(12) United States Patent
Sharei et al.

(10) Patent No.: US 12,130,281 B2
(45) Date of Patent: Oct. 29, 2024

(54) GENE EDITING THROUGH MICROFLUIDIC DELIVERY

(71) Applicants: Massachusetts Institute of Technology, Cambridge, MA (US); President and Fellows of Harvard College, Cambridge, MA (US)

(72) Inventors: Armon R. Sharei, Cambridge, MA (US); Marc Lajoie, Seattle, WA (US); Klavs F. Jensen, Lexington, MA (US); Robert S. Langer, Newton, MA (US)

(73) Assignees: Massachusetts Institute of Technology, Cambridge, MA (US); President and Fellows of Harvard College, Cambridge, MA (US)

( * ) Notice: Subject to any disclaimer, the term of this patent is extended or adjusted under 35 U.S.C. 154(b) by 200 days.

(21) Appl. No.: 17/404,286

(22) Filed: Aug. 17, 2021

(65) Prior Publication Data

US 2022/0091099 A1  Mar. 24, 2022

Related U.S. Application Data

(62) Division of application No. 15/542,892, filed as application No. PCT/US2016/013113 on Jan. 12, 2016, now Pat. No. 11,125,739.

(60) Provisional application No. 62/102,347, filed on Jan. 12, 2015.

(51) Int. Cl.
| | | |
|---|---|---|
| *G01N 33/487* | (2006.01) | |
| *C12N 15/87* | (2006.01) | |
| *G01N 33/50* | (2006.01) | |
| *C12Q 1/00* | (2006.01) | |

(52) U.S. Cl.
CPC ......... *G01N 33/5002* (2013.01); *C12N 15/87* (2013.01); *G01N 33/48721* (2013.01); *C12Q 1/00* (2013.01)

(58) Field of Classification Search
CPC ......... G01N 33/5002; G01N 33/48721; C12N 15/87; C12Q 1/00
See application file for complete search history.

(56) References Cited

U.S. PATENT DOCUMENTS

| | | | |
|---|---|---|---|
| 4,055,799 A | 10/1977 | Coster et al. | |
| 4,376,634 A | 3/1983 | Prior et al. | |
| 4,835,457 A | 5/1989 | Hanss et al. | |
| 5,023,054 A | 6/1991 | Sato et al. | |
| 5,643,577 A | 7/1997 | Pang et al. | |
| 5,658,892 A | 8/1997 | Flotte et al. | |
| 5,842,787 A | 12/1998 | Kopf-Sill et al. | |
| 5,951,976 A | 9/1999 | Segal | |
| 6,133,503 A | 10/2000 | Scheffler | |
| 6,156,181 A | 12/2000 | Parce et al. | |
| 6,186,660 B1 | 2/2001 | Kopf-Sill et al. | |
| 6,218,166 B1 | 4/2001 | Ravindranath et al. | |
| 6,410,329 B1 | 6/2002 | Hansen et al. | |
| 6,461,867 B1 | 10/2002 | Cai et al. | |
| 6,562,616 B1 | 5/2003 | Toner et al. | |
| 7,109,034 B2 | 9/2006 | Orwar et al. | |
| 7,704,743 B2 | 4/2010 | Fedorov et al. | |
| 7,993,821 B2 | 8/2011 | Chiu | |
| 8,211,656 B2 | 7/2012 | Hyde et al. | |
| 8,669,044 B2 | 3/2014 | Chiu | |
| 8,679,751 B2 | 3/2014 | Huang | |
| 8,697,359 B1 | 4/2014 | Zhang | |
| 8,844,570 B2 | 9/2014 | Glick | |
| 9,005,579 B2 | 4/2015 | Nowinski et al. | |
| 9,017,991 B2 | 4/2015 | Diefenbach | |
| 9,157,550 B2 | 10/2015 | Wheeler et al. | |
| 9,255,245 B2 | 2/2016 | Bernick et al. | |
| 9,364,504 B2 | 6/2016 | Godfrin et al. | |
| 9,458,489 B2 | 10/2016 | Lim et al. | |
| 9,526,823 B2 | 12/2016 | Yoshioka | |
| 9,950,049 B2 | 4/2018 | Godfrin et al. | |
| 10,124,336 B2 | 11/2018 | Sharei et al. | |
| 10,526,573 B2 | 1/2020 | Ding et al. | |
| 10,696,944 B2 | 6/2020 | Sharei et al. | |
| 10,870,112 B2 | 12/2020 | Sharei et al. | |
| 11,111,472 B2 | 9/2021 | Sharei et al. | |
| 11,125,739 B2 | 9/2021 | Sharei et al. | |
| 11,299,698 B2 | 4/2022 | Sharei et al. | |
| 11,806,714 B2 | 11/2023 | Sharei et al. | |
| 2003/0133922 A1 | 7/2003 | Kasha, Jr. | |
| 2004/0176282 A1 | 9/2004 | Dalby et al. | |
| 2004/0197898 A1 | 10/2004 | Nakatani et al. | |
| 2005/0026283 A1 | 2/2005 | Ormar et al. | |
| 2006/0134067 A1 | 6/2006 | Liu et al. | |
| 2006/0134772 A1 | 6/2006 | Miles et al. | |
| 2006/0223185 A1 | 10/2006 | Fedorov et al. | |

(Continued)

FOREIGN PATENT DOCUMENTS

| | | |
|---|---|---|
| CN | 101031339 A | 9/2007 |
| CN | 101031641 A | 9/2007 |

(Continued)

OTHER PUBLICATIONS

Sharei et al (PNAS 2013). (Year: 2013).*
Sharei et al (PNAS 2013; Supplemental Information; pp. 1-10). (Year: 2013).*
Sharei et al "Cell Squeezing as a Robust, Microfluidic Intracellular Delivery Platform" (Journal of Visualized Experiments: published Nov. 7, 2013; pp. 1-7). (Year: 2013).*

(Continued)

*Primary Examiner* — Catherine S Hibbert
(74) *Attorney, Agent, or Firm* — Wolf, Greenfield & Sacks, P.C.

(57) ABSTRACT

Gene editing can be performed by introducing gene-editing components into a cell by mechanical cell disruption. Related apparatus, systems, techniques, and articles are also described.

23 Claims, 75 Drawing Sheets

Specification includes a Sequence Listing.

(56) References Cited

U.S. PATENT DOCUMENTS

| | | |
|---|---|---|
| 2007/0243523 A1 | 10/2007 | Ionescu-Zanetti et al. |
| 2007/0249038 A1 | 10/2007 | Adamo et al. |
| 2008/0026465 A1 | 1/2008 | Nakata |
| 2008/0241844 A1 | 10/2008 | Kellogg |
| 2008/0311140 A1 | 12/2008 | Lee et al. |
| 2008/0318324 A1 | 12/2008 | Chiu et al. |
| 2009/0209039 A1 | 8/2009 | Adamo et al. |
| 2009/0280518 A1 | 11/2009 | Adamo et al. |
| 2010/0203068 A1 | 8/2010 | Betz et al. |
| 2010/0249621 A1 | 9/2010 | Ichitani et al. |
| 2010/0323388 A1 | 12/2010 | Chiu et al. |
| 2011/0014616 A1 | 1/2011 | Holmes et al. |
| 2011/0030808 A1 | 2/2011 | Chiou et al. |
| 2011/0091973 A1 | 4/2011 | Glaser |
| 2011/0300205 A1 | 12/2011 | Geall et al. |
| 2012/0064505 A1 | 3/2012 | Suresh et al. |
| 2012/0107925 A1 | 5/2012 | Li et al. |
| 2012/0207745 A1 | 8/2012 | Godfrin et al. |
| 2012/0222143 A1 | 8/2012 | Fahrenkrug et al. |
| 2013/0023051 A1 | 1/2013 | Bundock et al. |
| 2013/0045211 A1 | 2/2013 | Nowinski |
| 2013/0065314 A1 | 3/2013 | MacMillan |
| 2014/0011226 A1 | 1/2014 | Bernick et al. |
| 2014/0273229 A1 | 9/2014 | Meacham et al. |
| 2014/0287509 A1 | 9/2014 | Sharei et al. |
| 2015/0184127 A1 | 7/2015 | White et al. |
| 2015/0196913 A1 | 7/2015 | Liu |
| 2016/0017340 A1 | 1/2016 | Wu |
| 2016/0193605 A1 | 7/2016 | Sharei et al. |
| 2016/0199837 A1 | 7/2016 | Breinlinger et al. |
| 2017/0020926 A1 | 1/2017 | Mata-Fink et al. |
| 2017/0326213 A1 | 11/2017 | Jajosky et al. |
| 2018/0003696 A1 | 1/2018 | Sharei et al. |
| 2018/0016539 A1 | 1/2018 | Ding et al. |
| 2018/0085402 A1 | 3/2018 | Kahvejian et al. |
| 2018/0142198 A1 | 5/2018 | Sharei et al. |
| 2018/0201889 A1 | 7/2018 | Sharei et al. |
| 2018/0245089 A1 | 8/2018 | Sharei et al. |
| 2019/0017072 A1 | 1/2019 | Ditommaso et al. |
| 2019/0030536 A1 | 1/2019 | Sharei et al. |
| 2019/0093073 A1 | 3/2019 | Sharei et al. |
| 2019/0111082 A1 | 4/2019 | Gilbert et al. |
| 2019/0382796 A1 | 12/2019 | Gilbert et al. |
| 2020/0277566 A1 | 9/2020 | Sharei et al. |
| 2021/0138050 A1 | 5/2021 | Loughhead et al. |
| 2021/0170411 A1 | 6/2021 | Sharei et al. |
| 2022/0064584 A1 | 3/2022 | Sharei et al. |
| 2022/0195364 A1 | 6/2022 | Sharei et al. |
| 2023/0097861 A1 | 3/2023 | Ditommaso et al. |
| 2023/0130686 A1 | 4/2023 | Sharei et al. |
| 2023/0357782 A1 | 11/2023 | Sharei et al. |

FOREIGN PATENT DOCUMENTS

| | | |
|---|---|---|
| CN | 106244543 A | 12/2016 |
| EP | 882448 A1 | 12/1998 |
| EP | 1225228 A2 | 7/2002 |
| EP | 2169070 A1 | 3/2010 |
| JP | H01-196566 A | 8/1989 |
| JP | H03-257366 A | 11/1991 |
| JP | 2010-025852 A | 2/2010 |
| JP | 2011-163830 A | 8/2011 |
| JP | 2013-536848 A | 9/2013 |
| JP | 6235085 B2 | 11/2017 |
| KR | 100760309 B1 | 10/2007 |
| KR | 100891487 B1 | 4/2009 |
| KR | 20110009422 A | 1/2011 |
| KR | 2014-0115560 A | 10/2014 |
| KR | 20140134524 A | 11/2014 |
| WO | WO 85/00748 A1 | 2/1985 |
| WO | WO 97/20570 A1 | 6/1997 |
| WO | WO 00/07630 A1 | 2/2000 |
| WO | WO 02/67863 A2 | 9/2002 |
| WO | WO 03/20039 A1 | 3/2003 |
| WO | WO 2004/001424 A1 | 12/2003 |
| WO | WO 2006/010521 A1 | 2/2006 |
| WO | WO 2006/095330 A2 | 9/2006 |
| WO | WO 2006/105251 A2 | 10/2006 |
| WO | WO 2007/067032 A1 | 6/2007 |
| WO | WO 2007/097934 A2 | 8/2007 |
| WO | WO 2008/021465 A2 | 2/2008 |
| WO | WO 2009/056332 A1 | 5/2009 |
| WO | WO 2010/016800 A1 | 2/2010 |
| WO | WO 2010/077290 A1 | 7/2010 |
| WO | WO 2010/105135 A1 | 9/2010 |
| WO | WO 2010/129671 A2 | 11/2010 |
| WO | WO 2010/145849 A2 | 12/2010 |
| WO | WO 2011/051346 A1 | 5/2011 |
| WO | WO 2011/119492 A2 | 9/2011 |
| WO | WO 2012/069568 A2 | 5/2012 |
| WO | WO 2012/097450 A1 | 7/2012 |
| WO | WO 2012/106536 A2 | 8/2012 |
| WO | WO 2012/118799 A2 | 9/2012 |
| WO | WO 2012/162779 A1 | 12/2012 |
| WO | WO 2013/059343 A1 | 4/2013 |
| WO | WO 2013/185032 A1 | 12/2013 |
| WO | WO 2014/065596 A1 | 5/2014 |
| WO | WO 2014/106629 A1 | 7/2014 |
| WO | WO 2014/106631 A1 | 7/2014 |
| WO | WO 2014/120956 A1 | 8/2014 |
| WO | WO 2014/165707 A2 | 10/2014 |
| WO | WO 2015/023982 A1 | 2/2015 |
| WO | WO 2015/061458 A1 | 4/2015 |
| WO | WO 2015/153102 A1 | 10/2015 |
| WO | WO 2015/161276 A2 | 10/2015 |
| WO | WO 2016/003485 A1 | 1/2016 |
| WO | WO 2016/070136 A1 | 5/2016 |
| WO | WO 2016/077761 A1 | 5/2016 |
| WO | WO 2016/109864 A1 | 7/2016 |
| WO | WO 2016/115179 A1 | 7/2016 |
| WO | WO 2016/183482 A1 | 11/2016 |
| WO | WO 2017/005700 A1 | 1/2017 |
| WO | WO 2017/008063 A1 | 1/2017 |
| WO | WO 2017/041050 A1 | 3/2017 |
| WO | WO 2017/041051 A1 | 3/2017 |
| WO | WO 2017/106899 A2 | 6/2017 |
| WO | WO 2017/123644 A1 | 7/2017 |
| WO | WO 2017/123646 A1 | 7/2017 |
| WO | WO 2017/123663 A1 | 7/2017 |
| WO | WO 2017/192785 A1 | 11/2017 |
| WO | WO 2017/192786 A1 | 11/2017 |
| WO | WO 2018/089497 A1 | 5/2018 |

OTHER PUBLICATIONS

Lin et al in "Enhanced homology-directed human genome engineering by controlled timing of CRISPR/Cas9 delivery" (eLIFE 2014, pp. 1-13). (Year: 2014).*

Nemudryi et al.(Acta Naturae vol. 6, No. 3. 2014; pp. 19-40). (Year: 2014).*

Rivera-Torres et al.(PloS ONE vol. 9, No. 5: pp. 1-8; published May 1, 2014). (Year: 2014).*

Freitas Jr. Nanomedicine, vol. I: Basic Capabilities. 1999:1 page.

Hori et al., Control of regulatory T cell development by the transcription factor Foxp3. Science. Feb. 14, 2003;299(5609):1057-61. doi: 10.1126/science.1079490. Epub Jan. 9, 2003.

Loschko et al., Antigen targeting to plasmacytoid dendritic cells via Siglec-H inhibits Th cell- dependent autoimmunity. J Immunol. Dec. 15, 2011;187(12):6346-56. doi: 10.4049/jimmunol.1102307. Epub Nov. 11, 2011.

Ring et al., Targeting of autoantigens to DEC205+ dendritic cells in vivo suppresses experimental allergic encephalomyelitis in mice. J Immunol. Sep. 15, 2013;191(6):2938-47. doi: 10.4049/jimmunol.1202592. Epub Aug. 14, 2013.

Tsai et al., Reversal of autoimmunity by boosting memory-like autoregulatory T cells. Immunity. Apr. 23, 2010;32(4):568-80. doi: 10.1016/j.immuni.2010.03.015. Epub Apr. 8, 2010.

International Search Report and Written Opinion for PCT/US2016/013113 dated Mar. 21, 2016.

International Search Report and Written Opinion for PCT/US2015/060689 dated Feb. 1, 2016.

(56) References Cited

OTHER PUBLICATIONS

International Preliminary Report on Patentability (Chapter I) for PCT/US2015/060689 dated May 16, 2017.
International Search Report and Written Opinion for PCT/US2015/058489 dated Mar. 11, 2016.
International Preliminary Report on Patentability (Chapter I) for PCT/US2015/058489 dated May 2, 2017.
European Search Report for EP App. No. 14836593.5 dated Feb. 23, 2017.
International Search Report and Written Opinion for PCT/US2014/051343 dated Dec. 18, 2014.
International Preliminary Report on Patentability (Chapter I) for PCT/US2014/051343 dated Feb. 16, 2016.
European Search Report for EP App. No. 12841329.1 dated Apr. 30, 2015.
International Preliminary Report on Patentability (Chapter I) PCT/US2012/060646 dated Apr. 22, 2014.
International Search Report and Written Opinion for PCT/US2012/060646 dated Feb. 25, 2013.
International Search Report and Written Opinion for PCT/US2016/050287 dated Jan. 3, 2017.
International Search Report and Written Opinion for PCT/US2017/030933 dated Jul. 21, 2017.
International Search Report and Written Opinion for PCT/US2017/030932 dated Sep. 19, 2017.
Extended European Search Report for EP App. No. 16822078.8 dated Jan. 30, 2019.
International Search Report and Written Opinion for PCT/US2016/041653 dated Oct. 4, 2016.
International Preliminary Report on Patentability (Chapter I) for PCT/US2016/041653 dated Jan. 18, 2018.
Extended European Search Report for EP App. No. 16737769.6 dated May 3, 2018.
International Preliminary Report on Patentability (Chapter I) for PCT/US2016/013113 dated Jul. 27, 2017.
Partial Supplementary European Search Report for EP App. No. 15859824.3 dated Jun. 11, 2018.
Partial Supplementary European Search Report for EP App. No. 15855640.7 dated May 30, 2018.
Extended European Search Report dated Sep. 11, 2018 for Application No. EP 15859824.3.
Extended European Search Report dated Sep. 5, 2018 for Application No. EP 15855640.7.
International Search Report and Written Opinion for PCT/US2016/050288 dated Jan. 12, 2016.
Extended European Search Report dated Nov. 21, 2019 for Application No. EP 19187758.8.
Extended European Search Report for EP Application No. 21158382.8 dated Jun. 11, 2021.
[No Author Listed], SQZ Biotech and AskBio Announce Research Collaboration to Create Immune Tolerization Products for AAV Gene Therapies. AskBio. Press Release. Nov. 7, 2019. 3 pages.
[No Author Listed], SQZ Biotech Announces Pricing of Initial Public Offering. SQZ Biotech. Press Release. Oct. 29, 2020. 2 pages.
[No Author Listed], SQZ Biotech Closes $65 Million Series D Financing. SQZ Biotech. Press Release. May 18, 2020. 2 pages.
[No Author Listed], SQZ Biotechnologies Presents Preclinical Data for their SQZ Tolerizing Antigen Carrier Platform in Antigen-Specific Immune Tolerance (ASIT) Digital Summit Invited Talk. SQZ Biotech. Press Release. Jan. 27, 2021. 4 pages.
Adamo et al., Microfluidic Cell Deformation as a Robust, Vector-Free Method for Cystosolic Delivery of Macromolecules. 2012 AIChE Annual Meeting. Oct. 2012;8 pages.
Adamo, Andrea et al., "Microfluidics-Based Assessment of Cell Deformability," Analytical Chemistry (Aug. 7, 2012), vol. 84, No. 15, pp. 6438-6443.
Alberts et al., Chapter 11: Ion Channels and the Electrical Properties of Membranes. Molecular Biology of the Cell, 4th Ed. New York: Garland Science. 2002. 20 pages.

ATCC Thawing, Propagating, and Cryopreserving Protocol, NCI-PBCF-HTB81 (DU 145), Prostate Carcinoma (ATCC.RTM. htb-81), Version 1.6, 2012, 23 pages.
Augustsson et al. "Microfluidic, Label-Free Enrichment of Prostate Cancer Cells in Blood Based on Acoustophoresis," Analytical Chemistry, Aug. 28, 2012 (Aug. 28, 2012), vol. 84, No. 18, pp. 7954-7962.
Azarikia et al., Stabilization of biopolymer microgels formed by electrostatic complexation: Influence of enzyme (laccase) cross-linking on pH, thermal, and mechanical stability. Food Res Int. Dec. 2015;78:18-26. doi: 10.1016/j.foodres.2015.11.013. Epub Nov. 21, 2015.
Banz, A et al., "Tumor Growth Control Using Red Blood Cells as the Antigen Delivery System and Poly(I:C)," J Immunother 2012, 35(5), pp. 409-417.
Baumann et al., Hemolysis of human erythrocytes with saponin affects the membrane structure. Acta Histochem. Feb. 2000;102(1):21-35. doi: 10.1078/0065-1281-00534.
BD Bioscience FITC-labeled anti-CD45 antibody, 2 pages.
BD Bioscience PE-labeled anti-EpCAM antibody, 2 pages.
Berrington et al., Lymphocyte subsets in term and significantly preterm UK infants in the first year of life analysed by single platform flow cytometry. Clin Exp Immunol. May 2005;140(2):289-92. doi: 10.1111/j.1365-2249.2005.02767.x.
Blagovic et al., 165 Activating antigen carriers generated with microfluidics cell squeezing drive effective anti-tumor responses. JITC. Dec. 2020;8:A98-9. doi: 10.1136/jitc-2020-SITC2020.0165.
Boohaker et al. The Use of Therapeutic Peptides to Target and to Kill Cancer Cells. Curr Med Chem. (2012); 19(22), 26 page reprint.
Bosilkovski, This MIT PhD Just Raised $65 Million For His Clinical Stage Cell Therapy Company. Forbes. May 21, 2020. https://www.forbes.com/sites/igorbosilkovski/2020/05/21/meet-the-mit-phd-who-just-raised-65-million-for-his-clinical-stage-cell-therapy-company/?sh=1e9a48af9809 [last accessed Jan. 28, 2021]. 3 pages.
Cancer Facts & Figures 2012. Published by the American Cancer Society in Atlanta, 68 pages.
Carlson et al., Self-Sorting of White Blood Cells in a Lattice. PRL. Sep. 15, 1997;79(11):2149-52.
Chaw et al. Multi-step microfluidic device for studying cancer metastasis. Lab on a Chip (2007), v7, p. 1041-1047.
Chen et al., Patch clamping on plane glass-fabrication of hourglass aperture and high-yield ion channel recording. Lab Chip. Aug. 21, 2009;9(16):2370-80. Epub May 14, 2009. https://doi.org/10.1039/b901025d.
Cremel, L et al., "Innovative approach in Pompe disease therapy: Induction of immune tolerance by antigen-encapsulated red blood cells," Int J Pharm. Aug. 1, 2015;491(1-2), pp. 69-77.
Cremel, L. et al., "Red blood cells as innovative antigen carrier to induce specific immune tolerance," Int J Pharm. Feb. 25, 2013;443(1-2), pp. 39-49.
Cross et al., "Nanomechanical analysis of cells from cancer patients," Nature Nanotechnology (Dec. 2007), vol. 2, pp. 780-783.
De Clercq et al., Antiviral agents active against human herpesviruses HHV-6, HHV-7 and HHV-8. Rev Med Virol. Nov.-Dec. 2001;11(6):381-95. doi: 10.1002/rmv.336.
De Clercq, Antiviral drugs in current clinical use. J Clin Virol. Jun. 2004;30(2):115-33. doi: 10.1016/j.jcv.2004.02.009.
Ding, X et al., "High-throughput nuclear delivery and rapid expression of DNA via mechanical and electrical cell-membrane disruption," Nature Biomedical Engineering (2017), vol. 1, No. 3, 7 pages.
Ditommaso et al., Cell engineering with microfluidic squeezing preserves functionality of primary immune cells in vivo. PNAS. Oct. 2018;115(46):E10907-14.
Downs, C. A. et al. (May 14, 2011). "Cell Culture Models Using Rat Primary Alveolar type 1 Cells", Pulmonary Pharm. & Therapeutics 24(5)577-586.
Eixarch, H. et al. "Tolerance induction in experimental autoimmune encephalomyelitis using non-myeloablative hematopoietic gene therapy with autoantigen." Molecular Therapy 17.5 (2009): 897-905.
Escoffre et al., What is (still not) known of the mechanism by which electroporation mediates gene transfer and expression in cells and tissues. Mol Biotechnol. Mar. 2009;41(3):286-95. doi: 10.1007/s12033-008-9121-0. Epub Nov. 18, 2008.

(56) References Cited

OTHER PUBLICATIONS

Esposito et al., "Intraerythrocytic administration of a synthetic Plasmodium antigen elicits antibody response in mice, without carrier molecules or adjuvants," International Journal of Parasitology, vol. 20, No. 8, pp. 1109-1111 (1990).
Fagerlund et al., The Cpf1 CRISPR-Cas protein expands genome-editing tools. Genome Biol. Nov. 1, 20157;16:251. doi: 10.1186/s13059-015-0824-9.
Favretto, M. E. et al., "Human erythrocytes as drug carriers: Loading efficiency and side effects of hypotonic dialysis, chlorpromazine treatment and fusion with liposomes," Journal of Controlled Release 2013; 170: 343-351.
Gasteiger et al. The Proteomics Handbook (2005), Chapter 52, pp. 571-607.
Getasew et al., Advanced malaria treatment in pregnant women. Eur J Clin Pharm. Sep.-Oct. 2017;19(5):325-34.
Gilbert, T-cell-inducing vaccines—what's the future. Immunology. Jan. 2012;135(1):19-26. doi: 10.1111/j.1365-2567.2011.03517.x.
Golzio et al., Direct visualization at the single-cell level of electrically mediated gene delivery. Proc Natl Acad Sci U S A. Feb. 5, 2002;99(3):1292-7. doi: 10.1073/pnas.022646499. Epub Jan. 29, 2002.
Gossett et al., Hydrodynamic stretching of single cells for large population mechanical phenotyping. PNAS. May 2012;109(20):7630-5.
Griesbeck et al., "Sex Differences in Plasmacytoid Dendritic Cell Levels of IRF5 Drive higher IFN-alpha production in Women," The Journal of Immunology (Dec. 2015), vol. 195(11):5327-5336.
Grimm, A. J. et al., "Memory of tolerance and induction of regulatory T cells by erythrocyte-targeted antigens," Sci Rep. Oct. 29, 2015;5:15907, 11 pages.
Hallow et al., "Shear-Induced Intracellular Loading of Cells With Molecules by Controlled Microfluidics," Biotechnology and Bioengineering (2008), vol. 99(4):846-854.
Han, X et al., "CRISPR-Cas9 delivery to hard-to-transfect cells via membrane deformation," Sci. Adv., Aug. 14, 2015, e1500454, 8 pp.
Hillerdal et al., "Systemic treatment with CAR-engineered T cells against PSCA delays subcutaneous tumor growth and prolongs survival of mice," BMC Cancer (Jan. 18, 2014), vol. 14, No. 30, pp. 1-9.
Hoeppener A.E.L.M., Swennenhuis J.F., Terstappen L.W.M.M. (2012) Immunomagnetic Separation Technologies. In: Ignatiadis M., Sotiriou C., Pantel K. (eds) Minimal Residual Disease and Circulating Tumor Cells in Breast Cancer. Recent Results in CancerResearch, vol. 195. Springer, Berlin, Heidelberg.
Hoffman, On Red Blood Cells, Hemolysis and Resealed Ghosts. In: The Use of Resealed Erythrocytes as Carriers and Bioreactors. 1992. Magnani et al.,. Eds. Chapter 1:1-15.
Hoskin et al. Studies on anticancer activities of antimicrobial peptides. Biochimica et Biophyscia Acta (2008), v1778, p. 357-375.
Hosokawa et al. Size-Selective Microcavity Array for Rapid and Efficient Detection of Circulating Tumor Cells. Anal. Chem. (2010), v82, p. 6629-6635.
Howarth, M. et al. (May 2008). "Monovalent, Reduced-Size Quantum Dots for Imaging Receptors on Living Cells," Nature Methods 5(5):397-399.
Janeway Jr. et al. Immunobiology: The Immune System in Health and Disease. 5th edition (2001), Chapter "The structure of a typical antibody molecule", NCBI Bookshelf NBK27144, 5 page reprint.
Jiang, The immunopotentiators and delivery systems for use in vaccines. Prog Microbiol Immunol. Dec. 31, 2012;(3):1-8.
Johnson et al., Loss of resealing ability in erythrocyte membranes. Effect of divalent cations and spectrin release. Biochim Biophys Acta. May 4, 1978;509(1):58-66. doi: 10.1016/0005-2736(78)90007-x. Abstract only.
Kiani et al., Cas9 gRNA engineering for genome editing, activation and repression. Nature Methods. 2015;12:1051-4.
Kim, D., et al., "Microengineered Platforms for Cell Mechanobiology," Annual Review of Biomedical Engineering, 2009, vol. 11, pp. 203-233.

Kinosita Jr. et al., Survival of sucrose-loaded erythrocytes in the circulation. Nature. Mar. 16, 1978;272(5650):258-60. doi: 10.1038/272258a0.
Lee et al., "Nonendocytic delivery of functional engineered nanoparticles into the cytoplasm of live cells using a novel, high-throughput microfluidic device," Nano Letters (2012), vol. 12, pp. 6322-6327.
Lee et al., Kinetic studies of human erythrocyte membrane resealing. Biochim Biophys Acta. Apr. 26, 1985;815(1):128-34. doi: 10.1016/0005-2736(85)90482-1. Abstract only.
Li, J et al., "Microfluidic-Enabled Intracellular Delivery of Membrane Impermeable Inhibitors to Study Target Engagement in Human Primary Cells," ACS Chemical Biology 2017, vol. 12, No. 12, pp. 2970-2974.
Lin et al., "Highly selective biomechanical separation of cancer cells from leukocytes using microfluidic and hydrodynamic concentrator," Biomicrofluidics (Jun. 26, 2013), vol. 7, No. 3, pp. 34114-1-34114-11.
Liu et al., "Molecular imaging in tracking tumor-specific cytotoxic T lymphocytes (CTLs)," Theranostics (Jul. 28, 2014), vol. 4, No. 10, pp. 990-1001.
Liu et al., "Spatially selective reagent delivery into cancer cells using a two-layer microfluidic culture system," Analytica Chimica Acta (Sep. 1, 2012), vol. 743, pp. 125-130.
Liu, W. et al. (Jan. 20, 2010). "Compact Biocompatible Quantum Dots via RAFT-Mediated Synthesis of Imidazole-Based Random Copolymer Ligand," JACS 132(2):472-483.
Lizano et al., Mouse erythrocytes as carriers for coencapsulated alcohol and aldehyde dehydrogenase obtained by electroporation in vivo survival rate in circulation, organ distribution and ethanol degradation. Life Sci. Mar. 16, 2001;68(17):2001-16. doi: 10.1016/s0024-3205(01)00991-2.
Lorentz, K. M. et al., "Engineered binding to erythrocytes induces immunological tolerance to E. coli asparaginase," Sci Adv. Jul. 17, 2015;1(6):e1500112, 11 pages.
Magnani et al., Erythrocyte engineering for drug delivery and targeting. Biotechnol Appl Biochem. Aug. 1998;28(1):1-6.
Mali, P. et al., "RNA-guided human Genome Engineering via Cas9," Science (2013), vol. 339, No. 6121, pp. 823-826.
Maratou et al., Glucose transporter expression on the plasma membrane of resting and activated while blood cells. European Journal of Clinical Investigation. 2007;37:282-90.
Matthews, B.D., et al., "Cellular adaptation to mechanical stress: role of integrins, Rho, cytoskeletal tension and mechanosensitive ion channels," Journal of Cell Science, vol. 119, pp. 508-518, 2006.
McNeil et al., Coping with the inevitable: how cells repair a torn surface membrane. Nat Cell Biol. May 2001;3(5):E124-9. doi: 10.1038/35074652. Abstract only.
McNeil et al., Plasma membrane disruption: repair, prevention, adaptation. Annu Rev Cell Dev Biol. 2003;19:697-731. doi: 10.1146/annurev.cellbio.19.111301.140101.
McNeil et al., The endomembrane requirement for cell surface repair. Proc Natl Acad Sci U S A. Apr. 15, 2003;100(8):4592-7. doi: 10.1073/pnas.0736739100. Epub Apr. 2, 2003.
McNeil, Repairing a torn cell surface: make way, lysosomes to the rescue. J Cell Sci. Mar. 1, 2002;115(Pt 5):873-9.
Milo, R. "What is the total number of protein molecules per cell volume? A call to rethink some published values." Bioessays 35.12 (2013): 1050-1055.
Murphy, J. S. et al. (Sep. 1, 1956, e-pub May 2004). "Measurement of Wall Shearing Stress in the Boundary Layer by Means of an Evaporating Liquid Film," Journal of Applied Physics 27(9):1097-1103.
Nagel et al., HbS-oman heterozygote: a new dominant sickle syndrome. Blood. Dec. 1, 1998;92(11):4375-82.
Nic an Tsaoir et al., Scalable Antibody Production from CHO Cell Line of Choice Using Flow Electroporation. MaxCyte. Jun. 2016. 1 page.
Novokhatskiy et al., Problema kontaminatsii kletkami I novyie podkhody k kontroliu perevivaiemykh liniy. Voprosy virusologii. 1977;4:396-408.
Ogurtsov et al., Biotechnology. Principles and Application Training Manual. Ministry of Education and Science. 2012. 344 pages.

(56) References Cited

OTHER PUBLICATIONS

Paganin-Gioanni et al., Direct visualization at the single-cell level of siRNA electrotransfer into cancer cells. Proc Natl Acad Sci U S A. Jun. 28, 2011;108(26):10443-7. doi: 10.1073/pnas.1103519108. Epub Jun. 13, 2011.
Patel et al., Drug loaded erythrocytes: as novel drug delivery system. Curr Pharm Des. 2008;14(1):63-70. doi: 10.2174/138161208783330772.
Polvani et al., "Murine Red Blood Cells as Efficient Carriers of Three Bacterial Antigens for the Production of Specific and Neutralizing Antibodies," Biotechnology and Applied Biochemistry, vol. 14, pp. 347-356 (1991).
Ramakrishnan et al., 1743-P: Engineering Erythrocytes with the SQZ Cell Therapy Platform to Enhance Immunotolerance. Diabetes. Jun. 2019;68(Supplement 1). https://doi.org/10.2337/db19-1743-P. Abstract.
Ravilla et al., "Erythrocytes as Carrier for Drugs, Enzymes and Peptides," Journal of Applied Pharmaceutical Science, vol. 2, No. 2, pp. 166-176 (2012).
Razizadeh et al., Coarse-Grained Modeling of Pore Dynamics on the Red Blood Cell Membrane under Large Deformations. Biophys J. Aug. 4, 2020;119(3):471-482. doi: 10.1016/j.bpj.2020.06.016. Epub Jun. 24, 2020.
Reddy et al., Plasma membrane repair is mediated by Ca(2+)-regulated exocytosis of lysosomes. Cell. Jul. 27, 2001;106(2):157-69. doi: 10.1016/s0092-8674(01)00421-4.
Redman, Phospholipid metabolism in intact and modified erythrocyte membranes. J Cell Biol. Apr. 1971;49(1):35-49. doi: 10.1083/jcb.49.1.35.
Rossi, L. et al., "Erythrocyte-mediated delivery of phenylalanine ammonia lyase for the treatment of phenylketonuria in BTBR-Pah.sup.enu2 mice," Journal of Controlled Release 194; 37-44 (2014).
Rughetti, A. et al., "Transfected human dendritic cells to induce antitumor immunity," Gene Therapy, vol. 7, pp. 1458-1466 (2000).
Rutella et al., "Tolerogenic dendritic cells: cytokine modulation comes of age," Blood, vol. 108, No. 5, pp. 1435-1440 (2006).
Sachs, Potassium-potassium exchange as part of the over-all reaction mechanism of the sodium pump of the human red blood cell. J Physiol. May 1986;374:221-44. doi: 10.1113/jphysiol.1986.sp016076.
Salgado et al., Red blood cell membrane-facilitated release of nitrite-derived nitric oxide bioactivity. Biochemistry. Nov. 10, 2015;54(44):6712-23. doi: 10.1021/acs.biochem.5b00643. Epub Oct. 28, 2015. Abstract only.
Saulis, The loading of human erythrocytes with small molecules by electroporation. Cell Mol Biol Lett. 2005;10(1):23-35.
Schatzmann et al., Calcium movements across the membrane of human red cells. J Physiol. Apr. 1969;201(2):369-95. doi: 10.1113/jphysiol.1969.sp008761.
Sharei et al., "Ex vivo Cytosolic Delivery of Functional Macromolecules to Immune Cells," (Apr. 13, 2015), PLoS One, vol. 10, No. 4, 12 pp. e0118803.
Sharei et al., "A vector-free microfluidic platform for intracellular delivery," Proc. Natl. Acad. Sci. USA (Feb. 5, 2013), vol. 110, No. 6, Supporting Information. 10 pages.
Sharei et al., "A vector-free microfluidic platform for intracellular delivery," Proc. Natl. Acad. Sci. USA (Feb. 5, 2013), vol. 110, No. 6, pp. 2082-2087.
Sharei et al., "Cell Squeezing as a Robust, Microfluidic Intracellular Delivery Platform," Journal of Visualized Experiments (Nov. 7, 2013), No. 81, 9 pp.
Sharei et al., "Plasma membrane recovery kinetics of a microfluidic intracellular delivery platform," Integrative Biology (2014), vol. 6, pp. 470-475.
Shelby et al., "A microfluidic model for single-cell capillary obstruction by Plasmodium falciparum infected erythrocytes," (Dec. 9, 2003), Proc. Nat. Acad. Sci., vol. 100, No. 25, pp. 14618-14622.
Song et al., Scientific basis for the use of hypotonic solutions with ultrasonic liposuction. Aesthetic Plast Surg. Mar.-Apr. 2006;30(2):233-8. doi: 10.1007/s00266-005-0087-z.
Steinman et al., "Tolerogenic dendritic cells," Annual Review of Immunology, vol. 21, pp. 685-711 (2003).
Stevenson, D. J. et al., "Single cell optical transfection," IEEE Transactions on Ultrasonics, Ferroelectrics and Frequency Control, vol. 53, No. 1, 863-871 (2010).
Stevenson, D. J. et al., "Single cell optical transfection," J. R. Soc. Interface, vol. 7, 863-871 (2010).
Stewart et al., "In vitro and ex vivo strategies for intracellular delivery," Nature, vol. 538, No. 7624, pp. 183-192 (2016).
Swaminathan et al. Mechanical Stiffness Grades Metastatic Potential in Patient Tumor Cells and in Cancer Cell Lines. Cancer Research (2011) , v71(15), p. 5075-5080.
Szeto et al., "Microfluidic squeezing for intracellular antigen loading in polyclonal B-cells as cellular vaccines," Scientific Reports, vol. 5, 10276 (May 2015), 13 pages.
Tlaxca, J. L. et al., "Analysis of in vitro Transfection by Sonoporation Using Cationic and Neutral Microbubbles," Ultrasound in Medicine and Biology, vol. 36, No. 11, 1907-1918 (2010).
Tran et al., Expansion of immature, nucleated red blood cells by transient low-dose methotrexate immune tolerance induction in mice. Clin Exp Immunol. Nov. 18, 2020;0:1-15. doi: 10.1111/cei.13552.
Vechkanov et al., Osnovy kletochnoy inzhenerii: Study guide. Rostov-on-Don. 2012; 133 pages. Relevant pp. 15-16.
Vinulan, SQZ Biotech Lines Up an IPO on the NYSE to Fund Cell Therapy R&D. Xconomy. Oct. 12, 2020. https://xconomy.com/boston/2020/10/12/sqz-biotech-lines-up-an-ipo-on-the-nyse-to-fund-cell-therapy-rd/ [last accessed Jan. 28, 2021]. 3 pages.
Weaver et al., A brief overview of electroporation pulse strength-duration space: A region where additional intracellular effects are expected. Bioelectrochemistry. Oct. 2012;87:236-43.
Wen et al., Shear Effects on Stability of DNA Complexes in the Presence of Serum. Biomacromolecules. Oct. 9, 2017;18(10):3252-3259. doi: 10.1021/acs.biomac.7b00900. Epub Sep. 1, 2017.
Williams, A.R. et al. (Nov. 5, 1999). "Filtroporation: A Simple, Reliable Technique for Transfection and Macromolecular Loading of Cells", Biotechnology and Bioengineering 65(3)341-346.
Wright et al., Rational design of a split-Cas9 enzyme complex. PNAS. Mar. 2015;112(10):2984-9.
Yangulov et al., Vliyaniye razlichnykh kriozashchitnykh sred na zhiznesposobnost kriokonservirovannykh limfoblastnykh kletochnyk liniy H-9 I U-937. Problemy kriobiologii. 1991;3:46-9.
Ye, Complexation between milk proteins and polysaccharides via electrostatic interaction: principles and applications—a review. Int J Food Sci Technol. Jan. 31, 2008;43(3):406-15.
Yin et al., "Delivery technologies for genome editing," Nature Reviews (2017), vol. 16, No. 6, pp. 387-399.
Zarnitsyn et al., "Electrosonic ejector microarray for drug and gene delivery," Biomed Microdevices (2008) 10:299-308.
Zdobnova et al., Self-Assembling Complexes of Quantum Dots and scFv Antibodies for Cancer Cell Targeting and Imaging. PLoS One. 2012;7(10):e48248. 8 pages.
Zhdanov et al., Tayna tretiego tsarstva. Znaniye. 1975; 176 pages. Relevant pp. 124-125.
Brahmer et al., Safety and activity of anti-PD-L1 antibody in patients with advanced cancer. N Engl J Med. Jun. 28, 2012;366(26):2455-65. doi: 10.1056/NEJMoa1200694. Epub Jun. 2, 2012.
Cobb et al., Development of a HIV-1 lipopeptide antigen pulsed therapeutic dendritic cell vaccine. J Immunol Methods. Feb. 28, 2011;365(1-2):27-37. doi: 10.1016/j.jim.2010.11.002. Epub Nov. 18, 2010.
Hombach et al., Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule. J Immunol. Dec. 1, 2001;167(11):6123-31. doi: 10.4049/jimmunol.167.11.6123.
Kim et al., Blocking the immunosuppressive axis with small interfering RNA targeting interleukin (IL)-10 receptor enhances dendritic cell-based vaccine potency. Clin Exp Immunol. Aug. 2011;165(2):180-9. doi: 10.1111/j.1365-2249.2011.04410.x. Epub May 18, 2011.

(56) References Cited

OTHER PUBLICATIONS

Liu et al., Plasma cells from multiple myeloma patients express B7-H1 (PD-L1) and increase expression after stimulation with IFN-{gamma} and TLR ligands via a MyD88-, TRAF6-, and MEK-dependent pathway. Blood. Jul. 1, 2007;110(1):296-304. doi: 10.1182/blood-2006-10-051482. Epub Mar. 15, 2007.

Madan et al., Ipilimumab and a poxviral vaccine targeting prostate-specific antigen in metastatic castration-resistant prostate cancer: a phase 1 dose-escalation trial. Lancet Oncol. May 2012;13(5):501-8. doi: 10.1016/S1470-2045(12)70006-2. Epub Feb. 10, 2012.

Stronen et al., Dendritic cells engineered to express defined allo-HLA peptide complexes induce antigen-specific cytotoxic T cells efficiently killing tumour cells. Scand J Immunol. Apr. 2009;69(4):319-28. doi: 10.1111/j.1365-3083.2008.02223.x.

Wang et al., Delivery of siRNA therapeutics: barriers and carriers. AAPS J. Dec. 2010;12(4):492-503. doi: 10.1208/s12248-010-9210-4. Epub Jun. 11, 2010.

\* cited by examiner

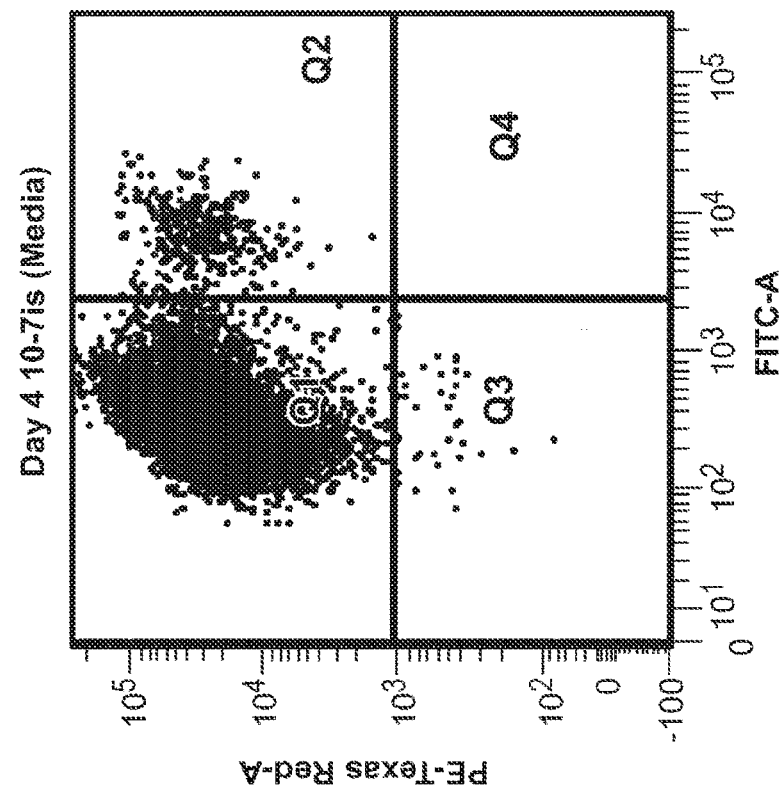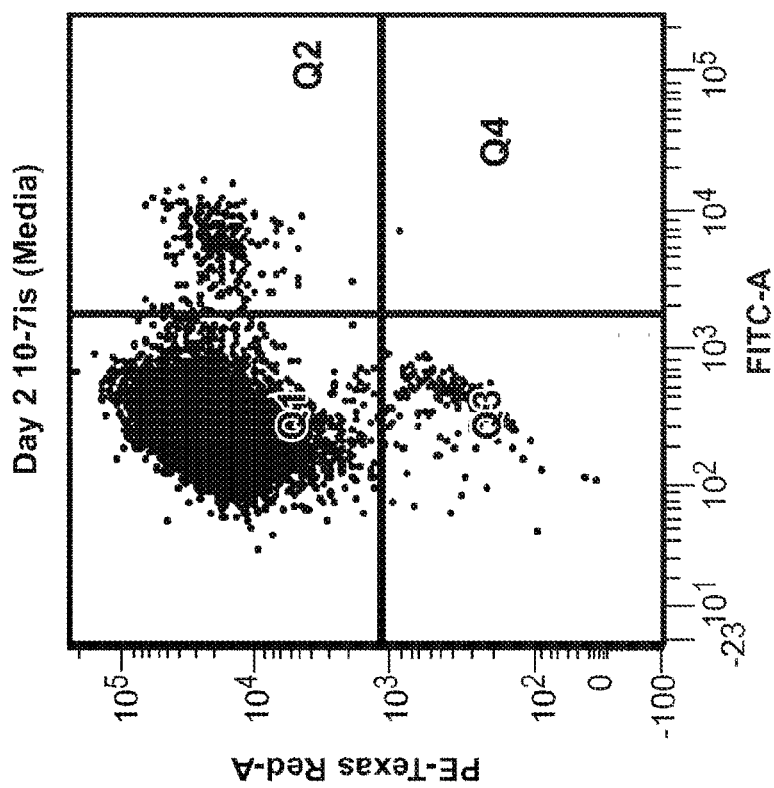
FIG. 3A

```
TTGGGGCGGGGGGCAGGGAGGAGCACTTCACACCATTGTCAACCGTAGTTTTAGCTGTGTGGA
CCTACCCAGACTGTGCATGCAGGAGAGTGTGTGACCAGAGTCCATATTCAGGAAGCAAACAGGTTGTT
CAGGGCTGGGTGAGCTCGATTCTGCAGCTTAGCACAGCGTTTGGCACAAGTAAGTGC
TCACGAAGTGTTAGCTATTAGTATTTCTGTAACAAATTAGAATCATGCTATATATTGGT
TTTGTTCCTGCTTTATTCAATTAACACAGTAGTGTTTTGAAGCTTACTAAAAATTGTTGA
ACACATGATCTTCATGATGGACAAGACTGTCCTCACATCAGACATGAACTTTGATTGATT
TGACCAAGTGCCGATTGTTGACATTCCGGTTGTTCTCGTTTTTTCTATAAACATCCC
TGACTGCTTCCTTGGATTCCTGAAAAGGGAGTTGCTGGGGCAAAGGGGCGTGCATTTTT
AAAGTTTATGACCCCTCTCTGCTAATTCTCCAAAGTTGTCCTATTTATGCTCCC
TCTACTTAAGCTAACCCTAGGTGAGTATTATTAGTTTAATTATTCCAACATGACAG
GTAAGAAAAACACATTATCACATTGTGAAATTGCATCTTGTGATTACTTTACTATTC
ATTGGCCATTCATGCTTTTTTTTTTTTTTTTGGTGTGCTGGTCTCAIGTCCTACTCCTA
ATAGGGTTGCATCTTATTTTCCCTTATTGATTGCCACAGCTCTTATTGAAIGT
TATTAACTTTCATCAGCCATTACATATATAGCAAATATTTCCCAATTCATCATTTGC
TTTTTTTCTATTTGTTTTTTTTCTGCTTCCTGTTTTTGTGATGCTTATGATGGTTTATACAGTCAAA
TAGGTTAGTCTTTTTTTCTCTGTTTGGCCTATGTTGGCTTCAGTCTTTTATGGCTTCAT
TACTTGAAAATGAGATAAAATGTTCACCTAGTGGCTTCTAGTCTCTTTTATGGCTTCAT
TTTTTCCATTTACTATAGAGGGTTAAGAGAGTGTGTAAGAGAGCCAGACTGTCTGGGACAA
ACCCAGCGTCACCCAAGCCTATGTGTGATTTTAGCCAGGCACTTAACCTCTCCATAC
CTCCATTTCCTCATATGTACTGCAATGTTATAATACTTCCTCAGGAGTCTTTGTT
TAGATTAAAATTTTAACCAGTAGTTAAACTTATATCTTGAATGATCTGGCATTTTAGGTATA
AAGATCAGCATTAGGTGTTAAAACTTGTTAAACTCTTGAATGATCTGGCATTTTAGGTATA
TGATGATGGTGACATTTCAAACTGGGCAGGAGGGTTGTTGGGATAATGGACTGACTAT
TCACTCAATAACTTTATCTTCCTCCCTAATTATCTCAGACACATTGTTAAACCATACTCC
ATGGTCCTCCCAGTTTGAAATGCCACATTCATCATTCCTCCCAGTATCGTTCTTATACCATGGGT
CCATGCCAAGCTTTCTATTCTATTTCTGTTCTTCTCCCCAGTATCAATACCCAGTGGTGTCCCTGG
ACTGTTTTGCTTGATTGTTGCTTTGCAATACAATTCAATACCCAGCCATGGTGTCCCTGG
```

FIG. 6 (continued)

```
CACCTTGCCCTTCTTTATTCTTGATTATTTCAGGCAGCATCAGTTGAACCAGCCAGAGAC
CAGCAAATGTTCTTATTGAGGCAATCCTCCTCACTATCTCTTGTTCTCTTGCTCTGCTCAT
GCATGTGTCCATTTCTCTCAATGTCTCTCACTATCTCTTGTTCTCTTGCTCTGCTCTTT
GTGTGTGTCTCTTTGTCTCTCTATGTATCTCTCAGCCAGTCCCCCTGGATAGAGGGG
CAATTGTCAACTTGAAGCCCTGCAGACACCTAATGACTTAACCAGACAGCGTAGAAGGC
CCTGGCCCTGTCTACTCCACGCCTCTCCGTGCTCAGTGTAGAAGGCAAATTGAAGACC
AGAGATCCAGGCCTCACCGAAATGCAGGGCAGAGTTGAAATCCAAGCCTAGATCTCA
GGACTCTAGTGGGACCCTGGTTCTGGCTCTCCCCAACTGCAGCCTCAGTTTACCCC
TCAGCACCCAGAAGGGGAAGGGGCTACCATTCCCCCTTCTGCCTTCTCACA
CGTTGGACCCCAACTTCCCACAGTTGGACGATCCACGATCACAGTGTGGGCCAGCCT
CACAAGAGCTGGGCTAGTGAGGCCCCGACTCAGTCAGGCGTCAGGAGGCTAGTTGGCCAG
AGCGTGGTGATGATGGAGGCATGTCAGTCAGGCCTGTGTCCCCAGAGCTGGTGCT
GGTCCCCGAAAACCTTGATTGTGGGCCCCTCTAGAGAGTCTGATGATGGGCTCTGTATT
GGCGAAGGCTGAGGCTTTCCAGCTCCCCCCCAGCCAGACCAAAGGCACACCAGCC
TCAACCTCCTCCCCCTGTTGCCATCTCTGGCGGAGTGGCCATGTATTTGGAACGTT
GTTCCAGATGGACAGGGAGACTGAGGCCTAGGAGCAAGCTGGCTCTGTTTCCAGGCCTGG
TAGGCAAGAGCCCTATGAAGCAGCAAGCTGCCTGACTTTCAGATGGTTCCAAGGAGTT
GGACCAGGAGCCCTACACAGGCTACACATACTTTGGACCGTAGACTTTGGACCCCCACAGTCT
GTGGTTTGAGATTCTAGGATCCTTTAAATCTAAGAAATGCTGTTCTATGATTCTGAGGT
CCTGGTGGGTATACTATTGAAGACCCCAGGGTCCCAACCAGGGGCTCCAAATCAACCAGGGCAGTCA
CTCTCAGAGCTTCAAACCTGGGTCCTCCACAGGGACTCCAACCAGTCTTCAGAGC
TAGGGCTTGTCATAGTGGCCAGATGGACATCACCATCACCAGACCACCATGTC
ACCCCACCTGGCCAGCCTGCAGACGCAGTTCTCGGAACGACATCTTCGAAACCTGT
GGGGTGGGGTATCTGCCCCTCTTCTTCCTTCCGTGGTGTCGATGAAGCCCGGCATCCG
GCCGCCATGACGTCAATGAGCCCCCGGGGAAAAATCTGGCAAGTCGGGGGCTGTGACAACAGGGC
CAGATGCAGACCCCAGTGAGTCAGATATGAGAAAACATAATCTGTGTCCCAACAGAGACGTC
TCTGAGAAACCCAGTGAGGACGTCCCAACAGAGACAGTGCAGGAAGCCGGCTGCCCA
```

GCCCGGCCCTCTAGTGTCCTCTACCCCCAGACAGATCATTCCATGTCCCTGTGTCTGAGAAT
GTATCTATGTGCTTGTGAGTCAGGCCATCAGGCCATCCCACATGTGTTTGGGAGAATTCTTAGCTCT
GGCCAAGTGTCCAGGCAGCTTCAGAAGCTTCAGCTTGCACCAGGCCACATGGGCCAGGCCAGA
GTGGTGGAAAACATCCATTTGCACCGAAATCGGTTAGTTTGTTCTGGCTGTATAACA
AAGTACCACACTGAGTGGCTTCAGCAACAGAAATTGATCATCTCACAGTTCTGGAGGCC
AGAGTCCAAGATCAAGGTGTTGCCAGGGTTGGTTCCTTCTGGGCCATAAGGGAGAAGC
TGCTCCAGGCCTCTCCCCAGTTCTGTGGTTGCTGTGTTGCTGCAATCTTTGTTATTTCTTGGCT
TGAAGGAGCATCACCCCCATCTCTGGCTTCATTCATTCACTCACCTTCATTCTCACCAGT
GCTCTCCAGGCCCTTGTTCGGAGACTAAGAACTTAATACCCTGGATTCTCACACTCATCTCCCT
ATGTTCTAAGCCCCCAGGAGAGACTAAGAACTTAATACCCTGACTTCTCACACTCATCTCCCT
CAGCCACAGCTCTGACAACCACCCCCAGGAGGTGACAGCAGTGTGACCAGCTGTGCCCAACT
TGCTCCCCAGAACCCTTCTATACTCCCCGGGCTGCTCTCAGCAGTGTGCCAACT
CAGTGCTGTGAGGTGCACACGGAACTCCTAAAGAAGACACACACCAGAGTTTA
TAAAATGTGCACAGGAAACACTTCCTAAAGAAGAAGAGTGGAGTTCAGTCACTATGG
GACTACGGAACTCGGCATCTGAGCATCCCCTTCTGTATAATAGGGCCCGGAGCCAGTGCTGGCTGGCAGTCC
CTTCCAGCTCTCGGCTTCCTCAGAGGATTATAGATCCTGAAAAGCCAGTGCTTCC
CTCAGGGAGTGGAAGGTTCTGCAGGCTCAGCAGGGGCCCAGAGCCATTGTGGAGGCTTT
CAAGGTGAGGACAATAGAGGGGGTGCAGGCTTGAGGCCAAAGAGGAGAAGG
AGTGGGCATTTGAGGCAGGGGGTGTAGAGAAGCTTCTACAGGCCCCCCAGCTCAAGGAGGAGAAGG
GAACTCTGATGGGGCTGGTAGAGAAGCTTCTACAGGCCCCCCATCAGCTTGATCATCTGTATGCCAAGAGGAGACCCATC
TCTCCTCCCTCGTGAGATCTTCACTTGCCATGAGTGCCATGATCACACCTCAGCTTGACTCGC
CTCCTTGCCCTGAGATCTCACTTGCCAGATCCAGTATTCAGCTGCCCCTCAGCTCTCCACTCACA
TATTTAATGCCAGACTCTTCATGTCTATCTACACCTGCACTTTTGCACCAATCCAACTC
CCCGCCATCCATCACAGTAATGTCAGCTCGGTCCCCTTGCCACTACCTCGCCAGTCTCCAAGCTAAA
ACCCAGTCACTGTTTGACTTCCCTTTGCCACTACCTCGCCTTCGCCTTCTCCTGCCACCA
GATCCAGTCACTGTTTGACTTCCCTTTGCCACTACCTCGCCTTCGCCTTCTCCTGCCACCA
GCCCATTCGTGCCAGCATCACTTGCCAGGACTGTTACAATAGCCTCCTCACTAGCC

ACATGATATACCAGATATTCCCGACTGTCTCTGAACTGAAACCCTGACCTAGCCCATCCT
GACTGATAGCCTCACTGCAATCATCATCGCTCTGACTCTGTAATCCTGAATCCTGAATCCAAA
CTGATCAAATTCCCTGACCCCTCAGCCCTCACTCCAACCGAACCCACACTAACCTCATC
CTTGCCCTGAGCCTAACCCTGACCCCTAACCATGTCCCTGACACGTAAGATACTCGATAATTCAA
ACCATCTCTGGCTTCTGACCTAAAGCCAAGTCATCCCCATCCCCTAGACCCCCCA
CCTGAGTCCAACCCCAGCCTGACCTTAACCCTCCCTGACCCTTCACCTTCCCAAGTTGGCCTG
GCCCTTTACCCTCCAAATCCTTGACCCCACTTCGACCCTTCACCTTCCCCAACCCTG
AAATGTCACCTCCACAGAGAACAAGACCACCAACTCCAACTCCAACCCTTTCACTT
CAGCCCTAGCCCCTGAACAAGACCCCACTCCCAACTCCAACCAGTCCCTACCCTCACTTCC
CAGAACAACCATACCACACCCATCTAACCCTGCCCAACCGACACTTCACCCTTTCT
AACCCCATCTTTGACCCCCATGCTTCACCCCACATCTAGTCCCTGATTACCCGCCC
CTACAATTCCGCCCCCATGTCAGATGCCCCTCGGGTAGGTCATAGCCCCTAAACCCCAA
GTTTGGGAATGTGCCCCATGCCCCTACCCCAACTTGCCAGCCCATCCAG...

MPNPRPGKPSAPSLALGPSPGASPSWRAAPKASDLLGARGPGGTFQGRDLRGGAHASSSS
LNPMPPSQLQLPTLPLVMVAPSGARLGPLPHLQALLQDRPHFMHQLSTVDAHARTPVLQV
HPLESPAMISLTPPTTATGVFSLKARPGLPPGTNVASLEWVSREPALLCTFPNPSAPRKD
STLSAVPQSSYPLLANGVCKWPGCEKVFEEPEDFLKHCQADHLLDEKGRAQCLLQREMVQ
SLEQQLVLEKEKLSAMQAHLAGKMALTKASSVASSDKGSCCIVAAGSQGPVVPAWSGPRE
APDSLFAVRRHLWGSHGNSTFPEFLHNMDYFKFHNMRPPFTYATLIRWAILEAPEKQRTL
NETYHWFTRMFAFFRNHPATWKNAIRHNLSLHKCFVRVESEKGAVWTVDELEFRKKRSQR
PSRCSNPTPGP

SEQ ID NO: 57

```
CGCAGAAAATAGACAGCCTTGGCCGGGTGTAGTGGTTCACACCTGTGATCCCAGCACTGT
GGGAGGCTGAGGCGAGAGGATTGCTTGAGCCAGGAGTTTGAGACCAGCCTGGCCAATAT
AGTGAGACCCTGTCTCTACAAAAATAAGAAATTAGCTGGGTGTGGTGGCACACGTCCTG
TGGTTCCAGCTATGGAGAGGCTAAGGTGAGAGAATGAACCAGTTCATATGCTAGCAAGCT
GCAGTCAGCGATGATTGCACCACTGCACAGCCTGGGCGACAGAGTGAGACCCTTGTCT
CAAAAAAAAAAAAAGAAAATGAACCAGTTCATATGCTAGCAAGTGACTGGGTG
TGCAGGTGACATTACTAGCTGGAGGATCAGGGAGGCCCTCCGAGGAGGTGACATTGA
GCTGAGACCCGATGAGGAGGAAGAGAGAGCTGGCCATGTGACGTAGTGATCAAGAGTCAA
GCATCTCTGGGCAGAGGAGATGGTGAGCACAAAGCCCTAATGTGGAGCCAGGCCACAGTTAG
GGACAGTGTGCCCGTGGCAGAGGACCCTAGTGGAGGCGAGGGCCACAGCAGGTTAG
ACCATGTTGGAGCTAGGATGTTGAAAGTGAAAACCTGAGAGTGAGGTGGCGCACGTCT
GTGATCCCAGCACTTTGGGAGGCCGAAGATTGCTGAGCTCAGGAGTTTAAAA
CCAGCTGGGCAACATAGAGAGACCCATCTCTATTAAAAAATACTGGTATGATGG
CCCAAGCATGTGGTAGTCCTAGCAGTTTGGGAGGCTGGGGATCACTTGAGCCC
AAGAGTTCAAGACCACCCTGGGCAACATGGAGAGACCTCATCTCTACTACGA
CTACTACTACTAATAATAGCTGGATGTAGTGGCATGCACCTGTGGTCTCAGTTACT
TGGAAGGCTGAGGCAGGATCACCTGAGCCAAGGAGGTCGACGCTGAGTTGA
TTGTGACACTGCACTTCAGCCTGGGTGATAAAGCAAGATTCTGTGTCAAAAAAAAAAA
AAAGAGAGGGAAGAGGGAAGAAGAAGAAGAAGAAGAAGAAGAAGAAGAAGAAAG
AGGAAGAGCGAGAAAAGTGACACCCAGTCGAAAGAAAAGTGACAACCGGCTGGGCATGGT
AAAAGAAAAAGAAAAAGTGACACCCAGTCGAAAGAAAAGTGACAACCGGCTGGGCATGGT
CGGTCGAAAGAAAAAAAGTGACACTTTGGGAGGCCGAGGCAGGTCACGAGGTTCAAGACCAT
CCCAGCACTTTGGGAGGCCGAGGCAGGTGGATCACGAGGTTCAAGACCAT
GCCCAACATGGTGAAACCCTGTCTCAACTAAAGATACAAAAAAATTAGCTGGCACA
GTGGTGCGCACCTGTGAGTCCCAGCTACTAGGGAGGCTGAGGCAGGAGAATTGCTTGAAC
```

FIG. 8 (continued)

CCAGGAGGCGGAGGTTGCAGTGAGCCGAGATTGCGTCACTGCACTCCAGCCTGAGTGCAG
CGGGAGAGAGACTCCATCTCAAAAAAAAGAAAAAGAAAAAAGTGACAACCTGCTTA
CAGAGTACTGGCGAGTTTGTGGGTGGGTGCTCCCTAGCCCTGCTGATTCTTGCTTCTCA
CACTCATGTCTGCCCCTGCCCCAGTGCACATCTTGTCACTGTCGGCCCCACCGATGGGGT
TCCTACTGAGTCTTCTGGTCCCTGATCCCTGGTGTCATTTCCTGCCAGGTAGCTTG
GCCAGGCCTCCCCTGGTGCAGATTTCATCCTGGTTTCTCAGCCTGGCCTGAATGACCC
TCTACAGACAGGTCCCCATGCCCAGCCACCTCTCAGAACAACTTGCTCCAGCCACATGGCTTGCTCACG
GCCAGGCACTGCGCCCATGTGGACTCTGTGCGTGCCACCTCTTTGCCCTGACCCATGTTGCC
TCTGGGGAGCACTTCTTCCCACCTTCCATCATGGCTGTGGGAGAAGGGCACCAGGCTCCGGCG
TGCCCCCGACGCGTCGTGTTTTACCCACCTTCCTACTCAGTCTTGTGACCTTGGGCAATTACT
TCTGACAGCCGTGTTTTACCCACCTTAGTTTCTGTTTCTAAAATTGGGTGAATAACACCTAAGTAG
TAACATCTCGAGTCTTAGTTTCTGTTTCTAAAATTGGGTGAATAACACCTAAGTAG
GGTTGGCCTGAGGATTAATAGTATAAAGCTGGCACTGAAACCCTGCCACTT
ACCAGCTTTCACATCAGTTCCAGAACTTGTAAGCTCATTGTCAGGCGGGATT
CTGAGCCTATCTTCTTGTATCACCATTGATCTTGATCGTATGGTTTTAATTTTTTT
GACTGCCTATCTTCTTGTATCACCATTGATCTTGATCGTATGGTTTTAATTTTTTT
TTTTGAGACCTTCCACCTCGTGTTGCCAGGCTGGAGTGCGGTGGCGATGATCTCGGCTC
ACTGCAACCTCCACCTCCCTGAGAAGCTGGGATTACAGGCATGTGCCACACCCGGCTA
ATCTTTGTATTTTTAGTAGAGTTGGGGTTTCACTATGTTGGCCAGGCTGGTCTCGATCTC
CTGACCTCGTGATCCGCCAACTTCACGTTTATACACACCCATGTTGGCCCTGCCA
CTGCGCCCGGCCAACTTCACGTTTATACACACCCAAGTTGCCATGGCCA
AAGAGCCTTCCCTGTACCCCTAAAAGTTTCCCAGAAATTGTTCCCAGTTAGCATATTTATT
TTTATAAAGGTAATGCATGCCCATCATATAACATTCAAAAAGGTATGTAGAGAACCAAGT
GTCTCCCCCAGCCCTGCCTCCACCCAGTTCCCTAGGGAAGCCACCAATA
TGTGTTTCTTAGTATCCCCTGTTGAGCTGCTTTCCTCGTTTTGGCGGTTGA

```
CAGTGTGCCACCCCAGGCTGCCAGGTGCCCAGGTCCCAGGGTCAGGGTCACCCATAGGGTCAAGTCAT
GTCGCTGTAAGGCAGGCCAGGCGGGGGGGAGCCCTCTGCTGAGGCTCCTGTCTGTGACCA
CAGTGTGGGCTGGGCAGGGAGGGGTCTGCCTGGGCTTGAATTCAAGGCTGAGACCCAGGAG
GGAGACTCAAGTCCTGTGAATGGCCTAATTTGCTCCCCCAGGGTGACTACAGT
GGCTGTTGCCTCAGCCAGCCCTTGTCTCTGCCAGTCAGGGTGGGCCAGCTG
GATGGAGGTGTCAGGGGTCGACTACAGGGTCCGAGGATACAGCTGCC
CCTCCCCACTTCCCCTGAGCTGTGAGCTTCTGGATCTCTGAGTTGCTG
ACTTCTGCTCTTCCCACCCAGGCCTTATCCAGGGTGATGCCGCCTGACATT
GAGAACGAGTGTACTGCAGGAGAAGTCAGAGTACAGCAGCTGGC
TTCTGCTGTTCAGTGCATGGTCCCCAGGCCAGGGCCAGGGCAGCTGAGGTGGT
GGCAGGCGGCCTGTGGGGCCCCAGGGACCCTTCCCCTTGCCACCTCTGCTCCTGAC
CCACCCCACGTGAGCTCCCCCGATGAGCTCCCTCTTTGGAGCTGATGCTCATTTCCCCA
CCCACATCTCAGATTCAGAGAGGGTGAGAACTTCCACCAGGTCTGAAGGGTGAGCACCCA
CCCCCAGCTCAGACGACCTAGACATTCCCCTGTGAGCACCCA
GGCTGCCCATTCACCCAGGATACCCAGAGTGCCTGCCCCAGAGCCTCCCCTT
TCTCCACCCACGCCAGGAGGGCCATCTCCCACACCTCCCCACAGAGCCTCCCCTT
CTCCAAAGGCCCTACTCCTCCCAGAAGTGCCTCACTCCTCCCCCACAGCAGGTTGCCC
CCTGCTCCCAACCTCCTGTGAACTCCCAGGCTTCCCATACAGATCCCCCACCCC
TGCTGCCACAGTCCCCGCAAGCCTCATGGCTTCCCTGGCTAACCCTGTAGCTC
AGGAGGGTCTGACCCAGGTGTGAGTGTGAACGCCAGACCATCTCGCCCTCCTCT
CCGCCCACTCCCAGTGACCCGAGTCCTGGCACTCACAGGGACGGGACAGTAACATCCC
CCGGTGGACTGCATAGTCACTCACATCAGGTCAGCAGTGTGGGCCACGTGGGAGG
AGAGGCTGGGCCTGGGAATTCCCTGTCTGTTGCATGGTGCTGAGGTGGACCCTAGATCCAGAGACAGCTG
GGCAAAGCCGAAGCTCTGCTTCTCTTGGGTGCATGGTGCAGTGTTCAGGCCTGCT
GGGCCAAGGGCTCACTGTCTCTTGGGGTGCGTCTCCACGTTGCGTCCAGAACCAGTG
```

```
ATTCTGGAGATTTGGCATTACCAGTAGTTGCTGCCTGACCATGGGGTCCCAGTGAG
CCTGGGGTGTCCTGAGCTTCCTGGACCAGTGACCAGCGGAAGTCTGCCTCAC
GCAGGGCCCATGTCGCACTGCCAGTGATGATAATCCTGATGGTAGTGACAG
CTGAGAAGTAAATACTGCTAAGTGCCATGAGCTGTTATAAGCAATATAAACGTTAGCTCG
CACATTGAGTGCCCTCCGCTTCACCCCGGTTCCTCTCCGGTGTCCCTGGCTCCAGAAC
CCTGGGTGGATCGTGGAACAGCCCCAGCAGCCCCACTTTGCCCTCTGCCGTGGTATCTTCC
TCAGAGCCCTCTCCGGATGTACCATCTCGCCCAACCCTGCCAAATACAGAGGAGGAGCCC
GGGACCCAGTTGCTGGCCAGGCCCAAGCTAGTCAGGCAAGGCCGGCAGGCACCCACAG
TAGGCCTGTGTCCCCGCTGCCTCCGGCTTTCTCTCTGCGAGGTCCCCATTCTGGTTTCTTCTC
CCAGGAACATCTATGAGGCATGTGCTCCCCATTCCTCCTCCCAGTCCCAGGCAGTGCCCATC
GGGCTTCGGCTTCTTCTGACTCTGCCTCTGCCCCAGCTTCCTCTTTGGGCTGCACATAACCCTC
CTGGCCCCAGGGCTGTGTGGGGATGGGTCAGGGCTCTTCTTTGGGCTGCAGAGGTGGGGC
TGTCTATCTACCCGCATGTTGTGATCAGGAGACCCTCTGGTAAGGTGCAGAGTGCCTGGGGTGGAT
TGCAAGGAGGAGCAGGGGTTCCACAGTGAGCCCACTGAGCTGAGCTGGCCTGGGTGGAT
GAGAGGCAGTGGGTGCAGGGCCCCTCCGCTTACCAGCTGTGTGGTCTTGGACAAATTACT
TAACTTTTTCTAACCCTCAGCTCCCTATCTCAGCCTCATCTGTAAAATCAGGATCTCAGCCCTC
AACTCAATGAGAAGCTGTGTAACTCACATCAGGCAGAGAATAGGGGAACCTGCCTTGCCC
GTTACTAGTTTAGTAACTCACATCAGGACCCCTGGGACCAGGGCTGCCAAGTCGGCTGAATCTAGAGGTGCCCCC
CGGTCCCCTTCCCACTCCCCCCAGCAGCTGTTTGTCCTGGGACGGCAAGTCGGCTGAATCTAGAGGTGCCCCC
TTCCCCCCAGCAGCTGTTTGTCCTGGGACGGCAAGTCGGCTGAATCTAGAGGTGCCCCC
GATGGGCTGTCCGGGACGCGTCACCCGCCACACATTCACACACTTCTTGAAAGCCCATG
AGAGCTACCCTGCTCACCCGCCACACATTCACACACTTCTTGAAAGCCCATG
GCCTTTATTTAGACGTTACAGGAAGTGGGGGTTATTTTGACAATCTGG
```

MVRWFHRDLSGLDAETLLLKGRGVHGSFLARPSRKNQGDFSLSVRVGDQVTHIRIQNSGDF
YDLYGGEKFATLTELVEYTQQGVLQDRDGTIIHLKYPLNCSDPTSERWYHGHMSGGQA
ETLLQAKGEPWTFLVRESLSQPGDFVLSVLSDQPKAGPGSPLRVTHIKVMCEGGRYTVGG
LETFDSLTDLVEHFKKTGIEEASGAFVYLRQPYYATRVNAADIENRVLELNKKQESEDTA
KAGFWEEFESLQKQEVKNLHQRLEGQRPENKGKNRYKNILPFDHSRVILQGRDSNIPGSD
YINANYIKNQLLGPDENAKTYIASQGCLEATVNDFWQMAWQENSRVIVMTTREVEKGRNK
CVPYWPEVGMQRAYGPYSVTNCGEHDTTEYKLRTLQVSPLDNGDLIREIWHYQYLSWPDH
GVPSEPGGVLSFLDQINQRESLPHAGPIIVHCSAGIGRTGTIIVIDMLMENISTKGLDC
DIDIQKTIQMVRAQRSGMVQTEAQYKFIYAIAQFIETTKKKLEVLQSQKGQESEYGNIT
YPPAMKNAHAKASRTSSKSLESSAGTVAASPVRRGGQRGLPVPGPPVLSPDLHQLPVLAP
LHPAADTRRMCMRTCTLRTRGRRK

SEQ ID NO: 59

FIG. 9

AGGCTCAAGCAATCCTCTCACCTCAGCCTCCCGAGTAGCTGGGACTACAGGCGCGCGCCA
CCACGCCCGGCTAATTTTTGTATTTTTTGTAGAGATGGGATTTCACTATTTTGCCCGGGC
TGGTTCCCAACTCCTGGACTCAAGCGATTCGCCCGCCTCAGCCTCCCAAAGGGAAGTGCT
GGGATTTCAGGCGTGTGCCACCGCTCCCACCCCAAAGTAGTATTTATTGTAATTATTATT
ATTATTTTGAGACGGAGTCTCGCTCTATTGCCAGGCTGGAGTGCAGTGGCGCGATCTCGG
CTCAATGCAACCTCTGCCTCCCGGGTTCAAGCGATTCTCCTGCTTCAGACTCCCAAGCAG
CTGGGACTACAGGCGCCCCCCACCACGCCAGGCTAATTCTTGAATTTTTAGTGGAGACGG
GGTTTCACCATGTTGGCCAGGATGGTCTCGATCTCTTGACCTCGTGATCCGCCCACCTCG
GCCTCCCAAAGTGCTGGGATTACAGGCGTGAGCCACCGCGCCCAGCCTATTATTATTTTT
TTAGGCAGTGTCTTGCCCTGTCGCTCAGGGTGTAGTGCAGTGGCGTGATCACGACTCACT
GCAGCCTCGACTTCTGGGCTTAAGCGATCTCCCGCCGCAGCCTCGACCCGGTTAGT
TTTTTGCATTTTTTGTAGAGATGAGGTCTTGCTTTTTTGCCCAGGCTGGCCTCGAACTCC
TTGGCTTAAGCGAACCTCTTGCCGCAGCCTCCCAAAGTGTTGGGATTACGGGCGTGAACC
ACCGCGCCCAGCCTACTATCTTTATCTTACAGAAGAAAGAATGAGCAAACCGACCT
GAGACGTAGCTAATTCCCACGGTCACATAATCTGCACGGCATTGT
GAACAATCAATCGATGTGCAGCGCCCGACGGGTCGTGCCTATACCG
AGCGCAGCTCACTTGCCGCCGCCTCAGGAGGAGCAACATGCTTGGA
ACTTGCGTCCGCCGCGAGCCCGCTGCCATCCCACCGTGCTCGACT
GCTCACGGAAGCACTAGTGCGGCGCGTCCAGCTGACATCACAGGCC
CGCCGCGAGGCGCGGCCAGGACGAGCGCCCCGCCGCGGCAGTGCATGTC
TCCCAATCCCCAGGCTGAGCGGGTCTGTGCCGGCCGTGCCTCTGCCGCT
CGCCCCAGCGGCTCCTTGGGCAGCCCTGTGACCGAGCCAGCCAGCCTGAG
CAGCAGCGGTTCGTCCGGACTGGACGCCGCCGAATCGACATCGCCGGTGAG
GAGCCCCGAGGGGCCCGGCGCGGGCCTCGGCCCGGCCACCGCCGCGTTCGGTTAGCCCCG
TCCGGAAGGGGGCGCCCCGGCCGGGCTTCGGGCTCCCGCCCGGGTCGGGGTTGGGGGCC
GGTTCCCTCCTCGTCCCCTCGCCCTCCAGGGGCCGGGGGCCGGCCCCACCGCGCCCCCAC
CCCTCGGGTCCCCATTCATTTCCTGCCTCCCCGAGTTCCGGCTGCGGCAGCCCCGGGGAT
GCCCGTCAGGCCCGGGGCAGGTAGAGCCGCCGAGGGAACCACGGGTGCCAGCGGCCAGGC
TCAGCGCCGCATTCCTGACCCATTGCCTCATGAGAATTGCCTCATGGTGATTCCGAAATA
ACCCTGCTCACTTGGGGAGGCTCCTTGGGACACGAGAGGGGAGTTGCGCGGGGCCGGGCC
CCCAGTGGTCTAGTCGTTCTGGCTCACTGTGCCACTTTCGTGCATTTGGGGACTTCACGC
AGGACCCCTGACCCTTTTATATGCCTCTTTGTGTCTTCTTTTCCTCCTACCCCTCACGTG
CCAGAAATGGAAAAACTGACTGTATCTGCAGCCACTAGAAGTATTTCCTTCCTCTGCGAT
CTTCGCTTTGGGAGATGGAAAGGAAGGGAGCCGCATCTCGTTATTTAATCCTTCACTGCA
ACCTTAACAGTCAGGTCACTTTACTGGTACCCGTTTTATGGATGAGGAAACCGAGGCCCA

```
GAAGCAACATGCTAGTAAATGACAAGATTGAAACTTAGGAGGATTAGTGAGTTAATGAG
ATCCTTTGAAAGGTCAGGGTAATACTACTACTAATAGCTAACATTTGCTTAGTTCTGACC
ACAGCCCTATCAGATGGCTACTATTATCCCCATTGTAAAGATGAGTAAACCGAGTTTCAG
AGGTTAAGTAAATTGCCTAACCTCACAGCTAGTAGGTGGTGGAGACAGAATCCCTACTTT
TAATCACTATGTTGCTTCTATTATTTTGTAACTATTGCTAACCATTTGTAAGCCTTAATT
TTGTTGTCAAACAGTAGTGTGACCTGTTGTTTTCAGATAGTGATCCTGCTATTTTGTATA
GTCACTCTATATACCACTCACACTTAAGACCCATTGTCTATTCTTTTCCATGATTGTTCA
ATTATGGTCACTGTCTCAGACATTTAAAAAACGATTCAAGCTATTGAGGCTATTTGAATG
AGATTTTCTTTTCTTTTTTTCTTTTTTTTTTGGAGACGGAGCTCACTCTGTTGCCCAG
GCTGGAGTGCAGTGGCGCAATCTCGGCTCACCACAATCTCCGCCTCCTAGGTTCAAGCGA
TTCTCCTGCCTCAGCCTCCCAAGTAACTAGGACTACAGGCGCACCACTATGCCCGGCTAA
TTTTTGTATTTTTAGTAGAGACAGGGTTTCACTATGTTGGCCAGGCTGGTCTCAAACTCC
TGACCTCGTGATCCGCCCGCCTTGGCCTCCCAAAGTGCTGGAATTACAGGCGTGAGCCAC
CGTACCCAGCCTGAATGAGATTTTTCAAAATATTAGGAATGTCTCCTCCAAACACACCTG
GCATGTTATTCATACATGGATCTGGAATTTAAAAGGGGAGAAAAAGAAAACTGAGAACT
CGTAGGAAGTGAGTGACTTGGACAGGTCGGTTGGCAAGTGCTTACAGATCTGGGTAATAT
ATAACTGCATTTCAACAGAACAGTGTATAGCCTCAAATGTTCTAATTCTTTAGGGAGCTT
TTAAATAAACAGTTGTCTATTCTTTAATCTGTCAAATAGTCATTGAGCCTTTTGTTCCTG
GTGTCTGCTCTTCCAGACAAGTAAGGATCTGCTGCTTTAGGAGACATCAGACGGGGCTGG
GGGTTGGGAAAAGGTCTGGGTAGTAATAGACCCTACATTGTCCAGTTTGTTCATTTAGAA
GCATAGAAGTGTGGGCATAGTCAAAGTAGCAAGTGGTAAAGATGACAGTTTGAAATGGAG
TAATTCCTTCTCCCCTCCAGCCCTGGTATTATGCACCACCCAAAAAGCCGGGTTATGAAC
ATAATACACATAATTTTGAATGATTCATTATTTTTTGGATTATAAGCCTGTTTTATTTGT
TAACCAGCCTTAATGAGGTATAAATGACATGCAATTAATTGCATATATTTAAATGTACAA
TTTGATCAGTTTTGACATACATATACACTTGGGAAACCACCACCATAGTCAAGATAATGA
ACACATCTATCACCCCTGGTAATTTTGCCTTATGTTCTTTATAATCCTTCCTTTGTTCTT
AGGCAGCCACTATTCTGCTTTCTGTCACTATGTATTAGTTTGCATTTCCTAGAATTTTAT
TTTTAAAAATTTTAAAATTGTTTGAATAGAGATGGGGTCTCACTGTGTTGCCCAGGGCAG
TCTCAAACTCCTGGGTTCAAGTGATCCTCTCACCTTGGCCTCCTGAAGTGTTGGGATTAT
AGGCATGAGACACCCTGCCCAGCCCTAGAATTTTATTATTATTGTTATTATTGTGTTTTT
TTGAGATAGGGTCTCACTTTGTTGCCCAGGCTGGAGTGCAGTGGTGCAATCACTGCAGCC
TTGTTTTCCTAGGCTCAATCCATCCCCCCTCCTCAGCTTTCCGGTTACTGGGCTACAGG
TGTGCACCACCACACCCGGCTAATTTTTGTATTTTTTATAGAGACAGGGTTTTGCCATG
TTGGCCAGGCTGGTCTCAAACTCCCGGGCTCAAGCGATCTTCCTGCCTCGGCCTCCCAAA
GTGCTGGGATTACAGGCATGAGCTATTGCGTCCGCCTTCAAATTACTTTAACCTAGTAT
```

FIG. 10
(continued)

```
TAATTCATTCAACAGGAAGTTAATGAGCCAGGCAGGATAAAGCAGTAAGATAGGAAAATA
TTGCTATTTTCATGGCTGAGAGAGAGCAGACAAACACATGACTAAATAGGGCAATTTCAG
GTAGTAATAAATTCTAGGAGGGAAAAAATCCCACAGAAATGTGAGGATGGGAGAATGCAG
TTAGTTTTGATAGGTGGTTTAGAGAAGGTGATCGTGTGAGCTGACACCTGAATGACAATT
AGTAGTCTGAATTTTGTTTTGCTTAATTATCAAAATAACTCCTCTTGGGTTCGGCTTTTA
TATGCATCCAGTAATTAAAATGTAAGTATATTCAATGTACTGATATCTCTCAGCATCATA
GGTAGGAAAACTAAGGCATTCAGCAATTAAGTGACTCCTCCCTTGATCATGTAGCAGTGA
TAGTACTGGATTTAGATTTTGAGGTTGCTTCTCTGCCCTTTTCTGCCTTTGTGAAACCAA
CAAAGCTGCCTGTATTTTCCAACTCTTCCTTCAGCATGTGGTACCTCCTTTACATCTGTT
TTTGTTGCTCTGAAATCCATACGCGACGATGAGCTGAGAGGGCAGAAAATTGAGCTTGT
TCTGAGACTGGAGGCTTTTGGTTTATCTCTTGCAGGTCAAGTACATTTTGTCCTGGGCTC
TCCCTGGTCGCCACGTTTGTTTATCTCCTGCGGAGTAAATAAACTTGCCTTGCTGAAAA
ATAACAGTTCTGTGTCTTTGCAGTGGAAACTGGGATGTCTTTATTAACGTTAGGTCCTGA
TGTAAGGCCAAGTTTTTGGTTAGAGTTGCTCAAGTGCAGAGGCCACTGCTAAGATGACTT
ACCCCTCGTGTCCATGGTCAATGTGGAGACTGTTATGAGTGGCACATGATGCTGGAAAAG
CAGAGCCAACTCATGTTTGTAATTGTCCTAGCAGGCCGTGGTGTACTTTGTTAGGCAGCC
ACAGAACAATAGAGAAACTCAGCTTATTCCCCTTCCCTCTGGGAAACACAGACAGTACTT
GCCATCCAACGCCAATGTTTTTAAGGAAGAAAGAGGCAAAAAGTGATGTTGGCAAGGTCT
CTGGGAGTTGTGGACCCCAACCAAGGATTGGAGACCCTGAAATGGATTCAGATGCCCTAA
AATGCAGCCCAGTTCATTACTATGAATTTTGGAGGACTTTGTGCCTTGAGCAAATGTGTA
TATGTGACGCTCTTTGACAACACTGAAATAGGAAAAATACTATCCATGTTCGCGAGGAGC
ACTGAATTTAGAGAGGGAGACAGACTTTTATGCCAGCATCAAATGAATTTGATAAAGCTA
GTACCAAAATGAAATTTGAAATTTTTTTTTTTTTGAAATAGAGTCTTACTCAGTCACCCAG
GCTGGAGTGCAGTGATACAATATTGGCTCACTGCAACCTCCACCTCTTGGGTTCAAACAA
TTCTTGTGCCTCAGTCTCCTGAGTAGCTGGGATTACAGGTGCGTGCCACCATGTCTGGCT
AATTTTATATTTTAGTAGGGATGGGGTTTCACCATGTTGGCCAGGCCGGTCTTGAACT
CCTGGCCTCAAGTGATCTGCCCACCTTGGCCTTCCAAAGTGCTGGGATTATAGGCATGAG
CTACCACACAAGCCTGAAATTTGAAATGTATTGGTATAGAATATACTGTTTAGAATGTAT
GTGTATATATGTATATTTGTATACTCATATAAACACAAATACACATTGTATGTGTTCTG
TAATATGTATATCTGTCTACACATACATGTATATACACATACAATGTCTTTTTTTTTT
TTTTTTTTTTTGAGACAGGGTCTTACCCTGTTGCCCAGGCTGGAGACTGCAGTGGCATA
ATCTTGGCTCACTGCAGCCTCGACCTCCTGGGCTCAAGTGATCCTCCCATCTCAGCCTCC
TGAGTAGCTGGGACTGACTACAGGCACGTGGCATCAAACTTGTCCAATTTTTCTATTTTT
TTGTAGAGTTAGGGTCTTGCTCTGTTGCCCAGGCTGGTCTCAAATTCCTGGGCTCAAGCT
GTCTGCCTGCCTCGGCCTTCCAAAGTACTAGGATTACAGATGTGAACCACTGTACCTGGC
```

FIG. 10 (continued)

```
CTTTACAATGTCTATTTTAAAGATAATGGTTCAAGTTTTTATCATCCCACTGGCCTACTC
TAATGAAACATCTATCCATTCATTGAAGAATTATTTATGGTGGGATAACTCTGTGCCAGG
TACCGTGCTAGGCATTGAGTATTCCAGGTTTTAGGAAACAGCACATGCAAAAGTGCTGAA
GTGGGAGAAGATCTCGGAGTGATTGAAGGCTAGGAGAGAGCAAGTGTGGGAGCTGTGAGG
CTGGGAAGGTGGGAGGTAGGTGGGAGCAGACCACATAGGGATTCTTAATGTCTTTAGTGT
CATGTGGACCATGGAGAGGAGTGTAGATTGTATTTTTAGAGCAATGCAAAATCATAGAAG
GATGTGATCGGGGGAGTGGCATGAGCTGATCTATTTAAAAATATTTCTCTGGCTGCTGTG
AAGGAAGGATTGTAGGAGGCAGGAGTAGATTCAGGGAGATGAGACAAGTGATGAGAGAGG
CTTTGAACTTGGGTAAAAGTAGTTTGTGGAAAGTCTTTTTTGGAGGTAGTTTTTGTTTAT
TGCCTTGTCATCAAAGCAGAGATGCTGACCAATGAAACTCCATGAGAAAATAGTGATTTA
TAAAGACATATCTATGCACTGCCATTAAAAAGCTGCTTGGAAAAAAGGATAAAAAGCTG
CTTTAACAACTTTTTTTTTTTGAGATGGGGTCTTACTCTGTCACCCAGGCTCACGACCTCA
GCTCACTGCAACCTCTGCCTCCCAGGCTCAAGCATTCTCCCACCTCAGCCTCCCGAGTGG
CTGGGACTGCAGGCACACGCCACCATGTCAGGCTAATTGTGTGTGTGTGTGTGTGTGTGT
ATGTGTGTGTGTGTGTGTGTGTGTGTGCTGGGACTGCAGGCACACACCACCATGTCAG
GCTAATTGTGTGTGTGTGTGTGTGTGTGTGTGTGTGTGTGTGTGTGTGTGTGTGTGTGTA
TGTAGAGATGGGGTTTTGCCATGTTGCCCAGGCTGGTCTCAAAATGTTGCCCAGGCTGGT
CTCAAACTCCTGAGCTCAGGTGATCCACCCGCCTCGGCCTCCAAAGTGCTGGAGATTACA
GACGTGAGCCACTGTGCCCACCTAACAACTTTAAAAAAATTTTGACATTTAGTAGGATAT
TTATTGCATTATTGTTGAGATGGCAAAATATTGGAGACAACTGAAATGTTCATCAGTGGG
GGGGGCTAGTTAAATGAAATACAGTGTAGCATGCATTAGAACACTTTTCAAGAATTTAAC
TTTTTTTGTAGCCTTTTACTTATAATGCTTGTCCCTATTGATGCCTTTTTTTCAGCATG
ACTTACTCTTTTACTATAGGATATTAAAATTTAATTAGATTAGAAATGAGGAATATTCTT
GTAATCTGTAGAAAGTAACAAACTATAAACTTATTCCCCAAGAACAAATATAATAATTTT
TCTGGAGTAGCAGGTAAGAAAGATATAAATTTATATGTATACAAGAAACTGAAATTAGAC
TTTATACATTTAAAGGTTACAAGTGCAGTTTATTACATGAATGTATTATCCAGCATTGA
AGTCTGGGCTTTTAGTGTAACCAGCACCTGAATAACATACATTGTACCCATTAAGTAATT
TCTCATCCCTCAAACCCCTCCCACCCTGAAATTAGACTTTGGATCCCTAGTTTAAATTCC
ACCCCTCTCTTTTTTGAGACAAGGTCTCACTCTGTCACCCAGGCTGGAGGGCAATGTTG
CAATGATAGCTTACTGTAGCCTCAACCTCCTGGGCTCAAGGGATACACCCTCCTCAGCCT
CCTGAGTAGCTGGAACTGCAGGCGTGCACCACCACATTCAGCTAATTTTTTGATTTTTTT
ATAGAGATGAGGTCGGAACTCCTGGGCTCAAGCGATTCTCCCCAAGTGCTGGGGTTACAC
ACATGGGCCACTGCCCCAGCCTAAACCTCCTTTCTCAGTATAGCAGCCTTGAGATGAAG
TTCCTGAAATTACTGGCCAGCTTGACTGTTTCCCCACATCACTGGAGGAGGGGATGCAT
AGATAAAACAAAATATTCAGCATCATTGTATTTTCTTTTTGTTTCATCAGCATCTTTTTT
```

FIG. 10 *(continued)*

```
TAAAACTCACTTGACATAAGTCCCTAGCCTCAAAGAGTAAAGCCTTTGCAGAATCTGCAT
TCAGATTTCGGGTGTGATTTCCTGACAGATAGTTCAGGTTTGTAAACTCTTTTTTTTTTC
TTTGAGACAGAGTTTCACTCTTGTAGCGCAGGCTGGAGTGCAGTGGCACCATCTTGCCTC
ACTGCAACTTCTGCCCCCTTGATTCACGCGATTCTCCTGCCTCAGCCTCCTGAGTAGCTG
GGATTACAGGCATGCGCCACCACACCTGGGTAATTTTTGTATTTTTAGTAGAGATGGGGT
TTCACCATGTTGGCCAGGCTGGTTTTGAACTCCTGACTTCAGGTGATCTACCTGCCTCAG
CCTCCCAAAGTGATGGGATTACAGGTGTGAGCCACCGCAGCCGGCCAAAACTTTGTTTTT
TTTCCTCTTTTGTTGCTGAGAAATGTAAACTCTTACAGACACAAATTATGTCTCCCATT
TTTTAAAACCCACTCAACACAGGGGTCATGTGTAATAGGCCCTGGAGCTTATTTTAGACA
TTGATTTGAGGCTCTTTTCCCCAAGTGCTGGTTTGTGTGTGTGTGTATGTGTGTGTAAGT
CTTTCTATGAGATGAGTGGTACCTACCTCGGCTGTGTGATCTTTTTTATTTTATTTATTT
TATTTTTGTAGATACGAGGTCTCACTATGTTGCTCAGGCTGGTCTTGAACTCTGGGGCTC
AACCTATCCTCCCTCCTTGGCCTCCTAGAGTGCTGAGATTACAGGTGTGAGCCACTGCAC
CTGGCCAGCGATCCTTAATAAATATAGATAATGGCCGGGCGTGGTGGCTCACACCTATAA
TACCAGTACTTTGAGGGGCCGAGGCTGGCAGGTCACCTGAGCTGAGGAGTTTGAGACCAG
CCTGGGTAACGTGGGTGAAACCCTGTCTCTACAGAAAATAGAAAAATTAGCCAGGTGTGG
TGGTGCATGCCTGTAGTCACAGCTACTTGGGAGGTTGAGACAGGAGAATTGCTTGAACCT
GGAAGGTGGAGGTTGCAGTGAGCCGAGATCGTGTCTTTGAACTCCAGCCTGGGTGACAGA
GTGAGACCTTGTCTCAAAAAAAAATATAGATATAGGCTGGGCGTGGTGGCTCACACCTGT
AATCCCAGCACTTTGGGAGGCCGAGGCGGGTGGATCAGGAGGTCAGGAGATCGAGACCAT
CCTAGCTAACATGGTGAAACCCTGTCTCTACTAAAAATACAAACAATTAGCCAGGCCTGG
TGGTGGGTGCCTGTAGTCCCAGCTACTCGGGAGGCTGAGGCAGGAGAATGGCGTGAACCC
GGGAGGTGGAGGTTGCAGTGAGCCGAGACTGTGCCACTGCCCTCCAGCCTGGGCGACAGA
GCGAGACTCTGTCTCAAAAAAAAAAATCTATATATCTATATATCTATATCTATATAGAT
ATAGATATAGATAATGCCAGATGATGGCTGGTTAGAAGGGATTGTCAGGGGCTGGCAGGT
TTTGCAGGTGTTAGAATGAGCAAGATGAGGAGAAGGATGCTTACTTCCCTCTCCTTGTAA
CTCTCTACCCCCTCCCCTCAGTGTTTTTTTATTTTTATTTTTATTTATTTATTTTTTTG
AGACAAGGTCTTGCTCTGTCACCCACACTGGATTGCAGTGATGCAATCATAGCTCATTGA
AGCCCAAACTCCTGGGCTCAAGTGATCCTCTTGCCTCAGCCTCCCAAGTAACTGGGACCA
CAGGTGCGTACAACTATGCCCAGTTAAGTTTTTCATTTTTTATACAGACGGGGTCTTGCT
ATGCTGTCCAGGCTGGACTTGCACTTCTGGCTTCAAGTGATTCTCTTGCCTCAGTTTCCC
AAAGTGCTGGCATTATGGGCATAAGCCACTGTGCCTAGCCCATCAGTGTCTTTTTATCCT
TTACTCCTATCAAAATTCATTCACTCAGCAGCCATTGATCAAGTGCCTACTATATACATG
TTGAGGACTGGAAATTTATTTGTCTCTTCTCATCTTATCTGGACCCTCTGTGTTAATTGT
AATTAACTGTAATCATTCTGTATTAATTGTAATAAACTTGTTGATAAACTCAAATGAGGC
```

FIG. 10 (continued)

```
CATACCGTTTTGCCACTTCCCCTCCTTCCAGGTTATATGGATGTACTTACATTGCAGGTT
TCATTTGTTGGTTCAGTTTTTAAACTAAGCCCTATTGTGTCAAATTATGCTAGGTGTGAG
ATGGGGAGTTCAAGCTGTGTGTTGTCTTTTTTTTTTTTTTTTTTTTGCCTCACTTACTA
ATATACAAGCGCTTATAACCTTTGAGGCTGGCCCTATACATTAAGATTTTTATTAATTCC
ACTGTTCTTTATCTTCTCTTACTAAGTTCTCAGGGTCGAATGAACTCTAACTGCTCCTTG
CTAGTGATAAGCAAGTTGCAAATTACAGAATTGTCAGTGATTGAATACACGTATTAAACC
TGTAACTGGGAAGCATTTTTGGTAATTATGAATACTTTTGGAAAAAAAAAAGCTATGGAA
GGAAAGTTTAAAATCTACGAAAGCTCAAGTAGATGGTCATGGAATAGCTATTTCAATTTC
TAACTATATATTACTTATTTATTTATTTATTTTTGAGACGGAGTTTAGCTCTTGTTGCCC
AGGCTGGAGTGTAATGGCGTGATCTCAGCTCACTGCAACCTCCACCTCCCGGGTTCAAGC
TATTCTCCTGCCTCAGCCTCCCGAGTAGCTGGGATTATAGACATGTGCCACCACGCCAGG
CTAATTTTGTATTTTTAGTAGAGACGGGGTTTCTCCACATTGGTCAGGCTGGTCTCGAAC
TCCCAACCTCAGCTGATCCGCCTGCCTCGGCCTCCCAAAGTGCTGGGATTACAGGCGTGA
GCCACCGCGTCCGGCCTCTTAACTATTGTTTGAAATAATGTAGAGACAGCTCCAGAGCCA
TGAAGAAGTGTATGAAGAAGCAGTGTTAGCTTAAATGACATACATGTCACAATTGCCTAT
GTGAAACTATCATAATTATGCATGAGAAGTATCTATCCTGCATAACCTCCACCAATAATA
ATAATGTTAATAATAGTGAAAACTAATGTTTATTAAGTCCTTACTGTCTCCAGCCTCTGT
GCTAAATACTGGTTACTAAGTTTCCCTGAAAATACTATTCTCATCTGTTTGTTCTTAATA
ACAGGATAGCATAATTGTAAGTTGTAAATGAAATAATACAGTTTATGTAATAAAAGGGTA
AAAGAGAAGACCACCTACCTTATCTTCTGTTGCTGATCTGGATGGATGTAGGTGGTGTTT
ACCTAGTTTCACCTTTGGCAGTTGAAACTACTTTTTTTTTTTTTTTTTTTTTTTTAAGA
GACAGGGTGGGCCAGGCGCAGTGGCTCACGCCTGTAATCCCCGCACTTTGGGAGGCTGAG
GCGGACAGATCACTTGAGGTCAGAAGTTCGAGACCAGCCTGGCCAACATGGTGAAACCCT
GTCTCTACTAAAAATACAGAAAAATTAACTGGGTGTGGTGGTACACACCTGTAATTCCAG
CTACGTGGGAGGCTGAAGCAGGAGAATCGCTTGAACCCGGGAGTGGAGGTTGCAGTGAGC
TGAGATTGTGCCACTGCACTCCAGCCTGGGTGACAGAGCAGGACTCCGTCTCAAAAAAAA
AAACAACAACAAAAAAGAAATTTTTAGAAATATGAGATGACAGCAAGAATGAGGGTATT
AAAAAGAAATTTTTAGAACTAAATAGCAGAATGTAATGGTGAAAGTTTGATTTCTCAAG
TCTGCTTTGCACACAGGCATGTGGCAAACATTCAGTAAGTATAGCTGTAATTTTAACCAG
CTGTAATGTATAATAGCCAACATATCACATTTTTCTTTTTTCTTTTTGAGACAGAGTCT
TGCTCTGTTGCCCAGGCTGGAGTGCAGTGGCACCATCTCGGCTCACTGCAACCTCTGCCT
CCTGAGTTCAAGTGATTCTTGTGCCTCAGCCTCTCAAGTAGCTGGGATTACAGGTGTGTG
CCACCACACTCGGCTATTTTTTGCATTTTTAGTAGAGATGGGGCTGGTCTTGAACTCCCA
GCCTCAGGTGATCTGCCTGCCTCAGCCTCCCAAAGTGCTGAGATTACAGGTGTGAGCCAC
AGCGCCTGGCCATATATTGCTTTTTTCTTATTATCAGAGCCAGTTCATAATTGTGGAAAA
```

FIG. 10
(continued)

```
ATAGTGTTTGTAACAATGTAAGTATGGATAAATCATCTTTTTAATTTTGTGATTCATATA
GGTTTGTTGTTGTTGTTGTTTGTTTTTATCTTGAGACAGAGTCTTGGTCTGTCACC
CAGGCTGGAGTGTAATGGCACAACCATGGCTCACTGCAGCCTCAGATGCCTGGGTTCAAG
CAATCCTCCCGTCTCAGCCTCTAGAGTAGATGGGACCACAGGTGTGGGCCACCATGCCTG
GGTAATTACAAAACTTTTTTTTTTTTTCTAGAGATGAGGTCTCACTATGTTGCCCAGGC
TGGTCTCAAACCTTTGACCTCGCTTCAGCCTTTAGAGTAGCTATGACTATAGGCATGTGC
CATCACCCAGCTAATTAAAATTTTTTTCTTTTTTTTTTGGTGGAGATGCGGTCTTACT
TTGTTACCCAGACTGCAAGTTAGTTTCAGATATCAACATTTGGTGTTTCCAAATGCACGG
GGAGGCTTTGGAGCAAGTTTTTGGCTCATATGCATAGGTGTCCTAGACATTCACTTTGCA
AATTCTTATTAAAATGACTACAGTAGCATACAGATAGGGAAAAATATCCTTGTCAGTACC
ACCGATTGGGTGAGAAGAGACTGTATATTAAAAACAATGACCATCTTTTTGCCACATAAA
TTGCTGGTGGGGCCAGTTTGAAGAGGGCTTTGTCAGCTGCCTTCTGCCTCTTCCTCTTGA
GTACGTGGAGTTGGAGTCATCCTTGACAGCCTCCTGTTGACACCACCGGGTCACAGATG
TGAAACTGTGTGGATGTAGGAGAGAGCAGTGATGGGCTTACCCCAAGGTTGCTCTTCCT
TCCCTCTGGCCACAAATGTTTAGTAAGGAACTGCTCTGTATTAACCATTTGCTAGGGCT
GCAGATACGGTGGTGAAGAAATAGACATGTTCCTACTCGGGATGCTGAGGTGGGAGGATT
GCTTGAGCCCAGGAGTTGGAGCTGCAGTGAGCCATGATCACACCACTGCACTCCAGCCTG
GGGGACAGAGCGAGACCCTATCTCTAAAAACAATAAAAGAAATAGATGTGTCCTTCACC
CTCATGGAACTGCCAGTCTAGCCTTCAACCTGGTGACTGTAGAAATGTGTGATTAGATGC
TATATTGCCATGTTGAGTGTCACCCCTGAGAAGCAGGGTTTTTTTTGAGAAGGTAGGATG
GGGGATCTGACTGTGGGACCACCAGAGGGAAAAGCACATGTAAAAGCTGCGTGTACCAAC
TGGAGGAAATCGGAGACGTGATCAGAGAACCAGAGTCAACCAGGGGCCATGCCGTACAGG
GTCCTGTTAAGATCTGTGACTTTTTTCTAAACGTTTTCTTCTGGATAACATCTAAATTTC
TAGTTCCAAATGTGAAACTCCAAGGGCGTTCTGTGCTAAACATTTTGCATGTATTAATTA
ATTTCCACCACACAACATTGCTGTGAATTAAGACAGTTTCTAAGCATGGCAAGAAACCCA
GAAATCATAATGGAAAAATCTGATAAATTTAACAATGCCAACATGAACCTCTGTAGGAAA
AAAAATACCACAGACTAAAAAGGGGGGAAAAAAACCAGAGACAAATATTTGCAACACATA
CAGTAAAGGGTAATTTTCTGGTTATATCAAGAGCTCCTACAAATCAGTAAGAAAAAAAT
CTAATAGGAAATGAGCAACGACAAACTGACAACTCATAGAAAAGGAAACACAAGTGGTCT
GAAAACATGAAAAGTGCTCAGTCTCACAAAGAAATGCAAACTAACATGGTACCATTTTC
CATTAATCAGATAGACAAAGATGAAAGAGTTTGGTAATGTATGTAGTATTGGCACAAGTG
AGGGAAAACAGGGGATTTCACACTCTATGCCCGTCCAAACCAGTACCTTATTTTGAGGGT
GGTTTGACAATATTTGTCAAAATAAAAAAATTATATATAGTCATTTGCCACATAATGATG
GTTCAGTTGATGATGGACGGCATACATAATGGTGGTCCCATAAGAATATAATGGGCTGGG
TGCAGTGGCTCTCACCTGCAATCCCAGCACTTTGGGAGGCCGAGGTGGGTGGATTGCCTG
```

FIG. 10
*(continued)*

```
AGGTCAGGAGTTTGAGACCAGCCTGGCCAACATGGTGAAACCCTGTCTCTGCTAAAAACA
TACAAACAATTAGCCAGGCATGGTGGCGGGTGCCTGTAATCCCAGCTACTCAGGAGGCAG
AGGCAGGAGAATCGCTTGAACCCGGAAGGCGGAGGTTGCAGTGAGGTGAGATTGGGCCAC
TGCACTCCCATCTAGATGACAAGGCAAAACTCCATCTCAAAAAAAAAAAAAAAAAAGAAT
ATTATGGGCCCAGCCACAGTGGCTCACACCTGTAATCCCAGTACTTTGGTAGGCCAAGGC
AGGAGAATCATTTGAACTCAGGAGTTTGAGACTAGTGGGGACAACATAGCAAGACCCCAT
CTCAAAAAAAAAAGATTATGGTGGAGCTGTCCTGTATAGACATACCATTTTAACTTTTT
TTTTTTTTGAGATGGAGTCTTGCTGTGTCACCCAGGCTGATGTGTAGTGGCGTGATCTGG
GCTTACTGAAACCTCCACCTCCTGGGTTCAAGCGATTCTCCTGCCTCAGCTTCCTGAGTA
GCTGGGACTGCAGGCGCAGGACACCATATCTGGCTAATTTTTATATATTTAGTAGAGATG
GGGTTTCACCATGTTGGCCAGGCTGGTCTTGAACTCCTGACCTCAAGTGATCCGCCTGCC
TCAGCCTCCCAAAGTGCTGGGATTACAGGCATTAGCCACCATTACAGGCACCTGGCCAC
CATTTTAATCTTTTATATTGTATTTAAACTGTACCTTTCTATGTATGGATGTGTTTAG
ATACACAAATACCATTGTGTTACAGTTACTTACAGTATTCAGTACAGTAGCATGCTGTAC
AGGTGTGTAGCCTAGGAGCAATAGGTTATACCATATAGCCCAGGTGTGTAGTAGGCTCTG
CCATCTAGGTTTGTGTAAGTACGCTCCATGATGTTACCACAGTGACGAAATCGCCTAATG
ATGCATTTCTCAGAACATATTCCTGTTGTTAAGCAATGCATGACCGTATCTTGACAAAGC
CATTTATTTCTAAAACTTTAATTTTACAGATTTATTTGTAAAAGTATGTAAAAATGATT
GTAAAGGATATGTTCTGCTGCATTATTTGTAATAACAAAAAACCAGAGGATAACATAAAT
GTCCTATAAGAAGGGTTAGATTATGGATGGCACATTCATACAATGGGTATTATGTAGCC
ATTGAATAAAAGGGTACTGGCTGGGCGCAGTGGCTCATGCCTATAATCTCAACACTTTGG
GTGGCCAAAGAAGGAGGATTGCTTGAAGCCAGGAGCTTGGGGCCAGCCTGGGCAACATAG
CAAGACCCTATCTCTACAAAGGAAAAATAAAACAATTAGCCAGGTTTGGTATTGGACACC
TTCATGGTCCCAGCTACTGAGGAGGCTGAGATTGGAGGGATCGCTTGTGCCTGGCAGGTT
GAGGCTGTAGTGAGCCATGATTGTGCCACTGCACTCCAGGCTGGGAGATAGAGTGGGACC
CTATCTCAAAAAACAAAAACAAAAACAAAACCTCCTGTAAAATGTCAAGAAGTCCTAGA
TGTGGGCCAGGTGTGGTGGCTCACACTTGTAATCCCTGCACTTTGGGAGGCTGAGGCCAG
GAGTTTGAGACCAGGCAGAGCAAGATAGCAAGACTCCATTTCTACAAAAAATAAAAAAAA
TTAGTTGGGCATAGTGGTGCATTCCTGTAGTCCCAGCTACTCAGGAGGCTGAGGTGGGAG
GATTGCTTGAGCCTGGGAGGTTGAGGCTGCAGTGAGCCATGATCACACCTCTGCACTCCA
ACCTGCGCAACAGAGTGAGACCCTGTCTCTAAAACAACAACCAAAAAACCCAGCAAAG
TACTGATAAAGATCTTTGGCTGGGCGCAGTGGCTCACACCTGTAATCCCAACACTTCAGG
AGGCTGAGGCGGGCAGGTCACAAGATCAAGAGATCAAGACCATCCTGGCCAACATGGTGA
AACCCGGTCTCTACTAAAAATACAAAAATTAGCTGGGCATGGTGGCGTGCACCTGTAGTC
TCTGCTACTCGGGAGGCTGAGGCAGGAGAATCACTTGAACCCAGGTGGCAGAGGTTGCAG
```

FIG. 10
(continued)

```
TGAGCCGAGATCACGCCACTGCATTCCAGCCTGGCGACAGAGCAAGACTCCGTCTCAAAA
AAAAAAAAAAGAGAGAAAGATCTTCAAGTTGTAGTATGTGAAAAAATCAGGGTGTAAAAC
AAGAGAATCCCATTTGTGTGTGTGTCGAGTGTGTTTCACACAGGCTCAGAGGGAGTAGTG
TGTATATGCACATGAACATACGTGTCAGTGTATATATGTATATATACAAGGTTGTGGGTT
TGTTTGTTTTTTTTGAGACAGAGTCTTACTCTGTTGCCCAGGCTGGGGTGCAGTGGTGCA
ATCTTGACCCACTGCAACCTTCACCTCCCAGGTTCAAGTGATTCTTGTGCCTCAGCCTCC
CAAGTAGCTGAGACTACAGGCACGCACCACCATGCCCAGTTAATTTTTGTATTTTTAGTA
GAGATGGGGTTTCATCATGTTGCCCAGGCTGGTCTGGAACTCCTGGCCTCAAGTGCTCTG
CCCGCCTTGGCCTCCGAAAGTGCTGTTGCCCAGGCTGGAGCTCAGTGGCACAATCGCAGC
TCACTGCAACCCCGACGTCCCAGGCTCAGGCAATCTTTCCGTCTTAGCTTCCCAAGTAAC
TGGGACTACAGGTGTGTGCCATCAATGCCCCACCAATTTTTTAATTTTTTGTAGAGATGG
GGTTTCCCTACGTTGCCCAGGCTGATCTTGAACTCCTGGTCTCAAGCAATCCTCCCACCT
CAGCCTCCCAAAGTGCTGCGATTACAGGTGTGAGCCACCTTGCCCTGCCCTGTACAAAGA
TCTGCATAAAAGCAGTTAATAATACTATGTTTGAGGCTGCCATCACAGGGGTGAGGTCAA
GGACAAGTGTGAGAAATTCTTTTAGAATCTATTTAAAAAAGAAGAGATGACAGTGGTG
ACAGTCAGGGAACAGATAAGCAGGTAGATTGTGGGGTCTAGGCTGTCTAACTGGTGTTT
AAAATGAAGCAACCGCTGAGCCTGCTGTATTTCATTTAATGGAGACTAGTAAAACAACAG
CCAGAAATTCTTCACTTTCCATCTAAGAGAGGCAAAAGTTATTTTCCCTTCAATAACCTG
GGACTGTAGGATTAAGGTTTTTTTTTTTTTTTTTTAAATACTACAATATGACTACCAGT
ATAATTTAAAAATGATTAGAATTCTATTTGAGTAAGAAATAGGTGTCTGCCTGAAGTAGA
CAGTCACTGAAGTCACTAAGTGGCAAAAGACAGAAAAAAAATTGAAAGTAGGAAACAATC
AGCAGATATGATACCAAACATGAGCTGTCAGTGATAATGGATTAAGTCCTTCAATAATGG
CTGAGCCAGATGGAATTAAAAGAAAAAATCCAGGCCGGGCATGGTGGCTCACACCTGTAA
TCCCAGCACTTTGGGAGGCTGAGGTGGGAGGATCACTTGAGTCCAGGAGTTTGAGACCAG
CCTGAACAACATAGTGGGACCCCATCTCTATTTTATAAAAATATTTTGAAAAAAGAAAAA
AAAATTCAGTTGTGTTCTGCTTTAAAAGACAAATTGGCACAGAATGTCAAAGAATAAAT
AAAACAAACATGGGCAAAAGAGATTCAGGTGGTACCAATATCGGGCTAAGTAGCATTCAA
GATAAAGATTATTAAATAATAAGTTAGTTAATACTAGAGTAATTGCATATTAATGAAACA
TAATCTATGGTAGAGATATTATAGTCAATAATTGTTTATGTATTCATTAAGGTAACAAC
AAGCAAACAAGCTTTAATAGTTTTAAATGCTTTATATGCTTTATAGTTCTTTTATGTGCA
TTAATTCATTAATTCTCATTTCCTATGAGGTAAACACTATTATTATCCACATTTTACAGA
TGTAAAAACCGAAGCAGAGAGATTAATTAGCTTGCCCAGGAGATGTGGCATTCTGGGATT
TGAGACAGTGGTTTGGCTCTGTAGGTTGCTTCAATAACCAAGAGATGCTTCAAATCAGAT
TTTTAAAATATGTTTTCAGAAGCATTTTCCTGATACTTCTCCCCTTACATGGGTGTTAG
TCTTTTGGGTTGAAAAACATGAGTAAGTGCTAGAAGAGCAAAATATGCATCCAGATTTAA
```

FIG. 10
(continued)

```
TAGTATGTCTGTTTTCTGAGCCTTGGCATTTCATTGCTTTTATAATAGAAATGAAGGCT
TTTTTTTTTTTTGGCTGAGAATAGCACTGAACTCAGTGGGAGGGACTGTGGGTTGTAAG
TTGTCCGCCTCTGAATGGAGTTGAATTTAAGTTTCTTGGTTTCCAAAGAATGATTGATTT
AAAGACCCTCAAATTGCAAGTTAGAACTGACTTCAGTCCTTGAGGTTTTTTACCATTTAA
TGAATAATTAAATTTATGGTAATAAATGGTAATAAATGGTAAAAATGGTAATAAATTTTA
CCATTTAATGAATTTTCTTAAAAAGCAATTGAATTGTTGATGAAAGGTGATGTTAAAAT
TATCCCAGATTTATCAATCTTTTTTTTATTGCCCCTGGATTTTGAGTCATAGAAAGCCTT
TCCTTATTCTAAGGTTAACAAGACATTCACCCATGTTTTCCTCTAGTATTGCATTGTTTC
ATCTTTTACGTTTATTATTTATTTTATTTTATTTTTTGAGACAGGGTCTCACTGTGTCA
CTCAGGCTGGAGTGCAGTGGAATGATCTTGGCTCACTGCAGCCTCTGCCTCCCGCCTCCC
GGGTTCAAGCGATTCTGCTGCCTCGGCCTCCCAAGTAGCTGGGATTACAGGCACCTGCCA
CCGCGCCTGGCTAATTTTTGTATTTTTTTTTAGTACAGATGGGGTTTTGCTGTTGGCCA
GGCTGGTCTCGAACTCCTGACCTTAAGTGATCCACCCGCCTTGGCCTCCCAAAGTGCTGG
GATTACAGGCATGAGCCACCGTGCCCGGCCTAAAATTTATTCTGATATGTGATATGATGT
ATGGTTCTAACTACTTTGTTACGGTGCATTATTTCTAAATGTGGTATTGGATTCTTTTA
TATTTTGTTTAGAAGTTCTGCATCAATATTCATGAGTACCATTGGTCTCTGTTGTTTTC
TTGTGCCATCTTTATTGGTATAGGTATCAGTGTTATATTTAGTTTGTAAAAGGAAGTTGG
AAGTTTTCCTTTCTTTTTAGTACTCAGGAATGATTTTAAGAATTGAGACTATTTGGTCTT
TGAAGGTTTGGTAGAAGTCCATTGGGAATCCATCTGGGCCTGGTGATTTTCTGTGCGGTA
GTTCCTTAATTGTTTTCCCTATTTTTTCTTATTTTTAATCAGGTAGCCTCTGAACCAGAA
TAGGTTCAGAGAGGCTCCCTCTATTTTTTTTAATACAAGTTGGTCTGCCTAAGTTTTCTT
ACTCTAATGGGTTAATTTTTGTAGACTGCATTTCCCTGAAAAATTACACGTTTGTTCTAG
GTTTTCTGACTTATTTCCACAACTTTTTAGTCTTTCCCCCTGGAATCATGCCCCTTTCCA
TAAACAGGACTCTGATGTACCTGAAGTATTTTCACACTTCGGGTGGACTTTCTGTTTCTG
GGGGTGGTTTTAGAGCAATTTTAGGCCTGCCACTAGCTACCCTGTTCTCTACACCATGCT
GTTTTTCTCAGAATGCTCTTCTTTTGCACAAAGGCTTGGAGTAGGAGGTTGAGCAGTCAC
TCACTGACGTTTGGTATATTTCTTTTTTTTGCTTACAGGTAATCTGGAAGTTTGGGCAT
TCTCTTTAAGTTGAGGGTGTGGTTTTCATGTCATTTATTTGTTTATTGTTTTCTTGTGT
GTGTTTCTTAGAGACAGGGTCCCACTCTTGCCCTGGCTGGAGTGCAGTGGCGTCTTGATC
ATAGCTTACTGCATCCTCAAGCTGCTGGGCTTAGATGAACCTCCCACCTCAGCCTCCTGA
GTAGCTGGGACTACAGGAGCACACCACCATACCTAATTTTTTTTTTTGAGACGAAGTC
TTGCTCTGTCCCCAGATTGGAGTGTAGTGGTGCAATCTCGGCTCACTGCAACCTCTGCC
TCCCGGGTTCAAGCGATTCTCTCACCTCAGCCTCCCGAGTAGCTGAGACTGCAGGTGCAT
GCCACCATACCCGGCTAATTTTTGTATTTTTTAGTAGAAACAGGGTTTCACCATGTTGGC
TAGGCTGGTCTCAAACTCTTGACCTCAAGTGATCCACCCACCTTGGCCTCCCAAAGTGCT
```

FIG. 10
(continued)

```
GGGATTACAGGCTTGAGCCACTGTGCCTGGTCCCTGGCTAATTTTTAATTTTTTTGTAGA
GATGGGATCTTGCTATGTTGCCCAGGCTGGTCTTGAACACCTGGCCTTAAGCAATCCTCC
CACCCTAGCCTGCCAAAACACTGGGATTTACAGGCATGAACCATTGTGCCTGGCTTGTTT
TGTTTTTAATTCTATGTTGTTTTGAAGGATGTATGGGGAGAGATGGATTTAGGCAATCA
TCGTTGTCCTTGGCTACCTGAAAGTCCAGGCACTCTTCTAGATACTTTATAAATATTAAC
TCATTTTATCCTCTCAACAACACTATGACATGGGTACTGTTACACCTTCCATTTTATAGG
ACTTAACAGAGAGGTTAAATATGTAGCCCAGGGTCACAGAGAGCTGGGCTTCAGACCAAG
ACAATCTGGCACCAGAGTCTATGTGGCTACCCTAAGGCTTTGCCACCATGTGTTAGTGA
TTCTCAGCCTGTCATTTGGGGAGGGGATTGCCCTTTTTTTAAACTTTTTAAAAAATTTA
TTCTTATTTTATTATATTTTTGAGACAGAGTCTCCCTCTTTTGCCGAGGCTGGAGTGGAG
TGGTGTGATTTCAGCTCACTGTAACCTCTGCCTCTGGGTTCAAGTGATTCTCATGCCTC
AGCCTCCCAAGTAGCTGGGATTACAGTTGCCAGCCACCATGCCCAGCTAATTTTTGTATT
ATTATTATTATTTGAGACGGAGTCTCGCTCTTTTGTTCAGGCTGGAGTGCAGTGCTG
TGATCTCGGCTCTCTGTAACCTTCGTCTCCTGGGTTCAGGTGATTCTCCTGCCTCAGCCT
CCGGAGTAGCTGGGACTATAGGCGCGCACCACCATACTTGGCTAATTTTTTGTATTTTTA
GTAGAGACGGGGTTTCACTATGTTGGCCAGGCTGGTCTCGAACTCCTGACCTCAGGTGAT
CTACCTGCCTTGGCCTTCCAAAGTGCTGGGATTACAGGTGTGAGCCACCATGCATGGCTG
GATTGTCCTTTTTTAAAAAAAAAAACAAAAACAAAAAAAAAAACCCAAACCATAAACCCA
ATATTCTGAAAGATTTGGTCTCCACACCTGTGTTATATAATAATTAGTTTTTCCATTTTT
TTCCTCTTGGTAGAAGGCACATATGCCACTCAGTTTCCAGTTGCCACACCCAATTAACAT
AATTGTTTTGCAGCCAAAAGCAAAAGAGAGTTCACATTTTAATTAGCTTATGTAGGTAGA
CAAATTGAGGCCTAATGTAAGAGTTTCATTATACCTTTTTGAAAAACTATAAATAGCTAG
AAGCCAGTTGTCATTACTTTTTGATTCCTTAGAATTCTGGGCATCTTTCATCTGGAACCA
CAGATGAAAGAAGCTGCAAGGAAGGATTTTTTTTCTTAACGGAATAGTTTAACCATTCTG
AATGCAAAAGTATTGGATGCTAGAATAATAGGTATCACATAAATTGAGGTTGACGTTTTC
CCGGGTGAAATTCTATTCTGTCTCAATTTTCCTTTTTTTTGAGACGGAATCTTGCTCTG
TCGCCCAGGCTGGAGTGCAGTGGCATGATCTCGGCTCACTGCAAGCTCCACCTCCTGGGT
TCATGCCATTTTCCTGCCTCAGCCTCCCGAGTAGCTGGGATTACAGGGGCCTGCCACAAC
ACCCAGCTAATTTTTTGTATTTTTAGTAGAGACGGGGTTTCCCAGGATGGTCTCAATCT
CCTGACCTCGTGATCCGCCTGCCTCGGCCTCCCAAAGTGCCGGGATTACAGGCGTGAGCC
ACTGTGCCTGGCCTTTTTTTTTTTTTTTTTTTTTTTTTAAGACAGAGTCTCGCTTTG
TTGCCTAGGCTGGAGCGCAGTGGCATGATCTCAGCTATTGCAACCTCCGCCTCCCGGGT
TCAAGTGATTCTCCTGCCTCAGCCTCCCGAGTATCTGAGATTACAGATGTGTGCCACCAT
GCCTGGCTAATTTTTGTATTTTTAGTACAGATGAGGTTTTGCCATGTTGCCCAGGCTGGC
CTCAAACTCCTGACCTCAGGTAATCCTCCTGCCTCAGCTCTTCCCAAAGTGCTGGGATTA
```

FIG. 10
(continued)

```
TAGGCATGAGTCACCGGGCCCAGACTCAATCTTCTGACAAGCTCTCAGAGAGAGTAAAAA
GCAAATGAATATTTCATTATTTTGATCTGAGCTTTACGATTTTTCTTTTCTTTTCTTTTT
TTTTTTTTTTGAGATGGAGTTTTGCGTTGTTGCCCAGGCTAGAGTGCAGTGGTGGCGAT
CTTGGCTCACCGCACCCTCCGCTTCCCGGGTTCAAGCGATTCTTCTGCCTCAGCCTCCTG
AGTAACTGGGATTACAGGCATGCGCCACCATGCCCGGCTGATTTTGTATTTTTAGTAGGG
ACAGGGTTTCTCCATGTTGGTCAGGCTGGTCTTAAGCTCCCGACCTCAGGTGATCCACCT
GCCTCGGCCTCCCAAAGTGCTGGGATTACAAGCATGAGCCACCTTGCCCAGCCTTTTTTT
TTTAAATCTGAGAAGAGGTCTTGCTCGATTGCCTAGGCTGGAGTGCAGTGGTGCGATCTC
TGCTCACTGCATTCTCTGCCTCCCAGACTCAAGCAATCCTCCCACCTTAGCCTCCTGAGT
AGCTGGGACTACAGGCATATGCCACCACACCTGGCTAATGTTCGTATTTTTTGTAGAGA
CAGGGTTTTGCCATTTTGCCCAGGCTGGTCTTGAACTCCTGACCTCAGGTGATCCTCCCA
CCTTGGCCTCCCAAAGTGCTGGGATTACAGGTGTGAGCCACTGTGCCTGGTCTCCTTCAC
TGTTGTAAGATACTTGAATTGGGTCAATATTTGTGGAGAAGTCTCTTAAAAGTTCACTTG
ATTGTCAGTACTAGAACTCTACATTTAATATTGACATATTCCTGGGAGCATTTCAGAGCA
TTCTATTAGCTTAGAAAGGTCCAGGATAATTTGACTTTAGAAGTTACTGTTACCATGAAT
CTCAATGACTTTTGAAATCCATGAAGAATATCTTTTTTTTTTTTTTTGAGACGGAGTCTCA
CTCTGTCGCCCAGGCTGGAGTGCAGTGGTGATCTGGGCTCACTGCAAGCTCCGCCTACTG
GGTTCACGCCATTCTCCTGCCTCAGCCTCCCGAGTAGCTGGGATTACAGGCACATGCCAC
CACGCCTGGCTAATTTTTTGCATTTTTAGTAGAGAGGGGGTTTCACTGTGTTAGCCAGG
ATGGTCTCGATCTCCTGACCTTGTGATCCGCCCGCCTCGGCCTCCCAAAGTGCTGGGATT
ACAGGCGTGAGCCACCGCGCCTGCCCAAGAATATCTTTTTGCTGGTAACTAGAGAGGACT
CCTCTGAAGCAGATGCCATTCATGATGGATTTCATCATTTATGGGTTTTAAAAAACATTT
TATTTTGAAATAATTTCAAATTTAAATAAGAGTTGCAAAATAGTACAAATAATTCGTGTT
AACTTTTCATCCAGATTTACAAGTCAACCTTATACAGGTTGAGTATCCCTTATCCAAAAT
GCTTGGGACCAGAAGTGTTTTGGATTTCAGATTTTTTCGAATTTTGGAATATTTTTATTA
TATACTTAAGCATCTCTAATCCCCAAATCTCAAATCTGAAATATCTGAAATGCTATGATG
AGCATTTCCTTTGAGTGTTATGTGGGCACTTTTTAAATTTATTTAATTAATTTATTTTTT
GAGATGGAGTATTGCTCCATCACCCAGGCTGGAGTGCAGTGAGCGATCTTGGCTTATTGC
AAACTTCACCTTCTGGGTTCAAGTGATTCTCCTGCCTCAGCCCCTGAGTAGTTGGGACT
ATAGGCGCTTGCCACCACGGCCGGCTAATTTTTGTATTTTTAGTAGACAGGGTTTCAC
CGTGTTGGCCAGGCTGGTCTCGAACTCCTGACCTCAGGTGGTCCACCTGCCTCCGCCTCC
CAAAGTGCTGGGATTACAGGAGTGAACCACCGCGCCTGGCCATGGATTTTGCAGCATTTT
AGATTGGGATACTCAACCTGTACCATGTTTACTCTCTCCTCTCTCTCTCTCTTTT
TATATATATATATATATATATATATATATATATATATATATATATAAATTATATATAC
ACTACACATATATGTATGTATATGTATGTATTTTATATATAAAATACATATCTACATATA
```

FIG. 10
(continued)

```
AAATACACATGTATATATACATGTGTACATATATGTGTCTCTATATTTAAGTTTTGTTGG
AACCACTTGAGGGTAAGTTGCAGACATGGCGTCTCATTGCTCCAAAATACTTCAGTGTGT
ATTTCTAAATACAAGGACACTTGGTTACATAACCACAGTATATCACCAAATGTATATTA
TAACAAGACTACCATCAAATCCTTATATCTCTTTCAAATTGTTTTAGTAATATCCTTATA
GCAAAAGACAAAACAACAACAAAAACTGTTCCCTTTTATTTTGTTTGTTTTGGTCCATTA
TATGTCCAGGTTATGCATTAATGCATTGTGTTACTTGCTAAGTCTTGTTACTGGCCTTTA
ATTAGGATATTTCTTTGCATCCCGCCAAACTCCTCTTCATGGTTGTATCTTTTTTTTTTT
TTTTGGAGATGGAATTTTGCTTATGTTGCCCAGGCTGGAGTATAATGATGCGATCTTGGC
TCACTGCAACCTCCGTCTCCCGGGTTCAAGCGATTCTCCTGCCTCAGCCTCCCGAGTAAC
TGGGATTGCAGGCCTGCGCCACCTTGCCCAGCTAATTTTGGAATTTTGTGAGACGGGGTT
TTGCCATGTTGGTCAGACTAGTCTCGAACTCCTGACCTCATGATCCGCCCGCCTTGGCCT
CCCAAACTGTTGGGATTACAGGTGTGAGCCACTGTGCCCGGTCTTTTTTTTTTTTTTTTT
GAGACAGGGTCTTATTCTGTTGCCTGGCCTGGAGTGCAGTGGTATGATCTTGGCTCACTG
CAACCTGGACCTCCTGGGCTCAGGCGATCCTCCCACCTCAGCCTCCTTAGTAGCTGGGAC
TATAGGCACACACCACCATGCATGGCTAATTTTATATTTTTTGTAGAGACTGGGTTTC
GCCATGTTGCCCAAGCTGGTCTTGAACTCCTGGGCTCAAGTGATCCACCTGCCTTGGCCT
CCCAAAATGCTAGGATTACAGGTGTAAGCCACTGCGCCTGGCCCTAATTTTTGCATTTTT
TGTAGAGATGGGGTTTCACTATATTGCCCAGGCTGGTCTTGAACTCCTGGGCTCAAGTGA
TCTTCCCATCACAGCCCCCTAAAGTGCTGGGATTATAGGCGTGAACCACTGTGCCTGGCT
GAGGATTAAGTTTCAACCTCAGGGGAGCGGCATTCAAACTATAGCATTGTCCTTTAGTGA
CTGGCTTAGTTCACTTAGAATGTTTGTCTATTCATCCATCTATAGACACTGTTTTCTTTC
ACCTTTTGGCTTTGCAAATAATGCTGCTGTGAATATGAGTTATAGAAAAATACCAATTTG
AATCCGTGTTTTCAATTACTTTGAGTATATACCTGGAAGTGGAATTTCTGGATCATATGG
TACTTCCAAGTTTTTTTTTTTTCTTTTTTGAGACAAGGTCTCACTCTGTCACCCAGGCTG
GAGTGTAGTGGCACGATCTTGGCTCACTGCAACCTCCGCCTCCCGGGTTCAAGCGATTCT
CCTGCCTCAGCCTCTCAAGTAGCTGGGATTACAGGCACGCGCCACCACGCCCAACTAATT
TTGTATTTTTAGTAGAGATGGGTTTCTCCATGTTGGTCAGGCTGCTCCCGAACTCCCGAC
CTCAGGTGATCTGCCTGCCTCAGCCTCCCAAAATTCTGGGATTACAGGTGTGAGCCACCG
CACCTGGCCTCCATGTTTCAATTTTTAAACAAACAATTAGTTAAAAAAATAGGAAACTAA
GAGAATGAACTATTTCCTGTTTTATTCAGTGGGTTATAATCTGTTACTATCATTGTTTAT
TTTGAGGTACAAATTGTCCCTACTTTGGCCAGCAGAGGATCCTGCAGTTTGTCTCCTGTG
TCCTTTTCATAGCTCCTTGTTGGAACTCTTACTGGCCCACAATAGGATGTTCCAAGTTCA
TCTTCTTACTTTTACTGCCCCAACGCTGGGATCAGCCATTTCTTCAAGGAGGCCAGTTCC
TTTCATTGGAGAATGGAAAACCCAATATGTAGAAACCAAGATAGAGGTGTTAGGTGTGAT
TGCTACTGGAGTGTCATTGCTTCCAAACCCTTTCAGAAGAGACCTAGGAAATGTGTGTGT
```

FIG. 10 (continued)

```
GTGTGTATATATATGTGTGTGTGTGTGTATTCATAAAAGCACATACACATACACAT
ACCCCGAAGCATGTATTTCTGTATTATTATTATTTTTTGAGATGGAGTCTTGCTCTGTC
GCCCAGGCTGGAGTACAGTGGCACGATCATGGCTCACTGCAACCTCTGCCTCCTGGATTC
AAGCAATTCTCCTGTCTCAGCCTCCTGAGTAGCTGGGATTACAGGTGTCCACCACCACGC
CCACCTAATTTTTGTATTTTAGTAGAGATGGGGTTTCACCACATTGGCCAGGATGGTCT
TGAACTCCTGACGTCAAGTGATCTGCCCGCCTCGGCCTCCCAAAGTGCTGGGATTATAGG
CGTGAGCCACTGTTCCCATCCAGAAGCATACATATCTATTTCTATATCTACATTTCTGTC
TTTACATGTATATATTAAAAATTACAGTTTGCACTAATACCTCCAATTACAATCTAACAT
CATGGATTTATTCTGGCTTTCTCCCTTCTCATATTTGTGTCTCCCCAACAGTGAGAAAC
CTGGCTTGCTATCCTCAACATGGTAACTTATTTATTAAGAAACTTATTCTTTTTTTTTTT
TTTTTTCTGAGATTGAGTTTCGCTCTTGTTGCCCAAGCTGGAGTGCAGTGGTGTGATCTT
GGCTCACCGCAACCTCTGCCTCCTGGGTCAAGCGATTCTCCTGCCTCAGCTTCTCAAGT
AGCTGGGATTACAGGCATGCACCACCATGCCCAGCTAATTTCGTATTTTAGTAGAGATG
GGTTTCTCCATGTTGGTCAGGCTGCTCTGGAACTCCCGACCCCAGCTGATCTGCCTGCCT
CGGCCTCCCAAAGTCCTGGGATTACAGGCGTGAGCCACCGTGCCCTGCCTCTAGTTTATT
TATTTTTATTCCATGTGCTCAGTCTTGCGAGCACGTGGTCTGTTTCTTGGGCCTGGCCC
CCTCAGTGCACTGTCTTAATACCCTAGCCCCCAGTCCCTCTGATCATATCCCCAGACACC
CCTACTGAATCCCAGGTCTCTACCAAGGGAAAGGCAGGGAGGAGGCATTGACCAAGGAGA
AGAGGGGAAGGGACAGGGAAGGTCTTGATTTGTATTTTCTAAAATTTCTACTCTGCTC
ATAATGCGTCTTAGCTGTGTTGTTGTGGAAAGTAGTGCTGACAGTGTCTTGTTTTTTTAT
TACTTACTTTGTCTTTCTTTTTAAGTGTTTCACCGAAATATACTGTGTCGATGCA
AAAACCTACTGTTACAAGACGAGTTGATGGAGTTTTTGGCAAGGCCTACTAAAGTA
ACCCTGGAAGACTTCACACTTTCCGTTAGTAAGTTGGAATGAAAAGAGAGGATCCTGAGA
GTGTTTCTAGGTAGGAAGTGGTAAAACCATGCTTGGATAGCTTGCTGCCTGCATTTCGA
GTTTGAAGGCCTTATCTGAGCCCTGGGCTGCCTTCAGGGTTTGGGGAGTGGCCTCCTGGA
CATTTAGCAGAAGAGGAGTAAGGAGGGCCCTTCTTCTCCCTCTGAGACCTCATGGAAGGT
GAGTTGGAGCAGGTCATAGAAGTTCTTAAGCCCTCCAGTGCTTGAGACTTGTTCCACACA
TCTTGAACCTGGTTTCTGCATTTTTCTTTCCTTCCTGTTGATTTATTTAAAAATTTTAT
TTCTTTTCAATTTTTTTTTTTTTTAAATAGAGGTGGGATCTTCCAATGTTGGCCAGGTT
GGCCTTGAACTTCTGGCCTCAAGCAATCCTGCCTCGGCCTCCCAAAGTGTTAGGATTACA
GGCGTGAGCCACTATGCCTGGCCTTCTTTTTTGAGACAAGCTGTTGCTCTGTTGCCCAG
GCTGGAGTGCAGTGGTACGATCACAGCTTACAGCAGCCTTGAACTCCTGGGCTTAAGTGA
TCCTCCCGCCTCAGCCTCCGGGTAGCTGGGACTCCAGGCTTGTGCCACCATGCTCAGCA
TTTTTAAAAAATATTTTTTGTAGAGATGAGGTCTCACTGTATTACCAAGGCTGATCTTTA
ACTCTTAGCCTCAAGTGATCCTCCTGCCTCAGCCTCCCAAAGTGTTGGGATTACAGGCAT
```

FIG. 10
(continued)

```
GAGCCACCACACTCAGACTTTGTTGACTTCTTAATAAGAAAAATACTTGTTAAGAGTTTC
TTCAGATCACTTTCCTTTATCAACAAGTAAAACATGACTGAGGAAGTTGTGGTCCCCTTT
GCTTCCCTGCCCAGGCCCGTTTCCCTCCCTCTTTCCCCAGAGGAAACCACCAAGAGGTTG
GCATATATTCTTCCTGAACGTGTTTTTATAGTTGTACTGCACTTGTACTGTGTATGAACA
ATATAAAGTTGGTTTGTGTGTTTAAAAAATTCACATACATGGATTTATAATGTATGTATC
ATTTTGCAACTTAAAAATTTTTTTTGAGCTCCATGCTGATTGATAACGATCTATTTTTT
TTTTTTGAGATGGAGTTTCAGTCTTATTGCCCAGGCTGAAGTGCAATGGCGTGATCTCAG
CTCACTGCAACCTCAGCCTCCTGGGTTCAAGCTATTCTCCTGTCTCAGCCTCCGGAGTGG
CTGGGATTACAGGTGCATGCCACCATGCCCAGCTAATTTTTGTATTTTTAGTAGAGATGG
GGTTTCACCATGTCGACCAGGCTGGTCTCAAACTCCTGACCTCAGGTGATCTGCCTGCCT
TGGCCTCCCAAAGTGCTGGAATTACAGGCATGAGCTACCATGCCTGGCCTTTTTTTTTTT
TTTTTTTTGAGACAAAGTCTTGCTCTTTTTCCCAGGCTGGAGTGCAGTGGCCACAATCTT
GGCTCACTGCAACCTCTGCCTCCTGAGTTCAAGCAGTTCTCCTGCCTCAGCCTCCTGAGT
AGCTGGGATTACAGACATGTACCACCATGCCAAGTTAATTTTTGTATTTTTTGTAGAGAC
TAGGTTTTACCATGTTGGCCAGGCTGGTCCTGAACTCCTGACTTAAAGTGATCCATCTGC
CTTGGCTTCCCAAAGTGCTGGGGTTACAGGCATGAGCTATCGCGCCTGGCCTGAGAAATC
TCATTCTTACTCCTACTCCCTTGCACACTATCTCCATTCTGTAGGTAGCCATTTCTATTA
ATTTCTTGTTTACCCTTCTGTGTTTCTTTCATTCTTTTTCTTTTTTCTTTTTTTTTTTT
GAGACAATCTTGCTCTGTTGCCCAGACTGGAGTGCAGTGGTGTGATCTTGGCTCACCGCA
ACCTCCACCTCCTGGGTTCAAGTGATTTTCATGACTCAGCCACCTAAGTAGTTGGGATTA
CAGCGCCTGGTGTACACTACCACACCCAGCTAATTTGTGTATTTTTAGTAGAGATGGGGT
TTCACCATGTTGTCCAGGCTAATCTCCAACTCTTGGCCTCAAGGGATCTGCCTGTCTCAG
CCTCCCAAAGTGCTGGGATTATAGGCATGAGCCACCATGCCTGGCCCTATGTTTCTTTTT
ATAAAAATAAGCAAATTAATATTTTTATTACTATTTTCCTTTTATTTTTACACATCAAGT
AGAACATTAAATATATTTCTCTGTAATTTTTTTCAGTTACCTAAATCTTTTAGTGATCTC
TCTCATCTTTTTAATCAGCTGGATCGCATTCTATCATGTGAATATTTTATAACTTCTATA
TACTGTCACCAGCAGGTAGCGATTTAGTTGTGTCTAATATTTTAAAATGATATATAATGC
CTCAATGAATATAGTAACCTTTTGCATATATTGTTTGTGCTTTGGGATAACACTACCTC
GTATTGGAAACTGTGTCATTACATGTGTCTTAAAATTACATGTGTCTTTTTATTTTTAT
TTTTATTTTTTTGAGTGGGAGTTTCACTCTTGTTGCCCAGGCTGGAGTGCAGTGGTGAG
ATCTCGGCCGACTGCAACTTCCGCCTCCCGGGTTCAAGCGATTCTCCTGCCTCAGCCTCC
CCAGTAGGTGAGATTACAGGTGCCTGCCACCACGCCCAGCTAATTTTTGTATTTTTAGTA
GGGACGGGGTTTCACCATGTTGGCCAGGCTGGTATCGGTCTGCTGACCTCAGGTGATCCT
CCCACCTCAGCCTCCCAAAGTGCTGGGATTACAGACGTGAGCCACCATGCCTGGCCATCA
CTTTTTTTTTTTCTTAATTGCTGCATAGTGGCCGGGCACAGTGGCTCACGCCTGTAATC
```

FIG. 10
(continued)

```
CCAGCACTTTGGGAGGCCAAGGCAGGCGGCGGATCATGAGGTCAGGAGACCAATACCATC
CTGGCTAACATGGTGAAACCCCGTCTCTACTAAAAATACAAAAAATTTAGCTGGGCGTC
GTGGCGGGCGCCTGTAGTCCCAGCTACTTGGGAGGTTGAGGCAGGAGAATGGTGTGAACC
CGGGACGTGGAGCTTGCAGTGAGCCAAGATTGCACCACTGCACTCCAGCCTGGGTGATGG
AGTGAGACTCTGTCTCAAAAACAAACAAACAAACAAAAAATTGCTGCATAGTATTCCAT
TGTATGAGTAGTAACACAACAATTTTTATAATGCATAGTATTCCATTGTATGAATAGTAA
TGTAGCACTATTTGTTTATACATTTTTATGATTAAAAACAAAATGTTTTTCTATTATGA
ATAAAGTGGCAATGAATATTTTTGTACAAGTGTTTTGGTAGCTATACAGTTATTGTCACT
TAATATATGCAATTCGATAGGCCAGTCATTCAAAATAGAAGATATACAAGGTAGGCCGGG
CGTGGTGGCTCACGCCTGTAATCTCAGCACTTTGGGAGGCCGAGGTGGGTGGATCACCTG
TGGTTAGGAGTTTCAGACCAGCCTGACCAACATGGAGAAACCTCATCTCTACTAAAAATA
CAAAAGTAGCTGAGCGTGGTGGCGCATTCCTGTAATCCCAGCTTCTTGGGAGGCTGAGGT
AGGAGAATCACTTGAACCTGGATTTATAATGTATGTAAATCCACCGCGAAGGTTGCGGTG
AACCGAGATCACGTCATTGCACTCCAGCCTGGGCAATAAGAGCGAAACTCCATCTCAAAA
AAAAAAAAAAAGATATGCAAGGTAAAGATACTAATAAAGACCTTTGTGTTGAGTTGGTT
GACATGTGGTTATTTCACCCATCGTATTTCTTATAGGGAATAGGTAAATTCGTTCCTTGG
GTTTCTTTCAACACTTAGGTAAAATCCGACGTGGAAGATGAGATCTGATTTTACTGGTGT
AACTCTTTATTTGTCCCCTTGCCTCCCTTTCCAATGGACTATTTTAG<mark>AAGRATKAGC</mark>
<mark>TGACCAKTCKGATCAGAACATGCATNACTNTGANTGRATGAGRCAKAA</mark>
<mark>TKCATTKCCTRGTRGTNAGTATNCATNAACATCAKGGKAATKAAAKAG</mark>
<mark>AAKATKGANTGTATNAGCKTAANTATKCTCKAANTGTKCAGATCCKACCKTGA</mark>
<mark>N</mark>GTCAGTAACATTTAGTGACCACAAAGTCTGCTGCTCCCTTGTGCCCTGAGTGTCAGA
AATGCATGACGGTCTGTGTATGACTCTCTGACTCCAAAGGCTTGTGACTGTTTTTGAGC
TGTAATCTTTAAAGAATTACTAAAGTGAGACTAATAGCATCAAATTATTTTCAGAGTACC
TTTTTCCTGCAAAAGTTTTAATCAGTGTTACTTACACTCATCCTATAGGGGTTGCATACC
ATTCCTGCATATACTTGGTACGTGTATTAGTTTTAAGACTTATTGAACTTCAGCAGATAA
TCTTTGAGAGTTATTAGAGGAAAACAAATGATAATGGAGACACCAAAATAGCAGCAGTTT
TCTATGGTGGCTCTCGACCAGTTATTCAGCAATGTCACCAACAGATGTCAGTTTAAGCTC
AGAAGTGGAAAAGCAGAGAGCTCAGAGGGTCAGCTTTTTCATCAGTTCTTTTAATGTTAT
CACCACAATTATGTGAGAATGACCTTGCTTAGAGAAAATTATGTTATTTCGAGATCTTT
CCCCCTGTGTTGGAACTAGGCTGATGAAAGCATGGGCTTGACTTATTTATTGATTGTATT
CGTTTTGTACATTCCCAATCTCCTCTCTGACTTGGTGCAAATTCAGGATCTCTTAGTTAG
TTTGTATATTTTGTGTCTTCAGGTATGATTTTTCAGCTTATACCTTTATGTCAGTGCTA
TTATGTGCTGATAATTTGTTTCTCTAGCTACCACCGTAGCTTCAGGCAAAAGGCTGTCAG
CCAACTCTGTACAGTTTATTTCTAAATTTACTGTTTCAGTTGAGTATGGATGAAGAAT
```

FIG. 10
(continued)

AACTCAAAGTTTATTCTTTTGATGATGAGCCCTTAACACCACCTGCCATGATAGTACTTG
CTTTCTGACCAAGATCCTGAGGGAAAAGCCACTTTATTATTAGAACTATGTTAAGATGC
TTCCCAAAAAACATGGAGCAGTATTGTCTCAAAGTCTGTCCTTGGATGGCTTTGGATGCC
TACATCAGGACTGTCTGATGTGCTGGTTAAAATGCAGATTCCTGGGCCTCATTCAGACTT
ACATGTATTGATATTGCTGGTTGTGGAGCCTGGGAATTCATATTTTAGCAAAATCCCTC
ATTTTTACTCCAAGTCTTATGTGCATTATACAGTTTGAGATGATCACCCAGGATATAGTC
CAAAGACACTGGAGGCTGTTGAAGTATAGGTTGTATATATGGAAAAGGTTGGAATGTTTG
AATTAATTTATAATGAAGATCCTTTTTAATTGAGTGTTCACATGCCAAGGCAAGGACAAA
CATTCAAAATGATTTTCTGTCTCTGTTACAACTTTTTCTTTCTTTTTTTAATTTATTTA
TTTGAGATGGAGTCTCACTCTGTCACCCAGGCTGGAGTCAAGTGACGCGATCTCGGCTCA
CTACAACCTCCGCCTCCAGATTCAAGTAATTCTCTTGCCTCAGCCTCCCGAGTAGCTGG
GACTACAGGCATGTGCCACCATGCCCAGTTAATTTTTGTATTTTTAGTAGAGACAGGGTT
TTGTCATGTTTGCCAGGCTGGTCTCAAACTCCTGAACTCAGGTGATCCGCCCACCTTGAC
CTCTCAAAGTGCTGGGATTATAGGCGTGAGCCACCGTGCCTGTCTCTATTACAACTTTTT
ATTACAACTTCTTTATTTTGACTTTATTTTTACAAATTATTTATTTATTTTTTTGAGAT
GGAGTTTCGCTCGTCACCCAGGCTGGAGTGCAATGGTGCGATCTCAGCTCACTGCAACCT
CCGCCTCCCAGGTTCAAGTGATTCTCCTGCCTCAGCCTCCTGAGTAGCTGGGATTACAGG
CACTTGCCACCACACCCGGCCAATTTTGTATTTTTAGCAGAGACAGGGTTTCACCATGTT
GGTCAGGCTGGTCTCGAATTCTTGACCTCAGGTGATCCACCTGCCTCGGCCTCCCAAAGT
GTTGGGATTACAGGCATGAGCCACCACGTCCGGCCGACTTTTATTTTTTTTCTTGAGAC
AGGGTCTTGCTCTGTCACCCAAGCTGGAGTGCGGTGGCATGATCATAGCGCACTGCAGCC
TCGACCTCCTGGACTCAAGTGATCCTCCTGCCTCGGCCTTGTGTATAGCTGGGATTACAG
GCAGTTGCCACCATGCCAGGCTAATTTTTAATTGTTTTGTGAAGATGGGGATTTCACTGT
GTTGCCCAGACTGGTCTTGAACTCCTGGCCTCAAGTGATCTTCCTGCCTTGGCCTTCCAA
AGTGTTGGGATTACAGGCATAAGCCACTATGCATGGCCTGTAACTTCTTTAAATGGCTAT
AATTAAACAGTTGGTCCTTTTAAGATTGGGCAATGGACGAATGGCAAATTGCATTTTAA
AAGAGGAGGGATTTAAAAAAAAACAGGAAAGATTGGGGCATTTGTCTCTAAAGGACTGTG
GACTCATTTAAGAAGTTTAGTGGTCATTCTTACCATCTTTGTGGTTTTTCCTGCCTGCAT
GGGATGCAGATTTTCTGTCTCAGGTGGGATTGATCAATCCCTTGGAGGAATGTGTCTACT
TTTTAATTGTGTTTAGGAGAGCTGACTGTATACAGTAGTTTTGTGAAAGAACAACATGAA
CCCATAGTAGAGCTAAATTCTTTTTTATTTTTTAAAAACTTTAG<mark>AGGTGTCATGCGCAT</mark>
<mark>CTTGGAAGAAGAGAAATTATCTAAAACGAACATTGTAGTTTCT</mark>
<mark>ACAGAGACCAGACCACCTGGAGATTTTTTTGTTCGTACTGTAATGA</mark>
<mark>AAATGGGACAATGATGCAGTTAAGTGACCATGTTTGATTCCTGTGA</mark>GTA
AATCTCCAGTTGAAAAATGGGTCTGGCAAGATGTTACCTTTGGGTGATTTTCTGCTGAC FIG. 10
(continued)

AGAAGACAGACACCATTACATTCAAAGTCAGATTGTCTTTTATTTATTTATTTATTTATT
TATTTATTTGAGACAGGGTCTTGCTCTATCACCTACAGATGGGGTTTCACCACGTTGGGT
CTGGTGACCCAAATCTTTGGGTGATTTTTCTGCTGGAAGAGGACAAACACCATTACATTC
AAAGTCAGATTTTCTGTTTTTTTTTTTTTTTGTTTTTGTTTTTTAATATTCATTTGTT
TATTCATTTGAGACTGGGTCTTGCTCTGTCACGCAGGCTGGAGTGCAACCTCCCTGGGCT
CAGTTGATCTTCCCTCAGCCTCTTGAGTAGCTGGGACTACAGGTGTGTGCCACCATGCCC
AGCTAGTGTTTGTATTTTTTGTGGAGATGGTGTTTTGCCGCATTGCCCAGTGTGGTCTTG
AACTAGTGCTCAAGAGGCCTGCCTCCTTCAACCTCTCAAAGTGTTAGGATTACAGATGTG
AACTACTGTCCTGATCCAAAGTCAGATTTTCTTTCCTTACTTAGTCAAGTTCGTCTATG
CTTTTATTATACTTAATATATTAGTATAGTTACTGTATTAGTATATTAGCATATTTAATA
TATTATTATACTTATCATACTTGAGTATATTGAGTATATTTACACTTTTAGTATATTTGT
ATACACACCACATTTTTATTATTTATCTTTTTTTGAGACAGAGTCTCCCTCTGTCTC
CCAGGCTGAAGCACAGTTGGCTCACTGCAACCTCTGCCTCTTGGGCTCAAGTGATTCTCG
TGCCTCACCCTCCTGAGTAGCAGGGATTACAGGTGTCCACCACCAAGCCTGGCTAATTTT
TGTATTTTTAGTGGATATGGGGTTTTACCATGTTGGCCAGGCTGGTCTCGAACTCCTGAC
CTCAAATGATCTGCCCGCCTTGGCCTCCCAAAGTGCTGGAATTACTGGCGTGAGCCACTG
CACCCAGCCTATTATCTGTCTTTTGATGGACATTTAAGTTGTCTCTATATACTAGCTATT
GTGAATAATGCTGCAGTGAACATGAGAGTGCTTGAAAACACTAATGTAACATAAAGGTAA
CAAATAATAAATGTCATGTGTTTATCTTGAAAG{highlighted sequence begins}GAGCTGAATACACCTGGTGCAGGA
GAACGGTTCACTTCTTACAACATCCTGCTGAACATTATAAGAACAATCCTATGGCTGGAA
ACATTGGTACATACTCAACTCAAGCAG{highlighted sequence ends}GTGAGCAGATTGGAAAGCTCAAGCTTTCTC
CTTAAAAACTTAAAACAAATCCTAATAGAGAATTTTGCAAACATACAGAGGTAGACAGAA
TAGTATCATCAGCCTCCATGTACCCATTGCAGCTTCAACTATCAAATCTTTTTTTTTTTT
TTTTTTTTTGAGACAGTCTTACTCTGTCACCCAGTCTGGAGTACAGTGTTGCAATCTTGG
CTCACTACAACCTCTGCTTCCTGGGTTCAAGCGATTCTCCTGCCTCAGCCTCCTGAGTAG
CTGGGACTACAGGTGCCCACCACCATGCCCGGCTAGTTTTGTGTTTTTAATAGAGATGG
GGTTTCACCATGTTGGCCTGGCTGGTCTTGAATTCCCGACCTCAGGTTTTCTGCCCGCCT
TGGCCTCCCGAAGTTTTGGGATTACAGGCGTGAGCTACCACGCCCGGCCCTAAATCTTTT
CTTATTATGATTCCACTCACTGACTGCCGCTATAGTACTTGGAAACATATTCCAGATTTA
TATTATTCCCATATTTATCTGTAAAAGGCATTACAGAGGTTCTTTTTTTTTTTTTTTTT
TTTGAGATGGAGTTTTGCTCTGTCGCCCAGGCTGGAGTGCAGTGGCGTGTTCTTGGCTCA
CTGCAACCTCTGCGTCCCGGGTTCAAGAGCTTCTCCTGCCTCAGCCTCCTGAGTAGCTGG
GATTATAGGTGGTGCCACTACACCCAGCTAATTTTGTATTTTTAGTAGAGATGGGGTTT
CACCATGTTAGCCAGGCTGGTCTTGAACTCCTGACCTCAAGTGATCTGCCTGCCTCAGCC
TCTCAAAGTGCTGGGATTATAGGCATGAGCCACTGCATCTGGCCTAAGGCTGTACAGAGT FIG. 10
(continued)

```
TTTAAAGCAAGTTTTCATTATAGATCCACTTCTGGTTACCTTTAGGTAACCTCACTTATT
CACTTTGGCATTGTTGCTATTTCAAATTTCACCTTTATGATAGTGGAAAATGATATAATC
TCTCTAAATAATGTGGTCTATTCATAAAGAAAAATAGGCTTGAATTTATATCAGCAGAGT
AAAGTGTATGTGAAGACTGAAGAAAGATACATTTTCTGGCTGAACAGAAAACACGGTGAA
ACGATTTGAAAACTTTTATTGTGAATTACAGGGTCCTATGAACCCTCTGTCCGTGCCTTT
ATGAATATCAACATAGACATGTTTTTTTTTTTTTTTGCATTAACACCGTTTTCTGTAA
TATTTTCTTTATTTTACATCAACTGCTGTACTCGATCAGCCCCTTAACACGACTCGTATA
AATATGCAGAATAGAAGCAGACTTGAAGTAAGCAAATTAGCTGAGACCACAGAT
AAAGTCAAACAGGCTTTGGAAGAATTGAGGTAAGTTATTAAAAAACTGTTTTTACG
TGAGTTGTTATATCCTATTTTTAGTGGAGGAGAAGTTGCTCTTGTGTTTGGAATTGGACC
TGAGAGACTTGAAACTGACGTCCTTTTTTAATTCGGCCATTGATTGACACGGAGCAAGTT
GCTGAGAGGGCTTCTTCGAAACAGAAGAGCATTGTGTTCTGAGGGAAGGGAGTTGGCAGT
GAGTAGTCAATGGATGTGCTAGCCGCTCCATTTGGCTCTTTTGGTTTGGACTGGTGGCAA
AATCTCAGAGAAACAAAAGGATCTAATTTCTTCGAAAGATTTCCAGCATGCACTGGGGTC
TTTAGAAACAATCTATAGCCTTAGTGCAGCAAATGAGTATGAGTAAAAGAGAAACACCTT
GTGGTGGCTTTTTTTTTTTTTTTTGAGACAGGGTCTCGCTCTGTCGCCGAAGCTGGAG
TGTAGTGGCGTGATCTCGGTTACTGCAGCCCCGTCCTCCCTGGGCTCAAGTGATCTTCC
CATCTCAGCCTACTGAGTAGCTGGGACTACAGGCACATGCCCCTATGCCTGGCTAATTTT
TGTATTTTTGGTAGAGATGAGGTTTTGCAGTGTTGCCCAGGCTGGTCTTGAACTCTTGGG
CTCAAGTGATCCTCCTACTTAAGCTTCCCGAGTAGCTGGGACTACAGGCACACGATACCA
TGCCCATCTAATTTTTGTATTTTTTTGTAGAGATGGGGTTTTGCAGTGTTGCCCAGGCTG
GTCTTGAACTCTGGGCTCAAGTGATCCTCCAGCTTTGACGTGCCAAATGTGGTGGCTTT
AATTTCAGAGTTCAAATTGATAACTCTGGTAAGTTAAGTGAACTGATTTCTTTTTTTTT
AAATTATTTTTGTTGATTATACTTTAAGTTCTGGGATATATGTGCAGAACGTGCAGGTTT
GTACATAGGTATACATGTGCCATCATGGTTTGCTGCACACATTAACCCATCATTTAGGTT
TTAAGTCCTGCATGCATTAGGTGTTTGTCCTAATGCTCTCCCTCCCCTTTAATGCATCAG
TGAAAAAGTGATGATAGGCTGGGCGTGGTGGCTCACTCCTGTAATCTCAGCACTTTGAGA
GGGTGAGGCAGGTGGACCACTTGAATCCAGGAGTTTGCCCCCATCCCCAGACAGTGTGTG
TGATGTTCCCCTCCCTGTGTCCATGTGTTCTCATTGTTTGGTTTTCTGTTCCTGTGTTAG
TTCGAAATATGCTTCCGCTCATATCACCCGAAGGATGAGCTATT
TGTTTTTGCAGAGTCATGCTGTATGTCAATATTCTTTATCGGT
CATCATTGATGGATTGGTGGTCAATCTTGCTATTGAATGTCTGCA
AATATGTGCATATGTCTTTATAGTAGAATGTTTATAATCCTTTGGGTATATAC
CCAGTAATGGGATTGCTGGGTCAAATGGTATTTCTGGTTCTAGATCCTTGAGGAGTCACC
ACACTGTCTTCCACAATGGTTCAACTAATTTACACTCCCACCAACAGTGTAAAAGCATTC
```

FIG. 10
(continued)

```
CTATTTCTCCACATCTTCTCCAGCATCTGTTGTTTCCTGACTTTAAGTGAACTGATCTCT
TTCCTGAAACTAACTTGGGTTGGAGAATGTCCCTGATGGGAATGTGCTGTGTTCCCATTG
CACTCTTCTATATCACTTACCCATTGACAATGTGATCTCTTTCATTTTCTCCTCATCCAT
TTGACAGAAAACTTCAAAAACAAGGATTCTGGCATATTTACCTTTGCAGTTGTCCCCAGC
ATGTAGCACGGTGCCTAGTACACAGAAGAAACTCCATAAATGTTTGTTGAATGAGATTTA
CATTTAACTCATGTTTACATCATTTTATTTTCCTGTTCTGTTTATGGGAATGATTATTC
TATGCTTTTTGAGGACTACAATTTATAAATATTTGTGGATTGAATGAATAAGTGAATACT
GGGCAAATAAAGTCCTTTTAGCCAGAGTATGTCTGAACAACTTGCTGAGATAGATATGAT
TTCCCATTTTCCAGCTGAGGGGCCTAAGGGAGGTTAAGTAAATTATTCAATCTTCATACC
ACAGTTTTTGTTTTGTTTTGTTTTGTTTTTTTCCTCCTGAGACAGAGTCTCACTTTGCT
GCCATACTGGAGTACAGTGGTGCAATCATAGCTCACTGCAGCGTCCAACTTCTGGGCTCA
CGCCATCCTCCCACCTCAGCCTCCTGAGTAGCTGGTACTACAGGTGTGCACCACCATAGC
CGGCTAATTTTTCATTTTTTGTAGATATGGGGTCTCACTGTGTTACTCAGGTTGGTCTTG
AACTTCTGAGCTCAAACAATTCTCCTGTCTTGGCCTCTCAAAGTGTTGGGATTACAGGTG
TGAGCCACTGTGCCCGGCCCATACCACAGATATTGATTGAATTCCAGCAGTGGGGAGGAG
TGTGGAATAGAACATTCTCAGTCCTTGCTCAACATTACTGAACAGAGACTTGAATTTGAG
TTTATTCTCTCATCCCAGGCTTCGCGTTAGGCTCTGAAGACACTAGTGAACAAGACAGAC
AGGGTTACTGCCTTTAAAGGGAGCTTTTAGTTGAGAGAAGGAAAACAGTGATGAAAAGCA
TCAGTGAAAAAGTGATGATAGGCTGGGGCGTAGTGGCTACTCCTGTAATCTCAGCACTTT
TAGAGGGTGAGGCAGGCAGCTCACTTGATTCCAGGAGTTTGAGACCAGGCTGGGCAACAT
GGTAAAACCCCGTCTCTACAAAAAATACAAAAAGTAGCTGGGTGTGGGGTGCGCACCCA
CAGTCCCAGCTACTCTGGGGGTTGAGGTGGGAGGATTGCTCGAGCCTGGGAGATTGAGGC
TGCAGTGAGCTGAGATCACGTCACTGCTCTCCAGCCTGAGCAACAGAGCCAGAACCTGTC
CCAAAAAAAAAAAAAAATTGATGATAAACATAGTGAGACAGAATTTTGAAATCTCAGCCTC
ACTGTTGCCTTCCTTGTCCCCTGCCTGCCTAAATAATAAAAGGCAGCATTTCAGCAGTCA
TTCATTTCATTACTTTCACTTCATTTCACCTTCATAAAGCCTCATGAGGTAAGATGGGAA
GATACAGAAGTTTTAGAAACCGCTCATCAAAATTGAATGGAAAGCCGATTGTTCCAAAAC
TTTTTAGTGTGGAAAATTTCTATTATATGCAAAAGTAGAGAGAATGGGATAGTTATAGCA
GTATACCTGACACCCAGCATTAACAACTGTTGATAATATGGCCAATCTTTTTCGACTCTG
CCCCACTCACTTCCCCAGCCCTGACTTGTCTTGAAGCAAATACTTTTTTTTTTTTTTTGA
GATAGAGTTTTGTTTTGTTTTGTTTTTGTTTTTGAGATGGAGTCTCACTCTGTCCCCCA
AGCTGGAGTGCTGTGGCTTGATCTTGGCTCACTACAACCTCCGCCTCCTGGGTTCAAGTG
ATTCTTGTGCCTCAGCCTCCTGAGTAACTGGGATTACAGGTGTGTACCACCATGCCCAGC
TAATTTTTGTATTTTTAGTAGGGACAGGGTTTTCACTATGTTGGCCACGCTGGTCTCAAA
CTCCTGACCTCAGGTGATCCGCCTGACTTGGCCTCCGAAAGTGCTGGGATTGTAGGTGTG
```

FIG. 10
(continued)

```
AGCCACTGCTCCCGGCCTTGAAGCAAATCTTAACACATCATTTCGTCTGTAACTATTTTA
TTTCAAAAAATTATAACCTGAATAGCATTATCATATCTAAAACTATTAACAGTATTTCCT
TAATATTAACACATATCAGTCACATTTTCCTGATTGCTACACACACACACACACACACAC
ACACACACACTTGCAATTGTGTTTTTTCTTTTAGATGGATCTCACTCTGTTGCCC
AGGCTGGAGTGCAATGGTGCATTCTCAGCTCACTGCAACCTCCACCTCCTGGGCTCAACT
GATTCTCTTGCCTCAGCCTCCTGAGTAGCTGGGACTACAGGTGCCCACCACCTCACCTGG
CTAGTTTTTGTATTTTTAGTAGAGGTGGGGTTTCACCATGTTGGCCAGGTTGGTCTCAAA
CTTCCGACCTCAGGTGATCCACCCACCTTGGCCTCCCAAAGTGCTGGGATTACAGGCATG
AGCCACTGTGCCCAGCAGCAATTTGTTTGAATTGGGAGTGCTTTCTTCCACCTTGATTAT
GAAAAAATTTCAAATGTGTATAAAACAGATTCATATAAAGGATCCTGATATGCCATTATC
AGCTTTATCAATTATCCCTGTCATCATATTTTTATTTATAAATATTTCAATATTTGTGG
AATCCTTAAAAATGCATCACATAACCCAACATTGTTCATATTATACCAATTGTCTTATAA
TTTAAAAATATTTTGTTCAATCATTTTTCAGATAAGCTTCACACACTGTGGTTGGCTAAG
TCTCATAATATTTCTGTTGTAAAAATCTTAAGTCTGGGCGTGGTGGCACACGGCTGTCAT
TCCAGCACTTTGGGAGGCTGAGGTGGGCGGATCACGAGGTCAAGAGATCGAGACCATCCT
GGCCAACATGGTGAAACCCGGTCTCTACTAAAAATACAAAAATTAGCTGGGCGTGGTAGT
GCGTGCCTGTAGTCCCAGCTACTCGGGAGGCTGAGGCAGGAGAATCGCTTGAACCCAGAA
GGTGGCAGTTGCAGTGAGCCGAGATCGCGCCACTGCACTCCAGCCTAGAGACAGAGTGCG
GCTTCATCTCAAAACGAAACAAAACAAAACAATCTTAAGTCTCTTAGAATACTTTGATGC
CCCTTCCATCTCTCTTTTTCTGTCTTCCTTCCCCCTCTCCCTGTCTTTTCTGCTGTTGAA
GAAAGCAGATCATTTGTCCTGAGAGTTACTTATAGTCTGAATTTTGCTGAGTGCCTCTCT
GTGGTGGACTTAAGCATGTATCCATCCCTTATATTTCTTGTAAGTTGATATATCTAGAGA
CTTCATTGGATACAAGTTTTCTTTGGCAAGATAGCATGTATGGTGGTGTATCAGGAGGTG
TTTATGTCCTGTTGTTTCTTCTCTGATTTTCTTAGCAGCTCCTGATCATTATTACTTAGA
TCCATTAATTCATAAGGGACTATATGGTAGTGATATTGTAATTTTATCATTCTTCTTCAT
TTGTTAGGTTGGCATATTTCTATAAAAGCTTTTCATCGCCGAGGGTTGATTTTTCCTT
CTTACTAAGCAGTTTTCTTTTCTTTTTCTTTTTTTTTTTTGAGGTAGGTCTCACTGTG
TTGCTCAGGCTGGTGTGCAGTGGCGCAAACACAGTTGCGAACTCTTGGGCTGAGGTGA
TCCTCCTGCCTCAGTTTCCTGTGTAGTTGGGACCACAGGTGCATGCCACCATGCCTGGCT
AATTTTTTGATTCTTTTGTAGAGATGAGGTCTCACTTTATTTCCCAGGCTGGTCTTGAAT
GTCTGGGCTCAAGCAATCTTTCTACCTCAGCCTCCTGAGTAGCTGGGACTACAGGCACAT
ACCACCATGCCCAGCTAATTTTTTAATTTTTATTTTTAGTAGAGATGTGGTCGTATTATG
TTGCTCAGGATGGTCTCGAACTGCAGAGCTCAAGTGATCCTCCTGCCTCAGCCTCCCAGT
GTGCTGGGATTATAGGTGTACTACAGGCAAGAGCCAATGAGCCTGGTCAGATTTTTTTTT
CCTGATTTGAAATCTGTTATGGGTTCAATTGATACTTCCAAATCAAACTCAGGGTTTCAG
```

FIG. 10 (continued)

```
GATTTTTACTAACCTCATTGATCTTACCCATGTATCTCCTTTCTCTAATGCCAAAAATCC
TACTTCTTGAAGCCATAATAAGATTATTCATTTGTTTTATCCCACATTACACACAACAAT
CTTAGAATAATGACTTCCCAATAATATGATTACTGAAAACAGTTTAATTTTTTTTGCGCT
TTTCAAAAAAATCCTTCAGAGATGTGTAGTCAAGTTACTGTATTCTGCTGGGCACAGTGG
CTCACGCCTATAATCCCAGTACTTTGGGAGGACAAGAAGGGAGGATCGCTGGACCTCAGG
AGTTTGAGACCAGCCGGGGCAATATAGTGAGACCCTGTCTCTACAAAAGAAAATTAAAAA
TTAACCAGACATGGTGGCATGTCCCTATAGTCCCAGCTATTGAGAGGCTGTGGCGAGAGT
AGGCTTAAGCCCAGGAGTTTGAAGCTGCAGTGAGATACGATTGTGACACTGTACTCTAGG
GTGACAGAGCAGGGACCCTGTTTTTAAAAAAAAAAATGAAAAACTTCCTGTGCCTTAG
ACTCATTTGTAATCGTCCTTCTCTCTGTGTGGCTATATGCTAACTGGGTATATGGTTAGT
TTATTTGTTTCATTTAAAAAATCTCTTTCTGTTAAGTTTTATTTATAATTACACAAATAC
TGGCTTTGATAGTCAAATTGAAAAAACAAAGTGTATTCAAAGAAGTCTACCTTCTATCCT
TGTCCTTTCCTATGTTTTAGCCATAGTATAAAAAGTTATGGTTTATCATTATATTTCAAA
AATATAAGAAGATATTCCCATATCCCACTTTTTCTTAAACAGTAGCATAACTTTACATAC
TTTTTTCTAACCTTGCTTTTTAAATATCCTGGACATCCTGGATATCCATAATAGTGTCT
AGAGATAGTCTTCATTCTTTTTTTACTGTATAGTAATCCACTGTGTACTTGTACCATAGT
TTATTCAACCTATTGATGGGCATTTGGGTAGTTTCCAAATGTATCACAGAGAGGATTACA
GTGAATAGCCTTGTGTATGCATCCTGCTTTACTTTTGCTGACTACTGGTAATATTAACAT
TTTTTATGTTCTGTATTTAAAAAATGGTGGTTATTATTCATCTATAACTTTTATTATACA
TGACTTTGGTTAGCATGCTTTAACCTTTTAGCATAACATTTGCAAGCTACTTGTTTTAAT
TAAAATTTTGGTTAAATGTAAAAAATAGTGAGCTATTTTGTAATCTAGATTCAATAGAAT
CTTATACTTCCTTTACAAATGATAGCTGAGTTGATCATTTGTGTAAATGACTGTGAACTT
AAAAATTACAGCATTTTTTAAAATAAATTTTTTAACATTTTAAAATTATTTAAAATAAT
AGACACACAAAGTAAAAGAGAAGAAAAAAAAAGAGACAGGGTCTTGCTATGTTGCCCA
GGCTGGTCTCAAACTCCCAGGCTCAAATGATCCTCCTGCCTTGGCCTCCTAAAGTGTAAG
CCACCACACTTGGCAAAAATTAGTTTCTTTAAAACAAAAACATTACAGGTTATCTGGTAC
CATGGTAGCTTCTTTAACACTAGGTTCACTTAGAACAAAGCTTAGGAACAAAGTCAGACT
TTCACAAAGAGCTTGTGTGGCAATGGGGTATTTTTTGCAAATTCCATTGGTGGGGTCAAG
ATGTGAGTTTAGAAGGAACTCTTAGCCTGACTCTTCTGGCCATGGAAAAGATGGTTGCT
TCTAAATGCTGACCTGGTGATTTTACACTGTCACATCTCAAATTGTGGTCATCTTTTATA
CATTATTAACAACAAAGGGAAAAATTGAGTTGACTTTAAGAGGAAGTGGAAAATAACGA
GATCACATCTGTACTCTACAGGCTCTCCACAGAGGTCAGACTGAGGTGGTAAAATTGTTG
TGCACTAAATTAGGGCATTAACGTTTCATGGAAACTGAAGCTATATCTAAATAGCTGATG
GCCTGCTTTCTAGATCTCCTATATACCTGCTTCTCAAATTCAGTCTGTTTTAAAAAATTG
CCCTTTGAGGTTGGAACCAGCGAAATAAGGCTGAAAACAGAATAAGCCATTATTGAAAAA
```

FIG. 10
(continued)

```
ATTAGGAACTTGGAAGCAGATACTCATAATCTAAATCCTCTGAAGCTAAAGTTTGATCCA
CAATAGCAAAGCATTATCATTTTAGTGATTGTACCTTAGTTGTTTCCTGGCAGGTGATAA
ATTTGGGATCACTTTCTTCTTACAGTGTGCTCTGATAGTCTTTAAAACAAACCAGAGCTC
TAAAATTGTAATGCCATTGGTAATTTAACTCTGATTTGTCTCTATGCCTGTCTCCTGGTGT
TCTGTAAAATTCTACACGTCATTTCAGGTATCACTATCCAGAAGACGTTACTTTTGCCTT
TGATGCACTTTAAAATGTGAAGTCTCTTGTGAAGCTCTTTGGTTATTTTCTCCTTTGCTG
CTGAAATAAATTCAGGTTGATGATTTTCTTGTAGGATATGTTGTGTGATCTAGACATTGC
AAACCCAAGTCTTTGATTTTTTTTTCCCTACAGATTGCCTGTTTCTTTTTTATTTTAATT
TTTATTAGTTATTATTATTTTTGAGATGGAGTCTCACTCTGTCACCCAGGCTGGAGTGCA
GAGGTGTGATAGCTCACTGCAACCTCCACCTCCCGGGTTCTTGTGCCTCAGCCACCCAGG
TAGCTGGGATTACAGGCACGTACCACCACTCTCAGCTAATTTTTTTGTATTTTTAGTAGG
GATGGGATTTCTCCATGTTGGCCAGGCTGATCTCAAACTCCTGACCTTAAGTGATCTTCC
TGCCTTGGTCTCTGAAAGTGTTGGGATTACAGGTGTGAGCCACTGTGCCTGGCCAGTTAT
TAATTTTTTTAAAGAGATGGGGTCTCACTATCTTGCCCAGGCTGGAGTGCAGTGGCTCTT
TACAGGCACTGTTGTAGTGCACTGCAGCCTTGAACTCCTGGGCTCAAGTGATCCTCCTGA
GAGGCTGGAATTACAGGCACACACCACTGTGTCCAACAGATTGCCCATTTGTGATCTGTG
TAAATATCTCTCACTTCCTGCAGTATCTCTGCTCAAGAATGTAAAGAGATGGATAATATT
TTTAGATTTGTTGAAACAAAGTAAAGTTCTGCTCAAATGAGAATGACACTAACTAAATGA
AAAGGCCGGTTATAATTCTGTAATTTTGTGCCTGCAATGTGTGTGTTATTGTACACTTGA
ATCGGCCCTGTGCATTGTGGCGAGGTGCATATTGCATGGTTGTATTGAAAAGGTGCTTGG
GCCGGGCGTGGTGGCTCACACCTGTAATCCCAGCAATTTGGGAGGCTGAGGCAGCTGGAT
TACCTGAGGTTAGGAGTTCAAGACCAGCCTGGCCAACATGGTGAAACCCTGTTTCTAGTA
AAAAATACAAAAAATTAGCTGGGTGTGGTGGTGGGTGCCTGTAATACCAGCTACTAGGGA
GGCTAAGGCAGGGAGAATTGCTTAAACCTGGGAGGCAGAGGTTGCAGTGAGCTGAGATTG
TGCCACTGCACTCCAGCCTGAGTGTATCACAAAAAAAAAAAAAAAAAGGTTTTTGCCCTCT
CTCTGTGCCTGCTGCTCCCTGTTGAGTCCTATAGGCCTGAGCTGCCAGGGGGTACTGTGG
GCTGAGACTGGACATTGCAACCGACTGCAAGGCACCGTGGGACCCAGGTTGTGGATGGAC
TGTCTCTCGGCTTTCTTCTTTCCATTCATCTTCCTCCTCTAACTCCCCTCTGTATCCAG
TATCCTTGCTCTCCATACACCTGCTTCATTCTTTTTCCTTCAGTAGATTTTTCTGCTTCT
TGACTTACAAACCCTACTTCTAGCCCCTTTCAGATATTGAAACTAGCAACTTTCAGGCTT
TGTACCAAAGTCTCAGAGATTCTCATTGACTCGGATGCCATCCATCTCTAGTCCAAAGAA
CAATGTCAAGGACATGAACATGTGGAACAAAAGTGTCTGCTGTGGACACCTTTGGGGAGA
AATAGTTTTCAGTGATGAGGGTTGTAGTGAGTTGGGCAGATATCCCAAAAATATCTGCCA
AAAACTATAGACACTTCTGGTTGCAGTGACTTATTCCTTCCTTCATTCAGCAAATACTGA
TTGAACACCGACTGTATGTCTGGATCTATTCTAGGTTTTGGGGGTGGAGCAGTGAACAAA
```

FIG. 10
(continued)

```
TCAGTCTTTATCTTTATAGAGTGTACAGTCAAGTGGGAGAGACAGGCAGTAAACAAAGAA
ACAGTTCAATATTCAATCTGTGAGATGGTGATAAGTGCTACAGAGAAACAAACTAGTGT
AAGATAAAAGGGTGTTTTGATAGGCCTTTACTATTTAGGTCTCTTTGATAAGGTGGCAT
TTGAACAAAGCTCTGAAGGAAATAATGGAGCCAACCATGCATATAACCTCAGGGAGAACA
TTCTAGGTAGAGGGAACAGCAAGTGCAAAGGCCCTGAAGTGGGGGTTTGTTTACCTTGTT
GCACAATCTGCACACAGGCCAGTACAATTGGAATGGATGGGAAATGTAAAAGAGAGAAGT
TGAAAAGGCCAGGTGCAGTGGCTCATGCCTACAATCCCAGCATTTTGGGAGGCTGAAGTG
GGAGGAATTTGAGATCAGCCTGGGCAACAGAACCAGACCTCGGGCTAATTTTTGTATTTT
TAGTAGAGACAGGGTTTCACCATATTGGCCAGGCTGATCTCAAACTCCTGACCTCAGGTG
ATCCTCCTGCCTCAGCCTCCCAAAGTGCTAGGATTACAGGTGTGAGCCATGGCCCCCAGC
CGTATCTTTGTCTTAAAAAGTAATCTCTGTGCTTGGTAGGCCAAGAATTTAAAATATAAA
AAATTTAAGAAAGAAAAAAATAAGTAAAGTAACTATACAGGTTGGTCTGGCCGTAATGG
TGAGTGTCATTATTTTTCTTCCCTAGGTATTTTGGCTCTGTTGCTCAGAGCAGTGCAGGC
GAAATGGTCATTAGGGCATCGTCATGGTGCCTGGGGATGCCTGGCTCAGCCAGTTTATTT
TCTGTCTGCCTCTCCTTGGTCCTTTTCCTCCACTTTCATTCATGAAATTCTAGTCAAG
AGCTGGGTCCAGTGGTTTTCAATCCAAGGGCTTTGGAAGCCTCTGGGGTCTATTTTGGTC
ATTGCAGTCACTGGGCTGCTGCTCCTGGCATTTAGGTTGGCAGGGGTCTGGGCTGGGAAG
CAGGAATGTTCAGTGGCCATAAATGTAAGGGTTGGTCTTACATTTACATAAGGGAGACAA
TGAAAACTTAACTCCTCCACAGTAGTGGAGTAGTGCCGTTGGGTACTCACAGTCAGTAGT
GCCGTTGGGTACTCACATGTACAACATGGATCAGGACATTGACTTTCTGTGGATACCTTT
TAATAGTTTATTAGATGTGTTAGGCTGTTTTGCACTGCTCTAAAGGAATATCTGAGTCTA
GGTAATTTATAAAGACAAGAGGTTTAATTGGCTCATGGTTCTGAAGGCTGTACAAGCATG
GCTCCAGCATCTGCTTCTGGTGAGGGCCTCAGGAAGCTTCCGGTCATAGTGGAAGGCAAA
AGGAGGGCAGACGATCACATGGCCGGAGTGGTGGCAAGGGTGGGGTGGGAGCCACGCTCT
TTTTTTAATTTTATTTTAATTTGAGACAGTGTCTCACTCTTTGCCCAGCCTGGAGTGCA
GTGGCGTGATCTCAGCTCACTGCAGCCTCTGCCTCCCAGGTTCAAGCAATTCTCCTGCCT
CAGCCTCCTGAGTAGTTGGGACTACAGGCGCGCATCACAATGCCCAGCTGATTTTTGTAT
TTTTAGCAGAGACAGGGTTTCACCATGTTGGCCAGGCTGGTCTCGGACTCCTGATCTCAA
GTAATCCGCCTGCCTCGGCCTCCCAAAGTGCTGGGATTACAGGCATGAGCCACTGCGCAC
GGCCACCACACTGTTTTAAACAACCAGATTGCACGTGAACTTAGAGTGAGAACTCACTGT
GAGGATGGCACCAAAACATTCATGAAGGATCCACCACCTTCCTTTAGGCCCCACCTCCAA
CACTGGAGGTCATATTTCAACTTGAGATTTGGAGGGACAGACATCCAAACCGTATCATT
AAATTTAATAGTTTTATGCAGTTTTTTTGGCTCTAGATCTGTTTAGACTCCTGCAGTCAG
GTGTCTGTAACTAGCCTCTGGTCCTTTTTGAGAGTTCACAGTTTGGTGCAAACCCTTTGG
ATGTATTATTTGGGAAAATGGGATATCTGGCAGCCTGTGTCCCTGCTTTACATTATCCTT
```

FIG. 10 (continued)

```
TTTGCTGCCTGCCCCAAGCCTCCTCATTAGCATCCCTGCCAAGGCCAGTGGAGAAGGATG
GAGATGCGGTGACATTCAGCTTGACAGGTCATTAGCAGCTTTTGTGCCCTAGGGACTGCT
GGTGGGAGGGAGGTTGTGGAAGATAAACCCTGACAGGAATGTATTCTCCTCGAGGGCAGG
GTTTATTTGATATTTTCTGGAGCTTAGAACCATAAGCCTGGTGCTGGGGAGGAAGCGCC
CTTAGCATTTGGTAGCCTCTGTGGGCAGAGCATGGAAAGTCACAACTTCTGAATTGTTTG
TATTTTCAGTCTCACTCTAGATGGATGGCATCTTCTGCTATGGGAAATGAAATATGTTTA
GGCAACTTGAGTCCCAGGTGCAGATGAGGCTGGGCTAATTGGTGCACTAGGGAAGGAGCC
GGGGGAGAGATGTGCTGTTAGCTATTATCAATCTGTGACAACTGTCAGCTGCTGGCAGTT
AGCACCCACCTGAGCCTGGGATGCAGGGGTGCCTCTCCTGTCCTCTGTGGAAGCCTCTGG
ACCCAGCAGCCATCTTGACTGTGCACTGTTCAAGCCCCAAGTCCGCCTGGAAGAGGTGAT
TGAGAACTTACTGCAGGATAAGGAAAGCGCAGGACAGGTGCAGTGGCTCACGCCTGTAAT
CTCAGTGCTTTGGGAGGCTGAGGCCGGAGGAGGGCTGGAGTCCTTGAGTGCGAGACCAGC
CTGGGCAACATAGTGAGACCCTGTCTTTACAAAAAGGAAAAGAATTAGCCAGATGTGGTG
GTGCGTGCCTGTAGTCCCAGCCACTCAAGAGGCTGAGGTGCGAGGATCACTTGAGCCCAG
GAGTTTGAGGTTACAGTGAGCTATGATCATACCACTGCATTCCAGCCTGGGTGAGAGAGC
ATGACTCTGTCCCAACAACAAAAAAAAGATTAAGGGAAGCCTCTGGCAGACCTGATGAT
GGGTGGCCCAGCCAAAATGAGTATTGATGAGGATTTCCCTGGTCTGGAACTCTGAATTTA
GTCTGGCAAAGTATTCCCTTTGTGTTGTGAGATGATTCTTGGTGTTACCCCATCACGGTA
GGTAAGATGAATTAGCAAATGAGAAAGGCTTTCTCTTTTTCATCCTTATCTAGTCCGTAG
ATGAAGCCTGAAGAAGGTCTCCATATGGTAGTAGTAAGTGTTTAACATCTACCTCTAACA
CTTGCCTGTGTCTTTTTTTTTTGCAAAGCCTCAGGAATGCCCCAGTATCTAGGTAGAAT
TTGATAATATTTCATTTTGTTATATTCCCTTTTCTGTTTACCTTCTATATACAGCAAAA
TGAAAAAATTTTTAAAATTTGTGCAAGTAAGGGCAATTTCTTTTTTCTTTTTTCTTTTTTT
TTGAGACAGGGTCTTGCTCTGGCACCCAGGCTGGAGTGCAGTGACACAATCTCGGCTCAC
TGCAACCTCTGCTTCCTGGGTTTAAGCGATTCTCCTGCCTCAGGCTTCCAAGTAGCTGGG
ATTACAGGTGCCTGCCACCACTCCCAGCTAATTTTCATATTTTTAGTAGAGACCAGGTTT
TGCCATGTTGACTGGGCTGGTCTTGAACTCCTGACCTCAGGTGATCCATCCACCTTGGCC
TCCCAAAGTGCTGGGATTATAGGCTTGAGCCACTGGGCCTGGCTGAGGCAGTTTCTTTTT
GAAATATATTTTGTGAAGGAGAAAAAGAGGAGTTCAGTTTAAAGAAACAAATGACATAAG
AGGTGGTATGCAGAGATGCCAAAGCATCTTGAAGGTGCTTTTTTTTTGGAAACAGAGTC
TTGCTTCATTGCCCAGTCTGGTCTGCAGTGGTGCAATCATGGTTCCCTGCAGCCTTGACC
TTCTGGGCTCAAGTAATCCTCCCACCTCAGCCTCTCAAGTAGCTGGGACTACAGATGCAT
GCCACTATGTCTGGCTAATCTTTAAATTTTTTGTAGAAGCCAGCTCTCACCATATTGCCC
AGGCTGGTCTTGACCTCCTGTCCTCGAGCAAAAATACCGATTTTGATTAAGTCTGGGGTA
GGACCTGGGGCTGGGATTCTAACCAGCTCCCAGGTGGTGCTAATGCTGCTGGTCTACAGA
```

FIG. 10
*(continued)*

```
CCACACGTGGAGTAGCCAGTGTAGAGTTCATGTAGCAATAGTGATGTCATAGAAATAGCC
AGTATCTGTATACTTGCTTTGTTGTATGTCACGCACTGTATAGTGATGTACATGCATCTC
ATTTGACCCTCACCCCGCCCCTTTGGGGGTAGAAAGGATTGTGCTCATTTCACACTCAAG
GAAACTGAGGCACAGACAGGCAAAGTAGCTTGGCGAAACAGAAAGGAACTTAGAGGCAGG
CCCTGATTAGCTCAGAGACTAGAAGGCCTTGTGCGTCATCCTGAACAGCTTGGACTTGAT
CTTGAAGGTGGAGGGAGAAATTGAAGGGTAATTAAACAGGAACTGTAGGAAATTCACCTT
GCATAGTGATTGCTTTGGCCACGTGTGCCCTGCCACCGCCCCCCACCTCAGTGAAGTGT
CATGCGAAGTTGGGTTCGTAAATGAAGGCCCGAATGCTTTCCTGACAAGTTTGTTTTAAA
TCAAGCTGCTAATTAGTCCCAGTCCCCCTCCCCCGGTATGTATTTTTTGTTGATGTCGT
TTCACTTCATTTAGTTGAAGTGATTGATTCAGTTCAGTGTTTGAACTTCTTTTTGAACCT
CACCTTAATAACCTGTCTAAACATCAAGGTTAAACCTTCTTGCTAACACAGCAGTATTGC
TTGGTAAGACTGGCTCACAGTCCAAGGAAATGCTTGCCCAGAGAGGGCAAACTGCCTTAA
CTCCTTAACCTGAGCTCATTAAAAAAAATTCAAATGACTGATTCCTTGTCACAGTTCTAC
CTACATTGTTTTATTTTTGTCCAGGTTTCAGCTAGTTAAATGCTTTTGTGATGAGCTTA
TGTCCAGGCTGAAGGTTGCATTTTGAAACTGAGCGTCAAATACCAATTTAAAGTCCAGAC
CTTTACACTTGTGAAATTCAGATAAATGAAATGGAAATAAAACAGGGCTGCTGTGTTGTG
AAATATGACTGTGTTTTTCCTTGTAGGACTCTTTGAGGGTAGCCATTTTGGCATTTTATA
TATAAATTTTCTTTTCTTAGCCTACCTTTTACTTTCTTGATTTGCCTATTTGTGATTTCC
CATTAAACACTAGGCTTTTTGTAAACCAATTATCCCTTGAAATTGACTTTTTTTTTTTT
GAGACAGGATCTTGTTTTGCCACACAGGCTGGAGTGCCGTGGCTCCATCATATGATAAAC
AGAAAGAGAGAGAGAGAGAGAGAGAGAGAGAGAGAGAGAGAGACCCTGTCTTATTTAAAACA
AAAAAGAAGAAGAAAAAAAGAATATAGATCACAGCTGTTATTTGTATATGCTACGCCAA
TCCTTGTTGGGTTTCATTCTTTATAATTGTTATTTTTAAAGATTTTTCTTATGAATATTC
TATTGTTTCATTGTAGAAAATTTAAGGGAGAACACAGTGGGAAAAAAAAAACAAGAAAAG
GACTTCATAATCCTGCTACCCTGGGAGAAAAAAAAATCACCATTACCTATTTGGTTCTT
CTCCCACTTTTTTTTTTTCGAGATGGAGTCTCCCTTTGTTACCCAGGCTGGAGGGCAGG
GACGTGATCTTGGCTCTCTGCAACCTCTGCCTCCTGGGTTCAAGCGATTCTCGTGCCTCA
GCCTCCCGAGTATCTGGGATTACAGGGGTGTGCCATCACACCTGGCTAATTTTTGTATTT
TTAGTAGAGACGGGGTTTTGTCATGTTGGCCAGGCTGGTTTGTTGGCCATGTCTGGTTTT
TTGTCATATTGGCCAGTCTGTTTGTCATGTCAGGCTGACATGTTTTGTCATGTTGGCCAG
GCTGGTCTTTAACTCCTGACTTCAGGTAATCCTGAAGTGCTAGGATTATAGGCGTGAGCC
ATTGCACCTGGCCTTCTGCCTTTTTTTAAAGAAAAAAAATTAAAACATTTTTTTCTTTT
TAAGATAGCGTCTCATTTTGTTGCCCAGGCTGGTCTTGAACTCCTGGGCTCAAGTGATCC
TCCAGCCTCAGCCTCTGGAGTAGCTGGGACTACAGATGCACATCATGGTGTCCTTATGCC
ATTTCTTTTGTACGTAGGTGAATGCAAGTGTATGATTACATCATATGCTATTTTGGAGGT
```

FIG. 10
*(continued)*

TTGACTTTCTTTTCACTTTCATCATCTTTCCAAGGTGTTATTTTCCTAGTACATCTTTTT
AAATGGACATAGAACATTCTTTTGTATGAACAAACAATAGTTTTATTTAGGCGGTCCTTT
CCTGTTGGACATTTATATTATTTTCAGCATTTCTCCACAGTTGTTGCAGCATTCAGATGA
ACCTTCTTTTTTTTTTTTTTGAGACGGAGTCTCGCTCTTTCGCCCAGGCTGGAGTGCAG
TGGCACAATCTCTCCTCAAGTGATTCCTGTGTCACCCTCCCACGTAGCTGGGATTACAGG
TGCCCATGTCTGGCTAATTTTTGTGTTTTTGGTAGAGCTGTGGTTTTACCATGTTGGCCA
GGCTGGTTTCGAACTCCTGCCCTGAAGTGATCTGCCCACCTCAGCCTCCCAAAGTGTGGG
GATTACAGGTGTAAGCCATCACGCCTGACCCAGATGAACATTCTTGTAGCTATCGCACAC
AATTCTGAACATTTCCTAGGATGAATTCCTTAAAGAAGTAATGCTGATCCAGGCTTTTTT
CTTTTTCTGTGACTCTTTGACACGTAATAATATTGACTTTTCTTTCTTTCCAGACACTAC
AACACAGCAGTCAGCTTTGTCAGCGAATAGAGGTTAATGCAGAATCAAT
ACAATACATATAAACATCTGCACTGTAAGTATCAATATTCCGCTCAGTAATAGT
CACTCTTGGAGATTTTGATTCCTAGCACCTCTGTACCTTTCCTCAGGGTCGTGTGCTCTT
GTTAGCACATCGGAGGCCTTAGCTTCTTTAATTGCAAGCAGTTTCCAAAATAATCAACCA
TGGTGGGTGTTGATGACTTCATTCACTGAGCTCCCGTGATGCTGATTACTGAGTAAAGTT
GCCACTAGGTGGCTTTGTCTGTGGTTGGTTCCTTCTGTTAATTAATTTTCTGTCTGCCCA
AGATAGATCATCTCAAGGCTTGGGATCTCTCAGTGTCAGGGACCTTAGGGTGCCAGATTT
GTGTCTTGACTCCTCCTCACTGGGCCTGTGAGTCCTGGGTAAGGCCTGCCTCCTTTCTGG
GACTCAGTTCCCTTAAGTGGGAAACAGACAAACACCTCCTGAGGGCTCCTAGAACTGTTC
TGCTTGCTGATCCCCTGAGCTCAAGTTACTGGAGAAAGGGTATATACCTAAACTGCTCAG
AAGAAGACTTTGTGGGCCGGGCGCAGTGGCTCACACCTGTAATCCCAGCACTTTCGGAGG
CCGAGGCAAGCGGATCACCTCTGATCAGGAGTTCAAGACCAGCCTGGCCAACATGGTGAA
ACCCCATCTCTACTAAAAATACAAAAATTAGCCATATGTGGTGGTGTGCGCCTGTAATCC
CAGCTACTCGGGAGGCTGAGGCGGGAAATTGGTTGAACCCAGGAGATGGAGGTTGCAGTG
AGCCGAGATGTGCCATTGCACTCCAGCCTGGGTGACAAGAGCAAAACTCCGTCTCAAAAA
AAAAAAAGGAAGACTTTGTGAATATTCGCAAAGCTGTAAAGCTGTACCTTTCAATTTTTT
TTTGAGACATAGTCTCACTCTGTTGCTCAGGGTGCAGTCACAGCTCACTGTAGCCTCAAC
CTCCTGGGCTCAAGCGATTCTCCCACCTCAGCCTCCTGATTAGCTGGGACAATAGGCAGG
CACCAGTACACCTGGTTGATTTTACAGTTTTTCTGTAGGCCGGCGCAGTGGCTTACGCCT
GTAATCCCAGCACCCTGGGAGGCCGAGGTGGGCGGATCACCTGAGGTTAGGAGTTCGAGA
GTAGCCTGGCCAACATGGTGAAACCCCATCTCTATTAAAAATTACAAAAATTAGCTGGGC
GTGGTGGTGGATGCCTGTAATCCCAGCTACTTGGGAGGCTGAGGCTGAGGCAGGAGAATC
GCTTGAACCTGGGAGGCGGAGGTTGCAATGAGCCGGAGGTGCTATGTGCACCACTGCACT
CCAGGCTGGGCGACAGAGTGAGACTCTGTCTCAAAACAAAAAACGATTTAAAAAATAATA
AAATTTTTTCTAGGGCGGGGTCTCCCTATGTTGCCCAGGCTGGTCTTGAACTCCTGGGCT

FIG. 10
(continued)

CAAGTAGTCCTCCTGCCTCAGCCTCCCAAACTGTTGGGATTACCAGTGCAAGCCATTGTG
CCTGGCTGTACCTTCTGTAACACCCAAATGCCACCTGGCAAAGCCCAAGTTGAATCATGA
GGAAAAAAGGCCTGGAAGGATGTAGACCTTCCTTTTTTCTACTTATTTATTTATTTATTT
TTGAGATAGGGTCTTACTCTGTTGCCCAGGCTGGAGTGCAGTGGCATGATCATGGGTCAC
TGCAGCCTCAACCTCCCGGGCTCAAGTGGTCCTTCCCACCCCAGCCTGCAATGTAGCTGG
GACTACAGGCATGTGCTACCATGCCCAGCTAATTTTTGTATTTTTGTAATTATTTTTT
TGTAGAGACAGGGTTTCGTCATGTTGCCTAGGCTGGTCTCGAATTCCTGGGCTCAAACGA
TCTGCCTGCATCGGCCTCCCAAAGTGTTGGGATTACAGGTGTGAACCACTGTGTCTGGCT
ATATCTTCTCTAACACCCAAATGCCACCAGGCAAAGCCCAAGTTGAACCAGGAGGGAAAA
AGGCCTGGCAGGATGTAGGCCTTGCATGAGGATCTCAGAAACTGCACTAAACCAGTCACA
GTTCCTCTCTCCCGAGGTCTAACTCTATGCTGAACTCTTTGCATTTTTATCTCACTTAAT
CCATATCACATGCACAGGAAGGAAGCATTCGTAGTATCCTGGTTTCCTAGACCATTTTAG
CAAGGTTATAAGTGAAGGGGAGTGGGTGGAGAACTGGCACTAGAGCCCCCAAAGTCACT
GTTCTTAGCACCACTCTAATGCATGGGGTTCTCCATTGATGTGCTATGCAAGGCAGTGCA
CTGAGGAGAAAGGAAGGAACATTTACAACTTCTCTTTATTTATATCCTGTCCCTAAAAAA
AAAAGAAAAAGAAAAATTTGTCTGAGGCCTAGATTGATTGCAGGGAGTGCATAATGTTTT
ATTGATTGATTGATTGATTGTATATAGAGATGGGGGGTCTCACTATATTGCCCAGGCTGA
TCTCGAACTCCTAGGCTCAAGCAATCCTCCTGCTTTGGCTTCCCAAAGTGCTGGGATTAC
AGGCATGAGCGACTGCACCTGGCTATGCATACTATATTTATCCAACTTACAAATAAGGCT
TGCTTGCCTGTAGTGCATATGTGTATACATTCAGCATAGAAAAACTGTGTGATTGGGGG
TTGTGATCAAATTTGGAGAGCATTGCTCTCATGTCTTATCAGGTCAGAGTCATTTTGTCA
AATCTTGTAAACCATTCTTTGTGTGTGTCTATGCATGAAACATAGTCTTTCTCTTTCTGC
ATGCATATGTACATATACATGGTATATATGTATATCATATCTACATGGATATTGTAATGT
ATATGTATGAGGATGGGGGAAAGTGGAGACATTTGTAATACTGAGAAAAGGCAGTGAGGA
ATTTGCAGAGAAGCAGTTTGAGCTGTAGCATGGTACTAGTGACCTTGAGGAAGCCTTATC
CTTTTTTTTTGGAATTTATTTTTTCAATTTTTAGAAATAGACAAGAGTTTCTCTATGTTG
CCCAGGCTGGTCTTGACCTCCTGGGCCCAAACTATCCTCCTGCCTTGGCTTCCCAAAGTG
CCAGGATTACAGGTGTGGACCACCATGCCTGGCCACCTTGTCCTTTCTATGTCTAAGTTG
TGACATCTGCTCAGGGTCAGGTGGTATTAAATGGTATAAAATGTATGGGAAAGTGAAGG
GATCAATGGTATGCAGTATCTAAATAGAATATCGCTTTTCCTCCCTTAAAGGTCTCATT
CAGATGTTTCCTCTGATGAACATCTCATTTCCTTAAAGATGAGGAGTCTGAAGCAAAAAA
GACATTATTCTTTTAAGACACATGGCTGTCTTACTAATTCCCATTGCAAAATATGTTGTT
TAGGTAGAGCACTCAGATTTTTATACGAATAATAGACTTTTGTACAGAATTTGGACAGTT
GATACTATCAGAGCCTTGTGATATTCCACTGCATTATGCTTCACTAAAAAATACCTGGCT
GGGTGCGGTGGCTCACAACTGTAATCCCAGCACTTTGGGAGGCTGAGGTGGGCAGATCAC

FIG. 10
(continued)

CTGAGGTCAGGAGTTCAAGATCAGCCTGGCTAACATGGCAAAACCCCATCTCTACTAAAA
ATACAAAAATTAGCCAGATGTGGTGGCACGCTCCTGTAATCCCAGTTACTCAGGAGGCTG
AGGTATGAGAATTGCTTGAGCCCAGGAGGCAGAGGTTGCAGAGAGCCGAGATAGTGCTAT
TGCACTCCAACCTGGGTGACAGAGGAAAACCCTGTCTCAAAAAATAAATTTAAAACAACA
ACAACAACAACAACAAAAACCCCTCTTTATTATGGAAATTTTCAAATATATTCAAGAGCA
TAAAGAACCCACATGTACCCATCACCCAGCTTCAACAATTATCAACTCATGCCCAGTCTT
GGTTTCATCTATACTCTGATCCACATCTCCTCTCTCCTTGAATTATTTGAAGCCCATCT
CAGACATCATGTCATATATGTATACTTCAATCTTCTTTTTTTTAAAACTCCCCCTCCCC
TTTTCTTTTTCTTGAGACTGTGTCTCACTCTGTCATCCAGGCTGGAGTGATCTTGGCTC
ACTGCAATGTCCGCCTCTCGGGTTCAAGCGATTTTTGTACCTCAGCCTCCCTAGTAGCTA
GGATTACAGATGTGGACCAACATGCCTGGCTAATTTTTGTATTTTTAATAGAGACAGGGT
TTTGTCATGTTGGCCAGGCTGGTCTTGACCTCCTGACCTCATATGATCCACCTGCCTTGG
CCTCCCAAAGTGCTGAAATTATAGGCCACTGCGCCCAGCCCAAAATTTCTTGGTTTGAAA
TAATTTTGGAACTCATAAGAAGTTACACATATAGTAGAGAATTTTCTTGTACCTTCTC
TGAGCTTCCTATATACCCAATGATAACATCCTATATACCCATAGTATATGATCAAAACTA
GGAAATTGTGAAGATGGCATTTTGAGACATCAGGCAGTGTTCACGTTACTGTTTTGCTTA
CCTGGGCTTTAATTTTTATGTGTTTTTTTTTCAATCATTGAATGAACAAAACTTGGACTA
GGCTGGGGAGTAACTGATTTGAACTGTTTTTTCCTGAAGCAGTCCAGGACTTATGTGACC
GTGGTCTCTTTTCTTCTAGTGATCATACCAGCTTGTCCTAACGATGGTGATCCAA
TCAGCTGTTCAATTAATCAAGCAAATATCATTATGTAAGCTTTGCTTTTCACAG
TGTTTTCTGACCATACATTTCTAGCCTATTTTGTATTTAAATCCTTCCTCATGTCCTG
AAAGTAACTTTAAGGTGTTTGAAGGATTTTCTTCCTAAATTTCTAGCTGATTTGAAAC
AAGTGCAAAATCAAAGCCAAAAGAGTTACATTGCCACAAGGCTGCCTTCAAA
CATTGATGATTTTGCATGTGTTGAAAATCCAGTATTTCATGC
ATGGAATAATGGCTGATTAAAGGTAAATCACAGAAACTTCTTTTCTGCTAAACTGTT
TTTAAAGTATCAGACATGTCAGATTGGCCATGTTTAGGAATTGAATAAATGAATTAAGCT
TACTGTAACTGATTCTCTGGAAAAAAGGGACTAGGAGAAATTTGATTATGTTATTCCTTG
GTGTAGTTTTCTTTATGTTTCTTCTGCTTGGGATTTGTTGAGCTTCTTGGCTCCATGGAT
TTGTAGTTTTCCTTAAATTTGGATAATGTTCAGTCTTAGTTTCTTCAGATACATATCCTG
GGCTGGGCATGGTGGCTCATGCCTGTAGTCCCAGCACTGTGGGTGTTGAGGTGGGCGGA
TCACTTGAGGTCAGGAGTTTGAGACCAGCCTGGGCAATGTAGTAAGACCCCATCTCTTAA
AAAAAAAAATGTACCCTGCACAACCTTGTCCTAGGACAGCAGTCATACGTGTATTAGAC
TACTTGAAGTTGTCTCATAGCCCACTGATACTTGGTTTATTTATTCAGTTTTTCTCCC
CGTGTTTCATTTCGAATAGCTTCTTTTGCTATGTCTCCAAGTTAATCTTCTGCAATATGT
CATCCGCTCTTAATCCTATCCAGAGTATTTTCATCACAGACATTGTATTTTTCATCTCT

FIG. 10
(continued)

```
AGAAGTGTTAATGTCATCTATAGCTTTCCTTTTAACATGTGTAGCATTTTCCTTACCTTT
TGAATGTATGGAGTATTTCTGTTGTTGTTTTTGTTTGTAGAGACAGGGTCTCGGTCTG
TTGCCCAGGCCGGAGTGCAGTGGCATGATCTCAGCTCACTGCAGCCTCTGCCTCCCGGTT
CAAATGATTCTCATGCCTCAGCCTCCCAAGTAGCTGGGACTACAGGTGCGTGCCACCACG
CCTGGCTAATTTTTGTATTTTTAGTAGAGATGGGGTTTTGCCATGTTGGCCAGGCTGGTT
TTGGAACCCCTGAGCTTAGGTGATCCACCTTCCTTGACCTCCCAAAGTGTTGGGATTATA
GGTGTGAGCCACCATGCCTGGCCATGTTGTCTGTTTTAATTAACTCTGCCTAACTGTCCT
CCCAAATGGTTGCTGCAGTGCTCACTCCCACCAGCAGCACCTGCCTAGGACTCATTACTC
CATACTCTTCAAGACACTTCAGATTAAAAAAATAAATTGTAACACCCCACACCTACAGAA
GAGCGGACAGATCTTATTGAGTGACAGCCCTCTGTGTTATCTCAAAGTGAGCCCACCATG
GTGGTTTTTTTTTAAATATGGAAAAGTTCTGTGTTTTTGTTTGTGTTCTAGTGAAAGTT
CTTTTTAGATATCCTTTAATTGGTTTATATAAGATTTATGTGGAATGTAGCAGTCATA
CCTATAAATTAAACCTAAGGCAGATGGAGAACTTTGGAGTTGAGCCTTCCTACTGTAATT
TTCATATTGGATGTGAAGGGCAGTGTGATTTTCATAAGACTTTCATTGTTGTACTCCTAG
TTGGTATACTTCTGAATACCTTTGAGGCCAGTTCTGGTCATCGTGAAACAAAGGTTTCCT
TCAGCAAATGCCTGTGGTAACATTAGGTGTTCTTGAATTAATGGACCAATGAAAACATCT
TTGTAGTTTCTGCTTCAGGCAAGGGTTTTTTGCCCTAAATGTGGATAGGAAGAATGAAGC
CCTTCATCCTCCTTTTTGCCTGATTATAGCTATAGGAGGTTCACCTGTTCTCAGAAGACA
TGAGGATTGTGAAGAGAGGGGTCTTGTGTTGCTTCAGAGGAATCAGTATCAGTCCCTTTC
AGAAGCTCTCCTGGATAGACAGGCATTAGGGCCAAATCACTCTGCCCCACCCCTCACCAC
CATGTCCTACTCTCTGCTCCCTGTCTCATTCTTCCTCTTTACTTTGGTGGTGCCGAGAGG
ATGACATGATGGGTATTGATTCTCTCCACAGACCTTTCTGACATCCTACTTTCAGTATCC
CCCCAGTGCACAGAAGACAAGCCAGACTGTGGACTGTGTTTGATTCCTGGGCTCTATTTT
AAAAGACAGTGTATTAGTTCTCACATTTTAGAATTTGTTTGCCAAGGTTTCCACGGGAGT
TTAGAAACTAGGGGAGGGCTGATGTTTAAAGTTAGCTAAAATGTTCTTTTCAGGGTCAT
GATTTAATTTTATATTCTCTGGTGAGTTCCCTATAGTGACTGGGAGCAGTCCTCAGTCTT
GATTGGCCAGTGACAGCATAGAGTACAATTAATATTAGGAGTGCTCATTTGGGGAAACTA
AAATTTGCATCAAATCTGTCAGAGGTGTTTGGATCTACAAAATACCGGAGGGAAAGCTGA
ATTGAGAATCATAATAAATAAAAGACCACATCGTTCTTTTTTTTTTTTTTTTTGGGACT
GTATCTTGCTCTGTCACTCAGGCTGCAGTGCAGTGGCACTATCTTGGATCACTGCAGGCT
CCGCCTCCCGGATTCAAGCGATTTTCCTGCCTCAGTGCCTGAGTAGCTGGGATTACAGGC
GTGTGCCACTACACCTGGCTAATTTTTGTAATTTTAGTAGAGACAGGTTTCACCATGTTG
GCCAGGCTGGTCTCAAACTCCTGGCCTCAAGTGATCCACCCGGCTTCCCAAAGTGCTGGG
ATTACAGGCGTGAGCCACTGCGCCCAACCAAGACCACATCCTTTTATTGAACGTTCCTCC
TACCATGTTTTCTTTTTTCTTTCAATTAATCATTGACTCATTGACTCTCACTGTTGATGT
```

FIG. 10
(continued)

```
CTGTAGCTGCTCTCTTATTTCCAGTTTTATAGCTGTAAATTTCTCTGTCTTCCTAAGATA
CAAGGTAAATTTCTCTTGCTGATATTGGTGGTTTTGGAAAGTGAGTGGTGTGGATGACTG
CCCAGAAAACAACAGAACACAAAAGCATTCTCTGCCCAGAACACATCACCAAATAGATAC
AAACTCATCTCTTACTGAGTGAAATAGCTTCCTTTTTGGCAGCAAGAATGATTTTCTTGG
TGCCATATTTTTCAATCCGCCTGCTCTTGAAGCCAGCAGCTATTGCAGACTTGGCATTCC
CAGGCACCCAGTTAAGGGAAAGTGACGTGTAGAGGAGGTATCAGATGGGTCTGGATATAG
AAAAAGCAGCTGGTTCAAAACCCCATGGGCTGCCTTTCTGTGATAGAGTTATTCACACTT
GGGTTAGATAAGGCACAGAGTCCTCCTACACTGGTGCGGAAATGAAACAGACAGTCTGGC
TCGTTGGGCAGCCTAGCCTCCTCCAGAATCTGTGCTTGCCTTCCCTATGGAGTGACTGGT
AGATCTTAGAATTCAGACCTCAGTGGTTGCTAGCCAGCACTCTCACATTGGTTGGTCCTT
CTCTCTGCATCTTTGATTCTTTAGAGATAGATAAACCAAGCACCGACTCTCCTTTGACAT
GTGCTTGGAACAGACACCTGCACGAGCTGCCTTTCTCCTCCCACTTCTGCCTGGTCTTCC
AAACACCTGCTTTTCTTGTTTGAACTCTTCCTTTTTTTTTGAGACAGAACCTCTCTCTGT
CACCCAGGCTGGAGTGCAGTGGCATGATCTCAGCTCACTGCAACCTCTGCCTCCCAGGTT
CAAATAATTCTCCTGCCTCAGCCTCCCAAGTAGCTGGGATTACAGGTGCCTGCTATCACG
CCTGGCTAATTTTTGTATTTTTAGTAGAGACACGGTTTCACCATTTGGCCAGGTTGGTCT
CAAACCTCTGGTCTCAAGTGATCTGCCCGCCTCGGCCACCCGAACTGCTGGGATTACAGG
CATGAGCCACTGCGCCCAGCTGATTCTTTACAGATAAACAAACATTGACTCTGCTTTGA
CATGTGCTTGGATCAGGTAACTGCACCAGCTGCCTTTCTCCTCCCACTTCTGCCTGGTCC
TCCGAATGCCTGCTTTTCTTATTTGAACTCTTCTGTCCTTTCTGAAAACCTAACAGATG
CGAAACAGGCCATTTTCCATGTTGGTGGTTATTAAGCAAGACTTGAACATTTGTTTGTTG
CTTGTTTAGGCTTTTATTTCAGAGTTCACAGAATTAACTTTCTTTTTTTCTGATCTCTTC
CAGAGTAAATGTCAAATACTGGCCTGATGAGTATGCTCTAAAGCATATTGCTCATG
TGTTGGCCGTTAAAAACGCCGTCAGACATACCTAGACACTTAACT
CAAAGTTGACAAGTAAGTATATTGTCGTATTCTAGAGACTTTGGGAACTGTTGATGG
TGTGTAGGAATTCAGGGTCTTGCCGTTACTCATGTTTGCATACATGCATGCATTCGCTCA
CTCATTGATTCAGTAGCCATTTATTAGCTTCCTTCTATGTGCCAGGTACAGTTTAAGCAG
TACTGGTACATTGTGAACAAGGCAGGTAGTGTTCCTGCCCTCATCGAGCCTAGGGAGATA
GACAATTAAAAACAAATAACTGGCCAGGCGCCGTGGCTCAGGCCTGTAATCCCAGCACT
TTGGGAGGCTGAGGTGGGTGGATCGCTTGAGCCGGGGAGTTCGAGACCAGCCCTGGGTGG
GAGACTGGGATAGGGTGACCTGAGTGGCTACAAGGTCTGTTAGGAGGCCTCCGCAGGGGC
CTATGTTGATGGCCTCCTCTCCAAGTATCCACAGACTTCAGCAGTTGTTCTTTTTTGTTC
CTTCCTTTGGAATGGAATATTATATAAAATGGCAGAATAAACTGGAAGAGAAGCAGTAGA
TGTGAGAGGTGCCGGGGGGTGAAGTCTGCAGGATGTGGGATTGTTTGGCTTTTGGAGGA
GGAAGGAGGGATTCAAGACACATTGTAGAGGTTTGAGTCTGAGCGGACAGTGGTGCTGTG
```

FIG. 10
*(continued)*

```
GCAGACACCACAAAAGCTGGAAGGAGAACTGATGTGGGCAGTGATTTGTTTTCTTCTGGA
TGTGTTCAGCTGGGCATCTGAACAGTCATGTGGACATTCATCTATTCATTCAGAGATATT
TGTTCAATGACCTCTTGGTTCCTGGCACCATGCTGCTTGCTGGAGATAGAGCTGGGGAAC
AAAACAGATGGAATCCCTGCACTCCCAAGTGTACACTATACTGGCCAGTAATCTACCAGC
CCAGTAATTGCACATATAAATATATCATTATAAACTGTAATCAGGGCTAGAAAGAAAAAA
TGCAGGAGTTTAGGGTTCATTTGGAGGGGAAGGGACTTTTTTTTTTTTTTTTTTGAAAC
AGAATCTTGTTCTGTCACCCAGACTGGAGTGCACTGGTGCATTCACGGCTCACTGCAGCC
ACAACCTCCTAAGCTCAAGTGATCCTCTCACCTCAGCCTCCCATGTAGCTGGGGGCTACA
GGTGTGTGCCACCATGCCCACCCAATTGTTAAATTTTTATAGAGACGGTTGTCTCATTA
TGTTGCCCAGGCTGGTCTTGAACTCCTGGGCTTAAGCGATCCTGCTGCCACATGCAGCCT
CCCAAGGTGCTGGAATTACAGGCGTGAGCCAGCGCACCCGGCCAAGGGAGGGGAGGTTCT
TAAGGCATAGGGAACAATGTGTTTGAGTCAGCAAAGGAGGTTGTGGGGTTTGTCCTAAG
TGTGGTAAGCAGCCAGAGTTGGATTTAAGTTTTTAAGAGATTCCCCTCCACCCTGTAGAG
ACTGGAGGGGCAGGAGTTGTTCTAGGGATTAGGACCAATTTGGAGGTAGTGCAGCCGTC
AGAGTAAAAATAATAGGGATTGAACTAGGCCAGTGCCCAGGGTGCCTGAAAGAAGAGGA
CCCAGTAGAGCTGACTGGAGGCAGACATGCAGGGATTCAGTGAAGGAGTGTACCAAGGGC
GAGGGTGGTGTGCAGGGTGACTGGCAATTTCTAGCTTGAGAAAGGTCCGGGGGATGGC
AGTGGAGTTGAGGAAGCTGGGAGGATCAAGGACCTTTTTGTGAACACACAAAGTTTGAGA
TGCCTTGGACACATTGAAGTGGAGCGGTCAGGGAGGCAAGGGTGGAGGTGGGATGCGGAG
GGGAGGTGGGATGCAGAGCGTCGTGGATGGATCAGTTTTGCTCGATAGAGGGACATGTTT
TTCTGTGGCAACAGGAGGGCAAAAGGAGAAGGTGGCCACAGATGCCGGTAGATGAGCTGA
GAGTGATTGTATTCCCTATCCTCTCGGAAGCTTGAGGCAAGGCCATCAACAGACAATCAG
AGGGAATAAGAAGAGATAGAATATATGAAGAAAGGGAGAAAAGATGAAATCGTAATTGTG
TAGCAGGGCAAGAAGTCCAGAAATTTCTGTGCTGTGCCAAGTTCCCAGTTGAGGCGGTGA
ACATGAAAATATACTGATACCCATTGCCTGGTTTTTCTCCAAGGACACTTGGCTCCTAGG
GCACAAAACAGAAAGTACGTGGTTTGTCCAGGCCGAGGGCTTTGCATAGTTGCAGTGGAT
GGAGAGGAGGTCAAGGAATGGAGGCACATGGTAGAGAGAGACTGTCCCCAGAGCACGGGG
ACTCCTGGCCGGATGAGGGGACAGGGGCAGGAGGAGGCAGGTGGAAAGTAGAGGGAGGG
CTCAGTGGTCTGGAGGCTACAGGAAGTGACGGGGGACCAGAAGGAGCTGGAAACCAGTG
TGGTTGTGGCCCAGGGTGGGATGTTTGGATTCTGATGTCAGAGAGGGTCCAGTCCTTCT
GATGATGGGGAGGGGTGGAGGCTGAATCTATGGTAGAGATAGTGAGAGGAACTGGAACAA
TGTAGCTGTCAAGTGGAAATGGGAGAAAGGCTGGGCGTGGTGGCTCACGCCTGTAATCC
CAGCATATTGGGAGGCTGAGGCAAGAGGATCGTGTTAGCTCAGGAGTTCTGGGCTGCATT
GAGCTGTGATTGTGCCACTGCACTCCAGCCTTGGCAACAGAGTGCCCAGTTAAAAATAAA
AATAAAATAAAATAAAAAAATTAAAAAAAAAGAAGAAGAAAAAGAGAAAAGTGTCCTT
```

FIG. 10
(continued)

TTACATCCCTTTTAAAAATGTCACTTAAGGCTGGGCAAAGTGGCTCATGCCTGTAATCCC
TGCACTTTGGGAGGCTGAAGTGGGTGGATTACTTGAGGTCAGGAGTACAAGACCAGCCTG
GCCAACATGGCGAAACTCCTTCTCTACTAAAATTAGCTGGATGTGGTACATGCCTGTAGT
CCCAGCTACTCGGGAGTCGAGTCTGAGGCCCAAGAATTGCTTGAATCGGGGAGGCGTAGG
TTGCAGTGAGCTGTGATCAGGTCACTGTGCACCAGCCTGGATGACAGAGTGAGACTCTGT
CTCAAAAAAAAAAGTCACTTAGCTTAGATTGTCTCTACATATATAGGAAGAAGATGTAGG
AATGAATGGTGCTGCTACAATTACGTCATCTGGATAGACCCAGAAACATGATACTTTTTG
GTTTTCTGTAGCCTTGGTGCCATTGTTGATCTTTATTAATTATCATTATCCTCAAAATAG
CCATAATGTGCTGAGTCTCTTCCTATTTGCTGGCAGAGGCTGAGTATTTCAGCGAGCTC
ACTGAGTCCTTAAAATTGCATTATGATAGAGAGAAAGAGATTATTATTTGCATTTTGCAA
AATGAAGAAATTGAGGTTTAGAGATACCCAAGGGCCACGTGAGTGTGAGTGCCTGGAATT
GGAGCCTAAATCTAGTCATCTGATAGCAAAGCCTGTTTTCTTATCTGCTTTGCATTAAAT
ATAAGTTTAAAATAGAACAATACTGGCCAGGCTGGGTGGCTCACGCCTGTAATCCCAGCA
CTTTGGGAGGTCGAGGCAGGCAGATCACCTGAGGTCAGGAGTTTGCAACCAGCCTGGCCA
ATATGGCGAAAGAAACCCCATCGCTACTAAAAATACAAAAATTAGCCAGGCATGGTGATG
TGTGCCTGTAATCCCAGCTACTTGGGAGGCTGAGGCAGGAGAATGGCTTGAACCCGGGAG
GCAGAGGTTGCAGTGAGCCAAGATCACGCCACTGCACTCCAGCCTGGGCAACAGAGTAAG
ACTCTGTCTTGGAAAAAAAAAAAAAAAAAGAATGATACTATAGTCTGTGTTTATATGGTGG
GGAAGGTTGAGTATCAAAAAAATAACAAAGAGGAATGAATGTCTTAAGTGAATGCCTGTT
TCCCCATCTGCTTCCTCTTCTGCTGGGAGGAGAGACCTGGATCCCTAGAGGTTTCAGTTG
CCTCCAGAGCTGAGTGCCACAGGGATGCAGGGGAATAGGGATGTTACCTGTCGCTGGTAA
TTCAGAGAGATGATTCAGGGTATAGTTACCTGAAAGAACAAATTGCCATGCCAGACGTCT
TGGTTCTTATGACAGAGGCAAAGAGTTGCCTCCAGGATTGCCCAAAAGGAGACGAGTTCT
GGGAACCTCACGAAGAGGACCTTTCAGTGGAACCTGGGGAGATTCTCTTCCTCTCCATTG
GATTTAGGAAAGCTTAGAACCGGGTGATTCCTCAACCTCTTGATTTATTTAATTCTTTTC
TGGTTTTTCTTGGCTTTACTCCAGGCGAATACGGAGAGAACGGTCTGGCAATACCACTTT
GGGACCTGGCCGGACCACGGCGTGCCCAGCGACCCTGGGGCCGTGCTGGACTTCCTGGAG
GAGGTGCACCATAAGCAGGAGAGCATCATGGATGCAGGGCCGGTCGTGGTGCACTGCAGC
TGCACACTCCTGCTGCCCCTCTAGCCCACACCTCTCCCTGTCTCCTAGCGCCCATGGCT
TGCTTTTACCTACCCACTCCTAGCTCTTTAACTGTAGGAAGAATTTAATATCTGTTTGAG
GCATAGAGCAACTGCATTGAGGGACATTTTGATCCCAAGGCATATTTCTCCTAGACCCTA
GAGCACTGCCATTGGCCATGGCCATGGCAACATGCTCAGTTAAAACAGCAAAGACTAAGT
CAGCATTATCTCTGAGTCCACCAGAAGTTGTGCATTAAACAACTTCATCCTGGCTCTGCA
GTTTCTCCTTATTCTTCATGATGTTTGCTTTGTAGCTGTTGACTGCTTTGTAGGTATTGA
GGTGGTGGGGGTGTGGTGGAAATAGGCCTGACTCTTGAGGATCCCTTAAGTCATTTTTGC

FIG. 10
*(continued)*

TTGGTTCTCTTTTTCCTTCTTTTCTTCTACTCTTCTATGATTCATCTCTTTGATTGTGAT
TCTGTTCTCTCTCTCTCTCTCTTTTTTTTTTTTCGTTTTTGAGACAGAGTCTTGTTTT
GTTGCCCAGGCTAGAGTGCAGTGGTGCCATCTTGGCTCACTGCAACCTCCGCCTCCCGGG
TTCAGGCCATTCTCCTGCCTCAGCCTCCCAAGTAGCTGGGATTACAGGCATCTGACACTA
CGCCCGGCTAATTTTTGTATTTTAATAGAGACAAGGTTTTGTCATGTTGGCCAGGCTGGT
CTCGAACCCTTGACCTCAGGTGATCCACCTGCCTTGTCCTTCCAAAGTGCTGGGATTACA
GGTATGAGCTACCATGCCCGGCCCATTCTGTTCTCTTCTACCATAAATATATTCTCCCC
TAACACTATATTTGTTTGCTTCACAAGATTCCAGCTGCTTTTCCACCAAGGCCTTTGATG
GAAGCTGTGCTGTGACCTCTGTAATGAGTCTGTGGGCTGCTGATTCTCCAGTTTGGGCTT
CATGATTATACTGGGGAATATTGGGTTTCCTAAATCTCATTCATTTCTTGGGCAAGTAGA
TATATGTGAAAGTGTTTATTTGTCCAGTTGTTAAAGAAGCTACCATTTATTGAGCCAGCC
TCTGAGCACAATGTTTTTTGTTTGTTTTGTTTTTAATTTTTAAAATTATTTACTTCTTC
TATTTCAATAACTTTATTATTATTATTTTTGAGACAGAGTCTCACTCTGTCACCCAGGC
TAGAGTGCAATTGAGCGATCTTAGCTCACTGCAACCTCTGCTTTCTGGGTTCAAGCAATT
CTCATGTCTCAGCCTCCCGAGTAGCTGGGATTACTGGTACGTGACAACATGCCTGGCTAA
TTTTTGTGTTTTTAGTAGAGACGAGGTTTTGCTATGTTGGCCAGGCTGGTCTGGAACTCC
TGGCCCCAAGTGATCCTCCTGCCTCGGCCTCCCAAAGTGCTGGTATTATAGGTGAGAGCC
ACTGCGCCCGGCCCTCTTTCAGTAATTTTGATGTATTTTTTGTATATGATTCCTGTTTC
ATTCTGTCCAACCAGCACTCTGTATGGTATGTGCTGTTGTCCCCATTTCACAGATGCAGA
AATTAAGGGTCAGAGAGGTTAAGGGACTTACCTCAGGCACGTTGTACTGGAGAAGCTGAA
CTCCAAGAGCAGGTTTGGGCTGACTCCAAAGCCCTATGCTTTTTGCCAACATATTTTCAA
ACATAAATAGACAATTTTATAAATAGCTCCAAAGAGTAGACATTGTTTCTGTTGATATTA
ATGGCTTGGTTTTGAGTCTGAAACCCCCATGAATGATTCTGTTGTCCCTGCTTTTTGTCC
TTCTGCCCGCAG<mark>TXTGXATXXLXGCACAGXXACTTXATTXGATGATATXXCTTXX</mark>
<mark>XGACXTXXTCXXABXGAAXG</mark>GTGGGTCATCTGGTGGGCAAGAAGCGACAGTTTCTGTTTT
TAGTTTATGGAAGGAAAGTGCTCACGAAAACAGTCTGGGGAAGAGAGGTTGAATGGGAAA
ATTCTTTCACAAAAATCTGGGCTGAAGACTTCAGTGTGTCTGCCTGAGAACAGAAGTGAC
ACTATTTGAGCTTTTGGCATAAAATGAAGTCTAGGAGCTGCAGAACCCACTGCCATGGCC
TTTTGTTGCATACACAGTGGTGGTCTCTATCCAGCCACCTGACCTTGTTTACAGTATGGG
GTGATTTGTTGGCAAGTGAGGGAATCCTGACTTCTGCCACTTCGTTATTTATGTAGTCTT
CTGGGATCATTGGTATTGGTCAGAAGTTCAACACTGTAGCCATTGCAACATGCTCAGTTA
AAACAGCAAAGACTAAATTAGCATTGTCTCTGAGTCCACTAAAAGTTGTGCATTAAACAA
CTTCATCCTGGCTCTGCAGTTTCTCTTTATTCTTCATGATGTTTCCTTCGTAG<mark>XXXXX</mark>
<mark>CTXXGATXTXACTTCXXAAXACXATCXAGATXGGTXCGXTCTXAGAXGGTXAGXXATGGT</mark>
<mark>CCXXACXGAXGXCAGXACXATTXATXTATAXGCGXCAGXATATXXTGXAAXGT</mark>

FIG. 10 (continued)

[XXXXXXXXXXXXXXXXXXXXXXXX]GTACCAGCCTGAGGGCTGGCATGCGGATTCTCATT
CTCTTGCTAGGCCTCTTGGATACGCTCTCCTTTTGAGCAGGAGGACAGGCTCTGATAGAC
AACTGTTTGATTTCGGAATGGGAAACAAACTCCCAACTAAAAGGGCCTCTGGAAACTGTC
AATTATTCTCCACTTCTCAGCTCTGATTTTTCACTGCAGAGGAGCTTAGGGAAGGGCACC
ATCCTATCAGCCTGGCCTGCCAGATTGAAGAACTGCCATGCAGAAAGGTTCTGATGTTCT
CAGGCTCATGTGGCAAGCGTAAAACTCAAAGCCTTGAAGTTTCTAGCCTGTTCCAGCCTT
GATCCAGGCCATGTTTATCCTGATTCCATCCTTTAAAACGAATGCCTCACTCTTAATAGC
GCACGGCAGTTTGAACCACTAATTTGGTCGAGTTGGAAACAGTGAAATTTCAATTTTAAT
AAGCTGTGCATAATGAAGAGGAATGTGGAATTGGAGCCTTTCCATCTGAAGCTATTCATA
ACAGGCACAAAGCTGAGTTAATTAGGAATATGCTGAGATGAAGGAAATGAGGAGAGCTGC
TCTTTTGGGGCTGTGCTTCTCTCCCCAACCCCTCAACCCCATTGCCATGCTGCAGATGG
GGTGGTGTCTAAACATCAGTGGCGAGTGCCTGCATTACTCTGCTCGTTGCCTTCCAGAGA
ACTCAGCTTCTCCAAATGCTGAGCTCTTTTCAGAATGGGACCTGCCACCAGTATTTGAAA
GATTTCTAGCCTAGCAGAACAGCAGCCACGTTATCAAAGTTTGGTTGGCCAAAGGAAGGT
ACTTGCTAATTAGTTTAGTAGGTTTTCAGTCCGCACAGACATACGGGATTGTTTTATTGT
ACATAGACATCTTCAGAAACAGTGTATGTATAGAAATGTAAGGTCAAAATTTGAACCTCA
GTGCTTTAAATCTGAATTTGTATTAACTGATATGAAATATTTAGACGGTTACTTTATTTT
ATATCTGTCTTCCATTATACTTAATTTGGCTCAAGAATAGTTAGGCAAAAAGTTGCCCAA
AGAGAAGGATCTCCTAGTAAATACAAAGAGAATGTAACATAGTTGCTACAAGTTGGAGCA
TGTTCAGGGATGTCTTTTTTTTTTTTTTTTTTGAGAGAGAGGTCTCTCTCTGTTGCCCA
GGCTGGAGTGCAGTGGTGTAATCATGGCTCACTGCAGCCTCAATCTCCCAGGCTTAAGCG
ATCCTCCCACCTCAGCCTCCCAAGTAGCTGGGACTATAGGCATGCGCCACCACACCTAGC
TAATTTTCGCATTTTTGTAGTGTCACAGTTTCGCCATGTTGCCCAGGCTAGTCTCGAAT
TCCTAGGCTCAAGCAGTGCTTCTGCCTCAGCCTCTCTGAGTAGTTAGGACTACAAATTTG
TGGCTCCATGCCCGGCTAATTTTTTTATCTTTATTTTGTAGAGACAAGGTCTCACTGTGT
TGCCCAGGCTAGTCTTGAACTCCTGGGCTCAAACAACCCTCCCACTTTGGGTTTCCAAAG
TGCTGGGATTACAAGTGTGAGCCACTGAGCCCAGTGACCTCTGGGTTTTAAAAATGTGTA
GGCTTCAATTATTTATTTTAAAAATGAAATCCTGCAATATATAGTTTTCTGCGTTGTGT
GGTTTGAATCAATCTGGGAACTGGCTTGCTGGCTGATTGTGGTAAAGTAAGAAGTACTTA
ATTTAGTAGAAAGTTTAAATGGCAGACATAACATTAAACCCAGCTGATTTATAAATGAAG
CAAAAGAACAAAACTCATTCAGGATAATTGGTTATTCTAAAATACAGTCATTTCTAAAAT
TATGAAGTGTTCAGGACCTTTGGGAGTGAAAGAATTTGCTAAAGAAGGATCAGTGAAAAA
AAGGAATGATGGGTGAAGAGCTGTGGAGAAGGAAGAGAAGAAACAGCACAAGGAAGGAAG
AATATAAAATCAGATGTGGGAATCCAGGGGAAAGTGCAAACGAAGCAAGATTGAGAAAAT
TCTCAAGTTTTTATAAACAGTTCTCACACTCTGCCAGTTCCTTGGAGGTAGACTTTTTTG

FIG. 10
*(continued)*

```
TTAACTTCCAACTACAGTAGTGAAAAAAAAAAAAAACCCTCAAATTTGCAAAAGCAGTC
TGTGGAATTTTCTTTACCCAGCTTTCCTGACTGTTAACTTTTTAGCACACTTAACTTTAT
CATTCGTTTATTCTCTCTGTTTAAAATTAAAAATGTAAATTTTAAAAAGTAAAATGTTTG
TTGGTTACAAACATTTATACCCCTTTGTCTCTAAATATCATTTCATTTTAAAAAATGAAT
AATCTAAGCCTACACATTCTAAATGTGTATATTTTCTAAAAATAAGGGCATTCTCTTAC
ATAACCAATGTCACAATTATTTGATACAGTGATCAAAATCAGGAAACTAACATTGATATA
ACACTATTATCTAACCTACAGACCATCTTCAAATTTTGTCCTGCTAGTATCTTTTATGGG
TCCAGGGTCACACAGTGCATTTGGCTATAATGTATCTTTTTCTCTTTTTTGAGACAGG
GTCTCACTTTGTTGCCCAGGTTGGAGTGCAGTGGTGCAATTATGGCTCACGGCAGCCTTG
ACCTCCTTGGGCTCAGGTGATCCTCCCACCTCAGCCTCTCGAGTAGCTGGAGACCACAGG
TGTGCACCACCATGCCTGGCTAAGTTTTGTATTTTTGTAGAGATGGAGCTTCGCCGTGT
TGCCCCGGCTGGCCTTGAACTCCTGGGCTCAAGTGACCTCCCGCCTTGGCCTCCCAAAG
TGCTGGGATTACAGGCGTGAGTCACCACACCTGGCCAGTTATTAGTATGTTAGTCTCTT
TAATCTGGAACAGTTTCTCAGTCATTCTTTATTTTTCATGACCTGGATGTTTTGAAGAG
TTTAGGCCAGCTATTTAGCAGAATGCCTTTCAGTTTGGATTTGTCCAGTGTTTTCTCTTG
ACTATATTCTAGTCATGCATTTTTGGCAGGACTGTCACAGAAATGTTGTTGTAGTCTTCT
TAGTACATCACATCAGGTACACACTGTTGATCTGATTCATTACTAGTGGTGTTAACTTTG
ATCACTTGAATAAGGTGGTGTCTGTCAAATTTGTCCACCGTAAAGTTACTTGAGCAAAAC
GTAGCTGGGACTACAGGCGTAGCAAAAAATGTAGCAAAAGTAGTATTTTTGCTACATTT
TTTTTTAGGAACAAAGTATTTTTCCCTTTTAAGTTAATCTCTTGTCCATAAAGTTATTA
TTTTTCCCTTTTAAGTTAATATCTTGTGGGTAGATACTGGAGACTGCGTAAATTACCTAT
TTCTCATAATACTTTTTTTTTTTTTGAGATGGAGTCTCGCACCGTCTCCCAGGCTGGAGT
GCAGTGGTGCAATCTCGGGTCACTGCAAGCTCCACCTCCCGGGTTGACGCCATTCTCCTG
CCTCAGCCTCCCAAGTAGTTGGGACTACAGGCGCCCGCCATCACACCTGGCTAATTTTTT
GTATTTTTAGTAGAGACGGGGTCTCACCGTGTTAGCCAGGATGGTCTTGATCTCCTGACC
TTGTGATCTGCCCGCCTTGGCCTCCCAAAGTGCTGGGATTACAGATGTGAGTCACTGCGC
CCGGCTCTCATAATACTTTTTGCCTACTAATTTTATATTCATTGATTAAATTCTTGCCTG
AAAAAATTATTACTGTGGTATTTGCCAAATGGCAATTTTCTGTTTCCATCATTGCCTTTC
CCCCGCTTTTAAAAGTATAAGTGACAAAGAAAAACTGTATATAAAGTGTACACCATGATA
TTTTGATATATGTATACTTTGTGAAATGATTATCAAAATTGAGTTAAATAATGCATCCAA
CATCTCAGTTACTTTTTTTTTTTTTGAGACAGAGTCTTGGTTTGTCACTAAGGCTGGAG
TGCAGTGCCACAATCTCGGCTCATTACAACCTCCACCTCCCAGGTTCAAGTGATTCTCCT
GCCTTGGCCTCCCCAGTAGCTGGGATTACAGGTGCCCACCATCACACCCGGCTAATTTTT
GTATTTTTAGTAGAGGTGGGGTTTCACTACGTTGGCCAGGCTGGTCTCGAACTCCTGACC
TCAAATGATCCTCCCGTCTCAGCTTTCCAAAGTGGTGGGATTACAGGCGTGAGCCACTGT
```

FIG. 10
(continued)

```
GCCCGGCCACTCTTAGTAAATTTTAAGTGTACATTTTTTTTTTTTTTTTTTGAGATGGA
GTCTCACTTTGTCACCCTGGCTGGAGTGCAGTGGCATGATCTTGCCACACTGGAACCTCT
GCCTCCTGGGTTCATTCAGGTGCTTCTCCCACCTCAGCCTCCCAAGTAGCTGAGACTACA
GGTACCCGCCACCATGCCTGGCTAATTATTGTATTTTTAGTAGAGATGGGGGTTCACCAT
GTTAGCCAGGCTGGCCTCAAACTCCTGACCTCAGGTGATCTACCCACCTCGGCCTCCCAA
AGTACTGAGATTACAGGCATGAGCCACCACACCCAGCCACATTACGTTAGTATTAACTAT
AATCACCATGCTGTACATTAGATCTCCAAAATGTATTCATCTTATGTAACTTCAAGTTTG
TACCCTTTGACCAAAGTCTCCTTGTTTCCCTACCCCCAACCCCTGGTAATCACTGCTTT
AATCTCAGTTTTTATGAGTTTGACTGGTTTAGATTCCACATACAAATGAGATCAGGCAGT
GATGGTTTATTTCACTTAGCATAATGTCATCCATGTTCTTGCAAATGACAGGATTTTCTT
CTTTTTAAAACTAATATCCATGCTGGACACGGTGGCTCATGCCTGTAATCCCAGCACTTT
GGAAGGCTGAGGAGGGTGGATCACTTGAGGTCAGGAGTTCGAGACCAGCCTGGCCAACAT
GGTGAAACCCCATCTCTACCAAAAATATAAAAAATTAGCTGGATGTGGTGGCGCACACCT
GTGATCCCAGCTACTTGGGACACTGAGGCAGGAGGATCGCTTGAACCCGGGAGGCGGAGG
TTGCAGTGAGCCAAGATGGTGCCACTGCACTTTAGCCTGGATGTTGATGTTGTTCCACTT
GTTTATTTTTATTTTGTTCCCTGTGCTTTTGGTATCAAATCCTAAAAACCATTGCCATGA
CCATTGTCATGTTACTTTCCCCATATGCTTTCTTCTAGAACTTTTAAGGTTCATCATTCC
CTTTTCTGTTTTAGTTGCAAGCCTACTATAAGGAAGGGCTTTTCTTTCTTCCTTATTTA
TTTATTCATGTCTATCAGAATGGGCACCTTACTACTATTTTGTTGTTATTGCTTGAATT
GACTTGAATTTGGCTAGTGGAAACCTTTCAGATCGGGTACTCTGTCCTTTTGATCTCTT
TCCATTTTCAAGCACTTCTTTAGACTTAAGATGGTCTAGGCTCATCTTCTCCTTTCCCAG
CCATTTTTCAAAGGAACCTGATTCCTTTTAGTGAAGAGCAGTATTTTGAAACCAAGATCT
GGGCACTGGGTCTACTTGTTTGTACTGGTACAGTGTTCTTTGAATTGCTAATTAGCTGAT
CAATTACTGCTCTATTTGAGTTCCCTCTTTCTAAAACCTCACATATGTGTACAGACGGTC
CCTGACTTATGATGGTTCGACTTATGATTTTTGATTTTATGATGGTTTGAGAGCAATACA
TCCATTCTGTTTTCACTTTTCATTCAACACTTTATTTTAAAATAGGGATTGTGAGATGA
TATTGCCCACGTGTAGGCTAATGTAAGTGTTCTGAGCACGTTTAAAGTAGGCTAGGCTAA
GCTGTGGTGTTTGGTAGGTTAGATATGTTAAATGCATTTTCGACTAGTGATATTTTCAAC
TTATGATGAGTTTATTGGGATGTATCCCATAAAGTCGAGGAGCATTATACATATCTCTG
TATAACAGAGTGAGTTCCTTATACCTTTCATCCACTTTCCCCTGAAGTTAACATTTTACC
TAACCATGATACATTTATCAAAACTAAAACATTAACATCAATACATTGCTATTAACTAAA
CTAGAGTTTAATTGGATTTTGCCAGTTTTCCAATGAATATCCTTTTTCTGTTCCTTGATC
CAATTCATGGTCACACACTGAGTTTGGTCACTTGTCACTGTAGTCTTCTCCAATCTGCGA
CAGCTTCTTAGGCTTTCCTTGTTTTTCATGTACTCTTGACGATTTTAAGAGTACTGGTC
AGATATCTTGTAGGATATCCCACAACTTGTGTTTAATCTTATGTTTTCTCATGATTAGAC
```

FIG. 10
(continued)

TTGAGTAATGGATTTTTGGGAAGAATACCACAGAGGTATATTGTTAAGTGTTCTCATCAC
TTGGAGGTAAATGTTATCAACATGGCCTGGTGATGTTAAACTTGTCAGTTTGTTTAGTTA
GTATCTGCCAGATTTTTCTCACTGCATAATTACAAATCCTCCTTAACTTATGATGGGGTT
ACAGCCTGATAAGCCCATCATAAATTGAAAATATCATAAGTCAAAAATGCATTTAATGCA
TCTAAACTACTAAACATCACAGCTTAGCCTAGCCTGCCTTGAACGTATTCAGGACACTTA
CATTAGCCTACAGTTGGGCAAAATCATCTCATGGGAAGCCTGTTTTATAATGTGTTGCAT
ATCTTATGTAATGTGTTGAGTACTGTACTCAGAATGAAAACAGAAGGGTTGTATTGCTT
TTGCACCATCATAAAATCAAAAAAACCATAAGGCAAACCATCATGAAGTTGGGGACTGCC
TGTACTTTTTTCCTCTTTCCCTGTTCAATTCCTTGAAGAAAGTCATTTAGTTCAGACCA
TACTCAAGAAAAGGGAAATAAAGCTCCATCTCTTGGAGCTTAATTGAAACTGGAATGACT
AGTTTCTATATACATTATTTAGAATCCTTTTGTAAGAAAGATTTGTTCCTTCTCTCCATT
TATTTATTCCATTATTTATATTGATAGAGACGCATGTACATTTATTTTATACTTTGGGTT
ATAATCTATTTTTCTTGCTCAAATTGTTACAGCTTTGGTCACTGGGAGGTTCTTCAGATT
GGCTCCTGTGTCATTTGACATGTCCCCACCCTCTCGTTTCTGAGTACTTCTCTACTTTGG
CATTACAAAAGATGTTCCAGGCTCCTCTTATATTTTCCCTGCCGGCAGCCCTAGAATCAT
CCATTTTCTATGGTGCCCTGGTTCCTTTTACTTTAGATGGGGGTTTAGAAACCAATCTG
GGTGTTGGGTGTGCTCATTGCTACTGGAATCACTGCTTCTAGGCCCTCTCAGCAGATAGA
GCTAGAAAACATATGGCTGTATATGAATCCATGGATTCATATATATCTATAATTGTTTTC
TGTATCTGGCCATCTATATATATATTAAGCTAAACATGAATTCATACTGATGTCTCAGAC
TCGAATCCATTGCCGCAGGGCTCATTCTTGCCTTCCTCTTGCTTATTTGTGACTTCTTTC
TCTAACAGGGAGAAACCCCAGTCTCATTATCACCAACCTATCTACTCATTTGTTCAACCC
TGGTATAGGTGTAAAGTAGTTTCAGAATTACTAACCTATACCCATGTGAGAATTGTATTT
GCACTTCTTGTTTGAAGGAAATACATACAACACAGGTAGCGTCTCTACACTTCAGTATAC
AGAGATCTGAACAGTGTTCTCTCTGAGTGAATCATATTGCAGGACAGAAATTACTTTTAA
AAATTCTGTAATGGGTCAGGCCTATAATCCTAGCACTTTGGGAGGCTGAGGTGGGCAGAT
CACCTGAGGTCAGGAGTTCGAGACCAGCCTGGCCAAAATGGTAAAACCCCATCTCTACAA
AAAATACAAAAATTAGCCAGGCGTAGTGGTGTGTGCCTGTAATCCCAGCTACTCAGGAGG
CTGAGGCACGAGAATCACTTGAACCTGGGAGGCAGAGCTTGCAGTGAGCTGAGATTGAGC
CACTGCACTCCAGTCTGGGCGACAGAGCGAGACTCTGTCTCAAAAAAAAAAAAAAAAAA
AATTCCATAATGATAGCAGAGCTGGAATAGAAATGGGATTGCACAGGCTGAATCTGAGTT
GTTGCAACAGTAAACGAGCAAGATTTAAACTGGCCTTGTGTAGCACTTGCTATTTGGCTC
CTCATATTTTATTAGACGCTTATTCTTTTTTGTTTGGTGTCATTCCTTTGAGAAATATTT
GAGTGCCTTTTCTGTTGCAGACATTGATTAGATGCTGAGGTTGTAACAATGAAGAAGATA
GCCATCGCTGTTGCCTCATGGAACTGAAGTTTTACTAGATGTAAAATTTGAGTTAACATG
AGGCCGTGCCCCTATGTGCCCTATTGTTTCTTCACACAGCTCCCTTCATCTCCTTGGTCC

FIG. 10
(continued)

```
AATGAAAAGGTTTTTTCATACTTGTTCATTCATTCCTGCATTAATTAAAGTAGGTTGTAC
TGTGCCAGGCACTGGGAATATTTAAGTAGTTGTGTTCCTGAATTGGAAATGAATCCAGCA
TGGTTGGAGTAGAAGGAGCTGGGGGGCAATGTGGAGTGTGATGGGGAGATTGGAAAAGTA
AGCTGAGACCAGATTTTTCAGTTTGGAGGGAGAGGTGGGCCTTGTAGGCCATATTACAGA
TTGTAGACTTTATTTGGAGGGACATGGAAGTCATTGAGGAGTCTGAAGCAGGGGAATGAC
ATAAAAGATCCTCATTTTAGGCCGGATGTGGTGGCTCACGCCTGTAATCCCAGCACTTT
GGGAGGTTGAAGTGGGTGGATTGCTTGAGGCCAAGAGTTTGAGACTAGCCTGGGCAACAT
GGTGAAACCCTGTCTCTATCAAAATACAAAATTAGCTGGGCATGGTGGCTCACACCTG
TAGTCCCAGCTACTTGGGAGGCTGAGGCATGAGAATCGCTTGAACCCGGGAGGCAGAGAT
TGCAGTGAGCCGAGATTGTGCCACTGCATTCCAGCCTGGGTGACAGAGTGAGACTTCGTG
TCAAAAAAAAACAAAAAACCCCTCATTTTGAAAGGGAACCCTGGCTTGAGGGTGAAGAA
TGGGTGGGCACTAGGCTAGAGCAGCTGCAGGGTCAGTGAGGAGCTGCCGCAGTGCTGCAC
GTGAGAACCCGTCATGGTTTGGTCAGGGTGGGCAGGACTGACAGTGAGCACAGAGCGAAG
TAAAACCAGCAAAATTTCATGATTGGATAGTGGAAGGAATCATGGTGTTTGTAGTCTTCA
AATGTGAACCCAGAGTGCACTGGACAAGTAGTCTAGGCTGCTCTGTAACCAAGGCAAGTG
TTTTCATTTTACCCTCTCTTCCTGCTCTTGGCCTTTGGATTTTTTGTAATTTAAGGTTTA
TGAATGTAATCAGTTACTTAACATGGAAGATACTTAATACCAGATGATTTTGGAGTCTT
GTGATCAATACCTTCTCTCAATCTTGGGTGTGTGTCAGTTGGCAAGGCCATAAAATTTGT
TATAAACATTGCAGAAGGCTTGGTTACTGTGCTGTGACGTTGAATTTGGGTGGAGATAGA
TCAATTTCAGTTGATTTTCTAGGCTTCAGAAACACATTACCCTCTACTCCACAAACACAA
ATCAAAACAAAACAATCCCTATTCCCTGAGCATTTCTCTTGATCTATAACACAGCCTGGG
CTGTCACAGTACTAAGACAAGCCCATCTGATTTGTGAGTCAGTTTTATTTCTTGGTCTTC
TACATAAGCTAAAAAGTTTCAACATTTTAATGCTTTTCCTTGGATTCCTTTGAGTCATTG
AAGTAATTCCTGTTTCATTTGTACTAATTATTCCACACTAGAAAATTCTGTTGTAATCAC
TTTATGTATTAATAGAAATACTGATTTTTATTTTCAAGGAAGTATTGAGTAGGGAGGGGG
AAATAGGGATTTGCTGTTCAATGGGTATAGAGTTTCAGTAATACAAGACAAAAAACTTCA
GAGATCTTCTATACAGCAGTGGGTATATAGTTAACAATACTGCACATCTAACAGTTTGTT
AAGAGGGTAGATCTCATGTCATGTGTTTTAAAAATTGCTTTTAAAAAAAGTATCGAGTA
AAAAAGCAGTTTTACTCCTCAGTTTCTATTTATATTTAAAATTTTTATTTAAAAGTGAG
TTGAGATTTTTAAACCTCAGGATAAGTTTTATTTTTTAAAAAATTTATTTTTTATTATTT
TTTGAGATGGAGTCTCACTCCATCTCAAGTCACCCAGGCTGGAGTGCAGTGGTGTCTTGG
CTCACTGCGACCTCTATCTCCCAGGTTCAAGTGTTTCTGCTGCTTCAGCCTCCTGAGTAG
CTGGGATTACAGGTCTGCACCACCACGCCTGGCTAATTTTTGTATTTTTAGTAGAGATGG
GGTGTCACCATGTTGGCCAGGTTTGTCTTGAACTCCTAACCTCAAGTGACCACCTGCCTT
GGCCTCTCAAAGTGCTGGGATTACAGGTATGAGCCACAGTGCCCGGCGGGATAAGTTTTA
```

FIG. 10
(continued)

AAATAATATTCTCTGCTGGCTGGGCATGGTGGCTCATGCCTGTAAACCCAGCACTTTGGG
AGGCTGAGGCAGGAGCATCACTCGAGGCCAAGAGTTTGAGACCAGTCTGGGCAACATAAT
GAGACCCCCTCTCTACAAAAAATAAAAAAATTTGGCTGAGTGTGGCATGTTCCTGTAGC
TATCGGGAGGCTGAGATGGGAGGATTGCTTGAGCCCAGGAGTTTGAGGCTGCAGTGAGCT
ATGATTGCACCACTGCGCTCTAGTCTGGGTGACAGTGTGAGACCCTGTCTCTTAAAAAAA
AAAAAAAAAAAGGCCAGGCACAGTGGCTCAGGCCTGTAACCCCAGCACTTTGGGAGGCCG
AGGCGGGTGGATCACTTGAGGCCAGGAATTTGAGACCAGGCTGGCCAACATGATGAAACC
CCGTCTCTACTAAAATACAAAAATAAGCTGGGTGTTGTGGTGCACACCTGTAATCCCAG
CTACTTGGGAGGCTGAGGGAGAGAATTGCTTGAACCTGGGAGGCAGAGGCTACAGTGAGC
CGAGATCACACCACTGCACTCCAGCCTGGGTGACAGAGCAAGACTCCATCTCAAAACAA
CAACAACAAAAAACCAAATGTTCTTGCCAATTCTTCCATTTAATATTTAATTTTGAATT
ATATTGTATCTTTCTAAGGATTGTTTCTTATATAAGCAAAGATTTTTCAGTGCTAAACAT
TTACGACTGCTATTCAGAAATGGTTATTTACAAGTCTTTTTGTTTAAGAAAATGGCTGT
TCAAAAATTAAAATAGTATATAAACCAAACAAAATATTTTTGCTTTGGATGTCTGTTTT
GCAGCTTCTTCCCTACACTATAAGTTCTTACTGACTGCTTTATCACTTAATAAATTGGTT
TGGCTACTTTAACAGAGGCAAATAGTATCAGGCAAAAAATTATTTTTTATTTTTATTTTT
TGAGACAGTCTCACTCCATCACCCAGGCTGCAGTGCAGTGGCCTGATCTTGGCTCACTGC
AACCTCCACCTCCCAGGTTCAAGCGATTCTCATGCCTCAGCCTCCTGAGTAGCTGGAATT
ATAGGCATGCACCACCACACTCAGCTAATTTTTGTATTTTTAGTAGAGACAGGGTTTTGC
CATGTTGACCAGGCTAGTCTTGAACTCCTGACCTCAAGTGATCCATCTGCTTTGGCCTCC
CAAAGTGCTGGGATAACAGGCATGAGCCACCATGCCCAGCCCTATTTTTTATTTTTTAGA
GATGGGTCTCGCTTTTTAGAGATGGGTCTTGTTGCCCAGGCCAGAGTGCAGTGGTGCGAT
CATAGCTTACTGCAGCCTTGAATTCCTGGGCTCAAGCAATTCTCCTGCCTCAGCCTCCCG
AGTAGCTGGGACTACAGGCCTGTGCCACCAGGCCTGGCTTGTACATTAGTATTTGATATG
GCTACCCTAAGGGCAATCCTATAGTGAAGTCAACATTAGATAATGATGCTCATCTGATGG
ATTAGATTTTCAGAGTTGGCTGTTTCCAGGTGCCTATAGGAGTAGAAAAGGGTGACAAAC
CTCCTAACTAGATGTCCTACCAAATATAGTTCACTCCACATCTGAGATGAGACTGCATGA
CTGCTGGTTTTCTTTGCCTTTTCCCCCCAGGGTATCATCAGAACCAAAAATAAAGTTTT
AAAGGTGGGTCAGGTGTGTTGGCTCATGCCTGTAATCCTAGCACTTTGGGAGGCTGAG
GCAGGTGGATCATCTGAGCTCAGGAGTTCAAGACCAGCCTGGCTAATAACATGGTTAAGC
CCCATCTCTACTAAAATACAAAAAGTTAGCTGGGCATGGTGGTGGGCACCTGTAATCCCA
GCTACTCAGGAGGCTGAGGCATGAAAATCGCTTGAACCCCAGAGGCGGGGGTTGCAGTGA
GCCGAGATCATGCCACTGCACACTAGCCTGAACAACAGAGCAAGGCTCTGTCTCCAAACA
AACAAAAATGGTGCCAGAGTCTTTTCCAGGGCTGAGGGGAGATACAATGAAGTGTGTTAT
TTTTTCTGATAAGAGTGCTACCATCTTTCATTCTTGTGTGCCATTTCTAGTTGGGGTGAA

FIG. 10
(continued)

TTTGTTTTCGGAGTTCCTTTCCCAGCTGTTTGCCTGAAAAACCATGAAATGTGTTCCACA
TGAACTATGAAATGATTAGATGCTAATGTGGCAAAGAAAGTGTGAATTCTCTTGTAGAAA
CAGGGACATTTGGTTCGGTACAGTAAGTTGTAATGCGTGACTCTGTGCTTTCAAATTCT
GTGGTTCAAAAGTACTTTTCACTCCTACTGTGTATTTACCTTGAGAAGGTGAATCCCCTA
ACAATTTGGTCAATGTATCAGTATTCTCAACCCGTCTATCAATTTTTTTTCTTTCTCCC
TCTTTTTCTTTTTTGGGCAAAATACCTTTTTGCTTTTTATCCCCTTAAAATAACCAT
TGTCCCTCACATGTGCACTCTTCCAAATTTCAGAAAGCAAGAGAAAUGCACGATTA
ACAAATATTAAGTATTCTTAGCGGACCAGACGAGTGGAGATAGAGCCCTCTCCGCCT
TGTACTCCAACTCCAGCCTGTGCAGAGTAAGTAGTGCTGAAGGAAATTCTTTTTACCTGG
TCATGGTGGTTTAAAAAGGTTTAAAAAACAAAAACAAAAACAAAACACAAGTTTGTAGCA
CATGCCTTTCACTGGTGCACGTTCCTGTTGCCCTACTGTTAGTGTATCTGTGACTGGTGA
TATCTATTGATTGTGTTAATGCTATCTCAACCACGTTTTAATTTTCCTAAGCTGGCCAGG
CACGGTGGCTAACGCCTGTAATCCCAGTGCTTTGGGAGGCCGAGGTTCATGGATTACTTT
GAAGTCAGGAGTTCGAGACCAGCCTGGCCAACATGGTGAAACCCTGTCTCTACTAAAAAT
ACAAAAATTAGCCGGGCATGGTGGCGCATGCCTGTAATCCCAGCTACTCAGGAGGCTGAG
GCAGGAGAATCGCTTGAACCCAGGAAACGGATGTTGCAGTGAGCCGAGATCATGCCACTG
CACTCCAGCCTGGGCGATAGAGTGAGCCTCTGTCTAAAAATAAAATAAAATAAAATAAAT
TCCTAAACTGAAGGCTGACTGCTATGCTAGCTAGGATTATATGGGATTTTAAGTATATCA
AGTGGTGGTTCTCCAAGAAGAATCTAATTTTTCTTTTGATGGGCTGGGGATTGTAACAAA
GGAAGGTCATATGTCTTAATGATGTGTTAAGGCTCTTTGCAAAATCAAAGTAAATAAATT
GACCACTAATGTGTCAGCCCAGCCATGTTCTGCTCATTTGCCACCAGTCAACAGAAATCT
ACTTTGGGTGTTTAAACCAGGAGTCAGCAAACTACAGCTCACAAGGCCAGATGTGGGCCA
TGGCCTGTTACTGTATGGCCTGTTAATGGTTTTAAAGGGTTGTAAAACAAAAGAACACAA
AACAAAGACCCAATAACAAAACAAAGCCCGAAGAATAATATGCGACAGAGACCATGTATG
GCATATAGAGCCTAAAATACTGACTCTCAAGCCCTTCCCAGAAATCCTTCCCGACTCCTT
GTTGAAAACACGGTAGGAAAGCATTTGTCAAATTGAGGATATGAATAGCAATTGTAAGTT
ATTATTTTCTATATATTCGAAAGTCACTTGCTAGTATAACATTTACCTTTTATTTTCC
CTAAGAATCTTCTCTCTGTTTGCTTTCGACATGGATTTTTAAACCCCTGCAGATTTTAAT
ATTCTATATAAATGTTTTAGGTGGCATATATGAGGTTTGTATTAACATTTGCTTTCTATT
TAACATTGAAATGAAATTATACAGCAGAGGTATTTTCTCGTCCAAGTTGCCACTTCTTTC
TATCTTTTTCTTTCTTTCCCAGTGGACTGCCTGGGAAATTGATATTTAAATTGCTC
TCTGCAATAATTTGCAATGGAACTGGAATGCCAGGGTTCTGAGTCCTTGCCAGACAGCTC
GTCCCTCCTGTTGGCATGACTGAGTCAGCTGTCATGATTCCCTCAGTACCAGTGGCATGC
CTGTGACAGACAGCCTGTCTGCCTTTCATTCCCGTCGTCTCCCTTGTAGGGTTCAGATCC
AGGATACACTGGTCCTGGAGCCCCTCTCAGCCTGGCACCCACAGCTGCTGGGTTCCTTAC

FIG. 10
(continued)

TCTCCTGGACTGCTCTGATGTCATCTCCCTGCTCAGCAGAAAGAAGTCTGGGATCTTGAT
GCTTTGGCCCTCTGTCCTAGGCCCTAAACCACCCATTGCCCTTCACATAACCTGAGCTGG
GGCTAAATAGATCTCTCATCACTGCCTGCCTGCTCCTGTATTTTCCCTTCTTGGAGCTTT
TGCCTGTTCAGATCCCTCTACTGGAAATTAATAGGATTTCATTCTATGTGTGCATTTCCA
ACCTTTCTTCACAGTGCGATCCAAATGCCTCATCCTACAGGCCTCCTTAAAACAACCTGC
TTTCTGCCAGACCCCAGGGAGCACCAGGACTTGAGGCTTTTATTGCACTTCTGTTGTTTT
TTTGAGATGGAGTCTCGCTCTGTCGCCCAGGCTGGAGTGCAGTGGCACGATCTCTGCTCA
CTGCAACCTCCATCTCCCGAGTTCAAGAGATTCTTCTGCCTCAGCCTCTCAAGCAGCTGG
GACTACAGGCATGTGCCATGACACCCGGATAATTTTTGTATTTTTAGTAGAGACGGGGTT
CACCATATTGGCCAGGCTGGTCTCAAACTCCTGACCTCGTGATCCACCCACCTGGGCCTC
CCAAAGTTCTGGGATTACAGGCGTGAGCCACCATGCCCAGCGTTATTTCACTTCTGCCTC
TGTAATTATATTGCTGTATGGCTATCTCTTCTCTCCCTGGGAATGTCAGGTCCTAGGCAC
AGGAACTGTGTCTGTACCATATCTGGTGCCCAAAGAATGTAGTATGTGTTTTATAGATAT
CATGTAAGCTTAAACAGCGTGGTCTACATTTTTGTAAATGTCTTTCTTTTCTTTTCTCT
CCAGAATAGGAAACATTGCAGATTCATGAAACTGCGCCTGATGCATCAGCAGA
AAATTTGAGTGAAAACCTCCAAACTTCAGCACAGAAATAGGTATTTAAATGCAA
GTGCTCTATTGGTTAATTGTTTATATAATTGGCAGTATTTTAAGCAGGCAAGCAATTTG
GGAATGTTTTAGCAAAGTGTACCATAATTGAGTTTTACAAACCAGGCTCCTTTTTCCTCT
CCCTGTACTTCTTTTTCCAAGATGGTTTTAGTTTAGAGTTCATTAAACATTAAAATCAAA
CACAGAATTAATTCTGCATGAGGCAAGGCTAGCACTTATTCCAGAGAAATGGCTGATACT
GGTGGTAGAGTGCAGGTATCACTGTTCCTGCAATTTTTATTAGAGTTGGTTAGCCCAGGC
TGTGCTGGGGATGATCTGTAGGGATCTGGGAAGCATCGGGACTCAGCACTGGGTGGTTG
GGAGTCAGGAAGCCTGAGTTCTCATTTCAGTCAGTCTCTGACCAACTGTGTGGCATGGGG
TGCTAGACCACTTGGCTGCCGACTGGGTCACCGACATCCCTTCCAGCTCTGCTGCTGGAA
ATTCATCTCTCCCATATGTTGCCTCCCCATCAATTACGTTTTTTAAGTGTGACCCAAGTA
TATGATGTATGTTTTCATGATAAATTAGAAACTTATCTGGGCATGGTGGCTCATACCTGT
AATCCCAGCACTTTGGGAGGCTGAGGTGGGCGGATCACCTGAGGTCAGGAGTTCGAGACC
AGCCTGACCAACTAAAATAGTAGAGACCAACCCGTCTCTACTAAAAATAGAAAATTAGCT
GAGCATGGTGGTGCATGCCTATAATCCCAGCTACTCAGGAGGCTGAGGCAGGAGAGGCAG
CGGTTGCAGTGTGCCAAGATCGCGCCATTGCACTCCACCTGGGCCACAAGAGTGAAACTC
CATCTCAAAAAAAAAAAAAAAAAAAAAAAACTCAGTGTCAGTATTTCATGTCGAAATTC
CACTTCAATGGGTAGTGTAGTTAAAAGCTCTAAGTCTACCTTAAAATCACCTAATGCTTT
GTTAAGCTTTTAGATATATGTTCCTTAAAAACTCTTAACTTATTTCTTCCCCAGAGTG
AGTTCAGCCTTCCTAAAAGATCAAGAAGAGCGAGTTATGAGAAG
AATTGCATTTGAAGCTTGCAATGTGCTTGACTACCTTGATAAGCAAATTTAAA

TGATGGCATTTGTCGTTTGCTTCATCAGAAATGTCCAGGAAAAAAATGGGATTATTGGTC
ACTCCACCTCTCACACTGGCAAAATACTGACATTTAGCAGCTCTTATCTAGAAGTGACTT
GGAACATAGAATAAAGGCATGAGTTCCTGAAGAATTCATTGAGTGTTTCCTGTAGAAATA
GCTTTAGGAGATAGGGAGTTCTATCTGGGAGAACATATGAGTAACTCAAGAGTAAAAAGT

ATAGTCTGTGTAAACTATAGAAGAAATGCTGGGCATGGTGGCGCGCCCCTGTAATCTCAG
CTACTTGGAGGCTGAGACGGGAGGATTCCTTGAACCCAGGAGCCCAGGAGTTTTAGACCA
GTCTGGGTAACATAGTGAGACCCTTTCTCACCTACTCTCACTGCATGCCCCCCAAAAATA
TATATGTGCGCGCACGCGCGCGCACACACACATACACACACACACACACACACACACACA
CAGAGGAAATTGTTAGAAAACACACAGAACTGAATGTAAATAGTATTAGGTGGGAATAAG
AAGTAAAGGGATGGTAAGGAGGCTTGGAGGAGGAGTAAATTATCTGCTATGGGACATCAG
CTC

FIG. 10
(continued)

MTSRRRWFHPNITGVEAENLLLTRGVDGSFLARPSKSNPGDFTLSVRRNGAVTHIKIQNTG
DYYDLYGGEKFATLAELVQYYMEHHGQLKEKNGDVIELKYPLNCADPTSERWFHGHLSGK
EAEKLLTEKGKHGSFLVRESQSHPGDFVLSVRTGDDKGESNDGKSKVTHVMIRCQELKYD
VGGGERFDSLTDLVEHYKKNPMVETLGTVLQLKQPLNTTRINAAEIESRVRELSKLAETT
DKVKQGFWEEFETLQQQECKLLYSRKEGQRQENKNKNRYKNILPFDHTRVVLHDGDPNEP
VSDYINANIIMPEFETKCNNSKPKKSYIATQGCLQNTVNDFWRMVFQENSRVIVMTTKEV
ERGKSKCVKYWPDEYALKEYGVMRVRNVKESAAHDYTLRELKLSKVGQGNTERTVWQYHF
RTWPDHGVPSDPGGVLDFLEEVHHKQESIMDAGPVVHCSAGIGRTGTFIVIDILIDIIR
EKGVDCDIDVPKTIQMVRSQRSGMVQTEAQYRFIYMAVQHYIETLQRRIEEEQKSRKGH
EYTNIKYSLADQTSGDQSPLPPCTPTPPCAEMREDSARVYENVGLMQQQKSFR

SEQ ID NO: 61

FIG. 11

GENE EDITING THROUGH MICROFLUIDIC DELIVERY

RELATED APPLICATIONS

This application is a divisional of U.S. patent application Ser. No. 15/542,892, filed Nov. 27, 2017, which claims the benefit of priority under 35 U.S.C. § 371 to PCT Application No. PCT/US2016/013113, filed Jan. 12, 2016, which claims the benefit of priority under 35 U.S.C. § 119(e) to U.S. Provisional Application No. 62/102,347, filed Jan. 12, 2015, each of which is incorporated herein by reference in their entireties.

STATEMENT AS TO FEDERALLY-SPONSORED RESEARCH

This invention was made with Government support under Grant No. R01 GM101420 awarded by the National Institutes of Health (NIH), and Grant No. DE-FG02-02ER63445 awarded by the Department of Energy (DOE). The Government has certain rights in the invention.

TECHNICAL FIELD

The subject matter described herein relates to gene editing by introducing gene-editing components into a cell by mechanical cell disruption.

REFERENCE TO THE SEQUENCE LISTING

The contents of the text file submitted electronically herewith are incorporated herein by reference in their entirety and comprise a computer readable format copy of the Sequence Listing (filename: M092570678US02-SEQ-JNL, date recorded Aug. 5, 2021, file size: 531,072 bytes).

BACKGROUND

Genome editing technologies, such as clustered regularly interspaced short palindromic repeats (CRISPR)-CRISPR associated protein 9 (Cas9) and transcription activator-like effector nucleases (TALENs), have shown much potential in their ability to change the genetic code of cells. These technologies could thus enable novel insights in drug discovery and lead to the development of next generation gene therapies. Gene editing complexes, which include a protein component and a nucleic acid component, e.g., deoxyribonucleic acid (DNA) and/or ribonucleic acid (RNA) cannot readily cross the cellular membrane. Thus, delivery of such complexes has been a challenge.

SUMMARY

The methods and systems of the invention solve the problem of intracellular delivery of gene editing components and gene editing complexes to target cells. The results described herein indicate that delivery of gene editing components, e.g., protein, ribonucleic acid (RNA), and deoxyribonucleic acid (DNA), by mechanical disruption of cell membranes leads to successful gene editing. Because intracellular delivery of gene editing materials is a current challenge, the methods provide a robust mechanism to engineer target cells without the use of potentially harmful viral vectors or electric fields. Moreover, the scalability and relative simplicity of the process make it suitable for broad adoption. The strategy and methods are suitable for genome engineering applications in research and therapeutics.

Accordingly, a method for delivering a protein-nucleic acid complex into a cell is carried out by providing a cell in a suspension solution; passing the solution through a microfluidic channel that includes a cell-deforming constriction; passing the cell through the constriction such that a pressure is applied to the cell causing perturbations of the cell large enough for said protein-nucleic acid complex to pass through; and incubating the cell in a complex-containing solution for a predetermined time before or after the cell passes through the constriction. An exemplary protein-nucleic acid complex comprises gene editing components. For example, the protein-nucleic acid complex comprises a Cas protein (such as a Cas9 protein) and a guide RNA (gRNA) or donor DNA. In other examples, the protein-nucleic acid complex comprises a TALEN protein, Zinc-finger nuclease (ZFN), mega nuclease, or Cre recombinase.

The methods and system is generally applicable to cytosolic delivery of complexes, e.g., a protein-protein complex, small molecule+RNA complex, etc.

A variety of target cells types are processed in this manner. For example, the cell comprises a mammalian cell such as an immune cell (e.g., T cell) or a stem cell such as a hematopoetic stem cell.

The microfluidic system may include a plurality of microfluidic channels. Each of the microfluidic channels of the plurality defines a lumen and is configured such that a cell suspended in a buffer can pass through the lumen. In some embodiments, microfluidic channels include one or more cell-deforming constrictions. In some embodiments, the diameter of the constriction is a function of the diameter of the cell. Thus, there may be many microfluidic channels within a microfluidic system of the invention. For example, the microfluidic system may include a plurality of the microfluidic channels arranged in parallel, e.g., 2, 5, 10, 20, 40, 45, 50, 75, 100, 500, 1,000 or more.

Microfluidic systems having a plurality of parallel microfluidic channels allow for the high-throughput delivery of payloads to cells. Many cells can be passed through each parallel channel one after the other. It will be understood that, depending on context, a reference to a "cell" herein may refer to more than one cell.

The diameter of the constriction is chosen depending on the dimensions of the cell type to be treated. In some embodiments, the cell may be primarily compressed by the fluid flow. In some embodiments, the diameter is less than the diameter of the cell. For example, the diameter of the constriction may be substantially or about 20, 25, 30, 35, 40, 45, 50, 55, 60, 65, 70, 75, 80, 85, 90, 95, or 20-99% of the diameter of the cell. For example, the constriction is substantially 20-99% of the diameter of the cell, e.g., a diameter of the constriction is substantially 60% of the diameter of the cell. Non-limiting examples of the diameter of the constriction include substantially or about 2, 3, 4, 5, 6, 7, 8, 9, 10, 15, 20, 2-10 µm, or 10-20 m. Different lengths of the constriction are also possible. Non-limiting examples of constriction lengths include substantially or about 10, 15, 20, 24, 30, 40, 50, 60, 70, 80, 90, 100, 10-40, 10-50, 10-60, or 10-100 m.

The subject matter described herein provides many technical advantages over methods that deliver components (or nucleic acids encoding the components) of the complex piecemeal. Most gene editing systems require complex formation to occur inside the cell, which may be an inefficient process. Advantages of delivering the RNA and Cas (such as Cas9) in complex form (or other protein/nucleic acid gene editing composite assemblies) include better efficiency and specificity compared to other methods. By obviating the need for mRNA or DNA manipulation to express the Cas protein (such as a Cas9 protein), one can reduce how much time the cell spends exposed to the protein thus reducing the chance of off-target effects. Having the editing components delivered to the cell in complexed form also eliminates/minimizes the risk of the Cas (such as Cas9) complexing with other RNA strands in the cell and cleaving the wrong sites. For example, the RNA alone may be detected by intracellular and extracellular Toll-like receptor (TLR) and pattern recognition receptors, prompting an interferon response or other antiviral pathways. The complexed form does not interact with these pathways and can thus avoid undesirable side effects.

By complexing in vitro prior to delivery into a cell, one can precisely control the Cas (such as Cas9) and gRNA complexing reaction thus ensuring optimal functionality, while complexes forming in the cytosol may not be as efficient. For example, delivering the complex cytosolically ensures simultaneous interaction of Cas (such as Cas9) and gRNA with the target DNA. The complexes formed in vitro and delivered to the cell as described herein are fully functional and ready-to-go upon gaining access to the cytoplasm of the target cell.

The approach described here is relevant to any protein+ RNA/DNA based system to guide the nuclease as the delivery process is independent of the exact size and composition of the complex and because complex formation of the editing materials occurs and is controlled in vitro under their optimal conditions.

Implementations of the invention may also provide one or more of the following features. Deforming the cell includes deforming the cell for substantially or about 1 μs to 10 ms, e.g., 10 μs, 50 μs, 100 μs, 500 μs, and 750 μs. Incubating occurs for 0.0001 seconds to 20 minutes or more, e.g., substantially or about 1 second, 30 seconds, 90 seconds, 270 seconds, and 900 seconds.

The pressure and speeds at which a cell is passed through a microfluidic channel may also vary. In some embodiments, a pressure of substantially or about 10-35 psi is used to pass the solution containing a cell through a microfluidic channel. The speed may be adjusted for a variety of reasons, including to improve viability of the treated cells while maintaining high payload delivery. In some embodiments, the cell passes through the microfluidic channel at a speed of substantially or about 300 mm/s, 400 mm/s, 500 mm/s, 600 mm/s, 700 mm/s, 800 mm/s, 900 mm/s, 100-300 mm/s, 200-700 mm/s, 250-400 mm/s, 1-1000 mm/s, 1 m/s, 2 m/s, 3 m/s, 4 m/s, 5 m/s, 6 m/s, 7 m/s, 8 m/s, 9 m/s, 10 m/s, 0.01-5 m/s, 5-10 m/s, or 0.01-10 m/s. Where the cell is a plurality of cells, substantially or about 5, 10, 20, 30, 40, 50, 60, 70, 75, 80, 85, 90, 91, 92, 93, 94, 95, 96, 97, 98, 99, 90-95, or 80-99% or more of the cells may be viable after passing through the constriction. In some embodiments, the cells are viable for at least about any of one hour, two hours, three hours, four hours, five hours, six hours, seven hours, eight hours, nine hours, ten hours, twelve hours, eighteen hours, twenty four hours, or forty eight hours after passing through the constriction.

In some examples, a device of the invention includes 2, 10, 20, 25, 45, 50, 75, 100 or more channels. In some embodiments, cells are moved, e.g., pushed, through the channels or conduits by application of pressure. In some embodiments, a cell driver can apply the pressure. A cell driver can include, for example, a pressure pump, a gas cylinder, a compressor, a vacuum pump, a syringe, a syringe pump, a peristaltic pump, a manual syringe, a pipette, a piston, a capillary actor, and gravity. As an alternative to channels, the cells may be passed through a constriction in the form of a net. In either case, the width of the constriction through which the cells traverse is 20-99% of the width or diameter of the cell to be treated in its unconstricted, i.e., suspended, state. Temperature can affect the uptake of compositions and affect viability.

In certain embodiments, a temperature of 0 to 45° C. is used during cell treatment, e.g., 0-25° C. In various embodiments, the methods are carried out at room temperature (e.g., 20° C.), physiological temperature (e.g., 39° C.), higher than physiological temperature, or reduced temperature (e.g., 0.1° C.), or temperatures between these exemplary temperatures (e.g., 0.1 to 40° C.).

In some embodiments relating to immune cells, treatment of unstimulated T cells, B cells and/or monocytes is carried out at temperature of 4-8° C., e.g., on ice. In another example, dendritic cells, activated T cells, and/or activated B cells are treated using the device at temperatures of 20-25° C., e.g., at typical ambient room temperature.

In some embodiments, following controlled injury (e.g., perturbations) to the cell by constriction, stretching, and/or a pulse of high shear rate, the cells are incubated in a delivery solution that contains the complex that one wishes to introduce into the cell. Controlled injury may be characterized as small, e.g., 200 nm in diameter, perturbation in the cell membrane. The recovery period for the cells is on the order of a few minutes to close the injury caused by passing through the constriction. The delivery period comprises 1-10 minutes or longer, e.g., 15, 20, 30, 60 minutes or more, with 2-5 minutes being optimal when operated at room temperature.

In some embodiments of the device and methods described herein, passage of stem cells or progenitor cells such as induced pluripotent stem cells (iPSCs) through a constriction channel does not induce differentiation, but does reliably induce uptake of compositions into the cell. For example, gene editing compounds are introduced into such cells without complications associated with the method by which the factor(s) was introduced into the cell.

The size and duration of temporary perturbations in cell membranes can be modified by adjusting various factors, such as the diameter of cell-deforming constrictions and the speed at which cells pass through the constrictions. Disclosures regarding the size and duration of perturbations provided herein should not be interpreted as limiting. Non-limiting descriptions of perturbations and recovery are provided in Sharei et al., (2014) Integr. Biol., 6, 470-475, the entire content of which is incorporated herein by reference. In some embodiments, the perturbations of the cell membrane may be characterized by a maximum diameter of substantially or about 1-20, 1-600, 4, 5, 6, 7, 8, 9, 10, 12, 14, 16, 18, 20, 25, 50, 75, 100, 150, 200, 250, 300, 350, 400, 450, 500, or 600 nm. In various embodiments, perturbations of the cell membrane having a maximum diameter of substantially or about 1-20, 1-600, 4, 5, 6, 7, 8, 9, 10, 12, 14, 16, 18, 20, 25, 50, 75, 100, 150, 200, 250, 300, 350, 400, 450, 500, or 600 nm persist on the cell membrane for at least substantially or about 1, 2, 3, 4, 5, 6, 7, 8, 9, 10, or 1-10 minutes or more (11, 13, 15, 18, 20 minutes or more).

In various embodiments, the diameter is less than the diameter of the cell. For example, the diameter of the constriction may be substantially or about 20, 25, 30, 35, 40, 45, 50, 55, 60, 65, 70, 75, 80, 85, 90, 95, or 20-99% of the diameter of the cell. Non-limiting examples of the diameter of the constriction include substantially or about 4, 5, 6, 7, 8, 9, 10, 15, 20 4-10 µm, or 10-20 m. Different lengths of the constriction are also possible. Non-limiting examples of constriction lengths include substantially or about 10, 15, 20, 24, 30, 40, 50, 60, 70, 80, 90, 100 10-40, 10-50, 10-60, or 10-100 m.

Many cells are between 5-20 µm in diameter, e.g. unstimulated T cells are 7-8 µm in diameter. For example, the diameter of the constriction portion is 4.5, 5, 5.5, 6, or 6.5 µm for processing of single cells. In another example, the size/diameter of the constricted portion for processing of a human egg is between 60 µm and 80 µm, although larger and smaller constrictions are possible (diameter of a human ovum is approximately 100 µm). In yet another example, embryos (e.g., clusters of 2-3 cells) are processed using a constriction diameter of between 12 µm and 17 µm. In a non-limiting example relating to unstimulated T and B cells, the device comprises a constriction having a length of about 10, 15, 20, 25, 30, or 10-30 µm, a width of about 3, 3.5, 4, or 3-4 µm, a depth of about 15, 20, 25, or 15-25 µm, and/or an about 5, 6, 7, 8, 9, 10, 11, 12, 13, 14, 15, or 5-15 degree angle. Examples of microfluidic devices useful for delivering payloads into immune cells are described in PCT International Patent Application No. PCT/US2015/058489, Delivery of Biomolecules to Immune Cells, filed Oct. 30, 2015, the entire contents of which are incorporated herein by reference.

In addition to single cells, even very large cells, e.g., eggs (approximately 200 µm in diameter), clusters of cells, e.g., 2-5 cell clusters such as an embryo comprising 2-3 cells, are treated to take up target compositions. The size of the aperture is adjusted accordingly, i.e., such that the width of the constriction is just below the size of the cluster. For example, the width of the channel is 20-99% of the width of the cell cluster.

Cells or cell clusters are purified/isolated or enriched for the desired cell type. Dendritic cells or other cells, e.g., immune cells such as macrophages, B cells, T cells, or stem cells such as embryonic stem cells or iPS, used in the methods are purified or enriched. For example, cells are isolated or enriched by virtue of their expression of cell surface markers or other identifying characteristics. Dendritic cells are identified and isolated by virtue of their expression of the β-intergrin, CD11c or other identifying cell surface markers. With regard to cells, the term "isolated" means that the cell is substantially free of other cell types or cellular material with which it naturally occurs. For example, a sample of cells of a particular tissue type or phenotype is "substantially pure" when it is at least 60% of the cell population. Preferably, the preparation is at least 75%, more preferably at least 90%, and most preferably at least 99% or 100%, of the cell population. Purity is measured by any appropriate standard method, for example, by fluorescence-activated cell sorting (FACS).

Payload compositions such as polynucleotides, polypeptides, or other agents (e.g., Cas9 and gRNA) are purified and/or isolated. Specifically, as used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) is free of the genes or sequences that flank it in its naturally-occurring state. Examples of a an isolated or purified nucleic acid molecule include: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones.

Complexes are prepared from purified modules or components, e.g., purified protein(s) and purified nucleic acids (RNA and/or DNA). Thus, the ratios of the components are controlled and tailored as desired to achieve a desired gene editing result. The present method is particularly suitable for delivery of sensitive payloads, e.g., protein-RNA/DNA complexes, e.g., complexes that are 40 kDa, 50 kDa, 75 kDa, 100 kDa, and up to 120, 130, 150, 200, 250, 300 kDa or more.

Surfactants (e.g., 0.1-10% w/w) are optionally used (e.g., poloxamer, animal derived serum, albumin protein) in the flow buffer. Delivery of molecules into cells is not affected by the presence of surfactants; however, surfactants are optionally used to reduce clogging of the device during operation.

In some aspects, the device is made from silicon, metal (e.g., stainless steel), plastic (e.g., polystyrene), ceramics, or any other material suitable for forming one or more appropriately sized channels or conduits. In some aspects, the device is formed of materials suitable for etching micron scaled features and includes one or more channels or conduits through which cells pass. Silicon is particularly well suited, because micro patterning methods are well established with this material, thus it is easier to fabricate new devices, change designs, etc. Additionally, the stiffness of silicon can provide advantages over more flexible substrates like Polydimethylsiloxane (PDMS), e.g., higher delivery rates. For example, the device includes 2, 10, 20, 25, 45, 50 75, 100 or more channels. The device is microfabricated by etching the silicon. Cells are moved, e.g., pushed, through the channels or conduits by application of pressure. A cell driver can apply the pressure. A cell driver can include, for example, a pressure pump, a gas cylinder, a compressor, a vacuum pump, a syringe, a syringe pump, a peristaltic pump, a manual syringe, a pipette, a piston, a capillary actor, and gravity. As an alternative to channels, the cells may be passed through a constriction in the form of a net. In either case, the width of the constriction through which the cells traverse is 20-99% of the width or diameter of the cell to be treated in its unconstricted, i.e., suspended state.

Various implementations of the invention may also provide one or more of the following clinical and research capabilities. Quantitative delivery of gene-editing complexes or components thereof to cell models for improved screening and dosage studies can be achieved. The method could be deployed as a high throughput method of screening protein activity in the cytosol to help identify protein therapeutics or understand disease mechanisms. The devices and techniques are useful for intracellular delivery of gene-editing complexes to a specific subset of circulating blood cells (e.g. lymphocytes) or even whole blood; high throughput delivery of complexes or components thereof into cells, especially oocytes and zygotes; targeted cell differentiation by introducing gene-editing (optionally together with genetic material such as donor DNA) to induce cell reprogramming to produce iPS cells; delivery of DNA and/or recombination enzymes into embryonic stem cells for the development of transgenic or mutant stem cell lines; delivery of DNA and/or recombination enzymes into zygotes for the development of transgenic or mutant organisms; dendritic cell (DC) cell activation; iPS cell generation; creating mutations in normal or diseased cells (such as cancer cells) to study the contribution of one or more genes to cellular function and/or disease; and stem cell differentiation. Skin cells used in connection with plastic surgery are also modified using the devices and method described herein. Methods of delivering gene-editing proteins disclosed herein may also be used to generate CAR-T cells or to genetically modify hematopoietic stem cells (HSCs) for treating genetic and other diseases. In embodiments relating to HSCs, a subject may receive an autologous, syngeneic, or an allogeneic edited HSC. In various embodiments, cells of a subject may be ablated before the subject receives a gene-edited cell. For example, bone marrow cells of a subject may be ablated with radiation or chemically before the subject receives a gene-edited HSC. In some embodiments, a gene associated with beta thalassemia or sickle cell anemia is edited using a method or composition disclosed herein. Cells processed ex vivo or in vitro, i.e., outside of the body of a subject, in accordance with the invention are useful for subsequent administration to a subject in need of treatment or diagnosis of a pathology. In alternative embodiments, in vivo cell processing is carried out.

In various embodiments, the SHP2 gene is edited/mutated to reduce the activity thereof or knock out or reduce SHP2 expression. In such embodiments relating to gene editing in T cells, the T cells become less responsive to immunosuppressive signals and have increased activity toward tumors. In such embodiments, the T cells may be more responsive to tumor antigens and more effective at treating cancer.

Aspects of the present subject matter relate to the rapid and transient delivery of protein-protein as well as protein-nucleic acid complexes, e.g., gene-editing complexes to cells. A nucleic acid component of the complex comprises a deoxynucleic acid (DNA), ribonucleic acid (RNA, e.g., mRNA, gRNA) or other double-stranded or single stranded nucleic acid compounds, respectively. For example, the delivery of a gene-editing complex (e.g., a ribonucleoprotein (RNP)) may achieve gene editing faster than if an expression vector encoding components of the gene editing complex (e.g. a Cas protein and a gRNA) was delivered to the cell. For example, the gene may be edited (e.g., mutated or replaced) in the cell 0.1, 0.5, 1, 1.5, 2, 2.5, 3, 3.5, 4, or 0.1-4 hours sooner than in a corresponding cell that has received microfluidic or electroporation-mediated delivery of an expression vector that encodes gene editing complex components.

Each embodiment disclosed herein is contemplated as being applicable to each of the other disclosed embodiments. Thus, all combinations of the various elements described herein are within the scope of the invention.

Related apparatus, systems, techniques, and articles are also described.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

FIGS. 3A and 3B are a series of flow cytometry plots (FIG. 3A) and a bar graph (FIG. 3B) of the recombination efficiency for K562 reporter cells that had genetic editing material delivered to cell cytoplasm using the microfluidic device illustrated in FIGS. 1-2. For the reporter used, there is a frame-shifted GFP gene in the cell line. To perform the editing the Cas9 gRNA complex and a donor oligonucleotide would be delivered. The complex would cut near the GFP site and the oligonucleotide would insert itself into the cut site. Successful insertion of the oligo would correct the gene and result in GFP expression which is what is seen in this figure. Thus, in this assay something turned on upon gene editing as opposed to turned off. A gene would be expected to be turned off in instances where a gene (or depending on the context, a nucleotide or portion thereof) was being deleted in the absence of a donor oligonucleotide.

Figure 6:
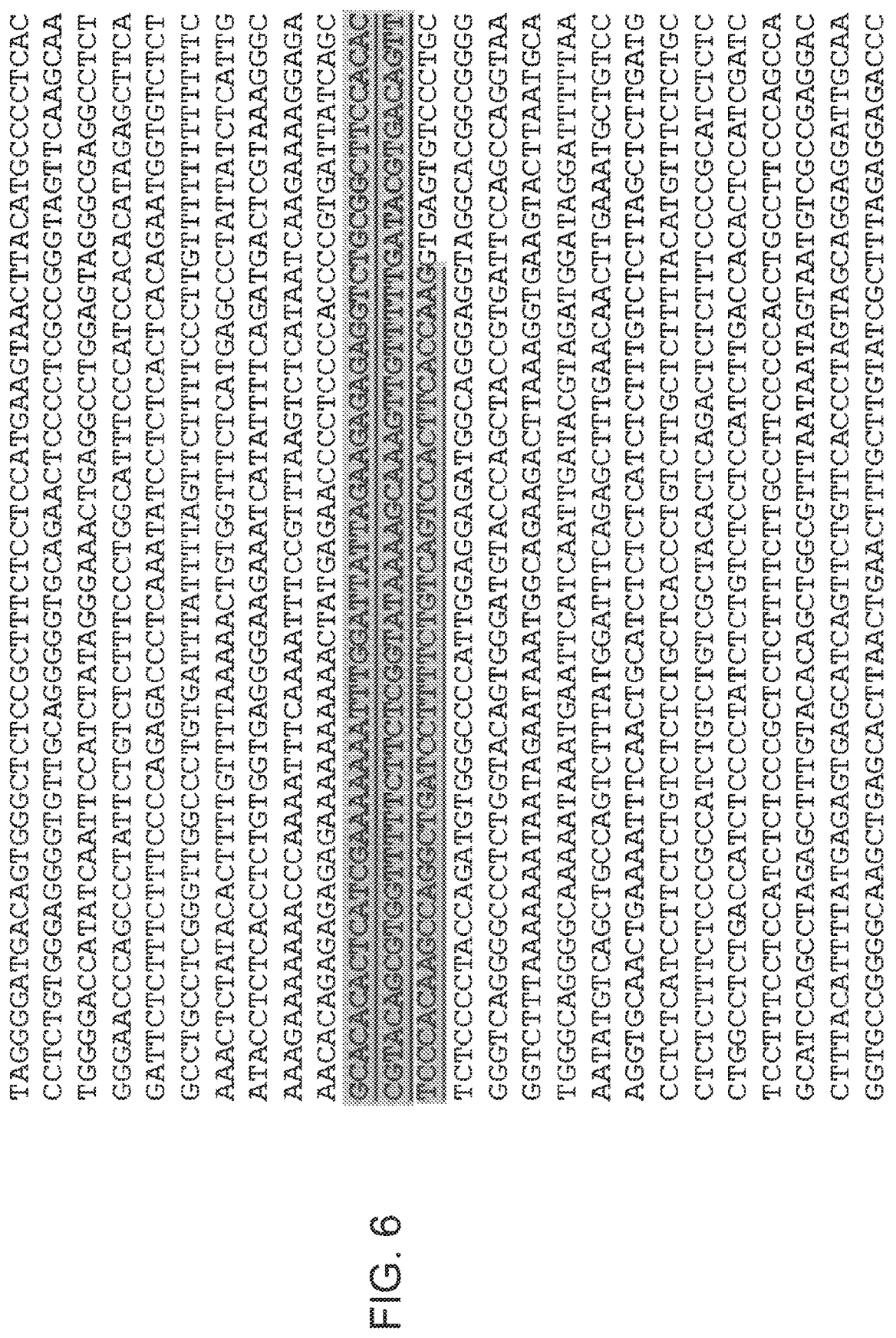
Figure 6:
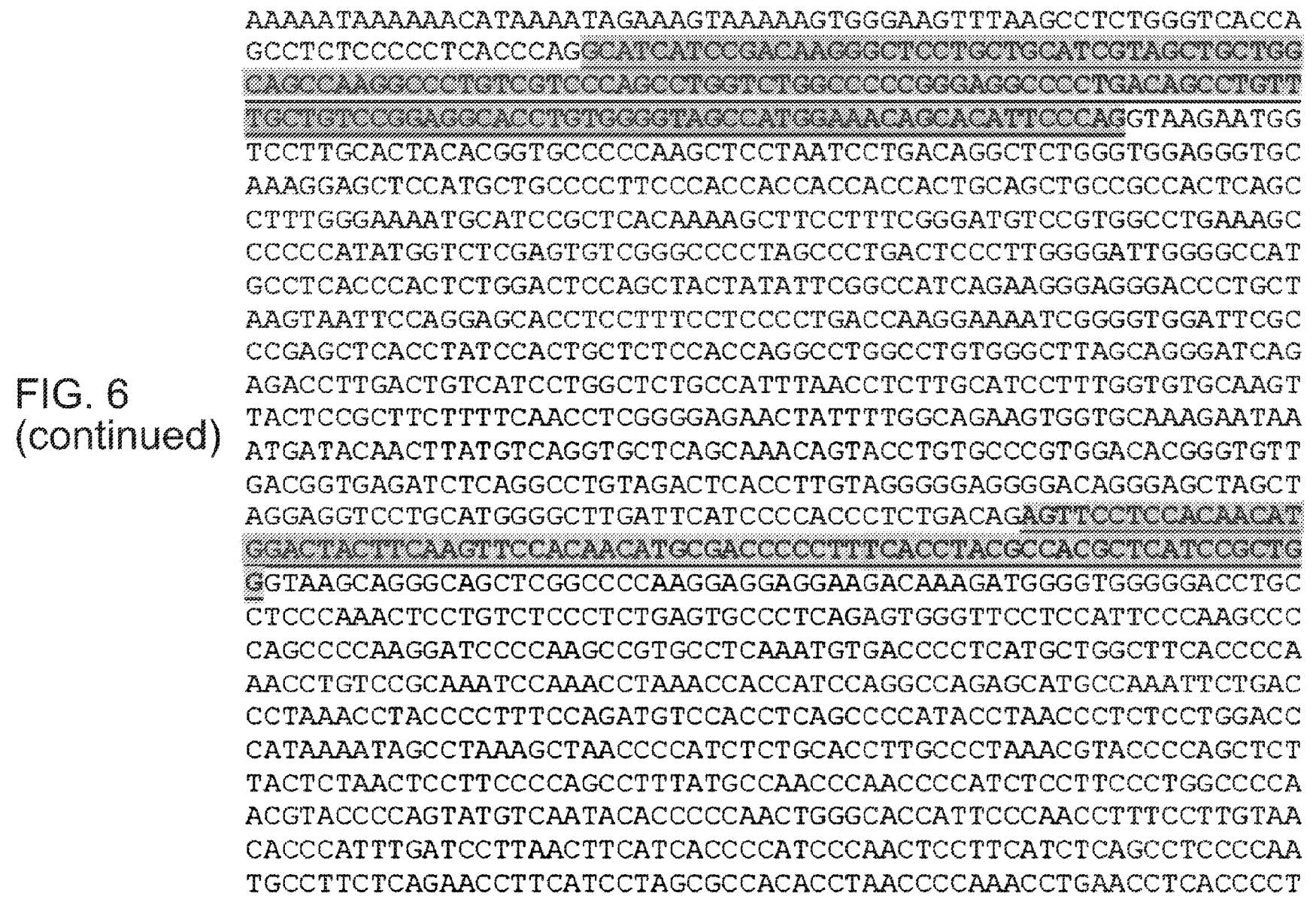
Figure 6:
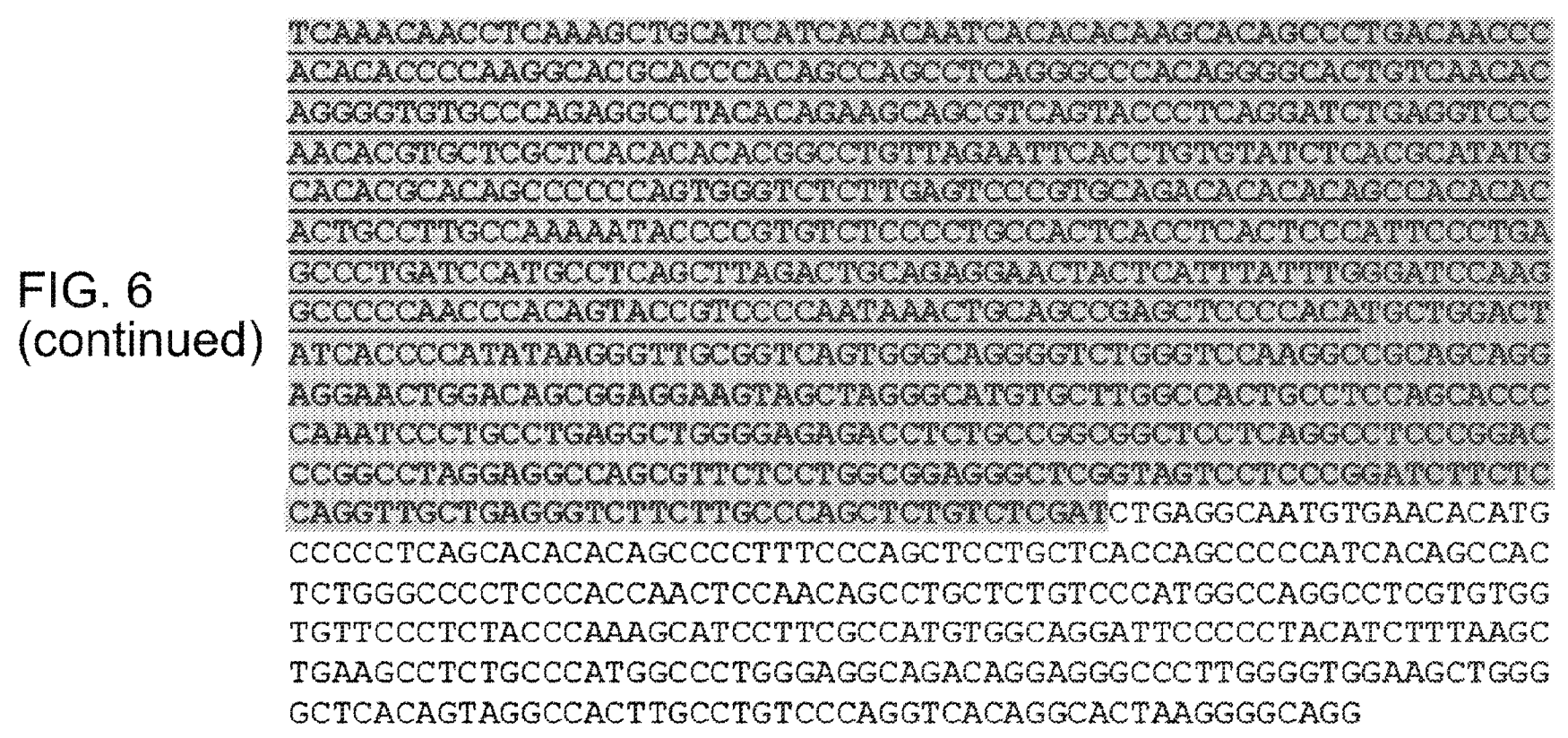

FIG. 6 shows a FoxP3 genomic sequence running from the first sheet of FIG. 6 to the last sheet of FIG. 6 (SEQ ID NO: 56). Exons belonging to FoxP3 are shown in underlined and highlighted letters. Other exons within this region that do not belong to FoxP3 are shown in non-underlined highlighted letters.

FIG. 7 shows a FoxP3 translated amino acid sequence (SEQ ID NO: 57). Alternating exons are underlined and non-underlined. Bold with italics indicate a residue overlap splice site.

Figure 8:
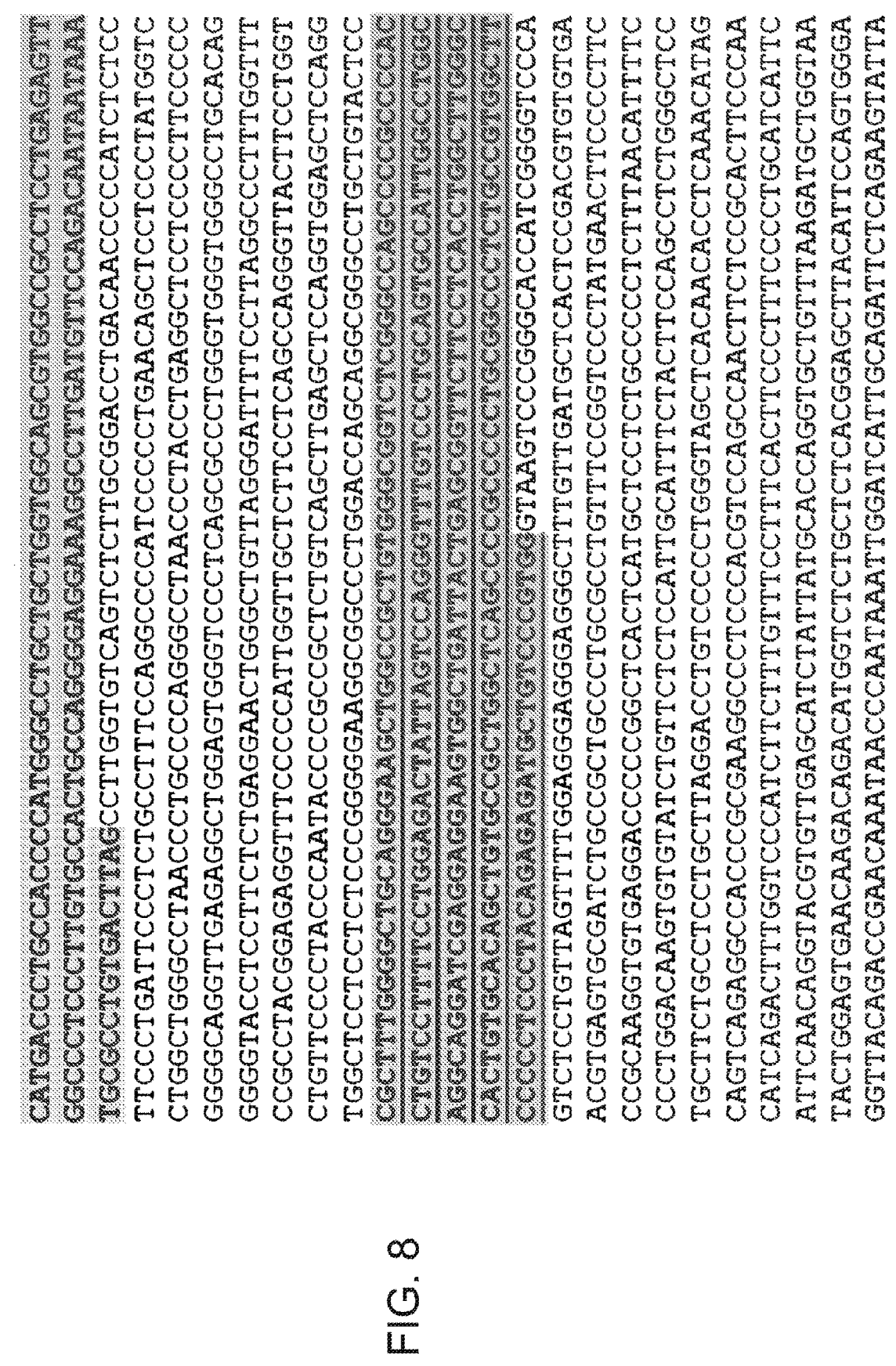
Figure 8:
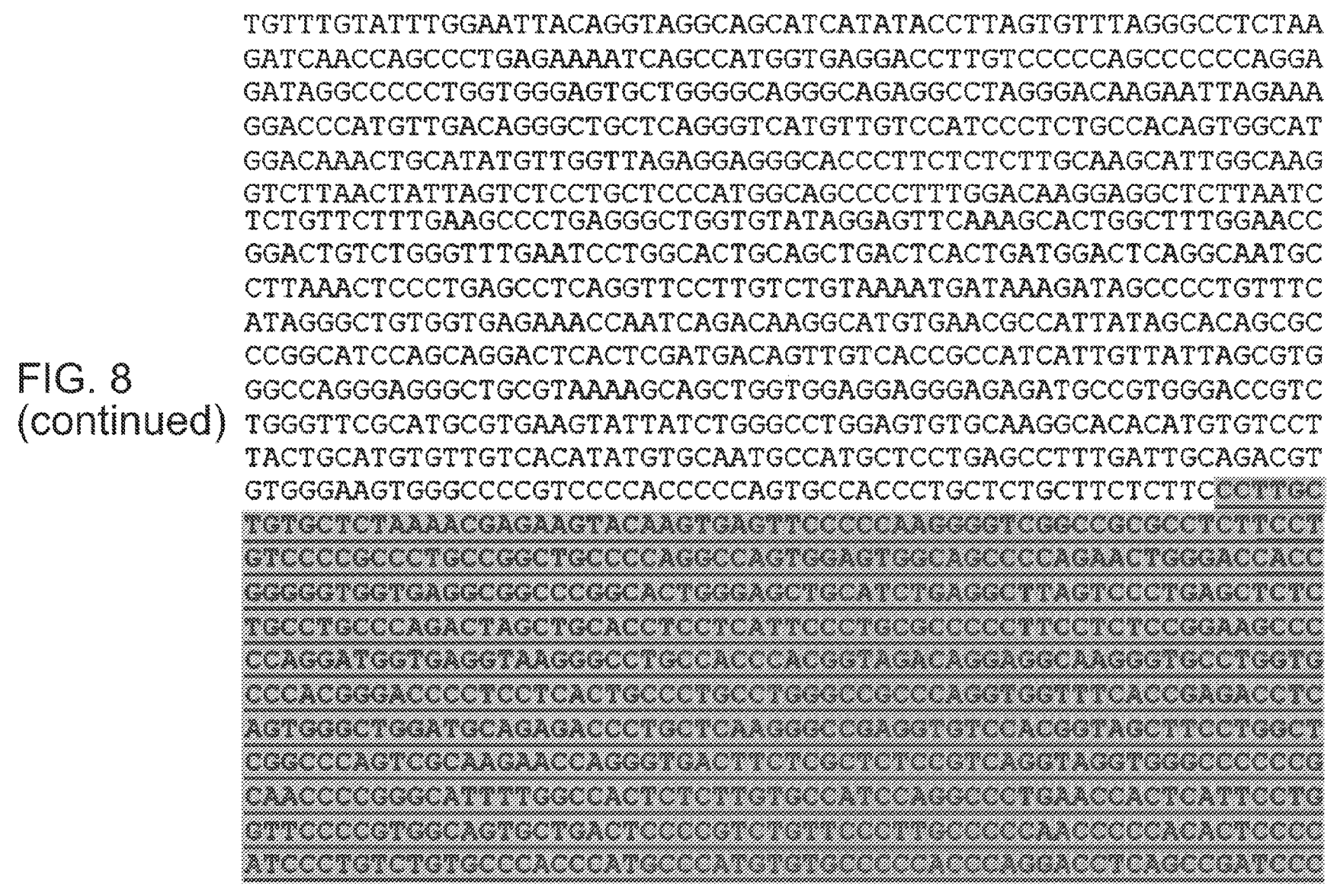
Figure 8:
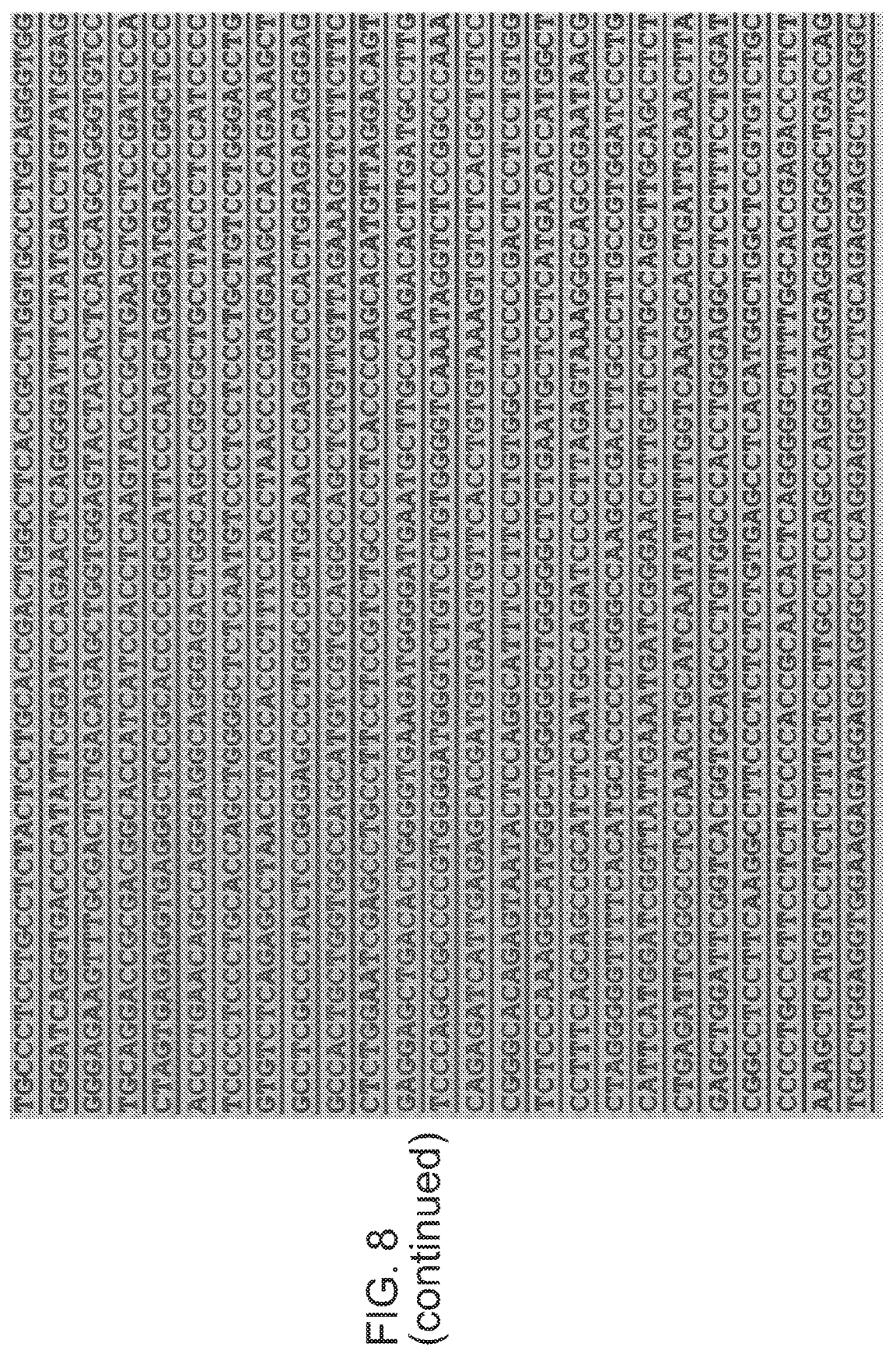
Figure 8:
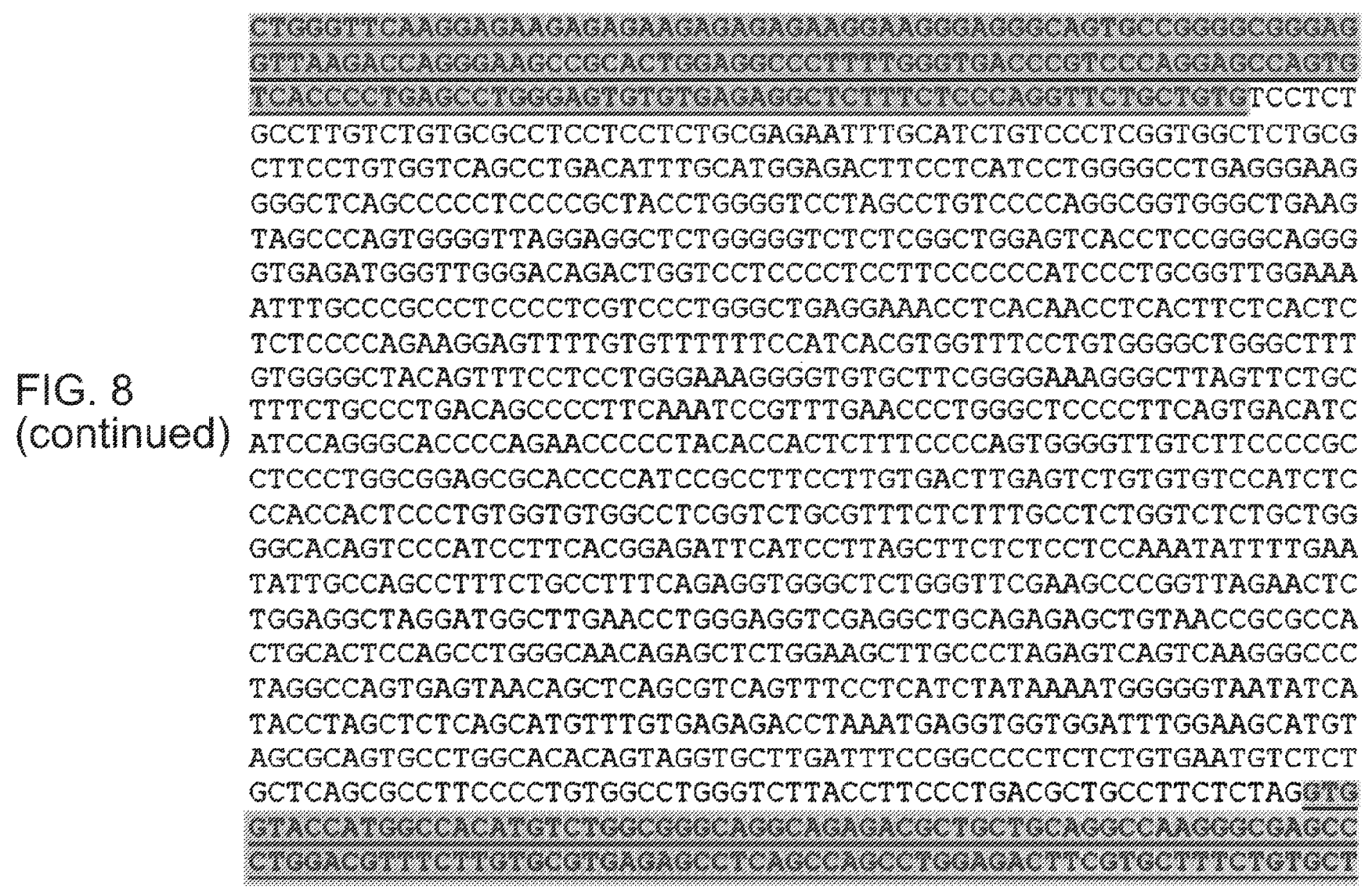
Figure 8:
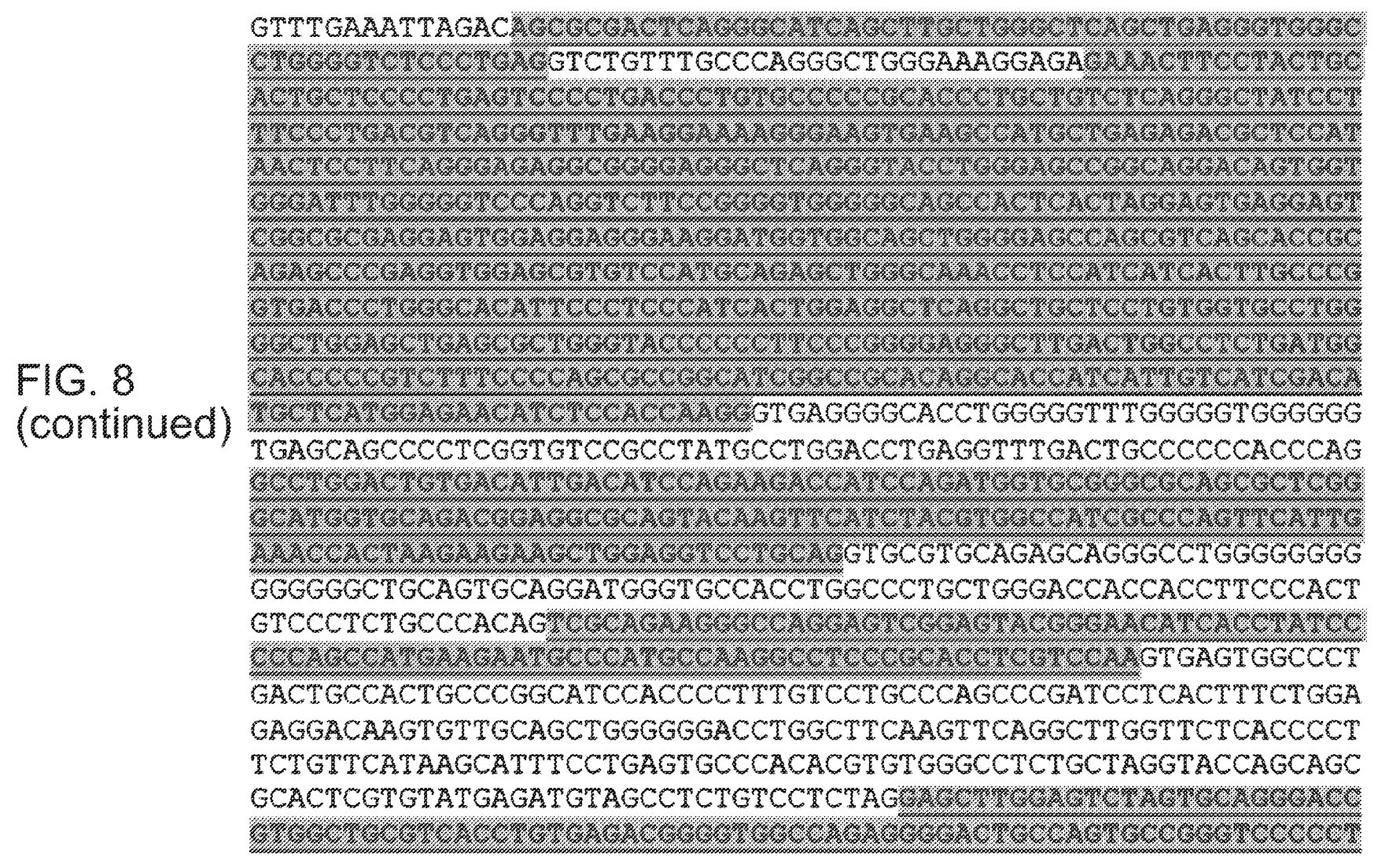

FIG. 8 shows a SHP1 genomic sequence running from the first sheet of FIG. 8 to the last sheet of FIG. 8 (SEQ ID NO: 58). Exons belonging to SHP1 are shown in underlined and highlighted letters. Other exons within this region that do not belong to SHP1 are shown in non-underlined highlighted letters.

FIG. 9 shows a SHP1 translated amino acid sequence (SEQ ID NO: 59). Alternating exons are underlined and non-underlined. Bold with italics indicate a residue overlap splice site.

FIG. 10 shows a SHP2 genomic sequence running from the first sheet of FIG. 10 to the last sheet of FIG. 10 (SEQ ID NO: 60). Exons belonging to SHP2 are shown in underlined and highlighted letters. SEQ ID NO: 60 is also as follows:

AGGCTCAAGCAATCCTCTCACCTCAGCCTCCCGAGTAGCTGGGACTACAGGCGCGCGCCA

CCACGCCCGGCTAATTTTTGTATTTTTTGTAGAGATGGGATTTCACTATTTTGCCCGGGC

TGGTTCCCAACTCCTGGACTCAAGCGATTCGCCCGCCTCAGCCTCCCAAAGGGAAGTGCT

GGGATTTCAGGCGTGTGCCACCGCTCCCACCCCAAAGTAGTATTTATTGTAATTATTATT

ATTATTTTGAGACGGAGTCTCGCTCTATTGCCAGGCTGGAGTGCAGTGGCGCGATCTCGG

CTCAATGCAACCTCTGCCTCCCGGGTTCAAGCGATTCTCCTGCTTCAGACTCCCAAGCAG

CTGGGACTACAGGCGCCCCCACCACGCCAGGCTAATTCTTGAATTTTTAGTGGAGACGG

GGTTTCACCATGTTGGCCAGGATGGTCTCGATCTCTTGACCTCGTGATCCGCCCACCTCG

GCCTCCCAAAGTGCTGGGATTACAGGCGTGAGCCACCGCGCCCAGCCTATTATTATTTTT

TTAGGCAGTGTCTTGCCCTGTCGCTCAGGGTGTAGTGCAGTGGCGTGATCACGACTCACT

GCAGCCCCGACTTCTCGGGCTTAAGTTATCTTCCCGCCGCAGCCTCCACGCCCGGTTAGT

TTTTTGCATTTTTTGTAGAGATGAGGTCTTGCTTTTTTGCCCAGGCTGGCCTCGAACTCC

TTGGCTTAAGCGAACCTCTTGCCGCAGCCTCCCAAAGTGTTGGGATTACGGGCGTGAACC

ACCGCGCCCAGCCTACTATCTTTATCTTACAGAAAGAAAAGAATGGAGGAAACCGAGGCT

CGGAGACAGTAGGTAATTTCCCCAAGGTTCCACAGCTAATGAGTGGAGCGGCGATTTGTG

GAACGAAATGAATGAAATCGATGTGGCAGCGGGCCCGGACGGGTCGGTGGCGTAGACGCG

GAGCGCGCAGCTCACACCTGGCGGCCGCGGTTTCCAGGAGGAAGCAAGGATGCTTTGGAC

ACTGTGCGTGGCGCCTCCGCGGAGCCCCGCGCTGCCATTCCCGGCCGTCGCTCGGTCCT

CCGCTGACGGGAAGCAGGAAGTGGCGGCGGGCGTCGCGAGCGGTGACATCACGGGGGCGA

CGGCGGCGAAGGGCGGGGCGGAGGAGGAGCGAGCCGGGCCGGGGGCAGCTGCACAGTC

TCCGGGATCCCCAGGCCTGGAGGGGGGTCTGTGCGCGGCCGGCTGGCTCTGCCCCGCGTC

CGGTCCCGAGCGGGCCTCCCTCGGGCCAGCCCGATGTGACCGAGCCCAGCGGAGCCTGAG

CAAGGAGCGGGTCCGTCGCGGAGCCGGAGGGCGGGAGGAACATGACATCGCGGAGGTGAG

GAGCCCCGAGGGGCCCGGCGCGGGCCTCGGCCCGGCCACCGCCGCGTTCGGTTAGCCCCG

TCCGGAAGGGGGCGCCCCGGCCGGGCTTCGGGCTCCCGCCCCGGGTCGGGGTTGGGGGCC

GGTTCCCTCCTCGTCCCCTCGCCCTCCAGGGGCCGGGGCCGGCCCCACCGCGCCCCCAC

CCCTCGGGTCCCCATTCATTTCCTGCCTCCCCGAGTTCCGGCTGCGGCAGCCCCGGGGAT

GCCCGTCAGGCCCGGGGCAGGTAGAGCCGCCGAGGGAACCACGGGTGCCAGCGGCCAGGC

TCAGCGCCGCATTCCTGACCCATTGCCTCATGAGAATTGCCTCATGGTGATTCCGAAATA

ACCCTGCTCACTTGGGGAGGCTCCTTGGGACACGAGAGGGGAGTTGCGCGGGGCCGGGCC

CCCAGTGGTCTAGTCGTTCTGGCTCACTGTGCCACTTTCGTGCATTTGGGGACTTCACGC

AGGACCCCTGACCCTTTTATATGCCTCTTTGTGTCTTCTTTTCCTCCTACCCCTCACGTG

CCAGAAATGGAAAAACTGACTGTATCTGCAGCCACTAGAAGTATTTCCTTCCTCTGCGAT

CTTCGCTTTGGGAGATGGAAAGGAAGGGAGCCGCATCTCGTTATTTAATCCTTCACTGCA

ACCTTAACAGTCAGGTCACTTTACTGGTACCCGTTTTATGGATGAGGAAACCGAGGCCCA

GAAGCAACATGCTAGTAAATGACAAGATTTGAAACTTAGGAGGATTAGTGAGTTAATGAG

ATCCTTTGAAAGGTCAGGGTAATACTACTACTAATAGCTAACATTTGCTTAGTTCTGACC

-continued

Figure 1A:
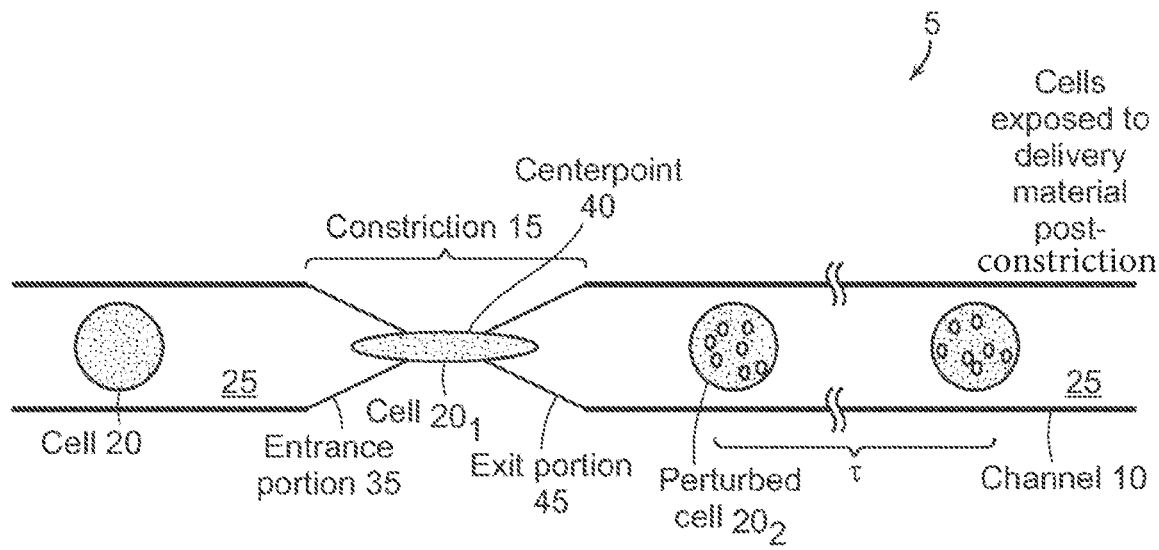
FIGS. 1A and 1B are schematic diagrams of a microfluidic system in which cells are exposed to the delivery material (payload) after passing through the constriction.

```
ACAGCCCTATCAGATGGCTACTATTATCCCCATTGTAAAGATGAGTAAACCGAGTTTCAG

AGGTTAAGTAAATTGCCTAACCTCACAGCTAGTAGGTGGTGGAGACAGAATCCCTACTTT

TAATCACTATGTTGCTTCTATTATTTTGTAACTATTGCTAACCATTTGTAAGCCTTAATT

TTGTTGTCAAACAGTAGTGTGACCTGTTGTTTTCAGATAGTGATCCTGCTATTTTGTATA

GTCACTCTATATACCACTCACACTTAAGACCCATTGTCTATTCTTTTCCATGATTGTTCA

ATTATGGTCACTGTCTCAGACATTTAAAAAACGATTCAAGCTATTGAGGCTATTTGAATG

AGATTTTCTTTTCTTTTTTCTTTTTTTTTTGGAGACGGAGGCTCACTCTGTTGCCCAG

GCTGGAGTGCAGTGGCGCAATCTCGGCTCACCACAATCTCCGCCTCCTAGGTTCAAGCGA

TTCTCCTGCCTCAGCCTCCCAAGTAACTAGGACTACAGGCGCACCACTATGCCCGGCTAA

TTTTTGTATTTTTAGTAGAGACAGGGTTTCACTATGTTGGCCAGGCTGGTCTCAAACTCC

TGACCTCGTGATCCGCCCGCCTTGGCCTCCCAAAGTGCTGGAATTACAGGCGTGAGCCAC

CGTACCCAGCCTGAATGAGATTTTTCAAAATATTAGGAATGTCTCCTCCAAACACACCTG

GCATGTTATTCATACATGGATCTGGAATTTAAAAAGGGGAGAAAAAGAAAACTGAGAACT

CGTAGGAAGTGAGTGACTTGGACAGGTCGGTTGGCAAGTGCTTACAGATCTGGGTAATAT

ATAACTGCATTTCAACAGAACAGTGTATAGCCTCAAATGTTCTAATTCTTTAGGGAGCTT

TTAAATAAACAGTTGTCTATTCTTTAATCTGTCAAATAGTCATTGAGCCTTTTGTTCCTG

GTGTCTGCTCTTCCAGACAAGTAAGGATCTGCTGCTTTAGGAGACATCAGACGGGGCTGG

GGGTTGGGAAAAGGTCTGGGTAGTAATAGACCCTACATTGTCCAGTTTGTTCATTTAGAA

GCATAGAAGTGTGGGCATAGTCAAAGTAGCAAGTGGTAAAGATGACAGTTTGAAATGGAG

TAATTCCTTCTCCCCTCCAGCCCTGGTATTATGCACCACCCAAAAAGCCGGGTTATGAAC

ATAATACACATAATTTTGAATGATTCATTATTTTTTGGATTATAAGCCTGTTTTATTTGT

TAACCAGCCTTAATGAGGTATAAATGACATGCAATTAATTGCATATATTTAAATGTACAA

TTTGATCAGTTTTGACATACATATACACTTGGGAAACCACCACCATAGTCAAGATAATGA

ACACATCTATCACCCCTGGTAATTTTGCCTTATGTTCTTTATAATCCTTCCTTTGTTCTT

AGGCAGCCACTATTCTGCTTTCTGTCACTATGTATTAGTTTGCATTTCCTAGAATTTTAT

TTTTAAAAATTTTAAAATTGTTTGAATAGAGATGGGGTCTCACTGTGTTGCCCAGGGCAG

TCTCAAACTCCTGGGTTCAAGTGATCCTCTCACCTTGGCCTCCTGAAGTGTTGGGATTAT

AGGCATGAGACACCCTGCCCAGCCCTAGAATTTTATTATTATTGTTATTATTGTGTTTTT

TTGAGATAGGGTCTCACTTTGTTGCCCAGGCTGGAGTGCAGTGGTGCAATCACTGCAGCC

TTGTTTTCCTAGGCTCAATCCATCCCCCCTCCTCAGCTTTCCGGTTACTGGGGCTACAGG

TGTGCACCACCACACCCGGCTAATTTTTGTATTTTTTATAGAGACAGGGTTTTGCCATG

TTGGCCAGGCTGGTCTCAAACTCCCGGGCTCAAGCGATCTTCCTGCCTCGGCCTCCCAAA

GTGCTGGGATTACAGGCATGAGCTATTGCGTCCCGCCTTCAAATTACTTTAACCTAGTAT

TAATTCATTCAACAGGAAGTTAATGAGCCAGGCAGGATAAAGCAGTAAGATAGGAAAATA

TTGCTATTTTCATGGCTGAGAGAGAGCAGACAAACACATGACTAAATAGGGCAATTTCAG

GTAGTAATAAATTCTAGGAGGGAAAAAATCCCACAGAAATGTGAGGATGGGAGAATGCAG

TTAGTTTTGATAGGTGGTTTAGAGAAGGTGATCGTGTGAGCTGACACCTGAATGACAATT

AGTAGTCTGAATTTTGTTTTGCTTAATTATCAAAATAACTCCTCTTGGGTTCGGCTTTTA

TATGCATCCAGTAATTAAAATGTAAGTATATTCAATGTACTGATATCTCTCAGCATCATA

GGTAGGAAAACTAAGGCATTCAGCAATTAAGTGACTCCTCCCTTGATCATGTAGCAGTGA

TAGTACTGGATTTAGATTTTGAGGTTGCTTCTCTGCCCTTTTCTGCCTTTGTGAAACCAA
```

-continued

```
CAAAGCTGCCTGTATTTTCCAACTCTTCCTTCAGCATGTGGTACCTCCTTTACATCTGTT

TTTGTTGCTCTGAAATCCATACGCGACGATGAGCTGAGAGGGGCAGAAAATTGAGCTTGT

TCTGAGACTGGAGGCTTTTGGTTTATCTCTTGCAGGTCAAGTACATTTTGTCCTGGGCTC

TCCCTGGTGGCCACGTTTGTTTATCTCCTGCGGGAGTAAATAAACTTGCCTTGCTGAAAA

ATAACAGTTCTGTGTCTTTGCAGTGGAAACTGGGATGTCTTTATTAACGTTAGGTCCTGA

TGTAAGGCCAAGTTTTTGGTTAGAGTTGCTCAAGTGCAGAGGCCACTGCTAAGATGACTT

ACCCCTCGTGTCCATGGTCAATGTGGAGACTGTTATGAGTGGCACATGATGCTGGAAAAG

CAGAGCCAACTCATGTTTGTAATTGTCCTAGCAGGCCGTGGTGTACTTTGTTAGGCAGCC

ACAGAACAATAGAGAAACTCAGCTTATTCCCCTTCCCTCTGGGAAACACAGACAGTACTT

GCCATCCAACGCCAATGTTTTTAAGGAAGAAAGAGGCAAAAAGTGATGTTGGCAAGGTCT

CTGGGAGTTGTGGACCCCAACCAAGGATTGGAGACCCTGAAATGGATTCAGATGCCCTAA

AATGCAGCCCAGTTCATTACTATGAATTTTGGAGGACTTTGTGCCTTGAGCAAATGTGTA

TATGTGACGCTCTTTGACAACACTGAAATAGGAAAAATACTATCCATGTTCGCGAGGAGC

ACTGAATTTAGAGAGGGAGACAGACTTTTATGCCAGCATCAAATGAATTTGATAAAGCTA

GTACCAAAATGAAATTTGAAATTTTTTTTTTTGAAATAGAGTCTTACTCAGTCACCCAG

GCTGGAGTGCAGTGATACAATATTGGCTCACTGCAACCTCCACCTCTTGGGTTCAAACAA

TTCTTGTGCCTCAGTCTCCTGAGTAGCTGGGATTACAGGTGCGTGCCACCATGTCTGGCT

AATTTTTATATTTTTAGTAGGGATGGGGTTTCACCATGTTGGCCAGGCCGGTCTTGAACT

CCTGGCCTCAAGTGATCTGCCCACCTTGGCCTTCCAAAGTGCTGGGATTATAGGCATGAG

CTACCACACAAGCCTGAAATTTGAAATGTATTGGTATAGAATATACTGTTTAGAATGTAT

GTGTATATATGTATATTTGTATACTCATATAAACACAAATACACATTGTATGTGTTTCTG

TAATATGTATATCTGTCTACACATACATGTATATACACACATACAATGTCTTTTTTTTT

TTTTTTTTTTTGAGACAGGGTCTTACCCTGTTGCCCAGGCTGGAGACTGCAGTGGCATA

ATCTTGGCTCACTGCAGCCTCGACCTCCTGGGCTCAAGTGATCCTCCCATCTCAGCCTCC

TGAGTAGCTGGGACTGACTACAGGCACGTGGCATCAAACTTGTCCAATTTTTCTATTTTT

TTGTAGAGTTAGGGTCTTGCTCTGTTGCCCAGGCTGGTCTCAAATTCCTGGGCTCAAGCT

GTCTGCCTGCCTCGGCCTTCCAAAGTACTAGGATTACAGATGTGAACCACTGTACCTGGC

CTTTACAATGTCTATTTTAAAGATAATGGTTCAAGTTTTTATCATCCCACTGGCCTACTC

TAATGAAACATCTATCCATTCATTGAAGAATTATTTATGGTGGGATAACTCTGTGCCAGG

TACCGTGCTAGGCATTGAGTATTCCAGGTTTTAGGAAACAGCACATGCAAAAGTGCTGAA

GTGGGAGAAGATCTCGGAGTGATTGAAGGCTAGGAGAGAGCAAGTGTGGGAGCTGTGAGG

CTGGGAAGGTGGGAGGTAGGTGGGAGCAGACCACATAGGGATTCTTAATGTCTTTAGTGT

CATGTGGACCATGGAGAGGAGTGTAGATTGTATTTTTAGAGCAATGCAAAATCATAGAAG

GATGTGATCGGGGAGTGGCATGAGCTGATCTATTTAAAAATATTTCTCTGGCTGCTGTG

AAGGAAGGATTGTAGGAGGCAGGAGTAGATTCAGGGAGATGAGACAAGTGATGAGAGAGG

CTTTGAACTTGGGTAAAAGTAGTTTGTGGAAAGTCTTTTTGGAGGTAGTTTTTGTTTAT

TGCCTTGTCATCAAAGCAGAGATGCTGACCAATGAAACTCCATGAGAAAATAGTGATTTA

TAAAGACATATCTATGCACTGCCATTAAAAAGCTGCTTGGAAAAAAAGGATAAAAAGCTG

CTTTAACAACTTTTTTTTTTGAGATGGGGTCTTACTCTGTCACCCAGGCTCACGACCTCA

GCTCACTGCAACCTCTGCCTCCCAGGCTCAAGCATTCTCCCACCTCAGCCTCCCGAGTGG
```

-continued

```
CTGGGACTGCAGGCACACGCCACCATGTCAGGCTAATTGTGTGTGTGTGTGTGTGTGTGT
ATGTGTGTGTGTGTGTGTGTGTGTGTGCTGGGACTGCAGGCACACACCACCATGTCAG
GCTAATTGTGTGTGTGTGTGTGTGTGTGTGTGTGTGTGTGTGTGTGTGTGTGTGTGTA
TGTAGAGATGGGGTTTTGCCATGTTGCCCAGGCTGGTCTCAAAATGTTGCCCAGGCTGGT
CTCAAACTCCTGAGCTCAGGTGATCCACCCGCCTCGGCCTCCAAAGTGCTGGAGATTACA
GACGTGAGCCACTGTGCCCACCTAACAACTTTAAAAAAATTTTGACATTTAGTAGGATAT
TTATTGCATTATTGTTGAGATGGCAAAATATTGGAGACAACTGAAATGTTCATCAGTGGG
GGGGGCTAGTTAAATGAAATACAGTGTAGCATGCATTAGAACACTTTTCAAGAATTTAAC
TTTTTTTGTAGCCTTTTACTTATAATGCTTGTCCCTATTGATGCCTTTTTTTTCAGCATG
ACTTACTCTTTTACTATAGGATATTAAAATTTAATTAGATTAGAAATGAGGAATATTCTT
GTAATCTGTAGAAAGTAACAAACTATAAACTTATTCCCCAAGAACAAATATAATAATTTT
TCTGGAGTAGCAGGTAAGAAAGATATAAATTTATATGTATACAAGAAACTGAAATTAGAC
TTTATACATTTAAAGGTTACAAGTGCAGTTTTATTACATGAATGTATTATCCAGCATTGA
AGTCTGGGCTTTTAGTGTAACCAGCACCTGAATAACATACATTGTACCCATTAAGTAATT
TCTCATCCCTCAAACCCCTCCCACCCTGAAATTAGACTTTGGATCCCTAGTTTAAATTCC
ACCCCTCTCTTTTTTTGAGACAAGGTCTCACTCTGTCACCCAGGCTGGAGGGCAATGTTG
CAATGATAGCTTACTGTAGCCTCAACCTCCTGGGCTCAAGGGATACACCCTCCTCAGCCT
CCTGAGTAGCTGGAACTGCAGGCGTGCACCACCACATTCAGCTAATTTTTTGATTTTTTT
ATAGAGATGAGGTCGGAACTCCTGGGCTCAAGCGATTCTCCCCAAGTGCTGGGGTTACAC
ACATGGGCCACTGCCCCCAGCCTAAACCTCCTTTCTCAGTATAGCAGCCTTGAGATGAAG
TTCCTGAAATTACTGGCCAGCTTGACTGTTTCCCCACATCACTGGAGGAGGGGGATGCAT
AGATAAAACAAAATATTCAGCATCATTGTATTTTCTTTTTGTTTCATCAGCATCTTTTTT
TAAAACTCACTTGACATAAGTCCCTAGCCTCAAAGAGTAAAGCCTTTGCAGAATCTGCAT
TCAGATTTCGGGTGTGATTTCCTGACAGATAGTTCAGGTTTGTAAACTCTTTTTTTTTTC
TTTGAGACAGAGTTTCACTCTTGTAGCGCAGGCTGGAGTGCAGTGGCACCATCTTGCCTC
ACTGCAACTTCTGCCCCCTTGATTCACGCGATTCTCCTGCCTCAGCCTCCTGAGTAGCTG
GGATTACAGGCATGCGCCACCACACCTGGGTAATTTTTGTATTTTTAGTAGAGATGGGGT
TTCACCATGTTGGCCAGGCTGGTTTTGAACTCCTGACTTCAGGTGATCTACCTGCCTCAG
CCTCCCAAAGTGATGGGATTACAGGTGTGAGCCACCGCAGCCGGCCAAAACTTTGTTTTT
TTTCCTCTTTTTGTTGCTGAGAAATGTAAACTCTTACAGACACAAATTATGTCTCCCATT
TTTTAAAACCCACTCAACACAGGGGTCATGTGTAATAGGCCCTGGAGCTTATTTTAGACA
TTGATTTGAGGCTCTTTTCCCCAAGTGCTGGTTTGTGTGTGTGTATGTGTGTGTAAGT
CTTTCTATGAGATGAGTGGTACCTACCTGGGCTGTGTGATCTTTTTTATTTTATTTATTT
TATTTTTGTAGATACGAGGTCTCACTATGTTGCTCAGGCTGGTCTTGAACTCTGGGCTC
AACCTATCCTCCCTCCTTGGCCTCCTAGAGTGCTGAGATTACAGGTGTGAGCCACTGCAC
CTGGCCAGCGATCCTTAATAAATATAGATAATGGCCGGGCGTGGTGGCTCACACCTATAA
TACCAGTACTTTGAGGGGCCGAGGCTGGCAGGTCACCTGAGCTGAGGAGTTTGAGACCAG
CCTGGGTAACGTGGGTGAAACCCTGTCTCTACAGAAAATAGAAAAATTAGCCAGGTGTGG
TGGTGCATGCCTGTAGTCACAGCTACTTGGGAGGTTGAGACAGGAGAATTGCTTGAACCT
GGAAGGTGGAGGTTGCAGTGAGCCGAGATCGTGTCTTTGAACTCCAGCCTGGGTGACAGA
GTGAGACCTTGTCTCAAAAAAAAATATAGATATAGGCTGGGCGTGGTGGCTCACACCTGT
```

-continued

```
AATCCCAGCACTTTGGGAGGCCGAGGCGGGTGGATCAGGAGGTCAGGAGATCGAGACCAT
CCTAGCTAACATGGTGAAACCCTGTCTCTACTAAAAATACAAACAATTAGCCAGGCCTGG
TGGTGGGTGCCTGTAGTCCCAGCTACTCGGGAGGCTGAGGCAGGAGAATGGCGTGAACCC
GGGAGGTGGAGGTTGCAGTGAGCCGAGACTGTGCCACTGCCCTCCAGCCTGGGCGACAGA
GCGAGACTCTGTCTCAAAAAAAAAAAATCTATATATCTATATATCTATATCTATATAGAT
ATAGATATAGATAATGCCAGATGATGGCTGGTTAGAAGGGATTGTCAGGGGCTGGCAGGT
TTTGCAGGTGTTAGAATGAGCAAGATGAGGAGAAGGATGCTTACTTCCCTCTCCTTGTAA
CTCTCTACCCCTCCCCTCAGTGTTTTTTATTTTTATTTTTATTTATTTATTTTTTTG
AGACAAGGTCTTGCTCTGTCACCCACACTGGATTGCAGTGATGCAATCATAGCTCATTGA
AGCCCAAACTCCTGGGCTCAAGTGATCCTCTTGCCTCAGCCTCCCAAGTAACTGGGACCA
CAGGTGCGTACAACTATGCCCAGTTAAGTTTTTCATTTTTTATACAGACGGGGTCTTGCT
ATGCTGTCCAGGCTGGACTTGCACTTCTGGCTTCAAGTGATTCTCTTGCCTCAGTTTCCC
AAAGTGCTGGCATTATGGGCATAAGCCACTGTGCCTAGCCCATCAGTGTCTTTTTATCCT
TTACTCCTATCAAAATTCATTCACTCAGCAGCCATTGATCAAGTGCCTACTATATACATG
TTGAGGACTGGAAATTTATTTGTCTCTTCTCATCTTATCTGGACCCTCTGTGTTAATTGT
AATTAACTGTAATCATTCTGTATTAATTGTAATAAACTTGTTGATAAACTCAAATGAGGC
CATACCGTTTTGCCACTTCCCCTCCTTCCAGGTTATATGGATGTACTTACATTGCAGGTT
TCATTTGTTGGTTCAGTTTTTAAACTAAGCCCTATTGTGTCAAATTATGCTAGGTGTGAG
ATGGGGAGTTCAAGCTGTGTGTTGTCTTTTTTTTTTTTTTTTTTTGCCTCACTTACTA
ATATACAAGCGCTTATAACCTTTGAGGCTGGCCCTATACATTAAGATTTTTATTAATTCC
ACTGTTCTTTATCTTCTCTTACTAAGTTCTCAGGGTCGAATGAACTCTAACTGCTCCTTG
CTAGTGATAAGCAAGTTGCAAATTACAGAATTGTCAGTGATTGAATACACGTATTAAACC
TGTAACTGGGAAGCATTTTTGGTAATTATGAATACTTTTGGAAAAAAAAAAGCTATGGAA
GGAAAGTTTAAAATCTACGAAAGCTCAAGTAGATGGTCATGGAATAGCTATTTCAATTTC
TAACTATATATTACTTATTTATTTATTTATTTTTGAGACGGAGTTTAGCTCTTGTTGCCC
AGGCTGGAGTGTAATGGCGTGATCTCAGCTCACTGCAACCTCCACCTCCCGGGTTCAAGC
TATTCTCCTGCCTCAGCCTCCCGAGTAGCTGGGATTATAGACATGTGCCACCACGCCAGG
CTAATTTTGTATTTTTAGTAGAGACGGGGTTTCTCCACATTGGTCAGGCTGGTCTCGAAC
TCCCAACCTCAGCTGATCCGCCTGCCTCGGCCTCCCAAAGTGCTGGGATTACAGGCGTGA
GCCACCGCGTCCGGCCTCTTAACTATTGTTTGAAATAATGTAGAGACAGCTCCAGAGCCA
TGAAGAAGTGTATGAAGAAGCAGTGTTAGCTTAAATGACATACATGTCACAATTGCCTAT
GTGAAACTATCATAATTATGCATGAGAAGTATCTATCCTGCATAACCTCCACCAATAATA
ATAATGTTAATAATAGTGAAAACTAATGTTTATTAAGTCCTTACTGTCTCCAGCCTCTGT
GCTAAATACTGGTTACTAAGTTTCCCTGAAAATACTATTCTCATCTGTTTGTTCTTAATA
ACAGGATAGCATAATTGTAAGTTGTAAATGAAATAATACAGTTTATGTAATAAAAGGGTA
AAAGAGAAGACCACCTACCTTATCTTCTGTTGCTGATCTGGATGGATGTAGGTGGTGTTT
ACCTAGTTTCACCTTTGGCAGTTGAAACTACTTTTTTTTTTTTTTTTTTTTAAGA
GACAGGGTGGGCCAGGCGCAGTGGCTCACGCCTGTAATCCCCGCACTTTGGGAGGCTGAG
GCGGACAGATCACTTGAGGTCAGAAGTTCGAGACCAGCCTGGCCAACATGGTGAAACCCT
GTCTCTACTAAAAATACAGAAAAATTAACTGGGTGTGGTGGTACACACCTGTAATTCCAG
```

-continued

```
CTACGTGGGAGGCTGAAGCAGGAGAATCGCTTGAACCCGGGAGTGGAGGTTGCAGTGAGC

TGAGATTGTGCCACTGCACTCCAGCCTGGGTGACAGAGCAGGACTCCGTCTCAAAAAAAA

AAACAACAACAAAAAAAGAAATTTTTAGAAATATGAGATGACAGCAAGAATGAGGGTATT

AAAAAGAAATTTTTAGAACTAAATAGCAGAATGTAATGGTGAAAAGTTTGATTTCTCAAG

TCTGCTTTGCACACAGGCATGTGGCAAACATTCAGTAAGTATAGCTGTAATTTTAACCAG

CTGTAATGTATAATAGCCAACATATCACATTTTTCTTTTTTCTTTTTTGAGACAGAGTCT

TGCTCTGTTGCCCAGGCTGGAGTGCAGTGGCACCATCTCGGCTCACTGCAACCTCTGCCT

CCTGAGTTCAAGTGATTCTTGTGCCTCAGCCTCTCAAGTAGCTGGGATTACAGGTGTGTG

CCACCACACTCGGCTATTTTTGCATTTTTAGTAGAGATGGGGCTGGTCTTGAACTCCCA

GCCTCAGGTGATCTGCCTGCCTCAGCCTCCCAAAGTGCTGAGATTACAGGTGTGAGCCAC

AGCGCCTGGCCATATATTGCTTTTTTCTTATTATCAGAGCCAGTTCATAATTGTGGAAAA

ATAGTGTTTGTAACAATGTAAGTATGGATAAATCATCTTTTTAATTTTGTGATTCATATA

GGTTTGTTGTTGTTGTTGTTTTGTTTTTATCTTGAGACAGAGTCTTGGTCTGTCACC

CAGGCTGGAGTGTAATGGCACAACCATGGCTCACTGCAGCCTCAGATGCCTGGGTTCAAG

CAATCCTCCCGTCTCAGCCTCTAGAGTAGATGGGACCACAGGTGTGGGCCACCATGCCTG

GGTAATTACAAAACTTTTTTTTTTTTTCTAGAGATGAGGTCTCACTATGTTGCCCAGGC

TGGTCTCAAACCTTTGACCTCGCTTCAGCCTTTAGAGTAGCTATGACTATAGGCATGTGC

CATCACCCAGCTAATTAAAATTTTTTTTCTTTTTTTTTTGGTGGAGATGCGGTCTTACT

TTGTTACCCAGACTGCAAGTTAGTTTCAGATATCAACATTTGGTGTTTCCAAATGCACGG

GGAGGCTTTGGAGCAAGTTTTTGGCTCATATGCATAGGTGTCCTAGACATTCACTTTGCA

AATTCTTATTAAAATGACTACAGTAGCATACAGATAGGGAAAAATATCCTTGTCAGTACC

ACCGATTGGGTGAGAAGAGACTGTATATTAAAAACAATGACCATCTTTTTGCCACATAAA

TTGCTGGTGGGGCCAGTTTGAAGAGGGCTTTGTCAGCTGCCTTCTGCCTCTTCCTCTTGA

GTACGTGGAGTTGGAGTCATCCTTGACAGCCTCCTGTTGACACCACCCGGGTCACAGATG

TGAAACTGTGTGGATGTAGGAGAGAGCAGTGATGGGGCTTACCCCAAGGTTGCTCTTCCT

TCCCTCTGGCCACAAATGTTTAGTAAGGAACTGCTCTGTATTAACCATTTGCTAGGGGCT

GCAGATACGGTGGTGAAGAAATAGACATGTTCCTACTCGGGATGCTGAGGTGGGAGGATT

GCTTGAGCCCAGGAGTTGGAGCTGCAGTGAGCCATGATCACACCACTGCACTCCAGCCTG

GGGGACAGAGCGAGACCCTATCTCTAAAAAACAATAAAAGAAATAGATGTGTCCTTCACC

CTCATGGAACTGCCAGTCTAGCCTTCAACCTGGTGACTGTAGAAATGTGTGATTAGATGC

TATATTGCCATGTTGAGTGTCACCCCTGAGAAGCAGGGTTTTTTTGAGAAGGTAGGATG

GGGGATCTGACTGTGGGACCACCAGAGGGAAAAGCACATGTAAAAGCTGCGTGTACCAAC

TGGAGGAAATCGGAGACGTGATCAGAGAACCAGAGTCAACCAGGGGCCATGCCGTACAGG

GTCCTGTTAAGATCTGTGACTTTTTTCTAAACGTTTTCTTCTGGATAACATCTAAATTTC

TAGTTCCAAATGTGAAACTCCAAGGGCGTTCTGTGCTAAACATTTTGCATGTATTAATTA

ATTTCCACCACACAACATTGCTGTGAATTAAGACAGTTTCTAAGCATGGCAAGAAACCCA

GAAATCATAATGGAAAATCTGATAAATTTAACAATGCCAACATGAACCTCTGTAGGAAA

AAAAATACCACAGACTAAAAGGGGGAAAAAAACCAGAGACAAATATTTGCAACACATA

CAGTAAAGGGTAATTTTCTGGTTATATCAAGAGCTCCTACAAATCAGTAAGAAAAAAAAT

CTAATAGGAAATGAGCAACGACAAACTGCAACTCATAGAAAAGGAAACACAAGTGGTCT

GAAAACATGAAAAAGTGCTCAGTCTCACAAAGAAATGCAAACTAACATGGTACCATTTTC
```

-continued

```
CATTAATCAGATAGACAAAGATGAAAGAGTTTGGTAATGTATGTAGTATTGGCACAAGTG
AGGGAAAACAGGGGATTTCACACTCTATGCCCGTCCAAACCAGTACCTTATTTTGAGGGT
GGTTTGACAATATTTGTCAAAATAAAAAAATTATATATAGTCATTTGCCACATAATGATG
GTTCAGTTGATGATGGACGGCATACATAATGGTGGTCCCATAAGAATATAATGGGCTGGG
TGCAGTGGCTCTCACCTGCAATCCCAGCACTTTGGGAGGCCGAGGTGGGTGGATTGCCTG
AGGTCAGGAGTTTGAGACCAGCCTGGCCAACATGGTGAAACCCTGTCTCTGCTAAAACA
TACAAACAATTAGCCAGGCATGGTGGCGGGTGCCTGTAATCCCAGCTACTCAGGAGGCAG
AGGCAGGAGAATCGCTTGAACCCGGAAGGCGGAGGTTGCAGTGAGGTGAGATTGGGCCAC
TGCACTCCCATCTAGATGACAAGGCAAAACTCCATCTCAAAAAAAAAAAAAAAAAGAAT
ATTATGGGCCCAGCCACAGTGGCTCACACCTGTAATCCCAGTACTTTGGTAGGCCAAGGC
AGGAGAATCATTTGAACTCAGGAGTTTGAGACTAGTGGGACAACATAGCAAGACCCCAT
CTCAAAAAAAAAAGATTATGGTGGAGCTGTCCTGTATAGACATACCATTTTTAACTTTTT
TTTTTTTTGAGATGGAGTCTTGCTGTGTCACCCAGGCTGATGTGTAGTGGCGTGATCTGG
GCTTACTGAAACCTCCACCTCCTGGGTTCAAGCGATTCTCCTGCCTCAGCTTCCTGAGTA
GCTGGGACTGCAGGCGCAGGACACCATATCGGCTAATTTTTATATATTTAGTAGAGATG
GGGTTTCACCATGTTGGCCAGGCTGGTCTTGAACTCCTGACCTCAAGTGATCCGCCTGCC
TCAGCCTCCCAAAGTGCTGGGATTACAGGCATTAGCCACCATTTACAGGCACCTGGCCAC
CATTTTTAATCTTTTATATTGTATTTAAACTGTACCTTTTCTATGTATGGATGTGTTTAG
ATACACAAATACCATTGTGTTACAGTTACTTACAGTATTCAGTACAGTAGCATGCTGTAC
AGGTGTGTAGCCTAGGAGCAATAGGTTATACCATATAGCCCAGGTGTGTAGTAGGCTCTG
CCATCTAGGTTTGTGTAAGTACGCTCCATGATGTTACCACAGTGACGAAATCGCCTAATG
ATGCATTTCTCAGAACATATTCCTGTTGTTAAGCAATGCATGACCGTATCTTGACAAAGC
CATTTTATTTCTAAAACTTTAATTTTACAGATTTATTTGTAAAAGTATGTAAAAATGATT
GTAAAGGATATGTTCTGCTGCATTATTTGTAATAACAAAAAACCAGAGGATAACATAAAT
GTCCTATAAGAAGGGTTAGATTATGGATGGCACATTCATACAATGGGGTATTATGTAGCC
ATTGAATAAAAGGGTACTGGCTGGGCGCAGTGGCTCATGCCTATAATCTCAACACTTTGG
GTGGCCAAAGAAGGAGGATTGCTTGAAGCCAGGAGCTTGGGGCCAGCCTGGGCAACATAG
CAAGACCCTATCTCTACAAAGGAAAAATAAAACAATTAGCCAGGTTTGGTATTGGACACC
TTCATGGTCCCAGCTACTGAGGAGGCTGAGATTGGAGGGATCGCTTGTGCCTGGCAGGTT
GAGGCTGTAGTGAGCCATGATTGTGCCACTGCACTCCAGGCTGGGAGATAGAGTGGGACC
CTATCTCAAAAAAACAAAAACAAAAACAAAACCTCCTGTAAAATGTCAAGAAGTCCTAGA
TGTGGGCCAGGTGTGGTGGCTCACACTTGTAATCCCTGCACTTTGGGAGGCTGAGGCCAG
GAGTTTGAGACCAGGCAGAGCAAGATAGCAAGACTCCATTTCTACAAAAAATAAAAAAAA
TTAGTTGGGCATAGTGGTGCATTCCTGTAGTCCCAGCTACTCAGGAGGCTGAGGTGGGAG
GATTGCTTGAGCCTGGGAGGTTGAGGCTGCAGTGAGCCATGATCACACCTCTGCACTCCA
ACCTGCGCAACAGAGTGAGACCCTGTCTCTAAAAACAACAACCAAAAAAACCCAGCAAAG
TACTGATAAAGATCTTTGGCTGGGCGCAGTGGCTCACACCTGTAATCCCAACACTTCAGG
AGGCTGAGGCGGGCAGGTCACAAGATCAAGAGATCAAGACCATCCTGGCCAACATGGTGA
AACCCGGTCTCTACTAAAAATACAAAAATTAGCTGGGCATGGTGGCGTGCACCTGTAGTC
TCTGCTACTCGGGAGGCTGAGGCAGGAGAATCACTTGAACCCAGGTGGCAGAGGTTGCAG
```

-continued

```
TGAGCCGAGATCACGCCACTGCATTCCAGCCTGGCGACAGAGCAAGACTCCGTCTCAAAA
AAAAAAAAAAGAGAGAAAGATCTTCAAGTTGTAGTATGTGAAAAAATCAGGGTGTAAAAC
AAGAGAATCCCATTTGTGTGTGTGTCGAGTGTGTTTCACACAGGCTCAGAGGGAGTAGTG
TGTATATGCACATGAACATACGTGTCAGTGTATATATGTATATATACAAGGTTGTGGGTT
TGTTTGTTTTTTTTGAGACAGAGTCTTACTCTGTTGCCCAGGCTGGGGTGCAGTGGTGCA
ATCTTGACCCACTGCAACCTTCACCTCCCAGGTTCAAGTGATTCTTGTGCCTCAGCCTCC
CAAGTAGCTGAGACTACAGGCACGCACCACCATGCCCAGTTAATTTTTGTATTTTTAGTA
GAGATGGGGTTTCATCATGTTGCCCAGGCTGGTCTGGAACTCCTGGCCTCAAGTGCTCTG
CCCGCCTTGGCCTCCGAAAGTGCTGTTGCCCAGGCTGGAGCTCAGTGGCACAATCGCAGC
TCACTGCAACCCCGACGTCCCAGGCTCAGGCAATCTTTCCGTCTTAGCTTCCCAAGTAAC
TGGGACTACAGGTGTGTGCCATCAATGCCCCACCAATTTTTTAATTTTTTGTAGAGATGG
GGTTTCCCTACGTTGCCCAGGCTGATCTTGAACTCCTGGTCTCAAGCAATCCTCCCACCT
CAGCCTCCCAAAGTGCTGCGATTACAGGTGTGAGCCACCTTGCCCTGCCCTGTACAAAGA
TCTGCATAAAAGCAGTTAATAATACTATGTTTGAGGCTGCCATCACAGGGGTGAGGTCAA
GGACAAGTGTGAGAAATTCTTTTAGAATCTATTTTAAAAAAAGAAGAGATGACAGTGGTG
ACAGTCAGGGAACAGATAAGCAGGTAGATTGTGGGGGTCTAGGCTGTCTAACTGGTGTTT
AAAATGAAGCAACCGCTGAGCCTGCTGTATTTCATTTAATGGAGACTAGTAAAACAACAG
CCAGAAATTCTTCACTTTCCATCTAAGAGAGGCAAAAGTTATTTTCCCTTCAATAACCTG
GGACTGTAGGATTAAGGTTTTTTTTTTTTTTTTAAATACTACAATATGACTACCAGT
ATAATTTAAAAATGATTAGAATTCTATTTGAGTAAGAAATAGGTGTCTGCCTGAAGTAGA
CAGTCACTGAAGTCACTAAGTGGCAAAAGACAGAAAAAAAATTGAAAGTAGGAAACAATC
AGCAGATATGATACCAAACATGAGCTGTCAGTGATAATGGATTAAGTCCTTCAATAATGG
CTGAGCCAGATGGAATTAAAAGAAAAAATCCAGGCCGGGCATGGTGGCTCACACCTGTAA
TCCCAGCACTTTGGGAGGCTGAGGTGGGAGGATCACTTGAGTCCAGGAGTTTGAGACCAG
CCTGAACAACATAGTGGGACCCCATCTCTATTTTATAAAAATATTTTGAAAAAGAAAAA
AAAATTCAGTTGTGTTCTGCTTTAAAAAGACAAATTGGCACAGAATGTCAAAGAATAAAT
AAAACAAACATGGGCAAAAGAGATTCAGGTGGTACCAATATCGGGCTAAGTAGCATTCAA
GATAAAGATTATTAAATAATAAGTTAGTTAATACTAGAGTAATTGCATATTAATGAAACA
TAATCTATGGTAGAGATATTATAGTCAATAATTGTTTTATGTATTCATTAAGGTAACAAC
AAGCAAACAAGCTTTAATAGTTTTAAATGCTTTATATGCTTTATAGTTCTTTTATGTGCA
TTAATTCATTAATTCTCATTTCCTATGAGGTAAACACTATTATTATCCACATTTTACAGA
TGTAAAAACCGAAGCAGAGAGATTAATTAGCTTGCCCAGGAGATGTGGCATTCTGGGATT
TGAGACAGTGGTTTGGCTCTGTAGGTTGCTTCAATAACCAAGAGATGCTTCAAATCAGAT
TTTTAAAATATGTTTTTCAGAAGCATTTTCCTGATACTTCTCCCCTTACATGGGTGTTAG
TCTTTTGGGTTGAAAAACATGAGTAAGTGCTAGAAGAGCAAAATATGCATCCAGATTTAA
TAGTATGTCTGTTTTTCTGAGCCTTGGCATTTCATTGCTTTTATAATAGAAATGAAGGCT
TTTTTTTTTTTTGGCTGAGAATAGCACTGAACTCAGTGGGAGGGACTGTGGGTTGTAAG
TTGTCCGCCTCTGAATGGAGTTGAATTTAAGTTTCTTGGTTTCCAAAGAATGATTGATTT
AAAGACCCTCAAATTGCAAGTTAGAACTGACTTCAGTCCTTGAGGTTTTTTACCATTTAA
TGAATAATTAAATTTATGGTAATAAATGGTAATAAATGGTAAAAATGGTAATAAATTTTA
CCATTTAATGAATTTTTCTTAAAAAGCAATTGAATTGTTGATGAAAGGTGATGTTAAAAT
```

-continued

```
TATCCCAGATTTATCAATCTTTTTTTTATTGCCCCTGGATTTTGAGTCATAGAAAGCCTT

TCCTTATTCTAAGGTTAACAAGACATTCACCCATGTTTTCCTCTAGTATTGCATTGTTTC

ATCTTTTACGTTTATTATTTATTTTATTTTATTTTTTTGAGACAGGGTCTCACTGTGTCA

CTCAGGCTGGAGTGCAGTGGAATGATCTTGGCTCACTGCAGCCTCTGCCTCCCGCCTCCC

GGGTTCAAGCGATTCTGCTGCCTCGGCCTCCCAAGTAGCTGGGATTACAGGCACCTGCCA

CCGCGCCTGGCTAATTTTTGTATTTTTTTTTAGTACAGATGGGGTTTTGCTGTTGGCCA

GGCTGGTCTCGAACTCCTGACCTTAAGTGATCCACCCGCCTTGGCCTCCCAAAGTGCTGG

GATTACAGGCATGAGCCACCGTGCCCGGCCTAAAATTTATTCTGATATGTGATATGATGT

ATGGTTCTAACTACTTTGTTACGGTGCATTATTTTCTAAATGTGGTATTGGATTCTTTTA

TATTTTGTTTAGAAGTTCTGCATCAATATTCATGAGTACCATTGGTCTCTGTTGTTTTTC

TTGTGCCATCTTTATTGGTATAGGTATCAGTGTTATATTTAGTTTGTAAAAGGAAGTTGG

AAGTTTTCCTTTCTTTTTAGTACTCAGGAATGATTTTAAGAATTGAGACTATTTGGTCTT

TGAAGGTTTGGTAGAAGTCCATTGGGAATCCATCTGGGCCTGGTGATTTTCTGTGCGGTA

GTTCCTTAATTGTTTTCCCTATTTTTTCTTATTTTTAATCAGGTAGCCTCTGAACCAGAA

TAGGTTCAGAGAGGCTCCCTCTATTTTTTTTAATACAAGTTGGTCTGCCTAAGTTTTCTT

ACTCTAATGGGTTAATTTTTGTAGACTGCATTTCCCTGAAAAATTACACGTTTGTTCTAG

GTTTTCTGACTTATTTCCACAACTTTTTAGTCTTTCCCCCTGGAATCATGCCCCTTTCCA

TAAACAGGACTCTGATGTACCTGAAGTATTTTCACACTTCGGGTGGACTTTCTGTTTCTG

GGGGTGGTTTTAGAGCAATTTTAGGCCTGCCACTAGCTACCCTGTTCTCTACACCATGCT

GTTTTTCTCAGAATGCTCTTCTTTTGCACAAAGGCTTGGAGTAGGAGGTTGAGCAGTCAC

TCACTGACGTTTGGTATATTTTCTTTTTTTGCTTACAGGTAATCTGGAAGTTTGGGCAT

TCTCTTTAAGTTGAGGGTGTGGTTTTCATGTCATTTTATTTGTTTATTGTTTTCTTGTGT

GTGTTTCTTAGAGACAGGGTCCCACTCTTGCCCTGGCTGGAGTGCAGTGGCGTCTTGATC

ATAGCTTACTGCATCCTCAAGCTGCTGGGCTTAGATGAACCTCCCACCTCAGCCTCCTGA

GTAGCTGGGACTACAGGAGCACACCACCATACCTAATTTTTTTTTTTTGAGACGAAGTC

TTGCTCTGTCCCCCAGATTGGAGTGTAGTGGTGCAATCTCGGCTCACTGCAACCTCTGCC

TCCCGGGTTCAAGCGATTCTCTCACCTCAGCCTCCCGAGTAGCTGAGACTGCAGGTGCAT

GCCACCATACCCGGCTAATTTTTGTATTTTTTAGTAGAAACAGGGTTTCACCATGTTGGC

TAGGCTGGTCTCAAACTCTTGACCTCAAGTGATCCACCCACCTTGGCCTCCCAAAGTGCT

GGGATTACAGGCTTGAGCCACTGTGCCTGGTCCCTGGCTAATTTTTAATTTTTTTGTAGA

GATGGGATCTTGCTATGTTGCCCAGGCTGGTCTTGAACACCTGGCCTTAAGCAATCCTCC

CACCCTAGCCTGCCAAAACACTGGGATTTACAGGCATGAACCATTGTGCCTGGCTTGTTT

TGTTTTTAATTCTATGTTGTTTTTGAAGGATGTATGGGAGAGATGGATTTAGGCAATCA

TCGTTGTCCTTGGCTACCTGAAAGTCCAGGCACTCTTCTAGATACTTTATAAATATTAAC

TCATTTTATCCTCTCAACAACACTATGACATGGGTACTGTTACACCTTCCATTTTATAGG

ACTTAACAGAGAGGTTAAATATGTAGCCCAGGGTCACAGAGAGCTGGGCTTCAGACCAAG

ACAATCTGGCACCAGAGTCTATGTGGCTACCCCTAAGGCTTTGCCACCATGTGTTAGTGA

TTCTCAGCCTGTCATTTGGGGAGGGGATTGCCCTTTTTTTAAACTTTTTAAAAAATTTA

TTCTTATTTTATTATATTTTTGAGACAGAGTCTCCCTCTTTTGCCGAGGCTGGAGTGGAG

TGGTGTGATTTCAGCTCACTGTAACCTCTGCCTCTGGGGTTCAAGTGATTCTCATGCCTC
```

-continued

```
AGCCTCCCAAGTAGCTGGGATTACAGTTGCCAGCCACCATGCCCAGCTAATTTTTGTATT
ATTATTATTATTATTTGAGACGGAGTCTCGCTCTTTTGTTCAGGCTGGAGTGCAGTGCTG
TGATCTCGGCTCTCTGTAACCTTCGTCTCCTGGGTTCAGGTGATTCTCCTGCCTCAGCCT
CCGGAGTAGCTGGGACTATAGGCGCGCACCACCATACTTGGCTAATTTTTTGTATTTTTA
GTAGAGACGGGGTTTCACTATGTTGGCCAGGCTGGTCTCGAACTCCTGACCTCAGGTGAT
CTACCTGCCTTGGCCTTCCAAAGTGCTGGGATTACAGGTGTGAGCCACCATGCATGGCTG
GATTGTCCTTTTTAAAAAAAAAAACAAAAACAAAAAAAAAAACCCAAACCATAAACCCA
ATATTCTGAAAGATTTGGTCTCCACACCTGTGTTATATAATAATTAGTTTTTCCATTTTT
TTCCTCTTGGTAGAAGGCACATATGCCACTCAGTTTCCAGTTGCCACACCCAATTAACAT
AATTGTTTTGCAGCCAAAAGCAAAAGAGAGTTGACATTTTAATTAGCTTATGTAGGTAGA
CAAATTGAGGCCTAATGTAAGAGTTTCATTATACCTTTTTGAAAAACTATAAATAGCTAG
AAGCCAGTTGTCATTACTTTTTGATTCCTTAGAATTCTGGGCATCTTTCATCTGGAACCA
CAGATGAAAGAAGCTGCAAGGAAGGATTTTTTTTCTTAACGGAATAGTTTAACCATTCTG
AATGCAAAAGTATTGGATGCTAGAATAATAGGTATCACATAAATTGAGGTTGACGTTTTC
CCGGGTGAAATTCTATTCTGTCTCAATTTTCCTTTTTTTTGAGACGGAATCTTGCTCTG
TCGCCCAGGCTGGAGTGCAGTGGCATGATCTCGGCTCACTGCAAGCTCCACCTCCTGGGT
TCATGCCATTTTCCTGCCTCAGCCTCCCGAGTAGCTGGGATTACAGGGGCCTGCCACAAC
ACCCAGCTAATTTTTTGTATTTTTAGTAGAGACGGGGTTTCCCAGGATGGTCTCAATCT
CCTGACCTCGTGATCCGCCTGCCTCGGCCTCCCAAAGTGCCGGGATTACAGGCGTGAGCC
ACTGTGCCTGGCCTTTTTTTTTTTTTTTTTTTTTTAAGACAGAGTCTCGCTTTG
TTGCCTAGGCTGGAGCGCAGTGGCATGATCTCAGCTTATTGCAACCTCCGCCTCCCGGGT
TCAAGTGATTCTCCTGCCTCAGCCTCCCGAGTATCTGAGATTACAGATGTGTGCCACCAT
GCCTGGCTAATTTTTGTATTTTTAGTACAGATGAGGTTTTGCCATGTTGCCCAGGCTGGC
CTCAAACTCCTGACCTCAGGTAATCCTCCTGCCTCAGCTCTTCCCAAAGTGCTGGGATTA
TAGGCATGAGTCACCGGGCCCAGACTCAATCTTCTGACAAGCTCTCAGAGAGAGTAAAAA
GCAAATGAATATTTCATTATTTTGATCTGAGCTTTACGATTTTTCTTTTCTTTTCTTTTT
TTTTTTTTTTGAGATGGAGTTTTGCGTTGTTGCCCAGGCTAGAGTGCAGTGGTGGCGAT
CTTGGCTCACCGCACCCTCCGCTTCCCGGGTTCAAGCGATTCTTCTGCCTCAGCCTCCTG
AGTAACTGGGATTACAGGCATGCGCCACCATGCCCGGCTGATTTTGTATTTTTAGTAGGG
ACAGGGTTTCTCCATGTTGGTCAGGCTGGTCTTAAGCTCCCGACCTCAGGTGATCCACCT
GCCTCGGCCTCCCAAAGTGCTGGGATTACAAGCATGAGCCACCTTGCCCAGCCTTTTTTT
TTTAAATCTGAGAAGAGGTCTTGCTCGATTGCCTAGGCTGGAGTGCAGTGGTGCGATCTC
TGCTCACTGCATTCTCTGCCTCCCAGACTCAAGCAATCCTCCCACCTTAGCCTCCTGAGT
AGCTGGGACTACAGGCATATGCCACCACACCTGGCTAATGTTCGTATTTTTTGTAGAGA
CAGGGTTTTGCCATTTTGCCCAGGCTGGTCTTGAACTCCTGACCTCAGGTGATCCTCCCA
CCTTGGCCTCCCAAAGTGCTGGGATTACAGGTGTGAGCCACTGTGCCTGGTCTCCTTCAC
TGTTGTAAGATACTTGAATTGGGTCAATATTTGTGGAGAAGTCTCTTAAAAGTTCACTTG
ATTGTCAGTACTAGAACTCTACATTTAATATTGACATATTCCTGGGAGCATTTCAGAGCA
TTCTATTAGCTTAGAAAGGTCCAGGATAATTTGACTTTAGAAGTTACTGTTACCATGAAT
CTCAATGACTTTTGAAATCCATGAAGAATATCTTTTTTTTTTTTTGAGACGGAGTCTCA
CTCTGTCGCCCAGGCTGGAGTGCAGTGGTGATCTGGGCTCACTGCAAGCTCCGCCTACTG
```

-continued

```
GGTTCACGCCATTCTCCTGCCTCAGCCTCCCGAGTAGCTGGGATTACAGGCACATGCCAC
CACGCCTGGCTAATTTTTTTGCATTTTTAGTAGAGAGGGGGTTTCACTGTGTTAGCCAGG
ATGGTCTCGATCTCCTGACCTTGTGATCCGCCCGCCTCGGCCTCCCAAAGTGCTGGGATT
ACAGGCGTGAGCCACCGCGCCTGCCCAAGAATATCTTTTTGCTGGTAACTAGAGAGGACT
CCTCTGAAGCAGATGCCATTCATGATGGATTTCATCATTTATGGGTTTTAAAAAACATTT
TATTTTGAAATAATTTCAAATTTAAATAAGAGTTGCAAAATAGTACAAATAATTCGTGTT
AACTTTTCATCCAGATTTACAAGTCAACCTTATACAGGTTGAGTATCCCTTATCCAAAAT
GCTTGGGACCAGAAGTGTTTTGGATTTCAGATTTTTTCGAATTTTGGAATATTTTTATTA
TATACTTAAGCATCTCTAATCCCCAAATCTCAAATCTGAAATATCTGAAATGCTATGATG
AGCATTTCCTTTGAGTGTTATGTGGGCACTTTTTAAATTTATTTAATTAATTTATTTTTT
GAGATGGAGTATTGCTCCATCACCCAGGCTGGAGTGCAGTGAGCGATCTTGGCTTATTGC
AAACTTCACCTTCTGGGTTCAAGTGATTCTCCTGCCTCAGCCCCCTGAGTAGTTGGGACT
ATAGGCGCTTGCCACCACGGCCGGCTAATTTTTGTATTTTTAGTAGAGACAGGGTTTCAC
CGTGTTGGCCAGGCTGGTCTCGAACTCCTGACCTCAGGTGGTCCACCTGCCTCCGCCTCC
CAAAGTGCTGGGATTACAGGAGTGAACCACCGCGCCTGGCCATGGATTTTGCAGCATTTT
AGATTTGGGATACTCAACCTGTACCATGTTTACTCTCTCCTCTCTCTCTCTCTTTT
TATATATATATATATATATATATATATATATATATATATATATAAATTATATATAC
ACTACACATATATGTATGTATATGTATGTATTTTATATATAAAATACATATCTACATATA
AAATACACATGTATATATACATGTGTACATATATGTGTCTCTATATTTAAGTTTTGTTGG
AACCACTTGAGGGTAAGTTGCAGACATGGCGTCTCATTGCTCCAAAATACTTCAGTGTGT
ATTTCTTAAATACAAGGACACTTGGTTACATAACCACAGTATATCACCAAATGTATATTA
TAACAAGACTACCATCAAATCCTTATATCTCTTTCAAATTGTTTTAGTAATATCCTTATA
GCAAAAGACAAAACAACAACAAAAACTGTTCCCTTTTATTTTGTTTGTTTTGGTCCATTA
TATGTCCAGGTTATGCATTAATGCATTGTGTTACTTGCTAAGTCTTGTTACTGGCCTTTA
ATTAGGATATTTCTTTGCATCCCGCCAAACTCCTCTTCATGGTTGTATCTTTTTTTTTTT
TTTTGGAGATGGAATTTTGCTTATGTTGCCCAGGCTGGAGTATAATGATGCGATCTTGGC
TCACTGCAACCTCCGTCTCCCGGGTTCAAGCGATTCTCCTGCCTCAGCCTCCCGAGTAAC
TGGGATTGCAGGCCTGCGCCACCTTGCCCAGCTAATTTTGGAATTTTGTGAGACGGGGTT
TTGCCATGTTGGTCAGACTAGTCTCGAACTCCTGACCTCATGATCCGCCCGCCTTGGCCT
CCCAAACTGTTGGGATTACAGGTGTGAGCCACTGTGCCCGGTCTTTTTTTTTTTTTTT
GAGACAGGGTCTTATTCTGTTGCCTGGCCTGGAGTGCAGTGGTATGATCTTGGCTCACTG
CAACCTGGACCTCCTGGGCTCAGGCGATCCTCCCACCTCAGCCTCCTTAGTAGCTGGGAC
TATAGGCACACACCACCATGCATGGCTAATTTTTATATTTTTTGTAGAGACTGGGTTTC
GCCATGTTGCCCAAGCTGGTCTTGAACTCCTGGGCTCAAGTGATCCACCTGCCTTGGCCT
CCCAAAATGCTAGGATTACAGGTGTAAGCCACTGCGCCTGGCCCTAATTTTTGCATTTTT
TGTAGAGATGGGGTTTCACTATATTGCCCAGGCTGGTCTTGAACTCCTGGGCTCAAGTGA
TCTTCCCATCACAGCCCCCTAAAGTGCTGGGATTATAGGCGTGAACCACTGTGCCTGGCT
GAGGATTAAGTTTCAACCTCAGGGGAGCGGCATTCAAACTATAGCATTGTCCTTTAGTGA
CTGGCTTAGTTCACTTAGAATGTTTGTCTATTCATCCATCTATAGACACTGTTTTCTTTC
ACCTTTTGGCTTTGCAAATAATGCTGCTGTGAATATGAGTTATAGAAAAATACCAATTTG
```

```
AATCCGTGTTTTCAATTACTTTGAGTATATACCTGGAAGTGGAATTTCTGGATCATATGG

TACTTCCAAGTTTTTTTTTTTCTTTTTTGAGACAAGGTCTCACTCTGTCACCCAGGCTG

GAGTGTAGTGGCACGATCTTGGCTCACTGCAACCTCCGCCTCCCGGGTTCAAGCGATTCT

CCTGCCTCAGCCTCTCAAGTAGCTGGGATTACAGGCACGCGCCACCACGCCCAACTAATT

TTGTATTTTTAGTAGAGATGGGTTTCTCCATGTTGGTCAGGCTGCTCCCGAACTCCCGAC

CTCAGGTGATCTGCCTGCCTCAGCCTCCCAAAATTCTGGGATTACAGGTGTGAGCCACCG

CACCTGGCCTCCATGTTTCAATTTTTAAACAAACAATTAGTTAAAAAAATAGGAAACTAA

GAGAATGAACTATTTCCTGTTTTATTCAGTGGGTTATAATCTGTTACTATCATTGTTTAT

TTTGAGGTACAAATTGTCCCTACTTTGGCCAGCAGAGGATCCTGCAGTTTGTCTCCTGTG

TCCTTTTCATAGCTCCTTGTTGGAACTCTTACTGGCCCACAATAGGATGTTCCAAGTTCA

TCTTCTTACTTTTACTGCCCCAACGCTGGGATCAGCCATTTCTTCAAGGAGGCCAGTTCC

TTTCATTGGAGAATGGAAAACCCAATATGTAGAAACCAAGATAGAGGTGTTAGGTGTGAT

TGCTACTGGAGTGTCATTGCTTCCAAACCCTTTCAGAAGAGACCTAGGAAATGTGTGTGT

GTGTGTATATATATGTGTGTGTGTGTGTATTCATAAAAGCACATACACATACACAT

ACCCCGAAGCATGTATTTCTGTATTATTATTATTTTTTGAGATGGAGTCTTGCTCTGTC

GCCCAGGCTGGAGTACAGTGGCACGATCATGGCTCACTGCAACCTCTGCCTCCTGGATTC

AAGCAATTCTCCTGTCTCAGCCTCCTGAGTAGCTGGGATTACAGGTGTCCACCACCACGC

CCACCTAATTTTTGTATTTTTAGTAGAGATGGGGTTTCACCACATTGGCCAGGATGGTCT

TGAACTCCTGACGTCAAGTGATCTGCCCGCCTCGGCCTCCCAAAGTGCTGGGATTATAGG

CGTGAGCCACTGTTCCCATCCAGAAGCATACATATCTATTTCTATATCTACATTTCTGTC

TTTACATGTATATATTAAAAATTACAGTTTGCACTAATACCTCCAATTACAATCTAACAT

CATGGGATTTATTCTGGCTTTCTCCCTTCTCATATTTGTGTCTCCCCAACAGTGAGAAAC

CTGGCTTGCTATCCTCAACATGGTAACTTATTTATTAAGAAACTTATTCTTTTTTTTTT

TTTTTTCTGAGATTGAGTTTCGCTCTTGTTGCCCAAGCTGGAGTGCAGTGGTGTGATCTT

GGCTCACCGCAACCTCTGCCTCCTGGGTTCAAGCGATTCTCCTGCCTCAGCTTCTCAAGT

AGCTGGGATTACAGGCATGCACCACCATGCCCAGCTAATTTCGTATTTTTAGTAGAGATG

GGTTTCTCCATGTTGGTCAGGCTGCTCTGGAACTCCCGACCCCAGCTGATCTGCCTGCCT

CGGCCTCCCAAAGTCCTGGGATTACAGGCGTGAGCCACCGTGCCCTGCCTCTAGTTTATT

TATTTTTATTCCATGTGCTCAGTCTTGCGAGCACGTGGTCTGTTTTCTTGGGCCTGGCCC

CCTCAGTGCACTGTCTTAATACCCTAGCCCCAGTCCCTCTGATCATATCCCCAGACACC

CCTACTGAATCCCAGGTCTCTACCAAGGGAAAGGCAGGGAGGAGGCATTGACCAAGGAGA

AGAGGGGGAAGGGACAGGGAAGGTCTTGATTTGTATTTTCTAAAATTTTCTACTCTGCTC

ATAATGCGTCTTAGCTGTGTTGTTGTGGAAAGTAGTGCTGACAGTGTCTTGTTTTTTTAT

TACTTACTTTGTCTTTCTTTTTAAGATGGTTTCACCCAAATATCACTGGTGTGGAGGCAG

AAAACCTACTGTTGACAAGAGGAGTTGATGGCAGTTTTTTGGCAAGGCCTAGTAAAAGTA

ACCCTGGAGACTTCACACTTTCCGTTAGGTAAGTTGGAATGAAAAGAGAGGATCCTGAGA

GTGTTTTCTAGGTAGGAAGTGGTAAAACCATGCTTGGATAGCTTGCTGCCTGCATTTCGA

GTTTGAAGGCCTTATCTGAGCCCTGGGCTGCCTTCAGGGTTTGGGGAGTGGCCTCCTGGA

CATTTAGCAGAAGAGGAGTAAGGAGGGCCCTTCTTCTCCCTCTGAGACCTCATGGAAGGT

GAGTTGGAGCAGGTCATAGAAGTTCTTAAGCCCTCCAGTGCTTGAGACTTGTTCCACACA

TCTTGAACCTGGTTTCTGCATTTTTCTTTTCCTTCCTGTTGATTTATTTAAAAATTTTAT
```

-continued

```
TTCTTTTCAATTTTTTTTTTTTTTAAATAGAGGTGGGATCTTCCAATGTTGGCCAGGTT
GGCCTTGAACTTCTGGCCTCAAGCAATCCTGCCTCGGCCTCCCAAAGTGTTAGGATTACA
GGCGTGAGCCACTATGCCTGGCCTTCTTTTTTTGAGACAAGCTGTTGCTCTGTTGCCCAG
GCTGGAGTGCAGTGGTACGATCACAGCTTACAGCAGCCTTGAACTCCTGGGCTTAAGTGA
TCCTCCCGCCTCAGCCTCCCGGGTAGCTGGGACTCCAGGCTTGTGCCACCATGCTCAGCA
TTTTTAAAAAATATTTTTTGTAGAGATGAGGTCTCACTGTATTACCAAGGCTGATCTTTA
ACTCTTAGCCTCAAGTGATCCTCCTGCCTCAGCCTCCCAAAGTGTTGGGATTACAGGCAT
GAGCCACCACACTCAGACTTTGTTGACTTCTTAATAAGAAAAATACTTGTTAAGAGTTTC
TTCAGATCACTTTCCTTTATCAACAAGTAAAACATGACTGAGGAAGTTGTGGTCCCCTTT
GCTTCCCTGCCCAGGCCCGTTTCCCTCCCTCTTTCCCCAGAGGAAACCACCAAGAGGTTG
GCATATATTCTTCCTGAACGTGTTTTTATAGTTGTACTGCACTTGTACTGTGTATGAACA
ATATAAAGTTGGTTTGTGTGTTTAAAAAATTCACATACATGGATTTATAATGTATGTATC
ATTTTGCAACTTAAAAATTTTTTTTGAGCTCCATGCTGATTGATAACGATCTATTTTTT
TTTTTTGAGATGGAGTTTCAGTCTTATTGCCCAGGCTGAAGTGCAATGGCGTGATCTCAG
CTCACTGCAACCTCAGCCTCCTGGGTTCAAGCTATTCTCCTGTCTCAGCCTCCGGAGTGG
CTGGGATTACAGGTGCATGCCACCATGCCCAGCTAATTTTTGTATTTTTAGTAGAGATGG
GGTTTCACCATGTCGACCAGGCTGGTCTCAAACTCCTGACCTCAGGTGATCTGCCTGCCT
TGGCCTCCCAAAGTGCTGGAATTACAGGCATGAGCTACCATGCCTGGCCTTTTTTTTTTT
TTTTTTTGAGACAAAGTCTTGCTCTTTTTCCCAGGCTGGAGTGCAGTGGCCACAATCTT
GGCTCACTGCAACCTCTGCCTCCTGAGTTCAAGCAGTTCTCCTGCCTCAGCCTCCTGAGT
AGCTGGGATTACAGACATGTACCACCATGCCAAGTTAATTTTTGTATTTTTTGTAGAGAC
TAGGTTTTACCATGTTGGCCAGGCTGGTCCTGAACTCCTGACTTAAAGTGATCCATCTGC
CTTGGCTTCCCAAAGTGCTGGGGTTACAGGCATGAGCTATCGCGCCTGGCCTGAGAAATC
TCATTCTTACTCCTACTCCCTTGCACACTATCTCCATTCTGTAGGTAGCCATTTCTATTA
ATTTCTTGTTTACCCTTCTGTGTTTCTTTCATTCTTTTTCTTTTTTTCTTTTTTTTTTT
GAGACAATCTTGCTCTGTTGCCCAGACTGGAGTGCAGTGGTGTGATCTTGGCTCACCGCA
ACCTCCACCTCCTGGGTTCAAGTGATTTTCATGACTCAGCCACCTAAGTAGTTGGGATTA
CAGCGCCTGGTGTACACTACCACACCCAGCTAATTTGTGTATTTTTAGTAGAGATGGGGT
TTCACCATGTTGTCCAGGCTAATCTCCAACTCTTGGCCTCAAGGGATCTGCCTGTCTCAG
CCTCCCAAAGTGCTGGGATTATAGGCATGAGCCACCATGCCTGGCCCTATGTTTCTTTTT
ATAAAAATAAGCAAATTAATATTTTTATTACTATTTTCCTTTTATTTTTACACATCAAGT
AGAACATTAAATATATTTCTCTGTAATTTTTTTCAGTTACCTAAATCTTTTAGTGATCTC
TCTCATCTTTTTAATCAGCTGGATCGCATTCTATCATGTGAATATTTTATAACTTCTATA
TACTGTCACCAGCAGGTAGCGATTTAGTTGTGTCTAATATTTTAAAATGATATATAATGC
CTCAATGAATATAGTAACCTTTTGCATATATTGTTTTGTGCTTTGGGATAACACTACCTC
GTATTGGAAACTGTGTCATTACATGTGTCTTTAAAATTACATGTGTCTTTTTATTTTTAT
TTTTATTTTTTTGAGTGGGAGTTTCACTCTTGTTGCCCAGGCTGGAGTGCAGTGGTGAG
ATCTCGGCCGACTGCAACTTCCGCCTCCCGGGTTCAAGCGATTCTCCTGCCTCAGCCTCC
CCAGTAGGTGAGATTACAGGTGCCTGCCACCACGCCCAGCTAATTTTTGTATTTTTAGTA
GGGACGGGGTTTCACCATGTTGGCCAGGCTGGTATCGGTCTGCTGACCTCAGGTGATCCT
```

-continued

```
CCCACCTCAGCCTCCCAAAGTGCTGGGATTACAGACGTGAGCCACCATGCCTGGCCATCA
CTTTTTTTTTTTTCTTAATTGCTGCATAGTGGCCGGGCACAGTGGCTCACGCCTGTAATC
CCAGCACTTTGGGAGGCCAAGGCAGGCGGCGGATCATGAGGTCAGGAGACCAATACCATC
CTGGCTAACATGGTGAAACCCCGTCTCTACTAAAAATACAAAAAAATTTAGCTGGGCGTC
GTGGCGGGCGCCTGTAGTCCCAGCTACTTGGGAGGTTGAGGCAGGAGAATGGTGTGAACC
CGGGACGTGGAGCTTGCAGTGAGCCAAGATTGCACCACTGCACTCCAGCCTGGGTGATGG
AGTGAGACTCTGTCTCAAAACAAACAAACAAACAAAAAAATTGCTGCATAGTATTCCAT
TGTATGAGTAGTAACACAACAATTTTTATAATGCATAGTATTCCATTGTATGAATAGTAA
TGTAGCACTATTTGTTTATACATTTTTATGATTAAAAAACAAAATGTTTTTCTATTATGA
ATAAAGTGGCAATGAATATTTTTGTACAAGTGTTTTGGTAGCTATACAGTTATTGTCACT
TAATATATGCAATTCGATAGGCCAGTCATTCAAAATAGAAGATATACAAGGTAGGCCGGG
CGTGGTGGCTCACGCCTGTAATCTCAGCACTTTGGGAGGCCGAGGTGGGTGGATCACCTG
TGGTTAGGAGTTTCAGACCAGCCTGACCAACATGGAGAAACCTCATCTCTACTAAAAATA
CAAAAGTAGCTGAGCGTGGTGGCGCATTCCTGTAATCCCAGCTTCTTGGGAGGCTGAGGT
AGGAGAATCACTTGAACCTGGATTTATAATGTATGTAAATCCACCGCGAAGGTTGCGGTG
AACCGAGATCACGTCATTGCACTCCAGCCTGGGCAATAAGAGCGAAACTCCATCTCAAAA
AAAAAAAAAAAGATATGCAAGGTAAAGATACTAATAAAGACCTTTGTGTTGAGTTGGTT
GACATGTGGTTATTTCACCCATCGTATTTCTTATAGGGAATAGGTAAATTCGTTCCTTGG
GTTTCTTTCAACACTTAGGTAAAATCCGACGTGGAAGATGAGATCTGATTTTACTGGTGT
AACTCTTTATTTGTCCCCTTGCCTCCCTTTCCAATGGACTATTTTAGAAGAAATGGAGCT
GTCACCCACATCAAGATTCAGAACACTGGTGATTACTATGACCTGTATGGAGGGAGAAA
TTTGCCACTTTGGCTGAGTTGGTCCAGTATTACATGGAACATCACGGGCAATTAAAAGAG
AAGAATGGAGATGTCATTGAGCTTAAATATCCTCTGAACTGTGCAGATCCTACCTCTGAA
AGGTCAGTAACATTTTAGTGACCACAAAGTCTGCTGCTCCCTTGTGCCCTGAGTGTCAGA
AATGCATGACGGTCTGTGTATGACTCTCTGACTCCAAAGGCTTGTGACTGTTTTTTGAGC
TGTAATCTTTAAAGAATTACTAAAGTGAGACTAATAGCATCAAATTATTTTCAGAGTACC
TTTTTCCTGCAAAAGTTTTAATCAGTGTTACTTACACTCATCCTATAGGGGTTGCATACC
ATTCCTGCATATACTTGGTACGTGTATTAGTTTTAAGACTTATTGAACTTCAGCAGATAA
TCTTTGAGAGTTATTAGAGGAAAACAAATGATAATGGAGACACCAAAATAGCAGCAGTTT
TCTATGGTGGCTCTCGACCAGTTATTCAGCAATGTCACCAACAGATGTCAGTTTAAGCTC
AGAAGTGGAAAAGCAGAGAGCTCAGAGGGTCAGCTTTTTCATCAGTTCTTTTAATGTTAT
CACCACAATTATGTGAGAATGACCTTGCTTAGAGAAAATTATGTTATTTTCGAGATCTTT
CCCCCTGTGTTGGAACTAGGCTGATGAAAGCATGGGCTTGACTTATTTATTGATTGTATT
CGTTTTGTACATTCCCAATCTCCTCTCTGACTTGGTGCAAATTCAGGATCTCTTAGTTAG
TTTGTATATTTTGTGTCTTCAGGTATGATTTTTTCAGCTTATACCTTTATGTCAGTGCTA
TTATGTGCTGATAATTTGTTTCTCTAGCTACCACCGTAGCTTCAGGCAAAAGGCTGTCAG
CCAACTCTGTACAGTTTATTTCTAAATTTTACTGTTTTCAGTTGAGTATGGATGAAGAAT
AACTCAAAGTTTATTCTTTTGATGATGAGCCCTTAACACCACCTGCCATGATAGTACTTG
CTTTCTGACCAAGATCCTGAGGGAAAAAGCCACTTTATTATTAGAACTATGTTAAGATGC
TTCCCAAAAAACATGGAGCAGTATTGTCTCAAAGTCTGTCCTTGGATGGCTTTGGATGCC
TACATCAGGACTGTCTGATGTGCTGGTTAAAATGCAGATTCCTGGGCCTCATTCAGACTT
```

```
ACATGTATTGATATTGCTGGTTGTGGAGCCTGGGAATTCATATTTTTAGCAAAATCCCTC

ATTTTTACTCCAAGTCTTATGTGCATTATACAGTTTGAGATGATCACCCAGGATATAGTC

CAAAGACACTGGAGGCTGTTGAAGTATAGGTTGTATATATGGAAAAGGTTGGAATGTTTG

AATTAATTTATAATGAAGATCCTTTTTAATTGAGTGTTCACATGCCAAGGCAAGGACAAA

CATTCAAAATGATTTTCTGTCTCTGTTACAACTTTTTCTTTCTTTTTTTAATTTATTTA

TTTGAGATGGAGTCTCACTCTGTCACCCAGGCTGGAGTCAAGTGACGCGATCTCGGCTCA

CTACAACCTCCGCCTCCCAGATTCAAGTAATTCTCTTGCCTCAGCCTCCCGAGTAGCTGG

GACTACAGGCATGTGCCACCATGCCCAGTTAATTTTTGTATTTTTAGTAGAGACAGGGTT

TTGTCATGTTTGCCAGGCTGGTCTCAAACTCCTGAACTCAGGTGATCCGCCCACCTTGAC

CTCTCAAAGTGCTGGGATTATAGGCGTGAGCCACCGTGCCTGTCTATTACAACTTTTT

ATTACAACTTCTTTATTTTGACTTTATTTTTACAAATTATTTATTTATTTTTTTGAGAT

GGAGTTTCGCTCGTCACCCAGGCTGGAGTGCAATGGTGCGATCTCAGCTCACTGCAACCT

CCGCCTCCCAGGTTCAAGTGATTCTCCTGCCTCAGCCTCCTGAGTAGCTGGGATTACAGG

CACTTGCCACCACACCCGGCCAATTTTGTATTTTTAGCAGAGACAGGGTTTCACCATGTT

GGTCAGGCTGGTCTCGAATTCTTGACCTCAGGTGATCCACCTGCCTCGGCCTCCCAAAGT

GTTGGGATTACAGGCATGAGCCACCACGTCCGGCCGACTTTTATTTTTTTTCTTGAGAC

AGGGTCTTGCTCTGTCACCCAAGCTGGAGTGCGGTGGCATGATCATAGCGCACTGCAGCC

TCGACCTCCTGGACTCAAGTGATCCTCCTGCCTCGGCCTTGTGTATAGCTGGGATTACAG

GCAGTTGCCACCATGCCAGGCTAATTTTTAATTGTTTTGTGAAGATGGGGATTTCACTGT

GTTGCCCAGACTGGTCTTGAACTCCTGGCCTCAAGTGATCTTCCTGCCTTGGCCTTCCAA

AGTGTTGGGATTACAGGCATAAGCCACTATGCATGGCCTGTAACTTCTTTAAATGGCTAT

AATTAAACAGTTGGTCCTTTTAAGATTGGGCAATGGACGAATGGCAAATTGCATTTTTAA

AAGAGGAGGGATTTAAAAAAAAACAGGAAAGATTGGGGCATTTGTCTCTAAAGGACTGTG

GACTCATTTAAGAAGTTTAGTGGTCATTCTTACCATCTTTGTGGTTTTTCCTGCCTGCAT

GGGATGCAGATTTTCTGTCTCAGGTGGGATTGATCAATCCCTTGGAGGAATGTGTCTACT

TTTTAATTGTGTTTAGGAGAGCTGACTGTATACAGTAGTTTTGTGAAAGAACAACATGAA

CCCATAGTAGAGCTAAATTCTTTTTTATTTTTTAAAAACTTTAGGTGGTTTCATGGACAT

CTCTCTGGGAAAGAAGCAGAGAAATTATTAACTGAAAAAGGAAAACATGGTAGTTTTCTT

GTACGAGAGAGCCAGAGCCACCCTGGAGATTTTGTTCTTTCTGTGCGCACTGGTGATGAC

AAAGGGGAGAGCAATGACGGCAAGTCTAAAGTGACCCATGTTATGATTCGCTGTCAGGTA

AATCTCCAGTTGAAAAATGGGTCTGGCAAGATGTTACCTTTGGGTGATTTTCTGCTGAC

AGAAGACAGACACCATTACATTCAAAGTCAGATTGTCTTTTATTTATTTATTTATTTATT

TATTTATTTGAGACAGGGTCTTGCTCTATCACCTACAGATGGGGTTTCACCACGTTGGGT

CTGGTGACCCAAATCTTTGGGTGATTTTCTGCTGGAAGAGGACAAACACCATTACATTC

AAAGTCAGATTTTCTGTTTTTTTTTTTTTTGTTTTGTTTTTTAATATTCATTTGTT

TATTCATTTGAGACTGGGTCTTGCTCTGTCACGCAGGCTGGAGTGCAACCTCCCTGGGCT

CAGTTGATCTTCCCTCAGCCTCTTGAGTAGCTGGGACTACAGGTGTGTGCCACCATGCCC

AGCTAGTGTTTGTATTTTTTGTGGAGATGGTGTTTTGCCGCATTGCCCAGTGTGGTCTTG

AACTAGTGCTCAAGAGGCCTGCCTCCTTCAACCTCTCAAAGTGTTAGGATTACAGATGTG

AACTACTGTGCCTGATCCAAAGTCAGATTTTCTTTGCTTACTTAGTCAAGTTCGTCTATG
```

```
CTTTTATTATACTTAATATATTAGTATAGTTACTGTATTAGTATATTAGCATATTTAATA

TATTATTATACTTATCATACTTGAGTATATTGAGTATATTTACACTTTTAGTATATTTGT

ATACACACACCACATTTTTATTATTTATCTTTTTTTTGAGACAGAGTCTCCCTCTGTCTC

CCAGGCTGAAGCACAGTTGGCTCACTGCAACCTCTGCCTCTTGGGCTCAAGTGATTCTCG

TGCCTCACCCTCCTGAGTAGCAGGGATTACAGGTGTCCACCACCAAGCCTGGCTAATTTT

TGTATTTTTAGTGGATATGGGGTTTTACCATGTTGGCCAGGCTGGTCTCGAACTCCTGAC

CTCAAATGATCTGCCCGCCTTGGCCTCCCAAAGTGCTGGAATTACTGGCGTGAGCCACTG

CACCCAGCCTATTATCTGTCTTTTGATGGACATTTAAGTTGTCTCTATATACTAGCTATT

GTGAATAATGCTGCAGTGAACATGAGAGTGCTTGAAAACACTAATGTAACATAAAGGTAA

CAAATAATAAATGTCATGTGTTTATCTTGAAAGGAACTGAAATACGACGTTGGTGGAGGA

GAACGGTTTGATTCTTTGACAGATCTTGTGGAACATTATAAGAAGAATCCTATGGTGGAA

ACATTGGGTACAGTACTACAACTCAAGCAGGTGAGCAGATTGGAAAGCTCAAGCTTTCTC

CTTAAAAACTTAAAACAAATCCTAATAGAGAATTTTGCAAACATACAGAGGTAGACAGAA

TAGTATCATCAGCCTCCATGTACCCATTGCAGCTTCAACTATCAAATCTTTTTTTTTTT

TTTTTTTTTGAGACAGTCTTACTCTGTCACCCAGTCTGGAGTACAGTGTTGCAATCTTGG

CTCACTACAACCTCTGCTTCCTGGGTTCAAGCGATTCTCCTGCCTCAGCCTCCTGAGTAG

CTGGGACTACAGGTGCCCACCACCATGCCCGGCTAGTTTTTGTGTTTTTAATAGAGATGG

GGTTTCACCATGTTGGCCTGGCTGGTCTTGAATTCCCGACCTCAGGTTTTCTGCCCGCCT

TGGCCTCCCGAAGTTTTGGGATTACAGGCGTGAGCTACCACGCCCGGCCCTAAATCTTTT

CTTATTATGATTCCACTCACTGACTGCCGCTATAGTACTTGGAAACATATTCCAGATTTA

TATTATTCCCATATTTATCTGTAAAAGGCATTACAGAGGTTCTTTTTTTTTTTTTTTT

TTTGAGATGGAGTTTTGCTCTGTCGCCCAGGCTGGAGTGCAGTGGCGTGTTCTTGGCTCA

CTGCAACCTCTGCGTCCCGGGTTCAAGAGCTTCTCCTGCCTCAGCCTCCTGAGTAGCTGG

GATTATAGGTGGTGCCACTACACCCAGCTAATTTTTGTATTTTTAGTAGAGATGGGGTTT

CACCATGTTAGCCAGGCTGGTCTTGAACTCCTGACCTCAAGTGATCTGCCTGCCTCAGCC

TCTCAAAGTGCTGGGATTATAGGCATGAGCCACTGCATCTGGCCTAAGGCTGTACAGAGT

TTTAAAGCAAGTTTTCATTATAGATCCACTTCTGGTTACCTTTAGGTAACCTCACTTATT

CACTTTGGCATTGTTGCTATTTCAAATTTCACCTTTATGATAGTGGAAAATGATATAATC

TCTCTAAATAATGTGGTCTATTCATAAAGAAAAATAGGCTTGAATTTATATCAGCAGAGT

AAAGTGTATGTGAAGACTGAAGAAAGATACATTTTCTGGCTGAACAGAAAACACGGTGAA

ACGATTTGAAAACTTTTATTGTGAATTACAGGGTCCTATGAACCCTCTGTCCGTGCCTTT

ATGAATATCAACATAGACATGTTTTTTTTTTTTTTGCATTAACACCGTTTTCTGTAA

TATTTTCTTTATTTTACATCAACTGCTGTACTCGATCAGCCCCTTAACACGACTCGTATA

AATGCTGCTGAAATAGAAAGCAGAGTTCGAGAACTAAGCAAATTAGCTGAGACCACAGAT

AAAGTCAAACAAGGCTTTTGGGAAGAATTTGAGGTAAGTTATTAAAAAACTGTTTTTACG

TGAGTTGTTATATCCTATTTTTAGTGGAGGAGAAGTTGCTCTTGTGTTTGGAATTGGACC

TGAGAGACTTGAAACTGACGTCCTTTTTTAATTCGGCCATTGATTGACACGGAGCAAGTT

GCTGAGAGGGCTTCTTCGAAACAGAAGAGCATTGTGTTCTGAGGGAAGGGAGTTGGCAGT

GAGTAGTCAATGGATGTGCTAGCCGCTCCATTTGGCTCTTTTGGTTTGGACTGGTGGCAA

AATCTCAGAGAAACAAAAGGATCTAATTTCTTCGAAAGATTTCCAGCATGCACTGGGGTC

TTTAGAAACAATCTATAGCCTTAGTGCAGCAAATGAGTATGAGTAAAAGAGAAACACCTT
```

-continued

GTGGTGGCTTTTTTTTTTTTTTTTTGAGACAGGGTCTCGCTCTGTCGCCGAAGCTGGAG

TGTAGTGGCGTGATCTCGGTTTACTGCAGCCCCGTCCTCCCTGGGCTCAAGTGATCTTCC

CATCTCAGCCTACTGAGTAGCTGGGACTACAGGCACATGCCCCTATGCCTGGCTAATTTT

TGTATTTTTGGTAGAGATGAGGTTTTGCAGTGTTGCCCAGGCTGGTCTTGAACTCTTGGG

CTCAAGTGATCCTCCTACTTAAGCTTCCCGAGTAGCTGGGACTACAGGCACACGATACCA

TGCCCATCTAATTTTTGTATTTTTTGTAGAGATGGGGTTTTGCAGTGTTGCCCAGGCTG

GTCTTGAACTCTTGGGCTCAAGTGATCCTCCAGCTTTGACGTGCCAAATGTGGTGGCTTT

AATTTCAGAGTTCAAATTGATAACTCTGGTAAGTTAAGTGAACTGATTTCTTTTTTTTTT

AAATTATTTTTGTTGATTATACTTTAAGTTCTGGGATATATGTGCAGAACGTGCAGGTTT

GTACATAGGTATACATGTGCCATCATGGTTTGCTGCACACATTAACCCATCATTTAGGTT

TTAAGTCCTGCATGCATTAGGTGTTTGTCCTAATGCTCTCCCTCCCCTTTAATGCATCAG

TGAAAAAGTGATGATAGGCTGGGCGTGGTGGCTCACTCCTGTAATCTCAGCACTTTGAGA

GGGTGAGGCAGGTGGACCACTTGAATCCAGGAGTTTGCCCCCATCCCCAGACAGTGTGTG

TGATGTTCCCTCCCTGTGTCCATGTGTTCTCATTGTTTGGTTTTCTGTTCCTGTGTTAG

TTTGCTGAGAATGATGGTTTCCAGCTTCATCCATGACCCTGCAAAGGACATGAACTCATT

CTTTTTTTATGGCTGCATAGTATTCCATGGTGTGTATGTGCCACATTTTCTTTATCCGGT

CTATCATTGATGGGCATTTGGGTTGGTTCCAAGTCTTTGCTATTGTAAATAGTGCTGCAA

TAAACATATGTGTGCATATGTCTTTATAGTAGAATGTTTTATAATCCTTTGGGTATATAC

CCAGTAATGGGATTGCTGGGTCAAATGGTATTTCTGGTTCTAGATCCTTGAGGAGTCACC

ACACTGTCTTCCACAATGGTTCAACTAATTTACACTCCCACCAACAGTGTAAAAGCATTC

CTATTTCTCCACATCTTCTCCAGCATCTGTTGTTTCCTGACTTTAAGTGAACTGATCTCT

TTCCTGAAACTAACTTGGGTTGGAGAATGTCCCTGATGGGAATGTGCTGTGTTCCCATTG

CACTCTTCTATATCACTTACCCATTGACAATGTGATCTCTTTCATTTTCTCCTCATCCAT

TTGACAGAAAACTTCAAAAACAAGGATTCTGGCATATTTACCTTTGCAGTTGTCCCCAGC

ATGTAGCACGGTGCCTAGTACACAGAAGAAACTCCATAAATGTTTGTTGAATGAGATTTA

CATTTAACTCATGTTTACATCATTTTATTTTCCTGTTCTGTTTTATGGGAATGATTATTC

TATGCTTTTTGAGGACTACAATTTATAAATATTTGTGGATTGAATGAATAAGTGAATACT

GGGCAAATAAAGTCCTTTTAGCCAGAGTATGTCTGAACAACTTGCTGAGATAGATATGAT

TTCCCATTTTCCAGCTGAGGGGCCTAAGGGAGGTAAGTAAATTATTCAATCTTCATACC

ACAGTTTTGTTTTGTTTTGTTTTGTTTTTTTTCCTCCTGAGACAGAGTCTCACTTTGCT

GCCATACTGGAGTACAGTGGTGCAATCATAGCTCACTGCAGCGTCCAACTTCTGGGCTCA

CGCCATCCTCCCACCTCAGCCTCCTGAGTAGCTGGTACTACAGGTGTGCACCACCATAGC

CGGCTAATTTTTCATTTTTTGTAGATATGGGGTCTCACTGTGTTACTCAGGTTGGTCTTG

AACTTCTGAGCTCAAACAATTCTCCTGTCTTGGCCTCTCAAAGTGTTGGGATTACAGGTG

TGAGCCACTGTGCCCGGCCCATACCACAGATATTGATTGAATTCCAGCAGTGGGGAGGAG

TGTGGAATAGAACATTCTCAGTCCTTGCTCAACATTACTGAACAGAGACTTGAATTTGAG

TTTATTCTCTCATCCCAGGCTTCGCGTTAGGCTCTGAAGACACTAGTGAACAAGACAGAC

AGGGTTACTGCCTTTAAAGGGAGCTTTTAGTTGAGAGAAGGAAAACAGTGATGAAAAGCA

TCAGTGAAAAGTGATGATAGGCTGGGCGTAGTGGCTACTCCTGTAATCTCAGCACTTT

TAGAGGGTGAGGCAGGCAGCTCACTTGATTCCAGGAGTTTGAGACCAGGCTGGGCAACAT

-continued

```
GGTAAAACCCCGTCTCTACAAAAAATACAAAAAGTAGCTGGGTGTGGGGGTGCGCACCCA
CAGTCCCAGCTACTCTGGGGGTTGAGGTGGGAGGATTGCTCGAGCCTGGGAGATTGAGGC
TGCAGTGAGCTGAGATCACGTCACTGCTCTCCAGCCTGAGCAACAGAGCCAGAACCTGTC
CCAAAAAAAAAAAAAATTGATGATAAACATAGTGAGACAGAATTTTGAAATCTCAGCCTC
ACTGTTGCCTTCCTTGTCCCCTGCCTGCCTAAATAATAAAAGGCAGCATTTCAGCAGTCA
TTCATTTCATTACTTTCACTTCATTTCACCTTCATAAAGCCTCATGAGGTAAGATGGGAA
GATACAGAAGTTTTAGAAACCGCTCATCAAAATTGAATGGAAAGCCGATTGTTCCAAAAC
TTTTTAGTGTGGAAAATTTCTATTATATGCAAAAGTAGAGAGAATGGGATAGTTATAGCA
GTATACCTGACACCCAGCATTAACAACTGTTGATAATATGGCCAATCTTTTTCGACTCTG
CCCCACTCACTTCCCCAGCCCTGACTTGTCTTGAAGCAAATACTTTTTTTTTTTTTTGA
GATAGAGTTTTGTTTTGTTTTGTTTTTGTTTTTGAGATGGAGTCTCACTCTGTCCCCCA
AGCTGGAGTGCTGTGGCTTGATCTTGGCTCACTACAACCTCCGCCTCCTGGGTTCAAGTG
ATTCTTGTGCCTCAGCCTCCTGAGTAACTGGGATTACAGGTGTGTACCACCATGCCCAGC
TAATTTTTGTATTTTTAGTAGGGACAGGGTTTTCACTATGTTGGCCACGCTGGTCTCAAA
CTCCTGACCTCAGGTGATCCGCCTGACTTGGCCTCCGAAAGTGCTGGGATTGTAGGTGTG
AGCCACTGCTCCCGGCCTTGAAGCAAATCTTAACACATCATTTCGTCTGTAACTATTTTA
TTTCAAAAAATTATAACCTGAATAGCATTATCATATCTAAAACTATTAACAGTATTTCCT
TAATATTAACACATATCAGTCACATTTTCCTGATTGCTACACACACACACACACACACAC
ACACACACACTTGCAATTTGTGTTTTTTCTTTTTAGATGGATCTCACTCTGTTGCCC
AGGCTGGAGTGCAATGGTGCATTCTCAGCTCACTGCAACCTCCACCTCCTGGGCTCAACT
GATTCTCTTGCCTCAGCCTCCTGAGTAGCTGGGACTACAGGTGCCCACCACCTCACCTGG
CTAGTTTTTGTATTTTTAGTAGAGGTGGGGTTTCACCATGTTGGCCAGGTTGGTCTCAAA
CTTCCGACCTCAGGTGATCCACCCACCTTGGCCTCCCAAAGTGCTGGGATTACAGGCATG
AGCCACTGTGCCCAGCAGCAATTTGTTTGAATTGGGAGTGCTTTCTTCCACCTTGATTAT
GAAAAAATTTCAAATGTGTATAAAACAGATTCATATAAAGGATCCTGATATGCCATTATC
AGCTTTATCAATTATCCCTGTCATCATATTTTTATTTATAAATATTTCAATATTTGTGG
AATCCTTAAAAATGCATCACATAACCCAACATTGTTCATATTATACCAATTGTCTTATAA
TTTAAAAATATTTTGTTCAATCATTTTTCAGATAAGCTTCACACACTGTGGTTGGCTAAG
TCTCATAATATTTCTGTTGTAAAAATCTTAAGTCTGGGCGTGGTGGCACACGGCTGTCAT
TCCAGCACTTTGGGAGGCTGAGGTGGGCGGATCACGAGGTCAAGAGATCGAGACCATCCT
GGCCAACATGGTGAAACCCGGTCTCTACTAAAAATACAAAAATTAGCTGGGCGTGGTAGT
GCGTGCCTGTAGTCCCAGCTACTCGGGAGGCTGAGGCAGGAGAATCGCTTGAACCCAGAA
GGTGGCAGTTGCAGTGAGCCGAGATCGCGCCACTGCACTCCAGCCTAGAGACAGAGTGCG
GCTTCATCTCAAAACGAAACAAAACAAAACAATCTTAAGTCTCTTAGAATACTTTGATGC
CCCTTCCATCTCTCTTTTTCTGTCTTCCTTCCCCCTCTCCCTGTCTTTTCTGCTGTTGAA
GAAAGCAGATCATTTGTCCTGAGAGTTACTTATAGTCTGAATTTTGCTGAGTGCCTCTCT
GTGGTGGACTTAAGCATGTATCCATCCCTTATATTTCTTGTAAGTTGATATATCTAGAGA
CTTCATTGGATACAAGTTTTCTTTGGCAAGATAGCATGTATGGTGGTGTATCAGGAGGTG
TTTATGTCCTGTTGTTTCTTCTCTGATTTTCTTAGCAGCTCCTGATCATTATTACTTAGA
TCCATTAATTCATAAGGGACTATATGGTAGTGATATTGTAATTTTATCATTCTTCTTCAT
TTGTTAGGTTGGCATATTTCTATAAAAAGCTTTTCATCGCCGAGGGTTGATTTTTCCTT
```

-continued

```
CTTACTAAGCAGTTTTCTTTTCTTTTTCTTTTTTTTTTTTGAGGTAGGTCTCACTGTG
TTGCTCAGGCTGGTGTGCAGTGGCGCAAACACACAGTTGCGAACTCTTGGGCTGAGGTGA
TCCTCCTGCCTCAGTTTCCTGTGTAGTTGGGACCACAGGTGCATGCCACCATGCCTGGCT
AATTTTTTGATTCTTTTGTAGAGATGAGGTCTCACTTTATTTCCCAGGCTGGTCTTGAAT
GTCTGGGCTCAAGCAATCTTTCTACCTCAGCCTCCTGAGTAGCTGGGACTACAGGCACAT
ACCACCATGCCCAGCTAATTTTTTAATTTTTATTTTTAGTAGAGATGTGGTCGTATTATG
TTGCTCAGGATGGTCTCGAACTGCAGAGCTCAAGTGATCCTCCTGCCTCAGCCTCCCAGT
GTGCTGGGATTATAGGTGTACTACAGGCAAGAGCCAATGAGCCTGGTCAGATTTTTTTT
CCTGATTTGAAATCTGTTATGGGTTCAATTGATACTTCCAAATCAAACTCAGGGTTTCAG
GATTTTTACTAACCTCATTGATCTTACCCATGTATCTCCTTTCTCTAATGCCAAAAATCC
TACTTCTTGAAGCCATAATAAGATTATTCATTTGTTTTATCCCACATTACACACAACAAT
CTTAGAATAATGACTTCCCAATAATATGATTACTGAAAACAGTTTAATTTTTTTGCGCT
TTTCAAAAAAATCCTTCAGAGATGTGTAGTCAAGTTACTGTATTCTGCTGGGCACAGTGG
CTCACGCCTATAATCCCAGTACTTTGGGAGGACAAGAAGGGAGGATCGCTGGACCTCAGG
AGTTTGAGACCAGCCGGGGCAATATAGTGAGACCCTGTCTCTACAAAAGAAAATTAAAAA
TTAACCAGACATGGTGGCATGTCCCTATAGTCCCAGCTATTGAGAGGCTGTGGCGAGAGT
AGGCTTAAGCCCAGGAGTTTGAAGCTGCAGTGAGATACGATTGTGACACTGTACTCTAGG
GTGACAGAGCAGGGACCCTGTTTTAAAAAAAAAAAATGAAAAAACTTCCTGTGCCTTAG
ACTCATTTGTAATCGTCCTTCTCTCTGTGTGGCTATATGCTAACTGGGTATATGGTTAGT
TTATTTGTTTCATTTAAAAAATCTCTTTCTGTTAAGTTTTATTTATAATTACACAAATAC
TGGCTTTGATAGTCAAATTGAAAAAACAAAGTGTATTCAAAGAAGTCTACCTTCTATCCT
TGTCCTTTCCTATGTTTTAGCCATAGTATAAAAAGTTATGGTTTATCATTATATTTCAAA
AATATAAGAAGATATTCCCATATCCCACTTTTTCTTAAACAGTAGCATAACTTTACATAC
TTTTTTCTAACCTTGCTTTTTTAAATATCCTGGACATCCTGGATATCCATAATAGTGTCT
AGAGATAGTCTTCATTCTTTTTTTACTGTATAGTAATCCACTGTGTACTTGTACCATAGT
TTATTCAACCTATTGATGGGCATTTGGGTAGTTTCCAAATGTATCACAGAGAGGATTACA
GTGAATAGCCTTGTGTATGCATCCTGCTTTACTTTTGCTGACTACTGGTAATATTAACAT
TTTTTATGTTCTGTATTTAAAAAATGGTGGTTATTATTCATCTATAACTTTTATTATACA
TGACTTTGGTTAGCATGCTTTAACCTTTTAGCATAACATTTGCAAGCTACTTGTTTTAAT
TAAAATTTTGGTTAAATGTAAAAAATAGTGAGCTATTTTGTAATCTAGATTCAATAGAAT
CTTATACTTCCTTTACAAATGATAGCTGAGTTGATCATTTGTGTAAATGACTGTGAACTT
AAAAATTACAGCATTTTTAAAATAAATTTTTTAACATTTTAAAATTATTTAAAATAAT
AGACACACAAAGTAAAAAGAGAAGAAAAAAAAAGAGACAGGGTCTTGCTATGTTGCCCA
GGCTGGTCTCAAACTCCCAGGCTCAAATGATCCTCCTGCCTTGGCCTCCTAAAGTGTAAG
CCACCACACTTGGCAAAAATTAGTTTCTTTAAAACAAAAACATTACAGGTTATCTGGTAC
CATGGTAGCTTCTTTAACACTAGGTTCACTTAGAACAAAGCTTAGGAACAAAGTCAGACT
TTCACAAAGAGCTTGTGTGGCAATGGGGTATTTTTTGCAAATTCCATTGGTGGGGTCAAG
ATGTGAGTTTAGAAGGAACTCTTAGCCTGACTCTTCTGGCCATGGAAAAAGATGGTTGCT
TCTAAATGCTGACCTGGTGATTTTACACTGTCACATCTCAAATTGTGGTCATCTTTTATA
CATTATTAACAACAAAAGGGAAAAATTGAGTTGACTTTAAGAGGAAGTGGAAAATAACGA
```

-continued

```
GATCACATCTGTACTCTACAGGCTCTCCACAGAGGTCAGACTGAGGTGGTAAAATTGTTG

TGCACTAAATTAGGGCATTAACGTTTCATGGAAACTGAAGCTATATCTAAATAGCTGATG

GCCTGCTTTCTAGATCTCCTATATACCTGCTTCTCAAATTCAGTCTGTTTTAAAAAATTG

CCCTTTGAGGTTGGAACCAGCGAAATAAGGCTGAAAACAGAATAAGCCATTATTGAAAAA

ATTAGGAACTTGGAAGCAGATACTCATAATCTAAATCCTCTGAAGCTAAAGTTTGATCCA

CAATAGCAAAGCATTATCATTTTAGTGATTGTACCTTAGTTGTTTCCTGGCAGGTGATAA

ATTTGGGATCACTTTCTTCTTACAGTGTGCTCTGATAGTCTTTAAAACAAACCAGAGCTC

TAAATTGTAATGCCATTGGTAATTTAACTCTGATTTGTCTCTATGCCTGTCTCCTGGTGT

TCTGTAAAATTCTACACGTCATTTCAGGTATCACTATCCAGAAGACGTTACTTTTGCCTT

TGATGCACTTTAAAATGTGAAGTCTCTTGTGAAGCTCTTTGGTTATTTTCTCCTTTGCTG

CTGAAATAAATTCAGGTTGATGATTTTCTTGTAGGATATGTTGTGTGATCTAGACATTGC

AAACCCAAGTCTTTGATTTTTTTTCCCTACAGATTGCCTGTTTCTTTTTTATTTTAATT

TTTATTAGTTATTATTATTTTTGAGATGGAGTCTCACTCTGTCACCCAGGCTGGAGTGCA

GAGGTGTGATAGCTCACTGCAACCTCCACCTCCCGGGTTCTTGTGCCTCAGCCACCCAGG

TAGCTGGGATTACAGGCACGTACCACCACTCTCAGCTAATTTTTTGTATTTTTAGTAGG

GATGGGATTTCTCCATGTTGGCCAGGCTGATCTCAAACTCCTGACCTTAAGTGATCTTCC

TGCCTTGGTCTCTGAAAGTGTTGGGATTACAGGTGTGAGCCACTGTGCCTGGCCAGTTAT

TAATTTTTTTAAAGAGATGGGGTCTCACTATCTTGCCCAGGCTGGAGTGCAGTGGCTCTT

TACAGGCACTGTTGTAGTGCACTGCAGCCTTGAACTCCTGGGCTCAAGTGATCCTCCTGA

GAGGCTGGAATTACAGGCACACACCACTGTGTCCAACAGATTGCCCATTTGTGATCTGTG

TAAATATCTCTCACTTCCTGCAGTATCTCTGCTCAAGAATGTAAAGAGATGGATAATATT

TTTAGATTTGTTGAAACAAAGTAAAGTTCTGCTCAAATGAGAATGACACTAACTAAATGA

AAAGGCCGGTTATAATTCTGTAATTTTGTGCCTGCAATGTGTGTTATTGTACACTTGA

ATCGGCCCTGTGCATTGTGGCGAGGTGCATATTGCATGGTTGTATTGAAAAGGTGCTTGG

GCCGGGCGTGGTGGCTCACACCTGTAATCCCAGCAATTTGGGAGGCTGAGGCAGCTGGAT

TACCTGAGGTTAGGAGTTCAAGACCAGCCTGGCCAACATGGTGAAACCCTGTTTCTAGTA

AAAAATACAAAAAATTAGCTGGGTGTGGTGGTGGGTGCCTGTAATACCAGCTACTAGGGA

GGCTAAGGCAGGGAGAATTGCTTAAACCTGGGAGGCAGAGGTTGCAGTGAGCTGAGATTG

TGCCACTGCACTCCAGCCTGAGTGTATCACAAAAAAAAAAAAAAAAAGGTTTTTGCCCTCT

CTCTGTGCCTGCTGCTCCCTGTTGAGTCCTATAGGCCTGAGCTGCCAGGGGGTACTGTGG

GCTGAGACTGGACATTGCAACCGACTGCAAGGCACCGTGGGACCCAGGTTGTGGATGGAC

TGTCTCTCGGGCTTTCTTCTTTCCATTCATCTTCCTCCTCTAACTCCCCTCTGTATCCAG

TATCCTTGCTCTCCATACACCTGCTTCATTCTTTTTCCTTCAGTAGATTTTTCTGCTTCT

TGACTTACAAACCCTACTTCTAGCCCCTTTCAGATATTGAAACTAGCAACTTTCAGGCTT

TGTACCAAAGTCTCAGAGATTCTCATTGACTCGGATGCCATCCATCTCTAGTCCAAAGAA

CAATGTCAAGGACATGAACATGTGGAACAAAAGTGTCTGCTGTGGACACCTTTGGGGAGA

AATAGTTTTCAGTGATGAGGGTTGTAGTGAGTTGGGCAGATATCCCAAAAATATCTGCCA

AAAACTATAGACACTTCTGGTTGCAGTGACTTATTCCTTCCTTCATTCAGCAAATACTGA

TTGAACACCGACTGTATGTCTGGATCTATTCTAGGTTTTGGGGGTGGAGCAGTGAACAAA

TCAGTCTTTATCTTTATAGAGTGTACAGTCAAGTGGGAGAGACAGGCAGTAAACAAAGAA

ACAGTTCAATATTCAATCTGTGAGATGGTGATAAGTGCTACAGAGAAAACAAACTAGTGT
```

-continued

```
AAGATAAAAAGGGTGTTTTGATAGGCCTTTACTATTTAGGTCTCTTTGATAAGGTGGCAT

TTGAACAAAGCTCTGAAGGAAATAATGGAGCCAACCATGCATATAACCTCAGGGAGAACA

TTCTAGGTAGAGGGAACAGCAAGTGCAAAGGCCCTGAAGTGGGGGTTTGTTTACCTTGTT

GCACAATCTGCACACAGGCCAGTACAATTGGAATGGATGGGAAATGTAAAAGAGAGAAGT

TGAAAAGGCCAGGTGCAGTGGCTCATGCCTACAATCCCAGCATTTTGGGAGGCTGAAGTG

GGAGGAATTTGAGATCAGCCTGGGCAACAGAACCAGACCTCGGGCTAATTTTTGTATTTT

TAGTAGAGACAGGGTTTCACCATATTGGCCAGGCTGATCTCAAACTCCTGACCTCAGGTG

ATCCTCCTGCCTCAGCCTCCCAAAGTGCTAGGATTACAGGTGTGAGCCATGGCCCCCAGC

CGTATCTTTGTCTTAAAAAGTAATCTCTGTGCTTGGTAGGCCAAGAATTTAAAATATAAA

AAATTTAAGAAAGAAAAAAAATAAGTAAAGTAACTATACAGGTTGGTCTGGCCGTAATGG

TGAGTGTCATTATTTTTCTTCCCTAGGTATTTTGGCTCTGTTGCTCAGAGCAGTGCAGGC

GAAATGGTCATTAGGGCATCGTCATGGTGCCTGGGGATGCCTGGCTCAGCCAGTTTATTT

TCTGTCTGCCTCTCTCCTTGGTCCTTTTCCTCCACTTTCATTCATGAAATTCTAGTCAAG

AGCTGGGTCCAGTGGTTTTCAATCCAAGGGCTTTGGAAGCCTCTGGGGTCTATTTTGGTC

ATTGCAGTCACTGGGCTGCTGCTCCTGGCATTTAGGTTGGCAGGGGTCTGGGCTGGGAAG

CAGGAATGTTCAGTGGCCATAAATGTAAGGGTTGGTCTTACATTTACATAAGGGAGACAA

TGAAAACTTAACTCCTCCACAGTAGTGGAGTAGTGCCGTTGGGTACTCACAGTCAGTAGT

GCCGTTGGGTACTCACATGTACAACATGGATCAGGACATTGACTTTCTGTGGATACCTTT

TAATAGTTTATTAGATGTGTTAGGCTGTTTTGCACTGCTCTAAAGGAATATCTGAGTCTA

GGTAATTTATAAAGACAAGAGGTTTAATTGGCTCATGGTTCTGAAGGCTGTACAAGCATG

GCTCCAGCATCTGCTTCTGGTGAGGGCCTCAGGAAGCTTCCGGTCATAGTGGAAGGCAAA

AGGAGGGCAGACGATCACATGGCCGGAGTGGTGGCAAGGGTGGGGTGGGAGCCACGCTCT

TTTTTTAATTTTATTTTAATTTGAGACAGTGTCTCACTCTTTTGCCCAGCCTGGAGTGCA

GTGGCGTGATCTCAGCTCACTGCAGCCTCTGCCTCCCAGGTTCAAGCAATTCTCCTGCCT

CAGCCTCCTGAGTAGTTGGGACTACAGGCGCGCATCACAATGCCCAGCTGATTTTTGTAT

TTTTAGCAGAGACAGGGTTTCACCATGTTGGCCAGGCTGGTCTCGGACTCCTGATCTCAA

GTAATCCGCCTGCCTCGGCCTCCCAAAGTGCTGGGATTACAGGCATGAGCCACTGCGCAC

GGCCACCACACTGTTTTAAACAACCAGATTGCACGTGAACTTAGAGTGAGAACTCACTGT

GAGGATGGCACCAAAACATTCATGAAGGATCCACCACCTTCCTTTAGGCCCCACCTCCAA

CACTGGAGGTCATATTTCAACTTGAGATTTGGAGGGGACAGACATCCAAACCGTATCATT

AAATTTAATAGTTTTATGCAGTTTTTTTGGCTCTAGATCTGTTTAGACTCCTGCAGTCAG

GTGTCTGTAACTAGCCTCTGGTCCTTTTTGAGAGTTCACAGTTTGGTGCAAACCCTTTGG

ATGTATTATTTGGGAAAATGGGATATCTGGCAGCCTGTGTCCCTGCTTTACATTATCCTT

TTTGCTGCCTGCCCCAAGCCTCCTCATTAGCATCCCTGCCAAGGCCAGTGGAGAAGGATG

GAGATGCGGTGACATTCAGCTTGACAGGTCATTAGCAGCTTTTGTGCCCTAGGGACTGCT

GGTGGGAGGGAGGTTGTGGAAGATAAACCCTGACAGGAATGTATTCTCCTCGAGGGCAGG

GTTTATTTGATATTTTTCTGGAGCTTAGAACCATAAGCCTGGTGCTGGGGAGGAAGCGCC

CTTAGCATTTGGTAGCCTCTGTGGGCAGAGCATGGAAAGTCACAACTTCTGAATTGTTTG

TATTTTCAGTCTCACTCTAGATGGATGGCATCTTCTGCTATGGGAAATGAAATATGTTTA

GGCAACTTGAGTCCCAGGTGCAGATGAGGCTGGGCTAATTGGTGCACTAGGGAAGGAGCC
```

-continued

```
GGGGGAGAGATGTGCTGTTAGCTATTATCAATCTGTGACAACTGTCAGCTGCTGGCAGTT
AGCACCCACCTGAGCCTGGGATGCAGGGGTGCCTCTCCTGTCCTCTGTGGAAGCCTCTGG
ACCCAGCAGCCATCTTGACTGTGCACTGTTCAAGCCCCAAGTCCGCCTGGAAGAGGTGAT
TGAGAACTTACTGCAGGATAAGGAAAGCGCAGGACAGGTGCAGTGGCTCACGCCTGTAAT
CTCAGTGCTTTGGGAGGCTGAGGCCGGAGGAGGGCTGGAGTCCTTGAGTGCGAGACCAGC
CTGGGCAACATAGTGAGACCCTGTCTTTACAAAAAGGAAAAGAATTAGCCAGATGTGGTG
GTGCGTGCCTGTAGTCCCAGCCACTCAAGAGGCTGAGGTGCGAGGATCACTTGAGCCCAG
GAGTTTGAGGTTACAGTGAGCTATGATCATACCACTGCATTCCAGCCTGGGTGAGAGAGC
ATGACTCTGTCCCAACAACAAAAAAAAAGATTAAGGGAAGCCTCTGGCAGACCTGATGAT
GGGTGGCCCAGCCAAAATGAGTATTGATGAGGATTTCCCTGGTCTGGAACTCTGAATTTA
GTCTGGCAAAGTATTCCCTTTGTGTTGTGAGATGATTCTTGGTGTTACCCCATCACGGTA
GGTAAGATGAATTAGCAAATGAGAAAGGCTTTCTCTTTTTCATCCTTATCTAGTCCGTAG
ATGAAGCCTGAAGAAGGTCTCCATATGGTAGTAGTAAGTGTTTAACATCTACCTCTAACA
CTTGCCTGTGTCTTTTTTTTTTGCAAAGCCTCAGGAATGCCCCAGTATCTAGGTAGAAT
TTGATAATATTTCATTTTTGTTATATTCCCTTTTCTGTTTACCTTCTATATACAGCAAAA
TGAAAAAATTTTTAAAATTTGTGCAAGTAAGGGCAATTTCTTTTTTCTTTTTCTTTTTTT
TTGAGACAGGGTCTTGCTCTGGCACCCAGGCTGGAGTGCAGTGACACAATCTCGGCTCAC
TGCAACCTCTGCTTCCTGGGTTTAAGCGATTCTCCTGCCTCAGGCTTCCAAGTAGCTGGG
ATTACAGGTGCCTGCCACCACTCCCAGCTAATTTTCATATTTTTAGTAGAGACCAGGTTT
TGCCATGTTGACTGGGCTGGTCTTGAACTCCTGACCTCAGGTGATCCATCCACCTTGGCC
TCCCAAAGTGCTGGGATTATAGGCTTGAGCCACTGGGCCTGGCTGAGGCAGTTTCTTTTT
GAAATATATTTTGTGAAGGAGAAAAAGAGGAGTTCAGTTTAAAGAAACAAATGACATAAG
AGGTGGTATGCAGAGATGCCAAAGCATCTTGAAGGTGCTTTTTTTTTGGAAACAGAGTC
TTGCTTCATTGCCCAGTCTGGTCTGCAGTGGTGCAATCATGGTTCCCTGCAGCCTTGACC
TTCTGGGCTCAAGTAATCCTCCCACCTCAGCCTCTCAAGTAGCTGGGACTACAGATGCAT
GCCACTATGTCTGGCTAATCTTTAAATTTTTTGTAGAAGCCAGCTCTCACCATATTGCCC
AGGCTGGTCTTGACCTCCTGTCCTCGAGCAAAAATACCGATTTTGATTAAGTCTGGGGTA
GGACCTGGGGCTGGGATTCTAACCAGCTCCCAGGTGGTGCTAATGCTGCTGGTCTACAGA
CCACACGTGGAGTAGCCAGTGTAGAGTTCATGTAGCAATAGTGATGTCATAGAAATAGCC
AGTATCTGTATACTTGCTTTGTTGTATGTCACGCACTGTATAGTGATGTACATGCATCTC
ATTTGACCCTCACCCCGCCCCTTTGGGGGTAGAAAGGATTGTGCTCATTTCACACTCAAG
GAAACTGAGGCACAGACAGGCAAAGTAGCTTGGCGAAACAGAAAGGAACTTAGAGGCAGG
CCCTGATTAGCTCAGAGACTAGAAGGCCTTGTGCGTCATCCTGAACAGCTTGGACTTGAT
CTTGAAGGTGGAGGGAGAAATTGAAGGGTAATTAAACAGGAACTGTAGGAAATTCACCTT
GCATAGTGATTGCTTTGGCCACGTGTGCCCTGCCACCGCCCCCCCACCTCAGTGAAGTGT
CATGCGAAGTTGGGTTCGTAAATGAAGGCCCGAATGCTTTCCTGACAAGTTTGTTTTAAA
TCAAGCTGCTAATTAGTCCCAGTCCCCCTCCCCCGGTATGTATTTTTTGTTGATGTCGT
TTCACTTCATTTAGTTGAAGTGATTGATTCAGTTCAGTGTTTGAACTTCTTTTTGAACCT
CACCTTAATAACCTGTCTAAACATCAAGGTTAAACCTTCTTGCTAACACAGCAGTATTGC
TTGGTAAGACTGGCTCACAGTCCAAGGAAATGCTTGCCCAGAGAGGGCAAACTGCCTTAA
CTCCTTAACCTGAGCTCATTAAAAAAAATTCAAATGACTGATTCCTTGTCACAGTTCTAC
```

-continued

```
CTACATTGTTTTTATTTTTGTCCAGGTTTCAGCTAGTTAAATGCTTTTGTGATGAGCTTA

TGTCCAGGCTGAAGGTTGCATTTTGAAACTGAGCGTCAAATACCAATTTAAAGTCCAGAC

CTTTACACTTGTGAAATTCAGATAAATGAAATGGAAATAAAACAGGGCTGCTGTGTTGTG

AAATATGACTGTGTTTTTCCTTGTAGGACTCTTTGAGGGTAGCCATTTTGGCATTTTATA

TATAAATTTTCTTTTCTTAGCCTACCTTTTACTTTCTTGATTTGCCTATTTGTGATTTCC

CATTAAACACTAGGCTTTTTGTAAACCAATTATCCCTTGAAATTGACTTTTTTTTTTTT

GAGACAGGATCTTGTTTTGCCACACAGGCTGGAGTGCCGTGGCTCCATCATATGATAAAC

AGAAAGAGAGAGAGAGAGAGAGAGAGAGAGAGAGAGAGAGACCCTGTCTTATTTAAAACA

AAAAAGAAGAAGAAAAAAAGAATATAGATCACAGCTGTTATTTGTATATGCTACGCCAA

TCCTTGTTGGGTTTCATTCTTTATAATTGTTATTTTTAAAGATTTTTCTTATGAATATTC

TATTGTTTCATTGTAGAAAATTTAAGGGAGAACACAGTGGGAAAAAAAAAACAAGAAAAG

GACTTCATAATCCTGCTACCCTGGGAGAAAAAAAAAATCACCATTACCTATTTGGTTCTT

CTCCCACTTTTTTTTTTTCGAGATGGAGTCTCCCTTTGTTACCCAGGCTGGAGGGCAGG

GACGTGATCTTGGCTCTCTGCAACCTCTGCCTCCTGGGTTCAAGCGATTCTCGTGCCTCA

GCCTCCCGAGTATCTGGGATTACAGGGGTGTGCCATCACACCTGGCTAATTTTTGTATTT

TTAGTAGAGACGGGGTTTTGTCATGTTGGCCAGGCTGGTTTGTTGGCCATGTCTGGTTTT

TTGTCATATTGGCCAGTCTGTTTGTCATGTCAGGCTGACATGTTTTGTCATGTTGGCCAG

GCTGGTCTTTAACTCCTGACTTCAGGTAATCCTGAAGTGCTAGGATTATAGGCGTGAGCC

ATTGCACCTGGCCTTCTGCCTTTTTTTAAAGAAAAAAAATTAAAACATTTTTTTCTTTT

TAAGATAGCGTCTCATTTTGTTGCCCAGGCTGGTCTTGAACTCCTGGGCTCAAGTGATCC

TCCAGCCTCAGCCTCTGGAGTAGCTGGGACTACAGATGCACATCATGGTGTCCTTATGCC

ATTTCTTTTGTACGTAGGTGAATGCAAGTGTATGATTACATCATATGCTATTTTGGAGGT

TTGACTTTCTTTTCACTTTCATCATCTTTCCAAGGTGTTATTTTCCTAGTACATCTTTTT

AAATGGACATAGAACATTCTTTTGTATGAACAAACAATAGTTTTATTTAGGCGGTCCTTT

CCTGTTGGACATTTATATTATTTTCAGCATTTCTCCACAGTTGTTGCAGCATTCAGATGA

ACCTTCTTTTTTTTTTTTTGAGACGGAGTCTCGCTCTTTCGCCCAGGCTGGAGTGCAG

TGGCACAATCTCTCCTCAAGTGATTCCTGTGTCACCCTCCCACGTAGCTGGGATTACAGG

TGCCCATGTCTGGCTAATTTTTGTGTTTTTGGTAGAGCTGTGGTTTTACCATGTTGGCCA

GGCTGGTTTCGAACTCCTGCCCTGAAGTGATCTGCCCACCTCAGCCTCCCAAAGTGTGGG

GATTACAGGTGTAAGCCATCACGCCTGACCCAGATGAACATTCTTGTAGCTATCGCACAC

AATTCTGAACATTTCCTAGGATGAATTCCTTAAAGAAGTAATGCTGATCCAGGCTTTTTT

CTTTTTCTGTGACTCTTTGACACGTAATAATATTGACTTTTCTTTCTTTCCAGACACTAC

AACAACAGGAGTGCAAACTTCTCTACAGCCGAAAAGAGGGTCAAAGGCAAGAAAACAAAA

ACAAAAATAGATATAAAAACATCCTGCCCTGTAAGTATCAATATTCCGCTCAGTAATAGT

CACTCTTGGAGATTTTGATTCCTAGCACCTCTGTACCTTTCCTCAGGGTCGTGTGCTCTT

GTTAGCACATCGGAGGCCTTAGCTTCTTTAATTGCAAGCAGTTTCCAAAATAATCAACCA

TGGTGGGTGTTGATGACTTCATTCACTGAGCTCCCGTGATGCTGATTACTGAGTAAAGTT

GCCACTAGGTGGCTTTGTCTGTGGTTGGTTCCTTCTGTTAATTAATTTTCTGTCTGCCCA

AGATAGATCATCTCAAGGCTTGGGATCTCTCAGTGTCAGGGACCTTAGGGTGCCAGATTT

GTGTCTTGACTCCTCCTCACTGGGCCTGTGAGTCCTGGGTAAGGCCTGCCTCCTTTCTGG
```

-continued
```
GACTCAGTTCCCTTAAGTGGGAAACAGACAAACACCTCCTGAGGGCTCCTAGAACTGTTC

TGCTTGCTGATCCCCTGAGCTCAAGTTACTGGAGAAAGGGTATATACCTAAACTGCTCAG

AAGAAGACTTTGTGGGCCGGGCGCAGTGGCTCACACCTGTAATCCCAGCACTTTCGGAGG

CCGAGGCAAGCGGATCACCTCTGATCAGGAGTTCAAGACCAGCCTGGCCAACATGGTGAA

ACCCCATCTCTACTAAAAATACAAAAATTAGCCATATGTGGTGGTGTGCGCCTGTAATCC

CAGCTACTCGGGAGGCTGAGGCGGGAAATTGGTTGAACCCAGGAGATGGAGGTTGCAGTG

AGCCGAGATGTGCCATTGCACTCCAGCCTGGGTGACAAGAGCAAAACTCCGTCTCAAAAA

AAAAAAAGGAAGACTTTGTGAATATTCGCAAAGCTGTAAAGCTGTACCTTTCAATTTTTT

TTTGAGACATAGTCTCACTCTGTTGCTCAGGGTGCAGTCACAGCTCACTGTAGCCTCAAC

CTCCTGGGCTCAAGCGATTCTCCCACCTCAGCCTCCTGATTAGCTGGGACAATAGGCAGG

CACCAGTACACCTGGTTGATTTTACAGTTTTTCTGTAGGCCGGCGCAGTGGCTTACGCCT

GTAATCCCAGCACCCTGGGAGGCCGAGGTGGGCGGATCACCTGAGGTTAGGAGTTCGAGA

GTAGCCTGGCCAACATGGTGAAACCCCATCTCTATTAAAAATTACAAAAATTAGCTGGGC

GTGGTGGTGGATGCCTGTAATCCCAGCTACTTGGGAGGCTGAGGCTGAGGCAGGAGAATC

GCTTGAACCTGGGAGGCGGAGGTTGCAATGAGCCGGAGGTGCTATGTGCACCACTGCACT

CCAGGCTGGGCGACAGAGTGAGACTCTGTCTCAAAACAAAAAACGATTTAAAAAATAATA

AAATTTTTTCTAGGGCGGGGTCTCCCTATGTTGCCCAGGCTGGTCTTGAACTCCTGGGCT

CAAGTAGTCCTCCTGCCTCAGCCTCCCAAACTGTTGGGATTACCAGTGCAAGCCATTGTG

CCTGGCTGTACCTTCTGTAACACCCAAATGCCACCTGGCAAAGCCCAAGTTGAATCATGA

GGAAAAAAGGCCTGGAAGGATGTAGACCTTCCTTTTTTCTACTTATTTATTTATTTATTT

TTGAGATAGGGTCTTACTCTGTTGCCCAGGCTGGAGTGCAGTGGCATGATCATGGGTCAC

TGCAGCCTCAACCTCCCGGGCTCAAGTGGTCCTTCCCACCCCAGCCTGCAATGTAGCTGG

GACTACAGGCATGTGCTACCATGCCCAGCTAATTTTTGTATTTTTTGTAATTATTTTTTT

TGTAGAGACAGGGTTTCGTCATGTTGCCTAGGCTGGTCTCGAATTCCTGGGCTCAAACGA

TCTGCCTGCATCGGCCTCCCAAAGTGTTGGGATTACAGGTGTGAACCACTGTGTCTGGCT

ATATCTTCTGTAACACCCAAATGCCACCAGGCAAAGCCCAAGTTGAACCAGGAGGGAAAA

AGGCCTGGCAGGATGTAGGCCTTGCATGAGGATCTCAGAAACTGCACTAAACCAGTCACA

GTTCCTCTCTCCCGAGGTCTAACTCTATGCTGAACTCTTTGCATTTTTATCTCACTTAAT

CCATATCACATGCACAGGAAGGAAGCATTCGTAGTATCCTGGTTTCCTAGACCATTTTAG

CAAGGTTATAAGTGAAGGGGAGTGGGTGGGAGAACTGGCACTAGAGCCCCCAAAGTCACT

GTTCTTAGCACCACTCTAATGCATGGGGTTCTCCATTGATGTGCTATGCAAGGCAGTGCA

CTGAGGAGAAAGGAAGGAACATTTACAACTTCTCTTTATTTATATCCTGTCCCTAAAAAA

AAAGAAAAAGAAAAATTTGTCTGAGGCCTAGATTGATTGCAGGGAGTGCATAATGTTTT

ATTGATTGATTGATTGATTGTATATAGAGATGGGGGGTCTCACTATATTGCCCAGGCTGA

TCTCGAACTCCTAGGCTCAAGCAATCCTCCTGCTTTGGCTTCCCAAAGTGCTGGGATTAC

AGGCATGAGCGACTGCACCTGGCTATGCATACTATATTTATCCAACTTACAAATAAGGCT

TGCTTGCCTGTAGTGCATATGTGTATACATTTCAGCATAGAAAACTGTGTGATTGGGGG

TTGTGATCAAATTTGGAGAGCATTGCTCTCATGTCTTATCAGGTCAGAGTCATTTTGTCA

AATCTTGTAAACCATTCTTTGTGTGTGTCTATGCATGAAACATAGTCTTTCTCTTTCTGC

ATGCATATGTACATATACATGGTATATATGTATATCATATCTACATGGATATTGTAATGT

ATATGTATGAGGATGGGGGAAAGTGGAGACATTTGTAATACTGAGAAAAGGCAGTGAGGA
```

-continued

```
ATTTGCAGAGAAGCAGTTTGAGCTGTAGCATGGTACTAGTGACCTTGAGGAAGCCTTATC

CTTTTTTTTTGGAATTTATTTTTTCAATTTTTAGAAATAGACAAGAGTTTCTCTATGTTG

CCCAGGCTGGTCTTGACCTCCTGGGCCCAAACTATCCTCCTGCCTTGGCTTCCCAAAGTG

CCAGGATTACAGGTGTGGACCACCATGCCTGGCCACCTTGTCCTTTCTATGTCTAAGTTG

TGACATCTGCTCAGGGGTCAGGTGGTATTAAATGGTATAAAATGTATGGGAAAGTGAAGG

GATCAATGGTATGCAGTATCTAAATAGAATATCGCTTTTTCCTCCCTTAAAGGTCTCATT

CAGATGTTTCCTCTGATGAACATCTCATTTCCTTAAAGATGAGGAGTCTGAAGCAAAAAA

GACATTATTCTTTTAAGACACATGGCTGTCTTACTAATTCCCATTGCAAAATATGTTGTT

TAGGTAGAGCACTCAGATTTTTATACGAATAATAGACTTTTGTACAGAATTTGGACAGTT

GATACTATCAGAGCCTTGTGATATTCCACTGCATTATGCTTCACTAAAAAATACCTGGCT

GGGTGCGGTGGCTCACAACTGTAATCCCAGCACTTTGGGAGGCTGAGGTGGGCAGATCAC

CTGAGGTCAGGAGTTCAAGATCAGCCTGGCTAACATGGCAAAACCCCATCTCTACTAAAA

ATACAAAAATTAGCCAGATGTGGTGGCACGCTCCTGTAATCCCAGTTACTCAGGAGGCTG

AGGTATGAGAATTGCTTGAGCCCAGGAGGCAGAGGTTGCAGAGAGCCGAGATAGTGCTAT

TGCACTCCAACCTGGGTGACAGAGGAAAACCCTGTCTCAAAAAATAAATTTAAAACAACA

ACAACAACAACAAAAACCCCTCTTTATTATGGAAATTTTCAAATATATTCAAGAGCA

TAAAGAACCCACATGTACCCATCACCCAGCTTCAACAATTATCAACTCATGCCCAGTCTT

GGTTTCATCTATACTCTGATCCACATCTCCTCTCTCCTTGAATTATTTTGAAGCCCATCT

CAGACATCATGTCATATATGTATACTTCAATCTTCTTTTTTTTTAAAACTCCCCCTCCCC

TTTTCTTTTTTCTTGAGACTGTGTCTCACTCTGTCATCCAGGCTGGAGTGATCTTGGCTC

ACTGCAATGTCCGCCTCTCGGGTTCAAGCGATTTTTGTACCTCAGCCTCCCTAGTAGCTA

GGATTACAGATGTGGACCAACATGCCTGGCTAATTTTTGTATTTTTAATAGAGACAGGGT

TTTGTCATGTTGGCCAGGCTGGTCTTGACCTCCTGACCTCATATGATCCACCTGCCTTGG

CCTCCCAAAGTGCTGAAATTATAGGCCACTGCGCCCAGCCCAAAATTTCTTGGTTTGAAA

TAATTTTGGAACTCATAAGAAGTTACACATATAGTAGAGAGAATTTTCTTGTACCTTCTC

TGAGCTTCCTATATACCCAATGATAACATCCTATATACCCATAGTATATGATCAAAACTA

GGAAATTGTGAAGATGGCATTTTGAGACATCAGGCAGTGTTCACGTTACTGTTTTGCTTA

CCTGGGCTTTAATTTTTATGTGTTTTTTTTTCAATCATTGAATGAACAAAACTTGGACTA

GGCTGGGGAGTAACTGATTTGAACTGTTTTTTCCTGAAGCAGTCCAGGACTTATGTGACC

GTGGTCTCTTTTTCTTCTAGTTGATCATACCAGGGTTGTCCTACACGATGGTGATCCCAA

TGAGCCTGTTTCAGATTACATCAATGCAAATATCATCATGGTAAGCTTTGCTTTTCACAG

TGTTTTCTGACCATACATTTCTAGCCTATTTTTGTATTTTAAATCCTTCCTCATGTCCTG

AAAGTAACTTTAAGGTGTTTGAAGGATTTTCTTCCTAAATTTCTAGCCTGAATTTGAAAC

CAAGTGCAACAATTCAAAGCCCAAAAAGAGTTACATTGCCACACAAGGCTGCCTGCAAAA

CACGGTGAATGACTTTTGGCGGATGGTGTTCCAAGAAAACTCCCGAGTGATTGTCATGAC

AACGAAAGAAGTGGAGAGAGGAAAGGTAAATCACAGAAACTTCTTTTCTGCTAAACTGTT

TTTAAAGTATCAGACATGTCAGATTGGCCATGTTTAGGAATTGAATAAATGAATTAAGCT

TACTGTAACTGATTCTCTGGAAAAAAGGGACTAGGAGAAATTTGATTATGTTATTCCTTG

GTGTAGTTTTCTTTATGTTTCTTCTGCTTGGGATTTGTTGAGCTTCTTGGCTCCATGGAT

TTGTAGTTTTCCTTAAATTTGGATAATGTTCAGTCTTAGTTTCTTCAGATACATATCCTG
```

-continued

```
GGCTGGGCATGGTGGCTCATGCCTGTAGTCCCAGCACTGTGGGGTGTTGAGGTGGGCGGA

TCACTTGAGGTCAGGAGTTTGAGACCAGCCTGGGCAATGTAGTAAGACCCCATCTCTTAA

AAAAAAAAAATGTACCCTGCACAACCTTGTCCTAGGACAGCAGTCATACGTGTATTAGAC

TACTTGAAGTTGTCTCATAGCCCACTGATACTTGGTTTATTTTATTCAGTTTTTTCTCCC

CGTGTTTCATTTCGAATAGCTTCTTTTGCTATGTCTCCAAGTTAATCTTCTGCAATATGT

CATCCGCTCTTAATCCTATCCAGAGTATTTTTCATCACAGACATTGTATTTTTCATCTCT

AGAAGTGTTAATGTCATCTATAGCTTTCCTTTTAACATGTGTAGCATTTTCCTTACCTTT

TGAATGTATGGAGTATTTCTGTTGTTGTTTTTTGTTTTGTAGAGACAGGGTCTCGGTCTG

TTGCCCAGGCCGGAGTGCAGTGGCATGATCTCAGCTCACTGCAGCCTCTGCCTCCCGGTT

CAAATGATTCTCATGCCTCAGCCTCCCAAGTAGCTGGGACTACAGGTGCGTGCCACCACG

CCTGGCTAATTTTTGTATTTTTAGTAGAGATGGGGTTTTGCCATGTTGGCCAGGCTGGTT

TTGGAACCCCTGAGCTTAGGTGATCCACCTTCCTTGACCTCCCAAAGTGTTGGGATTATA

GGTGTGAGCCACCATGCCTGGCCATGTTGTCTGTTTTAATTAACTCTGCCTAACTGTCCT

CCCAAATGGTTGCTGCAGTGCTCACTCCCACCAGCAGCACCTGCCTAGGACTCATTACTC

CATACTCTTCAAGACACTTCAGATTAAAAAAATAAATTGTAACACCCCACACCTACAGAA

GAGCGGACAGATCTTATTGAGTGACAGCCCTCTGTGTTATCTCAAAGTGAGCCCACCATG

GTGGTTTTTTTTAAATATGGAAAAGTTCTGTGTTTTTGTTTGTGTTCTAGTGAAAGTT

CTTTTTTAGATATCCTTTAATTGGTTTATATAAGATTTTATGTGGAATGTAGCAGTCATA

CCTATAAATTAAACCTAAGGCAGATGGAGAACTTTGGAGTTGAGCCTTCCTACTGTAATT

TTCATATTGGATGTGAAGGGCAGTGTGATTTTCATAAGACTTTCATTGTTGTACTCCTAG

TTGGTATACTTCTGAATACCTTTGAGGCCAGTTCTGGTCATCGTGAAACAAAGGTTTCCT

TCAGCAAATGCCTGTGGTAACATTAGGTGTTCTTGAATTAATGGACCAATGAAAACATCT

TTGTAGTTTCTGCTTCAGGCAAGGGTTTTTTGCCCTAAATGTGGATAGGAAGAATGAAGC

CCTTCATCCTCCTTTTTGCCTGATTATAGCTATAGGAGGTTCACCTGTTCTCAGAAGACA

TGAGGATTGTGAAGAGAGGGGTCTTGTGTTGCTTCAGAGGAATCAGTATCAGTCCCTTTC

AGAAGCTCTCCTGGATAGACAGGCATTAGGGCCAAATCACTCTGCCCCACCCCTCACCAC

CATGTCCTACTCTCTGCTCCCTGTCTCATTCTTCCTCTTTACTTTGGTGGTGCCGAGAGG

ATGACATGATGGGTATTGATTCTCTCCACAGACCTTTCTGACATCCTACTTTCAGTATCC

CCCCAGTGCACAGAAGACAAGCCAGACTGTGGACTGTGTTTGATTCCTGGGCTCTATTTT

AAAAGACAGTGTATTAGTTCTCACATTTTAGAATTTGTTTGCCAAGGTTTCCACGGGAGT

TTAGAAACTAGGGGGAGGGCTGATGTTTAAAGTTAGCTAAAATGTTCTTTTCAGGGTCAT

GATTTAATTTTATATTCTCTGGTGAGTTCCCTATAGTGACTGGGAGCAGTCCTCAGTCTT

GATTGGCCAGTGACAGCATAGAGTACAATTAATATTAGGAGTGCTCATTTGGGGAAACTA

AAATTTGCATCAAATCTGTCAGAGGTGTTTGGATCTACAAAATACCGGAGGGAAAGCTGA

ATTGAGAATCATAATAAATAAAAGACCACATCGTTCTTTTTTTTTTTTTTTGGGACT

GTATCTTGCTCTGTCACTCAGGCTGCAGTGCAGTGGCACTATCTTGGATCACTGCAGGCT

CCGCCTCCCGGATTCAAGCGATTTTCCTGCCTCAGTGCCTGAGTAGCTGGGATTACAGGC

GTGTGCCACTACACCTGGCTAATTTTTGTAATTTTAGTAGAGACAGGTTTCACCATGTTG

GCCAGGCTGGTCTCAAACTCCTGGCCTCAAGTGATCCACCCGGCTTCCCAAAGTGCTGGG

ATTACAGGCGTGAGCCACTGCGCCCAACCAAGACCACATCCTTTTATTGAACGTTCCTCC

TACCATGTTTTCTTTTTTCTTTCAATTAATCATTGACTCATTGACTCTCACTGTTGATGT
```

```
CTGTAGCTGCTCTCTTATTTCCAGTTTTATAGCTGTAAATTTCTCTGTCTTCCTAAGATA

CAAGGTAAATTTCTCTTGCTGATATTGGTGGTTTTGGAAAGTGAGTGGTGTGGATGACTG

CCCAGAAAACAACAGAACACAAAAGCATTCTCTGCCCAGAACACATCACCAAATAGATAC

AAACTCATCTCTTACTGAGTGAAATAGCTTCCTTTTTGGCAGCAAGAATGATTTTCTTGG

TGCCATATTTTTCAATCCGCCTGCTCTTGAAGCCAGCAGCTATTGCAGACTTGGCATTCC

CAGGCACCCAGTTAAGGGAAAGTGACGTGTAGAGGAGGTATCAGATGGGTCTGGATATAG

AAAAAGCAGCTGGTTCAAAACCCCATGGGCTGCCTTTCTGTGATAGAGTTATTCACACTT

GGGTTAGATAAGGCACAGAGTCCTCCTACACTGGTGCGGAAATGAAACAGACAGTCTGGC

TCGTTGGGCAGCCTAGCCTCCTCCAGAATCTGTGCTTGCCTTCCCTATGGAGTGACTGGT

AGATCTTAGAATTCAGACCTCAGTGGTTGCTAGCCAGCACTCTCACATTGGTTGGTCCTT

CTCTCTGCATCTTTGATTCTTTAGAGATAGATAAACCAAGCACCGACTCTCCTTTGACAT

GTGCTTGGAACAGACACCTGCACGAGCTGCCTTTCTCCTCCCACTTCTGCCTGGTCTTCC

AAACACCTGCTTTTCTTGTTTGAACTCTTCCTTTTTTTTGAGACAGAACCTCTCTCTGT

CACCCAGGCTGGAGTGCAGTGGCATGATCTCAGCTCACTGCAACCTCTGCCTCCCAGGTT

CAAATAATTCTCCTGCCTCAGCCTCCCAAGTAGCTGGGATTACAGGTGCCTGCTATCACG

CCTGGCTAATTTTTGTATTTTTAGTAGAGACACGGTTTCACCATTTGGCCAGGTTGGTCT

CAAACCTCTGGTCTCAAGTGATCTGCCCGCCTCGGCCACCCGAACTGCTGGGATTACAGG

CATGAGCCACTGCGCCCCAGCTGATTCTTTACAGATAAACAAACATTGACTCTGCTTTGA

CATGTGCTTGGATCAGGTAACTGCACCAGCTGCCTTTCTCCTCCCACTTCTGCCTGGTCC

TCCGAATGCCTGCTTTTCTTATTTGAACTCTTCTGTCCTTTTCTGAAAACCTAACAGATG

CGAAACAGGCCATTTTCCATGTTGGTGGTTATTAAGCAAGACTTGAACATTTGTTTGTTG

CTTGTTTAGGCTTTTATTTCAGAGTTCACAGAATTAACTTTCTTTTTTTCTGATCTCTTC

CAGAGTAAATGTGTCAAATACTGGCCTGATGAGTATGCTCTAAAAGAATATGGCGTCATG

CGTGTTAGGAACGTCAAAGAAAGCGCCGCTCATGACTATACGCTAAGAGAACTTAAACTT

TCAAAGGTTGGACAAGTAAGTATATTGTCGTATTCTAGAGACTTTGGGAACTGTTGATGG

TGTGTAGGAATTCAGGGTCTTGCCGTTACTCATGTTTGCATACATGCATGCATTCGCTCA

CTCATTGATTCAGTAGCCATTTATTAGCTTCCTTCTATGTGCCAGGTACAGTTTAAGCAG

TACTGGTACATTGTGAACAAGGCAGGTAGTGTTCCTGCCCTCATCGAGCCTAGGGAGATA

GACAATTTAAAAACAAATAACTGGCCAGGCGCCGTGGCTCAGGCCTGTAATCCCAGCACT

TTGGGAGGCTGAGGTGGGTGGATCGCTTGAGCCGGGGAGTTCGAGACCAGCCCTGGGTGG

GAGACTGGGATAGGGTGACCTGAGTGGCTACAAGGTCTGTTAGGAGGCCTCCGCAGGGGC

CTATGTTGATGGCCTCCTCTCCAAGTATCCACAGACTTCAGCAGTTGTTCTTTTTTGTTC

CTTCCTTTGGAATGGAATATTATATAAAATGGCAGAATAAACTGGAAGAGAAGCAGTAGA

TGTGAGAGGTGCCGGGGGGTGAAGTCTGCAGGATGTGGGGATTGTTTGGCTTTTGGAGGA

GGAAGGAGGGATTCAAGACACATTGTAGAGGTTTGAGTCTGAGCGGACAGTGGTGCTGTG

GCAGACACCACAAAAGCTGGAAGGAGAACTGATGTGGGCAGTGATTTGTTTCTTCTGGA

TGTGTTCAGCTGGGCATCTGAACAGTCATGTGGACATTCATCTATTCATTCAGAGATATT

TGTTCAATGACCTCTTGGTTCCTGGCACCATGCTGCTTGCTGGAGATAGAGCTGGGGAAC

AAAACAGATGGAATCCCTGCACTCCCAAGTGTACACTATACTGGCCAGTAATCTACCAGC

CCAGTAATTGCACATATAAATATATCATTATAAACTGTAATCAGGGCTAGAAAGAAAAA
```

-continued

```
TGCAGGAGTTTAGGGTTCATTTGGAGGGGAAGGGACTTTTTTTTTTTTTTTTGAAAC
AGAATCTTGTTCTGTCACCCAGACTGGAGTGCACTGGTGCATTCACGGCTCACTGCAGCC
ACAACCTCCTAAGCTCAAGTGATCCTCTCACCTCAGCCTCCCATGTAGCTGGGGCTACA
GGTGTGTGCCACCATGCCCACCCAATTGTTAAATTTTTATAGAGACGGTTGTCTCATTA
TGTTGCCCAGGCTGGTCTTGAACTCCTGGGCTTAAGCGATCCTGCTGCCACATGCAGCCT
CCCAAGGTGCTGGAATTACAGGCGTGAGCCAGCGCACCCGGCCAAGGGAGGGGAGGTTCT
TAAGGCATAGGGAACAATGTGTTTGAGTCAGCAAAGGAGGTTGTGGGGGTTTGTCCTAAG
TGTGGTAAGCAGCCAGAGTTGGATTTAAGTTTTTAAGAGATTCCCCTCCACCCTGTAGAG
ACTGGAGGGGGCAGGAGTTGTTCTAGGGATTAGGACCAATTTGGAGGTAGTGCAGCCGTC
AGAGTAAAAAATAATAGGGATTGAACTAGGCCAGTGCCCAGGGTGCCTGAAAGAAGAGGA
CCCAGTAGAGCTGACTGGAGGCAGACATGCAGGGATTCAGTGAAGGAGTGTACCAAGGGC
GAGGGTGGTGTGCAGGGTGACTGGCAATTTTCTAGCTTGAGAAAGGTCCGGGGGGATGGC
AGTGGAGTTGAGGAAGCTGGGAGGATCAAGGACCTTTTTGTGAACACACAAAGTTTGAGA
TGCCTTGGACACATTGAAGTGGAGCGGTCAGGGAGGCAAGGGTGGAGGTGGGATGCGGAG
GGGAGGTGGGATGCAGAGCGTCGTGGATGGATCAGTTTTGCTCGATAGAGGGACATGTTT
TTCTGTGGCAACAGGAGGGCAAAAGGAGAAGGTGGCCACAGATGCCGGTAGATGAGCTGA
GAGTGATTGTATTCCCTATCCTCTCGGAAGCTTGAGGCAAGGCCATCAACAGACAATCAG
AGGGAATAAGAAGAGATAGAATATATGAAGAAAGGGAGAAAAGATGAAATCGTAATTGTG
TAGCAGGGCAAGAAGTCCAGAAATTTCTGTGCTGTGCCAAGTTCCCAGTTGAGGCGGTGA
ACATGAAAATATACTGATACCCATTGCCTGGTTTTTCTCCAAGGACACTTGGCTCCTAGG
GCACAAAACAGAAAGTACGTGGTTTGTCCAGGCCGAGGGCTTTGCATAGTTGCAGTGGAT
GGAGAGGAGGTCAAGGAATGGAGGCACATGGTAGAGAGAGACTGTCCCCAGAGCACGGGG
ACTCCTGGCCGGATGAGGGGGACAGGGGCAGGAGGAGGCAGGTGGAAAGTAGAGGGAGGG
CTCAGTGGTCTGGAGGCTACAGGAAGTGACGGGGGGACCAGAAGGAGCTGGAAACCAGTG
TGGTTGTGGCCCAGGGTGGGATGTTTGGATTTCTGATGTCAGAGAGGGTCCAGTCCTTCT
GATGATGGGGAGGGGTGGAGGCTGAATCTATGGTAGAGATAGTGAGAGGAACTGGAACAA
TGTAGCTGTCAAGTGGAAATGGGAGAAAGGGCTGGGCGTGGTGGCTCACGCCTGTAATCC
CAGCATATTGGGAGGCTGAGGCAAGAGGATCGTGTTAGCTCAGGAGTTCTGGGCTGCATT
GAGCTGTGATTGTGCCACTGCACTCCAGCCTTGGCAACAGAGTGCCCAGTTAAAAATAAA
AATAAAATAAAATAAAAAAATTAAAAAAAAAAGAAGAAGAAAAAAGAGAAAAGTGTCCTT
TTACATCCCTTTTAAAAATGTCACTTAAGGCTGGGCAAAGTGGCTCATGCCTGTAATCCC
TGCACTTTGGGAGGCTGAAGTGGGTGGATTACTTGAGGTCAGGAGTACAAGACCAGCCTG
GCCAACATGGCGAAACTCCTTCTCTACTAAAATTAGCTGGATGTGGTACATGCCTGTAGT
CCCAGCTACTCGGGAGTCGAGTCTGAGGCCCAAGAATTGCTTGAATCGGGGAGGCGTAGG
TTGCAGTGAGCTGTGATCAGGTCACTGTGCACCAGCCTGGATGACAGAGTGAGACTCTGT
CTCAAAAAAAAAAGTCACTTAGCTTAGATTGTCTCTACATATATAGGAAGAAGATGTAGG
AATGAATGGTGCTGCTACAATTACGTCATCTGGATAGACCCAGAAACATGATACTTTTTG
GTTTTCTGTAGCCTTGGTGCCATTGTTGATCTTTATTAATTATCATTATCCTCAAAATAG
CCATAATGTGCTGAGTCTCTTCCTATTTGCTGGGCAGAGGCTGAGTATTTCAGCGAGCTC
ACTGAGTCCTTAAAATTGCATTATGATAGAGAGAAAGAGATTATTATTTGCATTTTGCAA
AATGAAGAAATTGAGGTTTAGAGATACCCAAGGGCCACGTGAGTGTGAGTGCCTGGAATT
```

-continued

```
GGAGCCTAAATCTAGTCATCTGATAGCAAAGCCTGTTTTCTTATCTGCTTTGCATTAAAT

ATAAGTTTAAAATAGAACAATACTGGCCAGGCTGGGTGGCTCACGCCTGTAATCCCAGCA

CTTTGGGAGGTCGAGGCAGGCAGATCACCTGAGGTCAGGAGTTTGCAACCAGCCTGGCCA

ATATGGCGAAAGAAACCCCATCGCTACTAAAAATACAAAAATTAGCCAGGCATGGTGATG

TGTGCCTGTAATCCCAGCTACTTGGGAGGCTGAGGCAGGAGAATGGCTTGAACCCGGGAG

GCAGAGGTTGCAGTGAGCCAAGATCACGCCACTGCACTCCAGCCTGGGCAACAGAGTAAG

ACTCTGTCTTGGAAAAAAAAAAAAAAAAGAATGATACTATAGTCTGTGTTTATATGGTGG

GGAAGGTTGAGTATCAAAAAAATAACAAAGAGGAATGAATGTCTTAAGTGAATGCCTGTT

TCCCCATCTGCTTCCTCTTCTGCTGGGAGGAGAGACCTGGATCCCTAGAGGTTTCAGTTG

CCTCCAGAGCTGAGTGCCACAGGGATGCAGGGGAATAGGGATGTTACCTGTCGCTGGTAA

TTCAGAGAGATGATTCAGGGTATAGTTACCTGAAAGAACAAATTGCCATGCCAGACGTCT

TGGTTCTTATGACAGAGGCAAAGAGTTGCCTCCAGGATTGCCCAAAAGGAGACGAGTTCT

GGGAACCTCACGAAGAGGACCTTTCAGTGGAACCTGGGGAGATTCTCTTCCTCTCCATTG

GATTTAGGAAAGCTTAGAACCGGGTGATTCCTCAACCTCTTGATTTATTTAATTCTTTTC

TGGTTTTTCTTGGCTCTACTCCAGGGGAATACGGAGAGAACGGTCTGGCAATACCACTTT

CGGACCTGGCCGGACCACGGCGTGCCCAGCGACCCTGGGGGCGTGCTGGACTTCCTGGAG

GAGGTGCACCATAAGCAGGAGAGCATCATGGATGCAGGGCCGGTCGTGGTGCACTGCAGG

TGACAGCTCCTGCTGCCCCTCTAGGCCACAGCCTGTCCCTGTCTCCTAGCGCCCAGGGCT

TGCTTTTACCTACCCACTCCTAGCTCTTTAACTGTAGGAAGAATTTAATATCTGTTTGAG

GCATAGAGCAACTGCATTGAGGGACATTTTGATCCCAAGGCATATTTCTCCTAGACCCTA

CAGCACTGCCATTGGCCATGCCATGGCAACATGCTCAGTTAAAACAGCAAAGACTAAGT

CAGCATTATCTCTGAGTCCACCAGAAGTTGTGCATTAAACAACTTCATCCTGGCTCTGCA

GTTTCTCCTTATTCTTCATGATGTTTGCTTTGTAGCTGTTGACTGCTTTGTAGGTATTGA

GGTGGTGGGGGTGTGGTGGAAATAGGCCTGACTCTTGAGGATCCCTTAAGTCATTTTTGC

TTGGTTCTCTTTTTCCTTCTTTTCTTCTACTCTTCTATGATTCATCTCTTTGATTGTGAT

TCTGTTCTCTCTCTCTCTCTCTTTTTTTTTTTCGTTTTTGAGACAGAGTCTTGTTTT

GTTGCCCAGGCTAGAGTGCAGTGGTGCCATCTTGGCTCACTGCAACCTCCGCCTCCCGGG

TTCAGGCCATTCTCCTGCCTCAGCCTCCCAAGTAGCTGGGATTACAGGCATCTGACACTA

CGCCCGGCTAATTTTTGTATTTTAATAGAGACAAGGTTTTGTCATGTTGGCCAGGCTGGT

CTCGAACCCTTGACCTCAGGTGATCCACCTGCCTTGTCCTTCCAAAGTGCTGGGATTACA

GGTATGAGCTACCATGCCCGGCCCATTCTGTTCTCTTCTACCATAAATATATTTCTCCCC

TAACACTATATTTGTTTGCTTCACAAGATTCCAGCTGCTTTTCCACCAAGGCCTTTGATG

GAAGCTGTGCTGTGACCTCTGTAATGAGTCTGTGGGCTGCTGATTCTCCAGTTTGGGCTT

CATGATTATACTGGGGAATATTGGGTTTCCTAAATCTCATTCATTTCTTGGGCAAGTAGA

TATATGTGAAAGTGTTTATTTGTCCAGTTGTTAAAGAAGCTACCATTTATTGAGCCAGCC

TCTGAGCACAATGTTTTTGTTTTGTTTTGTTTTAATTTTAAAATTATTTACTTCTTC

TATTTCAATAACTTTATTATTATTATTTTTTGAGACAGAGTCTCACTCTGTCACCCAGGC

TAGAGTGCAATTGAGCGATCTTAGCTCACTGCAACCTCTGCTTTCTGGGTTCAAGCAATT

CTCATGTCTCAGCCTCCCGAGTAGCTGGGATTACTGGTACGTGACAACATGCCTGGCTAA

TTTTTGTGTTTTTAGTAGAGACGAGGTTTTGCTATGTTGGCCAGGCTGGTCTGGAACTCC
```

-continued
TGGCCCCAAGTGATCCTCCTGCCTCGGCCTCCCAAAGTGCTGGTATTATAGGTGAGAGCC

ACTGCGCCCGGCCCTCTTTCAGTAATTTTGATGTATTTTTTTGTATATGATTCCTGTTTC

ATTCTGTCCAACCAGCACTCTGTATGGTATGTGCTGTTGTCCCCATTTCACAGATGCAGA

AATTAAGGGTCAGAGAGGTTAAGGGACTTACCTCAGGCACGTTGTACTGGAGAAGCTGAA

CTCCAAGAGCAGGTTTGGGCTGACTCCAAAGCCCTATGCTTTTTGCCAACATATTTTCAA

ACATAAATAGACAATTTTATAAATAGCTCCAAAGAGTAGACATTGTTTCTGTTGATATTA

ATGGCTTGGTTTTGAGTCTGAAACCCCATGAATGATTCTGTTGTCCCTGCTTTTTGTCC

TTCTGCCCGCAGTGCTGGAATTGGCCGGACAGGGACGTTCATTGTGATTGATATTCTTAT

TGACATCATCAGAGAGAAAGGTGGGTCATCTGGTGGGCAAGAAGCGACAGTTTCTGTTTT

TAGTTTATGGAAGGAAAGTGCTCACGAAAACAGTCTGGGGAAGAGAGGTTGAATGGGAAA

ATTCTTTCACAAAAATCTGGGCTGAAGACTTCAGTGTGTCTGCCTGAGAACAGAAGTGAC

ACTATTTGAGCTTTTGGCATAAAATGAAGTCTAGGAGCTGCAGAACCCACTGCCATGGCC

TTTTGTTGCATACACAGTGGTGGTCTCTATCCAGCCACCTGACCTTGTTTACAGTATGGG

GTGATTTGTTGGCAAGTGAGGGAATCCTGACTTCTGCCACTTCGTTATTTATGTAGTCTT

CTGGGATCATTGGTATTGGTCAGAAGTTCAACACTGTAGCCATTGCAACATGCTCAGTTA

AAACAGCAAAGACTAAATTAGCATTGTCTCTGAGTCCACTAAAAGTTGTGCATTAAACAA

CTTCATCCTGGCTCTGCAGTTTCTCTTTATTCTTCATGATGTTTCCTTCGTAGGTGTTGA

CTGCGATATTGACGTTCCCAAAACCATCCAGATGGTGCGGTCTCAGAGGTCAGGGATGGT

CCAGACAGAAGCACAGTACCGATTTATCTATATGGCGGTCCAGCATTATATTGAAACACT

ACAGCGCAGGATTGAAGAAGAGCAGGTACCAGCCTGAGGGCTGGCATGCGGATTCTCATT

CTCTTGCTAGGCCTCTTGGATACGCTCTCCTTTTGAGCAGGAGGACAGGCTCTGATAGAC

AACTGTTTGATTTCGGAATGGGAAACAAACTCCCAACTAAAAGGGCCTCTGGAAACTGTC

AATTATTCTCCACTTCTCAGCTCTGATTTTTCACTGCAGAGGAGCTTAGGGAAGGGCACC

ATCCTATCAGCCTGGCCTGCCAGATTGAAGAACTGCCATGCAGAAAGGTTCTGATGTTCT

CAGGCTCATGTGGCAAGCGTAAAACTCAAAGCCTTGAAGTTTCTAGCCTGTTCCAGCCTT

GATCCAGGCCATGTTTATCCTGATTCCATCCTTTAAAACGAATGCCTCACTCTTAATAGC

GCACGGCAGTTTGAACCACTAATTTGGTCGAGTTGGAAACAGTGAAATTTCAATTTTAAT

AAGCTGTGCATAATGAAGAGGAATGTGGAATTGGAGCCTTTCCATCTGAAGCTATTCATA

ACAGGCACAAAGCTGAGTTAATTAGGAATATGCTGAGATGAAGGAAATGAGGAGAGCTGC

TCTTTTGGGGCTGTGCTTCTCTCCCCAACCCCTCAACCCCATTGCCATGCTGCAGATGG

GGTGGTGTCTAAACATCAGTGGCGAGTGCCTGCATTACTCTGCTCGTTGCCTTCCAGAGA

ACTCAGCTTCTCCAAATGCTGAGCTCTTTTCAGAATGGGACCTGCCACCAGTATTTGAAA

GATTTCTAGCCTAGCAGAACAGCAGCCACGTTATCAAAGTTTGGTTGGCCAAAGGAAGGT

ACTTGCTAATTAGTTTAGTAGGTTTTCAGTCCGCACAGACATACGGGATTGTTTTATTGT

ACATAGACATCTTCAGAAACAGTGTATGTATAGAAATGTAAGGTCAAAATTTGAACCTCA

GTGCTTTAAATCTGAATTTGTATTAACTGATATGAAATATTTAGACGGTTACTTTATTTT

ATATCTGTCTTCCATTATACTTAATTTGGCTCAAGAATAGTTAGGCAAAAAGTTGCCCAA

AGAGAAGGATCTCCTAGTAAATACAAAGAGAATGTAACATAGTTGCTACAAGTTGGAGCA

TGTTCAGGGATGTCTTTTTTTTTTTTTTTTTGAGAGAGAGGTCTCTCTCTGTTGCCCA

GGCTGGAGTGCAGTGGTGTAATCATGGCTCACTGCAGCCTCAATCTCCCAGGCTTAAGCG

ATCCTCCCACCTCAGCCTCCCAAGTAGCTGGGACTATAGGCATGCGCCACCACACCTAGC

```
TAATTTTCGCATTTTTTGTAGTGTCACAGTTTCGCCATGTTGCCCAGGCTAGTCTCGAAT

TCCTAGGCTCAAGCAGTGCTTCTGCCTCAGCCTCTCTGAGTAGTTAGGACTACAAATTTG

TGGCTCCATGCCCGGCTAATTTTTTATCTTTATTTTGTAGAGACAAGGTCTCACTGTGT

TGCCCAGGCTAGTCTTGAACTCCTGGGCTCAAACAACCCTCCCACTTTGGGTTTCCAAAG

TGCTGGGATTACAAGTGTGAGCCACTGAGCCCAGTGACCTCTGGGTTTTAAAAATGTGTA

GGCTTCAATTATTTATTTAAAAAATGAAATCCTGCAATATATAGTTTTCTGCGTTGTGT

GGTTTGAATCAATCTGGGAACTGGCTTGCTGGCTGATTGTGGTAAAGTAAGAAGTACTTA

ATTTAGTAGAAAGTTTAAATGGCAGACATAACATTAAACCCAGCTGATTTATAAATGAAG

CAAAAGAACAAAACTCATTCAGGATAATTGGTTATTCTAAAATACAGTCATTTCTAAAAT

TATGAAGTGTTCAGGACCTTTGGGAGTGAAAGAATTTGCTAAAGAAGGATCAGTGAAAAA

AAGGAATGATGGGTGAAGAGCTGTGGAGAAGGAAGAGAAGAAACAGCACAAGGAAGGAAG

AATATAAAATCAGATGTGGGAATCCAGGGGAAAGTGCAAACGAAGCAAGATTGAGAAAAT

TCTCAAGTTTTTATAAACAGTTCTCACACTCTGCCAGTTCCTTGGAGGTAGACTTTTTTG

TTAACTTCCAACTACAGTAGTGAAAAAAAAAAAAAAAACCCTCAAATTTGCAAAAGCAGTC

TGTGGAATTTTCTTTACCCAGCTTTCCTGACTGTTAACTTTTTAGCACACTTAACTTTAT

CATTCGTTTATTCTCTGTTTAAAATTAAAAATGTAAATTTTAAAAAGTAAATGTTTG

TTGGTTACAAACATTTATACCCCTTTGTCTCTAAATATCATTTCATTTTAAAAAATGAAT

AATCTAAGCCTACACATTCTAAAATGTGTATATTTTCTAAAAATAAGGGCATTCTCTTAC

ATAACCAATGTCACAATTATTTGATACAGTGATCAAAATCAGGAAACTAACATTGATATA

ACACTATTATCTAACCTACAGACCATCTTCAAATTTTGTCCTGCTAGTATCTTTTATGGG

TCCAGGGTCACACAGTGCATTTGGCTATAATGTATCTTTTTTCTCTTTTTTTGAGACAGG

GTCTCACTTTGTTGCCCAGGTTGGAGTGCAGTGGTGCAATTATGGCTCACGGCAGCCTTG

ACCTCCTTGGGCTCAGGTGATCCTCCCACCTCAGCCTCTCGAGTAGCTGGAGACCACAGG

TGTGCACCACCATGCCTGGCTAAGTTTTGTATTTTTTGTAGAGATGGAGCTTCGCCGTGT

TGCCCCGGCTGGCCTTGAACTCCTGGGCTCAAGTGACCCTCCCGCCTTGGCCTCCCAAAG

TGCTGGGATTACAGGCGTGAGTCACCACACCTGGCCAGTTATTAGTATGTTTAGTCTCTT

TAATCTGGAACAGTTTCTCAGTCATTCTTTATTTTTCATGACCTGGATGTTTTTGAAGAG

TTTAGGCCAGCTATTTAGCAGAATGCCTTTCAGTTTGGATTTGTCCAGTGTTTTCTCTTG

ACTATATTCTAGTCATGCATTTTTGGCAGGACTGTCACAGAAATGTTGTTGTAGTCTTCT

TAGTACATCACATCAGGTACACACTGTTGATCTGATTCATTACTAGTGGTGTTAACTTTG

ATCACTTGAATAAGGTGGTGTCTGTCAAATTTGTCCACCGTAAAGTTACTTGAGCAAAAC

GTAGCTGGGACTACAGGCGTAGCAAAAAATGTAGCAAAAAGTAGTATTTTTGCTACATTT

TTTTTTTAGGAACAAAGTATTTTTCCCTTTTAAGTTAATCTCTTGTCCATAAAGTTATTA

TTTTTCCCTTTTAAGTTAATATCTTGTGGGTAGATACTGGAGACTGCGTAAATTACCTAT

TTCTCATAATACTTTTTTTTTTTGAGATGGAGTCTCGCACCGTCTCCCAGGCTGGAGT

GCAGTGGTGCAATCTCGGGTCACTGCAAGCTCCACCTCCCGGGTTGACGCCATTCTCCTG

CCTCAGCCTCCCAAGTAGTTGGGACTACAGGCGCCCGCCATCACACCTGGCTAATTTTTT

GTATTTTTAGTAGAGACGGGGTCTCACCGTGTTAGCCAGGATGGTCTTGATCTCCTGACC

TTGTGATCTGCCCGCCTTGGCCTCCCAAAGTGCTGGGATTACAGATGTGAGTCACTGCGC

CCGGCTCTCATAATACTTTTTGCCTACTAATTTTATATTCATTGATTAAATTCTTGCCTG
```

-continued

```
AAAAAATTATTACTGTGGTATTTGCCAAATGGCAATTTTCTGTTTCCATCATTGCCTTTC
CCCCGCTTTTAAAAGTATAAGTGACAAAGAAAAACTGTATATAAAGTGTACACCATGATA
TTTTGATATATGTATACTTTGTGAAATGATTATCAAAATTGAGTTAAATAATGCATCCAA
CATCTCAGTTACTTTTTTTTTTTTGAGACAGAGTCTTGGTTTGTCACTAAGGCTGGAG
TGCAGTGCCACAATCTCGGCTCATTACAACCTCCACCTCCCAGGTTCAAGTGATTCTCCT
GCCTTGGCCTCCCCAGTAGCTGGGATTACAGGTGCCCACCATCACACCCGGCTAATTTTT
GTATTTTTAGTAGAGGTGGGGTTTCACTACGTTGGCCAGGCTGGTCTCGAACTCCTGACC
TCAAATGATCCTCCCGTCTCAGCTTTCCAAAGTGGTGGGATTACAGGCGTGAGCCACTGT
GCCCGGCCACTCTTAGTAAATTTTAAGTGTACATTTTTTTTTTTTTTTTGAGATGGA
GTCTCACTTTGTCACCCTGGCTGGAGTGCAGTGGCATGATCTTGCCACACTGGAACCTCT
GCCTCCTGGGTTCATTCAGGTGCTTCTCCCACCTCAGCCTCCCAAGTAGCTGAGACTACA
GGTACCCGCCACCATGCCTGGCTAATTATTGTATTTTTAGTAGAGATGGGGGTTCACCAT
GTTAGCCAGGCTGGCCTCAAACTCCTGACCTCAGGTGATCTACCCACCTCGGCCTCCCAA
AGTACTGAGATTACAGGCATGAGCCACCACACCCAGCCACATTACGTTAGTATTAACTAT
AATCACCATGCTGTACATTAGATCTCCAAAATGTATTCATCTTATGTAACTTCAAGTTTG
TACCCTTTGACCAAAGTCTCCTTGTTTTCCCTACCCCCAACCCCTGGTAATCACTGCTTT
AATCTCAGTTTTTATGAGTTTGACTGGTTTAGATTCCACATACAAATGAGATCAGGCAGT
GATGGTTTATTTCACTTAGCATAATGTCATCCATGTTCTTGCAAATGACAGGATTTTCTT
CTTTTTAAAACTAATATCCATGCTGGACACGGTGGCTCATGCCTGTAATCCCAGCACTTT
GGAAGGCTGAGGAGGGTGGATCACTTGAGGTCAGGAGTTCGAGACCAGCCTGGCCAACAT
GGTGAAACCCCATCTCTACCAAAAATATAAAAAATTAGCTGGATGTGGTGGCGCACACCT
GTGATCCCAGCTACTTGGGACACTGAGGCAGGAGGATCGCTTGAACCCGGGAGGCGGAGG
TTGCAGTGAGCCAAGATGGTGCCACTGCACTTTAGCCTGGATGTTGATGTTGTTCCACTT
GTTTATTTTTATTTTGTTCCCTGTGCTTTTGGTATCAAATCCTAAAAACCATTGCCATGA
CCATTGTCATGTTACTTTCCCCATATGCTTTCTTCTAGAACTTTTAAGGTTCATCATTCC
CTTTTCTGTTTTAGTTGCAAGCCTACTATAAGGAAGGGCTTTTCTTTCTTCCTTATTTA
TTTATTCATGTCTATCAGAATGGGCACCTTACTACTATTTTTGTTGTTATTGCTTGAATT
GACTTGAATTTGGCTAGTGGAAACCTTTTCAGATCGGGTACTCTGTCCTTTTGATCTCTT
TCCATTTTCAAGCACTTCTTTAGACTTAAGATGGTCTAGGCTCATCTTCTCCTTTCCCAG
CCATTTTTCAAAGGAACCTGATTCCTTTTAGTGAAGAGCAGTATTTTGAAACCAAGATCT
GGGCACTGGGTCTACTTGTTTGTACTGGTACAGTGTTCTTTGAATTGCTAATTAGCTGAT
CAATTACTGCTCTATTTGAGTTCCCTCTTTCTAAAACCTCACATATGTGTACAGACGGTC
CCTGACTTATGATGGTTCGACTTATGATTTTTGATTTTATGATGGTTTGAGAGCAATACA
TCCATTCTGTTTTTCACTTTTCATTCAACACTTTATTTTAAAATAGGGATTGTGAGATGA
TATTGCCCACGTGTAGGCTAATGTAAGTGTTCTGAGCACGTTTAAAGTAGGCTAGGCTAA
GCTGTGGTGTTTGGTAGGTTAGATATGTTAAATGCATTTTCGACTAGTGATATTTTCAAC
TTATGATGAGTTTATTGGGATGTATCCCCATAAAGTCGAGGAGCATTATACATATCTCTG
TATAACAGAGTGAGTTCCTTATACCTTTCATCCACTTTCCCCTGAAGTTAACATTTTACC
TAACCATGATACATTTATCAAAACTAAAACATTAACATCAATACATTGCTATTAACTAAA
CTAGAGTTTAATTGGATTTTGCCAGTTTTCCAATGAATATCCTTTTTCTGTTCCTTGATC
CAATTCATGGTCACACACTGAGTTTGGTCACTTGTCACTGTAGTCTTCTCCAATCTGCGA
```

-continued

```
CAGCTTCTTAGGCTTTCCTTGTTTTTCATGTACTCTTGACGATTTTTAAGAGTACTGGTC

AGATATCTTGTAGGATATCCCACAACTTGTGTTTAATCTTATGTTTTCTCATGATTAGAC

TTGAGTAATGGATTTTTGGGAAGAATACCACAGAGGTATATTGTTAAGTGTTCTCATCAC

TTGGAGGTAAATGTTATCAACATGGCCTGGTGATGTTAAACTTGTCAGTTTGTTTAGTTA

GTATCTGCCAGATTTTTCTCACTGCATAATTACAAATCCTCCTTAACTTATGATGGGGTT

ACAGCCTGATAAGCCCATCATAAATTGAAAATATCATAAGTCAAAATGCATTTAATGCA

TCTAAACTACTAAACATCACAGCTTAGCCTAGCCTGCCTTGAACGTATTCAGGACACTTA

CATTAGCCTACAGTTGGGCAAAATCATCTCATGGGAAGCCTGTTTTATAATGTGTTGCAT

ATCTTATGTAATGTGTTGAGTACTGTACTCAGAATGAAAAACAGAAGGGTTGTATTGCTT

TTGCACCATCATAAAATCAAAAAAACCATAAGGCAAACCATCATGAAGTTGGGGACTGCC

TGTACTTTTTTCCTCTTTCCCTGTTCAATTCCTTGGAAGAAAGTCATTTAGTTCAGACCA

TACTCAAGAAAAGGGAAATAAAGCTCCATCTCTTGGAGCTTAATTGAAACTGGAATGACT

AGTTTCTATATACATTATTTAGAATCCTTTTGTAAGAAAGATTTGTTCCTTCTCTCCATT

TATTTATTCCATTATTTATATTGATAGAGACGCATGTACATTTATTTTATACTTTGGGTT

ATAATCTATTTTTCTTGCTCAAATTGTTACAGCTTTGGTCACTGGGAGGTTCTTCAGATT

GGCTCCTGTGTCATTTGACATGTCCCCACCCTCTCGTTTCTGAGTACTTCTCTACTTTGG

CATTACAAAAGATGTTCCAGGCTCCTCTTATATTTTTCCCTGCCGCAGCCCTAGAATCAT

CCATTTTTCTATGGTGCCCTGGTTCCTTTTACTTTAGATGGGGGTTTAGAAACCAATCTG

GGTGTTGGGTGTGCTCATTGCTACTGGAATCACTGCTTCTAGGCCCTCTCAGCAGATAGA

GCTAGAAAACATATGGCTGTATATGAATCCATGGATTCATATATATCTATAATTGTTTTC

TGTATCTGGCCATCTATATATATATTAAGCTAAACATGAATTCATACTGATGTCTCAGAC

TCGAATCCATTGCCGCAGGGCTCATTCTTGCCTTCCTCTTGCTTATTTGTGACTTCTTTC

TCTAACAGGGAGAAACCCCAGTCTCATTATCACCAACCTATCTACTCATTTGTTCAACCC

TGGTATAGGTGTAAAGTAGTTTCAGAATTACTAACCTATACCCATGTGAGAATTGTATTT

GCACTTCTTGTTTGAAGGAAATACATACAACACAGGTAGCGTCTCTACACTTCAGTATAC

AGAGATCTGAACAGTGTTCTCTCTGAGTGAATCATATTGCAGGACAGAAATTACTTTTAA

AAATTCTGTAATGGGTCAGGCCTATAATCCTAGCACTTTGGGAGGCTGAGGTGGGCAGAT

CACCTGAGGTCAGGAGTTCGAGACCAGCCTGGCCAAAATGGTAAAACCCCATCTCTACAA

AAAATACAAAAATTAGCCAGGCGTAGTGGTGTGTGCCTGTAATCCCAGCTACTCAGGAGG

CTGAGGCACGAGAATCACTTGAACCTGGGAGGCAGAGCTTGCAGTGAGCTGAGATTGAGC

CACTGCACTCCAGTCTGGGCGACAGAGCGAGACTCTGTCTCAAAAAAAAAAAAAAAAAAA

AATTCCATAATGATAGCAGAGCTGGAATAGAAATGGGATTGCACAGGCTGAATCTGAGTT

GTTGCAACAGTAAACGAGCAAGATTTAAACTGGCCTTGTGTAGCACTTGCTATTTGGCTC

CTCATATTTTATTAGACGCTTATTCTTTTTTGTTTGGTGTCATTCCTTTGAGAAATATTT

GAGTGCCTTTTCTGTTGCAGACATTGATTAGATGCTGAGGTTGTAACAATGAAGAAGATA

GCCATCGCTGTTGCCTCATGGAACTGAAGTTTTACTAGATGTAAAATTTGAGTTAACATG

AGGCCGTGCCCCTATGTGCCCATTGTTTCTTCACACAGCTCCCTTCATCTCCTTGGTCC

AATGAAAAGGTTTTTTCATACTTGTTCATTCATTCCTGCATTAATTAAAGTAGGTTGTAC

TGTGCCAGGCACTGGGAATATTTAAGTAGTTGTGTTCCTGAATTGGAAATGAATCCAGCA

TGGTTGGAGTAGAAGGAGCTGGGGGGCAATGTGGAGTGTGATGGGGAGATTGGAAAAGTA
```

-continued

```
AGCTGAGACCAGATTTTTCAGTTTGGAGGGAGAGGTGGGCCTTGTAGGCCATATTACAGA

TTGTAGACTTTATTTGGAGGGACATGGAAGTCATTGAGGAGTCTGAAGCAGGGGAATGAC

ATAAAAAGATCCTCATTTTAGGCCGGATGTGGTGGCTCACGCCTGTAATCCCAGCACTTT

GGGAGGTTGAAGTGGGTGGATTGCTTGAGGCCAAGAGTTTGAGACTAGCCTGGGCAACAT

GGTGAAACCCTGTCTCTATCAAAAATACAAAAATTAGCTGGGCATGGTGGCTCACACCTG

TAGTCCCAGCTACTTGGGAGGCTGAGGCATGAGAATCGCTTGAACCCGGGAGGCAGAGAT

TGCAGTGAGCCGAGATTGTGCCACTGCATTCCAGCCTGGGTGACAGAGTGAGACTTCGTG

TCAAAAAAAAAACAAAAAACCCCTCATTTTGAAAGGGAACCCTGGCTTGAGGGTGAAGAA

TGGGTGGGCACTAGGCTAGAGCAGCTGCAGGGTCAGTGAGGAGCTGCCGCAGTGCTGCAC

GTGAGAACCCGTCATGGTTTGGTCAGGGTGGGCAGGACTGACAGTGAGCACAGAGCGAAG

TAAAACCAGCAAAATTTCATGATTGGATAGTGGAAGGAATCATGGTGTTTGTAGTCTTCA

AATGTGAACCCAGAGTGCACTGGACAAGTAGTCTAGGCTGCTCTGTAACCAAGGCAAGTG

TTTTCATTTTACCCTCTCTTCCTGCTCTTGGCCTTTGGATTTTTTGTAATTTAAGGTTTA

TGAATGTAATCAGTTACTTAACATGGAAAGATACTTAATACCAGATGATTTTGGAGTCTT

GTGATCAATACCTTCTCTCAATCTTGGGTGTGTCAGTTGGCAAGGCCATAAAATTTGT

TATAAACATTGCAGAAGGCTTGGTTACTGTGCTGTGACGTTGAATTTGGGTGGAGATAGA

TCAATTTCAGTTGATTTTCTAGGCTTCAGAAACACATTACCCTCTACTCCACAAACACAA

ATCAAAACAAAACAATCCCTATTCCCTGAGCATTTCTCTTGATCTATAACACAGCCTGGG

CTGTCACAGTACTAAGACAAGCCCATCTGATTTGTGAGTCAGTTTTATTTCTTGGTCTTC

TACATAAGCTAAAAAGTTTCAACATTTTAATGCTTTTCCTTGGATTCCTTTGAGTCATTG

AAGTAATTCCTGTTTCATTTGTACTAATTATTCCACACTAGAAAATTCTGTTGTAATCAC

TTTATGTATTAATAGAAATACTGATTTTTATTTTCAAGGAAGTATTGAGTAGGGAGGGGG

AAATAGGGATTTGCTGTTCAATGGGTATAGAGTTTCAGTAATACAAGACAAAAAACTTCA

GAGATCTTCTATACAGCAGTGGGTATATAGTTAACAATACTGCACATCTAACAGTTTGTT

AAGAGGGTAGATCTCATGTCATGTGTTTTAAAAATTGCTTTTAAAAAAAGTATCGAGTA

AAAAAGCAGTTTTACTCCTCAGTTTCTATTTATATTTAAAATTTTTATTTAAAAAGTGAG

TTGAGATTTTTAAACCTCAGGATAAGTTTTATTTTTTAAAAAATTTATTTTTTATTATTT

TTTGAGATGGAGTCTCACTCCATCTCAAGTCACCCAGGCTGGAGTGCAGTGGTGTCTTGG

CTCACTGCGACCTCTATCTCCCAGGTTCAAGTGTTTCTGCTGCTTCAGCCTCCTGAGTAG

CTGGGATTACAGGTCTGCACCACCACGCCTGGCTAATTTTTGTATTTTTAGTAGAGATGG

GGTGTCACCATGTTGGCCAGGTTTGTCTTGAACTCCTAACCTCAAGTGACCACCTGCCTT

GGCCTCTCAAAGTGCTGGGATTACAGGTATGAGCCACAGTGCCCGGCGGGATAAGTTTTA

AAATAATATTCTCTGCTGGCTGGGCATGGTGGCTCATGCCTGTAAACCCAGCACTTTGGG

AGGCTGAGGCAGGAGCATCACTCGAGGCCAAGAGTTTGAGACCAGTCTGGGCAACATAAT

GAGACCCCTCTCTACAAAAAATAAAAAAATTTGGCTGAGTGTGGCATGTTCCTGTAGC

TATCGGGAGGCTGAGATGGAGGATTGCTTGAGCCCAGGAGTTTGAGGCTGCAGTGAGCT

ATGATTGCACCACTGCGCTCTAGTCTGGGTGACAGTGTGAGACCCTGTCTCTTAAAAAAA

AAAAAAAAAAAGGCCAGGCACAGTGGCTCAGGCCTGTAACCCCAGCACTTTGGGAGGCCG

AGGCGGGTGGATCACTTGAGGCCAGGAATTTGAGACCAGGCTGGCCAACATGATGAAACC

CCGTCTCTACTAAAAATACAAAAATAAGCTGGGTGTTGTGGTGCACACCTGTAATCCCAG

CTACTTGGGAGGCTGAGGGAGAGAATTGCTTGAACCTGGGAGGCAGAGGCTACAGTGAGC
```

-continued

```
CGAGATCACACCACTGCACTCCAGCCTGGGTGACAGAGCAAGACTCCATCTCAAAAACAA

CAACAACAAAAAAACCAAATGTTCTTGCCAATTCTTCCATTTAATATTTAATTTTGAATT

ATATTGTATCTTTCTAAGGATTGTTTCTTATATAAGCAAAGATTTTTCAGTGCTAAACAT

TTACGACTGCTATTCAGAAATGGTTATTTACAAGTCTTTTTGTTTTAAGAAAATGGCTGT

TCAAAAAATTAAAATAGTATATAAACCAAACAAAATATTTTTGCTTTGGATGTCTGTTTT

GCAGCTTCTTCCCTACACTATAAGTTCTTACTGACTGCTTTATCACTTAATAAATTGGTT

TGGCTACTTTAACAGAGGCAAATAGTATCAGGCAAAAATTATTTTTTATTTTTATTTTT

TGAGACAGTCTCACTCCATCACCCAGGCTGCAGTGCAGTGGCCTGATCTTGGCTCACTGC

AACCTCCACCTCCCAGGTTCAAGCGATTCTCATGCCTCAGCCTCCTGAGTAGCTGGAATT

ATAGGCATGCACCACCACACTCAGCTAATTTTTGTATTTTTAGTAGAGACAGGGTTTTGC

CATGTTGACCAGGCTAGTCTTGAACTCCTGACCTCAAGTGATCCATCTGCTTTGGCCTCC

CAAAGTGCTGGGATAACAGGCATGAGCCACCATGCCCAGCCCTATTTTTATTTTTTAGA

GATGGGTCTCGCTTTTTAGAGATGGGTCTTGTTGCCCAGGCCAGAGTGCAGTGGTGCGAT

CATAGCTTACTGCAGCCTTGAATTCCTGGGCTCAAGCAATTCTCCTGCCTCAGCCTCCCG

AGTAGCTGGGACTACAGGCCTGTGCCACCAGGCCTGGCTTGTACATTAGTATTTGATATG

GCTACCCTAAGGGCAATCCTATAGTGAAGTCAACATTAGATAATGATGCTCATCTGATGG

ATTAGATTTTCAGAGTTGGCTGTTTCCAGGTGCCTATAGGAGTAGAAAAGGGTGACAAAC

CTCCTAACTAGATGTCCTACCAAATATAGTTCACTCCACATCTGAGATGAGACTGCATGA

CTGCTGGTTTTCTTTGCCTTTTCCCCCCCAGGGTATCATCAGAACCAAAAATAAAGTTTT

AAAGGTGGGTCAGGTGTGTGTTGGCTCATGCCTGTAATCCTAGCACTTTGGGAGGCTGAG

GCAGGTGGATCATCTGAGCTCAGGAGTTCAAGACCAGCCTGGCTAATAACATGGTTAAGC

CCCATCTCTACTAAAATACAAAAAGTTAGCTGGGCATGGTGGTGGGCACCTGTAATCCCA

GCTACTCAGGAGGCTGAGGCATGAAAATCGCTTGAACCCCAGAGGCGGGGGTTGCAGTGA

GCCGAGATCATGCCACTGCACACTAGCCTGAACAACAGAGCAAGGCTCTGTCTCCAAACA

AACAAAAATGGTGCCAGAGTCTTTTCCAGGGCTGAGGGGAGATACAATGAAGTGTGTTAT

TTTTTCTGATAAGAGTGCTACCATCTTTCATTCTTGTGTGCCATTTCTAGTTGGGGTGAA

TTTGTTTTCGGAGTTCCTTTCCCAGCTGTTTGCCTGAAAAACCATGAAATGTGTTCCACA

TGAACTATGAAATGATTAGATGCTAATGTGGCAAAGAAAGTGTGAATTCTCTTGTAGAAA

CAGGGACATTTGGTTCGGTACAGTAAGTTGTTAATGCGTGACTCTGTGCTTTCAAATTCT

GTGGTTCAAAAGTACTTTTCACTCCTACTGTGTATTTACCTTGAGAAGGTGAATCCCCTA

ACAATTTGGTCAATGTATCAGTATTCTCAACCCGTCTATCAATTTTTTTTCTTTCTCCC

TCTTTTTTCTTTTTTGGGCAAAATACCTTTTTGCTTTTTATCCCCTTAAAATAACCAT

TGTCCCTCACATGTGCACTCTTCCAAATTTCAGAAAAGCAAGAGGAAAGGGCACGAATAT

ACAAATATTAAGTATTCTCTAGCGGACCAGACGAGTGGAGATCAGAGCCCTCTCCCGCCT

TGTACTCCAACGCCACCCTGTGCAGAGTAAGTAGTGCTGAAGGAAATTCTTTTTACCTGG

TCATGGTGGTTTAAAAAGGTTTAAAAAACAAAAACAAAAACAAAACACAAGTTTGTAGCA

CATGCCTTTCACTGGTGCACGTTCCTGTTGCCCTACTGTTAGTGTATCTGTGACTGGTGA

TATCTATTGATTGTGTTAATGCTATCTCAACCACGTTTTAATTTTCCTAAGCTGGCCAGG

CACGGTGGCTAACGCCTGTAATCCCAGTGCTTTGGGAGGCCGAGGTTCATGGATTACTTT

GAAGTCAGGAGTTCGAGACCAGCCTGGCCAACATGGTGAAACCCTGTCTCTACTAAAAAT
```

-continued

```
ACAAAAATTAGCCGGGCATGGTGGCGCATGCCTGTAATCCCAGCTACTCAGGAGGCTGAG
GCAGGAGAATCGCTTGAACCCAGGAAACGGATGTTGCAGTGAGCCGAGATCATGCCACTG
CACTCCAGCCTGGGCGATAGAGTGAGCCTCTGTCTAAAAATAAAATAAAATAAAATAAAT
TCCTAAACTGAAGGCTGACTGCTATGCTAGCTAGGATTATATGGGATTTTAAGTATATCA
AGTGGTGGTTCTCCAAGAAGAATCTAATTTTTCTTTTGATGGGCTGGGGATTGTAACAAA
GGAAGGTCATATGTCTTAATGATGTGTTAAGGCTCTTTGCAAAATCAAAGTAAATAAATT
GACCACTAATGTGTCAGCCCAGCCATGTTCTGCTCATTTGCCACCAGTCAACAGAAATCT
ACTTTGGGTGTTTAAACCAGGAGTCAGCAAACTACAGCTCACAAGGCCAGATGTGGGCCA
TGGCCTGTTACTGTATGGCCTGTTAATGGTTTTAAAGGGTTGTAAAACAAAAGAACACAA
AACAAAGACCCAATAACAAAACAAAGCCCGAAGAATAATATGCGACAGAGACCATGTATG
GCATATAGAGCCTAAAATACTGACTCTCAAGCCCTTCCCAGAAATCCTTCCCGACTCCTT
GTTGAAAACACGGTAGGAAAGCATTTGTCAAATTGAGGATATGAATAGCAATTGTAAGTT
ATTATTTTTCTATATATTCGAAAGTCACTTGCTAGTATAACATTTACCTTTTATTTTTCC
CTAAGAATCTTCTCTCTGTTTGCTTTCGACATGGATTTTTAAACCCCTGCAGATTTTAAT
ATTCTATATAAATGTTTTAGGTGGCATATATGAGGTTTGTATTAACATTTGCTTTCTATT
TAACATTGAAATGAAATTATACAGCAGAGGTATTTTCTCGTCCAAGTTGCCACTTCTTTC
TATCTTTTTTCTTTTCTTTCCCAGTGGACTGCCTGGGAAAATTGATATTTTAAATTGCTC
TCTGCAATAATTTGCAATGGAACTGGAATGCCAGGGTTCTGAGTCCTTGCCAGACAGCTC
GTCCCTCCTGTTGGCATGACTGAGTCAGCTGTCATGATTCCCTCAGTACCAGTGGCATGC
CTGTGACAGACAGCCTGTCTGCCTTTCATTCCCGTCGTCTCCCTTGTAGGGTTCAGATCC
AGGATACACTGGTCCTGGAGCCCCTCTCAGCCTGGCACCCACAGCTGCTGGGTTCCTTAC
TCTCCTGGACTGCTCTGATGTCATCTCCCTGCTCAGCAGAAAGAAGTCTGGGATCTTGAT
GCTTTGGCCCTCTGTCCTAGGCCCTAAACCACCCATTGCCCTTCACATAACCTGAGCTGG
GGCTAAATAGATCTCTCATCACTGCCTGCCTGCTCCTGTATTTTCCCTTCTTGGAGCTTT
TGCCTGTTCAGATCCCTCTACTGGAAATTAATAGGATTTCATTCTATGTGTGCATTTCCA
ACCTTTCTTCACAGTGCGATCCAAATGCCTCATCCTACAGGCCTCCTTAAAACAACCTGC
TTTCTGCCAGACCCCAGGGAGCACCAGGACTTGAGGCTTTTATTGCACTTCTGTTGTTTT
TTTGAGATGGAGTCTCGCTCTGTCGCCCAGGCTGGAGTGCAGTGGCACGATCTCTGCTCA
CTGCAACCTCCATCTCCCGAGTTCAAGAGATTCTTCTGCCTCAGCCTCTCAAGCAGCTGG
GACTACAGGCATGTGCCATGACACCCGGATAATTTTTGTATTTTTAGTAGAGACGGGGTT
CACCATATTGGCCAGGCTGGTCTCAAACTCCTGACCTCGTGATCCACCCACCTGGGCCTC
CCAAAGTTCTGGGATTACAGGCGTGAGCCACCATGCCCAGCGTTATTTCACTTCTGCCTC
TGTAATTATATTGCTGTATGGCTATCTCTTCTCTCCCTGGGAATGTCAGGTCCTAGGCAC
AGGAACTGTGTCTGTACCATATCTGGTGCCCAAAGAATGTAGTATGTGTTTATAGATAT
CATGTAAGCTTAAACAGCGTGGTCTACATTTTTGTAAATGTCTTTCTTTTTCTTTTCTCT
CCAGAATGAGAGAAGACAGTGCTAGAGTCTATGAAAACGTGGGCCTGATGCAACAGCAGA
AAAGTTTCAGATGAGAAAACCTGCCAAAACTTCAGCACAGAAATAGGTATTTAAATGCAA
GTGCTCTATTGGTTAATTGTTTATATAATTGGCAGTATTTTTAAGCAGGCAAGCAATTTG
GGAATGTTTTAGCAAAGTGTACCATAATTGAGTTTTACAAACCAGGCTCCTTTTTCCTCT
CCCTGTACTTCTTTTTCCAAGATGGTTTTAGTTTAGAGTTCATTAAACATTAAAATCAAA
CACAGAATTAATTCTGCATGAGGCAAGGCTAGCACTTATTCCAGAGAAATGGCTGATACT
```

-continued

```
GGTGGTAGAGTGCAGGTATCACTGTTCCTGCAATTTTTATTAGAGTTGGTTAGCCCAGGC

TGTGCTGGGGATGATCTGTAGGGATCTGGGAAGCATCGGGACTCAGCACTGGGTGGTTG

GGAGTCAGGAAGCCTGAGTTCTCATTTCAGTCAGTCTCTGACCAACTGTGTGGCATGGGG

TGCTAGACCACTTGGCTGCCGACTGGGTCACCGACATCCCTTCCAGCTCTGCTGCTGGAA

ATTCATCTCTCCCATATGTTGCCTCCCCATCAATTACGTTTTTTAAGTGTGACCCAAGTA

TATGATGTATGTTTTCATGATAAATTAGAAACTTATCTGGGCATGGTGGCTCATACCTGT

AATCCCAGCACTTTGGGAGGCTGAGGTGGGCGGATCACCTGAGGTCAGGAGTTCGAGACC

AGCCTGACCAACTAAAATAGTAGAGACCAACCCGTCTCTACTAAAAATAGAAAATTAGCT

GAGCATGGTGGTGCATGCCTATAATCCCAGCTACTCAGGAGGCTGAGGCAGGAGAGGCAG

CGGTTGCAGTGTGCCAAGATCGCGCCATTGCACTCCACCTGGGCCACAAGAGTGAAACTC

CATCTCAAAAAAAAAAAAAAAAAAAAAAAACTCAGTGTCAGTATTTCATGTCGAAATTC

CACTTCAATGGGTAGTGTAGTTAAAAGCTCTAAGTCTACCTTAAAATCACCTAATGCTTT

GTTAAGCTTTTAGATATATGTTCCTTAAAAACTCTTAACTTATTTCTTCCCCAGATGTGG

ACTTTCACCCTCTCCCTAAAAAGATCAAGAACAGACGCAAGAAAGTTTATGTGAAGACAG

AATTTGGATTTGGAAGGCTTGCAATGTGGTTGACTACCTTTTGATAAGCAAAATTTGAAA

CCATTTAAAGACCACTGTATTTTAACTCAACAATACCTGCTTCCCAATTACTCATTTCCT

CAGATAAGAAGAAATCATCTCTACAATGTAGACAACATTATATTTTATAGAATTTGTTTG

AAATTGAGGAAGCAGTTAAATTGTGCGCTGTATTTTGCAGATTATGGGGATTCAAATTCT

AGTAATAGGCTTTTTTATTTTTATTTTTATACCCTTAACCAGTTTAATTTTTTTTTCCT

CATTGTTGGGGATGATGAGAAGAAATGATTTGGGAAAATTAAGTAACAACGACCTAGAAA

AGTGAGAACAATCTCATTTACCATCATGTATCCAGTAGTGGATAATTCATTTTGATGGCT

TCTATTTTGGCCAAATGAGAATTAAGCCAGTGCCTGAGACTGTCAGAAGTTGACCTTTG

CACTGGCATTAAAGAGTCATAGAAAAAGAATCATGGATATTTATGAATTAAGGTAAGAGG

TGTGGCTTTTTTTTTTCTTTTTTCCAGCCGTTGACCAATTATAGTTCGGCTGTTGACT

GAGAAGTTTGTGGTGGGAAAACGTTTGCCATATTTTCTTTGCATTTGAATAATTGTCTTG

TACTTAGAAAAAAGGCGTCTATGAATGACCAGTGTTTTTGGTCGCCAAATGTTGCTGACA

AACTTATCCCAAAACTTTAGTGGCTTAAAAAAACCTGCCCCCAACTGTTAGTCAATCTGA

GCTGGGCTCAGCTGGGCTGTTCTTCTGCCAGCCTGCAGGTGGCCACTCATGTGGTCAGCA

GGTCGGCGGAGAGACTGGGATGGCTGGGCTTCTCTCTCTGCCTGCAGTCCTGAGTCTCTC

CTTCTTCGTGTAGTCTCTTTCAGTGGCCTGGCTGGCAGGGTAGCTAGACCTCTCACATGC

AGCTCAGAGCTCCCAAGAGCTCAAAAGCAGAAATGGCCAGGCCTTCTGAAAACTTAAGTC

CAGAATTGTCACAGTGTCCCTTCTACTTCCCTCTATTGATGATGATGATGATGATGATGA

TGATGATGATGATGATGATGGTTTTTTCTAATCAGAAGAAAGCTGGGGTATGCCCTC

TACTTACTAAACAAGTCACAAGCCCAGCTCAGATTCAAGAAAGGGTGTGAAGTAGAGGT

GCAGTTAAGTGGGGGGCCACTAGTCTAACAGACGGTCACAACCAGTGCCATGGAAAACCA

AGGATATTAGCAAAAGCAGAAGTTGCTAGTGACCTTGGGAAGCCGAAGCTGCTTACAGTA

GCTGGGACAAGCTGAAAGTCAGACTAAGAAATAAAGAGAGGGCCTTCAAGAAGCTTCCTG

AATGATTTCTGCTAGCCCTGAGCCTATTTTTGGAACCAGCACTTGGGGAAACTGATCTTG

TGAGGATGGATGTGTTTAGGGACACAGGGCTTTTGAGAGCAGCACCACCCCACTGGGGCA

TCCCCAGACTTGGGAAACGTGACTCTTTCTTAATGCCACTGGGTTTTAGTCAGGCCACAG
```

-continued

TGAGAAGGAACAGCCCTAACAGGCCTCCAGCCAGGTTGAATGAGCTCATTTTTGTTGTAG

CCAACCAGTAAGATTTGCTAATGTTCTACATTAAGTGCCTTCTCCAAAGACATCCCTCTT

TGCCTCATATGTTGAATCATCCAGTGCGGATATTTCAATGAAAATATCATTGGTTGACTT

TTGTGATGGTAATAATGCTATGGCATCTTTGCCATGAAGTTGTGGCCTCCTTGGATTCTT

CTGACTTTGGCTTCTGAAAGGAAGGCCTAGATCCAGCCCTGGTGGTAGTTCCTTTCTGAG

GTCTCTCAGTCCCTTGAGACTTTGGGGTAGTTTGGCTGCCATTCTCACTGACAAAATGTA

TATCAGCCCCCACCTCCACCCCCCAATATTCCTTGAACTTTGAATTGCTTCAGAACACAG

GTGTGGCCTGAAGGTATTCCCTTATTAGGGAAGTGTCACTGCTGTCTTCTAGTCAAACTT

GTAAAGAAAAAGATTCCAGTTCAGTATTTGCAGCAAGAAGCTTGAATGCTGTTCTTTTTA

TCGCATTGTTACATCGACTCATTCTCCATTTTGCTTTGGTTTTGTCTTGACTTGACTTGA

CTTTGGGGGTAAAGTCTTTCACCAGCACACAAGAGTTTGATTGTACAAATATATCTTCTG

CATTAACATCTCTGCCTGTTGCTTAAGATCAGTTGCTTTTATACTCAGAATGGAAATACC

TGATCTTGGCTAGTTTTGTTATAAGATATTGATTTCATTTAGATTTCCCTCCACGAGGTC

AGCAAACTATCATGTTCTTATGTAAACTTAGGCCAAGGCCAGAGTTATCATAGTCCCTAG

GTTGCTACGGCTTATCATGTGCTTGGTAAAAGGTGATCGCAGGTTCTCAGACGAGTTTAC

TTTACATGAGATGGAATCAGGCAGAGAGGCTGGGATGATGGAGAAAGCTCGAGGTGAAGT

TTTAAAAAAAAGTTGTGGAAAGGAAAGTTCCAAAGAGGTGGTTTCTGAGGAAGTCAGAG

CGCCCAGGGCCAGAGCAGTCAGTAATGGGTGAATGAGGTTGTTTGGAAAGTCGGTGTGAC

AGACACATGGATGCCATCTACTTCTAGGTTGCTGGTGGGTATTAAATATGCACAATATTC

CATAGCTCACTGAGGATTTTAAAATTATAAGCATAGGATTTTATATTTTGGGGTGAAAGA

ATTATCTGGCACATTAGGTATTGGAGTTTAAAAAAAAAGCCAAATTTCACAGTCTTAATA

ACTTTTTTTAAAAAAAACTAAAAGGCGCTTCATGTCCAGTGTGTGGCCCTTCTGAAACTT

ATGGTCATCTCTCCCACTGAAACCAAGGTCTTTTCAAATGTGGCTAAATGGGGATGAGGA

GACACGGGTAGGACTTTCTTGGTGTGTGTGCATTCTTTAAAGAGCCAAGTTGCTTCGGGG

AAACAGCCAGGAAAATGGTCAAGATTATTTTTAGAGGTTATTTTATTGGGGATTTTAAGA

ACTAATAACATCTTGAGTTATTTTAATTCAGGGGGATGTGGAAAGGTTTGCAATTGTCA

AGTGTTTTGTTGTAGCTTAGTATCCATAAGGGAAACTTAGACTATAGACATAACTACAAA

GCCAGTGCAGCTTTTGTTTTCTGTATGTTGTTGGGGGATCAACTTTCACACATAGCAAGC

ACATGGCCTCCCTGATGTCAGGATGCCTTTGTTAGGATCTGTATTTGCCCTTAATTTTGT

TGAAATCTTTTTCCTTCTTCCTCTTGAAAAGTTCCAAAATATAGTTTATTGTATCTTTC

ATCACTAAAAATTTGTTCCTTTTTCACTATGGGCAGTTCACACAAGGCAAAAACTATTGA

ACAGTTGGTTTTAGTGTGTTGTATAACTTTGCTGTATATCAAACTAATTTTGACAAGTTT

TCATCCTAAGCCTCAAATCATGTAATTAATAATTTGCCTGTTTATTTATGACCTAATTGT

GATTCTTTTATTAATAAAAGCTAATGGGAAAAGGATCCCTGATTAAGCTGATGACTAGAC

CTACAATTAATTTTCCTGCAGTATATGAAGTATTGTACCAGAGTATTAAAAGATATGTAA

TATTTTATTGATAAATCTATCCTTTAAAAGGAATACGTTTTAGGATGTCATCATTTTGAT

GTGAATCATGTAAATGTTGATAATATGCTGTTTATTATACATTTAGTGTTTCAAGAGATT

CACTTAATTGCCTTTTTGCCCACGTATATTATGTAGTCTATTTGCAACTGTTCTTAAAAA

AATGACATTAAAAGAATAGTTTATGTAGAGAAACATTAGTGGATGTTAATTGTCTCCCCA

CCTATATTTATGGGTGTTAGCGCAACTGCTTTGCTAGTTGCAAAGCTGTATTATCAGAGT

AAAAGTGTATTTGTAAACTGTATGGGAACTAAAAATTAGGAATAAAACCATTTTCTTATA

```
TGATGGCATTTGTCGTTTGCTTCATCAGAAATGTCCAGGAAAAAAATGGGATTATTGGTC

ACTCCACCTCTCACACTGGCAAAATACTGACATTTAGCAGCTCTTATCTAGAAGTGACTT

GGAACATAGAATAAAGGCATGAGTTCCTGAAGAATTCATTGAGTGTTTCCTGTAGAAATA

GCTTTAGGAGATAGGGAGTTCTATCTGGGAGAACATATGAGTAACTCAAGAGTAAAAAGT

ATAGTCTGTGTAAACTATAGAAGAAATGCTGGGCATGGTGGCGCGCCCCTGTAATCTCAG

CTACTTGGAGGCTGAGACGGGAGGATTCCTTGAACCCAGGAGCCCAGGAGTTTTAGACCA

GTCTGGGTAACATAGTGAGACCCTTTCTCACCTACTCTCACTGCATGCCCCCCAAAAATA

TATATGTGCGCGCACGCGCGCGCACACACACATACACACACACACACACACACACACACA

CAGAGGAAATTGTTAGAAAACACACAGAACTGAATGTAAATAGTATTAGGTGGGAATAAG

AAGTAAAGGGATGGTAAGGAGGCTTGGAGGAGGAGTAAATTATCTGCTATGGGACATCAG

CTC
```

FIG. 11 shows a SHP2 translated amino acid sequence (SEQ ID NO: 61). Alternating exons are underlined and non-underlined. Bold with italics indicate a residue overlap splice site.

Like reference symbols in the various drawings indicate like elements.

DETAILED DESCRIPTION OF THE INVENTION

Protein/nucleic acid complexes or assemblies are difficult to manipulate due to their fragility and requirement for structural integrity (e.g., 3-dimensional conformation. Genome editing technologies, such as clustered regularly interspaced short palindromic repeats (CRISPR)-Cas9, transcription activator-like effector nucleases (TALENS), and others, have shown much potential in their ability to change the genetic code of cells. However, their activity is highly dependent on structural and conformational integrity.

Zinc-finger nucleases (ZFNs) and transcription activator-like effector nucleases (TALENs) are examples of a class of gene editing tools. These chimeric nucleases are composed of programmable, sequence-specific DNA-binding modules linked to a nonspecific DNA cleavage domain. ZFNs and TALENs enable a broad range of genetic modifications by inducing DNA double-strand breaks that stimulate error-prone nonhomologous end joining or homology-directed repair at specific genomic locations (Gaj et al., 2013, Trends Biotechnol. 31(7):397-405; hereby incorporated by reference).

Numerous publications describe the use of viruses, mRNA and plasmids to code for the Cas9 and/or gRNA and/or donor oligonucleotides (where relevant). Compared to these methods, the methods and systems described herein utilize a different strategy—delivery of the protein itself, complexed with the guide RNA. This process is fundamentally different, because it does not require the cell to translate/transcribe anything for the editing to work. For that reason, and because the protein/guide complex has a short half-life, the approach of the invention results in faster and more efficient editing with fewer off-target effects.

Other Approaches Such as Liposome Mediated Protein Delivery, Microinjection, and Cell-Penetrating Peptides (CPP).

One example of liposome mediated protein delivery uses GFP fused to Cas-9, has also been used (Zuris et al., 2015, Nature Biotechnology 33:73-80). The GFP is capable of complexing with conventional lipofection agents (e.g. lipofectamine) due to charge interactions and appears to mediate a gene editing response. The main advantages of the invention relative to this approach are: 1) does not require a fusion protein 2) does not require lipofection agents which can have toxicity, endosome escape problems, and issues/problems translating to primary cells.

Microinjection mediated complex delivery is characterized by extremely low throughput and can be difficult to implement for most mammalian cell types. The latter drawback is highlighted by the fact that the work was done with embryos, i.e., cells that are much larger than a fibroblast or a T cell (cells which are desirable target cells for gene editing endeavors). By enabling high throughput and translatability to smaller primary cells, e.g., fibroblasts, T cells, stem cells, the methods described herein have a big advantage.

A CPP-based strategy does not involve a complex. One example of such as strategy is described in Ramakrishna et al., 2014, Genome Res. 24(6):1020-7. CPP mediated delivery of individual components is also associated with drawbacks. Conjugating a CPP to the guide and Cas9 requires extra modification that may inhibit function, limit scalability. CPP mediated delivery is known to go through endocytosis and is inefficient or ineffective in many primary cells (particularly immune cells).

Target Cells and Payload Compositions

Any gene can be manipulated using the gene editing strategies described. Some target genes/proteins are particularly relevant in clinical disease and thus gene editing of such target genes/proteins is useful for therapy. Examples include C—C chemokine receptor type 5 (CCR5): prevent human immunodeficiency virus (HIV) infection; major histocompatibility complex class I (MHC-I): reduce graft vs. host disease; cluster of differentiation 1 (CD1): reduce graft vs. host disease; programmed cell death protein 1 (PD-1), programmed death-ligand 1 (PDL-1), Cytotoxic T-Lymphocyte-Associated Protein 4 (CTLA-4), interferon-regulatory factor (IRF) protein family, TLR protein family, pattern recognition receptors (PRRs): modulate immunity to enhance or dampen effector/antiviral responses; forkhead box P3 (FoxP3): eliminate Treg mediated tolerance; cluster of differentiation 80 (CD80), cluster of differentiation 86 (CD86) and other costimulatory molecules: knockout costimulation abilities to promote tolerance; T cell receptor (TCR), B-cell receptor (BCR): eliminate endogenous TCR or BCR to allow for engineering of T cells and B cells with desired specificity; oncogenes (e.g., Kras, Myc, Tp53): cancer therapy. In another example, targeting transcription factors is used to change cell fate, e.g., delete FoxP3 to remove Treg type function. Delete nuclear factor-kappa B (NF-kB), t-bet, Eomesodermin (Eomes), etc. to alter T cell differentiation.

A protein coding sequence for forkhead box P3 (FoxP3) is as follows:

(SEQ ID NO: 62)
ATGCCCAACCCCAGGCCTGGCAAGCCCTCGGCCCCTTCC
TTGGCCCTTGGCCCATCCCCAGGAGCCTCGCCCAGCTGGAGGGCTGCACC
CAAAGCCTCAGACCTGCTGGGGGCCCGGGGCCCAGGGGGAACCTTCAG
GGCCGAGATCTTCGAGGCGGGGCCCATGCCTCCTCTTCTTCCTTGAACCC
CATGCCACCATCGCAGCTGCAGCTGCCCACACTGCCCCTAGTCATGGTGG
CACCCTCCGGGGCACGGCTGGGCCCCTTGCCCCACTTACAGGCACTCCTC
CAGGACAGGCCACATTTCATGCACCAGCTCTCAACGGTGGATGCCCACGC
CCGGACCCCTGTGCTGCAGGTGCACCCCCTGGAGAGCCCAGCCATGATCA
GCCTCACACCACCCACCACCGCCACTGGGGTCTTCTCCCTCAAGGCCCGG
CCTGGCCTCCCACCTGGGATCAACGTGGCCAGCCTGGAATGGGTGTCCAG
GGAGCCGGCACTGCTCTGCACCTTCCCAAATCCCAGTGCACCCAGGAAGG
ACAGCACCCTTTCGGCTGTGCCCCAGAGCTCCTACCCACTGCTGGCAAAT
GGTGTCTGCAAGTGGCCCGGATGTGAGAAGGTCTTCGAAGAGCCAGAGGA
CTTCCTCAAGCACTGCCAGGCGGACCATCTTCTGGATGAGAAGGGCAGGG
CACAATGTCTCCTCCAGAGAGAGATGGTACAGTCTCTGGAGCAGCAGCTG
GTGCTGGAGAAGGAGAAGCTGAGTGCCATGCAGGCCCACCTGGCTGGGAA
AATGGCACTGACCAAGGCTTCATCTGTGGCATCATCCGACAAGGGCTCCT
GCTGCATCGTAGCTGCTGGCAGCCAAGGCCCTGTCGTCCCAGCCTGGTCT
GGCCCCCGGGAGGCCCCTGACAGCCTGTTTGCTGTCCGGAGGCACCTGTG
GGGTAGCCATGGAAACAGCACATTCCCAGAGTTCCTCCACAACATGGACT
ACTTCAAGTTCCACAACATGCGACCCCCTTTCACCTACGCCACGCTCATC
CGCTGGGCCATCCTGGAGGCTCCAGAGAAGCAGCGGACACTCAATGAGAT
CTACCACTGGTTCACACGCATGTTTGCCTTCTTCAGAAACCATCCTGCCA
CCTGGAAGAACGCCATCCGCCACAACCTGAGTCTGCACAAGTGCTTTGTG
CGGGTGGAGAGCGAGAAGGGGGCTGTGTGGACCGTGGATGAGCTGGAGTT
CCGCAAGAAACGGAGCCAGAGGCCCAGCAGGTGTTCCAACCCTACACCTG
GCCCCTGA

Src homology region 2 domain-containing phosphatase-1 (SHP1) is also known as tyrosine-protein phosphatase non-receptor type 6 (PTPN6). A protein coding sequence for SHP1 is as follows:

(SEQ ID NO: 63)
ATGGTGAGGTGGTTTCACCGAGACCTCAGTGGGCTGGAT
GCAGAGACCCTGCTCAAGGGCCGAGGTGTCCACGGTAGCTTCCTGGCTCG
GCCCAGTCGCAAGAACCAGGGTGACTTCTCGCTCTCCGTCAGGGTGGGGG
ATCAGGTGACCCATATTCGGATCCAGAACTCAGGGGATTTCTATGACCTG
TATGGAGGGGAGAAGTTTGCGACTCTGACAGAGCTGGTGGAGTACTACAC
TCAGCAGCAGGGTGTCCTGCAGGACCGCGACGGCACCATCATCCACCTCA
AGTACCCGCTGAACTGCTCCGATCCCACTAGTGAGAGGTGGTACCATGGC
CACATGTCTGGCGGGCAGGCAGAGACGCTGCTGCAGGCCAAGGGCGAGCC
CTGGACGTTTCTTGTGCGTGAGAGCCTCAGCCAGCCTGGAGACTTCGTGC
TTTCTGTGCTCAGTGACCAGCCCAAGGCTGGCCCAGGCTCCCCGCTCAGG
GTCACCCACATCAAGGTCATGTGCGAGGGTGGACGCTACACAGTGGGTGG
TTTGGAGACCTTCGACAGCCTCACGGACCTGGTGGAGCATTTCAAGAAGA
CGGGGATTGAGGAGGCCTCAGGCGCCTTTGTCTACCTGCGGCAGCCGTAC
TATGCCACGAGGGTGAATGCGGCTGACATTGAGAACCGAGTGTTGGAACT
GAACAAGAAGCAGGAGTCCGAGGATACAGCCAAGGCTGGCTTCTGGGAGG
AGTTTGAGAGTTTGCAGAAGCAGGAGGTGAAGAACTTGCACCAGCGTCTG
GAAGGGCAGCGGCCAGAGAACAAGGGCAAGAACCGCTACAAGAACATTC
TCCCCTTTGACCACAGCCGAGTGATCCTGCAGGGACGGGACAGTAACATC
CCCGGGTCCGACTACATCAATGCCAACTACATCAAGAACCAGCTGCTAGG
CCCTGATGAGAACGCTAAGACCTACATCGCCAGCCAGGGTTGTCTGGAGG
CCACGGTCAATGACTTCTGGCAGATGGCGTGGCAGGAGAACAGCCGTGTC
ATCGTCATGACCACCCGAGAGGTGGAGAAAGGCCGGAACAAATGCGTCC
CATACTGGCCCGAGGTGGGCATGCAGCGTGCTTATGGGCCCTACTCTGTG
ACCAACTGCGGGGAGCATGACACAACCGAATACAAACTCCGTACCTTACA
GGTCTCCCCGCTGGACAATGGAGACCTGATTCGGGAGATCTGGCATTACC
AGTACCTGAGCTGGCCCGACCATGGGGTCCCCAGTGAGCCTGGGGGTGTC
CTCAGCTTCCTGGACCAGATCAACCAGCGGCAGGAAAGTCTGCCTCACGC
AGGGCCCATCATCGTGCACTGCAGCGCCGGCATCGGCCGCACAGGCACCA
TCATTGTCATCGACATGCTCATGGAGAACATCTCCACCAAGGGCCTGGAC
TGTGACATTGACATCCAGAAGACCATCCAGATGGTGCGGGCGCAGCGCTC
GGGCATGGTGCAGACGGAGGCGCAGTACAAGTTCATCTACGTGGCCATCG
CCCAGTTCATTGAAACCACTAAGAAGAAGCTGGAGGTCCTGCAGTCGCAG
AAGGGCCAGGAGTCGGAGTACGGGAACATCACCTATCCCCAGCCATGA
AGAATGCCCATGCCAAGGCCTCCCGCACCTCGTCCAAGAGCTTGGAGTCT
AGTGCAGGGACCGTGGCTGCGTCACCTGTGAGACGGGGTGGCCAGAGGG
GACTGCCAGTGCCGGGTCCCCCTGTGCTGTCTCCTGACCTGCACCAACTG
CCTGTACTTGCCCCCCTGCACCCGGCTGCAGACACAAGGAGGATGTGTAT
GAGAACCTGCACACTAAGAACAAGAGGGAGGAGAAAGTGA

Src homology region 2 domain-containing phosphatase-1 (SHP2) is also known as tyrosine-protein phosphatase non-receptor type 11 (PTPN11). A protein coding sequence for SHP2 is as follows:

(SEQ ID NO: 64)
ATGACATCGCGGAGATGGTTTCACCCAAATATCACT

GGTGTGGAGGCAGAAAACCTACTGTTGACAAGAGG

AGTTGATGGCAGTTTTTTGGCAAGGCCTAGTAAAA

GTAACCCTGGAGACTTCACACTTTCCGTTAGAAGA

AATGGAGCTGTCACCCACATCAAGATTCAGAACAC

TGGTGATTACTATGACCTGTATGGAGGGGAGAAAT

TTGCCACTTTGGCTGAGTTGGTCCAGTATTACATG

GAACATCACGGGCAATTAAAAGAGAAGAATGGAGA

TGTCATTGAGCTTAAATATCCTCTGAACTGTGCAG

ATCCTACCTCTGAAAGGTGGTTTCATGGACATCTC

TCTGGGAAGAAGCAGAGAAATTATTAACTGAAAA

AGGAAAACATGGTAGTTTTCTTGTACGAGAGAGCC

AGAGCCACCCTGGAGATTTTGTTCTTTCTGTGCGC

ACTGGTGATGACAAAGGGGAGAGCAATGACGGCAA

GTCTAAAGTGACCCATGTTATGATTCGCTGTCAGG

AACTGAAATACGACGTTGGTGGAGGAGAACGGTTT

GATTCTTTGACAGATCTTGTGGAACATTATAAGAA

GAATCCTATGGTGGAAACATTGGGTACAGTACTAC

AACTCAAGCAGCCCCTTAACACGACTCGTATAAAT

GCTGCTGAAATAGAAAGCAGAGTTCGAGAACTAAG

CAAATTAGCTGAGACCACAGATAAAGTCAAACAAG

GCTTTTGGGAAGAATTTGAGACACTACAACAACAG

GAGTGCAAACTTCTCTACAGCCGAAAAGAGGGTCA

AAGGCAAGAAAACAAAAACAAAAATAGATATAAAA

ACATCCTGCCCTTTGATCATACCAGGGTTGTCCTA

CACGATGGTGATCCCAATGAGCCTGTTTCAGATTA

CATCAATGCAAATATCATCATGCCTGAATTTGAAA

CCAAGTGCAACAATTCAAAGCCCAAAAGAGTTAC

ATTGCCACACAAGGCTGCCTGCAAAACACGGTGAA

TGACTTTTGGCGGATGGTGTTCCAAGAAAACTCCC

GAGTGATTGTCATGACAACGAAAGAAGTGGAGAGA

GGAAAGAGTAAATGTGTCAAATACTGGCCTGATGA

GTATGCTCTAAAAGAATATGGCGTCATGCGTGTTA

GGAACGTCAAAGAAAGCGCCGCTCATGACTATACG

CTAAGAGAACTTAAACTTTCAAAGGTTGGACAAGG

GAATACGGAGAGAACGGTCTGGCAATACCACTTTC

GGACCTGGCCGGACCACGGCGTGCCCAGCGACCCT

GGGGGCGTGCTGGACTTCCTGGAGGAGGTGCACCA

TAAGCAGGAGAGCATCATGGATGCAGGGCCGGTCG

TGGTGCACTGCAGTGCTGGAATTGGCCGGACAGGG

-continued
ACGTTCATTGTGATTGATATTCTTATTGACATCAT

CAGAGAGAAAGGTGTTGACTGCGATATTGACGTTC

CCAAAACCATCCAGATGGTGCGGTCTCAGAGGTCA

GGGATGGTCCAGACAGAAGCACAGTACCGATTTAT

CTATATGGCGGTCCAGCATTATATTGAAACACTAC

AGCGCAGGATTGAAGAAGAGCAGAAAAGCAAGAGG

AAAGGGCACGAATATACAAATATTAAGTATTCTCT

AGCGGACCAGACGAGTGGAGATCAGAGCCCTCTCC

CGCCTTGTACTCCAACGCCACCCTGTGCAGAAATG

AGAGAAGACAGTGCTAGAGTCTATGAAAACGTGGG

CCTGATGCAACAGCAGAAAAGTTTCAGATGA

Other targets include areas of the genome that can have a plasmid or donor DNA inserted into them so that the target cell can express a new gene, e.g. a recombinant TCR, a recombinant BCR, Chimerica Antigen Receptor, fluorescent protein, reprogramming factors.

In some embodiments, a genomic sequence is edited in a coding region. In certain embodiments, a genomic sequence is edited in a non-coding region.

In various embodiments relating to FoxP3, a genetic region upstream of FoxP3 may be edited. In such embodiments a region where a transcriptional repressor of Foxp3 might bind is edited. For example a site about 0.5, 1, 1.5, 2, 2.5, 3, 3.5, 4, 4.5, 5, 0.5-2.5, or 0.5-5 kb upstream of the FoxP3 transcriptional start site may be edited.

Treating Subjects

Aspects of the present invention relate to editing the genomes of a plurality of a subject's cells. In various embodiments, cells are removed from a subject, receive a gene-editing complex using a method of the present subject matter, and then are reintroduced back into the subject. For example, mutant cells may be produced in a process involving delivery of a gene-editing complex as described herein. The mutant cells may be heterozygous or homozygous for a mutated allele a gene involved in a disease. In certain embodiments, the mutant cells are null for the gene involved in a disease.

Cells, such as stem cells (e.g. hematopoietic stem cells) from bone marrow, or circulating immune cells in whole blood, may be treated using methods and devices described herein. Cells may be genetically modified to reduce the expression of a receptor for a pathogen (such as a viral or bacterial pathogen) or a toxin (such as a microbial pathogen toxin). Since a gene-editing protein complex or components thereof may be directly introduced into target cells without the need for expression, no transgene delivery is necessary. This approach has important advantages over traditional gene-therapy approaches, which suffer from aberrant expression, insertion, and silencing, as well as variable delivery of transgene copy number.

In one embodiment, a gene-editing complex that targets the C—C chemokine receptor type 5 (CCR5) gene is introduced into a blood (such as a CD4+ T cell) or bone marrow cell (such as a hematopoietic stem cell) of a subject who is infected with human immunodeficiency virus (HIV). The gene-editing complex may be designed to mutate the CCR5 gene such that cells receiving the gene-editing complex no longer express CCR5 or express CCR5 at a reduced level. In one example, hematopoietic stem cells expressing a version of CCR5 that binds HIV (or that produce progeny that express the CCR5) are removed from the subject, modified to no longer express a version of CCR5 that binds HIV, and then are transplanted into the subject. In another example, CCR5-expressing CD4+ T cells of the subject receive a gene-editing complex using methods and devices described herein such that the CD4+ T cells no longer express a version of CCR5 that binds HIV. The modified CD4+ T cells are then returned into the subject. Such treatment of the CD4+ T cell may be performed in whole blood from the subject. In these and other embodiments, bone marrow cells or blood cells are modified to no longer express a version of C—X—C chemokine receptor type 4 (CXCR4) to which HIV binds. Similarly, cells of a subject may be modified to have reduced CCR5 expression to treat or prevent an infection associates with *Yersinia pestis* (bubonic plague) or Variola major (small pox).

Subjects, other than humans, containing cells modified by methods and devices disclosed herein are also provided. Such subjects include non-human vertebrate, amphibian, mammalian, and primate subjects. Non-limiting examples include *Danio* sp., *Fugu* sp., *Xenopus* sp., *Mus* sp., *Rattus* sp., and others.

Introducing Gene-Editing Proteins and Complexes into Cells

The delivery of pre-formed protein complexes allows for the study of cellular processes without genetic modification of the cells being studied. The present subject matter is useful for delivering protein complexes and gene editing complexes to cells, including CRISPR.

The advantages of delivering protein complexes using the methods and devices described herein include the controlled and temporary introduction of test agents for the study of cell and protein complex function. Since transgene expression and cellular assembly of complex components is not needed, the timing and ratios (protein:RNA) of complex function can be controlled. Additionally, the transient nature of delivery enables the observation of changes due to temporary function, rather than prolonged expression which may result in off-target or secondary effects. From an in vivo homing perspective and a gene expression format, microfluidic delivery has far fewer side effects (10-fold) on treated cells rather than electroporation.

For example, microfluidic delivery results in fewer aberrant and non-specific gene expression changes compared to electroporation. Additionally, the structural and functional integrity of microfluidically squeezed cells is preserved compared to electroporation-mediated cargo delivery. As an example, an increased number of T cells exposed to microfluidic delivery ex vivo (and then introduced into a subject in vivo) home to lymph nodes compared to T cells that have undergone electroporation. Cells (e.g., T cells) treated by electroporation and then administered into a subject are more likely to be cleared from the subject compared to cells treated by microfluidic delivery. Such clearance is related to altered/aberrant gene expression following electroporation that marks such cells for destruction or clearance by the body.

Target Cells and Payload Compositions

Any eukaryotic, e.g., mammalian such as human, cell can be processed using the microfluidic device to alter the cell membrane for introduction of protein/nucleic acid complexes or assemblies into the cytosol of the target cell. Exemplary target cells include Lymphocytes/Immune cells: DCs, B cells, T cells, Natural killer cells (NK cells), neutrophils, basophils, eosinophils, innate lymphoid cells, monocytes, macrophages, hematopoietic stem cells, common lymphoid progenitor cells; Stem cells: Embryonic, mesenchymal, induced pluripotent; Other primary cells: Fibroblasts, hepatocytes, cardiomyocytes, neurons, epithelial, epidermal, endothelial, pancreatic islet cells; as well as Cell lines, e.g., cell lines for disease studies: T cell clones, Jurkat cells, HeLa cells, Human Embryonic Kidney 293 (HEK293) cells, U2OS cells, Chinese Hamster Ovary (CHO) cells. Prokaryotic cells can also be processed. The dimensions of the constriction of the device are tailored depending on the cell type to be processed.

In some embodiments, the cell is a prokaryotic cell. In other embodiments, the cell is a eukaryotic cell. Non-limiting examples of eukaryotic cells include protozoan, algal, fungi, yeast, plant, animal, vertebrate, invertebrate, arthropod, mammalian, rodent, primate, and human cells. The cell may be a cell, e.g., of a unicellular organism or a multicellular organism. The cell may be, e.g., a primary eukaryotic cell or an immortalized eukaryotic cell. In some embodiments, the cell is a cancer cell. In certain embodiments, the cell is other than a human cell. For example, a composition for treating cancer and/or a method of treating cancer or preparing a composition for treating cancer, comprises treating immune cells using the gene-editing methods described herein to reduce the expression/production of immune suppressing signals from tumor cells. An example includes reduction or SHP-2 knockout for increasing immune activity towards tumors.

In various embodiments, a cell may be in a mixture of two or more cell types or a plurality of cells may be a mixture of two or more cell types. A mixture of cell types may be a co-culture of multiple cell types (such as two or more of those disclosed herein) or a mixture of cell types that naturally occur together, such as in whole blood.

In some embodiments, the cell is a peripheral blood mononuclear cell. In various embodiments, the cell suspension comprises a purified cell population. In certain embodiments, the cell is a primary cell or a cell line cell.

In some embodiments, the cell is a blood cell. In some embodiments, the blood cell is an immune cell. In some embodiments, the immune cell is a lymphocyte. In some embodiments, the immune cell is a T cell, B cell, natural killer (NK) cell, dendritic cell (DC), Natural killer T (NKT) cell, mast cell, monocyte, macrophage, basophil, eosinophil, or neutrophil. In some embodiments, the immune cell is an adaptive immune cell such as a T cell and B cell. In some embodiments, the immune cell is an innate immune cell. Exemplary innate immune cells include innate lymphoid cells (ILCs; ILC1, ILC2, ILC3), basophils, eosinophils, mast cells, NK cells, neutrophils, and monocytes. In some embodiments, the immune cell is a memory cell. In some embodiments, the immune cell is a primary human T cell. In some embodiments, the cell is a mouse, dog, cat, horse, rat, goat, monkey, or rabbit cell.

In some embodiments, the cell is a human cell. In some embodiments, the cell suspension comprises a cell other than a human cell or a non-mammalian cell. In some embodiments, the cell is a chicken, frog, insect, or nematode cell.

Any physiologically-compatible or cell-compatible buffer system can be used as a solution to bathe/incubate the cells and process the cells through the device. For example, phosphate buffered saline (PBS), Opti-MEM®, Roswell Park Memorial Institute (RPMI), Dulbecco's Modified Eagle's Medium (DMEM). A reduced serum or serum-free media or buffer composition is preferable. The buffer or medium is chosen based to maintain and preserve the health or viability of the target cell and/or the effect on gene expression. For example, in some cases the presence of calcium in the buffer is desirable to promote or support mRNA expression.

Payload compositions include a protein-nucleic acid complex or assembly. Exemplary complexes include components or modules of a gene editing system as described above, e.g., nuclease/guide nucleic acid combination or assembly. For example, gRNA:Cas9 molar ratio ranges from 1:100,000 to 100,000:1, e.g., a preferred range, 1:10 to 10:1, e.g., 1:1 or 1:2, 2:1. Complex concentration in the buffer to facilitate delivery (molar concentrations) typically ranges from 100 mM to 1 nM, e.g., 10 uM to 100 nM. Complexes can be mixed with cells before going through constriction or afterwards.

Microfluidic Delivery of Gene Editing Complexes

In order to effect gene editing manipulations, Cas protein (such as Cas9 protein), guide RNA and donor DNA can be delivered to a cell through mechanical deformation using, for example, a microfluidic platform (e.g., as described in U.S. Application Publication No. 20140287509, filed Apr. 17, 2014; PCT International Application No. PCT/US2014/051343 filed Aug. 15, 2014; PCT International Application No. PCT/US2015/060689 filed Nov. 13, 2015; and PCT International Application No. PCT/US2015/058489 filed Oct. 30, 2015, each of which is hereby incorporated by reference).

Figure 1B:
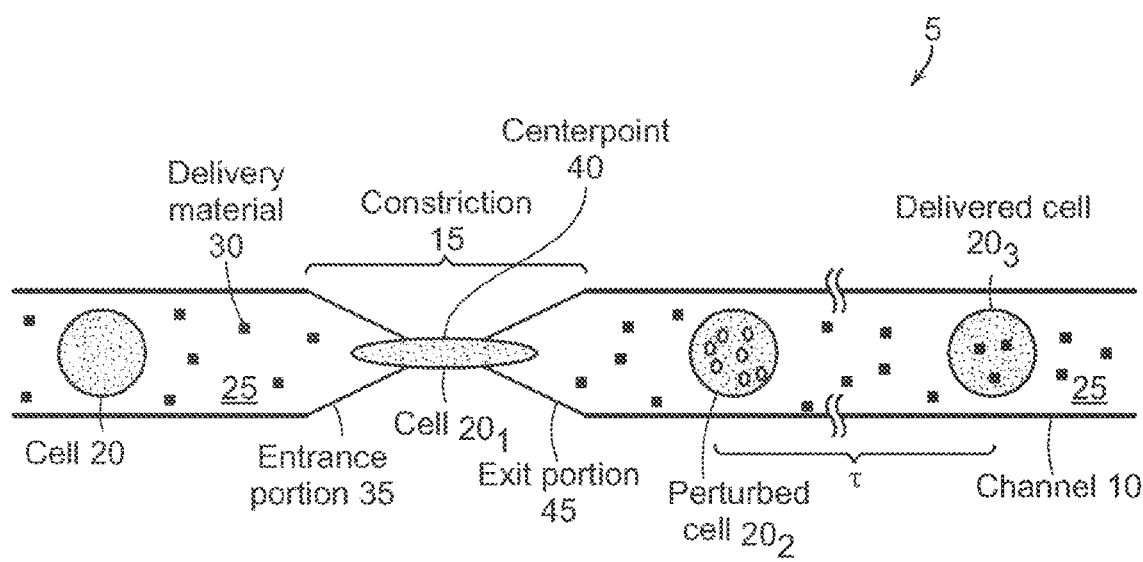
Figure 2A:
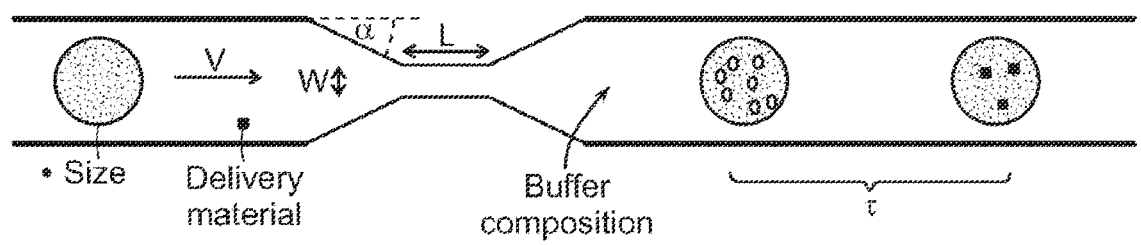
FIGS. 2A and 2B are schematic diagrams of an embodiment of a microfluidic system in depicting parameters such as channel depth, width, and length.
Figure 2B:
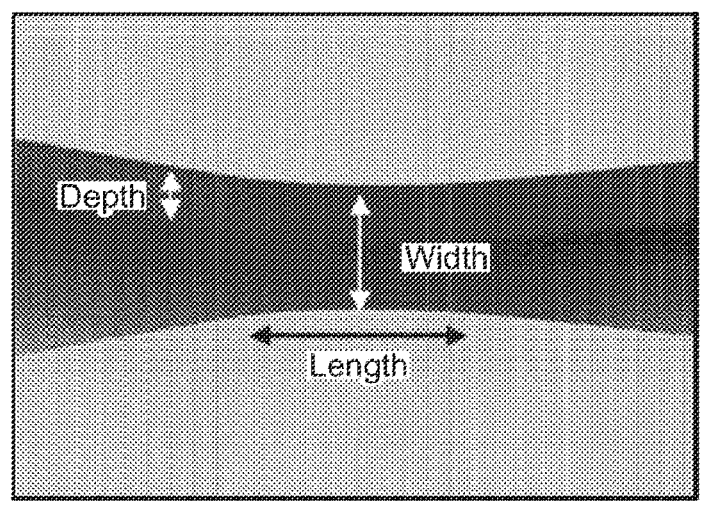

FIGS. 1-2 illustrate an example microfluidic system that can be used for the delivery of genome editing protein, RNA, and DNA. The microfluidic system 5 includes a channel 10 defining a tubular lumen. The microfluidic channel 10 includes a constriction 15 that is preferably configured such that only a single target cell 20 can pass through the constriction 15 at one time. Preferably, the cells 20 pass through the channel 10 suspended in a solution buffer 25 that also includes delivery materials 30, although the delivery materials can be added to the solution buffer 25 after the cells 20 pass through the constriction 15. As the cell 20 approaches and passes through the constriction 15, the constriction 15 applies pressure (e.g., mechanical compression) to the cell 20, squeezing the cell 20 (e.g., shown as cell $20_1$). The pressure applied to the cell by the constriction 15 causes perturbations (e.g., holes) in the cell membrane (e.g., cell $20_2$). Once the cell passes through the constriction 15, the cell 20 begins to uptake the material in the solution buffer 25 through the holes, including the delivery material 30 (e.g., cell $20_3$). The cell membrane recovers over time, and at least a portion of the delivery material 30 preferably remains trapped inside the cell.

In some embodiments, the device comprises a constriction length of about 5 µm to about 50 µm or any length or range of lengths therebetween. For example, the constriction length ranges from about 5 µm to about 40 µm, about 5 µm to about 30 µm, about 5 µm to about 20 µm, or about 5 µm to about 10 µm. In some embodiments, the constriction length ranges from about 10 µm to about 50 m, about 20 µm to about 50 µm, about 30 µm to about 50 µm, or about 40 µm to about 50 µm. In some embodiments, the constriction depth ranges from about 2 µm to about 200 µm or any depth or range of depths there between. For example, the constriction depth ranges from about 2 µm to about 150 m, about 2 µm to about 100 m, about 2 µm to about 50 µm, about 2 µm to about 25 µm, about 2 µm to about 15 µm, or about 2 µm to about 10 µm. In some embodiments, the constriction depth ranges from about 10 µm to about 200 m, about 25 µm to about 200 m, about 50 µm to about 200 m, about 100 µm to about 200 m, or about 150 µm to about 200 m. In some embodiments, the angle of the entrance or exit portion of the constriction ranges from about 0 degrees to about 90 degrees or any angle or range of angles therebetween. For example, the angle is about 5, about 10, about 15, about 20, about 30, about 40, about 50, about 60, about 70, about 80, or about 90 degrees or more. In some embodiments, the pressure ranges from about 50 psi to about 200 psi or any pressure or range of pressures there between. For example, the pressure ranges from about 50 psi to about 150 psi, about 50 psi to about 125 psi, about 50 psi to about 100 psi, or about 50 psi to about 75 psi. In some embodiments, the pressure ranges from about 75 psi to about 200 psi, about 100 psi to about 200 psi, about 125 psi to about 200 psi, about 150 psi to about 200 psi, or about 175 psi to about 200 psi. In some embodiments, the device comprises a constriction width of between about 2 µm and about 10 µm or any width or range of widths therebetween. For example, the constriction width can be any one of about 3 µm, about 4 µm, about 5 µm, about 6 µm, or about 7 µm.

The data described below was generated using the following materials and methods. Complexes were made as follows: Mix 10 µl of 1 mg/ml nuclear localization signal (NLS) tagged Cas9 protein with 5 µl of 1 mg/ml guide RNA. Incubate on ice for 20 min to allow complexes to form. For delivery, target cells are suspended at 10 million cells/ml in serum-free media. Cells and Cas9-gRNA complexes are mixed immediately before device treatment such that complex concentration is ~0.15 mg/ml. Cells are treated by the device using pressure, temperature, chip design and buffer conditions specific to the target cell type. For example, for primary human T cells, pressure is approximately 100 psi, on ice, through a 30 µm length, 4 µm width constriction. After a 2 min incubation post-treatment, cells are diluted in media and washed to remove undelivered complexes. Cells are then cultured to allow for gene editing to occur (e.g., 1, 2, 5, 12, 24 hours or more (for non-clinical applications, timeframe depends on assay readout, e.g., 24 hours or later). For clinical use, e.g., for patient therapy, the cells could be injected back into patient immediately after device treatment. Optionally, the cells are incubated in vitro for a time (e.g., 1, 2, 5, 12, 24 hours or more) prior to injecting the cells into a patient recipient. Temperatures, concentrations, iterations of the molecules vary depending on the target cell type.

Figure 3B:
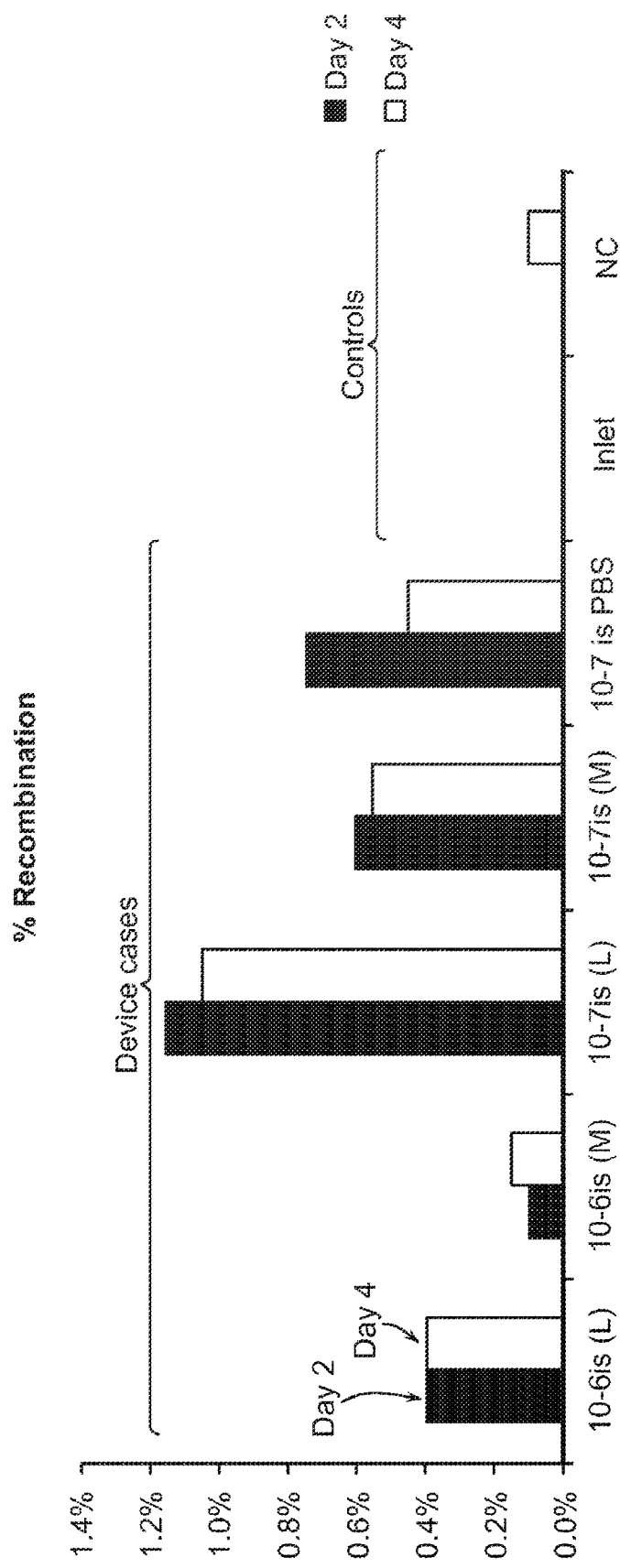

FIG. 3 is a series of flow cytometry plots and a bar graph of the recombination efficiency for K562 reporter cells (American Type Culture Collection (ATCC)® CCL-243™, bone marrow-derived cells derived from patient with chronic myelogenous leukemia; lymphoblast morphology) that had genetic editing material delivered to cell cytoplasm using the microfluidic device illustrated in FIGS. 1-2. At top are flow cytometry plots of K562 reporter cells that had a protein Cas9, site-specific gRNA, and donor oligonucleotide delivered. A CRISPR complex is ~150 kDa. These reporter cells had an mCherry gene and thus would normally appear in Q1 of the plots. If the site-specific DNA cleavage and insertion of donor oligonucleotide is successful it would lead to expression of green fluorescent protein (GFP), i.e., cells would appear in Q2. At bottom is a quantification of recombination efficiency based on flow cytometry for multiple device conditions as compared to endocytosis (inlet) and untreated (NC) controls. Delivery of Cas9 protein, guide RNA and donor DNA by cell squeezing led to successful changes in the genome of reporter cell lines. These data indicate that delivery of gene editing components (in the form of a complex or assembly) by mechanical cell disruption leads to effective changes in the genome.

Delivery of TALEN proteins or mRNA, zinc finger nucleases, mega nucleases, Cre recombinase or any other enzyme capable of cleaving DNA can also be delivered to the cytoplasm of a cell by mechanical disruption of the cell membrane. An exemplary TALEN genome-editing system, including exemplary TALEN proteins, is described in Ding et al., (2013) Cell Stem Cell, 12, 238-251, the entire content of which is incorporated herein by reference. Ding et al., (2013) Cell Stem Cell, 12, 238-251 describes non-limiting examples of generic TALEN amino acid sequences to recognize 15 base pair sequences. Non-limiting examples of generic TALEN amino acid sequences are:

```
                                      (SEQ ID NO: 65)
MDYKDHDGDYKDHDIDYKDDDDKMAPKKKRKVGI

HGVPSRVDLRTLGYSQQQQEKIKPKVRSTVAQHH

EALVGHGFTHAHIVALSQHPAALGTVAVTYQHII

TALPEATHEDIVGVGKQWSGARALEALLTDAGEL

RGPPLQLDTGQLVKIAKRGGVTAMEAVHASRNAL

TGAPLNLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALESIVAQSLR

PDPALAALTNDHLVALACLGGRPAMDAVKKGLPH

APELIRRVNRRIGERTGHRVAGSQLVKSELEEKK

SELRHKLKYVPHEYIELIEIARNPTQDRILEMKV

MEFFMKVYGYRGEHLGGSRKPDGAIYTVGSPIDY

GVIVDTKAYSGGYNLPIGQADEMQRYVKENQTRN

KHINPNEWWKVYPSSVTEFKFLFVSGHFKGNYKA

QLTRLNRKTNCNGAVLSVEELLIGGEMIKAGTLT

LEEVRRKFNNGEINF (SEQ ID NO: 66)
MDYKDHDGDYKDHDIDYKDDDDKMAPKKKRKVGI

HGVPARVDLRTLGYSQQQQEKIKPKVRSTVAQHH

EALVGHGFTHAHIVALSQHPAALGTVAVTYQHII

TALPEATHEDIVGVGKQWSGARALEALLTDAGEL

RGPPLQLDTGQLVKIAKRGGVTAMEAVHASRNAL

TGAPLNLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALETVQRLLPV

LCQAHGLTPEQVVAIASXXGGKQALESIVAQSLR

PDPALAALTNDHLVALACLGGRPAMDAVKKGLPH

APELIRRVNRRIGERTGHRVAGSQLVKSELEEKK

SELRHKLKYVPHEYIELIEIARNPTQDRILEMKV

MEFFMKVYGYRGEHLGGSRKPDGAIYTVGSPIDY

GVIVDTKAYSGGYNLPIGQADEMQRYVEENQTRD

KHLNPNEWWKVYPSSVTEFKFLFVSGHFKGNYKA

QLTRLNHITNCNGAVLSVEELLIGGEMIKAGTLT

LEEVRRKFNNGEINF
```

In SEQ ID NOS: 65 and 66, to recognize C: XX=HD; to recognize T: XX=NG; to recognize A: XX=NI; and to recognize G: XX=NN except in the last position where XX=NK. Underline indicates N-term and C-term of TAL effector.

Although a few variations have been described in detail above, other modifications or additions are possible. For example, genetic editing material can include TALEN proteins, TALEN mRNA, zinc finger nucleases, mega nucleases, Cre recombinase or any other enzyme capable of cleaving DNA delivered to the cytosol by mechanical disruption of the cell membrane.

Delivery of RNA and Cas9 in Complex Form

The results achieved were surprising in view of numerous factors that could potentially have impeded successful gene editing by microfluidic delivery of the gene complexes. For example, the Cas9-gRNA complex may have caused a Toll-like receptor (TLR) mediated or other PRR (pattern recognition receptor) mediated response that would have inhibited gene editing function and/or survival but this potential problem was not observed. Since the complex is not guaranteed to be stable once it enters the cytoplasm, it could have been degraded and rendered non-functional, but surprisingly, the delivered complexes were still able to edit.

The integrity of the gene editing complex was preserved using microfluidic based, cell-squeezing delivery to the cell. The complex does not have the same physical/chemical properties as a gRNA alone or protein alone and thus it was uncertain if the delivery process would behave the same in the context of delivering a complex vs. its individual components. Complexes are larger and less stable than their constituents. Complexes may fall apart due to, e.g., shear forces. Additionally, complexes may not survive membrane transit or in the cytosol because some other elements may break the complexes up before they are functional or have an opportunity to act on cellular targets. Complexes also have a different charge distribution which may affect the ability of a complex to be delivered. Shape and thus transport properties can also change compared to complex constituents. The delivery methods successfully preserved the structural and functional integrity of the complexes.

The shear forces involved with the delivery process could potentially have disrupted the Protein/gRNA complex and rendered it non-functional but surprisingly the delivery system was effective to introduce the complexes into the cell and the gene editing still worked. It was also not obvious that the complex would still have the appropriate nuclear localization behavior as compared to an uncomplexed Cas (such as Cas9) protein alone with NLS; however, the behavior and function was preserved throughout the process as demonstrated by the gene expression results described above.

The CRISPR-Cas system is known in the art. Non-limiting aspects of this system are described in U.S. Pat. No. 8,697,359, issued Apr. 15, 2014, the entire content of which is incorporated herein by reference.

Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologs thereof, or modified versions thereof. These enzymes are known; for example, the amino acid sequence of *S. pyogenes* Cas9 protein may be found in the SwissProt database under accession number Q99ZW2. In some embodiments, the unmodified CRISPR enzyme has DNA cleavage activity, such as Cas9. In some embodiments the CRISPR enzyme is Cas9, and may be Cas9 from *S. pyogenes* or *S. pneumoniae*. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In aspects of the invention, nickases may be used for genome editing via homologous recombination.

Non-limiting examples of Cas9 amino acid and cDNA sequences are provided below.

The amino acid sequence of a *Streptococcus pyogenes* Cas9 protein may be found in the SwissProt database under accession number Q99ZW2. This amino acid sequence is:

(SEQ ID NO: 1)

```
MDKKYSIGLDIGTNSVGWAVITDEYKVPSKKFKVL
GNTDRHSIKKNLIGALLFDSGETAEATRLKRTARR
RYTRRKNRICYLQEIFSNEMAKVDDSFFHRLEESF
LVEEDKKHERHPIFGNIVDEVAYHEKYPTIYHLRK
KLVDSTDKADLRLIYLALAHMIKFRGHFLIEGDLN
PDNSDVDKLFIQLVQTYNQLFEENPINASGVDAKA
ILSARLSKSRRLENLIAQLPGEKKNGLFGNLIALS
LGLTPNFKSNFDLAEDAKLQLSKDTYDDDLDNLLA
QIGDQYADLFLAAKNLSDAILLSDILRVNTEITKA
PLSASMIKRYDEHHQDLTLLKALVRQQLPEKYKEI
FFDQSKNGYAGYIDGGASQEEFYKFIKPILEKMDG
TEELLVKLNREDLLRKQRTFDNGSIPHQIHLGELH
AILRRQEDFYPFLKDNREKIEKILTFRIPYYVGPL
ARGNSRFAWMTRKSEETITPWNFEEVVDKGASAQS
FIERMTNFDKNLPNEKVLPKHSLLYEYFTVYNELT
KVKYVTEGMRKPAFLSGEQKKAIVDLLFKTNRKVT
VKQLKEDYFKKIECFDSVETSGVEDRFNASLGTYH
DLLKIIKDKDFLDNEENEDILEDIVLTLTLFEDRE
MIEERLKTYAHLFDDKVMKQLKRRRYTGWGRLSRK
LINGIRDKQSGKTILDFLKSDGFANRNFMQLIHDD
SLTFKEDIQKAQVSGQGDSLHEHIANLAGSPAIKK
GILQTVKVVDELVKVMGRHKPENIVIEMARENQTT
QKGQKNSRERMKRIEEGIKELGSQILKEHPVENTQ
LQNEKLYLYYLQNGRDMYVDQELDINRLSDYDVDH
IVPQSFLKDDSIDNKVLTRSDKNRGKSDNVPSEEV
VKKMKNYWRQLLNAKLITQRKFDNLTKAERGGLSE
LDKAGFIKRQLVETRQITKHVAQILDSRMNTKYDE
NDKLIREVKVITLKSKLVSDFRKDFQFYKVREINN
YHHAHDAYLNAVVGTALIKKYPKLESEFVYGDYKV
YDVRKMIAKSEQEIGKATAKYFFYSNIMNFFKTEI
TLANGEIRKRPLIETNGETGEIVWDKGRDFATVRK
VLSMPQVNIVKKTEVQTGGFSKESILPKRNSDKLI
ARKKDWDPKKYGGFDSPTVAYSVLVVAKVEKGKSK
KLKSVKELLGITIMERSSFEKNPIDFLEAKGYKEV
KKDLIIKLPKYSLFELENGRKRMLASAGELQKGNE
LALPSKYVNFLYLASHYEKLKGSPEDNEQKQLFVE
QHKHYLDEIIEQISEFSKRVILADANLDKVLSAYN
KHRDKPIREQAENIIHLFTLTNLGAPAAFKYFDTT
IDRKRYTSTKEVLDATLIHQSITGLYETRIDLSQL
GGD
```

SEQ ID NO: 1 may be encoded by the following nucleotide sequence found in the European Nucleotide Archive under accession number AAK33936.2:

(SEQ ID NO: 2)
ATGGATAAGAAATACTCAATAGGCTTAGATATCGG
CACAAATAGCGTCGGATGGGCGGTGATCACTGATG
AATATAAGGTTCCGTCTAAAAAGTTCAAGGTTCTG
GGAAATACAGACCGCCACAGTATCAAAAAAAATCT
TATAGGGGCTCTTTTATTTGACAGTGGAGAGACAG
CGGAAGCGACTCGTCTCAAACGGACAGCTCGTAGA
AGGTATACACGTCGGAAGAATCGTATTTGTTATCT
ACAGGAGATTTTTTCAAATGAGATGGCGAAAGTAG
ATGATAGTTTCTTTCATCGACTTGAAGAGTCTTTT
TTGGTGGAAGAAGACAAGAAGCATGAACGTCATCC
TATTTTTGGAAATATAGTAGATGAAGTTGCTTATC
ATGAGAAATATCCAACTATCTATCATCTGCGAAAA
AAATTGGTAGATTCTACTGATAAAGCGGATTTGCG
CTTAATCTATTTGGCCTTAGCGCATATGATTAAGT
TTCGTGGTCATTTTTTGATTGAGGGAGATTTAAAT
CCTGATAATAGTGATGTGGACAAACTATTTATCCA
GTTGGTACAAACCTACAATCAATTATTTGAAGAAA
ACCCTATTAACGCAAGTGGAGTAGATGCTAAAGCG
ATTCTTTCTGCACGATTGAGTAAATCAAGACGATT
AGAAAATCTCATTGCTCAGCTCCCCGGTGAGAAGA
AAAATGGCTTATTTGGGAATCTCATTGCTTTGTCA
TTGGGTTTGACCCCTAATTTTAAATCAAATTTTGA
TTTGGCAGAAGATGCTAAATTACAGCTTTCAAAAG
ATACTTACGATGATGATTTAGATAATTTATTGGCG
CAAATTGGAGATCAATATGCTGATTTGTTTTTGGC
AGCTAAGAATTTATCAGATGCTATTTTACTTTCAG
ATATCCTAAGAGTAAATACTGAAATAACTAAGGCT
CCCCTATCAGCTTCAATGATTAAACGCTACGATGA
ACATCATCAAGACTTGACTCTTTTAAAAGCTTTAG
TTCGACAACAACTTCCAGAAAAGTATAAAGAAATC
TTTTTTGATCAATCAAAAAACGGATATGCAGGTTA
TATTGATGGGGAGCTAGCCAAGAAGAATTTTATA
AATTTATCAAACCAATTTTAGAAAAAATGGATGGT
ACTGAGGAATTATTGGTGAAACTAAATCGTGAAGA
TTTGCTGCGCAAGCAACGGACCTTTGACAACGGCT
CTATTCCCCATCAAATTCACTTGGGTGAGCTGCAT
GCTATTTTGAGAAGACAAGAAGACTTTTATCCATT
TTTAAAAGACAATCGTGAGAAGATTGAAAAAATCT

TGACTTTTCGAATTCCTTATTATGTTGGTCCATTG
GCGCGTGGCAATAGTCGTTTTGCATGGATGACTCG
GAAGTCTGAAGAAACAATTACCCCATGGAATTTTG
AAGAAGTTGTCGATAAAGGTGCTTCAGCTCAATCA
TTTATTGAACGCATGACAAACTTTGATAAAAATCT
TCCAAATGAAAAAGTACTACCAAAACATAGTTTGC
TTTATGAGTATTTTACGGTTTATAACGAATTGACA
AAGGTCAAATATGTTACTGAAGGAATGCGAAAACC
AGCATTTCTTTCAGGTGAACAGAAGAAAGCCATTG
TTGATTTACTCTTCAAAACAAATCGAAAAGTAACC
GTTAAGCAATTAAAAGAAGATTATTTCAAAAAAAT
AGAATGTTTTGATAGTGTTGAAATTTCAGGAGTTG
AAGATAGATTTAATGCTTCATTAGGTACCTACCAT
GATTTGCTAAAAATTATTAAAGATAAAGATTTTTT
GGATAATGAAGAAATGAAGATATCTTAGAGGATA
TTGTTTTAACATTGACCTTATTTGAAGATAGGGAG
ATGATTGAGGAAAGACTTAAAACATATGCTCACCT
CTTTGATGATAAGGTGATGAAACAGCTTAAACGTC
GCCGTTATACTGGTTGGGGACGTTTGTCTCGAAAA
TTGATTAATGGTATTAGGGATAAGCAATCTGGCAA
AACAATATTAGATTTTTTGAAATCAGATGGTTTTG
CCAATCGCAATTTTATGCAGCTGATCCATGATGAT
AGTTTGACATTTAAAGAAGACATTCAAAAAGCACA
AGTGTCTGGACAAGGCGATAGTTTACATGAACATA
TTGCAAATTTAGCTGGTAGCCCTGCTATTAAAAAA
GGTATTTTACAGACTGTAAAAGTTGTTGATGAATT
GGTCAAAGTAATGGGCGGCATAAGCCAGAAAATA
TCGTTATTGAAATGGCACGTGAAAATCAGACAACT
CAAAAGGGCCAGAAAAATTCGCGAGAGCGTATGAA
ACGAATCGAAGAAGGTATCAAAGAATTAGGAAGTC
AGATTCTTAAAGAGCATCCTGTTGAAAATACTCAA
TTGCAAAATGAAAAGCTCTATCTCTATTATCTCCA
AAATGGAAGAGACATGTATGTGGACCAAGAATTAG
ATATTAATCGTTTAAGTGATTATGATGTCGATCAC
ATTGTTCCACAAAGTTTCCTTAAAGACGATTCAAT
AGACAATAAGGTCTTAACGCGTTCTGATAAAAATC
GTGGTAAATCGGATAACGTTCCAAGTGAAGAAGTA
GTCAAAAAGATGAAAAACTATTGGAGACAACTTCT
AAACGCCAAGTTAATCACTCAACGTAAGTTTGATA
ATTTAACGAAAGCTGAACGTGGAGGTTTGAGTGAA

```
-continued
CTTGATAAAGCTGGTTTTATCAAACGCCAATTGGT
TGAAACTCGCCAAATCACTAAGCATGTGGCACAAA
TTTTGGATAGTCGCATGAATACTAAATACGATGAA
AATGATAAACTTATTCGAGAGGTTAAAGTGATTAC
CTTAAAATCTAAATTAGTTTCTGACTTCCGAAAAG
ATTTCCAATTCTATAAAGTACGTGAGATTAACAAT
TACCATCATGCCCATGATGCGTATCTAAATGCCGT
CGTTGGAACTGCTTTGATTAAGAAATATCCAAAAC
TTGAATCGGAGTTTGTCTATGGTGATTATAAAGTT
TATGATGTTCGTAAAATGATTGCTAAGTCTGAGCA
AGAAATAGGCAAAGCAACCGCAAAATATTTCTTTT
ACTCTAATATCATGAACTTCTTCAAAACAGAAATT
ACACTTGCAAATGGAGAGATTCGCAAACGCCCTCT
AATCGAAACTAATGGGGAAACTGGAGAAATTGTCT
GGGATAAAGGGCGAGATTTTGCCACAGTGCGCAAA
GTATTGTCCATGCCCCAAGTCAATATTGTCAAGAA
AACAGAAGTACAGACAGGCGGATTCTCCAAGGAGT
CAATTTTACCAAAAGAAATTCGGACAAGCTTATT
GCTCGTAAAAAGACTGGGATCCAAAAAAATATGG
TGGTTTTGATAGTCCAACGGTAGCTTATTCAGTCC
TAGTGGTTGCTAAGGTGGAAAAAGGGAAATCGAAG
AAGTTAAAATCCGTTAAAGAGTTACTAGGGATCAC
AATTATGGAAAGAAGTTCCTTTGAAAAAAATCCGA
TTGACTTTTAGAAGCTAAAGGATATAAGGAAGTT
AAAAAAGACTTAATCATTAAACTACCTAAATATAG
TCTTTTTGAGTTAGAAAACGGTCGTAAACGGATGC
TGGCTAGTGCCGGAGAATTACAAAAAGGAAATGAG
CTGGCTCTGCCAAGCAAATATGTGAATTTTTTATA
TTTAGCTAGTCATTATGAAAAGTTGAAGGGTAGTC
CAGAAGATAACGAACAAAAACAATTGTTTGTGGAG
CAGCATAAGCATTATTTAGATGAGATTATTGAGCA
AATCAGTGAATTTTCTAAGCGTGTTATTTTAGCAG
ATGCCAATTTAGATAAAGTTCTTAGTGCATATAAC
AAACATAGAGACAAACCAATACGTGAACAAGCAGA
AAATATTATTCATTTATTTACGTTGACGAATCTTG
GAGCTCCCGCTGCTTTTAAATATTTTGATACAACA
ATTGATCGTAAACGATATACGTCTACAAAAGAAGT
TTTAGATGCCACTCTTATCCATCAATCCATCACTG
GTCTTTATGAAACACGCATTGATTTGAGTCAGCTA
GGAGGTGACTGA
```

The amino acid sequence of a *Streptococcus thermophilus* Cas9 protein may be found in the UniProt database under accession number Q03J16.1. See also, Sapranauskas et al., (2011) *Nucleic Acids Res.* 39:9275-9282. This amino acid sequence is:

(SEQ ID NO: 3)
MTKPYSIGLDIGTNSVGWAVTTDNYKVPSKKMKVL
GNTSKKYIKKNLLGVLLFDSGITAEGRRLKRTARR
RYTRRRNRILYLQEIFSTEMATLDDAFFQRLDDSF
LVPDDKRDSKYPIFGNLVEEKAYHDEFPTIYHLRK
YLADSTKKADLRLVYLALAHMIKYRGHFLIEGEFN
SKNNDIQKNFQDFLDTYNAIFESDLSLENSKQLEE
IVKDKISKLEKKDRILKLFPGEKNSGIFSEFLKLI
VGNQADFRKCFNLDEKASLHFSKESYDEDLETLLG
YIGDDYSDVFLKAKKLYDAILLSGFLTVTDNETEA
PLSSAMIKRYNEHKEDLALLKEYIRNISLKTYNEV
FKDDTKNGYAGYIDGKTNQEDFYVYLKKLLAEFEG
ADYFLEKIDREDFLRKQRTFDNGSIPYQIHLQE
MRAILDKQAKFYPPFLAKNKERIEKILT
FRIPYYVGPLARGNSDFAWSIRKRNEKITPWNFED
VIDKESSAEAFINRMTSFDLYLPEEKVLPKHSLLY
ETFNVYNELTKVRFIAESMRDYQFLDSKQKKDIVR
LYFKDKRKVTDKDIIEYLHAIYGYDGIELKGIEKQ
FNSSLSTYHDLLNIINDKEFLDDSSNEAIIEEIIH
TLTIFEDREMIKQRLSKFENIFDKSVLKKLSRRHY
TGWGKLSAKLINGIRDEKSGNTILDYLIDDGISNR
NFMQLIHDDALSFKKKIQKAQIIGDEDK
GNIKEVVKSLPGSPAIKKGILQSIKIVDELVKVMG
GRKPESIVVEMARENQYTNQGKSNSQQRLKRLEKS
LKELGSKILKENIPAKLSKIDNNALQNDRLYLYYL
QNGKDMYTGDDLDIDRLSNYDIDHIIPQAFLKDNS
IDNKVLVSSASNRGKSDDVPSLEVVKKRKTFWYQL
LKSKLISQRKFDNLTKAERGGLSPEDKAGFIQRQL
VETRQITKHVARLLDEKFNNKKDENNRAVRTVKII
TLKSTLVSQFRKDFELYKVREINDFHHAHDAYLNA
VVASALLKKYPKLEPEFVYGDYPKYNSFRERKSAT
EKVYFYSNIMNIFKKSISLADGRVIERPLIEVNEE
TGESVWNKESDLATVRRVLSYPQVNVVKKVEEQNH
GLDRGKPKGLFNANLSSKPKPNSNENLVGAKEYLD
PKKYGGYAGISNSFTVLVKGTIEKGAKKKITNVLE
FQGISILDRINYRKDKLNFLLEKGYKDIELIIELP
KYSLFELSDGSRRMLASILSTNNKRGEIHKGNQIF
LSQKFVKLLYHAKRISNTINENHRKYVENHKKEFE
ELFYYILEFNENYVGAKKNGKLLNSAFQSWQNHSI

DELCSSFIGPTGSERKGLFELTSRGSAADFEFLGV

KIPRYRDYTPSSLLKDATLIHQSVTGLYETRIDLA

KLGEG

SEQ ID NO: 3 may be encoded by the following nucleotide sequence found in the European Nucleotide Archive under accession number ABJ66636.1:

```
                                  (SEQ ID NO: 4)
ATGACTAAGCCATACTCAATTGGACTTGATATTGG

AACGAATAGTGTTGGATGGGCTGTAACAACTGATA

ATTACAAGGTTCCGTCTAAAAAAATGAAAGTCTTA

GGAAATACGAGTAAAAAGTATATCAAAAAGAACCT

GTTAGGTGTATTACTCTTTGACTCTGGAATCACAG

CAGAAGGAAGAAGATTGAAGCGTACTGCAAGAAGA

CGTTATACTAGACGCCGTAATCGTATCCTTTATTT

GCAGGAAATTTTTAGCACAGAGATGGCTACATTAG

ATGATGCTTTCTTTCAAAGACTTGACGATTCGTTT

TTAGTTCCTGATGATAAACGTGATAGTAAGTATCC

GATATTTGGAAACTTAGTAGAAGAAAAAGCCTATC

ATGATGAATTTCCAACTATCTATCATTTAAGGAAA

TATTTAGCAGATAGTACTAAAAAAGCAGATTTGCG

TCTAGTTTATCTTGCATTGGCTCATATGATTAAAT

ATAGAGGTCACTTCTTAATTGAAGGAGAGTTTAAT

TCAAAAAATAATGATATTCAGAAGAATTTTCAAGA

CTTTTTGGACACTTATAATGCTATTTTTGAATCGG

ATTTATCACTTGAGAATAGTAAACAACTTGAGGAA

ATTGTTAAAGATAAGATTAGTAAATTAGAAAAGAA

AGATCGTATTTTAAAACTCTTCCCTGGGGAGAAGA

ATTCGGGGATTTTTTCAGAGTTTCTAAAGTTGATT

GTAGGAAATCAAGCTGATTTTAGGAAATGTTTTAA

TTTAGACGAAAAAGCCTCCTTACATTTTTCCAAAG

AAAGCTATGATGAAGATTTAGAGACTTTGTTAGGT

TATATTGGAGATGATTACAGTGATGTCTTTCTCAA

AGCAAAGAAACTTTATGATGCTATTCTTTTATCGG

GTTTTCTGACTGTAACTGATAATGAGACAGAAGCA

CCTCTCTCTTCTGCTATGATAAAGCGATATAATGA

ACACAAAGAAGATTTAGCGTTACTAAAGGAATATA

TAAGAAATATTTCACTAAAAACGTATAATGAAGTA

TTTAAAGATGACACCAAAAATGGTTATGCTGGTTA

TATTGATGGAAAAACAAATCAGGAAGATTTCTACG

TATATCTAAAAAAACTATTGGCTGAATTTGAAGGT

GCGGATTATTTTCTTGAAAAAATTGATCGAGAAGA

TTTTTTGAGAAAGCAACGTACATTTGACAATGGTT

CGATACCATATCAGATTCATCTTCAAGAAATGAGA

GCAATTCTTGATAAGCAAGCTAAATTTTATCCTTT

CTTGGCTAAAAATAAAGAAAGAATCGAGAAGATTT

TAACCTTCCGAATTCCTTATTATGTAGGTCCACTT

GCGAGAGGGAATAGTGATTTTGCCTGGTCAATAAG

AAAACGAAATGAAAAAATTACACCTTGGAATTTTG

AGGACGTTATTGACAAAGAATCTTCGGCAGAGGCC

TTCATTAATCGAATGACTAGTTTTGATTTGTATTT

GCCAGAAGAGAAGGTACTTCCAAAGCATAGTCTCT

TATACGAAACTTTTAATGTATATAATGAATTAACA

AAAGTTAGATTTATTGCCGAAAGTATGAGAGATTA

TCAATTTTTAGATAGTAAGCAGAAGAAAGATATTG

TTAGACTTTATTTTAAAGATAAAAGGAAAGTTACT

GATAAGGATATTATTGAATATTTACATGCAATTTA

TGGGTATGATGGAATTGAATTAAAAGGCATAGAGA

AACAGTTTAATTCTAGTTTATCTACTTATCACGAT

CTTTTAAATATTATTAATGATAAAGAGTTTTTGGA

TGATAGTTCAAATGAAGCGATTATCGAAGAAATTA

TCCATACTTTGACAATTTTTGAAGATAGAGAGATG

ATAAAACAACGTCTTTCAAAATTTGAGAATATATT

CGATAAATCCGTTTTGAAAAAGTTATCTCGTAGAC

ATTACACTGGCTGGGGTAAGTTATCTGCTAAGCTT

ATTAATGGTATTCGAGATGAAAAATCTGGTAATAC

TATTCTTGATTACTTAATTGATGATGGTATTTCTA

ACCGTAATTTCATGCAACTTATTCACGATGATGCT

CTTTCTTTTAAAAAGAAGATACAGAAAGCACAAAT

TATTGGTGACGAAGATAAAGGTAATATTAAAGAGG

TCGTTAAGTCTTTGCCAGGTAGTCCTGCGATTAAA

AAAGGTATTTTACAAAGCATAAAAATTGTAGATGA

ATTGGTCAAAGTAATGGGAGGAAGAAAACCCGAGT

CAATTGTTGTTGAGATGGCTCGTGAAAATCAATAT

ACCAATCAAGGTAAGTCTAATTCCCAACAACGCTT

GAAACGTTTAGAAAAATCTCTCAAAGAGTTAGGTA

GTAAGATACTTAAGGAAAATATTCCTGCAAAACTT

TCTAAAATAGACAATAACGCACTTCAAAATGATCG

ACTTTACTTATACTATCTTCAAAATGGAAAAGATA

TGTATACCGGAGATGATTTAGATATTGATAGATTA

AGTAATTATGATATTGATCATATTATTCCTCAAGC

TTTTTTGAAAGATAATTCTATTGACAATAAAGTAC
```

```
TTGTTTCATCTGCTAGTAACCGTGGTAAATCAGAT
GATGTTCCAAGTTTAGAGGTTGTCAAAAAAGAAA
GACATTTTGGTATCAATTATTGAAATCAAAATTAA
TTTCTCAACGAAAATTTGATAATCTGACAAAAGCT
GAACGGGGAGGATTGTCACCTGAGGACAAAGCTGG
TTTTATTCAACGCCAGTTGGTTGAAACACGTCAAA
TAACAAAACATGTAGCTCGTTTACTTGATGAGAAA
TTTAATAATAAAAAGATGAAAATAATAGAGCGGT
ACGAACAGTAAAAATTATTACCTTGAAATCTACCT
TAGTTTCTCAATTTCGTAAGGATTTTGAACTTTAT
AAAGTTCGTGAAATCAATGATTTTCATCATGCTCA
TGATGCTTACTTGAATGCCGTTGTAGCAAGTGCTT
TACTTAAGAAATACCCTAAACTAGAGCCAGAATTT
GTGTACGGTGATTATCCAAAATACAATAGTTTTAG
AGAAAGAAAGTCCGCTACAGAAAAGGTATATTTCT
ATTCAAATATCATGAATATCTTTAAAAAATCTATT
TCTTTAGCTGATGGTAGAGTTATTGAAAGACCACT
TATTGAGGTAAATGAGGAGACCGGCGAATCCGTTT
GGAATAAAGAATCTGATTTAGCAACTGTAAGGAGA
GTACTCTCTTATCCGCAAGTAAATGTTGTGAAAAA
AGTTGAGGAACAGAATCACGGATTGGATAGAGGAA
AACCAAAGGGATTGTTTAATGCAAATCTTTCCTCA
AAGCCAAAACCAAATAGTAATGAAAATTTAGTAGG
TGCTAAAGAGTATCTTGACCCCAAAAAGTATGGGG
GGTATGCTGGAATTTCTAATTCTTTTACTGTTCTT
GTTAAAGGGACAATTGAAAAAGGTGCTAAGAAAAA
AATAACAAATGTACTAGAATTTCAAGGTATTTCTA
TTTTAGATAGGATTAATTATAGAAAAGATAAACTT
AATTTTTTACTTGAAAAAGGTTATAAAGATATTGA
GTTAATTATTGAACTACCTAAATATAGTTTATTTG
AACTTTCAGATGGTTCACGTCGTATGTTGGCTAGT
ATTTTGTCAACGAATAATAAGAGGGGAGAGATTCA
CAAAGGAAATCAGATTTTTCTTTCACAGAAGTTTG
TGAAATTACTTTATCATGCTAAGAGAATAAGTAAC
ACAATTAATGAGAATCATAGAAAATATGTTGAGAA
CCATAAAAAGAGTTTGAAGAATTATTTTACTACA
TTCTTGAGTTTAATGAGAATTATGTTGGAGCTAAA
AAGAATGGTAAACTCTTAAACTCTGCCTTTCAATC
TTGGCAAAATCATAGTATAGATGAACTCTGTAGTA
GTTTTATAGGACCTACCGGAAGTGAAAGAAAGGGG
CTATTTGAATTAACCTCTCGTGGAAGTGCTGCTGA
```

```
TTTTGAATTTTTAGGTGTTAAAATTCCAAGGTATA
GAGACTATACCCCATCATCCCTATTAAAAGATGCC
ACACTTATTCATCAATCTGTTACAGGCCTCTATGA
AACACGAATAGACCTTGCCAAACTAGGAGAGGGTT
AA
```

An example of a Cas9 protein comprising a nuclear localization signal (GGSGPPKKKRKV; SEQ ID NO: 5) at the C-terminus thereof has the following amino acid sequence:

(SEQ ID NO: 6)
```
MDKKYSIGLDIGTNSVGWAVITDEYKVPSKKFKVL
GNTDRHSIKKNLIGALLFDSGETAEATRLKRTARR
RYTRRKNRICYLQEIFSNEMAKVDDSFFHRLEESF
LVEEDKKHERHPIFGNIVDEVAYHEKYPTIYHLRK
KLVDSTDKADLRLIYLALAHMIKFRGHFLIEGDLN
PDNSDVDKLFIQLVQTYNQLFEENPINASGVDAKA
ILSARLSKSRRLENLIAQLPGEKKNGLFGNLIALS
LGLTPNFKSNFDLAEDAKLQLSKDTYDDDLDNLLA
QIGDQYADLFLAAKNLSDAILLSDILRVNTEITKA
PLSASMIKRYDEHHQDLTLLKALVRQQLPEKYKEI
FFDQSKNGYAGYIDGGASQEEFYKFIKPILEKMDG
TEELLVKLNREDLLRKQRTFDNGSIPHQIHLGELH
AILRRQEDFYPFLKDNREKIEKILTFRIPYYVGPL
ARGNSRFAWMTRKSEETITPWNFEEVVDKGASAQS
FIERMTNFDKNLPNEKVLPKHSLLYEYFTVYNELT
KVKYVTEGMRKPAFLSGEQKKAIVDLLFKTNRKVT
VKQLKEDYFKKIECFDSVEISGVEDRFNASLGTYH
DLLKIIKDKDFLDNEENEDILEDIVLTLTLFEDRE
MIEERLKTYAHLFDDKVMKQLKRRRYTGWGRLSRK
LINGIRDKQSGKTILDFLKSDGFANRNFMQLIHDD
SLTFKEDIQKAQVSGQGDSLHEHIANLAGSPAIKK
GILQTVKVVDELVKVMGRHKPENIVIEMARENQTT
QKGQKNSRERMKRIEEGIKELGSQILKEHPVENTQ
LQNEKLYLYYLQNGRDMYVDQELDINRLSDYDVDH
IVPQSFLKDDSIDNKVLTRSDKNRGKSDNVPSEEV
VKKMKNYWRQLLNAKLITQRKFDNLTKAERGGLSE
LDKAGFIKRQLVETRQITKHVAQILDSRMNTKYDE
NDKLIREVKVITLKSKLVSDFRKDFQFYKVREINN
YHHAHDAYLNAVVGTALIKKYPKLESEFVYGDYKV
YDVRKMIAKSEQEIGKATAKYFFYSNIMNFFKTEI
TLANGEIRKRPLIETNGETGEIVWDKGRDFATVRK
```

```
-continued
VLSMPQVNIVKKTEVQTGGFSKESILPKRNSDKLI

ARKKDWDPKKYGGFDSPTVAYSVLVVAKVEKGKSK

KLKSVKELLGITIMERSSFEKNPIDFLEAKGYKEV

KKDLIIKLPKYSLFELENGRKRMLASAGELQKGNE

LALPSKYVNFLYLASHYEKLKGSPEDNEQKQLFVE

QHKHYLDEIIEQISEFSKRVILADANLDKVLSAYN

KHRDKPIREQAENIIHLFTLTNLGAPAAFKYFDTT

IDRKRYTSTKEVLDATLIHQSITGLYETRIDLSQL

GGDGGSGPPKKKRKV
```

In some embodiments, a Cas9 nickase may be used in combination with guide sequence(s), e.g., two guide sequences, which target respectively sense and antisense strands of the DNA target. This combination allows both strands to be nicked and used to induce non-homologous end joining (NHEJ).

As a further example, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity (where the amino acid numbering is as in SEQ ID NO: 1). In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other CRISPR enzyme is from a species other than S. pyogenes, mutations in corresponding amino acids may be made to achieve similar effects.

In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g. 1, 2, 3, 4, 5, 10, 15, 20, 25, 50, or more, or all codons) in a sequence encoding a CRISPR enzyme corresponds to the most frequently used codon for a particular amino acid.

In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMNNNNNNNNNNNNXGG MMMMMMMMNNNNNNNNNNNNXXAGAAW where NNNNNNNNNNNNXGG (N is A, G, T, or C; and X can be a deoxynucleotide) has a single occurrence in the genome. A unique target sequence in a genome may include an S. pyogenes Cas9 target site of the form MMMMMMMMNNNNNNNNNNNNXGG where NNNNNNNNNNNNXGG (N is A, G, T, or C; and X can be a deoxynucleotide) has a single occurrence in the genome. For the S. thermophilus CRISPR1 Cas9, a unique target sequence in a genome may include a Cas9 target site of the form MMMMMMMMNNNNNNNNNNNNXXAGAAW (SEQ ID NO: 7) where NNNNNNNNNNNNXXAGAAW (SEQ ID NO: 8) (N is A, G, T, or C; X can be a deoxynucleotide; and W is A or T) has a single occurrence in the genome. A unique target sequence in a genome may include an *S. thermophilus* CRISPR1 Cas9 target site of the form MMMMMMMMMNNNNNNNNNNNXXAGAAW (SEQ ID NO: 9) where NNNNNNNNNNNXXAGAAW (SEQ ID NO: 10) (N is A, G, T, or C; X can be a deoxynucleotide; and W is A or T) has a single occurrence in the genome. For the *S. pyogenes* Cas9, a unique target sequence in a genome may include a Cas9 target site of the form MMMMMMMMMNNNNNNNNNNNXGGXG where NNNNNNNNNNNXGGXG (N is A, G, T, or C; and X can be a deoxynucleotide) has a single occurrence in the genome. A unique target sequence in a genome may include an *S. pyogenes* Cas9 target site of the form MMMMMMMMMNNNNNNNNNNNXGGXG where NNNNNNNNNNNXGGXG (N is A, G, T, or C; and X can be a deoxynucleotide) has a single occurrence in the genome. In each of these sequences "M" may be A, G, T, or C, and need not be considered in identifying a sequence as unique.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and P A Carr and G M Church, 2009, Nature Biotechnology 27(12): 1151-62). Further algorithms may be found in U.S. application Ser. No. 61/836,080; incorporated herein by reference.

Aspects of the present subject matter relate to delivery of CRISPR/CRISPR/CRISPR from *Prevotella* and *Francisella* 1 (Cpf1) gene editing complexes or components thereof (e.g., CPf1 proteins). Examples of human codon optimized Cpf1-family proteins are provided below.

Human Codon Optimized Cpf1-Family Proteins

Non-limiting examples of Cpf1-family protein sequences, and aspects of CRISPR/Cpf1 gene-editing, are described in Zetsche et al., Cell 163, 759-771, Oct. 22, 2015, the entire content of which is incorporated herein by reference.

*Francisella tularensis* subsp. *Novicida* U112 (FnCpf1; pY004)), including NLS and HA tag:

```
                                    (SEQ ID NO: 11)
MSIYQEFVNKYSLSKTLRFELIPQGKTLENIKARG

LILDDEKRAKDYKKAKQIIDKYHQFFIEEILSSVC

ISEDLLQNYSDVYFKLKKSDDDNLQKDFKSAKDTI

KKQISEYIKDSEKFKNLFNQNLIDAKKGQESDLIL

WLKQSKDNGIELFKANSDITDIDEALEIIKSFKGW

TTYFKGFHENRKNVYSSNDIPTSIIYRIVDDNLPK

FLENKAKYESLKDKAPEAINYEQIKKDLAEELTFD

IDYKTSEVNQRVFSLDEVFEIANFNNYLNQSGITK

FNTIIGGKFVNGENTKRKGINEYINLYSQQINDKT

LKKYKMSVLFKQILSDTESKSFVIDKLEDDSDVVT

TMQSFYEQIAAFKTVEEKSIKETLSLLFDDLKAQK

LDLSKIYFKNDKSLTDLSQQVFDDYSVIGTAVLEY

ITQQIAPKNLDNPSKKEQELIAKKTEKAKYLSLET

IKLALEEFNKHRDIDKQCRFEEILANFAAIPMIFD

EIAQNKDNLAQISIKYQNQGKKDLLQASAEDDVKA

IKDLLDQTNNLLHKLKIFHISQSEDKANILDKDEH

FYLVFEECYFELANIVPLYNKIRNYITQKPYSDEK

FKLNFENSTLANGWDKNKEPDNTAILFIKDDKYYL

GVMNKKNNKIFDDKAIKENKGEGYKKIVYKLLPGA

NKMLPKVFFSAKSIKFYNPSEDILRIRNHSTHTKN

GSPQKGYEKFEFNIEDCRKFIDFYKQSISKHPEWK

DFGFRFSDTQRYNSIDEFYREVENQGYKLTFENIS

ESYIDSVVNQGKLYLFQIYNKDFSAYSKGRPNLHT

LYWKALFDERNLQDVVYKLNGEAELFYRKQSIPKK

ITHPAKEAIANKNKDNPKKESVFEYDLIKDKRFTE

DKFFFHCPITINFKSSGANKFNDEINLLLKEKAND

VHILSIDRGERHLAYYTLVDGKGNIIKQDTFNIIG

NDRMKTNYHDKLAAIEKDRDSARKDWKKINNIKEM

KEGYLSQVVHEIAKLVIEYNAIVVFEDLNFGFKRG

RFKVEKQVYQKLEKMLIEKLNYLVFKDNEFDKTGG

VLRAYQLTAPFETFKKMGKQTGIIYYVPAGFTSKI

CPVTGFVNQLYPKYESVSKSQEFFSKFDKICYNLD

KGYFEFSFDYKNFGDKAAKGKWTIASFGSRLINFR

NSDKNHNWDTREVYPTKELEKLLKDYSIEYGHGEC

IKAAICGESDKKFFAKLTSVLNTILQMRNSKTGTE

LDYLISPVADVNGNFFDSRQAPKNMPQDADANGAY

HIGLKGLMLLGRIKNNQEGKKLNLVIKNEEYFEFV

QNRNNKRPAATKKAGQAKKKKGSYPYDVPDYAYPY

DVPDYAYPYDVPDYA
```

SEQ ID NO: 11 includes a nuclear localization signal (KRPAATKKAGQAKKKK) (SEQ ID NO: 12), followed by a glycine-serine linker (GS), followed by a Human influenza hemagglutinin (HA) tag (YPYDVPDYAYPYDVPDYAYPYDVPDYA) (SEQ ID NO: 13).

SEQ ID NO: 11 may be encoded by the following nucleotide sequence:

```
                                    (SEQ ID NO: 14)
ATGAGCATCTACCAGGAGTTCGTCAACAAGTATTC

ACTGAGTAAGACACTGCGGTTCGAGCTGATCCCAC

AGGGCAAGACACTGGAGAACATCAAGGCCCGAGGC

CTGATTCTGGACGATGAGAAGCGGGCAAAAGACTA

TAAGAAAGCCAAGCAGATCATTGATAAATACCACC
```

```
AGTTCTTTATCGAGGAAATTCTGAGCTCCGTGTGC
ATCAGTGAGGATCTGCTGCAGAATTACTCAGACGT
GTACTTCAAGCTGAAGAAGAGCGACGATGACAACC
TGCAGAAGGACTTCAAGTCCGCCAAGGACACCATC
AAGAAACAGATTAGCGAGTACATCAAGGACTCCGA
AAAGTTTAAAAATCTGTTCAACCAGAATCTGATCG
ATGCTAAGAAGGCCAGGAGTCCGACCTGATCCTG
TGGCTGAAACAGTCTAAGGACAATGGGATTGAACT
GTTCAAGGCTAACTCCGATATCACTGATATTGACG
AGGCACTGGAAATCATCAAGAGCTTCAAGGGATGG
ACCACATACTTTAAAGGCTTCCACGAGAACCGCAA
GAACGTGTACTCCAGCAACGACATTCCTACCTCCA
TCATCTACCGAATCGTCGATGACAATCTGCCAAAG
TTCCTGGAGAACAAGGCCAAATATGAATCTCTGAA
GGACAAAGCTCCCGAGGCAATTAATTACGAACAGA
TCAAGAAAGATCTGGCTGAGGAACTGACATTCGAT
ATCGACTATAAGACTAGCGAGGTGAACCAGAGGGT
CTTTTCCCTGGACGAGGTGTTTGAAATCGCCAATT
TCAACAATTACCTGAACCAGTCCGGCATTACTAAA
TTCAATACCATCATTGGCGGGAAGTTTGTGAACGG
GGAGAATACCAAGCGCAAGGGAATTAACGAATACA
TCAATCTGTATAGCCAGCAGATCAACGACAAAACT
CTGAAGAAATACAAGATGTCTGTGCTGTTCAAACA
GATCCTGAGTGATACCGAGTCCAAGTCTTTTGTCA
TTGATAAACTGGAAGATGACTCAGACGTGGTCACT
ACCATGCAGAGCTTTTATGAGCAGATCGCCGCTTT
CAAGACAGTGGAGGAAAAATCTATTAAGGAAACTC
TGAGTCTGCTGTTCGATGACCTGAAAGCCCAGAAG
CTGGACCTGAGTAAGATCTACTTCAAAAACGATAA
GAGTCTGACAGACCTGTCACAGCAGGTGTTTGATG
ACTATTCCGTGATTGGGACCGCCGTCCTGGAGTAC
ATTACACAGCAGATCGCTCCAAAGAACCTGGATAA
TCCCTCTAAGAAAGAGCAGGAACTGATCGCTAAGA
AAACCGAGAAGGCAAAATATCTGAGTCTGGAAACA
ATTAAGCTGGCACTGGAGGAGTTCAACAAGCACAG
GGATATTGACAAACAGTGCCGCTTTGAGGAAATCC
TGGCCAACTTCGCAGCCATCCCCATGATTTTTGAT
GAGATCGCCCAGAACAAAGACAATCTGGCTCAGAT
CAGTATTAAGTACCAGAACCAGGGCAAGAAAGACC
TGCTGCAGGCTTCAGCAGAAGATGACGTGAAAGCC
ATCAAGGATCTGCTGGACCAGACCAACAATCTGCT
```

```
GCACAAGCTGAAAATCTTCCATATTAGTCAGTCAG
AGGATAAGGCTAATATCCTGGATAAAGACGAACAC
TTCTACCTGGTGTTCGAGGAATGTTACTTCGAGCT
GGCAAACATTGTCCCCCTGTATAACAAGATTAGGA
ACTACATCACACAGAAGCCTTACTCTGACGAGAAG
TTTAAACTGAACTTCGAAAATAGTACCCTGGCCAA
CGGGTGGGATAAGAACAAGGAGCCTGACAACACAG
CTATCCTGTTCATCAAGGATGACAAGTACTATCTG
GGAGTGATGAATAAGAAAAACAATAAGATCTTCGA
TGACAAAGCCATTAAGGAGAACAAAGGGGAAGGAT
ACAAGAAAATCGTGTATAAGCTGCTGCCCGGCGCA
AATAAGATGCTGCCTAAGGTGTTCTTCAGCGCCAA
GAGTATCAAATTCTACAACCCATCCGAGGACATCC
TGCGGATTAGAAATCACTCAACACATACTAAGAAC
GGGAGCCCCCAGAAGGGATATGAGAAATTTGAGTT
CAACATCGAGGATTGCAGGAAGTTTATTGACTTCT
ACAAGCAGAGCATCTCCAAACACCCTGAATGGAAG
GATTTTGGCTTCCGGTTTTCCGACACACAGAGATA
TAACTCTATCGACGAGTTCTACCGCGAGGTGGAAA
ATCAGGGGTATAAGCTGACTTTTGAGAACATTTCT
GAAAGTTACATCGACAGCGTGGTCAATCAGGGAAA
GCTGTACCTGTTCCAGATCTATAACAAAGATTTTT
CAGCATACAGCAAGGGCAGACCAAACCTGCATACA
CTGTACTGGAAGGCCCTGTTCGATGAGAGGAATCT
GCAGGACGTGGTCTATAAACTGAACGGAGAGGCCG
AACTGTTTTACCGGAAGCAGTCTATTCCTAAGAAA
ATCACTCACCCAGCTAAGGAGGCCATCGCTAACAA
GAACAAGGACAATCCTAAGAAAGAGAGCGTGTTCG
AATACGATCTGATTAAGGACAAGCGGTTCACCGAA
GATAAGTTCTTTTTCCATTGTCCAATCACCATTAA
CTTCAAGTCAAGCGGCGCTAACAAGTTCAACGACG
AGATCAATCTGCTGCTGAAGGAAAAAGCAAACGAT
GTGCACATCCTGAGCATTGACCGAGGAGAGCGGCA
TCTGGCCTACTATACCCTGGTGGATGGCAAAGGGA
ATATCATTAAGCAGGATACATTCAACATCATTGGC
AATGACCGGATGAAAACCAACTACCACGATAAACT
GGCTGCAATCGAGAAGGATAGAGACTCAGCTAGGA
AGGACTGGAAGAAAATCAACAACATTAAGGAGATG
AAGGAAGGCTATCTGAGCCAGGTGGTCCATGAGAT
TGCAAAGCTGGTCATCGAATACAATGCCATTGTGG
```

-continued

```
TGTTCGAGGATCTGAACTTCGGCTTTAAGAGGGGG
CGCTTTAAGGTGGAAAAACAGGTCTATCAGAAGCT
GGAGAAAATGCTGATCGAAAAGCTGAATTACCTGG
TGTTTAAAGATAACGAGTTCGACAAGACCGGAGGC
GTCCTGAGAGCCTACCAGCTGACAGCTCCCTTTGA
AACTTTCAAGAAAATGGGAAAACAGACAGGCATCA
TCTACTATGTGCCAGCCGGATTCACTTCCAAGATC
TGCCCCGTGACCGGCTTTGTCAACCAGCTGTACCC
TAAATATGAGTCAGTGAGCAAGTCCCAGGAATTTT
TCAGCAAGTTCGATAAGATCTGTTATAATCTGGAC
AAGGGGTACTTCGAGTTTTCCTTCGATTACAAGAA
CTTCGGCGACAAGGCCGCTAAGGGGAAATGGACCA
TTGCCTCCTTCGGATCTCGCCTGATCAACTTTCGA
AATTCCGATAAAAACCACAATTGGGACACTAGGGA
GGTGTACCCAACCAAGGAGCTGGAAAAGCTGCTGA
AAGACTACTCTATCGAGTATGGACATGGCGAATGC
ATCAAGGCAGCCATCTGTGGCGAGAGTGATAAGAA
ATTTTTCGCCAAGCTGACCTCAGTGCTGAATACAA
TCCTGCAGATGCGGAACTCAAAGACCGGGACAGAA
CTGGACTATCTGATTAGCCCCGTGGCTGATGTCAA
CGGAAACTTCTTCGACAGCAGACAGGCACCCAAAA
ATATGCCTCAGGATGCAGACGCCAACGGGCCTAC
CACATCGGGCTGAAGGGACTGATGCTGCTGGGCCG
GATCAAGAACAATCAGGAGGGGAAGAAGCTGAACC
TGGTCATTAAGAACGAGGAATACTTCGAGTTTGTC
CAGAATAGAAATAACAAAAGGCCGGCGGCCACGAA
AAAGGCCGGCCAGGCAAAAAAGAAAAAGGGATCCT
ACCCATACGATGTTCCAGATTACGCTTATCCCTAC
GACGTGCCTGATTATGCATACCCATATGATGTCCC
CGACTATGCCTAA
```

*Lachnospiraceae bacterium* MC2017 (Lb3Cpf1; pY005), including NLS and HA tag:

(SEQ ID NO: 15)
```
MDYGNGQFERRAPLTKTITLRLKPIGETRETIREQ
KLLEQDAAFRKLVETVTPIVDDCIRKIADNALCHF
GTEYDFSCLGNAISKNDSKAIKKETEKVEKLLAKV
LTENLPDGLRKVNDINSAAFIQDTLTSFVQDDADK
RVLIQELKGKTVLMQRFLTTRITALTVWLPDRVFE
NFNIFIENAEKMRILLDSPLNEKIMKFDPDAEQYA
SLEFYGQCLSQKDIDSYNLIISGIYADDEVKNPGI
NEIVKEYNQQIRGDKDESPLPKLKKLHKQILMPVE
KAFFVRVLSNDSDARSILEKILKDTEMLPSKIIEA
MKEADAGDIAVYGSRLHELSHVIYGDHGKLSQIIY
DKESKRISELMETLSPKERKESKKRLEGLEEHIRK
STYTFDELNRYAEKNVMAAYIAAVEESCADIVIRK
EKDLRTLLSKEDVKIRGNRHNTLIVKNYFNAWTVF
RNLIRILRRKSEAEIDSDFYDVLDDSVEVLSLTY
KGENLCRSYITKKIGS
DLKPEIATYGSALRPNSRWWSPGEKFNVKFHTIVR
RDGRLYYFILPKGAKPVELEDMDGDIECLQMRKIP
NPTIFLPKLVFKDPEAFFRDNPEADEFVFLSGMKA
PVTITRETYEAYRYKLYTVGKLRDGEVSEEEYKRA
LLQVLTAYKEFLENRMIYADLNFGFKDLEEYKDSS
EFIKQVETHNTFMCWAKVSSSQLDDLVKSGNGLLF
EIWSERLESYYKYGNEKVLRGYEGVLLSILKDENL
VSMRTLLNSRPMLVYRPKESSKPMVVHRDGSRVVD
RFDKDGKYIPPEVHDELYRFFNNLLIKEKLGEKAR
KILDNKKVKVKVLESERVKWSKFYDEQFAVTFSVK
KNADCLDTTKDLNAEVMEQYSESNRLILIRNTTDI
LYYLVLDKNGKVLKQRSLNIINDGARDVDWKERFR
QVTKDRNEGYNEWDYSRTSNDLKEVYLNYALKEIA
EAVIEYNAILIIEKMSNAFKDKYSFLDDVTFKGFE
TKLLAKLSDLHFRGIKDGEPCSFTNPLQLCQNDSN
KILQDGVIFMVPNSMTRSLDPDTGFIFAINDHNIR
TKKAKLNFLSKFDQLKVSSEGCLIMKYSGDSLPTH
NTDNRVWNCCCNHPITNYDRETKKVEFIEEPVEEL
SRVLEENGIETDTELNKLNERENVPGKVVDAIYSL
VLNYLRGTVSGVAGQRAVYYSPVTGKKYDISFIQA
MNLNRKCDYYRIGSKERGEWTDFVAQLINKRPAAT
KKAGQAKKKKGSYPYDVPDYAYPYDVPDYAYPYDV
PDYA
```

*Lachnospiraceae bacterium* MC2017 (Lb3Cpf1;pY005), including NLS and HA tag:

(SEQ ID NO: 15)
```
MDYGNGQFERRAPLTKTITLRLKPIGETRETIREQKLLEQDAAFRKLVET
VTPIVDDCIRKIADNALCHFGTEYDFSCLGNAISKNDSKAIKKETEKVEK
LLAKVLTENLPDGLRKVNDINSAAFIQDTLTSFVQDDADKRVLIQELKGK
TVLMQRFLTTRITALTVWLPDRVFENFNIFIENAEKMRILLDSPLNEKIM
KFDPDAEQYASLEFYGQCLSQKDIDSYNLIISGIYADDEVKNPGINEIVK
EYNQQIRGDKDESPLPKLKKLHKQILMPVEKAFFVRVLSNDSDARSILEK
ILKDTEMLPSKIIEAMKEADAGDIAVYGSRLHELSHVIYGDHGKLSQIIY
DKESKRISELMETLSPKERKESKKRLEGLEEHIRKSTYTFDELNRYAEKN
```

```
VMAAYIAAVEESCAEIMRKEKDLRTLLSKEDVKIRGNRHNTLIVKNYFNA
WTVFRNLIRILRRKSEAEIDSDFYDVLDDSVEVLSLTYKGENLCRSYITK
KIGSDLKPEIATYGSALRPNSRWWSPGEKFNVKFHTIVRRDGRLYYFILP
KGAKPVELEDMDGDIECLQMRKIPNPTIFLPKLVFKDPEAFFRDNPEADE
FVFLSGMKAPVTITRETYEAYRYKLYTVGKLRDGEVSEEEYKRALLQVLT
AYKEFLENRMIYADLNFGFKDLEEYKDSSEFIKQVETHNTFMCWAKVSSS
QLDDLVKSGNGLLFEIWSERLESYYKYGNEKVLRGYEGVLLSILKDENLV
SMRTLLNSRPMLVYRPKESSKPMVVHRDGSRVVDRFDKDGKYIPPEVHDE
LYRFFNNLLIKEKLGEKARKILDNKKVKVKVLESERVKWSKFYDEQFAVT
FSVKKNADCLDTTKDLNAEVMEQYSESNRLILIRNTTDILYYLVLDKNGK
VLKQRSLNIINDGARDVDWKERFRQVTKDRNEGYNEWDYSRTSNDLKEVY
LNYALKEIAEAVIEYNAILIIEKMSNAFKDKYSFLDDVTFKGFETKLLAK
LSDLHFRGIKDGEPCSFTNPLQLCQNDSNKILQDGVIFMVPNSMTRSLDP
DTGFIFAINDHNIRTKKAKLNFLSKFDQLKVSSEGCLIMKYSGDSLPTHN
TDNRVWNCCCNHPITNYDRETKKVEFIEEPVEELSRVLEENGIETDTELN
KLNERENVPGKVVDAIYSLVLNYLRGTVSGVAGQRAVYYSPVTGKKYDIS
FIQAMNLNRKCDYYRIGSKERGEWTDFVAQLINKRPAATKKAGQAKKKKG
SYPYDVPDYAYPYDVPDYAYPYDVPDYA
```

SEQ ID NO: 15 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 15 may be encoded by the following nucleotide sequence:

```
ATGGATTACGGCAACGGCCAGTTTGAGCGGAGAGC
CCCCCTGACCAAGACAATCACCCTGCGCCTGAAGC
CTATCGGCGAGACACGGGAGACAATCCGCGAGCAG
AAGCTGCTGGAGCAGGACGCCGCCTTCAGAAAGCT
GGTGGAGACAGTGACCCCTATCGTGGACGATTGTA
TCAGGAAGATCGCCGATAACGCCCTGTGCCACTTT
GGCACCGAGTATGACTTCAGCTGTCTGGGCAACGC
CATCTCTAAGAATGACAGCAAGGCCATCAAGAAGG
AGACAGAGAAGGTGGAGAAGCTGCTGGCCAAGGTG
CTGACCGAGAATCTGCCAGATGGCCTGCGCAAGGT
GAACGACATCAATTCCGCCGCCTTTATCCAGGATA
CACTGACCTCTTTCGTGCAGGACGATGCCGACAAG
CGGGTGCTGATCCAGGAGCTGAAGGGCAAGACCGT
GCTGATGCAGCGGTTCCTGACCACACGGATCACAG
CCCTGACCGTGTGGCTGCCCGACAGAGTGTTCGAG
AACTTTAATATCTTCATCGAGAACGCCGAGAAGAT
GAGAATCCTGCTGGACTCCCCTCTGAATGAGAAGA
TCATGAAGTTTGACCCAGATGCCGAGCAGTACGCC
TCTCTGGAGTTCTATGGCCAGTGCCTGTCTCAGAA
GGACATCGATAGCTACAACCTGATCATCTCCGGCA
TCTATGCCGACGATGAGGTGAAGAACCCTGGCATC
AATGAGATCGTGAAGGAGTACAATCAGCAGATCCG
GGGCGACAAGGATGAGTCCCCACTGCCCAAGCTGA
AGAAGCTGCACAAGCAGATCCTGATGCCAGTGGAG
AAGGCCTTCTTTGTGCGCGTGCTGTCTAACGACAG
CGATGCCCGGAGCATCCTGGAGAAGATCCTGAAGG
ACACAGAGATGCTGCCCTCCAAGATCATCGAGGCC
ATGAAGGAGGCAGATGCAGGCGACATCGCCGTGTA
CGGCAGCCGGCTGCACGAGCTGAGCCACGTGATCT
ACGGCGATCACGGCAAGCTGTCCCAGATCATCTAT
GACAAGGAGTCCAAGAGGATCTCTGAGCTGATGGA
GACACTGTCTCCAAAGGAGCGCAAGGAGAGCAAGA
AGCGGCTGGAGGGCCTGGAGGAGCACATCAGAAAG
TCTACATACACCTTCGACGAGCTGAACAGGTATGC
CGAGAAGAATGTGATGGCAGCATACATCGCAGCAG
TGGAGGAGTCTTGTGCCGAGATCATGAGAAAGGAG
AAGGATCTGAGGACCCTGCTGAGCAAGGAGGACGT
GAAGATCCGGGGCAACAGACACAATACACTGATCG
TGAAGAACTACTTTAATGCCTGGACCGTGTTCCGG
AACCTGATCAGAATCCTGAGGCGCAAGTCCGAGGC
CGAGATCGACTCTGACTTCTACGATGTGCTGGACG
ATTCCGTGGAGGTGCTGTCTCTGACATACAAGGGC
GAGAATCTGTGCCGCAGCTATATCACCAAGAAGAT
CGGCTCCGACCTGAAGCCCGAGATCGCCACATACG
GCAGCGCCCTGAGGCCTAACAGCCGCTGGTGGTCC
CCAGGAGAGAAGTTTAATGTGAAGTTCCACACCAT
CGTGCGGAGAGATGGCCGGCTGTACTATTTCATCC
TGCCCAAGGGCGCCAAGCCTGTGGAGCTGGAGGAC
ATGGATGGCGACATCGAGTGTCTGCAGATGAGAAA
GATCCCTAACCCAACAATCTTTCTGCCCAAGCTGG
TGTTCAAGGACCCTGAGGCCTTCTTTAGGGATAAT
CCAGAGGCCGACGAGTTCGTGTTTCTGAGCGGCAT
GAAGGCCCCCGTGACAATCACCAGAGAGACATACG
AGGCCTACAGGTATAAGCTGTATACCGTGGGCAAG
CTGCGCGATGGCGAGGTGTCCGAAGAGGAGTACAA
GCGGGCCCTGCTGCAGGTGCTGACCGCCTACAAGG
AGTTTCTGGAGAACAGAATGATCTATGCCGACCTG
AATTTCGGCTTTAAGGATCTGGAGGAGTATAAGGA
```

CAGCTCCGAGTTTATCAAGCAGGTGGAGACACACA

ACACCTTCATGTGCTGGGCCAAGGTGTCTAGCTCC

CAGCTGGACGATCTGGTGAAGTCTGGCAACGGCCT

GCTGTTCGAGATCTGGAGCGAGCGCCTGGAGTCCT

ACTATAAGTACGGCAATGAGAAGGTGCTGCGGGGC

TATGAGGGCGTGCTGCTGAGCATCCTGAAGGATGA

GAACCTGGTGTCCATGCGGACCCTGCTGAACAGCC

GGCCCATGCTGGTGTACCGGCCAAAGGAGTCTAGC

AAGCCTATGGTGGTGCACCGGGATGGCAGCAGAGT

GGTGGACAGGTTTGATAAGGACGGCAAGTACATCC

CCCCTGAGGTGCACGACGAGCTGTATCGCTTCTTT

AACAATCTGCTGATCAAGGAGAAGCTGGGCGAGAA

GGCCCGGAAGATCCTGGACAACAAGAAGGTGAAGG

TGAAGGTGCTGGAGAGCGAGAGAGTGAAGTGGTCC

AAGTTCTACGATGAGCAGTTTGCCGTGACCTTCAG

CGTGAAGAAGAACGCCGATTGTCTGGACACCACAA

AGGACCTGAATGCCGAAGTGATGGAGCAGTATAGC

GAGTCCAACAGACTGATCCTGATCAGGAATACCAC

AGATATCCTGTACTATCTGGTGCTGGACAAGAATG

GCAAGGTGCTGAAGCAGAGATCCCTGAACATCATC

AATGACGGCGCCAGGGATGTGGACTGGAAGGAGAG

GTTCCGCCAGGTGACAAAGGATAGAAACGAGGGCT

ACAATGAGTGGGATTATTCCAGGACCTCTAACGAC

CTGAAGGAGGTGTACCTGAATTATGCCCTGAAGGA

GATCGCCGAGGCCGTGATCGAGTACAACGCCATCC

TGATCATCGAGAAGATGTCTAATGCCTTTAAGGAC

AAGTATAGCTTCCTGGACGACGTGACCTTCAAGGG

CTTCGAGACAAAGCTGCTGGCCAAGCTGAGCGATC

TGCACTTTAGGGGCATCAAGGACGGCGAGCCATGT

TCCTTCACAAACCCCCTGCAGCTGTGCCAGAACGA

TTCTAATAAGATCCTGCAGGACGGCGTGATCTTTA

TGGTGCCAAATTCTATGACACGGAGCCTGGACCCC

GACACCGGCTTCATCTTTGCCATCAACGACCACAA

TATCAGGACCAAGAAGGCCAAGCTGAACTTTCTGA

GCAAGTTCGATCAGCTGAAGGTGCCTCTGAGGGC

TGCCTGATCATGAAGTACAGCGGCGATTCCCTGCC

TACACACAACACCGACAATCGCTGTGGAACTGCT

GTTGCAATCACCCAATCACAAACTATGACCGGGAG

ACAAAGAAGGTGGAGTTCATCGAGGAGCCCGTGGA

GGAGCTGTCCCGCGTGCTGGAGGAGAATGGCATCG

AGACAGACACCGAGCTGAACAAGCTGAATGAGCGG

GAGAACGTGCCTGGCAAGGTGGTGGATGCCATCTA

CTCTCTGGTGCTGAATTATCTGCGCGGCACAGTGA

GCGGAGTGGCAGGACAGAGGGCCGTGTACTATAGC

CCTGTGACCGGCAAGAAGTACGATATCTCCTTTAT

CCAGGCCATGAACCTGAATAGGAAGTGTGACTACT

ATAGGATCGGCTCCAAGGAGAGGGGAGAGTGGACC

GATTTCGTGGCCCAGCTGATCAACAAAAGGCCGGC

GGCCACGAAAAGGCCGGCCAGGCAAAAAGAAAA

AGGGATCCTACCCATACGATGTTCCAGATTACGCT

TATCCCTACGACGTGCCTGATTATGCATACCCATA

TGATGTCCCCGACTATGCCTAA

*Butyrivibrio proteoclasticus*
(BpCpf1; pY006), including NLS and
HA tag:
(SEQ ID NO: 17)
MSIYQEFVNKYSLSKTLRFELIPQGKTLENIKARG

LILDDEKRAKDYKKAKQIIDKYHQFFIEEILSSVC

ISEDLLQNYSDVYFKLKKSDDDNLQKDFKSAKDTI

KKQISEYIKDSEKFKNLFNQNLIDAKKGQESDLIL

WLKQSKDNGIELFKANSDITDIDEALEIIKSFKGW

TTYFKGFHENRKNVYSSNDIPTSIIYRIVDDNLPK

FLENKAKYESLKDKAPEAINYEQIKKDLAEELTFD

IDYKTSEVNQRVFSLDEVFEIANFNNYLNQSGITK

FNTIIGGKFVNGENTKRKGINEYINLYSQQINDKT

LKKYKMSVLFKQILSDTESKSFVIDKLEDDSDVVT

TMQSFYEQIAAFKTVEEKSIKETLSLLFDDLKAQK

LDLSKIYFKNDKSLTDLSQQVFDDYSVIGTAVLEY

ITQQIAPKNLDNPSKKEQELIAKKTEKAKYLSLET

IKLALEEFNKHRDIDKQCRFEEILANFAAIPMI

FDEIAQNKDNLAQISIKYQNQGKKDLLQASAE

DDVKAIKDLLDQTNNLLHKLKIFHISQSEDKANIL

DKDEHFYLVFEECYFELANIVPLYNKIRNYITQKP

YSDEKFKLNFENSTLANGWDKNKEPDNTAILFIKD

DKYYLGVMNKKNNKIFDDKAIKENKGEGYKKIVYK

LLPGANKMLPKVFFSAKSIKFYNPSEDILRIRNHS

THTKNGSPQKGYEKFEFNIEDCRKFIDFYKQSISK

HPEWKDFGFRFSDTQRYNSIDEFYREVENQGYKLT

FENISESYIDSVVNQGKLYLFQIYNKDFSAYSKGR

PNLHTLYWKALFDERNLQDVVYKLNGEAELFYRKQ

SIPKKITHPAKEAIANKNKDNPKKESVFEYDLIKD

KRFTEDKFFFHCPITINFKSSGANKFNDEINLLLK

EKANDVHILSIDRGERHLAYYTLVDGKGNIIKQDT

-continued

FNIIGNDRMKTNYHDKLAAIEKDRDSARKDWKKIN

NIKEMKEGYLSQVVHEIAKLVIEYNAIVVFEDLNF

GFKRGRFKVEKQVYQKLEKMLIEKLNYLVFKDNEF

DKTGGVLRAYQLTAPFETFKKMGKQTGIIYYVPAG

FTSKICPVTGFVNQLYPKYESVSKSQEFFSKFDKI

CYNLDKGYFEFSFDYKNFGDKAAKGKWTIASFGSR

LINFRNSDKNHNWDTREVYPTKELEKLLKDYSIEY

GHGECIKAAICGESDKKFFAKLTSVLNTILQMRNS

KTGTELDYLISPVADVNGNFFDSRQAPKNMPQDAD

ANGAYHIGLKGLMLLGRIKNNQEGKKLNLVIKNEE

YFEFVQNRNNKRPAATKKAGQAKKKKGSYPYDVPD

YAYPYDVPDYAYPYDVPDYA

*Butyrivibrio* proteoclasticus (BpCpf1; pY006), including NLS and HA tag:

(SEQ ID NO: 17)
MSIYQEFVNKYSLSKTLRFELIPQGKTLENIKARGLILDDEKRAKDYKKA

KQIIDKYHQFFIEEILSSVCISEDLLQNYSDVYFKLKKSDDDNLQKDFKS

AKDTIKKQISEYIKDSEKFKNLFNQNLIDAKKGQESDLILWLKQSKDNGI

ELFKANSDITDIDEALEIIKSFKGWTTYFKGFHENRKNVYSSNDIPTSII

YRIVDDNLPKFLENKAKYESLKDKAPEAINYEQIKKDLAEELTFDIDYKT

SEVNQRVFSLDEVFEIANFNNYLNQSGITKFNTIIGGKFVNGENTKRKGI

NEYINLYSQQINDKTLKKYKMSVLFKQILSDTESKSFVIDKLEDDSDVVT

TMQSFYEQIAAFKTVEEKSIKETLSLLFDDLKAQKLDLSKIYFKNDKSLT

DLSQQVFDDYSVIGTAVLEYITQQIAPKNLDNPSKKEQELIAKKTEKAKY

LSLETIKLALEEFNKHRDIDKQCRFEEILANFAAIPMIFDEIAQNKDNLA

QISIKYQNQGKKDLLQASAEDDVKAIKDLLDQTNNLLHKLKIFHISQSED

KANILDKDEHFYLVFEECYFELANIVPLYNKIRNYITQKPYSDEKFKLNF

ENSTLANGWDKNKEPDNTAILFIKDDKYYLGVMNKKNNKIFDDKAIKENK

GEGYKKIVYKLLPGANKMLPKVFFSAKSIKFYNPSEDILRIRNHSTHTKN

GSPQKGYEKFEFNIEDCRKFIDFYKQSISKHPEWKDFGFRFSDTQRYNSI

DEFYREVENQGYKLTFENISESYIDSVVNQGKLYLFQIYNKDFSAYSKGR

PNLHTLYWKALFDERNLQDVVYKLNGEAELFYRKQSIPKKITHPAKEAIA

NKNKDNPKKESVFEYDLIKDKRFTEDKFFFHCPITINFKSSGANKFNDEI

NLLLKEKANDVHILSIDRGERHLAYYTLVDGKGNIIKQDTFNIIGNDRMK

TNYHDKLAAIEKDRDSARKDWKKINNIKEMKEGYLSQVVHEIAKLVIEYN

AIVVFEDLNFGFKRGRFKVEKQVYQKLEKMLIEKLNYLVFKDNEFDKTGG

VLRAYQLTAPFETFKKMGKQTGIIYYVPAGFTSKICPVTGFVNQLYPKYE

SVSKSQEFFSKFDKICYNLDKGYFEFSFDYKNFGDKAAKGKWTIASFGSR

LINFRNSDKNHNWDTREVYPTKELEKLLKDYSIEYGHGECIKAAICGESD

KKFFAKLTSVLNTILQMRNSKTGTELDYLISPVADVNGNFFDSRQAPKNM

-continued
PQDADANGAYHIGLKGLMLLGRIKNNQEGKKLNLVIKNEEYFEFVQNRNN

KRPAATKKAGQAKKKKGSYPYDVPDYAYPYDVPDYAYPYDVPDYA

SEQ ID NO: 17 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 17 may be encoded by the following nucleotide sequence:

(SEQ ID NO: 18)
ATGAGCATCTACCAGGAGTTCGTCAACAAGTATTC

ACTGAGTAAGACACTGCGGTTCGAGCTGATCCCAC

AGGGCAAGACACTGGAGAACATCAAGGCCCGAGGC

CTGATTCTGGACGATGAGAAGCGGGCAAAAGACTA

TAAGAAAGCCAAGCAGATCATTGATAAATACCACC

AGTTCTTTATCGAGGAAATTCTGAGCTCCGTGTGC

ATCAGTGAGGATCTGCTGCAGAATTACTCAGACGT

GTACTTCAAGCTGAAGAAGAGCGACGATGACAACC

TGCAGAAGGACTTCAAGTCCGCCAAGGACACCATC

AAGAAACAGATTAGCGAGTACATCAAGGACTCCGA

AAAGTTTAAAAATCTGTTCAACCAGAATCTGATCG

ATGCTAAGAAAGGCCAGGAGTCCGACCTGATCCTG

TGGCTGAAACAGTCTAAGGACAATGGGATTGAACT

GTTCAAGGCTAACTCCGATATCACTGATATTGACG

AGGCACTGGAAATCATCAAGAGCTTCAAGGGATGG

ACCACATACTTTAAAGGCTTCCACGAGAACCGCAA

GAACGTGTACTCCAGCAACGACATTCCTACCTCCA

TCATCTACCGAATCGTCGATGACAATCTGCCAAAG

TTCCTGGAGAACAAGGCCAAATATGAATCTCTGAA

GGACAAAGCTCCCGAGGCAATTAATTACGAACAGA

TCAAGAAAGATCTGGCTGAGGAACTGACATTCGAT

ATCGACTATAAGACTAGCGAGGTGAACCAGAGGGT

CTTTTCCCTGGACGAGGTGTTTGAAATCGCCAATT

TCAACAATTACCTGAACCAGTCCGGCATTACTAAA

TTCAATACCATCATTGGCGGGAAGTTTGTGAACGG

GGAGAATACCAAGCGCAAGGGAATTAACGAATACA

TCAATCTGTATAGCCAGCAGATCAACGACAAAACT

CTGAAGAAATACAAGATGTCTGTGCTGTTCAAACA

GATCCTGAGTGATACCGAGTCCAAGTCTTTTGTCA

TTGATAAACTGGAAGATGACTCAGACGTGGTCACT

ACCATGCAGAGCTTTTATGAGCAGATCGCCGCTTT

CAAGACAGTGGAGGAAAAATCTATTAAGGAAACTC

TGAGTCTGCTGTTCGATGACCTGAAAGCCCAGAAG

-continued

CTGGACCTGAGTAAGATCTACTTCAAAAACGATAA
GAGTCTGACAGACCTGTCACAGCAGGTGTTTGATG
ACTATTCCGTGATTGGGACCGCCGTCCTGGAGTAC
ATTACACAGCAGATCGCTCCAAAGAACCTGGATAA
TCCCTCTAAGAAAGAGCAGGAACTGATCGCTAAGA
AAACCGAGAAGGCAAAATATCTGAGTCTGGAAACA
ATTAAGCTGGCACTGGAGGAGTTCAACAAGCACAG
GGATATTGACAAACAGTGCCGCTTTGAGGAAATCC
TGGCCAACTTCGCAGCCATCCCCATGATTTTTGAT
GAGATCGCCCAGAACAAAGACAATCTGGCTCAGAT
CAGTATTAAGTACCAGAACCAGGGCAAGAAAGACC
TGCTGCAGGCTTCAGCAGAAGATGACGTGAAAGCC
ATCAAGGATCTGCTGGACCAGACCAACAATCTGCT
GCACAAGCTGAAAATCTTCCATATTAGTCAGTCAG
AGGATAAGGCTAATATCCTGGATAAAGACGAACAC
TTCTACCTGGTGTTCGAGGAATGTTACTTCGAGCT
GGCAAACATTGTCCCCCTGTATAACAAGATTAGGA
ACTACATCACACAGAAGCCTTACTCTGACGAGAAG
TTTAAACTGAACTTCGAAAATAGTACCCTGGCCAA
CGGGTGGGATAAGAACAAGGAGCCTGACAACACAG
CTATCCTGTTCATCAAGGATGACAAGTACTATCTG
GGAGTGATGAATAAGAAAAACAATAAGATCTTCGA
TGACAAAGCCATTAAGGAGAACAAAGGGGAAGGAT
ACAAGAAAATCGTGTATAAGCTGCTGCCCGGCGCA
AATAAGATGCTGCCTAAGGTGTTCTTCAGCGCCAA
GAGTATCAAATTCTACAACCCATCCGAGGACATCC
TGCGGATTAGAAATCACTCAACACATACTAAGAAC
GGGAGCCCCCAGAAGGGATATGAGAAATTTGAGTT
CAACATCGAGGATTGCAGGAAGTTTATTGACTTCT
ACAAGCAGAGCATCTCCAAACACCCTGAATGGAAG
GATTTTGGCTTCCGGTTTTCCGACACACAGAGATA
TAACTCTATCGACGAGTTCTACCGCGAGGTGGAAA
ATCAGGGGTATAAGCTGACTTTTGAGAACATTTCT
GAAAGTTACATCGACAGCGTGGTCAATCAGGGAAA
GCTGTACCTGTTCCAGATCTATAACAAAGATTTTT
CAGCATACAGCAAGGGCAGACCAAACCTGCATACA
CTGTACTGGAAGGCCCTGTTCGATGAGAGGAATCT
GCAGGACGTGGTCTATAAACTGAACGGAGAGGCCG
AACTGTTTTACCGGAAGCAGTCTATTCCTAAGAAA
ATCACTCACCCAGCTAAGGAGGCCATCGCTAACAA

-continued

GAACAAGGACAATCCTAAGAAAGAGAGCGTGTTCG
AATACGATCTGATTAAGGACAAGCGGTTCACCGAA
GATAAGTTCTTTTTCCATTGTCCAATCACCATTAA
CTTCAAGTCAAGCGGCGCTAACAAGTTCAACGACG
AGATCAATCTGCTGCTGAAGGAAAAAGCAAACGAT
GTGCACATCCTGAGCATTGACCGAGGAGAGCGGCA
TCTGGCCTACTATACCCTGGTGGATGGCAAAGGGA
ATATCATTAAGCAGGATACATTCAACATCATTGGC
AATGACCGGATGAAAACCAACTACCACGATAAACT
GGCTGCAATCGAGAAGGATAGAGACTCAGCTAGGA
AGGACTGGAAGAAAATCAACAACATTAAGGAGATG
AAGGAAGGCTATCTGAGCCAGGTGGTCCATGAGAT
TGCAAAGCTGGTCATCGAATACAATGCCATTGTGG
TGTTCGAGGATCTGAACTTCGGCTTTAAGAGGGGG
CGCTTTAAGGTGGAAAAACAGGTCTATCAGAAGCT
GGAGAAAATGCTGATCGAAAAGCTGAATTACCTGG
TGTTTAAAGATAACGAGTTCGACAAGACCGGAGGC
GTCCTGAGAGCCTACCAGCTGACAGCTCCCTTTGA
AACTTTCAAGAAAATGGGAAAACAGACAGGCATCA
TCTACTATGTGCCAGCCGGATTCACTTCCAAGATC
TGCCCCGTGACCGGCTTTGTCAACCAGCTGTACCC
TAAATATGAGTCAGTGAGCAAGTCCCAGGAATTTT
TCAGCAAGTTCGATAAGATCTGTTATAATCTGGAC
AAGGGGTACTTCGAGTTTTCCTTCGATTACAAGAA
CTTCGGCGACAAGGCCGCTAAGGGGAAATGGACCA
TTGCCTCCTTCGGATCTCGCCTGATCAACTTTCGA
AATTCCGATAAAAACCACAATTGGGACACTAGGGA
GGTGTACCCAACCAAGGAGCTGGAAAAGCTGCTGA
AAGACTACTCTATCGAGTATGGACATGGCGAATGC
ATCAAGGCAGCCATCTGTGGCGAGAGTGATAAGAA
ATTTTTCGCCAAGCTGACCTCAGTGCTGAATACAA
TCCTGCAGATGCGGAACTCAAAGACCGGGACAGAA
CTGGACTATCTGATTAGCCCCGTGGCTGATGTCAA
CGGAAACTTCTTCGACAGCAGACAGGCACCCAAAA
ATATGCCTCAGGATGCAGACGCCAACGGGCCTAC
CACATCGGGCTGAAGGGACTGATGCTGCTGGGCCG
GATCAAGAACAATCAGGAGGGGAAGAAGCTGAACC
TGGTCATTAAGAACGAGGAATACTTCGAGTTTGTC
CAGAATAGAAATAACAAAAGGCCGGCGGCCACGAA
AAAGGCCGGCCAGGCAAAAAAGAAAAAGGGATCCT
ACCCATACGATGTTCCAGATTACGCTTATCCCTAC

-continued

```
GACGTGCCTGATTATGCATACCCATATGATGTCCC
CGACTATGCCTAA
```

Peregrinibacteria bacterium GW2011
GWA 33 10 (PeCpf1; pY007),
including NLS and HA tag:

(SEQ ID NO: 19)
```
MSNFFKNFTNLYELSKTLRFELKPVGDTLTNMKDH
LEYDEKLQTFLKDQNIDDAYQALKPQFDEIHEEFI
TDSLESKKAKEIDFSEYLDLFQEKKELNDSEKKLR
NKIGETFNKAGEKWKKEKYPQYEWKKGSKIANGAD
ILSCQDMLQFIKYKNPEDEKIKNYIDDTLKGFFTY
FGGFNQNRANYYETKKEASTAVATRIVHENLPKFC
DNVIQFKHIIKRKKDGTVEKTERKTEYLNAYQYLK
NNNKITQIKDAETEKMIESTPIAEKIFDVYYFSSC
LSQKQIEEYNRIIGHYNLLINLYNQAKRSEGKHLS
ANEKKYKDLPKFKTLYKQIGCGKKKDLFYTIKCDT
EEEANKSRNEGKESHSVEEIINKAQEAINKYFKSN
NDCENINTVPDFINYILTKENYEGVYWSKAAMNTI
SDKYFANYHDLQDRLKEAKVFQKADKKSEDDIKIP
EAIELSGLFGVLDSLADWQTTLFKSSILSNEDKLK
IITDSQTPSEALLKMIFNDIEKNMESFLKETNDII
TLKKYKGNKEGTEKIKQWFDYTLAINRMLKYFLVK
ENKIKGNSLDTNISEALKTLIYSDDAEWFKWYDAL
RNYLTQKPQDEAKENKLKLNFDNPSLAGGWDVNKE
CSNFCVILKDKNEKKYLAIMKKGENTLFQKEWTEG
RGKNLTKKSNPLFEINNCEILSKMEYDFWADVSKM
IPKCSTQLKAVVNHFKQSDNEFIFPIGYKVTSGEK
FREECKISKQDFELNNKVFNKNELSVTAMRYDLSS
TQEKQYIKAFQKEYWELLFKQEKRDTKLTNNEIFN
EWINFCNKKYSELLSWERKYKDALTNWINFCKYFL
SKYPKTTLFNYSFKESENYNSLDEFYRDVDICSYK
LNINTTINKSILDRLVEEGKLYLFEIKNQDSNDGK
SIGHKNNLHTIYWNAIFENFDNRPKLNGEAEIFYR
KAISKDKLGIVKGKKTKNGTEIIKNYRFSKEKFIL
HVPITLNFCSNNEYVNDIVNTKFYNFSNLHFLGID
RGEKHLAYYSLVNKNGEIVDQGTLNLPFTDKDGNQ
RSIKKEKYFYNKQEDKWEAKEVDCWNYNDLLDAMA
SNRDMARKNWQRIGTIKEAKNGYVSLVIRKIADLA
VNNERPAFIVLEDLNTGFKRSRQKIDKSVYQKFEL
ALAKKLNFLVDKNAKRDEIGSPTKALQLTPPVNNY
GDIENKKQAGIMLYTRANYTSQTDPATGWRKTIYL
KAGPEETTYKKDGKIKNKSVKDQIIETFTDIGFDG
KDYYFEYDKGEFVDEKTGEIKPKKWRLYSGENGKS
LDRFRGEREKDKYEWKIDKIDIVKILDDLFVNFDK
NISLLKQLKEGVELTRNNEHGTGESLRFAINLIQQ
IRNTGNNERDNDFILSPVRDENGKHFDSREYWDKE
TKGEKISMPSSGDANGAFNIARKGIIMNAHILANS
DSKDLSLFVSDEEWDLHLNNKTEWKKQLNIFSSRK
AMAKRKKKRPAATKKAGQAKKKKGSYPYDVPDYAY
PYDVPDYAYPYDVPDYA
```

Peregrinibacteria bacterium GW2011_GWA_33_10 (PeCpf1; pY007), including NLS and HA tag:

(SEQ ID NO: 19)
```
MSNFFKNFTNLYELSKTLRFELKPVGDTLTNMKDHLEYDEKLQTFLKDQN
IDDAYQALKPQFDEIHEEFITDSLESKKAKEIDFSEYLDLFQEKKELNDS
EKKLRNKIGETFNKAGEKWKKEKYPQYEWKKGSKIANGADILSCQDMLQF
IKYKNPEDEKIKNYIDDTLKGFFTYFGGFNQNRANYYETKKEASTAVATR
IVHENLPKFCDNVIQFKHIIKRKKDGTVEKTERKTEYLNAYQYLKNNNKI
TQIKDAETEKMIESTPIAEKIFDVYYFSSCLSQKQIEEYNRIIGHYNLLI
NLYNQAKRSEGKHLSANEKKYKDLPKFKTLYKQIGCGKKKDLFYTIKCDT
EEEANKSRNEGKESHSVEEIINKAQEAINKYFKSNNDCENINTVPDFINY
ILTKENYEGVYWSKAAMNTISDKYFANYHDLQDRLKEAKVFQKADKKSED
DIKIPEAIELSGLFGVLDSLADWQTTLFKSSILSNEDKLKIITDSQTPSE
ALLKMIFNDIEKNMESFLKETNDIITLKKYKGNKEGTEKIKQWFDYTLAI
NRMLKYFLVKENKIKGNSLDTNISEALKTLIYSDDAEWFKWYDALRNYLT
QKPQDEAKENKLKLNFDNPSLAGGWDVNKECSNFCVILKDKNEKKYLAIM
KKGENTLFQKEWTEGRGKNLTKKSNPLFEINNCEILSKMEYDFWADVSKM
IPKCSTQLKAVVNHFKQSDNEFIFPIGYKVTSGEKFREECKISKQDFELN
NKVFNKNELSVTAMRYDLSSTQEKQYIKAFQKEYWELLFKQEKRDTKLTN
NEIFNEWINFCNKKYSELLSWERKYKDALTNWINFCKYFLSKYPKTTLFN
YSFKESENYNSLDEFYRDVDICSYKLNINTTINKSILDRLVEEGKLYLFE
IKNQDSNDGKSIGHKNNLHTIYWNAIFENFDNRPKLNGEAEIFYRKAISK
DKLGIVKGKKTKNGTEIIKNYRFSKEKFILHVPITLNFCSNNEYVNDIVN
TKFYNFSNLHFLGIDRGEKHLAYYSLVNKNGEIVDQGTLNLPFTDKDGNQ
RSIKKEKYFYNKQEDKWEAKEVDCWNYNDLLDAMASNRDMARKNWQRIGT
IKEAKNGYVSLVIRKIADLAVNNERPAFIVLEDLNTGFKRSRQKIDKSVY
QKFELALAKKLNFLVDKNAKRDEIGSPTKALQLTPPVNNYGDIENKKQAG
IMLYTRANYTSQTDPATGWRKTIYLKAGPEETTYKKDGKIKNKSVKDQII
ETFTDIGFDGKDYYFEYDKGEFVDEKTGEIKPKKWRLYSGENGKSLDRFR
GEREKDKYEWKIDKIDIVKILDDLFVNFDKNISLLKQLKEGVELTRNNEH
GTGESLRFAINLIQQIRNTGNNERDNDFILSPVRDENGKHFDSREYWDKE
TKGEKISMPSSGDANGAFNIARKGIIMNAHILANSDSKDLSLFVSDEEWD
```

LHLNNKTEWKKQLNIFSSRKAMAKRKKKRPAATKKAGQAKKKKGSYPYDV

PDYAYPYDVPDYAYPYDVPDYA

SEQ ID NO: 19 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 19 may be encoded by the following nucleotide sequence:

(SEQ ID NO: 20)
ATGTCCAACTTCTTTAAGAATTTCACCAACCTGTATGAGCTGTCCAAGAC

ACTGAGGTTTGAGCTGAAGCCCGTGGGCGACACCCTGACAAACATGAAGG

ACCACCTGGAGTACGATGAGAAGCTGCAGACCTTCCTGAAGGATCAGAAT

ATCGACGATGCCTATCAGGCCCTGAAGCCTCAGTTCGACGAGATCCACGA

GGAGTTTATCACAGATTCTCTGGAGAGCAAGAAGGCCAAGGAGATCGACT

TCTCCGAGTACCTGGATCTGTTTCAGGAGAAGAAGGAGCTGAACGACTCT

GAGAAGAAGCTGCGCAACAAGATCGGCGAGACATTCAACAAGGCCGGCGA

GAAGTGGAAGAAGGAGAAGTACCCTCAGTATGAGTGGAAGAAGGGCTCCA

AGATCGCCAATGGCGCCGACATCCTGTCTTGCCAGGATATGCTGCAGTTT

ATCAAGTATAAGAACCCAGAGGATGAGAAGATCAAGAATTACATCGACGA

TACACTGAAGGGCTTCTTTACCTATTTCGGCGGCTTTAATCAGAACAGGG

CCAACTACTATGAGACAAAGAAGGAGGCCTCCACCGCAGTGGCAACAAGG

ATCGTGCACGAGAACCTGCCAAAGTTCTGTGACAATGTGATCCAGTTTAA

GCACATCATCAAGCGGAAGAAGGATGGCACCGTGGAGAAAACCGAGAGAA

AGACCGAGTACCTGAACGCCTACCAGTATCTGAAGAACAATAACAAGATC

ACACAGATCAAGGACGCCGAGACAGAGAAGATGATCGAGTCTACACCCAT

CGCCGAGAAGATCTTCGACGTGTACTACTTCAGCAGCTGCCTGAGCCAGA

AGCAGATCGAGGAGTACAACCGGATCATCGGCCACTATAATCTGCTGATC

AACCTGTATAACCAGGCCAAGAGATCTGAGGGCAAGCACCTGAGCGCCAA

CGAGAAGAAGTATAAGGACCTGCCTAAGTTCAAGACCCTGTATAAGCAGA

TCGGCTGCGGCAAGAAGAAGGACCTGTTTTACACAATCAAGTGTGATACC

GAGGAGGAGGCCAATAAGTCCCGGAACGAGGGCAAGGAGTCCCACTCTGT

GGAGGAGATCATCAACAAGGCCCAGGAGGCCATCAATAAGTACTTCAAGT

CTAATAACGACTGTGAGAATATCAACACCGTGCCCGACTTCATCAACTAT

ATCCTGACAAAGGAGAATTACGAGGGCGTGTATTGGAGCAAGGCCGCCAT

GAACACCATCTCCGACAAGTACTTCGCCAATTATCACGACCTGCAGGATA

GACTGAAGGAGGCCAAGGTGTTTCAGAAGGCCGATAAGAAGTCCGAGGAC

GATATCAAGATCCCAGAGGCCATCGAGCTGTCTGGCCTGTTCGGCGTGCT

GGACAGCCTGGCCGATTGGCAGACCACACTGTTTAAGTCTAGCATCCTGA

GCAACGAGGACAAGCTGAAGATCATCACAGATTCCCAGACCCCCTCTGAG

GCCCTGCTGAAGATGATCTTCAATGACATCGAGAAGAACATGGAGTCCTT

TCTGAAGGAGACAAACGATATCATCACCCTGAAGAAGTATAAGGGCAATA

AGGAGGGCACCGAGAAGATCAAGCAGTGGTTCGACTATACACTGGCCATC

AACCGGATGCTGAAGTACTTTCTGGTGAAGGAGAATAAGATCAAGGGCAA

CTCCCTGGATACCAATATCTCTGAGGCCCTGAAAACCCTGATCTACAGCG

ACGATGCCGAGTGGTTCAAGTGGTACGACGCCCTGAGAAACTATCTGACC

CAGAAGCCTCAGGATGAGGCCAAGGAGAATAAGCTGAAGCTGAATTTCGA

CAACCCATCTCTGGCCGGCGGCTGGGATGTGAACAAGGAGTGCAGCAATT

TTTGCGTGATCCTGAAGGACAAGAACGAGAAGAAGTACCTGGCCATCATG

AAGAAGGGCGAGAATACCCTGTTCCAGAAGGAGTGGACAGAGGGCCGGGG

CAAGAACCTGACAAAGAAGTCTAATCCACTGTTCGAGATCAATAACTGCG

AGATCCTGAGCAAGATGGAGTATGACTTTTGGGCCGACGTGAGCAAGATG

ATCCCCAAGTGTAGCACCCAGCTGAAGGCCGTGGTGAACCACTTCAAGCA

GTCCGACAATGAGTTCATCTTTCCTATCGGCTACAAGGTGACAAGCGGCG

AGAAGTTTAGGGAGGAGTGCAAGATCTCCAAGCAGGACTTCGAGCTGAAT

AACAAGGTGTTTAATAAGAACGAGCTGAGCGTGACCGCCATGCGCTACGA

TCTGTCCTCTACACAGGAGAAGCAGTATATCAAGGCCTTCCAGAAGGAGT

ACTGGGAGCTGCTGTTTAAGCAGGAGAAGCGGGACACCAAGCTGACAAAT

AACGAGATCTTCAACGAGTGGATCAATTTTTGCAACAAGAAGTATAGCGA

GCTGCTGTCCTGGGAGAGAAAGTACAAGGATGCCCTGACCAATTGGATCA

ACTTCTGTAAGTACTTTCTGAGCAAGTATCCCAAGACCACACTGTTCAAC

TACTCTTTTAAGGAGAGCGAGAATTATAACTCCCTGGACGAGTTCTACCG

GGACGTGGATATCTGTTCTTACAAGCTGAATATCAACACCACAATCAATA

AGAGCATCCTGGATAGACTGGTGGAGGAGGGCAAGCTGTACCTGTTTGAG

ATCAAGAATCAGGACAGCAACGATGGCAAGTCCATCGGCCACAAGAATAA

CCTGCACACCATCTACTGGAACGCCATCTTCGAGAATTTTGACAACAGGC

CTAAGCTGAATGGCGAGGCCGAGATCTTCTATCGCAAGGCCATCTCCAAG

GATAAGCTGGGCATCGTGAAGGGCAAGAAAACCAAGAACGGCACCGAGAT

CATCAAGAATTACAGATTCAGCAAGGAGAAGTTTATCCTGCACGTGCCAA

TCACCCTGAACTTCTGCTCCAATAACGAGTATGTGAATGACATCGTGAAC

ACAAAGTTCTACAATTTTTCCAACCTGCACTTTCTGGGCATCGATAGGGG

CGAGAAGCACCTGGCCTACTATTCTCTGGTGAATAAGAACGGCGAGATCG

TGGACCAGGGCACACTGAACCTGCCTTTCACCGACAAGGATGGCAATCAG

CGCAGCATCAAGAAGGAGAAGTACTTTTATAACAAGCAGGAGGACAAGTG

GGAGGCCAAGGAGGTGGATTGTTGGAATTATAACGACCTGCTGGATGCCA

TGGCCTCTAACCGGGACATGGCCAGAAAGAATTGGCAGAGGATCGGCACC

ATCAAGGAGGCCAAGAACGGCTACGTGAGCCTGGTCATCAGGAAGATCGC

CGATCTGGCCGTGAATAACGAGCGCCCCGCCTTCATCGTGCTGGAGGACC

TGAATACAGGCTTTAAGCGGTCCAGACAGAAGATCGATAAGAGCGTGTAC

CAGAAGTTCGAGCTGGCCCTGGCCAAGAAGCTGAACTTTCTGGTGGACAA

GAATGCCAAGCGCGATGAGATCGGCTCCCCTACAAAGGCCCTGCAGCTGA

CCCCCCCTGTGAATAACTACGGCGACATTGAGAACAAGAAGCAGGCCGGC

ATCATGCTGTATACCCGGGCCAATTATACCTCTCAGACAGATCCAGCCAC

```
AGGCTGGAGAAAGACCATCTATCTGAAGGCCGGCCCCGAGGAGACAACAT
ACAAGAAGGACGGCAAGATCAAGAACAAGAGCGTGAAGGACCAGATCATC
GAGACATTCACCGATATCGGCTTTGACGGCAAGGATTACTATTTCGAGTA
CGACAAGGGCGAGTTTGTGGATGAGAAAACCGGCGAGATCAAGCCCAAGA
AGTGGCGGCTGTACTCCGGCGAGAATGGCAAGTCCCTGGACAGGTTCCGC
GGGAGAGAGGGAGAAGGATAAGTATGAGTGGAAGATCGACAAGATCGATAT
CGTGAAGATCCTGGACGATCTGTTCGTGAATTTTGACAAGAACATCAGCC
TGCTGAAGCAGCTGAAGGAGGGCGTGGAGCTGACCCGGAATAACGAGCAC
GGCACAGGCGAGTCCCTGAGATTCGCCATCAACCTGATCCAGCAGATCCG
GAATACCGGCAATAACGAGAGAGACAACGATTTCATCCTGTCCCCAGTGA
GGGACGAGAATGGCAAGCACTTTGACTCTCGCGAGTACTGGGATAAGGAG
ACAAAGGGCGAGAAGATCAGCATGCCCAGCTCCGGCGATGCCAATGGCGC
CTTCAACATCGCCCGGAAGGGCATCATCATGAACGCCCACATCCTGGCCA
ATAGCGACTCCAAGGATCTGTCCCTGTTCGTGTCTGACGAGGAGTGGGAT
CTGCACCTGAATAACAAGACCGAGTGGAAGAAGCAGCTGAACATCTTTTC
TAGCAGGAAGGCCATGGCCAAGCGCAAGAAGAAAAGGCCGGCGGCCACGA
AAAAGGCCGGCCAGGCAAAAAAGAAAAAGGGATCCTACCCATACGATGTT
CCAGATTACGCTTATCCCTACGACGTGCCTGATTATGCATACCCATATGA
TGTCCCCGACTATGCCTAA
```

*Parcubacteria bacterium* GWC2011_GWC2_44_17 (PbCpf1; pY008), including NLS and HA tag:

(SEQ ID NO: 21)
MENIFDQFIGKYSLSKTLRFELKPVGKTEDFLKINKVFEKDQTIDDSYNQ
AKFYFDSLHQKFIDAALASDKTSELSFQNFADVLEKQNKIILDKKREMGA
LRKRDKNAVGIDRLQKEINDAEDIIQKEKEKIYKDVRTLFDNEAESWKTY
YQEREVDGKKITFSKADLKQKGADFLTAAGILKVLKYEFPEEKEKEFQAK
NQPSLFVEEKENPGQKRYIFDSFDKFAGYLTKFQQTKKNLYAADGTSTAV
ATRIADNFIIFHQNTKVFRDKYKNNHTDLGFDEENIFEIERYKNCLLQRE
IEHIKNENSYNKIIGRINKKIKEYRDQKAKDTKLTKSDFPFFKNLDKQIL
GEVEKEKQLIEKTREKTEEDVLIERFKEFIENNEERFTAAKKLMNAFCNG
EFESEYEGIYLKNKAINTISRRWFVSDRDFELKLPQQKSKNKSEKNEPKV
KKFISIAEIKNAVEELDGDIFKAVFYDKKIIAQGGSKLEQFLVIWKYEFE
YLFRDIERENGEKLLGYDSCLKIAKQLGIFPQEKEAREKATAVIKNYADA
GLGIFQMMKYFSLDDKDRKNTPGQLSTNFYAEYDGYYKDFEFIKYYNEFR
NFITKKPFDEDKIKLNFENGALLKGWDENKEYDFMGVILKKEGRLYLGIM
HKNHRKLFQSMGNAKGDNANRYQKMIYKQIADASKDVPRLLLTSKKAMEK
FKPSQEILRIKKEKTFKRESKNFSLRDLHALIEYYRNCIPQYSNWSFYDF
QFQDTGKYQNIKEFTDDVQKYGYKISFRDIDDEYINQALNEGKMYLFEVV
NKDIYNTKNGSKNLHTLYFEHILSAENLNDPVFKLSGMAEIFQRQPSVNE
REKITTQKNQCILDKGDRAYKYRRYTEKKIMFHMSLVLNTGKGEIKQVQF
NKIIINQRISSSDNEMRVNVIGIDRGEKNLLYYSVVKQNGEIIEQASLNEI
NGVNYRDKLIEREKERLKNRQSWKPVVKIDLKKGYISHVIHKICQLIEK
YSAIVVLEDLNMRFKQIRGGIERSVYQQFEKALIDKLGYLVFKDNRDLRA
PGGVLNGYQLSAPFVSFEKMRKQTGILFYTQAEYTSKTDPITGFRKNVYI
SNSASLDKIKEAVKKFDAIGWDGKEQSYFFKYNPYNLADEKYKNSTVSKE
WAIFASAPRIRRQKGEDGYWKYDRVKVNEEFEKLLKVWNFVNPKATDIKQ
EIIKKEKAGDLQGEKELDGRLRNFWHSFIYLFNLVLELRNSFSLQIKIKA
GEVIAVDEGVDFIASPVKPFFTTPNPYIPSNLCWLAVENADANGAYNIAR
KGVMILKKIREHAKKDPEFKKLPNLFISNAEWDEAARDWGKYAGTTALNL
DHKRPAATKKAGQAKKKKGSYPYDVPDYAYPYDVPDYAYPYDVPDYA

SEQ ID NO: 21 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 21 may be encoded by the following nucleotide sequence:

(SEQ ID NO: 22)
ATGGAGAACATCTTCGACCAGTTTATCGGCAAGTACAGCCTGTCCAAGAC

CCTGAGATTCGAGCTGAAGCCCGTGGGCAAGACAGAGGACTTCCTGAAGA

TCAACAAGGTGTTTGAGAAGGATCAGACCATCGACGATAGCTACAATCAG

GCCAAGTTCTATTTTGATTCCCTGCACCAGAAGTTTATCGACGCCGCCCT

GGCCTCCGATAAGACATCCGAGCTGTCTTTCCAGAACTTTGCCGACGTGC

TGGAGAAGCAGAATAAGATCATCCTGGATAAGAAGAGAGAGATGGGCGCC

CTGAGGAAGCGCGACAAGAACGCCGTGGGCATCGATAGGCTGCAGAAGGA

GATCAATGACGCCGAGGATATCATCCAGAAGGAGAAGGAGAAGATCTACA

AGGACGTGCGCACCCTGTTCGATAACGAGGCCGAGTCTTGGAAAACCTAC

TATCAGGAGCGGGAGGTGGACGGCAAGAAGATCACCTTCAGCAAGGCCGA

CCTGAAGCAGAAGGGCGCCGATTTTCTGACAGCCGCCGGCATCCTGAAGG

TGCTGAAGTATGAGTTCCCCGAGGAGAAGGAGAAGGAGTTTCAGGCCAAG

AACCAGCCCTCCCTGTTCGTGGAGGAGAAGGAGAATCCTGGCCAGAAGAG

GTACATCTTCGACTCTTTTGATAAGTTCGCCGGCTATCTGACCAAGTTTC

AGCAGACAAAGAAGAATCTGTACGCAGCAGACGGCACCAGCACAGCAGTG

GCCACCCGCATCGCCGATAACTTTATCATCTTCCACCAGAATACCAAGGT

GTTCCGGGACAAGTACAAGAACAATCACACAGACCTGGGCTTCGATGAGG

AGAACATCTTTGAGATCGAGAGGTATAAGAATTGCCTGCTGCAGCGCGAG

ATCGAGCACATCAAGAATGAGAATAGCTACAACAAGATCATCGGCCGGAT

CAATAAGAAGATCAAGGAGTATCGGGACCAGAAGGCCAAGGATACCAAGC

TGACAAAGTCCGACTTCCCTTTCTTTAAGAACCTGGATAAGCAGATCCTG

GGCGAGGTGGAGAAGGAGAAGCAGCTGATCGAGAAAACCCGGGAGAAAAC

CGAGGAGGACGTGCTGATCGAGCGGTTCAAGGAGTTCATCGAGAACAATG

AGGAGAGGTTCACCGCCGCCAAGAAGCTGATGAATGCCTTCTGTAACGGC

GAGTTTGAGTCCGAGTACGAGGGCATCTATCTGAAGAATAAGGCCATCAA

CACAATCTCCCGGAGATGGTTCGTGTCTGACAGAGATTTTGAGCTGAAGC

TGCCTCAGCAGAAGTCCAAGAACAAGTCTGAGAAGAATGAGCCAAAGGTG

AAGAAGTTCATCTCCATCGCCGAGATCAAGAACGCCGTGGAGGAGCTGGA

CGGCGATATCTTTAAGGCCGTGTTCTACGACAAGAAGATCATCGCCCAGG

GCGGCTCTAAGCTGGAGCAGTTCCTGGTCATCTGGAAGTACGAGTTTGAG

TATCTGTTCCGGGACATCGAGAGAGAGAACGGCGAGAAGCTGCTGGGCTA

TGATAGCTGCCTGAAGATCGCCAAGCAGCTGGGCATCTTCCCACAGGAGA

AGGAGGCCCGCGAGAAGGCAACCGCCGTGATCAAGAATTACGCCGACGCC

GGCCTGGGCATCTTCCAGATGATGAAGTATTTTTCTCTGGACGATAAGGA

TCGGAAGAACACCCCCGGCCAGCTGAGCACAAATTTCTACGCCGAGTATG

ACGGCTACTACAAGGATTTCGAGTTTATCAAGTACTACAACGAGTTTAGG

AACTTCATCACCAAGAAGCCTTTCGACGAGGATAAGATCAAGCTGAACTT

TGAGAATGGCGCCCTGCTGAAGGGCTGGGACGAGAACAAGGAGTACGATT

TCATGGGCGTGATCCTGAAGAAGGAGGGCCGCCTGTATCTGGGCATCATG

CACAAGAACCACCGGAAGCTGTTTCAGTCCATGGGCAATGCCAAGGGCGA

CAACGCCAATAGATACCAGAAGATGATCTATAAGCAGATCGCCGACGCCT

CTAAGGATGTGCCCAGGCTGCTGCTGACCAGCAAGAAGGCCATGGAGAAG

TTCAAGCCTTCCCAGGAGATCCTGAGAATCAAGAAGGAGAAAACCTTCAA

GCGGGAGAGCAAGAACTTTTCCCTGAGAGATCTGCACGCCCTGATCGAGT

ACTATAGGAACTGCATCCCTCAGTACAGCAATTGGTCCTTTTATGACTTC

CAGTTTCAGGATACCGGCAAGTACCAGAATATCAAGGAGTTCACAGACGA

TGTGCAGAAGTACGGCTATAAGATCTCCTTTCGCGACATCGACGATGAGT

ATATCAATCAGGCCCTGAACGAGGGCAAGATGTACCTGTTCGAGGTGGTG

AACAAGGATATCTATAACACCAAGAATGGCTCCAAGAATCTGCACACACT

GTACTTTGAGCACATCCTGTCTGCCGAGAACCTGAATGACCCAGTGTTCA

AGCTGTCTGGCATGGCCGAGATCTTTCAGCGGCAGCCCAGCGTGAACGAA

AGAGAGAAGATCACCACACAGAAGAATCAGTGTATCCTGGACAAGGGCGA

TAGAGCCTACAAGTATAGGCGCTACACCGAGAAGAAGATCATGTTCCACA

TGAGCCTGGTGCTGAACACAGGCAAGGGCGAGATCAAGCAGGTGCAGTTT

AATAAGATCATCAACCAGAGGATCAGCTCCTCTGACAACGAGATGAGGGT

GAATGTGATCGGCATCGATCGCGGCGAGAAGAACCTGCTGTACTATAGCG

TGGTGAAGCAGAATGGCGAGATCATCGAGCAGGCCTCCCTGAACGAGATC

AATGGCGTGAACTACCGGGACAAGCTGATCGAGAGGGAGAAGGAGCGCCT

GAAGAACCGGCAGAGCTGGAAGCCTGTGGTGAAGATCAAGGATCTGAAGA

AGGGCTACATCTCCCACGTGATCCACAAGATCTGCCAGCTGATCGAGAAG

TATTCTGCCATCGTGGTGCTGGAGGACCTGAATATGAGATTCAAGCAGAT

CAGGGGAGGAATCGAGCGGAGCGTGTACCAGCAGTTCGAGAAGGCCCTGA

TCGATAAGCTGGGCTATCTGGTGTTTAAGGACAACAGGGATCTGAGGGCA

CCAGGAGGCGTGCTGAATGGCTACCAGCTGTCTGCCCCCTTTGTGAGCTT

CGAGAAGATGCGCAAGCAGACCGGCATCCTGTTCTACACACAGGCCGAGT

ATACCAGCAAGACAGACCCAATCACCGGCTTCGGAAGAACGTGTATATC

TCTAATAGCGCCTCCCTGGATAAGATCAAGGAGGCCGTGAAGAAGTTCGA

CGCCATCGGCTGGGATGGCAAGGAGCAGTCTTACTTCTTTAAGTACAACC

CTTACAACCTGGCCGACGAGAAGTATAAGAACTCTACCGTGAGCAAGGAG

TGGGCCATCTTTGCCAGCGCCCCAAGAATCCGGAGACAGAAGGGCGAGGA

CGGCTACTGGAAGTATGATAGGGTGAAAGTGAATGAGGAGTTCGAGAAGC

TGCTGAAGGTCTGGAATTTTGTGAACCCAAAGGCCACAGATATCAAGCAG

GAGATCATCAAGAAGGAGAAGGCAGGCGACCTGCAGGGAGAGAAGGAGCT

GGATGCCGGCTGAGAAACTTTTGGCACTCTTTCATCTACCTGTTTAACC

TGGTGCTGGAGCTGCGCAATTCTTTCAGCCTGCAGATCAAGATCAAGGCA

GGAGAAGTGATCGCAGTGGACGAGGGCGTGGACTTCATCGCCAGCCCAGT

GAAGCCCTTCTTTACCACACCCAACCCTTACATCCCCTCCAACCTGTGCT

```
GGCTGGCCGTGGAGAATGCAGACGCAAACGGAGCCTATAATATCGCCAGG

AAGGGCGTGATGATCCTGAAGAAGATCCGCGAGCACGCCAAGAAGGACCC

CGAGTTCAAGAAGCTGCCAAACCTGTTTATCAGCAATGCAGAGTGGGACG

AGGCAGCCCGGGATTGGGGCAAGTACGCAGGCACCACAGCCCTGAACCTG

GACCACAAAAGGCCGGCGGCCACGAAAAAGGCCGGCCAGGCAAAAAAGAA

AAAGGGATCCTACCCATACGATGTTCCAGATTACGCTTATCCCTACGACG

TGCCTGATTATGCATACCCATATGATGTCCCCGACTATGCCTAA
```

Smithella sp. SC_K08D17 (SsCpf1; pY009),
including NLS and HA tag:

(SEQ ID NO: 23)

```
MQTLFENFTNQYPVSKTLRFELIPQGKTKDFIEQKGLLKKDEDRAEKYKK
VKNIIDEYHKDFIEKSLNGLKLDGLEKYKTLYLKQEKDDKDKKAFDKEKE
NLRKQIANAFRNNEKFKTLFAKELIKNDLMSFACEEDKKNVKEFEAFTTY
FTGFHQNRANMYVADEKRTAIASRLIHENLPKFIDNIKIFEKMKKEAPEL
LSPFNQTLKDMKDVIKGTTLEEIFSLDYFNKTLTQSGIDIYNSVIGGRTP
EEGKTKIKGLNEYINTDFNQKQTDKKKRQPKFKQLYKQILSDRQSLSFIA
EAFKNDTEILEAIEKFYVNELLHFSNEGKSTNVLDAIKNAVSNLESFNLT
KMYFRSGASLTDVSRKVFGEWSIINRALDNYYATTYPIKPREKSEKYEER
KEKWLKQDFNVSLIQTAIDEYDNETVKGKNSGKVIADYFAKFCDDKETDL
IQKVNEGYIAVKDLLNTPCPENEKLGSNKDQVKQIKAFMDSIMDIMHFVR
PLSLKDTDKEKDETFYSLFTPLYDHLTQTIALYNKVRNYLTQKPYSTEKI
KLNFENSTLLGGWDLNKETDNTAIILRKDNLYYLGIMDKRHNRIFRNVPK
ADKKDFCYEKMVYKLLPGANKMLPKVFFSQSRIQEFTPSAKLLENYANET
HKKGDNFNLNHCHKLIDFFKDSINKHEDWKNFDFRFSATSTYADLSGFYH
EVEHQGYKISFQSVADSFIDDLVNEGKLYLFQIYNKDFSPFSKGKPNLHT
LYWKMLFDENNLKDVVYKLNGEAEVFYRKKSIAEKNTTIHKANESIINKN
PDNPKATSTFNYDIVKDKRYTIDKFQFHIPITMNFKAEGIFNMNQRVNQF
LKANPDINIIGIDRGERHLLYYALINQKGKILKQDTLNVIANEKQKVDYH
NLLDKKEGDRATARQEWGVIETIKELKEGYLSQVIHKLTDLMIENNAIIV
MEDLNFGFKRGRQKVEKQVYQKFEKMLIDKLNYLVDKNKKANELGGLLNA
FQLANKFESFQKMGKQNGFIFYVPAWNTSKTDPATGFIDFLKPRYENLNQ
AKDFFEKFDSIRLNSKADYFEFAFDFKNFTEKADGGRTKWTVCTTNEDRY
AWNRALNNNRGSQEKYDITAELKSLFDGKVDYKSGKDLKQQIASQESADF
FKALMKNLSITLSRHNNGEKGDNEQDYILSPVADSKGRFFDSRKADDDM
PKNADANGAYHIALKGLWCLEQISKTDDLKKVKLAISNKEWLEFVQTLKG
KRPAATKKAGQAKKKKGSYPYDVPDYAYPYDVPDYAYPYDVPDYA
```

Smithella sp. SC_K08D17 (SsCpf1; pY009), including NLS and HA tag:

(SEQ ID NO: 23)

```
MQTLFENFTNQYPVSKTLRFELIPQGKTKDFIEQKGLLKKDEDRAEKYKK
VKNIIDEYHKDFIEKSLNGLKLDGLEKYKTLYLKQEKDDKDKKAFDKEKE
NLRKQIANAFRNNEKFKTLFAKELIKNDLMSFACEEDKKNVKEFEAFTTY
FTGFHQNRANMYVADEKRTAIASRLIHENLPKFIDNIKIFEKMKKEAPEL
LSPFNQTLKDMKDVIKGTTLEEIFSLDYFNKTLTQSGIDIYNSVIGGRTP
EEGKTKIKGLNEYINTDFNQKQTDKKKRQPKFKQLYKQILSDRQSLSFIA
EAFKNDTEILEAIEKFYVNELLHFSNEGKSTNVLDAIKNAVSNLESFNLT
KMYFRSGASLTDVSRKVFGEWSIINRALDNYYATTYPIKPREKSEKYEER
KEKWLKQDFNVSLIQTAIDEYDNETVKGKNSGKVIADYFAKFCDDKETDL
IQKVNEGYIAVKDLLNTPCPENEKLGSNKDQVKQIKAFMDSIMDIMHFVR
PLSLKDTDKEKDETFYSLFTPLYDHLTQTIALYNKVRNYLTQKPYSTEKI
KLNFENSTLLGGWDLNKETDNTAIILRKDNLYYLGIMDKRHNRIFRNVPK
ADKKDFCYEKMVYKLLPGANKMLPKVFFSQSRIQEFTPSAKLLENYANET
HKKGDNFNLNHCHKLIDFFKDSINKHEDWKNFDFRFSATSTYADLSGFYH
EVEHQGYKISFQSVADSFIDDLVNEGKLYLFQIYNKDFSPFSKGKPNLHT
LYWKMLFDENNLKDVVYKLNGEAEVFYRKKSIAEKNTTIHKANESIINKN
PDNPKATSTFNYDIVKDKRYTIDKFQFHIPITMNFKAEGIFNMNQRVNQF
LKANPDINIIGIDRGERHLLYYALINQKGKILKQDTLNVIANEKQKVDYH
NLLDKKEGDRATARQEWGVIETIKELKEGYLSQVIHKLTDLMIENNAIIV
MEDLNFGFKRGRQKVEKQVYQKFEKMLIDKLNYLVDKNKKANELGGLLNA
FQLANKFESFQKMGKQNGFIFYVPAWNTSKTDPATGFIDFLKPRYENLNQ
AKDFFEKFDSIRLNSKADYFEFAFDFKNFTEKADGGRTKWTVCTTNEDRY
AWNRALNNNRGSQEKYDITAELKSLFDGKVDYKSGKDLKQQIASQESADF
FKALMKNLSITLSRHNNGEKGDNEQDYILSPVADSKGRFFDSRKADDDM
PKNADANGAYHIALKGLWCLEQISKTDDLKKVKLAISNKEWLEFVQTLKG
KRPAATKKAGQAKKKKGSYPYDVPDYAYPYDVPDYAYPYDVPDYA
```

SEQ ID NO: 23 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 23 may be encoded by the following nucleotide sequence:

(SEQ ID NO: 24)

```
ATGCAGACCCTGTTTGAGAACTTCACAAATCAGTACCCAGTGTCCAAGAC
CCTGCGCTTTGAGCTGATCCCCCAGGGCAAGACAAAGGACTTCATCGAGC
AGAAGGGCCTGCTGAAGAAGGATGAGGACCGGGCCGAGAAGTATAAGAAG
GTGAAGAACATCATCGATGAGTACCACAAGGACTTCATCGAGAAGTCTCT
GAATGGCCTGAAGCTGGACGGCCTGGAGAAGTACAAGACCCTGTATCTGA
AGCAGGAGAAGGACGATAAGGATAAGAAGGCCTTTGACAAGGAGAAGGAG
AACCTGCGCAAGCAGATCGCCAATGCCTTCCGGAACAATGAGAAGTTTAA
GACACTGTTCGCCAAGGAGCTGATCAAGAACGATCTGATGTCTTTCGCCT
GCGAGGAGGACAAGAAGAATGTGAAGGAGTTTGAGGCCTTCACCACATAC
TTCACCGGCTTCCACCAGAACCGCGCCAATATGTACGTGGCCGATGAGAA
GAGAACAGCCATCGCCAGCAGGCTGATCCACGAGAACCTGCCAAAGTTTA
TCGACAATATCAAGATCTTCGAGAAGATGAAGAAGGAGGCCCCCGAGCTG
```

-continued

CTGTCTCCTTTCAACCAGACCCTGAAGGATATGAAGGACGTGATCAAGGG
CACCACACTGGAGGAGATCTTTAGCCTGGATTATTTCAACAAGACCCTGA
CACAGAGCGGCATCGACATCTACAATTCCGTGATCGGCGGCAGAACCCCT
GAGGAGGGCAAGACAAAGATCAAGGGCCTGAACGAGTACATCAATACCGA
CTTCAACCAGAAGCAGACAGACAAGAAGAAGCGGCAGCCAAAGTTCAAGC
AGCTGTATAAGCAGATCCTGAGCGATAGGCAGAGCCTGTCCTTTATCGCC
GAGGCCTTCAAGAACGACACCGAGATCCTGGAGGCCATCGAGAAGTTTTA
CGTGAATGAGCTGCTGCACTTCAGCAATGAGGGCAAGTCCACAAACGTGC
TGGACGCCATCAAGAATGCCGTGTCTAACCTGGAGAGCTTTAACCTGACC
AAGATGTATTTCCGCTCCGGCGCCTCTCTGACAGACGTGAGCCGGAAGGT
GTTTGGCGAGTGGAGCATCATCAATAGAGCCCTGGACAACTACTATGCCA
CCACATATCCAATCAAGCCCAGAGAGAAGTCTGAGAAGTACGAGGAGAGG
AAGGAGAAGTGGCTGAAGCAGGACTTCAACGTGAGCCTGATCCAGACCGC
CATCGATGAGTACGACAACGAGACAGTGAAGGGCAAGAACAGCGGCAAAG
TGATCGCCGATTATTTTGCCAAGTTCTGCGACGATAAGGAGACAGACCTG
ATCCAGAAGGTGAACGAGGGCTACATCGCCGTGAAGGATCTGCTGAATAC
ACCCTGTCCTGAGAACGAGAAGCTGGGCAGCAATAAGGACCAGGTGAAGC
AGATCAAGGCCTTTATGGATTCTATCATGGACATCATGCACTTCGTGCGC
CCCCTGAGCCTGAAGGATACCGACAAGGAGAAGGATGAGACATTCTACTC
CCTGTTCACACCTCTGTACGACCACCTGACCCAGACAATCGCCCTGTATA
ACAAGGTGCGGAACTATCTGACCCAGAAGCCTTACAGCACAGAGAAGATC
AAGCTGAACTTCGAGAACAGCACCCTGCTGGGCGGCTGGGATCTGAATAA
GGAGACAGACAACACAGCCATCATCCTGAGGAAGGATAACCTGTACTATC
TGGGCATCATGGACAAGAGGCACAATCGCATCTTTCGGAACGTGCCCAAG
GCCGATAAGAAGGACTTCTGCTACGAGAAGATGGTGTATAAGCTGCTGCC
TGGCGCCAACAAGATGCTGCCAAAGGTGTTCTTTTCTCAGAGCAGAATCC
AGGAGTTTACCCCTTCCGCCAAGCTGCTGGAGAACTACGCCAATGAGACA
CACAAGAAGGGCGATAATTTCAACCTGAATCACTGTCACAAGCTGATCGA
TTTCTTTAAGGACTCTATCAACAAGCACGAGGATTGGAAGAATTTCGACT
TTAGGTTCAGCGCCACCTCCACCTACGCCGACCTGAGCGGCTTTTACCAC
GAGGTGGAGCACCAGGGCTACAAGATCTCTTTTCAGAGCGTGGCCGATTC
CTTCATCGACGATCTGGTGAACGAGGGCAAGCTGTACCTGTTCCAGATCT
ATAATAAGGACTTTTCCCCATTCTCTAAGGGCAAGCCCAACCTGCACACC
CTGTACTGGAAGATGCTGTTTGATGAGAACAATCTGAAGGACGTGGTGTA
TAAGCTGAATGGCGAGGCCGAGGTGTTCTACCGCAAGAAGAGCATTGCCG
AGAAGAACCACCAATCCACAAGGCCAATGAGTCCATCATCAACAAGAAT
CCTGATAACCCAAAGGCCACCAGCACCTTCAACTATGATATCGTGAAGGA
CAAGAGATACACCATCGACAAGTTTCAGTTCCACATCCCAATCACAATGA
ACTTTAAGGCCGAGGGCATCTTCAACATGAATCAGAGGGTGAATCAGTTC
CTGAAGGCCAATCCCGATATCAACATCATCGGCATCGACAGAGGCGAGAG

-continued

GCACCTGCTGTACTATGCCCTGATCAACCAGAAGGGCAAGATCCTGAAGC
AGGATACCCTGAATGTGATCGCCAACGAGAAGCAGAAGGTGGACTACCAC
AATCTGCTGGATAAGAAGGAGGGCGACCGCGCAACCGCAAGGCAGGAGTG
GGGCGTGATCGAGACAATCAAGGAGCTGAAGGAGGGCTATCTGTCCCAGG
TCATCCACAAGCTGACCGATCTGATGATCGAGAACAATGCCATCATCGTG
ATGGAGGACCTGAACTTTGGCTTCAAGCGGGGCAGACAGAAGGTGGAGAA
GCAGGTGTATCAGAAGTTTGAGAAGATGCTGATCGATAAGCTGAATTACC
TGGTGGACAAGAATAAGAAGGCAAACGAGCTGGGAGGCCTGCTGAACGCA
TTCCAGCTGGCCAATAAGTTTGAGTCCTTCCAGAAGATGGGCAAGCAGAA
CGGCTTTATCTTCTACGTGCCCGCCTGGAATACCTCTAAGACAGATCCTG
CCACCGGCTTTATCGACTTCCTGAAGCCCCGCTATGAGAACCTGAATCAG
GCCAAGGATTTCTTTGAGAAGTTTGACTCTATCCGGCTGAACAGCAAGGC
CGATTACTTTGAGTTCGCCTTTGACTTCAAGAATTTCACCGAGAAGGCCG
ATGGCGGCAGAACCAAGTGGACAGTGTGCACCACAAACGAGGACAGATAT
GCCTGGAATAGGGCCCTGAACAATAACAGGGGCAGCCAGGAGAAGTACGA
CATCACAGCCGAGCTGAAGTCCCTGTTCGATGGCAAGGTGGACTATAAGT
CTGGCAAGGATCTGAAGCAGCAGATCGCCAGCCAGGAGTCCGCCGACTTC
TTTAAGGCCCTGATGAAGAACCTGTCCATCACCCTGTCTCTGAGACACAA
TAACGGCGAGAAGGGCGATAATGAGCAGGACTACATCCTGTCCCCTGTGG
CCGATTCTAAGGGCCGCTTCTTTGACTCCCGGAAGGCCGACGATGACATG
CCAAAGAATGCCGACGCCAACGGCGCCTATCACATCGCCCTGAAGGGCCT
GTGGTGTCTGGAGCAGATCAGCAAGACCGATGACCTGAAGAAGGTGAAGC
TGGCCATCTCCAACAAGGAGTGGCTGGAGTTCGTGCAGACACTGAAGGGC
AAAAGGCCGGCGGCCACGAAAAAGGCCGGCCAGGCAAAAAAGAAAAAGGG
ATCCTACCCATACGATGTTCCAGATTACGCTTATCCCTACGACGTGCCTG
ATTATGCATACCCATATGATGTCCCCGACTATGCCTAA

*Acidaminococcus* sp. BV3L6 (AsCpf1; pY010),
including NLS and HAtag:

(SEQ ID NO: 25)
MTQFEGFTNLYQVSKTLRFELIPQGKTLKHIQEQGFIEEDKARNDHYKEL
KPIIDRIYKTYADQCLQLVQLDWENLSAAIDSYRKEKTEETRNALIEEQA
TYRNAIHDYFIGRTDNLTDAINKRHAEIYKGLFKAELFNGKVLKQLGTVT
TTEHENALLRSFDKFTTYFSGFYENRKNVFSAEDISTAIPHRIVQDNFPK
FKENCHIFTRLITAVPSLREHFENVKKAIGIFVSTSIEEVFSFPFYNQLL
TQTQIDLYNQLLGGISREAGTEKIKGLNEVLNLAIQKNDETAHIIASLPH
RFIPLFKQILSDRNTLSFILEEFKSDEEVIQSFCKYKTLLRNENVLETAE
ALFNELNSIDLTHIFISHKKLETISSALCDHWDTLRNALYERRISELTGK
ITKSAKEKVQRSLKHEDINLQEIISAAGKELSEAFKQKTSEILSHAHAAL
DQPLPTTLKKQEEKEILKSQLDSLLGLYHLLDWFAVDESNEVDPEFSARL
TGIKLEMEPSLSFYNKARNYATKKPYSVEKFKLNFQMPTLASGWDVNKEK
NNGAILFVKNGLYYLGIMPKQKGRYKALSFEPTEKTSEGFDKMYYDYFPD
AAKMIPKCSTQLKAVTAHFQTHTTPILLSNNFIEPLEITKEIYDLNNPEK

-continued

EPKKFQTAYAKKTGDQKGYREALCKWIDFTRDFLSKYTKTTSIDLSSLRP

SSQYKDLGEYYAELNPLLYHISFQRIAEKEIMDAVETGKLYLFQIYNKDF

AKGHHGKPNLHTLYWTGLFSPENLAKTSIKLNGQAELFYRPKSRMKRMAH

RLGEKMLNKKLKDQKTPIPDTLYQELYDYVNHRLSHDLSDEARALLPNVI

TKEVSHEIIKDRRFTSDKFFFHVPITLNYQAANSPSKFNQRVNAYLKEHP

ETPIIGIDRGERNLIYITVIDSTGKILEQRSLNTIQQFDYQKKLDNREKE

RVAARQAWSVVGTIKDLKQGYLSQVIHEIVDLMIHYQAVVVLENLNFGFK

SKRTGIAEKAVYQQFEKMLIDKLNCLVLKDYPAEKVGGVLNPYQLTDQFT

SFAKMGTQSGFLFYVPAPYTSKIDPLTGFVDPFVWKTIKNHESRKHFLEG

FDFLHYDVKTGDFILHFKMNRNLSFQRGLPGFMPAWDIVFEKNETQFDAK

GTPFIAGKRIVPVIENHRFTGRYRDLYPANELIALLEEKGIVFRDGSNIL

PKLLENDDSHAIDTMVALIRSVLQMRNSNAATGEDYINSPVRDLNGVCFD

SRFQNPEWPMDADANGAYHIALKGQLLLNHLKESKDLKLQNGISNQDWLA

YIQELRNKRPAATKKAGQAKKKKGSYPYDVPDYAYPYDVPDYAYPYDVPD

YA

*Acidaminococcus* sp. BV3L6 (AsCpf1;pY010), including NLS and HA tag:

(SEQ ID NO: 25)

MTQFEGFTNLYQVSKTLRFELIPQGKTLKHIQEQGFIEEDKARNDHYKEL

KPIIDRIYKTYADQCLQLVQLDWENLSAAIDSYRKEKTEETRNALIEEQA

TYRNAIHDYFIGRTDNLTDAINKRHAEIYKGLFKAELFNGKVLKQLGTVT

TTEHENALLRSFDKFTTYFSGFYENRKNVFSAEDISTAIPHRIVQDNFPK

FKENCHIFTRLITAVPSLREHFENVKKAIGIFVSTSIEEVFSFPFYNQLL

TQTQIDLYNQLLGGISREAGTEKIKGLNEVLNLAIQKNDETAHIIASLPH

RFIPLFKQILSDRNTLSFILEEFKSDEEVIQSFCKYKTLLRNENVLETAE

ALFNELNSIDLTHIFISHKKLETISSALCDHWDTLRNALYERRISELTGK

ITKSAKEKVQRSLKHEDINLQEIISAAGKELSEAFKQKTSEILSHAHAAL

DQPLPTTLKKQEEKEILKSQLDSLLGLYHLLDWFAVDESNEVDPEFSARL

TGIKLEMEPSLSFYNKARNYATKKPYSVEKFKLNFQMPTLASGWDVNKEK

NNGAILFVKNGLYYLGIMPKQKGRYKALSFEPTEKTSEGFDKMYYDYFPD

AAKMIPKCSTQLKAVTAHFQTHTTPILLSNNFIEPLEITKEIYDLNNPEK

EPKKFQTAYAKKTGDQKGYREALCKWIDFTRDFLSKYTKTTSIDLSSLRP

SSQYKDLGEYYAELNPLLYHISFQRIAEKEIMDAVETGKLYLFQIYNKDF

AKGHHGKPNLHTLYWTGLFSPENLAKTSIKLNGQAELFYRPKSRMKRMAH

RLGEKMLNKKLKDQKTPIPDTLYQELYDYVNHRLSHDLSDEARALLPNVI

TKEVSHEIIKDRRFTSDKFFFHVPITLNYQAANSPSKFNQRVNAYLKEHP

ETPIIGIDRGERNLIYITVIDSTGKILEQRSLNTIQQFDYQKKLDNREKE

RVAARQAWSVVGTIKDLKQGYLSQVIHEIVDLMIHYQAVVVLENLNFGFK

SKRTGIAEKAVYQQFEKMLIDKLNCLVLKDYPAEKVGGVLNPYQLTDQFT

SFAKMGTQSGFLFYVPAPYTSKIDPLTGFVDPFVWKTIKNHESRKHFLEG

FDFLHYDVKTGDFILHFKMNRNLSFQRGLPGFMPAWDIVFEKNETQFDAK

-continued

GTPFIAGKRIVPVIENHRFTGRYRDLYPANELIALLEEKGIVFRDGSNIL

PKLLENDDSHAIDTMVALIRSVLQMRNSNAATGEDYINSPVRDLNGVCFD

SRFQNPEWPMDADANGAYHIALKGQLLLNHLKESKDLKLQNGISNQDWLA

YIQELRNKRPAATKKAGQAKKKKGSYPYDVPDYAYPYDVPDYAYPYDVPD

YA

SEQ ID NO: 25 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 25 may be encoded by the following nucleotide sequence:

(SEQ ID NO: 26)

ATGACACAGTTCGAGGGCTTTACCAACCTGTATCAGGTGAGCAAGACACT

GCGGTTTGAGCTGATCCCACAGGGCAAGACCCTGAAGCACATCCAGGAGC

AGGGCTTCATCGAGGAGGACAAGGCCCGCAATGATCACTACAAGGAGCTG

AAGCCCATCATCGATCGGATCTACAAGACCTATGCCGACCAGTGCCTGCA

GCTGGTGCAGCTGGATTGGGAGAACCTGAGCGCCGCCATCGACTCCTATA

GAAAGGAGAAAACCGAGGAGACAAGGAACGCCCTGATCGAGGAGCAGGCC

ACATATCGCAATGCCATCCACGACTACTTCATCGGCCGGACAGACAACCT

GACCGATGCCATCAATAAGAGACACGCCGAGATCTACAAGGGCCTGTTCA

AGGCCGAGCTGTTTAATGGCAAGGTGCTGAAGCAGCTGGGCACCGTGACC

ACAACCGAGCACGAGAACGCCCTGCTGCGGAGCTTCGACAAGTTTACAAC

CTACTTCTCCGGCTTTTATGAGAACAGGAAGAACGTGTTCAGCGCCGAGG

ATATCAGCACAGCCATCCCACACCGCATCGTGCAGGACAACTTCCCCAAG

TTTAAGGAGAATTGTCACATCTTCACACGCCTGATCACCGCCGTGCCCAG

CCTGCGGGAGCACTTTGAGAACGTGAAGAAGGCCATCGGCATCTTCGTGA

GCACCTCCATCGAGGAGGTGTTTTCCTTCCCTTTTTATAACCAGCTGCTG

ACACAGACCCAGATCGACCTGTATAACCAGCTGCTGGGAGGAATCTCTCG

GGAGGCAGGCACCGAGAAGATCAAGGGCCTGAACGAGGTGCTGAATCTGG

CCATCCAGAAGAATGATGAGACAGCCCACATCATCGCCTCCCTGCCACAC

AGATTCATCCCCCTGTTTAAGCAGATCCTGTCCGATAGGAACACCCTGTC

TTTCATCCTGGAGGAGTTTAAGAGCGACGAGGAAGTGATCCAGTCCTTCT

GCAAGTACAAGACACTGCTGAGAAACGAGAACGTGCTGGAGACAGCCGAG

GCCCTGTTTAACGAGCTGAACAGCATCGACCTGACACACATCTTCATCAG

CCACAAGAAGCTGGAGACAATCAGCAGCGCCCTGTGCGACCACTGGGATA

CACTGAGGAATGCCCTGTATGAGCGGAGAATCTCCGAGCTGACAGGCAAG

ATCACCAAGTCTGCCAAGGAGAAGGTGCAGCGCAGCCTGAAGCACGAGGA

TATCAACCTGCAGGAGATCATCTCTGCCGCAGGCAAGGAGCTGAGCGAGG

CCTTCAAGCAGAAAACCAGCGAGATCCTGTCCCACGCACACGCCGCCCTG

GATCAGCCACTGCCTACAACCCTGAAGAAGCAGGAGGAGAAGGAGATCCT

GAAGTCTCAGCTGGACAGCCTGCTGGGCCTGTACCACCTGCTGGACTGGT

TTGCCGTGGATGAGTCCAACGAGGTGGACCCCGAGTTCTCTGCCCGGCTG
ACCGGCATCAAGCTGGAGATGGAGCCTTCTCTGAGCTTCTACAACAAGGC
CAGAAATTATGCCACCAAGAAGCCCTACTCCGTGGAGAAGTTCAAGCTGA
ACTTTCAGATGCCTACACTGGCCTCTGGCTGGGACGTGAATAAGGAGAAG
AACAATGGCGCCATCCTGTTTGTGAAGAACGGCCTGTACTATCTGGGCAT
CATGCCAAAGCAGAAGGGCAGGTATAAGGCCCTGAGCTTCGAGCCCACAG
AGAAAACCAGCGAGGGCTTTGATAAGATGTACTATGACTACTTCCCTGAT
GCCGCCAAGATGATCCCAAAGTGCAGCACCCAGCTGAAGGCCGTGACAGC
CCACTTTCAGACCCACACAACCCCCATCCTGCTGTCCAACAATTTCATCG
AGCCTCTGGAGATCACAAAGGAGATCTACGACCTGAACAATCCTGAGAAG
GAGCCAAAGAAGTTTCAGACAGCCTACGCCAAGAAAACCGGCGACCAGAA
GGGCTACAGAGAGGCCCTGTGCAAGTGGATCGACTTCACAAGGGATTTTC
TGTCCAAGTATACCAAGACAACCTCTATCGATCTGTCTAGCCTGCGGCCA
TCCTCTCAGTATAAGGACCTGGGCGAGTACTATGCCGAGCTGAATCCCCT
GCTGTACCACATCAGCTTCCAGAGAATCGCCGAGAAGGAGATCATGGATG
CCGTGGAGACAGGCAAGCTGTACCTGTTCCAGATCTATAACAAGGACTTT
GCCAAGGGCCACCACGGCAAGCCTAATCTGCACACACTGTATTGGACCGG
CCTGTTTTCTCCAGAGAACCTGGCCAAGACAAGCATCAAGCTGAATGGCC
AGGCCGAGCTGTTCTACCGCCCTAAGTCCAGGATGAAGAGGATGGCACAC
CGGCTGGGAGAGAAGATGCTGAACAAGAAGCTGAAGGATCAGAAAACCCC
AATCCCCGACACCCTGTACCAGGAGCTGTACGACTATGTGAATCACAGAC
TGTCCCACGACCTGTCTGATGAGGCCAGGGCCCTGCTGCCCAACGTGATC
ACCAAGGAGGTGTCTCACGAGATCATCAAGGATAGGCGCTTTACCAGCGA
CAAGTTCTTTTTCCACGTGCCTATCACACTGAACTATCAGGCCGCCAATT
CCCCATCTAAGTTCAACCAGAGGGTGAATGCCTACCTGAAGGAGCACCCC
GAGACACCTATCATCGGCATCGATCGGGGCGAGAGAAACCTGATCTATAT
CACAGTGATCGACTCCACCGGCAAGATCCTGGAGCAGCGGAGCCTGAACA
CCATCCAGCAGTTTGATTACCAGAAGAAGCTGGACAACAGGGAGAAGGAG
AGGGTGGCAGCAAGGCAGGCCTGGTCTGTGGTGGGCACAATCAAGGATCT
GAAGCAGGGCTATCTGAGCCAGGTCATCCACGAGATCGTGGACCTGATGA
TCCACTACCAGGCCGTGGTGGTGCTGGAGAACCTGAATTTCGGCTTTAAG
AGCAAGAGGACCGGCATCGCCGAGAAGGCCGTGTACCAGCAGTTCGAGAA
GATGCTGATCGATAAGCTGAATTGCCTGGTGCTGAAGGACTATCCAGCAG
AGAAAGTGGGAGGCGTGCTGAACCCATACCAGCTGACAGACCAGTTCACC
TCCTTTGCCAAGATGGGCACCCAGTCTGGCTTCCTGTTTTACGTGCCTGC
CCCATATACATCTAAGATCGATCCCCTGACCGGCTTCGTGGACCCCTTCG
TGTGGAAAACCATCAAGAATCACGAGAGCCGCAAGCACTTCCTGGAGGGC
TTCGACTTTCTGCACTACGACGTGAAAACCGGCGACTTCATCCTGCACTT
TAAGATGAACAGAAATCTGTCCTTCCAGAGGGGCCTGCCCGGCTTTATGC
CTGCATGGGATATCGTGTTCGAGAAGAACGAGACAGTTTGACGCCAAG
GGCACCCCTTTCATCGCCGGCAAGAGAATCGTGCCAGTGATCGAGAATCA

CAGATTCACCGGCAGATACCGGGACCTGTATCCTGCCAACGAGCTGATCG
CCCTGCTGGAGGAGAAGGGCATCGTGTTCAGGGATGGCTCCAACATCCTG
CCAAAGCTGCTGGAGAATGACGATTCTCACGCCATCGACACCATGGTGGC
CCTGATCCGCAGCGTGCTGCAGATGCGGAACTCCAATGCCGCCACAGGCG
AGGACTATATCAACAGCCCCGTGCGCGATCTGAATGGCGTGTGCTTCGAC
TCCCGGTTTCAGAACCCAGAGTGGCCCATGGACGCCGATGCCAATGGCGC
CTACCACATCGCCCTGAAGGGCCAGCTGCTGCTGAATCACCTGAAGGAGA
GCAAGGATCTGAAGCTGCAGAACGGCATCTCCAATCAGGACTGGCTGGCC
TACATCCAGGAGCTGCGCAACAAAGGCCGGCGGCCACGAAAAGGCCGG
CCAGGCAAAAAAGAAAAAGGGGATCCTACCCATACGATGTTCCAGATTACG
CTTATCCCTACGACGTGCCTGATTATGCATACCCATATGATGTCCCCGAC
TATGCCTAA

*Lachnospiraceae bacterium* MA2020 (Lb2Cpf1;
pY011), including NLS and HA tag:
(SEQ ID NO: 27)
MYYESLTKQYPVSKTIRNELIPIGKTLDNIRQNNILESDVKRKQNYEHVK
GILDEYHKQLINEALDNCTLPSLKIAAEIYLKNQKEVSDREDFNKTQDLL
RKEVVEKLKAHENFTKIGKKDILDLLEKLPSISEDDYNALESFRNFYTYF
TSYNKVRENLYSDKEKSSTVAYRLINENFPKFLDNVKSYRFVKTAGILAD
GLGEEEQDSLFIVETFNKTLTQDGIDTYNSQVGKINSSINLYNQKNQKAN
GFRKIPKMKMLYKQILSDREESFIDEFQSDEVLIDNVESYGSVLIESLKS
SKVSAFFDALRESKGKNVYVKNDLAKTAMSNIVFENWRTFDDLLNQEYDL
ANENKKKDDKYFEKRQKELKKNKSYSLEHLCNLSEDSCNLIENYIHQISD
DIENIIINNETFLRIVINEHDRSRKLAKNRKAVKAIKDFLDSIKVLEREL
KLINSSGQELEKDLIVYSAHEELLVELKQVDSLYNMTRNYLTKKPFSTEK
VKLNFNRSTLLNGWDRNKETDNLGVLLLKDGKYYLGIMNTSANKAFVNPP
VAKTEKVFKKVDYKLLPVPNQMLPKVFFAKSNIDFYNPSSEIYSNYKKGT
HKKGNMFSLEDCHNLIDFFKESISKHEDWSKFGFKFSDTASYNDISEFYR
EVEKQGYKLTYTDIDETYINDLIERNELYLFQIYNKDFSMYSKGKLNLHT
LYFMMLFDQRNIDDVVYKLNGEAEVFYRPASISEDELIIHKAGEEIKNKN
PNRARTKETSTFSYDIVKDKRYSKDKFTLHIPITMNFGVDEVKRFNDAVN
SAIRIDENVNVIGIDRGERNLLYVVVIDSKGNILEQISLNSIINKEYDIE
TDYHALLDEREGGRDKARKDWNTVENIRDLKAGYLSQVVNVVAKLVLKYN
AIICLEDLNFGFKRGRQKVEKQVYQKFEKMLIDKLNYLVIDKSREQTSPK
ELGGALNALQLTSKFKSFKELGKQSGVIYYVPAYLTSKIDPTTGFANLFY
MKCENVEKSKRFFDGFDFIRFNALENVFEFGFDYRSFTQRACGINSKWTV
CTNGERIIKYRNPDKNNMFDEKVVVVTDEMKNLFEQYK1PYEDGRNVKDM
IISNEEAEFYRRLYRLLQQTLQMRNSTSDGTRDYIISPVKNKREAYFNSE
LSDGSVPKDADANGAYNIARKGLWVLEQIRQKSEGEKINLAMTNAEWLEY
AQTHLLKRPAATKKAGQAKKKKGSYPYDVPDYAYPYDVPDYAYPYDVPDY
A Lachnospiraceae bacterium MA2020 (Lb2Cpf1;pY011), including NLS and HA tag:

(SEQ ID NO: 27)
MYYESLTKQYPVSKTIRNELIPIGKTLDNIRQNNILESDVKRKQNYEHVK

GILDEYHKQLINEALDNCTLPSLKIAAEIYLKNQKEVSDREDFNKTQDLL

RKEVVEKLKAHENFTKIGKKDILDLLEKLPSISEDDYNALESFRNFYTYF

TSYNKVRENLYSDKEKSSTVAYRLINENFPKFLDNVKSYRFVKTAGILAD

GLGEEEQDSLFIVETFNKTLTQDGIDTYNSQVGKINSSINLYNQKNQKAN

GFRKIPKMKMLYKQILSDREESFIDEFQSDEVLIDNVESYGSVLIESLKS

SKVSAFFDALRESKGKNVYVKNDLAKTAMSNIVFENWRTFDDLLNQEYDL

ANENKKKDDKYFEKRQKELKKNKSYSLEHLCNLSEDSCNLIENYIHQISD

DIENIIINNETFLRIVINEHDRSRKLAKNRKAVKAIKDFLDSIKVLEREL

KLINSSGQELEKDLIVYSAHEELLVELKQVDSLYNMTRNYLTKKPFSTEK

VKLNFNRSTLLNGWDRNKETDNLGVLLLKDGKYYLGIMNTSANKAFVNPP

VAKTEKVFKKVDYKLLPVPNQMLPKVFFAKSNIDFYNPSSEIYSNYKKGT

HKKGNMFSLEDCHNLIDFFKESISKHEDWSKFGFKFSDTASYNDISEFYR

EVEKQGYKLTYTDIDETYINDLIERNELYLFQIYNKDFSMYSKGKLNLHT

LYFMMLFDQRNIDDVVYKLNGEAEVFYRPASISEDELIIHKAGEEIKNKN

PNRARTKETSTFSYDIVKDKRYSKDKFTLHIPITMNFGVDEVKRFNDAVN

SAIRIDENVNVIGIDRGERNLLYVVVIDSKGNILEQISLNSIINKEYDIE

TDYHALLDEREGGRDKARKDWNTVENIRDLKAGYLSQVVNVVAKLVLKYN

AIICLEDLNFGFKRGRQKVEKQVYQKFEKMLIDKLNYLVIDKSREQTSPK

ELGGALNALQLTSKFKSFKELGKQSGVIYYVPAYLTSKIDPTTGFANLFY

MKCENVEKSKRFFDGFDFIRFNALENVFEFGFDYRSFTQRACGINSKWTV

CTNGERIIKYRNPDKNNMFDEKVVVVTDEMKNLFEQYKIPYEDGRNVKDM

IISNEEAEFYRRLYRLLQQTLQMRNSTSDGTRDYIISPVKNKREAYFNSE

LSDGSVPKDADANGAYNIARKGLWVLEQIRQKSEGEKINLAMTNAEWLEY

AQTHLLKRPAATKKAGQAKKKKGSYPYDVPDYAYPYDVPDYAYPYDVPDY

A

SEQ ID NO: 27 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 27 may be encoded by the following nucleotide sequence:

(SEQ ID NO: 28)
ATGTACTATGAGTCCCTGACCAAGCAGTACCCCGTGTCTAAGACAATCCG

GAATGAGCTGATCCCTATCGGCAAGACACTGGATAACATCCGCCAGAACA

ATATCCTGGAGAGCGACGTGAAGCGGAAGCAGAACTACGAGCACGTGAAG

GGCATCCTGGATGAGTATCACAAGCAGCTGATCAACGAGGCCCTGGACAA

TTGCACCCTGCCATCCCTGAAGATCGCCGCCGAGATCTACCTGAAGAATC

AGAAGGAGGTGTCTGACAGAGAGGATTTCAACAAGACACAGGACCTGCTG

AGGAAGGAGGTGGTGGAGAAGCTGAAGGCCCACGAGAACTTTACCAAGAT

CGGCAAGAAGGACATCCTGGATCTGCTGGAGAAGCTGCCTTCCATCTCTG

AGGACGATTACAATGCCCTGGAGAGCTTCCGCAACTTTTACACCTATTTC

ACATCCTACAACAAGGTGCGGGAGAATCTGTATTCTGATAAGGAGAAGAG

CTCCACAGTGGCCTACAGACTGATCAACGAGAATTTCCCAAAGTTTCTGG

ACAATGTGAAGAGCTATAGGTTTGTGAAAACCGCAGGCATCCTGGCAGAT

GGCCTGGGAGAGGAGGAGCAGGACTCCCTGTTCATCGTGGAGACATTCAA

CAAGACCCTGACACAGGACGGCATCGATACCTACAATTCTCAAGTGGGCA

AGATCAACTCTAGCATCAATCTGTATAACCAGAAGAATCAGAAGGCCAAT

GGCTTCAGAAAGATCCCCAAGATGAAGATGCTGTATAAGCAGATCCTGTC

CGATAGGGAGGAGTCTTTCATCGACGAGTTTCAGAGCGATGAGGTGCTGA

TCGACAACGTGGAGTCTTATGGCAGCGTGCTGATCGAGTCTCTGAAGTCC

TCTAAGGTGAGCGCCTTCTTTGATGCCCTGAGAGAGTCTAAGGGCAAGAA

CGTGTACGTGAAGAATGACCTGGCCAAGACAGCCATGAGCAACATCGTGT

TCGAGAATTGGAGGACCTTTGACGATCTGCTGAACCAGGAGTACGACCTG

GCCAACGAGAACAAGAAGAAGGACGATAAGTATTTCGAGAAGCGCCAGAA

GGAGCTGAAGAAGAATAAGAGCTACTCCCTGGAGCACCTGTGCAACCTGT

CCGAGGATTCTTGTAACCTGATCGAGAATTATATCCACCAGATCTCCGAC

GATATCGAGAATATCATCATCAACAATGAGACATTCCTGCGCATCGTGAT

CAATGAGCACGACAGGTCCCGCAAGCTGGCCAAGAACCGGAAGGCCGTGA

AGGCCATCAAGGACTTTCTGGATTCTATCAAGGTGCTGGAGCGGGAGCTG

AAGCTGATCAACAGCTCCGGCCAGGAGCTGGAGAAGGATCTGATCGTGTA

CTCTGCCCACGAGGAGCTGCTGGTGGAGCTGAAGCAGGTGGACAGCCTGT

ATAACATGACCAGAAATTATCTGACAAAGAAGCCTTTCTCTACCGAGAAG

GTGAAGCTGAACTTTAATCGCAGCACACTGCTGAACGGCTGGGATCGGAA

TAAGGAGACAGACAACCTGGGCGTGCTGCTGCTGAAGGACGGCAAGTACT

ATCTGGGCATCATGAACACAAGCGCCAATAAGGCCTTCGTGAATCCCCCT

GTGGCCAAGACCGAGAAGGTGTTTAAGAAGGTGGATTACAAGCTGCTGCC

AGTGCCCAACCAGATGCTGCCAAAGGTGTTCTTTGCCAAGAGCAATATCG

ACTTCTATAACCCCTCTAGCGAGATCTACTCCAATTATAAGAAGGGCACC

CACAAGAAGGGCAATATGTTTTCCCTGGAGGATTGTCACAACCTGATCGA

CTTCTTTAAGGAGTCTATCAGCAAGCACGAGGACTGGAGCAAGTTCGGCT

TTAAGTTCAGCGATACAGCCTCCTACAACGACATCTCCGAGTTCTATCGC

GAGGTGGAGAAGCAGGGCTACAAGCTGACCTATACAGACATCGATGAGAC

ATACATCAATGATCTGATCGAGCGGAACGAGCTGTACCTGTTCCAGATCT

ATAATAAGGACTTTAGCATGTACTCCAAGGGCAAGCTGAACCTGCACACA

CTGTATTTCATGATGCTGTTTGATCAGCGCAATATCGACGACGTGGTGTA

TAAGCTGAACGGAGAGGCAGAGGTGTTCTATAGGCCAGCCTCCATCTCTG

AGGACGAGCTGATCATCCACAAGGCCGGCGAGGAGATCAAGAACAAGAAT

CCTAACCGGGCCAGAACCAAGGAGACAAGCACCTTCAGCTACGACATCGT

GAAGGATAAGCGGTATAGCAAGGATAAGTTTACCCTGCACATCCCCATCA

-continued

```
CAATGAACTTCGGCGTGGATGAGGTGAAGCGGTTCAACGACGCCGTGAAC
AGCGCCATCCGGATCGATGAGAATGTGAACGTGATCGGCATCGACCGGG
CGAGAGAAATCTGCTGTACGTGGTGGTCATCGACTCTAAGGGCAACATCC
TGGAGCAGATCTCCCTGAACTCTATCATCAATAAGGAGTACGACATCGAG
ACAGATTATCACGCACTGCTGGATGAGAGGGAGGGCGGCAGAGATAAGGC
CCCGGAAGGACTGGAACACCGTGGAGAATATCAGGGACCTGAAGGCCGGCT
ACCTGAGCCAGGTGGTGAACGTGGTGGCCAAGCTGGTGCTGAAGTATAAT
GCCATCATCTGCCTGGAGGACCTGAACTTTGGCTTCAAGAGGGGCCGCCA
GAAGGTGGAGAAGCAGGTGTACCAGAAGTTCGAGAAGATGCTGATCGATA
AGCTGAATTACCTGGTCATCGACAAGAGCCGCGAGCAGACATCCCCTAAG
GAGCTGGAGGCGCCCTGAACGCACTGCAGCTGACCTCTAAGTTCAAGAG
CTTTAAGGAGCTGGGCAAGCAGTCCGGCGTGATCTACTATGTGCCTGCCT
ACCTGACCTCTAAGATCGATCCAACCACAGGCTTCGCCAATCTGTTTTAT
ATGAAGTGTGAGAACGTGGAGAAGTCCAAGAGATTCTTTGACGGCTTTGA
TTTCATCAGGTTCAACGCCCTGGAGAACGTGTTCGAGTTCGGCTTTGACT
ACCGGAGCTTCACCCAGAGGGCCTGCGGCATCAATTCCAAGTGGACCGTG
TGCACCAACGGCGAGCGCATCATCAAGTATCGGAATCCAGATAAGAACAA
TATGTTCGACGAGAAGGTGGTGGTGGTGACCGATGAGATGAAGAACCTGT
TTGAGCAGTACAAGATCCCCTATGAGGATGGCAGAAATGTGAAGGACATG
ATCATCAGCAACGAGGAGGCCGAGTTCTACCGGAGACTGTATAGGCTGCT
GCAGCAGACCCTGCAGATGAGAAACAGCACCTCCGACGGCACAAGGGATT
ACATCATCTCCCCTGTGAAGAATAAGAGAGAGGCCTACTTCAACAGCGAG
CTGTCCGACGGCTCTGTGCCAAAGGACGCCGATGCCAACGGCGCCTACAA
TATCGCCAGAAAGGGCCTGTGGGTGCTGGAGCAGATCAGGCAGAAGAGCG
AGGGCGAGAAGATCAATCTGGCCATGACCAACGCCGAGTGGCTGGAGTAT
GCCCAGACACACCTGCTGAAAAGGCCGGCGGCCACGAAAAAGGCCGGCCA
GGCAAAAAAGAAAAAGGGATCCTACCCATACGATGTTCCAGATTACGCTT
ATCCCTACGACGTGCCTGATTATGCATACCCATATGATGTCCCCGACTAT
GCCTAA
```

*Candidatus Methanoplasma termitum* (CMtCpf1; pY012), including NLS and HA tag:

(SEQ ID NO: 29)
MNNYDEFTKLYPIQKTIRFELKPQGRTMEHLETFNFFEEDRDRAEKYKIL
KEAIDEYHKKFIDEHLTNMSLDWNSLKQISEKYYKSREEKDKKVFLSEQK
RMRQEIVSEFKKDDRFKDLFSKKLFSELLKEEIYKKGNHQEIDALKSFDK
FSGYFIGLHENRKNMYSDGDEITAISNRIVNENFPKFLDNLQKYQEARKK
YPEWIIKAESALVAHNIKMDEVFSLEYFNKVLNQEGIQRYNLALGGYVTK
SGEKMMGLNDALNLAHQSEKSSKGRIHMTPLFKQILSEKESFSYIPDVFT
EDSQLLPSIGGFFAQIENDKDGNIFDRALELISSYAEYDTERIYIRQADI
NRVSNVIFGEWGTLGGLMREYKADSINDINLERTCKKVDKWLDSKEFALS
DVLEAIKRTGNNDAFNEYISKMRTAREKIDAARKEMKFISEKISGDEESI
HIIKTLLDSVQQFLHFFNLFKARQDIPLDGAFYAEFDEVHSKLFAIVPLY
NKVRNYLTKNNLNTKKIKLNFKNPTLANGWDQNKVYDYASLIFLRDGNYY
LGIINPKRKKNIKFEQGSGNGPFYRKMVYKQIPGPNKNLPRVFLTSTKGK
KEYKPSKEIIEGYEADKHIRGDKFDLDFCHKLIDFFKESIEKHKDWSKFN
FYFSPTESYGDISEFYLDVEKQGYRMHFENISAETIDEYVEKGDLFLFQI
YNKDFVKAATGKKDMHTIYWNAAFSPENLQDVVVKLNGEAELFYRDKSDI
KEIVHREGEILVNRTYNGRTPVPDKIHKKLTDYHNGRTKDLGEAKEYLDK
VRYFKAHYDITKDRRYLNDKIYFHVPLTLNFKANGKKNLNKMVIEKFLSD
EKAHIIGIDRGERNLLYYSIIDRSGKIIDQQSLNVIDGFDYREKLNQREI
EMKDARQSWNAIGKIKDLKEGYLSKAVHEITKMAIQYNAIVVMEELNYGF
KRGRFKVEKQIYQKFENMLIDKMNYLVFKDAPDESPGGVLNAYQLTNPLE
SFAKLGKQTGILFYVPAAYTSKIDPTTGFVNLFNTSSKTNAQERKEFLQK
FESISYSAKDGGIFAFAFDYRKFGTSKTDHKNVWTAYTNGERMRYIKEKK
RNELFDPSKEIKEALTSSGIKYDGGQNILPDILRSNNNGLIYTMYSSFIA
AIQMRVYDGKEDYIISPIKNSKGEFFRTDPKRRELPIDADANGAYNIALR
GELTMRAIAEKFDPDSEKMAKLELKHKDWFEFMQTRGDKRPAATKKAGQA
KKKKGSYPYDVPDYAYPYDVPDYAYPYDVPDYA

*Candidatus Methanoplasma termitum* (CMtCpf1; pY012), including NLS and HA tag:

(SEQ ID NO: 29)
MNNYDEFTKLYPIQKTIRFELKPQGRTMEHLETFNFFEEDRDRAEKYKIL
KEAIDEYHKKFIDEHLTNMSLDWNSLKQISEKYYKSREEKDKKVFLSEQK
RMRQEIVSEFKKDDRFKDLFSKKLFSELLKEEIYKKGNHQEIDALKSFDK
FSGYFIGLHENRKNMYSDGDEITAISNRIVNENFPKFLDNLQKYQEARKK
YPEWIIKAESALVAHNIKMDEVFSLEYFNKVLNQEGIQRYNLALGGYVTK
SGEKMMGLNDALNLAHQSEKSSKGRIHMTPLFKQILSEKESFSYIPDVFT
EDSQLLPSIGGFFAQIENDKDGNIFDRALELISSYAEYDTERIYIRQADI
NRVSNVIFGEWGTLGGLMREYKADSINDINLERTCKKVDKWLDSKEFALS
DVLEAIKRTGNNDAFNEYISKMRTAREKIDAARKEMKFISEKISGDEESI
HIIKTLLDSVQQFLHFFNLFKARQDIPLDGAFYAEFDEVHSKLFAIVPLY
NKVRNYLTKNNLNTKKIKLNFKNPTLANGWDQNKVYDYASLIFLRDGNYY
LGIINPKRKKNIKFEQGSGNGPFYRKMVYKQIPGPNKNLPRVFLTSTKGK
KEYKPSKEIIEGYEADKHIRGDKFDLDFCHKLIDFFKESIEKHKDWSKFN
FYFSPTESYGDISEFYLDVEKQGYRMHFENISAETIDEYVEKGDLFLFQI
YNKDFVKAATGKKDMHTIYWNAAFSPENLQDVVVKLNGEAELFYRDKSDI
KEIVHREGEILVNRTYNGRTPVPDKIHKKLTDYHNGRTKDLGEAKEYLDK
VRYFKAHYDITKDRRYLNDKIYFHVPLTLNFKANGKKNLNKMVIEKFLSD
EKAHIIGIDRGERNLLYYSIIDRSGKIIDQQSLNVIDGFDYREKLNQREI
EMKDARQSWNAIGKIKDLKEGYLSKAVHEITKMAIQYNAIVVMEELNYGF
KRGRFKVEKQIYQKFENMLIDKMNYLVFKDAPDESPGGVLNAYQLTNPLE
SFAKLGKQTGILFYVPAAYTSKIDPTTGFVNLFNTSSKTNAQERKEFLQK

```
FESISYSAKDGGIFAFAFDYRKFGTSKTDHKNVWTAYTNGERMRYIKEKK

RNELFDPSKEIKEALTSSGIKYDGGQNILPDILRSNNNGLIYTMYSSFIA

AIQMRVYDGKEDYIISPIKNSKGEFFRTDPKRRELPIDADANGAYNIALR

GELTMRAIAEKFDPDSEKMAKLELKHKDWFEFMQTRGDKRPAATKKAGQA

KKKKGSYPYDVPDYAYPYDVPDYAYPYDVPDYA
```

SEQ ID NO: 29 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 29 may be encoded by the following nucleotide sequence:

```
                                         (SEQ ID NO: 30)
ATGAACAATTACGACGAGTTCACCAAGCTGTATCCTATCCAGAAAACCAT

CCGGTTTGAGCTGAAGCCACAGGGCAGAACCATGGAGCACCTGGAGACAT

TCAACTTCTTTGAGGAGGACCGGGATAGAGCCGAGAAGTATAAGATCCTG

AAGGAGGCCATCGACGAGTACCACAAGAAGTTTATCGATGAGCACCTGAC

CAATATGTCCCTGGATTGGAACTCTCTGAAGCAGATCAGCGAGAAGTACT

ATAAGAGCAGGGAGGAGAAGGACAAGAAGGTGTTCCTGTCCGAGCAGAAG

AGGATGCGCCAGGAGATCGTGTCTGAGTTTAAGAAGGACGATCGCTTCAA

GGACCTGTTTTCCAAGAAGCTGTTCTCTGAGCTGCTGAAGGAGGAGATCT

ACAAGAAGGGCAACCACCAGGAGATCGACGCCCTGAAGAGCTTCGATAAG

TTTTCCGGCTATTTCATCGGCCTGCACGAGAATAGGAAGAACATGTACTC

CGACGGCGATGAGATCACCGCCATCTCCAATCGCATCGTGAATGAGAACT

TCCCCAAGTTTCTGGATAACCTGCAGAAGTACCAGGAGGCCAGGAAGAAG

TATCCTGAGTGGATCATCAAGGCCGAGAGCGCCCTGGTGGCCCACAATAT

CAAGATGGACGAGGTGTTCTCCCTGGAGTACTTTAATAAGGTGCTGAACC

AGGAGGGCATCCAGCGGTACAACCTGGCCCTGGGCGGCTATGTGACCAAG

AGCGGCGAGAAGATGATGGGCCTGAATGATGCCCTGAACCTGGCCCACCA

GTCCGAGAAGAGCTCCAAGGGCAGAATCCACATGACCCCCCTGTTCAAGC

AGATCCTGTCCGAGAAGGAGTCCTTCTCTTACATCCCCGACGTGTTTACA

GAGGATTCTCAGCTGCTGCCTAGCATCGGCGGCTTCTTTGCCCAGATCGA

GAATGACAAGGATGGCAACATCTTCGACCGGGCCCTGGAGCTGATCTCTA

GCTACGCCGAGTATGATACCGAGCGGATCTATATCAGACAGGCCGACATC

AATAGAGTGTCCAACGTGATCTTTGGAGAGTGGGGCACCCTGGGAGGCCT

GATGAGGGAGTACAAGGCCGACTCTATCAATGATATCAACCTGGAGCGCA

CATGCAAGAAGGTGGACAAGTGGCTGGATTCTAAGGAGTTTGCCCTGAGC

GATGTGCTGGAGGCCATCAAGAGGACCGGCAACAATGACGCCTTCAACGA

GTATATCTCCAAGATGCGGACAGCCAGAGAGAAGATCGATGCCGCCCGCA

AGGAGATGAAGTTCATCAGCGAGAAGATCTCCGGCGATGAGGAGTCTATC

CACATCATCAAGACCCTGCTGGACAGCGTGCAGCAGTTCCTGCACTTCTT

TAATCTGTTTAAGGCAAGGCAGGACATCCCACTGGATGGAGCCTTCTACG

CCGAGTTTGACGAGGTGCACAGCAAGCTGTTTGCCATCGTGCCCCTGTAT

AACAAGGTGCGGAACTATCTGACCAAGAACAATCTGAACACAAAGAAGAT

CAAGCTGAATTTCAAGAACCCTACACTGGCCAATGGCTGGGACCAGAACA

AGGTGTACGATTATGCCTCCCTGATCTTTCTGCGGGACGGCAATTACTAT

CTGGGCATCATCAATCCTAAGAGAAAGAAGAACATCAAGTTCGAGCAGGG

CTCTGGCAACGGCCCCTTCTACCGGAAGATGGTGTATAAGCAGATCCCCG

GCCCTAATAAGAACCTGCCAAGAGTGTTCCTGACCTCCACAAAGGGCAAG

AAGGAGTATAAGCCCTCTAAGGAGATCATCGAGGGCTACGAGGCCGACAA

GCACATCAGGGGCGATAAGTTCGACCTGGATTTTGTCACAAGCTGATCG

ATTTCTTTAAGGAGTCCATCGAGAAGCACAAGGACTGGTCTAAGTTCAAC

TTCTACTTCAGCCCAACCGAGAGCTATGGCGACATCTCTGAGTTCTACCT

GGATGTGGAGAAGCAGGGCTATCGCATGCACTTTGAGAATATCAGCGCCG

AGACAATCGACGAGTATGTGGAGAAGGGCGATCGTTTCTGTTCCAGATC

TACAACAAGGATTTTGTGAAGGCCGCCACCGGCAAGAAGGACATGCACAC

AATCTACTGGAATGCCGCCTTCAGCCCCGAGAACCTGCAGGACGTGGTGG

TGAAGCTGAACGGCGAGGCCGAGCTGTTTTATAGGGACAAGTCCGATATC

AAGGAGATCGTGCACCGCGAGGGCGAGATCCTGGTGAATAGGACCTACAA

CGGCCGCACACCAGTGCCCGACAAGATCCACAAGAAGCTGACCGATTATC

ACAATGGCCGGACAAAGGACCTGGGCGAGGCCAAGGAGTACCTGGATAAG

GTGAGATACTTCAAGGCCCACTATGACATCACCAAGGATCGGAGATACCT

GAACGACAAGATCTATTTCCACGTGCCTCTGACCCTGAACTTCAAGGCCA

ACGGCAAGAAGAATCTGAACAAGATGGTCATCGAGAAGTTCCTGTCCGAT

GAGAAGGCCCACATCATCGGCATCGACAGGGGCGAGCGCAATCTGCTGTA

CTATTCCATCATCGACAGGTCTGGCAAGATCATCGATCAGCAGAGCCTGA

ATGTGATCGACGGCTTTGATTATCGGGAGAAGCTGAACCAGAGAGAGATC

GAGATGAAGGATGCCCGCCAGTCTTGGAACGCCATCGGCAAGATCAAGGA

CCTGAAGGAGGGCTACCTGAGCAAGGCCGTGCACGAGATCACCAAGATGG

CCATCCAGTATAATGCCATCGTGGTCATGGAGGAGCTGAACTACGGCTTC

AAGCGGGGCCGGTTCAAGGTGGAGAAGCAGATCTATCAGAAGTTCGAGAA

TATGCTGATCGATAAGATGAACTACCTGGTGTTTAAGGACGCACCTGATG

AGTCCCCAGGAGGCGTGCTGAATGCCTACCAGCTGACAAACCCACTGGAG

TCTTTCGCCAAGCTGGGCAAGCAGACCGGCATCCTGTTTTACGTGCCAGC

CGCCTATACATCCAAGATCGACCCCACCACAGGCTTCGTGAATCTGTTTA

ACACCTCCTCTAAGACAAACGCCCAGGAGCGGAAGGAGTTCCTGCAGAAG

TTTGAGAGCATCTCCTATTCTGCCAAGGATGGCGGCATCTTTGCCTTCGC

CTTTGACTACAGAAAGTTCGGCACCAGCAAGACAGATCACAAGAACGTGT

GGACCGCCTATACAAACGGCGAGAGGATGCGCTACATCAAGGAGAAGAAG

CGGAATGAGCTGTTTGACCCTTCTAAGGAGATCAAGGAGGCCCTGACCAG

CTCCGGCATCAAGTACGATGGCGGCCAGAACATCCTGCCAGACATCCTGA

GGAGCAACAATAACGGCCTGATCTACACAATGTATTCTAGCTTCATCGCC

GCCATCCAGATGCGCGTGTACGACGGCAAGGAGGATTATATCATCAGCCC
```

-continued

```
CATCAAGAACTCCAAGGGCGAGTTCTTTAGGACCGACCCCAAGAGGCGCG

AGCTGCCTATCGACGCCGATGCCAATGGCGCCTACAACATCGCCCTGAGG

GGAGAGCTGACAATGAGGGCAATCGCAGAGAAGTTCGACCCTGATAGCGA

GAAGATGGCCAAGCTGGAGCTGAAGCACAAGGATTGGTTCGAGTTTATGC

AGACCAGAGGCGACAAAAGGCCGGCGGCCACGAAAAAGGCCGGCCAGGCA

AAAAAGAAAAAGGGATCCTACCCATACGATGTTCCAGATTACGCTTATCC

CTACGACGTGCCTGATTATGCATACCCATATGATGTCCCCGACTATGCCT

AA
```

*Eubacterium eligens* (EeCpf1; pY013), including NLS and HAtag:

(SEQ ID NO: 31)
```
MNGNRSIVYREFVGVIPVAKTLRNELRPVGHTQEHIIQNGLIQEDELRQE

KSTELKNIMDDYYREYIDKSLSGVTDLDFTLLFELMNLVQSSPSKDNKKA

LEKEQSKMREQICTHLQSDSNYKNIFNAKLLKEILPDFIKNYNQYDVKDK

AGKLETLALFNGFSTYFTDFFEKRKNVFTKEAVSTSIAYRIVHENSLIFL

ANMTSYKKISEKALDEIEVIEKNNQDKMGDWELNQIFNPDFYNMVLIQSG

IDFYNEICGVVNAHMNLYCQQTKNNYNLFKMRKLHKQILAYTSTSFEVPK

MFEDDMSVYNAVNAFIDETEKGNIIGKLKDIVNKYDELDEKRIYISKDFY

ETLSCFMSGNWNLITGCVENFYDENIHAKGKSKEEKVKKAVKEDKYKSIN

DVNDLVEKYIDEKERNEFKNSNAKQYIREISNIITDTETAHLEYDDHISL

IESEEKADEMKKRLDMYMNMYHWAKAFIVDEVLDRDEMFYSDIDDIYNIL

ENIVPLYNRVRNYVTQKPYNSKKIKLNFQSPTLANGWSQSKEFDNNAIIL

IRDNKYYLAIFNAKNKPDKKIIQGNSDKKNDNDYKKMVYNLLPGANKMLP

KVFLSKKGIETFKPSDYIISGYNAHKHIKTSENFDISFCRDLIDYFKNSI

EKHAEWRKYEFKFSATDSYSDISEFYREVEMQGYRIDWTYISEADINKLD

EEGKIYLFQIYNKDFAENSTGKENLHTMYFKNIFSEENLKDIIIKLNGQA

ELFYRRASVKNPVKHKKDSVLVNKTYKNQLDNGDVVRIPIPDDIYNEIYK

MYNGYIKESDLSEAAKEYLDKVEVRTAQKDIVKDYRYTVDKYFIHTPITI

NYKVTARNNVNDMVVKYIAQNDDIHVIGIDRGERNLIYISVIDSHGNIVK

QKSYNILNNYDYKKKLVEKEKTREYARKNWKSIGNIKELKEGYISGVVHE

IAMLIVEYNAIIAMEDLNYGFKRGRFKVERQVYQKFESMLINKLNYFASK

EKSVDEPGGLLKGYQLTYVPDNIKNLGKQCGVIFYVPAAFTSKIDPSTGF

ISAFNFKSISTNASRKQFFMQFDEIRYCAEKDMFSFGFDYNNFDTYNITM

GKTQWTVYTNGERLQSEFNNARRTGKTKSINLTETIKLLLEDNEINYADG

HDIRIDMEKMDEDKKSEFFAQLLSLYKLTVQMRNSYTEAEEQENGISYDK

IISPVINDEGEFFDSDNYKESDDKECKMPKDADANGAYCIALKGLYEVLK

IKSEWTEDGFDRNCLKLPHAEWLDFIQNKRYEKRPAATKKAGQAKKKKGS

YPYDVPDYAYPYDVPDYAYPYDVPDYA
```

*Eubacterium eligens* (EeCpf1;pY013), including NLS and HA tag:

(SEQ ID NO: 31)
```
MNGNRSIVYREFVGVIPVAKTLRNELRPVGHTQEHIIQNGLIQEDELRQE

KSTELKNIMDDYYREYIDKSLSGVTDLDFTLLFELMNLVQSSPSKDNKKA

LEKEQSKMREQICTHLQSDSNYKNIFNAKLLKEILPDFIKNYNQYDVKDK

AGKLETLALFNGFSTYFTDFFEKRKNVFTKEAVSTSIAYRIVHENSLIFL

ANMTSYKKISEKALDEIEVIEKNNQDKMGDWELNQIFNPDFYNMVLIQSG

IDFYNEICGVVNAHMNLYCQQTKNNYNLFKMRKLHKQILAYTSTSFEVPK

MFEDDMSVYNAVNAFIDETEKGNIIGKLKDIVNKYDELDEKRIYISKDFY

ETLSCFMSGNWNLITGCVENFYDENIHAKGKSKEEKVKKAVKEDKYKSIN

DVNDLVEKYIDEKERNEFKNSNAKQYIREISNIITDTETAHLEYDDHISL

IESEEKADEMKKRLDMYMNMYHWAKAFIVDEVLDRDEMFYSDIDDIYNIL

ENIVPLYNRVRNYVTQKPYNSKKIKLNFQSPTLANGWSQSKEFDNNAIIL

IRDNKYYLAIFNAKNKPDKKIIQGNSDKKNDNDYKKMVYNLLPGANKMLP

KVFLSKKGIETFKPSDYIISGYNAHKHIKTSENFDISFCRDLIDYFKNSI

EKHAEWRKYEFKFSATDSYSDISEFYREVEMQGYRIDWTYISEADINKLD

EEGKIYLFQIYNKDFAENSTGKENLHTMYFKNIFSEENLKDIIIKLNGQA

ELFYRRASVKNPVKHKKDSVLVNKTYKNQLDNGDVVRIPIPDDIYNEIYK

MYNGYIKESDLSEAAKEYLDKVEVRTAQKDIVKDYRYTVDKYFIHTPITI

NYKVTARNNVNDMVVKYIAQNDDIHVIGIDRGERNLIYISVIDSHGNIVK

QKSYNILNNYDYKKKLVEKEKTREYARKNWKSIGNIKELKEGYISGVVHE

IAMLIVEYNAIIAMEDLNYGFKRGRFKVERQVYQKFESMLINKLNYFASK

EKSVDEPGGLLKGYQLTYVPDNIKNLGKQCGVIFYVPAAFTSKIDPSTGF

ISAFNFKSISTNASRKQFFMQFDEIRYCAEKDMFSFGFDYNNFDTYNITM

GKTQWTVYTNGERLQSEFNNARRTGKTKSINLTETIKLLLEDNEINYADG

HDIRIDMEKMDEDKKSEFFAQLLSLYKLTVQMRNSYTEAEEQENGISYDK

IISPVINDEGEFFDSDNYKESDDKECKMPKDADANGAYCIALKGLYEVLK

IKSEWTEDGFDRNCLKLPHAEWLDFIQNKRYEKRPAATKKAGQAKKKKGS

YPYDVPDYAYPYDVPDYAYPYDVPDYA
```

SEQ ID NO: 31 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 31 may be encoded by the following nucleotide sequence:

SEQ ID NO: 31 may be encoded by the following nucleotide sequence:

(SEQ ID NO: 32)
```
ATGAACGGCAATAGGTCCATCGTGTACCGCGAGTTCGTG

GGCGTGATCCCCGTGGCCAAGACCCTGAGGAATGAGCTGCGCCCTGTGGG

CCACACACAGGAGCACATCATCCAGAACGGCCTGATCCAGGAGGACGAG

CTGCGGCAGGAGAAGAGCACCGAGCTGAAGAACATCATGGACGATTACT
```

```
ATAGAGAGTACATCGATAAGTCTCTGAGCGGCGTGACCGACCTGGACTTC
ACCCTGCTGTTCGAGCTGATGAACCTGGTGCAGAGCTCCCCCTCCAAGGA
CAATAAGAAGGCCCTGGAGAAGGAGCAGTCTAAGATGAGGGAGCAGATC
TGCACCCACCTGCAGTCCGACTCTAACTACAAGAATATCTTTAACGCCAA
GCTGCTGAAGGAGATCCTGCCTGATTTCATCAAGAACTACAATCAGTATG
ACGTGAAGGATAAGGCCGGCAAGCTGGAGACACTGGCCCTGTTTAATGGC
TTCAGCACATACTTTACCGACTTCTTTGAGAAGAGGAAGAACGTGTTCACC
AAGGAGGCCGTGAGCACATCCATCGCCTACCGCATCGTGCACGAGAACTC
CCTGATCTTCCTGGCCAATATGACCTCTTATAAGAAGATCAGCGAGAAGG
CCCTGGATGAGATCGAAGTGATCGAGAAGAACAATCAGGACAAGATGGG
CGATTGGGAGCTGAATCAGATCTTTAACCCTGACTTCTACAATATGGTGCT
GATCCAGTCCGGCATCGACTTCTACAACGAGATCTGCGGCGTGGTGAATG
CCCACATGAACCTGTACTGTCAGCAGACCAAGAACAATTATAACCTGTTC
AAGATGCGGAAGCTGCACAAGCAGATCCTGGCCTACACCAGCACCAGCTT
CGAGGTGCCCAAGATGTTCGAGGACGATATGAGCGTGTATAACGCCGTGA
ACGCCTTCATCGACGAGACAGAGAAGGGCAACATCATCGGCAAGCTGAA
GGATATCGTGAATAAGTACGACGAGCTGGATGAGAAGAGAATCTATATCA
GCAAGGACTTTTACGAGACACTGAGCTGCTTCATGTCCGGCAACTGGAAT
CTGATCACAGGCTGCGTGGAGAACTTCTACGATGAGAACATCCACGCCAA
GGGCAAGTCCAAGGAGGAGAAGGTGAAGAAGGCCGTGAAGGAGGACAA
GTACAAGTCTATCAATGACGTGAACGATCTGGTGGAGAAGTATATCGATG
AGAAGGAGAGGAATGAGTTCAAGAACAGCAATGCCAAGCAGTACATCCG
CGAGATCTCCAACATCATCACCGACACAGAGACAGCCCACCTGGAGTATG
ACGATCACATCTCTCTGATCGAGAGCGAGGAGAAGGCCGACGAGATGAA
GAAGCGGCTGGATATGTATATGAACATGTACCACTGGGCCAAGGCCTTTA
TCGTGGACGAGGTGCTGGACAGAGATGAGATGTTCTACAGCGATATCGAC
GATATCTATAATATCCTGGAGAACATCGTGCCACTGTATAATCGGGTGAG
AAACTACGTGACCCAGAAGCCCTACAACTCTAAGAAGATCAAGCTGAATT
TCCAGAGCCCTACACTGGCCAATGGCTGGTCCCAGTCTAAGGAGTTCGAC
AACAATGCCATCATCCTGATCAGAGATAACAAGTACTATCTGGCCATCTTC
AATGCCAAGAACAAGCCAGACAAGAAGATCATCCAGGGCAACTCCGATA
AGAAGAACGACAACGATTACAAGAAGATGGTGTATAACCTGCTGCCAGG
CGCCAACAAGATGCTGCCCAAGGTGTTTCTGTCTAAGAAGGGCATCGAGA
CATTCAAGCCCTCCGACTATATCATCTCTGGCTACAACGCCCACAAGCAC
ATCAAGACAAGCGAGAATTTTGATATCTCCTTCTGTCGGGACCTGATCGAT
TACTTCAAGAACAGCATCGAGAAGCACGCCGAGTGGAGAAAGTATGAGTT
CAAGTTTTCCGCCACCGACAGCTACTCCGATATCTCTGAGTTCTATCGGGA
GGTGGAGATGCAGGGCTACAGAATCGACTGGACATATATCAGCGAGGCC
GACATCAACAAGCTGGATGAGGAGGGCAAGATCTATCTGTTTCAGATCTA
CAATAAGGATTTCGCCGAGAACAGCACCGGCAAGGAGAATCTGCACACA
ATGTACTTTAAGAACATCTTCTCCGAGGAGAATCTGAAGGACATCATCAT
```
```
CAAGCTGAACGGCCAGGCCGAGCTGTTTTATCGGAGAGCCTCTGTGAAGA
ATCCCGTGAAGCACAAGAAGGATAGCGTGCTGGTGAACAAGACCTACAA
GAATCAGCTGGACAACGGCGACGTGGTGAGAATCCCCATCCCTGACGATA
TCTATAACGAGATCTACAAGATGTATAATGGCTACATCAAGGAGTCCGAC
CTGTCTGAGGCCGCCAAGGAGTACCTGGATAAGGTGGAGGTGAGGACCGC
CCAGAAGGACATCGTGAAGGATTACCGCTATACAGTGGACAAGTACTTCA
TCCACACACCTATCACCATCAACTATAAGGTGACCGCCCGCAACAATGTG
AATGATATGGTGGTGAAGTACATCGCCCAGAACGACGATATCCACGTGAT
CGGCATCGACCGGGGCGAGAGAAACCTGATCTACATCTCCGTGATCGATT
CTCACGGCAACATCGTGAAGCAGAAATCCTACAACATCCTGAACAACTAC
GACTACAAGAAGAAGCTGGTGGAGAAGGAGAAAACCCGGGAGTACGCCA
GAAAGAACTGGAAGAGCATCGGCAATATCAAGGAGCTGAAGGAGGGCTA
TATCTCCGGCGTGGTGCACGAGATCGCCATGCTGATCGTGGAGTACAACG
CCATCATCGCCATGGAGGACCTGAATTATGGCTTTAAGAGGGGCCGCTTC
AAGGTGGAGCGGCAGGTGTACCAGAAGTTTGAGAGCATGCTGATCAATAA
GCTGAACTATTTCGCCAGCAAGGAGAAGTCCGTGGACGAGCCAGGAGGCC
TGCTGAAGGGCTATCAGCTGACCTACGTGCCCGATAATATCAAGAACCTG
GGCAAGCAGTGCGGCGTGATCTTTTACGTGCCTGCCGCCTTCACCAGCAA
GATCGACCCATCCACAGGCTTTATCTCTGCCTTCAACTTTAAGTCTATCAG
CACAAATGCCTCTCGGAAGCAGTTCTTTATGCAGTTTGACGAGATCAGAT
ACTGTGCCGAGAAGGATATGTTCAGCTTTGGCTTCGACTACAACAACTTCG
ATACCTACAACATCACAATGGGCAAGACACAGTGGACCGTGTATACAAAC
GGCGAGAGACTGCAGTCTGAGTTCAACAATGCCAGGCGCACCGGCAAGA
CAAAGAGCATCAATCTGACAGAGACAATCAAGCTGCTGCTGGAGGACAAT
GAGATCAACTACGCCGACGGCCACGATATCAGGATCGATATGGAGAAGAT
GGACGAGGATAAGAAGAGCGAGTTCTTTGCCCAGCTGCTGAGCCTGTATA
AGCTGACCGTGCAGATGCGCAATTCCTATACAGAGGCCGAGGAGCAGGA
GAACGGCATCTCTTACGACAAGATCATCAGCCCTGTGATCAATGATGAGG
GCGAGTTCTTTGACTCCGATAACTATAAGGAGTCTGACGATAAGGAGTGC
AAGATGCCAAAGGACGCCGATGCCAACGGCGCCTACTGTATCGCCCTGAA
GGGCCTGTATGAGGTGCTGAAGATCAAGAGCGAGTGGACCGAGGACGGC
TTTGATAGGAATTGCCTGAAGCTGCCACACGCAGAGTGGCTGGACTTCAT
CCAGAACAAGCGGTACGAGAAAAGGCCGGCGGCCACGAAAAAGGCCGGC
CAGGCAAAAAGAAAAAGGGATCCTACCCATACGATGTTCCAGATTACGC
TTATCCCTACGACGTGCCTGATTATGCATACCCATATGATGTCCCCGACTA
TGCCTAA
```
*Moraxella bovoculi* 237 (MbCpf1; pY014), including NLS and HA tag:

(SEQ ID NO: 33)

MLFQDFTHLYPLSKTVRFELKPIDRTLEHIHAKNFLSQDETM
ADMHQKVKVILDDYHRDFIADMMGEVKLTKLAEFYDVYLKFRKNPKDDEL
QKQLKDLQAVLRKEIVKPIGNGGKYKAGYDRLFGAKLFKDGKELGDLAKFV

-continued

IAQEGESSPKLAHLAHFEKFSTYFTGFHDNRKNMYSDEDKHTAIAYRLIHE

NLPRFIDNLQILTTIKQKHSALYDQIINELTASGLDVSLASHLDGYHKLLT

QEGITAYNTLLGGISGEAGSPKIQGINELINSHHNQHCHKSERIAKLRPLH

KQILSDGMSVSFLPSKFADDSEMCQAVNEFYRHYADVFAKVQSLFDGFDDH

QKDGIYVEHKNLNELSKQAFGDFALLGRVLDGYYVDVVNPEFNERFAKAKT

DNAKAKLTKEKDKFIKGVHSLASLEQAIEHYTARHDDESVQAGKLGQYFKH

GLAGVDNPIQKIHNNHSTIKGFLERERPAGERALPKIKSGKNPEMTQLRQL

KELLDNALNVAHFAKLLTTKTTLDNQDGNFYGEFGVLYDELAKIPTLYNKV

RDYLSQKPFSTEKYKLNFGNPTLLNGWDLNKEKDNFGVILQKDGCYYLALL

DKAHKKVFDNAPNTGKSIYQKMIYKYLEVRKQFPKVFFSKEAIAINYHPSK

ELVEIKDKGRQRSDDERLKLYRFILECLKIHPKYDKKFEGAIGDIQLFKKD

KKGREVPISEKDLFDKINGIFSSKPKLEMEDFFIGEFKRYNPSQDLVDQYN

IYKKIDSNDNRKKENFYNNHPKFKKDLVRYYYESMCKHEEWEESFEFSKKL

QDIGCYVDVNELFTEIETRRLNYKISFCNINADYIDELVEQGQLYLFQIYN

KDFSPKAHGKPNLHTLYFKALFSEDNLADPIYKLNGEAQIFYRKASLDMNE

TTIHRAGEVLENKNPDNPKKRQFVYDIIKDKRYTQDKFMLHVPITMNFGVQ

GMTIKEFNKKVNQSIQQYDEVNVIGIDRGERHLLYLTVINSKGEILEQCSL

NDITTASANGTQMTTPYHKILDKREIERLNARVGWGEIETIKELKSGYLSH

VVHQISQLMLKYNAIVVLEDLNFGFKRGRFKVEKQIYQNFENALIKKLNHL

VLKDKADDEIGSYKNALQLTNNFTDLKSIGKQTGFLFYVPAWNTSKIDPET

GFVDLLKPRYENIAQSQAFFGKFDKICYNADKDYFEFHIDYAKFTDKAKNS

RQIWTICSHGDKRYVYDKTANQNKGAAKGINVNDELKSLFARHHINEKQPN

LVMDICQNNDKEFHKSLMYLLKTLLALRYSNASSDEDFILSPVANDEGVFF

NSALADDTQPQNADANGAYHIALKGLWLLNELKNSDDLNKVKLAIDNQTWL

NFAQNRKRPAATKKAGQAKKKKGSYPYDVPDYAYPYDVPDYAYPYDVPDYA

Moraxella bovoculi 237 (MbCpf1; pY014), including NLS and HA tag:

(SEQ ID NO: 33)
MLFQDFTHLYPLSKTVRFELKPIDRTLEHIHAKNFLSQDETMADMHQKVK

VILDDYHRDFIADMMGEVKLTKLAEFYDVYLKFRKNPKDDELQKQLKDLQ

AVLRKEIVKPIGNGGKYKAGYDRLFGAKLFKDGKELGDLAKFVIAQEGES

SPKLAHLAHFEKFSTYFTGFHDNRKNMYSDEDKHTAIAYRLIHENLPRFI

DNLQILTTIKQKHSALYDQIINELTASGLDVSLASHLDGYHKLLTQEGIT

AYNTLLGGISGEAGSPKIQGINELINSHHNQHCHKSERIAKLRPLHKQIL

SDGMSVSFLPSKFADDSEMCQAVNEFYRHYADVFAKVQSLFDGFDDHQKD

GIYVEHKNLNELSKQAFGDFALLGRVLDGYYVDVVNPEFNERFAKAKTDN

AKAKLTKEKDKFIKGVHSLASLEQAIEHYTARHDDESVQAGKLGQYFKHG

LAGVDNPIQKIHNNHSTIKGFLERERPAGERALPKIKSGKNPEMTQLRQL

KELLDNALNVAHFAKLLTTKTTLDNQDGNFYGEFGVLYDELAKIPTLYNK

VRDYLSQKPFSTEKYKLNFGNPTLLNGWDLNKEKDNFGVILQKDGCYYLA

-continued

LLDKAHKKVFDNAPNTGKSIYQKMIYKYLEVRKQFPKVFFSKEAIAINYH

PSKELVEIKDKGRQRSDDERLKLYRFILECLKIHPKYDKKFEGAIGDIQL

FKKDKKGREVPISEKDLFDKINGIFSSKPKLEMEDFFIGEFKRYNPSQDL

VDQYNIYKKIDSNDNRKKENFYNNHPKFKKDLVRYYYESMCKHEEWEESF

EFSKKLQDIGCYVDVNELFTEIETRRLNYKISFCNINADYIDELVEQGQL

YLFQIYNKDFSPKAHGKPNLHTLYFKALFSEDNLADPIYKLNGEAQIFYR

KASLDMNETTIHRAGEVLENKNPDNPKKRQFVYDIIKDKRYTQDKFMLHV

PITMNFGVQGMTIKEFNKKVNQSIQQYDEVNVIGIDRGERHLLYLTVINS

KGEILEQCSLNDITTASANGTQMTTPYHKILDKREIERLNARVGWGEIET

IKELKSGYLSHVVHQISQLMLKYNAIVVLEDLNFGFKRGRFKVEKQIYQN

FENALIKKLNHLVLKDKADDEIGSYKNALQLTNNFTDLKSIGKQTGFLFY

VPAWNTSKIDPETGFVDLLKPRYENIAQSQAFFGKFDKICYNADKDYFEF

HIDYAKFTDKAKNSRQIWTICSHGDKRYVYDKTANQNKGAAKGINVNDEL

KSLFARHHINEKQPNLVMDICQNNDKEFHKSLMYLLKTLLALRYSNASSD

EDFILSPVANDEGVFFNSALADDTQPQNADANGAYHIALKGLWLLNELKN

SDDLNKVKLAIDNQTWLNFAQNRKRPAATKKAGQAKKKKGSYPYDVPDYA

YPYDVPDYAYPYDVPDYA

SEQ ID NO: 33 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 33 may be encoded by the following nucleotide sequence:

```
SEQ ID NO: 33 may be encoded by the following
nucleotide sequence:
                                       (SEQ ID NO: 34)
ATGCTGTTCCAGGACTTTACCCACCTGTATCCACTGTCCA

AGACAGTGAGATTTGAGCTGAAGCCCATCGATAGGACCCTGGAGCACATC

CACGCCAAGAACTTCCTGTCTCAGGACGAGACAATGGCCGATATGCACCA

GAAGGTGAAAGTGATCCTGGACGATTACCACCGCGACTTCATCGCCGATA

TGATGGGCGAGGTGAAGCTGACCAAGCTGGCCGAGTTCTATGACGTGTAC

CTGAAGTTTCGGAAGAACCCAAAGGACGATGAGCTGCAGAAGCAGCTGA

AGGATCTGCAGGCCGTGCTGAGAAAGGAGATCGTGAAGCCCATCGGCAAT

GGCGGCAAGTATAAGGCCGGCTACGACAGGCTGTTCGGCGCCAAGCTGTT

TAAGGACGGCAAGGAGCTGGGCGATCTGGCCAAGTTCGTGATCGCACAGG

AGGGAGAGAGCTCCCCAAAGCTGGCCCACCTGGCCCACTTCGAGAAGTTT

TCCACCTATTTCACAGGCTTTCACGATAACCGGAAGAATATGTATTCTGAC

GAGGATAAGCACACCGCCATCGCCTACCGCCTGATCCACGAGAACCTGCC

CCGGTTTATCGACAATCTGCAGATCCTGACCACAATCAAGCAGAAGCACT

CTGCCCTGTACGATCAGATCATCAACGAGCTGACCGCCAGCGGCCTGGAC

GTGTCTCTGGCCAGCCACCTGGATGGCTATCACAAGCTGCTGACACAGGA

GGGCATCACCGCCTACAATACACTGCTGGGAGGAATCTCCGGAGAGGCAG

GCTCTCCTAAGATCCAGGGCATCAACGAGCTGATCAATTCTCACCACAAC
```

-continued

```
CAGCACTGCCACAAGAGCGAGAGAATCGCCAAGCTGAGGCCACTGCACA
AGCAGATCCTGTCCGACGGCATGAGCGTGTCCTTCCTGCCCTCTAAGTTTG
CCGACGATAGCGAGATGTGCCAGGCCGTGAACGAGTTCTATCGCCACTAC
GCCGACGTGTTCGCCAAGGTGCAGAGCCTGTTCGACGGCTTTGACGATCA
CCAGAAGGATGGCATCTACGTGGAGCACAAGAACCTGAATGAGCTGTCCA
AGCAGGCCTTCGGCGACTTTGCACTGCTGGGACGCGTGCTGGACGGATAC
TATGTGGATGTGGTGAATCCAGAGTTCAACGAGCGGTTTGCCAAGGCCAA
GACCGACAATGCCAAGGCCAAGCTGACAAAGGAGAAGGATAAGTTCATC
AAGGGCGTGCACTCCCTGGCCTCTCTGGAGCAGGCCATCGAGCACTATAC
CGCAAGGCACGACGATGAGAGCGTGCAGGCAGGCAAGCTGGGACAGTAC
TTCAAGCACGGCCTGGCCGGAGTGGACAACCCCATCCAGAAGATCCACAA
CAATCACAGCACCATCAAGGGCTTTCTGGAGAGGGAGCGCCCTGCAGGAG
AGAGAGCCCTGCCAAAGATCAAGTCCGGCAAGAATCCTGAGATGACACA
GCTGAGGCAGCTGAAGGAGCTGCTGGATAACGCCCTGAATGTGGCCCACT
TCGCCAAGCTGCTGACCACAAAGACCACACTGGACAATCAGGATGGCAAC
TTCTATGGCGAGTTTGGCGTGCTGTACGACGAGCTGGCCAAGATCCCCAC
CCTGTATAACAAGGTGAGAGATTACCTGAGCCAGAAGCCTTTCTCCACCG
AGAAGTACAAGCTGAACTTTGGCAATCCAACACTGCTGAATGGCTGGAC
CTGAACAAGGAGAAGGATAATTTCGGCGTGATCCTGCAGAAGGACGGCTG
CTACTATCTGGCCCTGCTGGACAAGGCCCACAAGAAGGTGTTTGATAACG
CCCCTAATACAGGCAAGAGCATCTATCAGAAGATGATCTATAAGTACCTG
GAGGTGAGGAAGCAGTTCCCCAAGGTGTTCTTTTCCAAGGAGGCCATCGC
CATCAACTACCACCCTTCTAAGGAGCTGGTGGAGATCAAGGACAAGGCC
GGCAGAGATCCGACGATGAGCGCCTGAAGCTGTATCGGTTTATCCTGGAG
TGTCTGAAGATCCACCCTAAGTACGATAAGAAGTTCGAGGGCGCCATCGG
CGACATCCAGCTGTTTAAGAAGGATAAGAAGGGCAGAGAGGTGCCAATC
AGCGAGAAGGACCTGTTCGATAAGATCAACGGCATCTTTTCTAGCAAGCC
TAAGCTGGAGATGGAGGACTTCTTTATCGGCGAGTTCAAGAGGTATAACC
CAAGCCAGGACCTGGTGGATCAGTATAATATCTACAAGAAGATCGACTCC
AACGATAATCGCAAGAAGGAGAATTTCTACAACAATCACCCCAAGTTTAA
GAAGGATCTGGTGCGGTACTATTACGAGTCTATGTGCAAGCACGAGGAGT
GGGAGGAGAGCTTCGAGTTTTCCAAGAAGCTGCAGGACATCGGCTGTTAC
GTGGATGTGAACAGCTGTTTACCGAGATCGAGACACGGAGACTGAATTA
TAAGATCTCCTTCTGCAACATCAATGCCGACTACATCGATGAGCTGGTGG
AGCAGGGCCAGCTGTATCTGTTCCAGATCTACAACAAGGACTTTTCCCCA
AAGGCCCACGGCAAGCCCAATCTGCACACCCTGTACTTCAAGGCCCTGTT
TTCTGAGGACAACCTGGCCGATCCTATCTATAAGCTGAATGGCGAGGCCC
AGATCTTCTACAGAAAGGCCTCCCTGGACATGAACGAGACAACAATCCAC
AGGGCCGGCGAGGTGCTGGAGAACAAGAATCCCGATAATCCTAAGAAGA
GACAGTTCGTGTACGACATCATCAAGGATAAGAGGTACACACAGGACAA
GTTCATGCTGCACGTGCCAATCACCATGAACTTTGGCGTGCAGGGCATGA
CAATCAAGGAGTTCAATAAGAAGGTGAACCAGTCTATCCAGCAGTATGAC
GAGGTGAACGTGATCGGCATCGATCGGGGCGAGAGACACCTGCTGTACCT
GACCGTGATCAATAGCAAGGGCGAGATCCTGGAGCAGTGTTCCCTGAACG
ACATCACCACAGCCTCTGCCAATGGCACACAGATGACCACACCTTACCAC
AAGATCCTGGATAAGAGGGAGATCGAGCGCCTGAACGCCCGGGTGGGAT
GGGGCGAGATCGAGACAATCAAGGAGCTGAAGTCTGGCTATCTGAGCCAC
GTGGTGCACCAGATCAGCCAGCTGATGCTGAAGTACAACGCCATCGTGGT
GCTGGAGGACCTGAATTTCGGCTTTAAGAGGGGCCGCTTTAAGGTGGAGA
AGCAGATCTATCAGACTTCGAGAATGCCCTGATCAAGAAGCTGAACCAC
CTGGTGCTGAAGGACAAGGCCGACGATGAGATCGGCTCTTACAAGAATGC
CCTGCAGCTGACCAACAATTTCACAGATCTGAAGAGCATCGGCAAGCAGA
CCGGCTTCCTGTTTTATGTGCCCGCCTGGAACACCTCTAAGATCGACCCTG
AGACAGGCTTTGTGGATCTGCTGAAGCCAAGATACGAGAACATCGCCCAG
AGCCAGGCCTTCTTTGGCAAGTTCGACAAGATCTGCTATAATGCCGACAA
GGATTACTTCGAGTTTCACATCGACTACGCCAAGTTTACCGATAAGGCCA
AGAATAGCCGCCAGATCTGGACAATCTGTTCCCACGGCGACAAGCGGTAC
GTGTACGATAAGACAGCCAACCAGAATAAGGGCGCCGCCAAGGGCATCA
ACGTGAATGATGAGCTGAAGTCCCTGTTCGCCCGCCACCACATCAACGAG
AAGCAGCCCAACCTGGTCATGGACATCTGCCAGAACAATGATAAGGAGTT
TCACAAGTCTCTGATGTACCTGCTGAAAACCCTGCTGGCCCTGCGGTACAG
CAACGCCTCCTCTGACGAGGATTTCATCCTGTCCCCCGTGGCAAACGACG
AGGGCGTGTTCTTTAATAGCGCCCTGGCCGACGATACACAGCCTCAGAAT
GCCGATGCCAACGGCGCCTACCACATCGCCCTGAAGGGCCTGTGGCTGCT
GAATGAGCTGAAGAACTCCGACGATCTGAACAAGGTGAAGCTGGCCATCG
ACAATCAGACCTGGCTGAATTTCGCCCAGAACAGGAAAAGGCCGGCGGC
CACGAAAAAGGCCGGCCAGGCAAAAAAGAAAAAGGGATCCTACCCATAC
GATGTTCCAGATTACGCTTATCCCTACGACGTGCCTGATTATGCATACC
CATATGATGTCCCCGACTATGCCTAA
```

*Leptospira inadai* (LiCpf1; pY015), including NLS and HA tag:

(SEQ ID NO: 35)
MEDYSGFVNIYSIQKTLRFELKPVGKTLEHIEKKGFLKKDKI
RAEDYKAVKKIIDKYHRAYIEEVFDSVLHQKKKKDKTRFSTQFIKEIKEFS
ELYYKTEKNIPDKERLEALSEKLRKMLVGAFKGEFSEEVAEKYKNLFSKEU
RNEIEKFCETDEERKQVSNFKSFTTYFTGFHSNRQNIYSDEKKSTAIGYRI
IHQNLPKFLDNLKIIESIQRRFKDFPWSDLKKNLKKIDKNIKLTEYFSIDG
FVNVLNQKGIDAYNTILGGKSEESGEKIQGLNEYINLYRQKNNIDRKNLPN
VKILFKQILGDRETKSFIPEAFPDDQSVLNSITEFAKYLKLDKKKKSIIAE
LKKFLSSFNRYELDGIYLANDNSLASISTFLFDDWSFIKKSVSFKYDESVG
DPKKKIKSPLKYEKEKEKWLKQKYYTISFLNDAIESYSKSQDEKRVKIRLE
AYFAEFKSKDDAKKQFDLLERIEEAYAIVEPLLGAEYPRDRNLKADKKEVG

KIKDFLDSIKSLQFFLKPLLSAEIFDEKDLGFYNQLEGYYEEIDSIGHLYN

KVRNYLTGKIYSKEKFKLNFENSTLLKGWDENREVANLCVIFREDQKYYLG

VMDKENNTILSDIPKVKPNELFYEKMVYKLIPTPHMQLPRIIFSSDNLSIY

NPSKSILKIREAKSFKEGKNFKLKDCHKFIDFYKESISKNEDWSRFDFKFS

KTSSYENISEFYREVERQGYNLDFKKVSKFYIDSLVEDGKLYLFQIYNKDF

SIFSKGKPNLHTIYFRSLFSKENLKDVCLKLNGEAEMFFRKKSINTYDEKK

KREGHHPELFEKLKYPILKDKRYSEDKFQFHLPISLNFKSKERLNFNLKVN

EFLKRNKDINIIGIDRGERNLLYLVMINQKGEILKQTLLDSMQSGKGRPEI

NYKEKLQEKEIERDKARKSWGTVENIKELKEGYLSIVIHQISKLMVENNAI

VVLEDLNIGFKRGRQKVERQVYQKFEKMLIDKLNFLVFKENKPTEPGGVLK

AYQLTDEFQSFEKLSKQTGFLFYVPSWNTSKIDPRTGFIDFLHPAYENIEK

AKQWINKFDSIRFNSKMDWFEFTADTRKFSENLMLGKNRVWVICTTNVERY

FTSKTANSSIQYNSIQITEKLKELFVDIPFSNGQDLKPEILRKNDAVFFKS

LLFYIKTTLSLRQNNGKKGEEEKDFILSPVVDSKGRFFNSLEASDDEPKDA

DANGAYHIALKGLMNLLVLNETKEENLSRPKWKIKNKDWLEFVWERNRKRP

AATKKAGQAKKKKGSYPYDVPDYAYPYDVPDYAYPYDVPDYA

*Leptospira inadai* (LiCpf1;pY015), including NLS and HA tag:

(SEQ ID NO: 35)
MEDYSGFVNIYSIQKTLRFELKPVGKTLEHIEKKGFLKKDKIRAEDYKAV

KKIIDKYHRAYIEEVFDSVLHQKKKKDKTRFSTQFIKEIKEFSELYYKTE

KNIPDKERLEALSEKLRKMLVGAFKGEFSEEVAEKYKNLFSKELIRNEIE

KFCETDEERKQVSNFKSFTTYFTGFHSNRQNIYSDEKKSTAIGYRIIHQN

LPKFLDNLKIIESIQRRFKDFPWSDLKKNLKKIDKNIKLTEYFSIDGFVN

VLNQKGIDAYNTILGGKSEESGEKIQGLNEYINLYRQKNNIDRKNLPNVK

ILFKQILGDRETKSFIPEAFPDDQSVLNSITEFAKYLKLDKKKKSIIAEL

KKFLSSFNRYELDGIYLANDNSLASISTFLFDDWSFIKKSVSFKYDESVG

DPKKKIKSPLKYEKEKEKWLKQKYYTISFLNDAIESYSKSQDEKRVKIRL

EAYFAEFKSKDDAKKQFDLLERIEEAYAIVEPLLGAEYPRDRNLKADKKE

VGKIKDFLDSIKSLQFFLKPLLSAEIFDEKDLGFYNQLEGYYEEIDSIGH

LYNKVRNYLTGKIYSKEKFKLNFENSTLLKGWDENREVANLCVIFREDQK

YYLGVMDKENNTILSDIPKVKPNELFYEKMVYKLIPTPHMQLPRIIFSSD

NLSIYNPSKSILKIREAKSFKEGKNFKLKDCHKFIDFYKESISKNEDWSR

FDFKFSKTSSYENISEFYREVERQGYNLDFKKVSKFYIDSLVEDGKLYLF

QIYNKDFSIFSKGKPNLHTIYFRSLFSKENLKDVCLKLNGEAEMFFRKKS

INTYDEKKKREGHHPELFEKLKYPILKDKRYSEDKFQFHLPISLNFKSKER

LNFNLKVNEFLKRNKDINIIGIDRGERNLLYLVMINQKGEILKQTLLDSM

QSGKGRPEINYKEKLQEKEIERDKARKSWGTVENIKELKEGYLSIVIHQI

SKLMVENNAIVVLEDLNIGFKRGRQKVERQVYQKFEKMLIDKLNFLVFKE

NKPTEPGGVLKAYQLTDEFQSFEKLSKQTGFLFYVPSWNTSKIDPRTGFI

DFLHPAYENIEKAKQWINKFDSIRFNSKMDWFEFTADTRKFSENLMLGKN

RVWVICTTNVERYFTSKTANSSIQYNSIQITEKLKELFVDIPFSNGQDLK

PEILRKNDAVFFKSLLFYIKTTLSLRQNNGKKGEEEKDFILSPVVDSKGR

FFNSLEASDDEPKDADANGAYHIALKGLMNLLVLNETKEENLSRPKWKIK

NKDWLEFVWERNRKRPAATKKAGQAKKKKGSYPYDVPDYAYPYDVPDYAY

PYDVPDYA

SEQ ID NO: 35 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 35 may be encoded by the following nucleotide sequence:

SEQ ID NO: 35 may be encoded by the following nucleotide sequence:

(SEQ ID NO: 36)
ATGGAGGACTATTCCGGCTTTGTGAACATCTACTCTATCC

AGAAAACCCTGAGGTTCGAGCTGAAGCCAGTGGGCAAGACACTGGAGCA

CATCGAGAAGAAGGGCTTCCTGAAGAAGGACAAGATCCGGGCCGAGGAT

TACAAGGCCGTGAAGAAGATCATCGATAAGTACCACAGAGCCTATATCGA

GGAGGTGTTTGATTCCGTGCTGCACCAGAAGAAGAAGAAGGACAAGACC

CGCTTTTCTACACAGTTCATCAAGGAGATCAAGGAGTTCAGCGAGCTGTA

CTATAAGACCGAGAAGAACATCCCCGACAAGGAGAGGCTGGAGGCCCTG

AGCGAGAAGCTGCGCAAGATGCTGGTGGGCGCCTTTAAGGGCGAGTTCTC

CGAGGAGGTGGCCGAGAAGTATAAGAACCTGTTTTCTAAGGAGCTGATCA

GGAATGAGATCGAGAAGTTCTGCGAGACAGACGAGGAGCGCAAGCAGGT

GTCTAACTTCAAGAGCTTCACCACATACTTTACCGGCTTCCACTCCAACAG

GCAGAATATCTATTCCGACGAGAAGAAGTCTACAGCCATCGGCTACCGCA

TCATCCACCAGAACCTGCCTAAGTTCCTGGATAATCTGAAGATCATCGAGT

CCATCCAGCGGCGGTTCAAGGACTTCCCATGGTCTGATCTGAAGAAGAAC

CTGAAGAAGATCGATAAGAATATCAAGCTGACCGAGTACTTCAGCATCGA

CGGCTTCGTGAACGTGCTGAATCAGAAGGGCATCGATGCCTACAACACAA

TCCTGGGCGGCAAGTCCGAGGAGTCTGGCGAGAAGATCCAGGGCCTGAAC

GAGTACATCAATCTGTATCGGCAGAAGAACAATATCGACAGAAAGAACCT

GCCCAATGTGAAGATCCTGTTTAAGCAGATCCTGGGCGATAGGGAGACAA

AGAGCTTTATCCCTGAGGCCTTCCCAGACGATCAGTCCGTGCTGAACTCTA

TCACAGAGTTCGCCAAGTACCTGAAGCTGGATAAGAAGAAGAAGAGCAT

CATCGCCGAGCTGAAGAAGTTTCTGAGCTCCTTCAATCGCTACGAGCTGG

ACGGCATCTATCTGGCCAACGATAATAGCCTGGCCTCTATCAGCACCTTCC

TGTTTGACGATTGGTCCTTTATCAAGAAGTCCGTGTCTTTCAAGTATGACG

AGTCCGTGGGCGACCCCAAGAAGAAGATCAAGTCTCCCCTGAAGTACGAG

AAGGAGAAGGAGAAGTGGCTGAAGCAGAAGTACTATACAATCTCTTTCCT

GAACGATGCCATCGAGAGCTATTCCAAGTCTCAGGACGAGAAGAGGGTG

AAGATCCGCCTGGAGGCCTACTTTGCCGAGTTCAAGAGCAAGGACGATGC

```
CAAGAAGCAGTTCGACCTGCTGGAGAGGATCGAGGAGGCCTATGCCATCG
TGGAGCCTCTGCTGGGAGCAGAGTACCCAAGGGACCGCAACCTGAAGGC
CGATAAGAAGGAAGTGGGCAAGATCAAGGACTTCCTGGATAGCATCAAG
TCCCTGCAGTTCTTTCTGAAGCCTCTGCTGTCCGCCGAGATCTTTGACGAG
AAGGATCTGGGCTTCTACAATCAGCTGGAGGGCTACTATGAGGAGATCGA
TTCTATCGGCCACCTGTATAACAAGGTGCGGAATTATCTGACCGGCAAGA
TCTACAGCAAGGAGAAGTTTAAGCTGAACTTCGAGAACAGCACCCTGCTG
AAGGGCTGGGACGAGAACCGGGAGGTGGCCAATCTGTGCGTGATCTTCAG
AGAGGACCAGAAGTACTATCTGGGCGTGATGGATAAGGAGAACAATACC
ATCCTGTCCGACATCCCCAAGGTGAAGCCTAACGAGCTGTTTTACGAGAA
GATGGTGTATAAGCTGATCCCCACACCTCACATGCAGCTGCCCCGGATCA
TCTTCTCTAGCGACAACCTGTCTATCTATAATCCTAGCAAGTCCATCCTGA
AGATCAGAGAGGCCAAGAGCTTTAAGGAGGGCAAGAACTTCAAGCTGAA
GGACTGTCACAAGTTTATCGATTTCTACAAGGAGTCTATCAGCAAGAATG
AGGACTGGAGCAGATTCGACTTCAAGTTCAGCAAGACCAGCAGCTACGAG
AACATCAGCGAGTTTTACCGGGAGGTGGAGAGACAGGGCTATAACCTGGA
CTTCAAGAAGGTGTCTAAGTTCTACATCGACAGCCTGGTGGAGGATGGCA
AGCTGTACCTGTTCCAGATCTATAACAAGGACTTTTCTATCTTCAGCAAGG
GCAAGCCCAATCTGCACACCATCTATTTTCGGTCCCTGTTCTCTAAGGAGA
ACCTGAAGGACGTGTGCCTGAAGCTGAATGGCGAGGCCGAGATGTTCTTT
CGGAAGAAGTCCATCAACTACGATGAGAAGAAGAAGCGGGAGGGCCACC
ACCCCGAGCTGTTTGAGAAGCTGAAGTATCCTATCCTGAAGGACAAGAGA
TACAGCGAGGATAAGTTTCAGTTCCACCTGCCCATCAGCCTGAACTTCAA
GTCCAAGGAGCGGCTGAACTTTAATCTGAAAGTGAATGAGTTCCTGAAGA
GAAACAAGGACATCAATATCATCGGCATCGATCGGGGCGAGAGAAACCT
GCTGTACCTGGTCATGATCAATCAGAAGGGCGAGATCCTGAAGCAGACCC
TGCTGGACAGCATGCAGTCCGGCAAGGGCCGGCCTGAGATCAACTACAAG
GAGAAGCTGCAGGAGAAGGAGATCGAGAGGGATAAGGCCCGCAAGAGCT
GGGGCACAGTGGAGAATATCAAGGAGCTGAAGGAGGGCTATCTGTCTATC
GTGATCCACCAGATCAGCAAGCTGATGGTGGAGAACAATGCCATCGTGGT
GCTGGAGGACCTGAACATCGGCTTTAAGCGGGGCAGACAGAAGGTGGAG
CGGCAGGTGTACCAGAAGTTCGAGAAGATGCTGATCGATAAGCTGAACTT
TCTGGTGTTCAAGGAGAATAAGCCAACCGAGCCAGGAGGCGTGCTGAAG
GCCTATCAGCTGACAGACGAGTTTCAGTCTTTCGAGAAGCTGAGCAAGCA
GACCGGCTTTCTGTTCTACGTGCCAAGCTGGAACACCTCCAAGATCGACC
CCAGAACAGGCTTTATCG ATTTCCTGCACCCTGCCTACGAGAATATCGAG
AAGGCCAAGCAGTGGATCAACAAGTTTGATTCCATCAGGTTCAATTCTAA
GATGACTGGTTTGAGTTCACCGCCGATACACGCAAGTTTTCCGAGAACC
TGATGCTGGGCAAGAATCGGGTGTGGGTCATCTGCACCACAAATGTGGAG
CGGTACTTCACCAGCAAGACCGCCAACAGCTCCATCCAGTACAATAGCAT
CCAGATCACCGAGAAGCTGAAGGAGCTGTTTGTGGACATCCCTTTCAGCA
```

```
ACGGCCAGGATCTGAAGCCAGAGATCCTGAGGAAGAATGACGCCGTGTTC
TTTAAGAGCCTGCTGTTTTACATCAAGACCACACTGTCCCTGCGCCAGAAC
AATGGCAAGAAGGGCGAGGAGGAGAAGGACTTCATCCTGAGCCCAGTGG
TGGATTCCAAGGGCCGGTTCTTTAACTCTCTGGAGGCCAGCGACGATGAG
CCCAAGGACGCCGATGCCAATGGCGCCTACCACATCGCCCTGAAGGGCCT
GATGAACCTGCTGGTGCTGAATGAGACAAAGGAGGAGAACCTGAGCAGA
CCAAAGTGGAAGATCAAGAATAAGGACTGGCTGGAGTTCGTGTGGGAGA
GGAACCGCAAAAGGCCGGCGGCCACGAAAAAGGCCGGCCAGGCAAAAA
AGAAAAAGGGATCCTACCCATACGATGTTCCAGATTACGCTTATCCCTAC
GACGTGCCTGATTATGCATACCCATATGATGTCCCCGACTATGCCTAA
```

Lachnospiraceae bacterium ND2006 (LbCpf1; pY016),
including NLS and HA tag:

(SEQ ID NO: 37)

MSKLEKFTNCYSLSKTLRFKAIPVGKTQENIDNKRLLVEDE
KRAEDYKGVKKLLDRYYLSFINDVLHSIKLKNLNNYISLFRKKTRTEKENK
ELENLEINLRKEIAKAFKGNEGYKSLFKKDIIETILPEFLDDKDEIALVNS
FNGFTTAFTGFFDNRENMFSEEAKSTSIAFRCINENLTRYISNMDIFEKVD
AIFDKHEVQEIKEKILNSDYDVEDFFEGEFFNFVLTQEGIDVYNAIIGGFV
TESGEKIKGLNEYINLYNQKTKQKLPKFKPLYKQVLSDRESLSFYGEGYTS
DEEVLEVFRNTLNKNSEIFSSIKKLEKLFKNFDEYSSAGIFVKNGPAISTI
SKDIFGEWNVIRDKWNAEYDDIHLKKKAVVTEKYEDDRRKSFKKIGSFSLE
QLQEYADADLSVVEKLKEIIIQKVDEIYKVYGSSEKLFDADFVLEKSLKKN
DAVVAIMKDLLDSVKSFENYIKAFFGEGKETNRDESFYGDFVLAYDILLKV
DHIYDAIRNYVTQKPYSKDKFKLYFQNPQFMGGWDKDKETDYRATILRYGS
KYYLAIMDKKYAKCLQKIDKDDVNGNYEKINYKLLPGPNKMLPKVFFSKKW
MAYYNPSEDIQKIYKNGTFKKGDMFNLNDCHKLIDFFKDSISRYPKWSNAY
DFNFSETEKYKDIAGFYREVEEQGYKVSFESASKKEVDKLVEEGKLYMFQI
YNKDFSDKSHGTPNLHTMYFKLLFDENNHGQIRLSGGAELFMRRASLKKEE
LVVHPANSPIANKNPDNPKKTTTLSYDVYKDKRFSEDQYELHIPIAINKCP
KNIPKINTEVRVLLKHDDNPYVIGIDRGERNLLYIVVVDGKGNIVEQYSLN
EIINNFNGIRIKTDYHSLLDKKEKERFEARQNWTSIENIKELKAGYISQVV
HKICELVEKYDAVIALEDLNSGFKNSRVKVEKQVYQKFEKMLIDKLNYMVD
KKSNPCATGGALKGYQITNKFESFKSMSTQNGFIFYIPAWLTSKIDPSTGF
VNLLKTKYTSIADSKKFISSFDRIMYVPEEDLFEFALDYKNFSRTDADYIK
KWKLYSYGNRIRIFRNPKKNNVFDWEEVCLTSAYKELFNKYGINYQQGDIR
ALLCEQSDKAFYSSFMALMSLMLQMRNSITGRTDVDFLISPVKNSDGIFYD
SRNYEAQENAILPKNADANGAYNIARKVLWAIGQFKKAEDEKLDKVKIAIS
NKEWLEYAQTSVKHKRPAATKKAGQAKKKKGSYPYDVPDYAYPYDVPDYAY
PYDVPDYA

Lachnospiraceae bacterium ND2006 (LbCpf1;pY016), including NLS and HA tag:

(SEQ ID NO: 37)
MSKLEKFTNCYSLSKTLRFKAIPVGKTQENIDNKRLLVEDEKRAEDYKGV
KKLLDRYYLSFINDVLHSIKLKNLNNYISLFRKKTRTEKENKELENLEIN
LRKEIAKAFKGNEGYKSLFKKDIIETILPEFLDDKDEIALVNSFNGFTTA
FTGFFDNRENMFSEEAKSTSIAFRCINENLTRYISNMDIFEKVDAIFDKH
EVQEIKEKILNSDYDVEDFFEGEFFNFVLTQEGIDVYNAIIGGFVTESGE
KIKGLNEYINLYNQKTKQKLPKFKPLYKQVLSDRESLSFYGEGYTSDEEV
LEVFRNTLNKNSEIFSSIKKLEKLFKNFDEYSSAGIFVKNGPAISTISKD
IFGEWNVIRDKWNAEYDDIHLKKKAVVTEKYEDDRRKSFKKIGSFSLEQL
QEYADADLSVVEKLKEIIQKVDEIYKVYGSSEKLFDADFVLEKSLKKND
AVVAIMKDLLDSVKSFENYIKAFFGEGKETNRDESFYGDFVLAYDILLKV
DHIYDAIRNYVTQKPYSKDKFKLYFQNPQFMGGWDKDKETDYRATILRYG
SKYYLAIMDKKYAKCLQKIDKDDVNGNYEKINYKLLPGPNKMLPKVFFSK
KWMAYYNPSEDIQKIYKNGTFKKGDMFNLNDCHKLIDFFKDSISRYPKWS
NAYDFNFSETEKYKDIAGFYREVEEQGYKVSFESASKKEVDKLVEEGKLY
MFQIYNKDFSDKSHGTPNLHTMYFKLLFDENNHGQIRLSGGAELFMRRAS
LKKEELVVHPANSPIANKNPDNPKKTTTLSYDVYKDKRFSEDQYELHIPI
AINKCPKNIFKINTEVRVLLKHDDNPYVIGIDRGERNLLYIVVVDGKGNI
VEQYSLNEIINNFNGIRIKTDYHSLLDKKEKERFEARQNWTSIENIKELK
AGYISQVVHKICELVEKYDAVIALEDLNSGFKNSRVKVEKQVYQKFEKML
IDKLNYMVDKKSNPCATGGALKGYQITNKFESFKSMSTQNGFIFYIPAWL
TSKIDPSTGFVNLLKTKYTSIADSKKFISSFDRIMYVPEEDLFEFALDYK
NFSRTDADYIKKWKLYSYGNRIRIFRNPKKNNVFDWEEVCLTSAYKELFN
KYGINYQQGDIRALLCEQSDKAFYSSFMALMSLMLQMRNSITGRTDVDFL
ISPVKNSDGIFYDSRNYEAQENAILPKNADANGAYNIARKVLWAIGQFKK
AEDEKLDKVKIAISNKEWLEYAQTSVKHKRPAATKKAGQAKKKKGSYPYD
VPDYAYPYDVPDYAYPYDVPDYA

SEQ ID NO: 37 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 37 may be encoded by the following nucleotide sequence:

```
SEQ ID NO: 37 may be encoded by the following
nucleotide sequence:
                                         (SEQ ID NO: 38)
ATGAGCAAGCTGGAGAAGTTTACAAACTGCTACTCCCTG

TCTAAGACCCTGAGGTTCAAGGCCATCCCTGTGGGCAAGACCCAGGAGAA

CATCGACAATAAGCGGCTGCTGGTGGAGGACGAGAAGAGAGCCGAGGAT

TATAAGGGCGTGAAGAAGCTGCTGGATCGCTACTATCTGTCTTTTATCAAC

GACGTGCTGCACAGCATCAAGCTGAAGAATCTGAACAATTACATCAGCCT

GTTCCGGAAGAAAACCAGAACCGAGAAGGAGAATAAGGAGCTGGAGAAC

CTGGAGATCAATCTGCGGAAGGAGATCGCCAAGGCCTTCAAGGGCAACG

AGGGCTACAAGTCCCTGTTTAAGAAGGATATCATCGAGACAATCCTGCCA

GAGTTCCTGGACGATAAGGACGAGATCGCCCTGGTGAACAGCTTCAATGG

CTTTACCACAGCCTTCACCGGCTTCTTTGATAACAGAGAGAATATGTTTTC

CGAGGAGGCCAAGAGCACATCCATCGCCTTCAGGTGTATCAACGAGAATC

TGACCCGCTACATCTCTAATATGGACATCTTCGAGAAGGTGGACGCCATCT

TTGATAAGCACGAGGTGCAGGAGATCAAGGAGAAGATCCTGAACAGCGA

CTATGATGTGGAGGATTTCTTTGAGGGCGAGTTCTTTAACTTTGTGCTGAC

ACAGGAGGGCATCGACGTGTATAACGCCATCATCGGCGGCTTCGTGACCG

AGAGCGGCGAGAAGATCAAGGGCCTGAACGAGTACATCAACCTGTATAA

TCAGAAAACCAAGCAGAAGCTGCCTAAGTTTAAGCCACTGTATAAGCAGG

TGCTGAGCGATCGGGAGTCTCTGAGCTTCTACGGCGAGGGCTATACATCC

GATGAGGAGGTGCTGGAGGTGTTTAGAAACACCCTGAACAAGAACAGCG

AGATCTTCAGCTCCATCAAGAAGCTGGAGAAGCTGTTCAAGAATTTTGAC

GAGTACTCTAGCGCCGGCATCTTTGTGAAGAACGGCCCCGCCATCAGCAC

AATCTCCAAGGATATCTTCGGCGAGTGGAACGTGATCCGGGACAAGTGGA

ATGCCGAGTATGACGATATCCACCTGAAGAAGAAGGCCGTGGTGACCGAG

AAGTACGAGGACGATCGGAGAAAGTCCTTCAAGAAGATCGGCTCCTTTTC

TCTGGAGCAGCTGCAGGAGTACGCCGACGCCGATCTGTCTGTGGTGGAGA

AGCTGAAGGAGATCATCATCCAGAAGGTGGATGAGATCTACAAGGTGTAT

GGCTCCTCTGAGAAGCTGTTCGACGCCGATTTTGTGCTGGAGAAGAGCCT

GAAGAAGAACGACGCCGTGGTGGCCATCATGAAGGACCTGCTGGATTCTG

TGAAGAGCTTCGAGAATTACATCAAGGCCTTCTTTGGCGAGGGCAAGGAG

ACAAACAGGGACGAGTCCTTCTATGGCGATTTTGTGCTGGCCTACGACAT

CCTGCTGAAGGTGGACCACATCTACGATGCCATCCGCAATTATGTGACCC

AGAAGCCCTACTCTAAGGATAAGTTCAAGCTGTATTTTCAGAACCCTCAGT

TCATGGGCGGCTGGGACAAGGATAAGGAGACAGACTATCGGGCCACCAT

CCTGAGATACGGCTCCAAGTACTATCTGGCCATCATGGATAAGAAGTACG

CCAAGTGCCTGCAGAAGATCGACAAGGACGATGTGAACGGCAATTACGA

GAAGATCAACTATAAGCTGCTGCCCGGCCCTAATAAGATGCTGCCAAAGG

TGTTCTTTTCTAAGAAGTGGATGGCCTACTATAACCCCAGCGAGGACATCC

AGAAGATCTACAAGAATGGCACATTCAAGAAGGGCGATATGTTTAACCTG

AATGACTGTCACAAGCTGATCGACTTCTTTAAGGATAGCATCTCCCGGTAT

CCAAAGTGGTCCAATGCCTACGATTTCAACTTTTCTGAGACAGAGAAGTA

TAAGGACATCGCCGGCTTTTACAGAGAGGTGGAGGAGCAGGGCTATAAG

GTGAGCTTCGAGTCTGCCAGCAAGAAGGAGGTGGATAAGCTGGTGGAGG

AGGGCAAGCTGTATATGTTCCAGATCTATAACAAGGACTTTTCCGATAAG

TCTCACGGCACACCCAATCTGCACACCATGTACTTCAAGCTGCTGTTTGAC

GAGAACAATCACGGACAGATCAGGCTGAGCGGAGGAGCAGAGCTGTTCA

TGAGGCGCGCCTCCCTGAAGAAGGAGGAGCTGGTGGTGCACCCAGCCAA
```

-continued
```
CTCCCCTATCGCCAACAAGAATCCAGATAATCCCAAGAAAACCACAACCC
TGTCCTACGACGTGTATAAGGATAAGAGGTTTTCTGAGGACCAGTACGAG
CTGCACATCCCAATCGCCATCAATAAGTGCCCCAAGAACATCTTCAAGAT
CAATACAGAGGTGCGCGTGCTGCTGAAGCACGACGATAACCCCTATGTGA
TCGGCATCGATAGGGGCGAGCGCAATCTGCTGTATATCGTGGTGGTGGAC
GGCAAGGGCAACATCGTGGAGCAGTATTCCCTGAACGAGATCATCAACAA
CTTCAACGGCATCAGGATCAAGACAGATTACCACTCTCTGCTGGACAAGA
AGGAGAAGGAGAGGTTCGAGGCCCGCCAGAACTGGACCTCCATCGAGAA
TATCAAGGAGCTGAAGGCCGGCTATATCTCTCAGGTGGTGCACAAGATCT
GCGAGCTGGTGGAGAAGTACGATGCCGTGATCGCCCTGGAGGACCTGAAC
TCTGGCTTTAAGAATAGCCGCGTGAAGGTGGAGAAGCAGGTGTATCAGAA
GTTCGAGAAGATGCTGATCGATAAGCTGAACTACATGGTGGACAAGAAGT
CTAATCCTTGTGCAACAGGCGGCGCCCTGAAGGGCTATCAGATCACCAAT
AAGTTCGAGAGCTTTAAGTCCATGTCTACCCAGAACGGCTTCATCTTTTAC
ATCCCTGCCTGGCTGACATCCAAGATCGATCCATCTACCGGCTTTGTGAAC
CTGCTGAAAACCAAGTATACCAGCATCGCCGATTCCAAGAAGTTCATCAG
CTCCTTTGACAGGATCATGTACGTGCCCGAGGAGGATCTGTTCGAGTTTGC
CCTGGACTATAAGAACTTCTCTCGCACAGACGCCGATTACATCAAGAAGT
GGAAGCTGTACTCCTACGGCAACCGGATCAGAATCTTCCGGAATCCTAAG
AAGAACAACGTGTTCGACTGGGAGGAGGTGTGCCTGACCAGCGCCTATAA
GGAGCTGTTCAACAAGTACGGCATCAATTATCAGCAGGGCGATATCAGAG
CCCTGCTGTGCGAGCAGTCCGACAAGGCCTTCTACTCTAGCTTTATGGCCC
TGATGAGCCTGATGCTGCAGATGCGGAACAGCATCACAGGCCGCACCGAC
GTGGATTTTCTGATCAGCCCTGTGAAGAACTCCGACGGCATCTTCTACGAT
AGCCGGAACTATGAGGCCCAGGAGAATGCCATCCTGCCAAAGAACGCCG
ACGCCAATGGCGCCTATAACATCGCCAGAAAGGTGCTGTGGGCCATCGGC
CAGTTCAAGAAGGCCGAGGACGAGAAGCTGGATAAGGTGAAGATCGCCA
TCTCTAACAAGGAGTGGCTGGAGTACGCCCAGACCAGCGTGAAGCACAAA
AGGCCGGCGGCCACGAAAAAGGCCGGCCAGGCAAAAAAGAAAAAGGGA
TCCTACCCATACGATGTTCCAGATTACGCTTATCCCTACGACGTGCCTGAT
TATGCATACCCATATGATGTCCCCGACTATGCCTAA
```

*Porphyromonas crevioricanis* (PcCpf1; pY017), including NLS and HA tag:

(SEQ ID NO: 39)
MDSLKDFTNLYPVSKTLRFELKPVGKTLENIEKAGILKEDEH
RAESYRRVKKIIDTYHKVFIDSSLENMAKMGIENEIKAMLQSFCELYKKDH
RTEGEDKALDKIRAVLRGLIVGAFTGVCGRRENTVQNEKYESLFKEKLIKE
ILPDFVLSTEAESLPFSVEEATRSLKEFDSFTSYFAGFYENRKNIYSTKPQ
STAIAYRLIHENLPKFIDNILVFQKIKEPIAKELEHIRADFSAGGYIKKDE
RLEDIFSLNYYIHVLSQAGIEKYNALIGKIVTEGDGEMKGLNEHINLYNQQ
RGREDRLPLFRPLYKQILSDREQLSYLPESFEKDEELLRALKEFYDHIAED
ILGRTQQLMTSISEYDLSRIYVRNDSQLTDISKKMLGDWNAIYMARERAYD

HEQAPKRITAKYERDRIKALKGEESISLANLNSCIAFLDNVRDCRVDTYLS
TLGQKEGPHGLSNLVENVFASYHEAEQLLSFPYPEENNLIQDKDNVVLIKN
LLDNISDLQRFLKPLWGMGDEPDKDERFYGEYNYIRGALDQVIPLYNKVRN
YLTRKPYSTRKVKLNFGNSQLLSGWDRNKEKDNSCVILRKGQNFYLAIMNN
RHKRSFENKMLPEYKEGEPYFEKMDYKFLPDPNKMLPKVFLSKKGIEIYKP
SPKLLEQYGHGTHKKGDTFSMDDLHELIDFFKHSIEAHEDWKQFGFKFSDT
ATYENVSSFYREVEDQGYKLSFRKVSESYVYSLIDQGKLYLFQIYNKDFSP
CSKGTPNLHTLYWRMLFDERNLADVIYKLDGKAEIFFREKSLKNDHPTHPA
GKPIKKKSRQKKGEESLFEYDLVKDRRYTMDKFQFHVPITMNFKCSAGSKV
NDMVNAHIREAKDMHVIGIDRGERNLLYICVIDSRGTILDQISLNTINDID
YHDLLESRDKDRQQEHRNWQTIEGIKELKQGYLSQAVHRIAELMVAYKAVV
ALEDLNMGFKRGRQKVESSVYQQFEKQLIDKLNYLVDKKKRPEDIGGLLRA
YQFTAPFKSFKEMGKQNGFLFYIPAWNTSNIDPTTGFVNLFHVQYENVDKA
KSFFQKFDSISYNPKKDWFEFAFDYKNFTKKAEGSRSMWILCTHGSRIKNF
RNSQKNGQWDSEEFALTEAFKSLFVRYEIDYTADLKTAIVDEKQKDFFVDL
LKLFKLTVQMRNSWKEKDLDYLISPVAGADGRFFDTREGNKSLPKDADANG
AYNIALKGLWALRQIRQTSEGGKLKLAISNKEWLQFVQERSYEKDKRPAAT
KKAGQAKKKKGSYPYDVPDYAYPYDVPDYAYPYDVPDYA

*Porphyromonas crevioricanis* (PcCpf1;pY017), including NLS and HA tag:

(SEQ ID NO: 39)
MDSLKDFTNLYPVSKTLRFELKPVGKTLENIEKAGILKEDEHRAESYRRV
KKIIDTYHKVFIDSSLENMAKMGIENEIKAMLQSFCELYKKDHRTEGEDK
ALDKIRAVLRGLIVGAFTGVCGRRENTVQNEKYESLFKEKLIKEILPDFV
LSTEAESLPFSVEEATRSLKEFDSFTSYFAGFYENRKNIYSTKPQSTAIA
YRLIHENLPKFIDNILVFQKIKEPIAKELEHIRADFSAGGYIKKDERLED
IFSLNYYIHVLSQAGIEKYNALIGKIVTEGDGEMKGLNEHINLYNQQRGR
EDRLPLFRPLYKQILSDREQLSYLPESFEKDEELLRALKEFYDHIAEDIL
GRTQQLMTSISEYDLSRIYVRNDSQLTDISKKMLGDWNAIYMARERAYDH
EQAPKRITAKYERDRIKALKGEESISLANLNSCIAFLDNVRDCRVDTYLS
TLGQKEGPHGLSNLVENVFASYHEAEQLLSFPYPEENNLIQDKDNVVLIK
NLLDNISDLQRFLKPLWGMGDEPDKDERFYGEYNYIRGALDQVIPLYNKV
RNYLTRKPYSTRKVKLNFGNSQLLSGWDRNKEKDNSCVILRKGQNFYLAI
MNNRHKRSFENKMLPEYKEGEPYFEKMDYKFLPDPNKMLPKVFLSKKGIE
IYKPSPKLLEQYGHGTHKKGDTFSMDDLHELIDFFKHSIEAHEDWKQFGF
KFSDTATYENVSSFYREVEDQGYKLSFRKVSESYVYSLIDQGKLYLFQIY
NKDFSPCSKGTPNLHTLYWRMLFDERNLADVIYKLDGKAEIFFREKSLKN
DHPTHPAGKPIKKKSRQKKGEESLFEYDLVKDRRYTMDKFQFHVPITMNF
KCSAGSKVNDMVNAHIREAKDMHVIGIDRGERNLLYICVIDSRGTILDQI
SLNTINDIDYHDLLESRDKDRQQEHRNWQTIEGIKELKQGYLSQAVHRIA

ELMVAYKAVVALEDLNMGFKRGRQKVESSVYQQFEKQLIDKLNYLVDKKK
RPEDIGGLLRAYQFTAPFKSFKEMGKQNGFLFYIPAWNTSNIDPTTGFVN
LFHVQYENVDKAKSFFQKFDSISYNPKKDWFEFAFDYKNFTKKAEGSRSM
WILCTHGSRIKNFRNSQKNGQWDSEEFALTEAFKSLFVRYEIDYTADLKT
AIVDEKQKDFFVDLLKLFKLTVQMRNSWKEKDLDYLISPVAGADGRFFDT
REGNKSLPKDADANGAYNIALKGLWALRQIRQTSEGGKLKLAISNKEWLQ
FVQERSYEKDKRPAATKKAGQAKKKKGSYPYDVPDYAYPYDVPDYAYPYD
VPDYA

SEQ ID NO: 39 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 39 may be encoded by the following nucleotide sequence:

```
SEQ ID NO: 39 may be encoded by the following
nucleotide sequence:
                                     (SEQ ID NO: 40)
ATGGACAGCCTGAAGGATTTCACCAACCTGTACCCCGTG

TCCAAGACACTGCGGTTTGAGCTGAAGCCTGTGGGCAAGACCCTGGAGAA

TATCGAGAAGGCCGGCATCCTGAAGGAGGATGAGCACAGAGCCGAGAGC

TACCGGAGAGTGAAGAAGATCATCGATACATATCACAAGGTGTTCATCGA

CAGCTCCCTGGAGAACATGGCCAAGATGGGCATCGAGAATGAGATCAAG

GCCATGCTGCAGTCCTTTTGCGAGCTGTATAAGAAGGACCACAGGACCGA

GGGAGAGGACAAGGCCCTGGATAAGATCAGGGCCGTGCTGAGGGGCCTG

ATCGTGGGAGCCTTCACCGGCGTGTGCGGCCGGCGGGAGAACACAGTGCA

GAATGAGAAGTATGAGAGCCTGTTTAAGGAGAAGCTGATCAAGGAGATC

CTGCCAGATTTCGTGCTGTCTACAGAGGCCGAGTCCCTGCCCTTTTCTGTG

GAGGAGGCCACCAGAAGCCTGAAGGAGTTCGACTCCTTTACATCTTACTT

CGCCGGCTTTTATGAGAACCGGAAGAATATCTACTCTACCAAGCCCCAGA

GCACAGCCATCGCCTATAGACTGATCCACGAGAACCTGCCTAAGTTCATC

GATAATATCCTGGTGTTTCAGAAGATCAAGGAGCCAATCGCCAAGGAGCT

GGAGCACATCAGGGCAGACTTCAGCGCCGGCGGCTACATCAAGAAGGAT

GAGCGCCTGGAGGACATCTTTTCCCTGAACTACTATATCCACGTGCTGTCT

CAGGCCGGCATCGAGAAGTACAATGCCCTGATCGGCAAGATCGTGACCGA

GGGCGATGGCGAGATGAAGGGCCTGAACGAGCACATCAACCTGTATAATC

AGCAGAGGGCCGCGAGGACCGGCTGCCACTGTTCAGACCCCTGTATAAG

CAGATCCTGTCTGATAGGGAGCAGCTGTCCTATCTGCCAGAGTCTTTCGAG

AAGGACGAGGAGCTGCTGAGGGCCCTGAAGGAGTTTTACGATCACATCGC

AGAGGACATCCTGGGAAGGACCCAGCAGCTGATGACAAGCATCTCCGAGT

ACGATCTGTCCCGGATCTATGTGAGAAACGATAGCCAGCTGACCGACATC

TCCAAGAAGATGCTGGGCGATTGGAATGCCATCTACATGGCCCGGGAGAG

AGCCTATGACCACGAGCAGGCCCCCAAGCGCATCACAGCCAAGTACGAG

AGGGACCGCATCAAGGCCCTGAAGGGCGAGGAGTCTATCAGCCTGGCCA

ACCTGAACAGCTGCATCGCCTTCCTGGACAACGTGAGGGATTGTCGCGTG

GACACCTATCTGTCTACACTGGGACAGAAGGAGGGACCTCACGGCCTGAG

CAACCTGGTGGAGAACGTGTTCGCCTCCTACCACGAGGCCGAGCAGCTGC

TGTCTTTTCCCTATCCTGAGGAGAACAATCTGATCCAGGACAAGGATAAC

GTGGTGCTGATCAAGAACCTGCTGGATAATATCAGCGACCTGCAGAGGTT

CCTGAAGCCACTGTGGGGCATGGGCGATGAGCCCGACAAGGATGAGAGG

TTTTACGGCGAGTACAATTATATCAGGGGCGCCCTGGACCAGGTCATCCCT

CTGTATAACAAGGTGCGGAATTATCTGACCCGCAAGCCATACTCCACACG

CAAGGTGAAGCTGAACTTCGGCAATAGCCAGCTGCTGTCCGGCTGGGATA

GGAACAAGGAGAAGGACAATTCTTGCGTGATCCTGCGCAAGGGCCAGAA

CTTCTACCTGGCCATCATGAACAATCGGCACAAGCGGAGCTTCGAGAATA

AGATGCTGCCCGAGTATAAGGAGGGCGAGCCTTACTTCGAGAAGATGGAT

TATAAGTTTCTGCCAGACCCCAACAAGATGCTGCCCAAGGTGTTCCTGTCT

AAGAAGGGCATCGAGATCTACAAGCCTAGCCCAAAGCTGCTGGAGCAGT

ATGGCCACGGCACCCACAAGAAGGGCGATACCTTCAGCATGGACGATCTG

CACGAGCTGATCGACTTCTTTAAGCACTCCATCGAGGCCCACGAGGATTG

GAAGCAGTTCGGCTTTAAGTTCAGCGACACCGCCACATACGAGAACGTGA

GCAGCTTCTACCGGGAGGTGGAGGACCAGGGCTACAAGCTGTCTTTTAGA

AAGGTGTCCGAGTCTTACGTGTATAGCCTGATCGATCAGGGCAAGCTGTA

CCTGTTCCAGATCTATAACAAGGACTTTAGCCCCTTGTTCCAAGGGCACCCC

AAATCTGCACACACTGTACTGGCGGATGCTGTTCGATGAGAGAAACCTGG

CCGACGTGATCTATAAGCTGGATGGCAAGGCCGAGATCTTCTTTCGGGAG

AAGTCCCTGAAGAATGACCACCCAACCCACCCTGCAGGCAAGCCCATCAA

GAAGAAGAGCCGGCAGAAGAAGGGCGAGGAGAGCCTGTTCGAGTACGAT

CTGGTGAAGGACCGGAGATATACCATGGATAAGTTTCAGTTCCACGTGCC

AATCACAATGAACTTTAAGTGCTCTGCCGGCAGCAAGGTGAACGACATGG

TGAATGCCCACATCAGGGAGGCCAAGGACATGCACGTGATCGGCATCGAT

AGGGGCGAGCGCAATCTGCTGTATATCTGCGTGATCGACAGCCGCGGCAC

CATCCTGGATCAGATCTCCCTGAACACAATCAATGACATCGATTATCACG

ATCTGCTGGAGTCCAGGGACAAGGATCGCCAGCAGGAGCACAGGAACTG

GCAGACCATCGAGGGCATCAAGGAGCTGAAGCAGGGCTACCTGTCTCAGG

CCGTGCACCGCATCGCCGAGCTGATGGTGGCCTATAAGGCCGTGGTGGCC

CTGGAGGACCTGAACATGGGCTTCAAGCGGGGCAGACAGAAGGTGGAGA

GCAGCGTGTACCAGCAGTTTGAGAAGCAGCTGATCGACAAGCTGAATTAT

CTGGTGGATAAGAAGAAGCGGCCCGAGGACATCGGAGGCCTGCTGAGAG

CCTACCAGTTCACCGCCCCTTTCAAGAGCTTTAAGGAGATGGGCAAGCAG

AACGGCTTTCTGTTCTATATCCCTGCCTGGAACACATCCAATATCGACCCA

ACCACAGGCTTCGTGAACCTGTTTCACGTGCAGTACGAGAATGTGGATAA

GGCCAAGAGCTTCTTTCAGAAGTTCGACAGCATCTCCTACAACCCTAAGA

AGGATTGGTTTGAGTTCGCCTTTGACTATAAGAACTTCACCAAGAAGGCC
```

```
GAGGGCTCTAGGAGCATGTGGATTCTGTGCACCCACGGCTCCCGGATCAA
GAACTTCAGAAATTCTCAGAAGAATGGCCAGTGGGATAGCGAGGAGTTTG
CCCTGACCGAGGCCTTCAAGTCCCTGTTTGTGCGGTACGAGATCGATTATA
CCGCCGACCTGAAAACCGCCATCGTGGACGAGAAGCAGAAGGATTCTTT
GTGGACCTGCTGAAGCTGTTCAAGCTGACCGTGCAGATGAGAAACTCCTG
GAAGGAGAAGGACCTGGATTACCTGATCTCTCCAGTGGCCGGCGCCGATG
GCAGGTTCTTTGACACACGCGAGGGCAATAAGAGCCTGCCCAAGGACGCA
GATGCAAACGGAGCCTATAATATCGCCCTGAAGGGCCTGTGGGCACTGAG
GCAGATCAGACAGACCTCCGAGGGCGGCAAGCTGAAGCTGGCCATCTCTA
ACAAGGAGTGGCTGCAGTTTGTGCAGGAGAGATCCTACGAGAAGGACAA
AAGGCCGGCGGCCACGAAAAAGGCCGGCCAGGCAAAAAAGAAAAAGGG
ATCCTACCCATACGATGTTCCAGATTACGCTTATCCCTACGACGTGCCTGA
TTATGCATACCCATATGATGTCCCCGACTATGCCTAA
```

*Prevotella disiens* (PdCpf1; pY018), including NLS and HA tag:

(SEQ ID NO: 41)
```
MENYQEFTNLFQLNKTLRFELKPIGKTCELLEEGKIFASGSF
LEKDKVRADNVSYVKKEIDKKHKIFIEETLSSFSISNDLLKQYFDCYNELK
AFKKDCKSDEEEVKKTALRNKCTSIQRAMREAISQAFLKSPQKKLLAIKNL
IENVFKADENVQHFSEFTSYFSGFETNRENFYSDEEKSTSIAYRLVHDNLP
IFIKNIYIFEKLKEQFDAKTLSEIFENYKLYVAGSSLDEVFSLEYFNNTLT
QKGIDNYNAVIGKIVKEDKQEIQGLNEHINLYNQKHKDRRLPFFISLKKQI
LSDREALSWLPDMFKNDSEVIKALKGFYIEDGFENNVLTPLATLLSSLDKY
NLNGIFIRNNEALSSLSQNVYRNFSIDEAIDANAELQTFNNYELIANALRA
KIKKETKQGRKSFEKYEEYIDKKVKAIDSLSIQEINELVENYVSEFNSNSG
NMPRKVEDYFSLMRKGDFGSNDLIENIKTKLSAAEKLLGTKYQETAKDIFK
KDENSKLIKELLDATKQFQHFIKPLLGTEEADRDLVFYGDFLPLYEKFEE
LTLLYNKVRNRLTQKPYSKDKIRLCFNKPKLMTGWVDSKTEKSDNGTQYGG
YLFRKKNEIGEYDYFLGISSKAQLFRKNEAVIGDYERLDYYQPKANTIYGS
AYEGENSYKEDKKRLNKVIIAYIEQIKQTNIKKSIIESISKYPNISDDDKV
TPSSLLEKIKKVSIDSYNGILSFKSFQSVNKEVIDNLLKTISPLKNKAEFL
DLINKDYQIFTEVQAVIDEICKQKTFIYFPISNVELEKEMGDKDKPLCLFQ
ISNKDLSFAKTFSANLRKKRGAENLHTMLFKALMEGNQDNLDLGSGAIFYR
AKSLDGNKPTHPANEAIKCRNVANKDKVSLFTYDIYKNRRYMENKFLFHLS
IVQNYKAANDSAQLNSSATEYIRKADDLHIIGIDRGERNLLYYSVIDMKGN
IVEQDSLNIIRNNDLETDYHDLLDKREKERKANRQNWEAVEGIKDLKKGYL
SQAVHQIAQLMLKYNAIIALEDLGQMFVTRGQKIEKAVYQQFEKSLVDKLS
YLVDKKRPYNELGGILKAYQLASSITKNNSDKQNGFLFYVPAWNTSKIDPV
TGFTDLLRPKAMTIKEAQDFFGAFDNISYNDKGYFEFETNYDKFKIRMKSA
QTRWTICTFGNRIKRKKDKNYWNYEEVELTEEFKKLFKDSNIDYENCNLKE
EIQNKDNRKFFDDLIKLLQLTLQMRNSDDKGNDYIISPVANAEGQFFDSRN
GDKKLPLDADANGAYNIARKGLWNIRQIKQTKNDKKLNLSISSTEWLDFVR
EKPYLKKRPAATKKAGQAKKKKGSYPYDVPDYAYPYDVPDYAYPYDVPDYA
```

*Prevotella disiens* (Pdef1;pY018), including NLS and HA tag:

(SEQ ID NO: 41)
```
MENYQEFTNLFQLNKTLRFELKPIGKTCELLEEGKIFASGSFLEKDKVRA
DNVSYVKKEIDKKHKIFIEETLSSFSISNDLLKQYFDCYNELKAFKKDCK
SDEEEVKKTALRNKCTSIQRAMREAISQAFLKSPQKKLLAIKNLIENVFK
ADENVQHFSEFTSYFSGFETNRENFYSDEEKSTSIAYRLVHDNLPIFIKN
IYIFEKLKEQFDAKTLSEIFENYKLYVAGSSLDEVFSLEYFNNTLTQKGI
DNYNAVIGKIVKEDKQEIQGLNEHINLYNQKHKDRRLPFFISLKKQILSD
REALSWLPDMFKNDSEVIKALKGFYIEDGFENNVLTPLATLLSSLDKYNL
NGIFIRNNEALSSLSQNVYRNFSIDEAIDANAELQTFNNYELIANALRAK
IKKETKQGRKSFEKYEEYIDKKVKAIDSLSIQEINELVENYVSEFNSNSG
NMPRKVEDYFSLMRKGDFGSNDLIENIKTKLSAAEKLLGTKYQETAKDIF
KKDENSKLIKELLDATKQFQHFIKPLLGTEEADRDLVFYGDFLPLYEKF
EELTLLYNKVRNRLTQKPYSKDKIRLCFNKPKLMTGWVDSKTEKSDNGTQ
YGGYLFRKKNEIGEYDYFLGISSKAQLFRKNEAVIGDYERLDYYQPKANT
IYGSAYEGENSYKEDKKRLNKVIIAYIEQIKQTNIKKSIIESISKYPNIS
DDDKVTPSSLLEKIKKVSIDSYNGILSFKSFQSVNKEVIDNLLKTISPLK
NKAEFLDLINKDYQIFTEVQAVIDEICKQKTFIYFPISNVELEKEMGDKD
KPLCLFQISNKDLSFAKTFSANLRKKRGAENLHTMLFKALMEGNQDNLDL
GSGAIFYRAKSLDGNKPTHPANEAIKCRNVANKDKVSLFTYDIYKNRRYM
ENKFLFHLSIVQNYKAANDSAQLNSSATEYIRKADDLHIIGIDRGERNLL
YYSVIDMKGNIVEQDSLNIIRNNDLETDYHDLLDKREKERKANRQNWEAV
EGIKDLKKGYLSQAVHQIAQLMLKYNAIIALEDLGQMFVTRGQKIEKAVY
QQFEKSLVDKLSYLVDKKRPYNELGGILKAYQLASSITKNNSDKQNGFLF
YVPAWNTSKIDPVTGFTDLLRPKAMTIKEAQDFFGAFDNISYNDKGYFEF
ETNYDKFKIRMKSAQTRWTICTFGNRIKRKKDKNYWNYEEVELTEEFKKL
FKDSNIDYENCNLKEEIQNKDNRKFFDDLIKLLQLTLQMRNSDDKGNDYI
ISPVANAEGQFFDSRNGDKKLPLDADANGAYNIARKGLWNIRQIKQTKND
KKLNLSISSTEWLDFVREKPYLKKRPAATKKAGQAKKKKGSYPYDVPDYA
YPYDVPDYAYPYDVPDYA
```

SEQ ID NO: 41 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 41 may be encoded by the following nucleotide sequence:

SEQ ID NO: 41 may be encoded by the following nucleotide sequence:

(SEQ ID NO: 42)
ATGGAGAACTATCAGGAGTTCACCAACCTGTTTCAGCTG

AATAAGACACTGAGATTCGAGCTGAAGCCCATCGGCAAGACCTGCGAGCT

GCTGGAGGAGGGCAAGATCTTCGCCAGCGGCTCCTTTCTGGAGAAGGACA

AGGTGAGGGCCGATAACGTGAGCTACGTGAAGAAGGAGATCGACAAGAA

GCACAAGATCTTTATCGAGGAGACACTGAGCTCCTTCTCTATCAGCAACG

ATCTGCTGAAGCAGTACTTTGACTGCTATAATGAGCTGAAGGCCTTCAAG

AAGGACTGTAAGAGCGATGAGGAGGAGGTGAAGAAAACCGCCCTGCGCA

ACAAGTGTACCTCCATCCAGAGGGCCATGCGCGAGGCCATCTCTCAGGCC

TTTCTGAAGAGCCCCCAGAAGAAGCTGCTGGCCATCAAGAACCTGATCGA

GAACGTGTTCAAGGCCGACGAGAATGTGCAGCACTTCTCCGAGTTTACCA

GCTATTTCTCCGGCTTTGAGACAAACAGAGAGAATTTCTACTCTGACAGG

GAGAAGTCCACATCTATCGCCTATAGGCTGGTGCACGATAACCTGCCTAT

CTTCATCAAGAACATCTACATCTTCGAGAAGCTGAAGGAGCAGTTCGACG

CCAAGACCCTGAGCGAGATCTTCGAGAACTACAAGCTGTATGTGGCCGGC

TCTAGCCTGGATGAGGTGTTCTCCCTGGAGTACTTTAACAATACCCTGACA

CAGAAGGGCATCGACAACTATAATGCCGTGATCGGCAAGATCGTGAAGG

AGGATAAGCAGGAGATCCAGGGCCTGAACGAGCACATCAACCTGTATAAT

CAGAAGCACAAGGACCGGAGACTGCCCTTCTTTATCTCCCTGAAGAAGCA

GATCCTGTCCGATCGGGAGGCCCTGTCTTGGCTGCCTGACATGTTCAAGAA

TGATTCTGAAGTGATCAAGGCCCTGAAGGGCTTCTACATCGAGGACGGCT

TTGAGAACAATGTGCTGACACCTCTGGCCACCCTGCTGTCCTCTCTGGATA

AGTACAACCTGAATGGCATCTTTATCCGCAACAATGAGGCCCTGAGCTCC

CTGTCCCAGAACGTGTATCGGAATTTTTCTATCGACGAGGCCATCGATGCC

AACGCCGAGCTGCAGACCTTCAACAATTACGAGCTGATCGCCAATGCCCT

GCGCGCCAAGATCAAGAAGGAGACAAAGCAGGGCCGGAAGTCTTTCGAG

AAGTACGAGGAGTATATCGATAAGAAGGTGAAGGCCATCGACAGCCTGTC

CATCCAGGAGATCAACGAGCTGGTGGAGAATTACGTGAGCGAGTTTAACT

CTAATAGCGGCAACATGCCAAGAAAGGTGGAGGACTACTTCAGCCTGATG

AGGAAGGGCGACTTCGGCTCCAACGATCTGATCGAAAATATCAAGACCAA

GCTGAGCGCCGCAGAGAAGCTGCTGGGCACAAAGTACCAGGAGACAGCC

AAGGACATCTTCAAGAAGGATGAGAACTCCAAGCTGATCAAGGAGCTGCT

GGACGCCACCAAGCAGTTCCAGCACTTTATCAAGCCACTGCTGGGCACAG

GCGAGGAGGCAGATCGGGACCTGGTGTTCTACGGCGATTTTCTGCCCCTG

TATGAGAAGTTTGAGGAGCTGACCCTGCTGTATAACAAGGTGCGGAATAG

ACTGACACAGAAGCCCTATTCCAAGGACAAGATCCGCCTGTGCTTCAACA

AGCCTAAGCTGATGACAGGCTGGGTGGATTCCAAGACCGAGAAGTCTGAC

AACGGCACACAGTACGGCGGCTATCTGTTTCGGAAGAAGAATGAGATCGG

-continued

CGAGTACGATTATTTTCTGGGCATCTCTAGCAAGGCCCAGCTGTTCAGAAA

GAACGAGGCCGTGATCGGCGACTACGAGAGGCTGGATTACTATCAGCCAA

AGGCCAATACCATCTACGGCTCTGCCTATGAGGGCGAGAACAGCTACAAG

GAGGACAAGAAGCGGCTGAACAAAGTGATCATCGCCTATATCGAGCAGA

TCAAGCAGACAAACATCAAGAAGTCTATCATCGAGTCCATCTCTAAGTAT

CCTAATATCAGCGACGATGACAAGGTGACCCCATCCTCTCTGCTGGAGAA

GATCAAGAAGGTGTCTATCGACAGCTACAACGGCATCCTGTCCTTCAAGT

CTTTTCAGAGCGTGAACAAGGAAGTGATCGATAACCTGCTGAAAACCATC

AGCCCCCTGAAGAACAAGGCCGAGTTTCTGGACCTGATCAATAAGGATTA

TCAGATCTTCACCGAGGTGCAGGCCGTGATCGACGAGATCTGCAAGCAGA

AAACCTTCATCTACTTTCCAATCTCCAACGTGGAGCTGGAGAAGGAGATG

GGCGATAAGGACAAGCCCCTGTGCCTGTTCCAGATCAGCAATAAGGATCT

GTCCTTCGCCAAGACCTTTAGCGCCAACCTGCGGAAGAAGAGAGGCGCCG

AGAATCTGCACACAATGCTGTTTAAGGCCCTGATGGAGGGCAACCAGGAT

AATCTGGACCTGGGCTCTGGCGCCATCTTCTACAGAGCCAAGAGCCTGGA

CGGCAACAAGCCCACACACCCTGCCAATGAGGCCATCAAGTGTAGGAAC

GTGGCCAATAAGGATAAGGTGTCCCTGTTCACCTACGACATCTATAAGAA

CAGGCGCTACATGGAGAATAAGTTCCTGTTTCACCTGAGCATCGTGCAGA

ACTATAAGGCCGCCAATGACTCCGCCCAGCTGAACAGCTCCGCCACCGAG

TATATCAGAAAGGCCGATGACCTGCACATCATCGGCATCGATAGGGGCGA

GCGCAATCTGCTGTACTATTCCGTGATCGATATGAAGGGCAACATCGTGG

AGCAGGACTCTCTGAATATCATCAGGAACAATGACCTGGAGACAGATTAC

CACGACCTGCTGGATAAGAGGGAGAAGGAGCGCAAGGCCAACCGGCAGA

ATTGGGAGGCCGTGGAGGGCATCAAGGACCTGAAGAAGGGCTACCTGAG

CCAGGCCGTGCACCAGATCGCCCAGCTGATGCTGAAGTATAACGCCATCA

TCGCCCTGGAGGATCTGGGCCAGATGTTTGTGACCCGCGGCCAGAAGATC

GAGAAGGCCGTGTACCAGCAGTTCGAGAAGAGCCTGGTGGATAAGCTGTC

CTACCTGGTGGACAAGAAGCGGCCTTATAATGAGCTGGGCGGCATCCTGA

AGGCCTACCAGCTGGCCTCTAGCATCACCAAGAACAATTCTGACAAGCAG

AACGGCTTCCTGTTTTATGTGCCAGCCTGGAATACAAGCAAGATCGATCCC

GTGACCGGCTTTACAGACCTGCTGCGGCCCAAGGCCATGACCATCAAGGA

GGCCCAGGACTTCTTTGGCGCCTTCGATAACATCTCTTACAATGACAAGGG

CTATTTCGAGTTTGAGACAAACTACGACAAGTTTAAGATCAGAATGAAGA

GCGCCCAGACCAGGTGGACAATCTGCACCTTCGGCAATCGGATCAAGAGA

AAGAAGGATAAGAACTACTGGAATTATGAGGAGGTGGAGCTGACCGAGG

AGTTCAAGAAGCTGTTTAAGGACAGCAACATCGATTACGAGAACTGTAAT

CTGAAGGAGGAGATCCAGAACAAGGACAATCGCAAGTTCTTTGATGACCT

GATCAAGCTGCTGCAGCTGACACTGCAGATGCGGAACTCCGATGACAAGG

GCAATGATTATATCATCTCTCCTGTGGCCAACGCCGAGGGCCAGTTCTTTG

ACTCCCGCAATGGCGATAAGAAGCTGCCACTGGATGCAGACGCAAACGG

AGCCTACAATATCGCCCGCAAGGGCCTGTGGAACATCCGGCAGATCAAGC

-continued

```
AGACCAAGAACGACAAGAAGCTGAATCTGAGCATCTCCTCTACAGAGTGG
CTGGATTTCGTGCGGGAGAAGCCTTACCTGAAGAAAAGGCCGGCGGCCAC
GAAAAAGGCCGGCCAGGCAAAAAGAAAAAGGGATCCTACCCATACGAT
GTTCCAGATTACGCTTATCCCTACGACGTGCCTGATTATGCATACCCATAT
GATGTCCCCGACTATGCCTAA
```

Porphyromonas macacae (PmCpf1; pY09), including NLS and HA tag:

(SEQ ID NO: 43)
```
MKTQHFFEDFTSLYSLSKTIRFELKPIGKTLENIKKNGLIRRD
EQRLDDYEKLKKVIDEYHEDFIANILSSFSFSEEILQSYIQNLSESEARAK
IEKTMRDTLAKAFSEDERYKSIFKKELVKKIAPVWCPAYKSLCKKFDNFTT
SLVPFHENRKNLYTSNEITASIPYRIVHVNLPKFIQNIEALCELQKKMGAD
LYLEMMENLRNVWPSFVKTPDDLCNLKTYNHLMVQSSISEYNRFVGGYSTE
DGTKHQGINEWINIYRQRNKEMRLPGLVFLHKQILAKVDSSSFISDTLEND
DQVFCVLRQFRKLFWNTVSSKEDDAASLKDLFCGLSGYDPEAIYVSDAHLA
TISKNIFDRWNYISDAIRRKTEVLMPRKKESVERYAEKISKQIKKRQSYSL
AELDDLLAHYSEESLPAGFSLLSYFTSLGGQKYLVSDGEVILYEEGSNIWD
EVLIAFRDLQVILDKDFTEKKLGKDEEAVSVIKKALDSALRLRKFFDLLSG
TGAEIRRDSSFYALYTDRMDKLKGLLKMYDKVRNYLTKKPYSIEKFKLHFD
NPSLLSGWDKNKELNNLSVIFRQNGYYYLGIMTPKGKNLFKTLPKLGAEEM
FYEKMEYKQIAEPMLMLPKVFFPKKTKPAFAPDQSVVDIYNKKTFKTGQKG
FNKKDLYRLIDFYKEALTVHEWKLFNFSFSPTEQYRNIGEFFDEVREQAYK
VSMVNVPASYIDEAVENGKLYLFQIYNKDFSPYSKGIPNLHTLYWKALFSE
QNQSRVYKLCGGGELFYRKASLHMQDTTVHPKGISIHKKNLNKKGETSLFN
YDLVKDKRFTEDKFFFHVPISINYKNKKITNVNQMVRDYIAQNDDLQIIGI
DRGERNLLYISRIDTRGNLLEQFSLNVIESDKGDLRTDYQKILGDREQERL
RRRQEWKSIESIKDLKDGYMSQVVHKICNMVVEHKAIVVLENLNLSFMKGR
KKVEKSVYEKFERMLVDKLNYLVVDKKNLSNEPGGLYAAYQLTNPLFSFEE
LHRYPQSGILFFVDPWNTSLTDPSTGFVNLLGRINYTNVGDARKFFDRFNA
IRYDGKGNILFDLDLSRFDVRVETQRKLWTLTTFGSRIAKSKKSGKWMVER
IENLSLCFLELFEQFNIGYRVEKDLKKAILSQDRKEFYVRLIYLFNLMMQI
RNSDGEEDYILSPALNEKNLQFDSRLIEAKDLPVDADANGAYNVARKGLMV
VQRIKRGDHESIHRIGRAQWLRYVQEGIVEKRPAATKKAGQAKKKKGSYPY
DVPDYAYPYDVPDYAYPYDVPDYA
```

Porphyromonas macacae (PmCpf1;pY09), including NLS and HA tag:

(SEQ ID NO: 43)
```
MKTQHFFEDFTSLYSLSKTIRFELKPIGKTLENIKKNGLIRRDEQRLDDY
EKLKKVIDEYHEDFIANILSSFSFSEEILQSYIQNLSESEARAKIEKTMR
DTLAKAFSEDERYKSIFKKELVKKDIPVWCPAYKSLCKKFDNFTTSLVPF
HENRKNLYTSNEITASIPYRIVHVNLPKFIQNIEALCELQKKMGADLYLE
MMENLRNVWPSFVKTPDDLCNLKTYNHLMVQSSISEYNRFVGGYSTEDGT
KHQGINEWINIYRQRNKEMRLPGLVFLHKQILAKVDSSSFISDTLENDDQ
VFCVLRQFRKLFWNTVSSKEDDAASLKDLFCGLSGYDPEAIYVSDAHLAT
ISKNIFDRWNYISDAIRRKTEVLMPRKKESVERYAEKISKQIKKRQSYSL
AELDDLLAHYSEESLPAGFSLLSYFTSLGGQKYLVSDGEVILYEEGSNIW
DEVLIAFRDLQVILDKDFTEKKLGKDEEAVSVIKKALDSALRLRKFFDLL
SGTGAEIRRDSSFYALYTDRMDKLKGLLKMYDKVRNYLTKKPYSIEKFKL
HFDNPSLLSGWDKNKELNNLSVIFRQNGYYYLGIMTPKGKNLFKTLPKLG
AEEMFYEKMEYKQIAEPMLMLPKVFFPKKTKPAFAPDQSVVDIYNKKTFK
TGQKGFNKKDLYRLIDFYKEALTVHEWKLFNFSFSPTEQYRNIGEFFDEV
REQAYKVSMVNVPASYIDEAVENGKLYLFQIYNKDFSPYSKGIPNLHTLY
WKALFSEQNQSRVYKLCGGGELFYRKASLHMQDTTVHPKGISIHKKNLNK
KGETSLFNYDLVKDKRFTEDKFFFHVPISINYKNKKITNVNQMVRDYIAQ
NDDLQIIGIDRGERNLLYISRIDTRGNLLEQFSLNVIESDKGDLRTDYQK
ILGDREQERLRRRQEWKSIESIKDLKDGYMSQVVHKICNMVVEHKAIVVL
ENLNLSFMKGRKKVEKSVYEKFERMLVDKLNYLVVDKKNLSNEPGGLYAA
YQLTNPLFSFEELHRYPQSGILFFVDPWNTSLTDPSTGFVNLLGRINYTN
VGDARKFFDRFNAIRYDGKGNILFDLDLSRFDVRVETQRKLWTLTTFGSR
IAKSKKSGKWMVERIENLSLCFLELFEQFNIGYRVEKDLKKAILSQDRKE
FYVRLIYLFNLMMQIRNSDGEEDYILSPALNEKNLQFDSRLIEAKDLPVD
ADANGAYNVARKGLMVVQRIKRGDHESIHRIGRAQWLRYVQEGIVEKRPA
ATKKAGQAKKKKGSYPYDVPDYAYPYDVPDYAYPYDVPDYA
```

SEQ ID NO: 43 includes a nuclear localization signal (KRPAATKKAGQAKKKK) (SEQ ID NO: 12), followed by a glycine-serine linker (GS), followed by a HA tag (YPYDVPDYAYPYDVPDYAYPYDVPDYA) (SEQ ID NO: 13).

SEQ ID NO: 43 may be encoded by the following nucleotide sequence:

SEQ ID NO: 43 may be encoded by the following nucleotide sequence:

(SEQ ID NO: 44)
```
ATGAAAACCCAGCACTTCTTTGAGGACTTCACAAGCCTG
TACTCTCTGAGCAAGACCATCCGGTTTGAGCTGAAGCCAATCGGCAAGAC
CCTGGAGAACATCAAGAAGAATGGCCTGATCCGGAGAGATGAGCAGAGA
CTGGACGATTACGAGAAGCTGAAGAAAGTGATCGACGAGTATCACGAGG
ATTTCATCGCCAACATCCTGAGCTCCTTTTCCTTCTCTGAGGAGATCCTGC
AGTCCTACATCCAGAATCTGAGCGAGTCCGAGGCCAGGGCCAAGATCGAG
AAAACCATGCGCGACACACTGGCCAAGGCCTTCTCTGAGGATGAGAGGTA
CAAGAGCATCTTTAAGAAGGAGCTGGTGAAGAAGGACATCCCCGTGTGGT
GCCCTGCCTATAAGAGCCTGTGCAAGAAGTTCGATAACTTTACCACATCTC
TGGTGCCCTTCCACGAGAACAGGAAGAACCTGTATACCAGCAATGAGATC
ACAGCCTCTATCCCTTATCGCATCGTGCACGTGAACCTGCCAAAGTTTATC
CAGAATATCGAGGCCCTGTGCGAGCTGCAGAAGAAGATGGGCGCCGACCT
```

```
-continued
GTACCTGGAGATGATGGAGAACCTGCGCAACGTGTGGCCCAGCTTCGTGA

AAACCCCAGACGACCTGTGCAACCTGAAAACCTATAATCACCTGATGGTG

CAGTCTAGCATCAGCGAGTACAACAGGTTTGTGGGCGGCTATTCCACCGA

GGACGGCACAAAGCACCAGGGCATCAACGAGTGGATCAATATCTACAGA

CAGAGGAATAAGGAGATGCGCCTGCCTGGCCTGGTGTTCCTGCACAAGCA

GATCCTGGCCAAGGTGGACTCCTCTAGCTTCATCAGCGATACACTGGAGA

ACGACGATCAGGTGTTTTGCGTGCTGAGACAGTTCAGGAAGCTGTTTTGG

AATACCGTGTCCTCTAAGGAGGACGATGCCGCCTCCCTGAAGGACCTGTT

CTGTGGCCTGTCTGGCTATGACCCTGAGGCCATCTACGTGAGCGATGCCCA

CCTGGCCACAATCTCCAAGAACATCTTTGACAGATGGAATTACATCTCCG

ATGCCATCAGGCGCAAGACCGAGGTGCTGATGCCACGGAAGAAGGAGAG

CGTGGAGAGATATGCCGAGAAGATCTCCAAGCAGATCAAGAAGAGACAG

TCTTACAGCCTGGCCGAGCTGGACGATCTGCTGGCCCACTATAGCGAGGA

GTCCCTGCCCGCAGGCTTCTCTCTGCTGAGCTACTTTACATCTCTGGGCGG

CCAGAAGTATCTGGTGAGCGACGGCGAAGTGATCCTGTACGAGGAGGGC

AGCAACATCTGGGACGAGGTGCTGATCGCCTTCAGGGATCTGCAGGTCAT

CCTGGACAAGGACTTCACCGAGAAGAAGCTGGGCAAGGATGAGGAGGCC

GTGTCTGTGATCAAGAAGGCCCTGGACAGCGCCCTGCGCCTGCGGAAGTT

CTTTGATCTGCTGTCCGGCACAGGCGCAGAGATCAGGAGAGACAGCTCCT

TCTATGCCCTGTATACCGACCGGATGGATAAGCTGAAGGGCCTGCTGAAG

ATGTATGATAAGGTGAGAAACTACCTGACCAAGAAGCCTTATTCCATCGA

GAAGTTCAAGCTGCACTTTGACAACCCATCCCTGCTGTCTGGCTGGGATAA

GAATAAGGAGCTGAACAATCTGTCTGTGATCTTCCGGCAGAACGGCTACT

ATTACCTGGGCATCATGACACCCAAGGGCAAGAATCTGTTCAAGACCCTG

CCTAAGCTGGGCGCCGAGGAGATGTTTTATGAGAAGATGGAGTACAAGCA

GATCGCCGAGCCTATGCTGATGCTGCCAAAGGTGTTCTTTCCCAAGAAAA

CCAAGCCAGCCTTCGCCCCAGACCAGAGCGTGGTGGATATCTACAACAAG

AAAACCTTCAAGACAGGCCAGAAGGGCTTTAATAAGAAGGACCTGTACCG

GCTGATCGACTTCTACAAGGAGGCCCTGACAGTGCACGAGTGGAAGCTGT

TTAACTTCTCCTTTTCTCCAACCGAGCAGTATCGGAATATCGGCGAGTTCT

TTGACGAGGTGAGAGAGCAGGCCTACAAGGTGTCCATGGTGAACGTGCCC

GCCTCTTATATCGACGAGGCCGTGGAGAACGGCAAGCTGTATCTGTTCCA

GATCTACAATAAGGACTTCAGCCCCTACTCCAAGGGCATCCCTAACCTGC

ACACACTGTATTGGAAGGCCCTGTTCAGCGAGCAGAATCAGAGCCGGGTG

TATAAGCTGTGCGGAGGAGGAGAGCTGTTTTATAGAAAGGCCAGCCTGCA

CATGCAGGACACCACAGTGCACCCCAAGGGCATCTCTATCCACAAGAAGA

ACCTGAATAAGAAGGGCGAGACAAGCCTGTTCAACTACGACCTGGTGAAG

GATAAGAGGTTTACCGAGGACAAGTTCTTTTTCCACGTGCCTATCTCTATC

AACTACAAGAATAAGAAGATCACCAACGTGAATCAGATGGTGCGCGATTA

TATCGCCCAGAACGACGATCTGCAGATCATCGGCATCGACCGCGGCGAGC

GGAATCTGCTGTATATCAGCCGGATCGATACAAGGGGCAACCTGCTGGAG

CAGTTCAGCCTGAATGTGATCGAGTCCGACAAGGGCGATCTGAGAACCGA

CTATCAGAAGATCCTGGGCGATCGCGAGCAGGAGCGGCTGAGGCGCCGG

CAGGAGTGGAAGTCTATCGAGAGCATCAAGGACCTGAAGGATGGCTACAT

GAGCCAGGTGGTGCACAAGATCTGTAACATGGTGGTGGAGCACAAGGCC

ATCGTGGTGCTGGAGAACCTGAATCTGAGCTTCATGAAGGGCAGGAAGAA

GGTGGAGAAGTCCGTGTACGAGAAGTTTGAGCGCATGCTGGTGGACAAGC

TGAACTATCTGGTGGTGGATAAGAAGAACCTGTCCAATGAGCCAGGAGGC

CTGTATGCAGCATACCAGCTGACCAATCCACTGTTCTCTTTTGAGGAGCTG

CACAGATACCCCCAGAGCGGCATCCTGTTTTTCGTGGACCCATGGAACAC

CTCTCTGACAGATCCCAGCACAGGCTTCGTGAATCTGCTGGGCAGAATCA

ACTACACCAATGTGGGCGACGCCCGCAAGTTTTTCGATCGGTTTAACGCC

ATCAGATATGACGGCAAGGGCAATATCCTGTTCGACCTGGATCTGTCCAG

ATTTGATGTGAGGGTGGAGACACAGAGGAAGCTGTGGACACTGACCACAT

TCGGCTCTCGCATCGCCAAATCCAAGAAGTCGGCAAGTGGATGGTGGAG

CGGATCGAGAACCTGAGCCTGTGCTTTCTGGAGCTGTTCGAGCAGTTTAAT

ATCGGCTACAGAGTGGAGAAGGACCTGAAGAAGGCCATCCTGAGCCAGG

ATAGGAAGGAGTTCTATGTGCGCCTGATCTACCTGTTTAACCTGATGATGC

AGATCCGGAACAGCGACGGCGAGGAGGATTATATCCTGTCTCCCGCCCTG

AACGAGAAGAATCTGCAGTTCGACAGCAGGCTGATCGAGGCCAAGGATCT

GCCTGTGGACGCAGATGCAAACGGAGCATACAATGTGGCCCGCAAGGGC

CTGATGGTGGTGCAGAGAATCAAGAGGGGCGACCACGAGTCCATCCACA

GGATCGGAAGGGCACAGTGGCTGAGATATGTGCAGGAGGGCATCGTGGA

GAAAAGGCCGGCGGCCACGAAAAAGGCCGGCCAGGCAAAAAGAAAAA

GGGATCCTACCCATACGATGTTCCAGATTACGCTTATCCCTACGACGTGCC

TGATTATGCATACCCATATGATGTCCCCGACTATGCCTAA
```

Some of the non-limiting sequences shown above include a sequence such as a nuclear localization signal and/or a tag sequence (such as a HA tags). In various embodiments, a different nuclear localization signal may be present. In some embodiments, no nuclear localization signal is used. In certain embodiments no tag (e.g., no HA tag) is used.

In various embodiments relating to a protein (such as a protein within a gene-editing complex) the protein may include a nuclear localization signal. For example, the protein (e.g., a Cas protein) may comprise a nuclear localization signal (NLS). Such signals are known in the art, and non-limiting examples are described in Kalderon et al., (1984) *Cell* 39 (3 Pt 2): 499-509; Makkerh et al., (1996) *Curr Biol.* 6 (8): 1025-7; and Dingwall et al., (1991) *Trends in Biochemical Sciences* 16 (12): 478-81, the contents of each of which are hereby incorporated herein by reference. Specific non-limiting examples of nuclear localization signals include GGSGPPKKKRKV (SEQ ID NO: 5), KRPAATKKAGQAKKKK (SEQ ID NO: 12), PKKKRKV (SEQ ID NO: 45), KR[PAATKKAGQA]KKKK (SEQ ID NO: 46), KR[XXXXXXXXXX]KKKK (SEQ ID NO: 47), KKXK (SEQ ID NO: 48), KRXK (SEQ ID NO: 49), KKXR (SEQ ID NO: 50), KRXR (SEQ ID NO: 51), AVKRPAATKKAGQAKKKKLD (SEQ ID NO: 52), MSRRR- KANPTKLSENAKKLAKEVEN (SEQ ID NO: 53), PAAKRVKLD (SEQ ID NO: 54), and KLKIKRPVK (SEQ ID NO: 55).

General Definitions and General Techniques

Unless specifically defined otherwise, all technical and scientific terms used herein shall be taken to have the same meaning as commonly understood by one of ordinary skill in the art (e.g., in cell culture, molecular genetics, and biochemistry).

As used herein, the term "about" in the context of a numerical value or range means±10% of the numerical value or range recited or claimed, unless the context requires a more limited range.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The terms "plasma membrane" and "cell membrane" are used interchangeably herein, and refer to the semipermeable membrane that separates the interior of a cell from the environment outside the cell.

As used herein, an "expression vector" is a DNA or RNA vector that is capable of effecting expression of one or more polynucleotides. Preferably, the expression vector is also capable of replicating within the host cell. Expression vectors can be either prokaryotic or eukaryotic, and are typically plasmids. Expression vectors of the present invention include any vectors that function (i.e., direct gene expression) in host cells of the present invention, including in one of the prokaryotic or eukaryotic cells described herein, e.g., protozoan, algal, fungi, yeast, plant, animal, vertebrate, invertebrate, arthropod, mammalian, rodent, primate, or human cells. Expression vectors of the present invention contain regulatory sequences such as transcription control sequences, translation control sequences, origins of replication, and other regulatory sequences that are compatible with the host cell and that control the expression of a polynucleotide. In particular, expression vectors of the present invention include transcription control sequences. Transcription control sequences are sequences which control the initiation, elongation, and termination of transcription. Particularly important transcription control sequences are those which control transcription initiation such as promoter, enhancer, operator and repressor sequences. Suitable transcription control sequences include any transcription control sequence that can function in at least one of the cells of the present invention. A variety of such transcription control sequences are known to those skilled in the art. In preferred embodiments, the methods do not comprise the use of viral vectors such as adenoviruses to deliver nucleic acid molecules or constructs.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to 5.0 mg.

Unless otherwise implicitly or explicitly contradicted by the context in which it is used, references to cell "squeeze" "squeezing" "deformation" and the like refer to a process used to deliver macromolecules directly into the cytosol of cells with minimal cytotoxicity. The principle underlying this approach is temporary membrane disruption by rapid mechanical deformation, or squeezing, of the target cell, which permits the uptake by diffusion of macromolecules in the fluid medium and is followed by cell membrane repair (see, e.g., U.S. Patent Application Publication No. 2014/0287509, published Sep. 25, 2014; PCT International Patent Application No. PCT/US2015/058489, filed Oct. 30, 2015; and PCT International Patent Application No. PCT/2015/060689, filed Nov. 13, 2015, the entire contents of each of which are incorporated herein by reference).

As used herein, "gRNA" refers to a CRISPR-Cas system guide RNA.

As used herein the term "protein complex" refers to a composite unit arising from the specific binding of a protein with a binding partner, wherein said binding partner can be one or more proteins, one or more nucleic acids, or a combination of one or more proteins and one or more nucleic acids, and the like, to form said protein complex. Protein complexes may be protein-protein complexes, protein-nucleic acid complexes, and the like. In certain embodiments, a protein complex may comprise protein-protein interactions, e.g. interactions between different proteins, or dimers, trimers, tetramers or higher oligomers of the same protein. Interactions between subunits of protein complexes (e.g., in protein-protein complexes or protein-nucleic acid complexes that comprise more than one protein) or between proteins and nucleic acids (e.g., in protein-nucleic acid complexes) are usually non-binding interactions, such as those interactions caused by hydrogen bridges, pi electron systems such as (optionally conjugated) C—C double bonds or aromatic rings, e.g. phenyl, and heteroaromatic rings, e.g. pyrrole, imidazole, indole, pyrimidine or purine rings, and interactions between metal atoms and oxygen, nitrogen or sulfur atoms, but may also be weak, and in particular reversible, covalent binding interactions, e.g. sulfur-sulfur bridges.

A "protein-protein complex" means a composite unit that is a combination of two or more proteins formed by interaction between the proteins. Typically but not necessarily, a "protein complex" is formed by the binding of two or more proteins together through specific non-covalent binding affinities. However, covalent bonds may also be present between the interacting partners. For instance, the two interacting partners can be covalently crosslinked so that the protein complex becomes more stable.

Similarly, a "protein-nucleic acid complex" means a composite unit that is a combination of at least one protein and at least one nucleic acid formed by interactions that include an interaction between a protein and a nucleic acid. Typically but not necessarily, a "protein-nucleic acid complex" is formed by the binding of a protein and a nucleic acid through non-covalent binding affinities.

In various embodiments, a gene-editing complex is a protein-nucleic acid complex, such as a RNP. A non-limiting example of an RNP is a CRISPR-Cas RNP comprising a Cas protein and a gRNA.

Methods and devices described herein deliver an intact and functional gene-editing complex into cells. The components of the gene-editing complex do not disassociate during delivery and remain functional after delivery into the cell.

Various assays are available to determine whether an intact and functional gene-editing complex has been delivered to a cell. For example, the detection of gene editing by the gene-editing complex may be used to indicate that an intact and functional gene-editing complex was delivered into a cell. Alternatively or in addition, cells to which the gene-editing complex has been delivered may be lysed using non-denaturing conditions (such as a non-denaturing buffer or a French press), and the lysate may be analyzed using a non-denaturing gel to determine whether the gene-editing complex was intact within the cells. Alternatively or in addition, the cells may be lysed using non-denaturing conditions and then immunoprecipitation may be used to isolate the gene-editing complex from the lysate (i.e., to verify that one component of the complex can be co-isolated with another using immunoprecipitation). The isolated gene-editing complex can be assayed before or after delivery to a cell using a non-denaturing gel or a denaturing assay (such as sodium dodecyl sulfate polyacrylamide gel electrophoresis) to determine whether the gene-editing complex was present in a pre-delivery/pre-cell squeeze buffer as well as whether the complex is present after microfluidic/squeeze processing and found intact and/or functional in the treated cells. In some embodiments relating to CRISPR-Cas9 RNPs, a band on a non-denaturing gel of about 145, 150, 155, or 145-160 kDa may indicate that the RNP was delivered as a complete and functional gene-editing complex into the cell.

As used herein, device dimensions are denoted by a series of numbers indicating length, width, and optionally number of constrictions (e.g., 30 μm-6 m×5 denotes a device with a 30 μm length, 6 μm width, and 5 constrictions).

Exemplary Embodiments

Aspects of the present subject matter provide a method for delivering a protein and a nucleic acid into a cell, the method comprising: providing a cell in a solution; passing the solution through a microfluidic channel that includes a cell-deforming constriction; passing the cell through the constriction such that a pressure is applied to the cell causing perturbations of the cell large enough for the protein and the nucleic acid to pass through; and contacting the cell with the protein and the nucleic acid before, during, and/or after the cell passes through the constriction.

In some embodiments, said solution comprises the protein and the nucleic acid before, during, and/or after the cell passes through the constriction.

In some embodiments, the protein and the nucleic acid form a protein-nucleic acid complex.

In some embodiments, the protein and the nucleic acid are the components of the protein-nucleic acid complex but are not complexed when delivered to the cell.

In some embodiments, the protein and the nucleic acid form a protein-nucleic acid complex after delivery into the cell.

In some embodiments, the protein and the nucleic acid form a protein-nucleic acid complex before delivery into the cell.

In some embodiments, the protein and the nucleic acid comprise gene editing components.

In some embodiments, said protein-nucleic acid complex comprises a ribonucleoprotein (RNP).

In some embodiments, (a) the protein is a Cas protein or a Cpf1 protein; and (b) the nucleic acid is a single guide RNA (sgRNA) or a CRISPR RNA (crRNA) and a trans-activating crRNA (tracrRNA).

In some embodiments, the complex is a RNP comprising a Cas protein or a Cpf1 protein and a sgRNA, wherein the Cas protein or the Cpf1 protein and the sgRNA were complexed using about a 0.5, 2.0, 2.5, or 3.0 molar excess of the Cas protein or Cpf1 protein.

In some embodiments, the Cas protein comprises a Cas9 protein.

In some embodiments, said protein-nucleic acid complex comprises a first RNP and a second RNP.

In some embodiments, the first RNP and the second RNP are both nickases.

In some embodiments, the first RNP nicks a target sequence different from the target sequence of the second RNP.

In some embodiments, said protein-nucleic acid complex comprises a TALEN protein, Zinc finger nuclease, mega nuclease, or Cre recombinase.

In some embodiments, the nucleic acid comprises an mRNA encoding a TALEN protein, a Zinc finger nuclease, a mega nuclease, or a Cre recombinase In some embodiments, said protein-nucleic acid complex comprises (a) a nucleic acid molecule that is complexed with a protein via electrostatic attraction; (b) a nucleic acid molecule wrapped around a protein; (c) DNA and a histone; (d) a ribonucleoprotein (RNP); (e) a ribosome, an enzyme telomerase, a vault ribonucleoprotein, RNase P, hnRNP, or a small nuclear RNP (snRNP); or (f) a chromosome comprising a protein.

In some embodiments, the solution further comprises donor DNA.

In some embodiments, the solution further comprises donor DNA before, during, and/or after the cell passes through the constriction.

In some embodiments, said cell comprises a mammalian cell.

In some embodiments, said cell comprises a human cell.

In some embodiments, the diameter of the constriction is selected to induce temporary perturbations of the cell membrane large enough for the protein and the nucleic acid to pass through.

In some embodiments, a diameter of the constriction is about 20-99% of the diameter of the cell.

In some embodiments, a diameter of the constriction is about 60% of the diameter of the cell.

In some embodiments, the microfluidic channel is one of a plurality of parallel microfluidic channels in the microfluidic system.

In some embodiments, the plurality of parallel microfluidic channels comprises at least about 2, 5, 10, 20, 25, 30, 40, 45, 50, 75, 100, 500, 1,000, or 2-1,000 microfluidic channels.

In some embodiments, the cell is a plurality of cells, and each cell is passed through one of a plurality of parallel microfluidic channels, and wherein each microfluidic channel of the plurality of parallel microfluidic channels includes a cell-deforming constriction.

In some embodiments, (a) the diameter of the constriction is about 2, 3, 4, 5, 6, 7, 8, 9, 10, 15, 20, 2-10 m, or 10-20 m; (b) the length of the constriction is about 10, 15, 20, 24, 30, 40, 50, 60, 70, 80, 90, 100, 10-40, 10-50, 10-60, or 10-100 μm; (c) a pressure of about 10, 20, 30, 40, 50, 60, 70, 80, 90, 100 or 10-100 psi is used to pass the solution through the microfluidic channel; (d) the cell passes through the microfluidic channel at a speed of about 300, 400, 500, 600, 700, 800, 900, 100-300, 200-700, 250-400, 100-1000 mm/s, 1-1000 mm/s, 1 m/s, 2 m/s, 3 m/s, 4 m/s, 5 m/s, 6 m/s, 7 m/s, 8 m/s, 9 m/s, 10 m/s, 0.01-5 m/s, 5-10 m/s, or 0.01-10 m/s; (e) said microfluidic channel comprises multiple cell-deforming constrictions in series; (f) said microfluidic channel comprises a single cell-deforming constriction; (g) the perturbations of the cell membrane include a maximum diameter of about 1-20, 1-600, 4, 5, 6, 7, 8, 9, 10, 12, 14, 16, 18, 20, 25, 50, 75, 100, 150, 200, 250, 300, 350, 400, 450, 500, or 600 nm; and/or (h) perturbations of the cell membrane having a maximum diameter of about 1-20, 1-600, 4, 5, 6, 7, 8, 9, 10, 12, 14, 16, 18, 20, 25, 50, 75, 100, 150, 200, 250, 300, 350, 400, 450, 500, or 600 nm persist on the cell membrane for at least about 1, 2, 3, 4, 5, 6, 7, 8, 9, 10, or 1-10 minutes.

In some embodiments, (a) the expression of a target gene in the cell is reduced by at least about 5, 10, 15, 20, 25, 30, 35, 40, 45, 50, 55, 60, 75, 80, 85, 90, 95, or 99% or more; or (b) the cell is a plurality of cells and the expression of a target gene in the plurality of cells is reduced by at least about 5, 10, 15, 20, 25, 30, 35, 40, 45, 50, 55, 60, 75, 80, 85, 90, 95, or 99% or more, after the protein and the nucleic acid are delivered to the cell.

In some embodiments, (a) the expression of a target gene in the cell is reduced by at least about 5, 10, 15, 20, 25, 30, 35, 40, 45, 50, 55, 60, 75, 80, 85, 90, 95, or 99% or more; or (b) the cell is a plurality of cells and the expression of a target gene in the plurality of cells is reduced by at least about 5, 10, 15, 20, 25, 30, 35, 40, 45, 50, 55, 60, 75, 80, 85, 90, 95, or 99% or more, about 1, 2, 5, 12, 24, 1-12, 6-12, 6-18, 12-24, or 1-24 hours after the protein and the nucleic acid are delivered to the cell.

In some embodiments, (a) the expression of a target gene in the cell is increased by at least about 5, 10, 25, 50, 75, 100, 250, 500% or more; or (b) the cell is a plurality of cells and the expression of a target gene in the plurality of cells is increased by at least about 5, 10, 25, 50, 75, 100, 250, 500% or more, after the protein and the nucleic acid are delivered to the cell.

In some embodiments, (a) the expression of a target gene in the cell is increased by at least about 5, 10, 25, 50, 75, 100, 250, 500% or more; or (b) the cell is a plurality of cells and the expression of a target gene in the plurality of cells is increased by at least about 5, 10, 25, 50, 75, 100, 250, 500% or more, about 1, 2, 5, 12, 24, 1-12, 6-12, 6-18, 12-24, or 1-24 hours after the protein and the nucleic acid are delivered to the cell.

Aspects of the present subject matter provide a device for delivering a protein-nucleic acid complex to a cell, comprising at least one microfluidic channel, wherein said channel comprises a constriction length of about 30 μm and a constriction width of about 4 μm.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1: Editing of the B2M Locus in Primary Human T Cells Using CellSqueeze (SQZ) to Deliver CRISPR/Cas9 Gene Editing Complex A series of experiments have been undertaken in unstimulated human T cells to demonstrate the ability of the SQZ platform to deliver Cas9 ribonucleoproteins (RNPs; recombinant Cas9 protein complexed with a single-guide RNA) and accomplish efficient genome editing of a model locus, the $\beta_2$ microglobulin component of MHC class 1 (B2M).

Delivery of Cas9 RNP to Unstimulated Human T Cells

Fresh PBMCs were isolated from human blood using a standard Ficoll gradient. Next, T cells were negatively selected (Human T cell enrichment kit (StemCell Technologies)) counted, washed and resuspended at $10\text{-}20\times10^6$ cells/mL in OptiMEM for delivery. Ten μg of recombinant CAS9 (PNA Bio) was pre-complexed with a 2.5 molar excess of unmodified gRNA (PNA Bio) designed to specifically target the B2M locus. Recombinant CAS9 is reconstituted to a solution with a final concentration of 20 mM Hepes, 150 mM KCl, 1% sucrose. gRNA is added directly to the CAS9 solution and incubated on ice for 20 minutes to form the complex. The complex is added directly to resuspended cells. RNP complexes were incubated on ice 20 minutes prior to SQZ-mediated delivery. The RNP (2.2 uM) was co-delivered with a 3 kD-Cascade Blue Dextran (0.15 mg/mL) used as a proxy for delivery efficiency. Two different chips, 10-4 and 30-4 were used to deliver the complex at a pressures of 60 and 90 psi. The chips have constrictions of the same width (4 microns) but have two different constriction lengths (30 vs. 10 microns).

Figure 4:
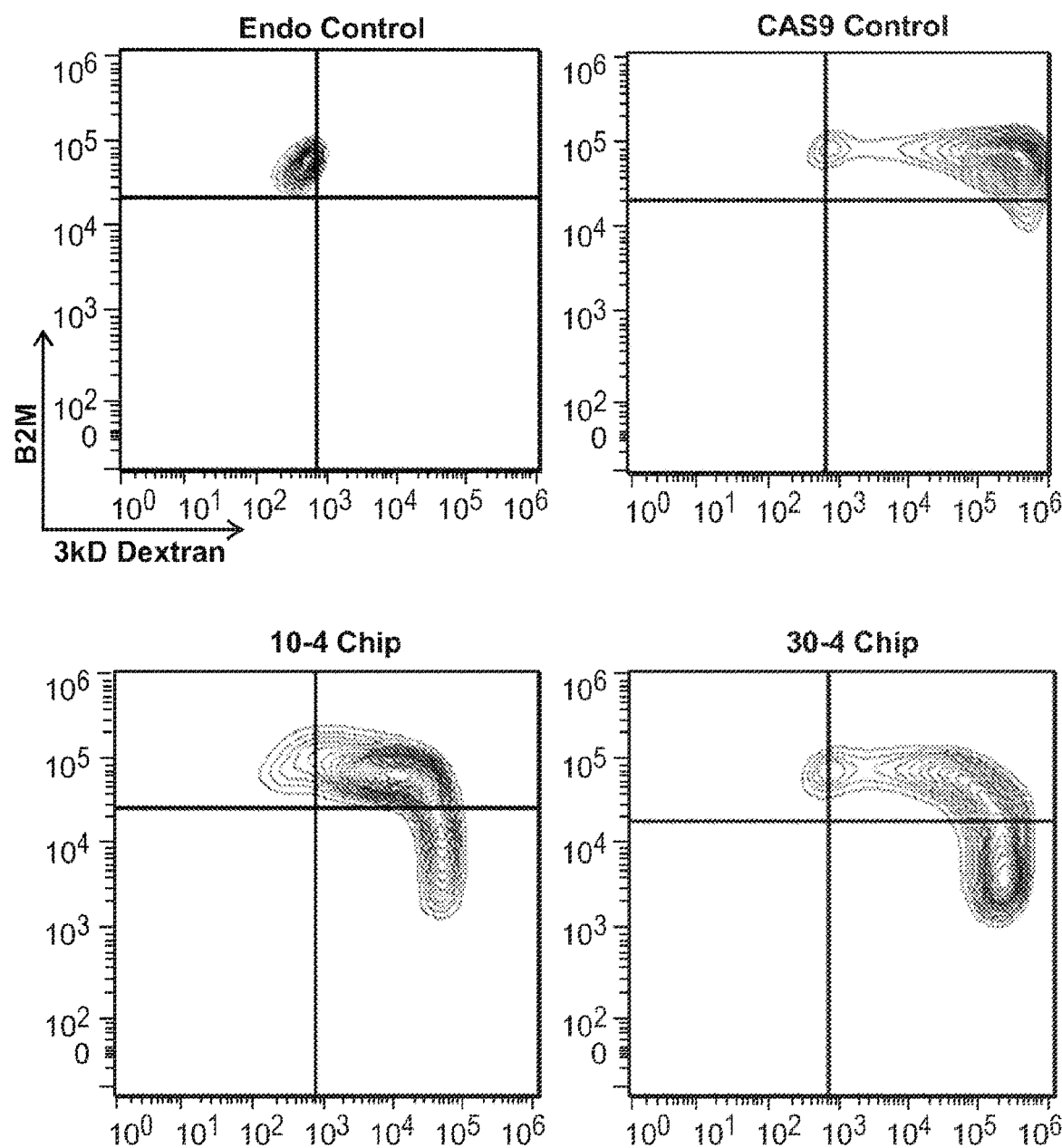
FIG. 4 is a series of FACs plots showing $\beta_2$ microglobulin component of MHC class 1 (B2M) expression vs. delivered dextran for four different cell populations obtained using FACS. The delivery of the RNP using the 30-4 chip at 90 psi results in a 54.4% reduction in B2M expression as compared to the endocytosis control whereas the 10-4 chip at 90 psi results in a 25.2% reduction in B2M expression. B2M expression on the CAS9 control is not significantly different than the endocytosis control. The longer constriction chip results in more delivery of the RNP complex and a larger reduction in B2M expression.

At 48 hours post-delivery, a FACS based readout was used to determine B2M protein levels. Reduced B2M expression was used as a measure of functional editing. Two controls were used; 1) T cells incubated with the RNP complex at room temperature for the same time as the delivery process using the *Cell* Squeeze process (endocytosis control; "endo control"), and 2) T cells squeezed with Cas9 protein but no gRNA. Plots of B2M expression vs. delivered dextran are shown (FIG. 4) for the four different cell populations. B2M expression on the Cas9 control was not significantly different than the endocytosis control. The delivery of the RNP using the 30-4 chip at 90 psi resulted in a 54.4% reduction in B2M expression as compared to the endo control whereas the 10-4 chip at 90 psi resulted in a 25.2% reduction in B2M expression. The longer constriction chip resulted in more delivery of the RNP complex and a larger reduction in B2M expression.

Dextran delivery was used to define low, mid and high delivered populations. The differences in efficiency of B2M knockdown for these specific populations was then determined using the mean fluorescence intensity (MFI) of B2M staining. For the 10-4 chip, the MFI of the highly delivered population was 18,637 versus 71,173 for the mid delivered populations and 83,676 for the low or non-delivered populations. This nearly 5-fold intensity drop in B2M staining for the high delivered populations demonstrates the degree to which delivery influences RNP activity. Similarly, for the 30-4 chip, the MFI of the highly delivered population was 16,460 versus 44,207 for the mid delivered populations and 54,159 for the low delivered population. These data demonstrated the importance that the cell squeezing delivery system of gene editing complexes to the cytosol of a cell has on editing efficiency, even within a single population.

To confirm the FACS readout, a second, sequence based analysis, was also employed in which DNA was extracted and amplified using primers flanking the target region thereby generating an amplicon of the edited region for Next Generation Sequencing (NGS). Sequencing results were analyzed using a simple algorithm designed to detect CRISPR variants from NGS reads. As expected, the sequence-based readout showed higher editing efficiencies. Indeed, some of the indels identified in sequencing still resulted in a functional, full length protein (i.e. single base substitutions that did not change the resultant amino acid).

TABLE

Comparison of FACS- and Sequence-based readouts from 10-4 editing experiment.

|  | Endo | Cas9 | RNP |
|---|---|---|---|
| FACS | 0.3 | 8.15 | 20.4 |
| Sequencing | 3.87 | 3.04 | 27.18 |

These data demonstrated successful editing ability of the RNP complex when delivered by the Cell Squeeze platform.

Effect of RNP Complex Amount on Editing Efficiency

Figure 5:
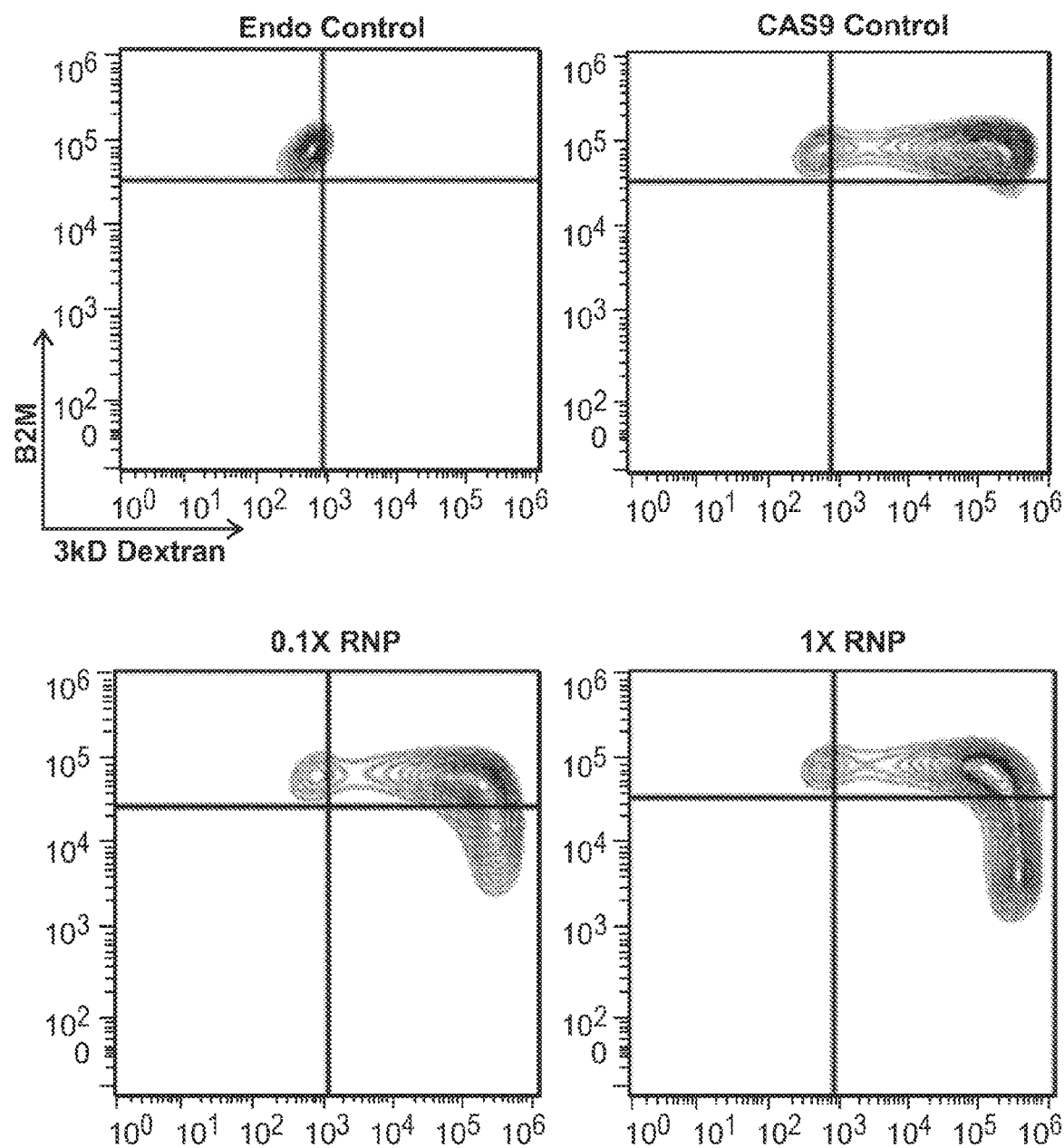
FIG. 5 is a series of FACs plots showing reduced B2M expression in a dose dependent manner determined by FACS as a measure of functional editing with the indicated conditions.

RNP complex was delivered to unstimulated human T cells using the 30-4 chip and at two different RNP amounts: 1) the standard 1×RNP complex (Mug Cas9, 2.5 molar excess of gRNA) and, 2) 0.1× the standard RNP complex amount. At 48 hours post-delivery, a FACS based readout was used to determine B2M protein levels. Reduced B2M expression was used as a measure of functional editing. Plots of B2M expression vs. delivered dextran are shown below for the four different cell populations. Two controls were used; 1) T cells incubated in 1×RNP complex at room temperature for the same time as the delivery process using the *Cell* Squeeze process (endocytosis control), and 2) T cells squeezed with Cas9 protein but no gRNA (FIG. 5).

B2M expression on the Cas9 control (Cas9 protein with no gRNA) is not significantly different than the endocytosis control. The lower amount of the RNP complex (0.1×RNP) resulted in a 20.7% reduction of B2M positive cells as compared to the 55.4% reduction in B2M positive cells at the higher amount of RNP complex (1×RNP complex (10 ug CAS9, 2.5 molar excess of gRNA)). This experiment demonstrates a dose-dependent response directly related to the delivery of the RNP.

Other Embodiments

Cited references are incorporated herein by reference. To the extent that any of the incorporated material is inconsistent with the present disclosure, the present disclosure shall control. Furthermore, to the extent necessary, material incorporated by reference herein should be disregarded if necessary to preserve the validity of the claims.

Further, while the description above refers to the invention, the description may include more than one invention.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A microfluidic system for delivering a complex comprising a protein and a nucleic acid (protein-nucleic acid complex) into a cell, comprising: (a) at least one microfluidic channel and (b) a protein-nucleic acid complex, wherein the at least one microfluidic channel comprises a cell-deforming constriction having a diameter that is 20-99% of the diameter of the cell and allows the delivery of the protein-nucleic acid complex in an intact form.

2. The microfluidic system of claim 1, wherein:
the microfluidic system further comprises the cell, wherein the cell is provided in a suspension; and
the microfluidic system is configured to pass the suspension comprising the cell through the microfluidic channel that includes the cell-deforming constriction such that a pressure is applied to the cell causing perturbations of the cell large enough for the protein-nucleic acid complex to pass through.

3. The microfluidic system of claim 2, wherein the system is configured such that the cell is contacted with the protein-nucleic acid complex (a) before the cell passes through the constriction; or (b) before and during the cell passes through the constriction.

4. The microfluidic system of claim 2, wherein the protein-nucleic acid complex comprises gene editing components.

5. The microfluidic system of claim 2, wherein the protein comprises a ribonucleoprotein (RNP).

6. The microfluidic system of claim 2, wherein
(a) the protein is a Cas protein or a Cpf1 protein; and
(b) the nucleic acid is a single guide RNA (sgRNA) or a CRISPR RNA (crRNA) and a trans-activating crRNA (tracrRNA).

7. The microfluidic system of claim 6, wherein the protein-nucleic acid complex is a RNP comprising a Cas protein or a Cpf1 protein and a sgRNA, wherein the Cas protein or the Cpf1 protein and the sgRNA were complexed using about a 0.5, 2.0, 2.5, or 3.0 molar excess of the Cas protein or Cpf1 protein.

8. The microfluidic system of claim 6, wherein the Cas protein comprises a Cas9 protein.

9. The microfluidic system of claim 5, wherein the protein-nucleic acid complex comprises a first RNP and a second RNP.

10. The microfluidic system of claim 9, wherein the first RNP and the second RNP are both nickases.

11. The microfluidic system of claim 10, wherein the first RNP nicks a target sequence different from the target sequence of the second RNP.

12. The microfluidic system of claim 2, wherein the protein comprises a TALEN protein, Zinc finger nuclease, mega nuclease, or Cre recombinase.

13. The microfluidic system of claim 2, wherein the nucleic acid comprises an mRNA encoding a TALEN protein, a Zinc finger nuclease, a mega nuclease, or a Cre recombinase.

14. The microfluidic system of claim 2, wherein the protein-nucleic acid complex comprises
(a) a nucleic acid molecule that is complexed with a protein via electrostatic attraction;
(b) a nucleic acid molecule wrapped around a protein;
(c) DNA and a histone;
(d) a ribonucleoprotein (RNP);
(e) a ribosome, an enzyme telomerase, a vault ribonucleoprotein, RNase P, hnRNP, or a small nuclear RNP (snRNP); or
(f) a chromosome comprising a protein.

15. The microfluidic system of claim 2, wherein the suspension further comprises a donor DNA.

16. The microfluidic system of claim 15, wherein the suspension comprises the donor DNA before, during, and/or after the cell passes through the constriction.

17. The microfluidic system of claim 2, wherein the cell comprises a mammalian cell.

18. The microfluidic system of claim 2, wherein the cell comprises a human cell.

19. The microfluidic system of claim 2, wherein a diameter of the constriction is about 60% of the diameter of the cell.

20. The microfluidic system of claim 2, wherein the microfluidic channel is one of a plurality of parallel microfluidic channels in the microfluidic system.

21. The microfluidic system of claim 20, wherein the plurality of parallel microfluidic channels comprises at least about 2, 5, 10, 20, 25, 30, 40, 45, 50, 75, 100, 500, 1,000, or 2-1,000 microfluidic channels.

22. The microfluidic system of claim 2, wherein the cell is a plurality of cells, and each cell is passed through one of a plurality of parallel microfluidic channels, and wherein each microfluidic channel of the plurality of parallel microfluidic channels includes a cell-deforming constriction.

23. The microfluidic system of claim 2, wherein
(a) the diameter of the constriction is about 2, 3, 4, 5, 6, 7, 8, 9, 10, 15, 20, 2-10 μm, or 10-20 μm;
(b) the length of the constriction is about 10, 15, 20, 24, 30, 40, 50, 60, 70, 80, 90, 100, 10-40, 10-50, 10-60, or 10-100 μm;
(c) a pressure of about 10, 20, 30, 40, 50, 60, 70, 80, 90, 100 or 10-100 psi is used to pass the suspension through the microfluidic channel;
(d) the cell passes through the microfluidic channel at a speed of about 300, 400, 500, 600, 700, 800, 900, 100-300, 200-700, 250-400, 100-1000 mm/s, 1-1000 mm/s, 1 m/s, 2 m/s, 3 m/s, 4 m/s, 5 m/s, 6 m/s, 7 m/s, 8 m/s, 9 m/s, 10 m/s, 0.01-5 m/s, 5-10 m/s, or 0.01-10 m/s;
(e) the microfluidic channel comprises multiple cell-deforming constrictions in series;
(f) the microfluidic channel comprises a single cell-deforming constriction;
(g) the perturbations of the cell membrane include a maximum diameter of about 1-20, 1-600, 4, 5, 6, 7, 8, 9, 10, 12, 14, 16, 18, 20, 25, 50, 75, 100, 150, 200, 250, 300, 350, 400, 450, 500, or 600 nm; and/or
(h) perturbations of the cell membrane having a maximum diameter of about 1-20, 1-600, 4, 5, 6, 7, 8, 9, 10, 12, 14, 16, 18, 20, 25, 50, 75, 100, 150, 200, 250, 300, 350, 400, 450, 500, or 600 nm persist on the cell membrane for about 1, 2, 3, 4, 5, 6, 7, 8, 9, 10, or 1-10 minutes.

\* \* \* \* \*

UNITED STATES PATENT AND TRADEMARK OFFICE
CERTIFICATE OF CORRECTION

Page 1 of 1

PATENT NO. : 12,130,281 B2
APPLICATION NO. : 17/404286
DATED : October 29, 2024
INVENTOR(S) : Armon R. Sharei et al.

It is certified that error appears in the above-identified patent and that said Letters Patent is hereby corrected as shown below:

In the Specification

At Column 1, Lines 18-22, in the paragraph under the heading "STATEMENT AS TO FEDERALLY-SPONSORED RESEARCH":
"This invention was made with Government support under Grant No. R01 GM101420 awarded by the National Institutes of Health, and Grant No. DE-FG02-02ER63445 awarded by the Department of Energy. The Government has certain rights in the invention."

Should read:
--This invention was made with government support under GM101420 awarded by the National Institutes of Health, and DE-FG02-02ER63445 awarded by the U.S. Department of Energy. The government has certain rights in the invention.--

In the Claims

Claim 1, Column 513, Lines 29-30:
"allows the delivery of the protein-nucleic acid complex in an intact form."

Should be:
--allows for the delivery of the protein-nucleic acid complex in an intact form.--

Claim 21, Column 514, Lines 59-62:
"The microfluidic system of claim 20, wherein the plurality of parallel microfluidic channels comprises at least about 2, 5, 10, 20, 25, 30, 40, 45, 50, 75, 100, 500, 1,000, or 2-1,000 microfluidic channels."

Should be:
--The microfluidic system of claim 20, wherein the plurality of parallel microfluidic channels comprises about 2, 5, 10, 20, 25, 30, 40, 45, 50, 75, 100, 500, 1,000, or 2-1,000 microfluidic channels.--

Signed and Sealed this
Seventh Day of January, 2025

Derrick Brent
*Acting Director of the United States Patent and Trademark Office*

SEQUENCE LISTING

```
<160> NUMBER OF SEQ ID NOS: 66

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
```

```
              115                 120                 125
His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540
```

-continued

```
Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
                675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960
```

```
Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
        1250                1255                1260

His Tyr Leu Asp Glu Ile Ile Glu Gln Ile Ser Glu Phe Ser Lys
        1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
        1295                1300                1305

Ile Ile His Leu Phe Thr Leu Thr Asn Leu Gly Ala Pro Ala Ala
        1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
        1340                1345                1350

Gly Leu Tyr Glu Thr Arg Ile Asp Leu Ser Gln Leu Gly Gly Asp
```

<210> SEQ ID NO 2
<211> LENGTH: 4107
<212> TYPE: DNA
<213> ORGANISM: Streptococcus pyogenes

<400> SEQUENCE: 2

| | | | | | |
|---|---|---|---|---|---|
| atggataaga | atactcaat | aggcttagat | atcggcacaa | atagcgtcgg | atgggcggtg | 60 |
| atcactgatg | aatataaggt | tccgtctaaa | aagttcaagg | ttctgggaaa | tacagaccgc | 120 |
| cacagtatca | aaaaaatct | tatagggct | cttttatttg | acagtggaga | gacagcggaa | 180 |
| gcgactcgtc | tcaaacggac | agctcgtaga | aggtatacac | gtcggaagaa | tcgtatttgt | 240 |
| tatctacagg | agatttttc | aaatgagatg | gcgaaagtag | atgatagttt | ctttcatcga | 300 |
| cttgaagagt | ctttttttggt | ggaagaagac | aagaagcatg | aacgtcatcc | tatttttgga | 360 |
| aatatagtag | atgaagttgc | ttatcatgag | aaatatccaa | ctatctatca | tctgcgaaaa | 420 |
| aaattggtag | attctactga | taaagcggat | ttgcgcttaa | tctatttggc | cttagcgcat | 480 |
| atgattaagt | tcgtggtca | tttttttgatt | gagggagatt | taaatcctga | taatagtgat | 540 |
| gtggacaaac | tatttatcca | gttggtacaa | acctacaatc | aattatttga | agaaaaccct | 600 |
| attaacgcaa | gtggagtaga | tgctaaagcg | attctttctg | cacgattgag | taaatcaaga | 660 |
| cgattagaaa | atctcattgc | tcagctcccc | ggtgagaaga | aaaatggctt | atttgggaat | 720 |
| ctcattgctt | tgtcattggg | tttgacccct | aattttaaat | caaattttga | tttggcagaa | 780 |
| gatgctaaat | tacagctttc | aaaagatact | tacgatgatg | atttagataa | tttattggcg | 840 |
| caaattggag | atcaatatgc | tgatttgttt | ttggcagcta | agaatttatc | agatgctatt | 900 |
| ttactttcag | atatcctaag | agtaaatact | gaaataacta | aggctcccct | atcagcttca | 960 |
| atgattaaac | gctacgatga | acatcatcaa | gacttgactc | ttttaaaagc | tttagttcga | 1020 |
| caacaacttc | cagaaaagta | taagaaaatc | ttttttgatc | aatcaaaaaa | cggatatgca | 1080 |
| ggttatattg | atgggggagc | tagccaagaa | gaatttttata | aatttatcaa | accaatttta | 1140 |
| gaaaaaatgg | atggtactga | ggaattattg | gtgaaactaa | atcgtgaaga | tttgctgcgc | 1200 |
| aagcaacgga | cctttgacaa | cggctctatt | ccccatcaaa | ttcacttggg | tgagctgcat | 1260 |
| gctattttga | agacaagaa | agactttttat | ccatttttaa | aagacaatcg | tgaagaagatt | 1320 |
| gaaaaaatct | tgacttttcg | aattccttat | tatgttggtc | cattggcgcg | tggcaatagt | 1380 |
| cgttttgcat | ggatgactcg | gaagtctgaa | gaaacaatta | ccccatggaa | ttttgaagaa | 1440 |
| gttgtcgata | aggtgcttc | agctcaatca | tttattgaac | gcatgacaaa | ctttgataaa | 1500 |
| aatcttccaa | atgaaaaagt | actaccaaaa | catagtttgc | tttatgagta | ttttacggtt | 1560 |
| tataacgaat | tgacaaaggt | caaatatgtt | actgaaggaa | tgcgaaaacc | agcatttctt | 1620 |
| tcaggtgaac | agaagaaagc | cattgttgat | ttactcttca | aaacaaatcg | aaaagtaacc | 1680 |
| gttaagcaat | taaaagaaga | ttatttcaaa | aaaatagaat | gttttgatag | tgttgaaatt | 1740 |
| tcaggagttg | aagatagatt | taatgcttca | ttaggtacct | accatgattt | gctaaaaatt | 1800 |
| attaaagata | aagatttttt | ggataatgaa | gaaatgaag | atatcttaga | ggatattgtt | 1860 |
| ttaacattga | cctatttga | agataggggag | atgattgagg | aaagacttaa | aacatatgct | 1920 |
| cacctctttg | atgataaggt | gatgaaacag | cttaaacgtc | gccgttatac | tggttgggga | 1980 |
| cgtttgtctc | gaaaattgat | taatggtatt | agggataagc | aatctggcaa | aacaatatta | 2040 |
| gattttttga | aatcagatgg | ttttgccaat | cgcaatttta | tgcagctgat | ccatgatgat | 2100 |

```
agtttgacat ttaaagaaga cattcaaaaa gcacaagtgt ctggacaagg cgatagttta   2160
catgaacata ttgcaaattt agctggtagc cctgctatta aaaaggtat  tttacagact   2220 gtaaagttg  ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aagatgaaa    2640 aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta agtgattac  cttaaaatct   2880 aaattagttt ctgacttccg aaaagatttc caattctata agtacgtga  gattaacaat   2940 taccatcatg cccatgatgc gtatctaaat gccgtcgttg gaactgcttt gattaagaaa   3000
tatccaaaac ttgaatcgga gtttgtctat ggtgattata agtttatga  tgttcgtaaa   3060 atgattgcta agtctgagca agaaataggc aaagcaaccg caaatatttt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aattatgaaa agaagttcct ttgaaaaaaa tccgattgac   3540 ttttagaag  ctaaaggata taaggaagtt aaaaaagact taatcattaa actacctaaa   3600
tatagtcttt ttgagttaga aaacggtcgt aaacggatgc tggctagtgc cggagaatta   3660
caaaaaggaa atgagctggc tctgccaagc aaatatgtga ttttttata  tttagctagt   3720 cattatgaaa agttgaaggg tagtccagaa gataacgaac aaaaacaatt gtttgtggag   3780
cagcataagc attatttaga tgagattatt gagcaaatca gtgaattttc taagcgtgtt   3840
attttagcag atgccaattt agataaagtt cttagtgcat ataacaaaca tagagacaaa   3900
ccaatacgtg aacaagcaga aaatattatt catttattta cgttgacgaa tcttggagct   3960
cccgctgctt ttaaatattt tgatacaaca attgatcgta aacgatatac gtctacaaaa   4020
gaagttttag atgccactct tatccatcaa tccatcactg gtctttatga aacacgcatt   4080
gatttgagtc agctaggagg tgactga                                       4107
```

<210> SEQ ID NO 3
<211> LENGTH: 1388
<212> TYPE: PRT
<213> ORGANISM: Streptococcus thermophilus

<400> SEQUENCE: 3

Met Thr Lys Pro Tyr Ser Ile Gly Leu Asp Ile Gly Thr Asn Ser Val
1               5                   10                  15

```
Gly Trp Ala Val Thr Thr Asp Asn Tyr Lys Val Pro Ser Lys Lys Met
            20              25              30
Lys Val Leu Gly Asn Thr Ser Lys Tyr Ile Lys Lys Asn Leu Leu
        35              40              45
Gly Val Leu Leu Phe Asp Ser Gly Ile Thr Ala Glu Gly Arg Arg Leu
    50              55              60
Lys Arg Thr Ala Arg Arg Arg Tyr Thr Arg Arg Arg Asn Arg Ile Leu
65              70              75              80
Tyr Leu Gln Glu Ile Phe Ser Thr Glu Met Ala Thr Leu Asp Asp Ala
            85              90              95
Phe Phe Gln Arg Leu Asp Asp Ser Phe Leu Val Pro Asp Lys Arg
            100             105             110
Asp Ser Lys Tyr Pro Ile Phe Gly Asn Leu Val Glu Glu Lys Ala Tyr
        115             120             125
His Asp Glu Phe Pro Thr Ile Tyr His Leu Arg Lys Tyr Leu Ala Asp
    130             135             140
Ser Thr Lys Lys Ala Asp Leu Arg Leu Val Tyr Leu Ala Leu Ala His
145             150             155             160
Met Ile Lys Tyr Arg Gly His Phe Leu Ile Glu Gly Glu Phe Asn Ser
            165             170             175
Lys Asn Asn Asp Ile Gln Lys Asn Phe Gln Asp Phe Leu Asp Thr Tyr
            180             185             190
Asn Ala Ile Phe Glu Ser Asp Leu Ser Leu Glu Asn Ser Lys Gln Leu
        195             200             205
Glu Glu Ile Val Lys Asp Lys Ile Ser Lys Leu Glu Lys Lys Asp Arg
    210             215             220
Ile Leu Lys Leu Phe Pro Gly Glu Lys Asn Ser Gly Ile Phe Ser Glu
225             230             235             240
Phe Leu Lys Leu Ile Val Gly Asn Gln Ala Asp Phe Arg Lys Cys Phe
            245             250             255
Asn Leu Asp Glu Lys Ala Ser Leu His Phe Ser Lys Glu Ser Tyr Asp
            260             265             270
Glu Asp Leu Glu Thr Leu Leu Gly Tyr Ile Gly Asp Asp Tyr Ser Asp
        275             280             285
Val Phe Leu Lys Ala Lys Lys Leu Tyr Asp Ala Ile Leu Leu Ser Gly
    290             295             300
Phe Leu Thr Val Thr Asp Asn Glu Thr Glu Ala Pro Leu Ser Ser Ala
305             310             315             320
Met Ile Lys Arg Tyr Asn Glu His Lys Glu Asp Leu Ala Leu Leu Lys
            325             330             335
Glu Tyr Ile Arg Asn Ile Ser Leu Lys Thr Tyr Asn Glu Val Phe Lys
            340             345             350
Asp Asp Thr Lys Asn Gly Tyr Ala Gly Tyr Ile Asp Gly Lys Thr Asn
        355             360             365
Gln Glu Asp Phe Tyr Val Tyr Leu Lys Lys Leu Leu Ala Glu Phe Glu
    370             375             380
Gly Ala Asp Tyr Phe Leu Glu Lys Ile Asp Arg Glu Asp Phe Leu Arg
385             390             395             400
Lys Gln Arg Thr Phe Asp Asn Gly Ser Ile Pro Tyr Gln Ile His Leu
            405             410             415
Gln Glu Met Arg Ala Ile Leu Asp Lys Gln Ala Lys Phe Tyr Pro Phe
            420             425             430
```

-continued

```
Leu Ala Lys Asn Lys Glu Arg Ile Glu Lys Ile Leu Thr Phe Arg Ile
            435                 440                 445

Pro Tyr Tyr Val Gly Pro Leu Ala Arg Gly Asn Ser Asp Phe Ala Trp
        450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510

Leu Leu Tyr Glu Thr Phe Asn Val Tyr Asn Glu Leu Thr Lys Val Arg
            515                 520                 525

Phe Ile Ala Glu Ser Met Arg Asp Tyr Gln Phe Leu Asp Ser Lys Gln
        530                 535                 540

Lys Lys Asp Ile Val Arg Leu Tyr Phe Lys Asp Lys Arg Lys Val Thr
545                 550                 555                 560

Asp Lys Asp Ile Ile Glu Tyr Leu His Ala Ile Tyr Gly Tyr Asp Gly
                565                 570                 575

Ile Glu Leu Lys Gly Ile Glu Lys Gln Phe Asn Ser Ser Leu Ser Thr
            580                 585                 590

Tyr His Asp Leu Leu Asn Ile Ile Asn Asp Lys Glu Phe Leu Asp Asp
            595                 600                 605

Ser Ser Asn Glu Ala Ile Ile Glu Glu Ile Ile His Thr Leu Thr Ile
        610                 615                 620

Phe Glu Asp Arg Glu Met Ile Lys Gln Arg Leu Ser Lys Phe Glu Asn
625                 630                 635                 640

Ile Phe Asp Lys Ser Val Leu Lys Lys Leu Ser Arg Arg His Tyr Thr
                645                 650                 655

Gly Trp Gly Lys Leu Ser Ala Lys Leu Ile Asn Gly Ile Arg Asp Glu
            660                 665                 670

Lys Ser Gly Asn Thr Ile Leu Asp Tyr Leu Ile Asp Asp Gly Ile Ser
            675                 680                 685

Asn Arg Asn Phe Met Gln Leu Ile His Asp Asp Ala Leu Ser Phe Lys
        690                 695                 700

Lys Lys Ile Gln Lys Ala Gln Ile Ile Gly Asp Glu Asp Lys Gly Asn
705                 710                 715                 720

Ile Lys Glu Val Val Lys Ser Leu Pro Gly Ser Pro Ala Ile Lys Lys
                725                 730                 735

Gly Ile Leu Gln Ser Ile Lys Ile Val Asp Glu Leu Val Lys Val Met
            740                 745                 750

Gly Gly Arg Lys Pro Glu Ser Ile Val Val Glu Met Ala Arg Glu Asn
            755                 760                 765

Gln Tyr Thr Asn Gln Gly Lys Ser Asn Ser Gln Gln Arg Leu Lys Arg
        770                 775                 780

Leu Glu Lys Ser Leu Lys Glu Leu Gly Ser Lys Ile Leu Lys Glu Asn
785                 790                 795                 800

Ile Pro Ala Lys Leu Ser Lys Ile Asp Asn Asn Ala Leu Gln Asn Asp
                805                 810                 815

Arg Leu Tyr Leu Tyr Tyr Leu Gln Asn Gly Lys Asp Met Tyr Thr Gly
            820                 825                 830

Asp Asp Leu Asp Ile Asp Arg Leu Ser Asn Tyr Asp Ile Asp His Ile
            835                 840                 845

Ile Pro Gln Ala Phe Leu Lys Asp Asn Ser Ile Asp Asn Lys Val Leu
```

-continued

```
            850                 855                 860
Val Ser Ser Ala Ser Asn Arg Gly Lys Ser Asp Val Pro Ser Leu
865                 870                 875                 880

Glu Val Val Lys Lys Arg Lys Thr Phe Trp Tyr Gln Leu Leu Lys Ser
                    885                 890                 895

Lys Leu Ile Ser Gln Arg Lys Phe Asp Asn Leu Thr Lys Ala Glu Arg
                900                 905                 910

Gly Gly Leu Ser Pro Glu Asp Lys Ala Gly Phe Ile Gln Arg Gln Leu
                915                 920                 925

Val Glu Thr Arg Gln Ile Thr Lys His Val Ala Arg Leu Leu Asp Glu
            930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
                965                 970                 975

Phe Glu Leu Tyr Lys Val Arg Glu Ile Asn Asp Phe His His Ala His
                980                 985                 990

Asp Ala Tyr Leu Asn Ala Val Val  Ala Ser Ala Leu Leu  Lys Lys Tyr
            995                 1000                1005

Pro Lys  Leu Glu Pro Glu Phe  Val Tyr Gly Asp Tyr  Pro Lys Tyr
    1010                1015                1020

Asn Ser  Phe Arg Glu Arg Lys  Ser Ala Thr Glu Lys  Val Tyr Phe
    1025                1030                1035

Tyr Ser  Asn Ile Met Asn Ile  Phe Lys Lys Ser Ile  Ser Leu Ala
    1040                1045                1050

Asp Gly  Arg Val Ile Glu Arg  Pro Leu Ile Glu Val  Asn Glu Glu
    1055                1060                1065

Thr Gly  Glu Ser Val Trp Asn  Lys Glu Ser Asp Leu  Ala Thr Val
    1070                1075                1080

Arg Arg  Val Leu Ser Tyr Pro  Gln Val Asn Val Val  Lys Lys Val
    1085                1090                1095

Glu Glu  Gln Asn His Gly Leu  Asp Arg Gly Lys Pro  Lys Gly Leu
    1100                1105                1110

Phe Asn  Ala Asn Leu Ser Ser  Lys Pro Lys Pro Asn  Ser Asn Glu
    1115                1120                1125

Asn Leu  Val Gly Ala Lys Glu  Tyr Leu Asp Pro Lys  Lys Tyr Gly
    1130                1135                1140

Gly Tyr  Ala Gly Ile Ser Asn  Ser Phe Thr Val Leu  Val Lys Gly
    1145                1150                1155

Thr Ile  Glu Lys Gly Ala Lys  Lys Lys Ile Thr Asn  Val Leu Glu
    1160                1165                1170

Phe Gln  Gly Ile Ser Ile Leu  Asp Arg Ile Asn Tyr  Arg Lys Asp
    1175                1180                1185

Lys Leu  Asn Phe Leu Leu Glu  Lys Gly Tyr Lys Asp  Ile Glu Leu
    1190                1195                1200

Ile Ile  Glu Leu Pro Lys Tyr  Ser Leu Phe Glu Leu  Ser Asp Gly
    1205                1210                1215

Ser Arg  Arg Met Leu Ala Ser  Ile Leu Ser Thr Asn  Asn Lys Arg
    1220                1225                1230

Gly Glu  Ile His Lys Gly Asn  Gln Ile Phe Leu Ser  Gln Lys Phe
    1235                1240                1245

Val Lys  Leu Leu Tyr His Ala  Lys Arg Ile Ser Asn  Thr Ile Asn
    1250                1255                1260
```

```
Glu Asn His Arg Lys Tyr Val Glu Asn His Lys Glu Phe Glu
    1265                1270            1275

Glu Leu Phe Tyr Tyr Ile Leu Glu Phe Asn Glu Asn Tyr Val Gly
    1280                1285            1290

Ala Lys Lys Asn Gly Lys Leu Leu Asn Ser Ala Phe Gln Ser Trp
    1295                1300            1305

Gln Asn His Ser Ile Asp Glu Leu Cys Ser Ser Phe Ile Gly Pro
    1310                1315            1320

Thr Gly Ser Glu Arg Lys Gly Leu Phe Glu Leu Thr Ser Arg Gly
    1325                1330            1335

Ser Ala Ala Asp Phe Glu Phe Leu Gly Val Lys Ile Pro Arg Tyr
    1340                1345            1350

Arg Asp Tyr Thr Pro Ser Ser Leu Leu Lys Asp Ala Thr Leu Ile
    1355                1360            1365

His Gln Ser Val Thr Gly Leu Tyr Glu Thr Arg Ile Asp Leu Ala
    1370                1375            1380

Lys Leu Gly Glu Gly
    1385

<210> SEQ ID NO 4
<211> LENGTH: 4167
<212> TYPE: DNA
<213> ORGANISM: Streptococcus thermophilus

<400> SEQUENCE: 4
atgactaagc atactcaat tggacttgat attggaacga atagtgttgg atgggctgta      60
acaactgata attacaaggt tccgtctaaa aaatgaaag tcttaggaaa tacgagtaaa     120
aagtatatca aaagaaacct gttaggtgta ttactctttg actctggaat cacagcagaa    180
ggaagaagat tgaagcgtac tgcaagaaga cgttatacta gacgccgtaa tcgtatcctt    240
tatttgcagg aaattttag cacagagatg gctacattag atgatgcttt ctttcaaaga    300
cttgacgatt cgtttttagt tcctgatgat aaacgtgata gtaagtatcc gatatttgga    360
aacttagtag aagaaaaagc ctatcatgat gaatttccaa ctatctatca tttaaggaaa    420
tatttagcag atagtactaa aaaagcagat ttgcgtctag tttatcttgc attggctcat    480
atgattaaat atagaggtca cttcttaatt gaaggagagt ttaattcaaa aaataatgat    540
attcagaaga attttcaaga ctttttggac acttataatg ctattttga atcggattta    600 tcacttgaga atagtaaaca acttgaggaa attgttaaag ataagattag taaattagaa    660
aagaaagatc gtatttaaa actcttccct ggggagaaga attcggggat ttttttcagag    720 tttctaaagt tgattgtagg aaatcaagct gattttagga aatgttttaa tttagacgaa    780
aaagcctcct tacatttttc caagaaaagc tatgatgaag atttagagac tttgttaggt    840
tatattggag atgattacag tgatgtcttt ctcaaagcaa agaaacttta tgatgctatt    900 ctttttatcgg gttttctgac tgtaactgat aatgagacag aagcacctct ctcttctgct    960
atgataaagc gatataatga acacaaagaa gatttagcgt tactaaagga atatataaga   1020
aatatttcac taaaaacgta taatgaagta tttaaagatg acaccaaaaa tggttatgct   1080
ggttatattg atggaaaaac aaatcaggaa gatttctacg tatatctaaa aaaactattg   1140
gctgaatttg aaggtgcgga ttattttctt gaaaaaattg atcgagaaga ttttttgaga   1200
aagcaacgta catttgacaa tggttcgata ccatatcaga ttcatcttca agaaatgaga   1260
gcaattcttg ataagcaagc taaattttat cctttcttgg ctaaaaataa agaaagaatc   1320
```

```
gagaagattt taaccttccg aattccttat tatgtaggtc cacttgcgag agggaatagt    1380
gattttgcct ggtcaataag aaaacgaaat gaaaaaatta caccttggaa ttttgaggac    1440
gttattgaca aagaatcttc ggcagaggcc ttcattaatc gaatgactag ttttgatttg    1500
tatttgccag aagagaaggt acttccaaag catagtctct tatacgaaac ttttaatgta    1560
tataatgaat taacaaaagt tagatttatt gccgaaagta tgagagatta tcaatttta     1620
gatagtaagc agaagaaaga tattgttaga ctttatttta aagataaaag gaaagttact    1680
gataaggata ttattgaata tttacatgca atttatgggt atgatggaat tgaattaaaa    1740
ggcatagaga aacagtttaa ttctagttta tctacttatc acgatctttt aaatattatt    1800
aatgataaag agttttttgga tgatagttca aatgaagcga ttatcgaaga aattatccat    1860
actttgacaa tttttgaaga tagagagatg ataaaacaac gtctttcaaa atttgagaat    1920
atattcgata aatccgtttt gaaaaagtta tctcgtagac attacactgg ctggggtaag    1980
ttatctgcta agcttattaa tggtattcga gatgaaaaat ctggtaatac tattcttgat    2040
tacttaattg atgatggtat ttctaaccgt aatttcatgc aacttattca cgatgatgct    2100
ctttctttta aaagaagat acagaaagca caaattattg gtgacgaaga taaaggtaat    2160
attaaagagg tcgttaagtc tttgccaggt agtcctgcga ttaaaaaagg tattttacaa    2220
agcataaaaa ttgtagatga attggtcaaa gtaatgggag gagaaaaacc cgagtcaatt    2280
gttgttgaga tggctcgtga aaatcaatat accaatcaag gtaagtctaa ttcccaacaa    2340
cgcttgaaac gtttagaaaa atctctcaaa gagttaggta gtaagatact taaggaaaat    2400
attcctgcaa aactttctaa aatagacaat aacgcacttc aaaatgatcg actttactta    2460
tactatcttc aaaatggaaa agatatgtat accggagatg atttagatat tgatagatta    2520
agtaattatg atattgatca tattattcct caagcttttt tgaaagataa ttctattgac    2580
aataaagtac ttgtttcatc tgctagtaac cgtggtaaat cagatgatgt tccaagttta    2640
gaggttgtca aaaaagaaa gacatttgg tatcaattat tgaaatcaaa attaatttct    2700
caacgaaaat ttgataatct gacaaaagct gaacggggag gattgtcacc tgaggacaaa    2760
gctggtttta ttcaacgcca gttggttgaa acacgtcaaa taacaaaaca tgtagctcgt    2820
ttacttgatg agaaatttaa taataaaaaa gatgaaaata atagagcggt acgaacagta    2880
aaaattatta ccttgaaatc taccttagtt tctcaatttc gtaaggattt tgaactttat    2940
aaagttcgtg aaatcaatga ttttcatcat gctcatgatg cttacttgaa tgccgttgta    3000
gcaagtgctt tacttaagaa atacctaaa ctagagccag aatttgtgta cggtgattat    3060
ccaaaataca atagttttag agaagaaag tccgctacag aaaaggtata tttctattca    3120
aatatcatga atatctttaa aaaatctatt tctttagctg atggtagagt tattgaaaga    3180
ccacttattg aggtaaatga ggagaccggc gaatccgttt ggaataaaga atctgattta    3240
gcaactgtaa ggagagtact ctcttatccg caagtaaatg ttgtgaaaaa agttgaggaa    3300
cagaatcacg gattggatag aggaaaacca aagggattgt taatgcaaa tctttcctca    3360
aagccaaaac caaatagtaa tgaaaattta gtaggtgcta agagtatct tgaccccaaa    3420
aagtatgggg ggtatgctgg aatttctaat tcttttactg ttcttgttaa agggacaatt    3480
gaaaaggtg ctaagaaaaa aataacaaat gtactagaat tcaaggtat ttctatttta    3540
gataggatta ttatagaaa agataaactt aatttttac ttgaaaaagg ttataaagat    3600
attgagttaa ttattgaact acctaaatat agtttatttg aactttcaga tggttcacgt    3660
```

```
cgtatgttgg ctagtatttt gtcaacgaat aataagaggg gagagattca caaaggaaat    3720 cagattttc tttcacagaa gtttgtgaaa ttactttatc atgctaagag aataagtaac     3780
acaattaatg agaatcatag aaaatatgtt gagaaccata aaaagagtt tgaagaatta     3840 ttttactaca ttcttgagtt taatgagaat tatgttggag ctaaaaagaa tggtaaactc    3900
ttaaactctg cctttcaatc ttggcaaaat catagtatag atgaactctg tagtagtttt    3960
ataggaccta ccggaagtga agaaagggg ctatttgaat taacctctcg tggaagtgct     4020
gctgattttg aatttttagg tgttaaaatt ccaaggtata gagactatac cccatcatcc    4080
ctattaaaag atgccacact tattcatcaa tctgttacag gcctctatga aacacgaata    4140
gaccttgcca aactaggaga gggttaa                                        4167
```

<210> SEQ ID NO 5
<211> LENGTH: 12
<212> TYPE: PRT
<213> ORGANISM: Artificial Sequence
<220> FEATURE:
<223> OTHER INFORMATION: Synthetic-Nuclear Localization Signal

<400> SEQUENCE: 5

Gly Gly Ser Gly Pro Pro Lys Lys Lys Arg Lys Val
1               5                   10

<210> SEQ ID NO 6
<211> LENGTH: 1380
<212> TYPE: PRT
<213> ORGANISM: Artificial Sequence
<220> FEATURE:
<223> OTHER INFORMATION: Synthetic-Cas9 protein comprising a C-terminal
      nuclear localization signal.

<400> SEQUENCE: 6

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala

-continued

```
            195                 200                 205
Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                    245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
                595                 600                 605

Asn Glu Glu Asn Glu Asp Ile Leu Glu Asp Ile Val Leu Thr Leu Thr
610                 615                 620
```

```
Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Tyr
            645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035
```

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Gly Gly Ser Gly Pro Pro Lys Lys Lys Arg Lys Val
    1370                1375                1380

<210> SEQ ID NO 7
<211> LENGTH: 27
<212> TYPE: DNA
<213> ORGANISM: Artificial Sequence
<220> FEATURE:
<223> OTHER INFORMATION: Synthetic-Cas9 target sequence
<220> FEATURE:
<221> NAME/KEY: misc_feature
<222> LOCATION: (1)..(20)

```
<223> OTHER INFORMATION: n is a, g, t, or c
<220> FEATURE:
<221> NAME/KEY: misc_feature
<222> LOCATION: (21)..(22)
<223> OTHER INFORMATION: n is a deoxynucleotide
<220> FEATURE:
<221> NAME/KEY: misc_feature
<222> LOCATION: (27)..(27)
<223> OTHER INFORMATION: n is a or t

<400> SEQUENCE: 7
nnnnnnnnnn nnnnnnnnnn nnagaan                                        27

<210> SEQ ID NO 8
<211> LENGTH: 19
<212> TYPE: DNA
<213> ORGANISM: Artificial Sequence
<220> FEATURE:
<223> OTHER INFORMATION: Synthetic-Cas9 target sequence
<220> FEATURE:
<221> NAME/KEY: misc_feature
<222> LOCATION: (1)..(12)
<223> OTHER INFORMATION: n is a, g, t, or c
<220> FEATURE:
<221> NAME/KEY: misc_feature
<222> LOCATION: (13)..(14)
<223> OTHER INFORMATION: n is a deoxynucleotide
<220> FEATURE:
<221> NAME/KEY: misc_feature
<222> LOCATION: (19)..(19)
<223> OTHER INFORMATION: n is a or t

<400> SEQUENCE: 8
nnnnnnnnnn nnnnagaan                                                 19

<210> SEQ ID NO 9
<211> LENGTH: 27
<212> TYPE: DNA
<213> ORGANISM: Artificial Sequence
<220> FEATURE:
<223> OTHER INFORMATION: Synthetic-Cas9 target sequence
<220> FEATURE:
<221> NAME/KEY: misc_feature
<222> LOCATION: (1)..(19)
<223> OTHER INFORMATION: n is a, c, g, or t
<220> FEATURE:
<221> NAME/KEY: misc_feature
<222> LOCATION: (20)..(21)
<223> OTHER INFORMATION: n is a, g, t, or c
<220> FEATURE:
<221> NAME/KEY: misc_feature
<222> LOCATION: (22)..(23)
<223> OTHER INFORMATION: n is a deoxynucleotide
<220> FEATURE:
<221> NAME/KEY: misc_feature
<222> LOCATION: (27)..(27)
<223> OTHER INFORMATION: n is a or t

<400> SEQUENCE: 9
nnnnnnnnnn nnnnnnnnnn nnagaan                                        27

<210> SEQ ID NO 10
<211> LENGTH: 18
<212> TYPE: DNA
<213> ORGANISM: Artificial Sequence
<220> FEATURE:
<223> OTHER INFORMATION: Synthetic-Cas9 target sequence
<220> FEATURE:
<221> NAME/KEY: misc_feature
<222> LOCATION: (1)..(11)
<223> OTHER INFORMATION: n is a, g, t, or c
<220> FEATURE:
<221> NAME/KEY: misc_feature
```

```
<222> LOCATION: (12)..(13)
<223> OTHER INFORMATION: n is a deoxynucleotide
<220> FEATURE:
<221> NAME/KEY: misc_feature
<222> LOCATION: (18)..(18)
<223> OTHER INFORMATION: n is a or t

<400> SEQUENCE: 10
nnnnnnnnnn nnnagaan                                                   18

<210> SEQ ID NO 11
<211> LENGTH: 1345
<212> TYPE: PRT
<213> ORGANISM: Artificial Sequence
<220> FEATURE:
<223> OTHER INFORMATION: Synthetic-Francisella tularensis subsp.
      Novicida U112 (FnCpf1; pY004)), including NLS and HA tag

<400> SEQUENCE: 11
```

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

```
Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
            325                 330                 335

Phe Val Ile Asp Lys Leu Glu Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
            405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
            435                 440                 445

Lys Tyr Leu Ser Leu Glu Thr Ile Lys Leu Ala Leu Glu Glu Phe Asn
450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Val Lys Ala Ile Lys Asp
515                 520                 525

Leu Leu Asp Gln Thr Asn Asn Leu Leu His Lys Leu Lys Ile Phe His
530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
            565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
            645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
            675                 680                 685

Leu Arg Ile Arg Asn His Ser Thr His Thr Lys Asn Gly Ser Pro Gln
            690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
```

-continued

```
                725                 730                 735
Phe Gly Phe Arg Phe Ser Asp Thr Gln Arg Tyr Asn Ser Ile Asp Glu
                740                 745                 750
Phe Tyr Arg Glu Val Glu Asn Gln Gly Tyr Lys Leu Thr Phe Glu Asn
                755                 760                 765
Ile Ser Glu Ser Tyr Ile Asp Ser Val Val Asn Gln Gly Lys Leu Tyr
                770                 775                 780
Leu Phe Gln Ile Tyr Asn Lys Asp Phe Ser Ala Tyr Ser Lys Gly Arg
785                 790                 795                 800
Pro Asn Leu His Thr Leu Tyr Trp Lys Ala Leu Phe Asp Glu Arg Asn
                805                 810                 815
Leu Gln Asp Val Val Tyr Lys Leu Asn Gly Glu Ala Glu Leu Phe Tyr
                820                 825                 830
Arg Lys Gln Ser Ile Pro Lys Lys Ile Thr His Pro Ala Lys Glu Ala
                835                 840                 845
Ile Ala Asn Lys Asn Lys Asp Asn Pro Lys Lys Glu Ser Val Phe Glu
850                 855                 860
Tyr Asp Leu Ile Lys Asp Lys Arg Phe Thr Glu Asp Lys Phe Phe Phe
865                 870                 875                 880
His Cys Pro Ile Thr Ile Asn Phe Lys Ser Ser Gly Ala Asn Lys Phe
                885                 890                 895
Asn Asp Glu Ile Asn Leu Leu Leu Lys Glu Lys Ala Asn Asp Val His
                900                 905                 910
Ile Leu Ser Ile Asp Arg Gly Glu Arg His Leu Ala Tyr Tyr Thr Leu
                915                 920                 925
Val Asp Gly Lys Gly Asn Ile Ile Lys Gln Asp Thr Phe Asn Ile Ile
930                 935                 940
Gly Asn Asp Arg Met Lys Thr Asn Tyr His Asp Lys Leu Ala Ala Ile
945                 950                 955                 960
Glu Lys Asp Arg Asp Ser Ala Arg Lys Asp Trp Lys Lys Ile Asn Asn
                965                 970                 975
Ile Lys Glu Met Lys Glu Gly Tyr Leu Ser Gln Val Val His Glu Ile
                980                 985                 990
Ala Lys Leu Val Ile Glu Tyr Asn Ala Ile Val Val Phe Glu Asp Leu
                995                 1000                1005
Asn Phe Gly Phe Lys Arg Gly Arg Phe Lys Val Glu Lys Gln Val
                1010                1015                1020
Tyr Gln Lys Leu Glu Lys Met Leu Ile Glu Lys Leu Asn Tyr Leu
                1025                1030                1035
Val Phe Lys Asp Asn Glu Phe Asp Lys Thr Gly Gly Val Leu Arg
                1040                1045                1050
Ala Tyr Gln Leu Thr Ala Pro Phe Glu Thr Phe Lys Lys Met Gly
                1055                1060                1065
Lys Gln Thr Gly Ile Ile Tyr Tyr Val Pro Ala Gly Phe Thr Ser
                1070                1075                1080
Lys Ile Cys Pro Val Thr Gly Phe Val Asn Gln Leu Tyr Pro Lys
                1085                1090                1095
Tyr Glu Ser Val Ser Lys Ser Gln Glu Phe Phe Ser Lys Phe Asp
                1100                1105                1110
Lys Ile Cys Tyr Asn Leu Asp Lys Gly Tyr Phe Glu Phe Ser Phe
                1115                1120                1125
Asp Tyr Lys Asn Phe Gly Asp Lys Ala Ala Lys Gly Lys Trp Thr
                1130                1135                1140
```

```
Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn Lys Arg Pro Ala Ala Thr Lys Lys
    1295                1300                1305

Ala Gly Gln Ala Lys Lys Lys Lys Gly Ser Tyr Pro Tyr Asp Val
    1310                1315                1320

Pro Asp Tyr Ala Tyr Pro Tyr Asp Val Pro Asp Tyr Ala Tyr Pro
    1325                1330                1335

Tyr Asp Val Pro Asp Tyr Ala
    1340            1345

<210> SEQ ID NO 12
<211> LENGTH: 16
<212> TYPE: PRT
<213> ORGANISM: Artificial Sequence
<220> FEATURE:
<223> OTHER INFORMATION: Synthetic-Nuclear Localization Signal

<400> SEQUENCE: 12

Lys Arg Pro Ala Ala Thr Lys Lys Ala Gly Gln Ala Lys Lys Lys Lys
1               5                   10                  15

<210> SEQ ID NO 13
<211> LENGTH: 27
<212> TYPE: PRT
<213> ORGANISM: Artificial Sequence
<220> FEATURE:
<223> OTHER INFORMATION: Synthetic-HA Tag

<400> SEQUENCE: 13

Tyr Pro Tyr Asp Val Pro Asp Tyr Ala Tyr Pro Tyr Asp Val Pro Asp
1               5                   10                  15

Tyr Ala Tyr Pro Tyr Asp Val Pro Asp Tyr Ala
            20                  25

<210> SEQ ID NO 14
<211> LENGTH: 4038
<212> TYPE: DNA
<213> ORGANISM: Artificial Sequence
<220> FEATURE:
<223> OTHER INFORMATION: Synthetic-Francisella tularensis subsp.
```

Novicida U112 (FnCpf1; pY004)), including NLS and HA tag

<400> SEQUENCE: 14

```
atgagcatct accaggagtt cgtcaacaag tattcactga gtaagacact gcggttcgag      60
ctgatcccac agggcaagac actggagaac atcaaggccc gaggcctgat tctggacgat     120
gagaagcggg caaaagacta taagaaagcc aagcagatca ttgataaata ccaccagttc     180
tttatcgagg aaattctgag ctccgtgtgc atcagtgagg atctgctgca gaattactca     240
gacgtgtact tcaagctgaa gaagagcgac gatgacaacc tgcagaagga cttcaagtcc     300
gccaaggaca ccatcaagaa acagattagc gagtacatca aggactccga aaagtttaaa     360
aatctgttca accagaatct gatcgatgct aagaaaggcc aggagtccga cctgatcctg     420
tggctgaaac agtctaagga caatgggatt gaactgttca aggctaactc cgatatcact     480
gatattgacg aggcactgga aatcatcaag agcttcaagg gatggaccac atactttaaa     540
ggcttccacg agaaccgcaa gaacgtgtac tccagcaacg acattcctac ctccatcatc     600
taccgaatcg tcgatgacaa tctgccaaag ttcctggaga caaggccaa atatgaatct     660
ctgaaggaca agctcccga ggcaattaat tacgaacaga tcaagaaaga tctggctgag     720
gaactgacat tcgatatcga ctataagact agcgaggtga ccagagggt cttttccctg     780
gacgaggtgt ttgaaatcgc caatttcaac aattacctga ccagtccgg cattactaaa     840
ttcaatacca tcattggcgg gaagtttgtg acgggggaga ataccaagcg caagggaatt     900
aacgaataca tcaatctgta tagccagcag atcaacgaca aaactctgaa gaaatacaag     960
atgtctgtgc tgttcaaaca gatcctgagt gataccgagt ccagtctttt tgtcattgat    1020
aaactggaag atgactcaga cgtggtcact accatgcaga gctttttatga gcagatcgcc    1080
gctttcaaga cagtggagga aaaatctatt aaggaaactc tgagtctgct gttcgatgac    1140
ctgaaagccc agaagctgga cctgagtaag atctacttca aaaacgataa gagtctgaca    1200
gacctgtcac agcaggtgtt tgatgactat tccgtgattg gaccgccgt cctggagtac    1260
attacacagc agatcgctcc aaagaacctg gataatccct ctaagaaaga gcaggaactg    1320
atcgctaaga aaaccgagaa ggcaaaatat ctgagtctgg aaacaattaa gctggcactg    1380
gaggagttca acaagcacag ggatattgac aaacagtgcc gctttgagga atcctggcc    1440
aacttcgcag ccatccccat gattttttgat gagatcgccc agaacaaaga caatctggct    1500
cagatcagta ttaagtacca gaaccagggc aagaaagacc tgctgcaggc ttcagcagaa    1560
gatgacgtga agccatcaa ggatctgctg gaccagacca caatctgct gcacaagctg    1620
aaaatcttcc atattagtca gtcagaggat aaggctaata tcctggataa agacgaacac    1680
ttctacctgg tgttcgagga atgttacttc gagctggcaa acattgtccc cctgtataac    1740
aagattagga actacatcac acagaagcct tactctgacg agaagtttaa actgaacttc    1800
gaaaatagta ccctggccaa cgggtgggat aagaacaagg agcctgacaa cacagctatc    1860
ctgttcatca aggatgacaa gtactatctg ggagtgatga ataagaaaaa caataagatc    1920
ttcgatgaca agccattaa ggagaacaaa ggggaaggat acaagaaaat cgtgtataag    1980
ctgctgcccg gcgcaaataa gatgctgcct aaggtgttct tcagcgccaa gagtatcaaa    2040
ttctacaacc catccgagga catcctgcgg attagaaatc actcaacaca tactaagaac    2100
gggagccccc agaagggata tgagaaattt gagttcaaca tcgaggattg caggaagttt    2160
attgacttct acaagcagag catctccaaa caccctgaat ggaaggattt tggcttccgg    2220
ttttccgaca cacagagata taactctatc gacgagttct accgcgaggt ggaaaatcag    2280
```

```
gggtataagc tgacttttga gaacatttct gaaagttaca tcgacagcgt ggtcaatcag    2340
ggaaagctgt acctgttcca gatctataac aaagattttt cagcatacag caagggcaga    2400
ccaaacctgc atacactgta ctggaaggcc ctgttcgatg agaggaatct gcaggacgtg    2460
gtctataaac tgaacggaga ggccgaactg ttttaccgga agcagtctat tcctaagaaa    2520
atcactcacc cagctaagga ggccatcgct aacaagaaca aggacaatcc taagaaagag    2580
agcgtgttcg aatacgatct gattaaggac aagcggttca ccgaagataa gttctttttc    2640
cattgtccaa tcaccattaa cttcaagtca agcggcgcta acaagttcaa cgacgagatc    2700
aatctgctgc tgaaggaaaa agcaaacgat gtgcacatcc tgagcattga ccgaggagag    2760
cggcatctgg cctactatac cctggtggat ggcaaaggga atatcattaa gcaggataca    2820
ttcaacatca ttggcaatga ccggatgaaa accaactacc acgataaact ggctgcaatc    2880
gagaaggata gagactcagc taggaaggac tggaagaaaa tcaacaacat taaggagatg    2940
aaggaaggct atctgagcca ggtggtccat gagattgcaa agctggtcat cgaatacaat    3000
gccattgtgg tgttcgagga tctgaacttc ggctttaaga gggggcgctt taaggtggaa    3060
aaacaggtct atcagaagct ggagaaaatg ctgatcgaaa agctgaatta cctggtgttt    3120
aaagataacg agttcgacaa gaccggaggc gtcctgagag cctaccagct gacagctccc    3180
tttgaaactt tcaagaaaat gggaaaacag acaggcatca tctactatgt gccagccgga    3240
ttcacttcca agatctgccc cgtgaccggc tttgtcaacc agctgtaccc taaatatgag    3300
tcagtgagca gtcccagga attttttcagc aagttcgata agatctgtta taatctggac    3360 aagggggtact tcgagttttc cttcgattac aagaacttcg gcgacaaggc cgctaagggg    3420
aaatggacca ttgcctcctt cggatctcgc ctgatcaact ttcgaaattc cgataaaaac    3480
cacaattggg acactaggga ggtgtaccca accaaggagc tggaaaagct gctgaaagac    3540
tactctatcg agtatggaca tggcgaatgc atcaaggcag ccatctgtgg cgagagtgat    3600
aagaaatttt tcgccaagct gacctcagtg ctgaatacaa tcctgcagat gcggaactca    3660
aagaccggga cagaactgga ctatctgatt agccccgtgg ctgatgtcaa cggaaacttc    3720
ttcgacagca gacaggcacc caaaaatatg cctcaggatg cagacgccaa cggggcctac    3780
cacatcgggc tgaagggact gatgctgctg ggccggatca agaacaatca ggaggggaag    3840
aagctgaacc tggtcattaa gaacgaggaa tacttcgagt ttgtccagaa tagaaataac    3900
aaaaggccgg cggccacgaa aaaggccggc caggcaaaaa agaaaaaggg atcctaccca    3960
tacgatgttc cagattacgc ttatccctac gacgtgcctg attatgcata cccatatgat    4020
gtccccgact atgcctaa                                                  4038
```

<210> SEQ ID NO 15
<211> LENGTH: 1278
<212> TYPE: PRT
<213> ORGANISM: Artificial Sequence
<220> FEATURE:
<223> OTHER INFORMATION: Synthetic-Lachnospiraceae bacterium MC2017
      (Lb3Cpf1; pY005), including NLS and HA tag

<400> SEQUENCE: 15

Met Asp Tyr Gly Asn Gly Gln Phe Glu Arg Arg Ala Pro Leu Thr Lys
1               5                   10                  15

Thr Ile Thr Leu Arg Leu Lys Pro Ile Gly Glu Thr Arg Glu Thr Ile
            20                  25                  30

Arg Glu Gln Lys Leu Leu Glu Gln Asp Ala Ala Phe Arg Lys Leu Val

```
                35                  40                  45
Glu Thr Val Thr Pro Ile Val Asp Asp Cys Ile Arg Lys Ile Ala Asp
 50                  55                  60

Asn Ala Leu Cys His Phe Gly Thr Glu Tyr Asp Phe Ser Cys Leu Gly
 65                  70                  75                  80

Asn Ala Ile Ser Lys Asn Asp Ser Lys Ala Ile Lys Lys Glu Thr Glu
                 85                  90                  95

Lys Val Glu Lys Leu Leu Ala Lys Val Leu Thr Glu Asn Leu Pro Asp
                100                 105                 110

Gly Leu Arg Lys Val Asn Asp Ile Asn Ser Ala Ala Phe Ile Gln Asp
            115                 120                 125

Thr Leu Thr Ser Phe Val Gln Asp Ala Asp Lys Arg Val Leu Ile
            130                 135                 140

Gln Glu Leu Lys Gly Lys Thr Val Leu Met Gln Arg Phe Leu Thr Thr
145                 150                 155                 160

Arg Ile Thr Ala Leu Thr Val Trp Leu Pro Asp Arg Val Phe Glu Asn
                165                 170                 175

Phe Asn Ile Phe Ile Glu Asn Ala Glu Lys Met Arg Ile Leu Leu Asp
                180                 185                 190

Ser Pro Leu Asn Glu Lys Ile Met Lys Phe Asp Pro Asp Ala Glu Gln
            195                 200                 205

Tyr Ala Ser Leu Glu Phe Tyr Gly Gln Cys Leu Ser Gln Lys Asp Ile
            210                 215                 220

Asp Ser Tyr Asn Leu Ile Ile Ser Gly Ile Tyr Ala Asp Asp Glu Val
225                 230                 235                 240

Lys Asn Pro Gly Ile Asn Glu Ile Val Lys Glu Tyr Asn Gln Gln Ile
                245                 250                 255

Arg Gly Asp Lys Asp Glu Ser Pro Leu Pro Lys Leu Lys Lys Leu His
            260                 265                 270

Lys Gln Ile Leu Met Pro Val Glu Lys Ala Phe Phe Val Arg Val Leu
            275                 280                 285

Ser Asn Asp Ser Asp Ala Arg Ser Ile Leu Glu Lys Ile Leu Lys Asp
290                 295                 300

Thr Glu Met Leu Pro Ser Lys Ile Ile Glu Ala Met Lys Glu Ala Asp
305                 310                 315                 320

Ala Gly Asp Ile Ala Val Tyr Gly Ser Arg Leu His Glu Leu Ser His
                325                 330                 335

Val Ile Tyr Gly Asp His Gly Lys Leu Ser Gln Ile Ile Tyr Asp Lys
            340                 345                 350

Glu Ser Lys Arg Ile Ser Glu Leu Met Glu Thr Leu Ser Pro Lys Glu
            355                 360                 365

Arg Lys Glu Ser Lys Lys Arg Leu Glu Gly Leu Glu Glu His Ile Arg
            370                 375                 380

Lys Ser Thr Tyr Thr Phe Asp Glu Leu Asn Arg Tyr Ala Glu Lys Asn
385                 390                 395                 400

Val Met Ala Ala Tyr Ile Ala Ala Val Glu Glu Ser Cys Ala Glu Ile
                405                 410                 415

Met Arg Lys Glu Lys Asp Leu Arg Thr Leu Leu Ser Lys Glu Asp Val
            420                 425                 430

Lys Ile Arg Gly Asn Arg His Asn Thr Leu Ile Val Lys Asn Tyr Phe
            435                 440                 445

Asn Ala Trp Thr Val Phe Arg Asn Leu Ile Arg Ile Leu Arg Arg Lys
450                 455                 460
```

```
Ser Glu Ala Glu Ile Asp Ser Asp Phe Tyr Asp Val Leu Asp Ser
465                 470                 475                 480

Val Glu Val Leu Ser Leu Thr Tyr Lys Gly Glu Asn Leu Cys Arg Ser
            485                 490                 495

Tyr Ile Thr Lys Lys Ile Gly Ser Asp Leu Lys Pro Glu Ile Ala Thr
            500                 505                 510

Tyr Gly Ser Ala Leu Arg Pro Asn Ser Arg Trp Trp Ser Pro Gly Glu
            515                 520                 525

Lys Phe Asn Val Lys Phe His Thr Ile Val Arg Arg Asp Gly Arg Leu
            530                 535                 540

Tyr Tyr Phe Ile Leu Pro Lys Gly Ala Lys Pro Val Glu Leu Glu Asp
545                 550                 555                 560

Met Asp Gly Asp Ile Glu Cys Leu Gln Met Arg Lys Ile Pro Asn Pro
                565                 570                 575

Thr Ile Phe Leu Pro Lys Leu Val Phe Lys Asp Pro Glu Ala Phe Phe
                580                 585                 590

Arg Asp Asn Pro Glu Ala Asp Glu Phe Val Phe Leu Ser Gly Met Lys
            595                 600                 605

Ala Pro Val Thr Ile Thr Arg Glu Thr Tyr Glu Ala Tyr Arg Tyr Lys
            610                 615                 620

Leu Tyr Thr Val Gly Lys Leu Arg Asp Gly Glu Val Ser Glu Glu
625                 630                 635                 640

Tyr Lys Arg Ala Leu Leu Gln Val Leu Thr Ala Tyr Lys Glu Phe Leu
                645                 650                 655

Glu Asn Arg Met Ile Tyr Ala Asp Leu Asn Phe Gly Phe Lys Asp Leu
            660                 665                 670

Glu Glu Tyr Lys Asp Ser Ser Glu Phe Ile Lys Gln Val Glu Thr His
            675                 680                 685

Asn Thr Phe Met Cys Trp Ala Lys Val Ser Ser Gln Leu Asp Asp
690                 695                 700

Leu Val Lys Ser Gly Asn Gly Leu Leu Phe Glu Ile Trp Ser Glu Arg
705                 710                 715                 720

Leu Glu Ser Tyr Tyr Lys Tyr Gly Asn Glu Lys Val Leu Arg Gly Tyr
                725                 730                 735

Glu Gly Val Leu Leu Ser Ile Leu Lys Asp Glu Asn Leu Val Ser Met
            740                 745                 750

Arg Thr Leu Leu Asn Ser Arg Pro Met Leu Val Tyr Arg Pro Lys Glu
            755                 760                 765

Ser Ser Lys Pro Met Val Val His Arg Asp Gly Ser Arg Val Val Asp
            770                 775                 780

Arg Phe Asp Lys Asp Gly Lys Tyr Ile Pro Pro Glu Val His Asp Glu
785                 790                 795                 800

Leu Tyr Arg Phe Phe Asn Asn Leu Leu Ile Lys Glu Lys Leu Gly Glu
                805                 810                 815

Lys Ala Arg Lys Ile Leu Asp Asn Lys Val Lys Val Lys Val Leu
                820                 825                 830

Glu Ser Glu Arg Val Lys Trp Ser Lys Phe Tyr Asp Glu Gln Phe Ala
            835                 840                 845

Val Thr Phe Ser Val Lys Lys Asn Ala Asp Cys Leu Asp Thr Thr Lys
            850                 855                 860

Asp Leu Asn Ala Glu Val Met Glu Gln Tyr Ser Glu Ser Asn Arg Leu
865                 870                 875                 880
```

```
Ile Leu Ile Arg Asn Thr Thr Asp Ile Leu Tyr Tyr Leu Val Leu Asp
                885                 890                 895

Lys Asn Gly Lys Val Leu Lys Gln Arg Ser Leu Asn Ile Ile Asn Asp
            900                 905                 910

Gly Ala Arg Asp Val Asp Trp Lys Glu Arg Phe Arg Gln Val Thr Lys
        915                 920                 925

Asp Arg Asn Glu Gly Tyr Asn Glu Trp Asp Tyr Ser Arg Thr Ser Asn
930                 935                 940

Asp Leu Lys Glu Val Tyr Leu Asn Tyr Ala Leu Lys Glu Ile Ala Glu
945                 950                 955                 960

Ala Val Ile Glu Tyr Asn Ala Ile Leu Ile Glu Lys Met Ser Asn
                965                 970                 975

Ala Phe Lys Asp Lys Tyr Ser Phe Leu Asp Asp Val Thr Phe Lys Gly
            980                 985                 990

Phe Glu Thr Lys Leu Leu Ala Lys Leu Ser Asp Leu His Phe Arg Gly
            995                 1000                1005

Ile Lys Asp Gly Glu Pro Cys Ser Phe Thr Asn Pro Leu Gln Leu
    1010                1015                1020

Cys Gln Asn Asp Ser Asn Lys Ile Leu Gln Asp Gly Val Ile Phe
    1025                1030                1035

Met Val Pro Asn Ser Met Thr Arg Ser Leu Asp Pro Asp Thr Gly
    1040                1045                1050

Phe Ile Phe Ala Ile Asn Asp His Asn Ile Arg Thr Lys Lys Ala
    1055                1060                1065

Lys Leu Asn Phe Leu Ser Lys Phe Asp Gln Leu Lys Val Ser Ser
    1070                1075                1080

Glu Gly Cys Leu Ile Met Lys Tyr Ser Gly Asp Ser Leu Pro Thr
    1085                1090                1095

His Asn Thr Asp Asn Arg Val Trp Asn Cys Cys Cys Asn His Pro
    1100                1105                1110

Ile Thr Asn Tyr Asp Arg Glu Thr Lys Lys Val Glu Phe Ile Glu
    1115                1120                1125

Glu Pro Val Glu Glu Leu Ser Arg Val Leu Glu Glu Asn Gly Ile
    1130                1135                1140

Glu Thr Asp Thr Glu Leu Asn Lys Leu Asn Glu Arg Glu Asn Val
    1145                1150                1155

Pro Gly Lys Val Val Asp Ala Ile Tyr Ser Leu Val Leu Asn Tyr
    1160                1165                1170

Leu Arg Gly Thr Val Ser Gly Val Ala Gly Gln Arg Ala Val Tyr
    1175                1180                1185

Tyr Ser Pro Val Thr Gly Lys Lys Tyr Asp Ile Ser Phe Ile Gln
    1190                1195                1200

Ala Met Asn Leu Asn Arg Lys Cys Asp Tyr Tyr Arg Ile Gly Ser
    1205                1210                1215

Lys Glu Arg Gly Glu Trp Thr Asp Phe Val Ala Gln Leu Ile Asn
    1220                1225                1230

Lys Arg Pro Ala Ala Thr Lys Lys Ala Gly Gln Ala Lys Lys Lys
    1235                1240                1245

Lys Gly Ser Tyr Pro Tyr Asp Val Pro Asp Tyr Ala Tyr Pro Tyr
    1250                1255                1260

Asp Val Pro Asp Tyr Ala Tyr Pro Tyr Asp Val Pro Asp Tyr Ala
    1265                1270                1275
```

<210> SEQ ID NO 16
<211> LENGTH: 3837
<212> TYPE: DNA
<213> ORGANISM: Artificial Sequence
<220> FEATURE:
<223> OTHER INFORMATION: Synthetic-Lachnospiraceae bacterium MC2017
(Lb3Cpf1; pY005), including NLS and HA tag

<400> SEQUENCE: 16

| | | | | | |
|---|---|---|---|---|---|
| atggattacg | gcaacggcca | gtttgagcgg | agagccccc | tgaccaagac | aatcaccctg | 60 |
| cgcctgaagc | ctatcggcga | gacacgggag | acaatccgcg | agcagaagct | gctggagcag | 120 |
| gacgccgcct | tcagaaagct | ggtggagaca | gtgacccta | tcgtggacga | ttgtatcagg | 180 |
| aagatcgccg | ataacgccct | gtgccacttt | ggcaccgagt | atgacttcag | ctgtctgggc | 240 |
| aacgccatct | ctaagaatga | cagcaaggcc | atcaagaagg | agacagagaa | ggtggagaag | 300 |
| ctgctggcca | aggtgctgac | cgagaatctg | ccagatggcc | tgcgcaaggt | gaacgacatc | 360 |
| aattccgccg | cctttatcca | ggatacactg | acctctttcg | tgcaggacga | tgccgacaag | 420 |
| cgggtgctga | tccaggagct | gaagggcaag | accgtgctga | tgcagcggtt | cctgaccaca | 480 |
| cggatcacag | ccctgaccgt | gtggctgccc | gacagagtgt | tcgagaactt | taatatcttc | 540 |
| atcgagaacg | ccgagaagat | gagaatcctg | ctggactccc | ctctgaatga | aagatcatg | 600 |
| aagtttgacc | cagatgccga | gcagtacgcc | tctctggagt | tctatggcca | gtgcctgtct | 660 |
| cagaaggaca | tcgatagcta | caacctgatc | atctccggca | tctatgccga | cgatgaggtg | 720 |
| aagaaccctg | gcatcaatga | gatcgtgaag | gagtacaatc | agcagatccg | gggcgacaag | 780 |
| gatgagtccc | cactgcccaa | gctgaagaag | ctgcacaagc | agatcctgat | gccagtggag | 840 |
| aaggccttct | tgtgcgcgt | gctgtctaac | gacagcgatg | cccggagcat | cctggagaag | 900 |
| atcctgaagg | acacagagat | gctgcccctc | aagatcatcg | aggccatgaa | ggaggcagat | 960 |
| gcaggcgaca | tcgccgtgta | cggcagccgg | ctgcacgagc | tgagccacgt | gatctacggc | 1020 |
| gatcacggca | gctgtcccca | gatcatctat | gacaaggagt | ccaagaggat | ctctgagctg | 1080 |
| atggagacac | tgtctccaaa | ggagcgcaag | gagagcaaga | gcggctgga | gggcctggag | 1140 |
| gagcacatca | gaaagtctac | atacaccttc | gacgagctga | acaggtatgc | cgagaagaat | 1200 |
| gtgatggcag | catacatcgc | agcagtggag | gagtcttgtg | ccgagatcat | gagaaggag | 1260 |
| aaggatctga | ggaccctgct | gagcaaggag | gacgtgaaga | tccggggcaa | cagacacaat | 1320 |
| acactgatcg | tgaagaacta | ctttaatgcc | tggaccgtgt | tccggaacct | gatcagaatc | 1380 |
| ctgaggcgca | gtccgaggc | cgagatcgac | tctgacttct | acgatgtgct | ggacgattcc | 1440 |
| gtggaggtgc | tgtctctgac | atacaagggc | gagaatctgt | gccgcagcta | tatcaccaag | 1500 |
| aagatcggct | ccgacctgaa | gcccgagatc | gccacatacg | cagcgccct | gaggcctaac | 1560 |
| agccgctggt | ggtccccagg | agagaagttt | aatgtgaagt | tccacaccat | cgtgcggaga | 1620 |
| gatggccggc | tgtactattt | catcctgccc | aagggcgcca | gcctgtgga | gctgaggac | 1680 |
| atggatggcg | acatcgagtg | tctgcagatg | agaaagatcc | ctaacccaac | aatctttctg | 1740 |
| cccaagctgg | tgttcaagga | ccctgaggcc | ttctttaggg | ataatccaga | ggccgacgag | 1800 |
| ttcgtgtttc | tgagcggcat | gaaggccccc | gtgacaatca | ccagagagac | atacgaggcc | 1860 |
| tacaggtata | agctgtatac | cgtgggcaag | ctgcgcgatg | gcgaggtgtc | cgaagaggag | 1920 |
| tacaagcggg | ccctgctgca | ggtgctgacc | gcctacaagg | agtttctgga | aacagaatg | 1980 |
| atctatgccg | acctgaattt | cggctttaag | gatctggagg | agtataagga | cagctccgag | 2040 |
| tttatcaagc | aggtggagac | acacaacacc | ttcatgtgct | gggccaaggt | gtctagctcc | 2100 |

```
cagctggacg atctggtgaa gtctggcaac ggcctgctgt tcgagatctg gagcgagcgc  2160
ctggagtcct actataagta cggcaatgag aaggtgctgc ggggctatga gggcgtgctg  2220
ctgagcatcc tgaaggatga gaacctggtg tccatgcgga ccctgctgaa cagccggccc  2280
atgctggtgt accggccaaa ggagtctagc aagcctatgg tggtgcaccg ggatggcagc  2340
agagtggtgg acaggtttga taaggacggc aagtacatcc ccctgaggt gcacgacgag  2400
ctgtatcgct tctttaacaa tctgctgatc aaggagaagc tgggcgagaa ggcccggaag  2460
atcctggaca caagaaggt gaaggtgaag gtgctggaga gcgagagagt gaagtggtcc  2520
aagttctacg atgagcagtt tgccgtgacc ttcagcgtga agaagaacgc cgattgtctg  2580
gacaccacaa aggacctgaa tgccgaagtg atggagcagt atagcgagtc caacagactg  2640
atcctgatca ggaataccac agatatcctg tactatctgg tgctggacaa gaatggcaag  2700
gtgctgaagc agagatccct gaacatcatc aatgacggcg ccaggatgt ggactggaag  2760
gagaggttcc gccaggtgac aaaggataga acgagggct acaatgagtg ggattattcc  2820
aggacctcta acgacctgaa ggaggtgtac ctgaattatg ccctgaagga gatcgccgag  2880
gccgtgatcg agtacaacgc catcctgatc atcgagaaga tgtctaatgc ctttaaggac  2940
aagtatagct tcctggacga cgtgaccttc aagggcttcg agacaaagct gctggccaag  3000
ctgagcgatc tgcactttag gggcatcaag gacggcgagc catgttcctt cacaaacccc  3060
ctgcagctgt gccagaacga ttctaataag atcctgcagg acggcgtgat ctttatggtg  3120
ccaaattcta tgcacggag cctggacccc gacaccggct tcatctttgc catcaacgac  3180
cacaatatca ggaccaagaa ggccaagctg aactttctga gcaagttcga tcagctgaag  3240
gtgtcctctg agggctgcct gatcatgaag tacagcggcg attccctgcc tacacacaac  3300
accgacaatc gcgtgtggaa ctgctgttgc aatcacccaa tcacaaacta tgaccgggag  3360
acaaagaagg tggagttcat cgaggagccc gtggaggagc tgtcccgcgt gctggaggag  3420
aatggcatcg agacagacac cgagctgaac aagctgaatg agcgggagaa cgtgcctggc  3480
aaggtggtgg atgccatcta ctctctggtg ctgaattatc tgcgcggcac agtgagcgga  3540
gtggcaggac agagggccgt gtactatagc cctgtgaccg gcaagaagta cgatatctcc  3600
tttatccagg ccatgaacct gaataggaag tgtgactact ataggatcgg ctccaaggag  3660
aggggagagt ggaccgattt cgtggcccag ctgatcaaca aaaggccggc ggccacgaaa  3720
aaggccggcc aggcaaaaaa gaaaagggga tcctacccat acgatgttcc agattacgct  3780
tatccctacg acgtgcctga ttatgcatac ccatatgatg tccccgacta tgcctaa     3837
```

<210> SEQ ID NO 17
<211> LENGTH: 1345
<212> TYPE: PRT
<213> ORGANISM: Artificial Sequence
<220> FEATURE:
<223> OTHER INFORMATION: Synthetic-Butyrivibrio proteoclasticus (BpCpf1;
      pY006), including NLS and HA tag

<400> SEQUENCE: 17

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

```
Lys Ala Lys Gln Ile Ile Asp Lys Tyr His Gln Phe Ile Glu Glu
    50              55                  60

Ile Leu Ser Ser Val Cys Ile Ser Glu Asp Leu Leu Gln Asn Tyr Ser
65              70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
                115                 120                 125

Asp Ala Lys Lys Gly Gln Glu Ser Asp Leu Ile Leu Trp Leu Lys Gln
        130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
            180                 185                 190

Asn Asp Ile Pro Thr Ser Ile Ile Tyr Arg Ile Val Asp Asp Asn Leu
                195                 200                 205

Pro Lys Phe Leu Glu Asn Lys Ala Lys Tyr Glu Ser Leu Lys Asp Lys
        210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
        290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
                340                 345                 350

Gln Ser Phe Tyr Glu Gln Ile Ala Ala Phe Lys Thr Val Glu Glu Lys
            355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
```

-continued

```
            465                 470                 475                 480
        Asn Phe Ala Ala Ile Pro Met Ile Phe Asp Glu Ile Ala Gln Asn Lys
                        485                 490                 495
        Asp Asn Leu Ala Gln Ile Ser Ile Lys Tyr Gln Asn Gln Gly Lys Lys
                        500                 505                 510
        Asp Leu Leu Gln Ala Ser Ala Glu Asp Val Lys Ala Ile Lys Asp
                        515                 520                 525
        Leu Leu Asp Gln Thr Asn Asn Leu Leu His Lys Leu Lys Ile Phe His
                530                 535                 540
        Ile Ser Gln Ser Glu Asp Lys Ala Asn Ile Leu Asp Lys Asp Glu His
        545                 550                 555                 560
        Phe Tyr Leu Val Phe Glu Glu Cys Tyr Phe Glu Leu Ala Asn Ile Val
                            565                 570                 575
        Pro Leu Tyr Asn Lys Ile Arg Asn Tyr Ile Thr Gln Lys Pro Tyr Ser
                        580                 585                 590
        Asp Glu Lys Phe Lys Leu Asn Phe Glu Asn Ser Thr Leu Ala Asn Gly
                        595                 600                 605
        Trp Asp Lys Asn Lys Glu Pro Asp Asn Thr Ala Ile Leu Phe Ile Lys
                        610                 615                 620
        Asp Asp Lys Tyr Tyr Leu Gly Val Met Asn Lys Lys Asn Asn Lys Ile
        625                 630                 635                 640
        Phe Asp Asp Lys Ala Ile Lys Glu Asn Lys Gly Glu Gly Tyr Lys Lys
                        645                 650                 655
        Ile Val Tyr Lys Leu Leu Pro Gly Ala Asn Lys Met Leu Pro Lys Val
                        660                 665                 670
        Phe Phe Ser Ala Lys Ser Ile Lys Phe Tyr Asn Pro Ser Glu Asp Ile
                        675                 680                 685
        Leu Arg Ile Arg Asn His Ser Thr His Thr Lys Asn Gly Ser Pro Gln
                        690                 695                 700
        Lys Gly Tyr Glu Lys Phe Glu Phe Asn Ile Glu Asp Cys Arg Lys Phe
        705                 710                 715                 720
        Ile Asp Phe Tyr Lys Gln Ser Ile Ser Lys His Pro Glu Trp Lys Asp
                        725                 730                 735
        Phe Gly Phe Arg Phe Ser Asp Thr Gln Arg Tyr Asn Ser Ile Asp Glu
                        740                 745                 750
        Phe Tyr Arg Glu Val Glu Asn Gln Gly Tyr Lys Leu Thr Phe Glu Asn
                        755                 760                 765
        Ile Ser Glu Ser Tyr Ile Asp Ser Val Val Asn Gln Gly Lys Leu Tyr
                770                 775                 780
        Leu Phe Gln Ile Tyr Asn Lys Asp Phe Ser Ala Tyr Ser Lys Gly Arg
        785                 790                 795                 800
        Pro Asn Leu His Thr Leu Tyr Trp Lys Ala Leu Phe Asp Glu Arg Asn
                        805                 810                 815
        Leu Gln Asp Val Val Tyr Lys Leu Asn Gly Glu Ala Glu Leu Phe Tyr
                        820                 825                 830
        Arg Lys Gln Ser Ile Pro Lys Lys Ile Thr His Pro Ala Lys Glu Ala
                        835                 840                 845
        Ile Ala Asn Lys Asn Lys Asp Asn Pro Lys Lys Glu Ser Val Phe Glu
                        850                 855                 860
        Tyr Asp Leu Ile Lys Asp Lys Arg Phe Thr Glu Asp Lys Phe Phe Phe
        865                 870                 875                 880
        His Cys Pro Ile Thr Ile Asn Phe Lys Ser Ser Gly Ala Asn Lys Phe
                        885                 890                 895
```

-continued

Asn Asp Glu Ile Asn Leu Leu Lys Glu Lys Ala Asn Asp Val His
            900                 905                 910

Ile Leu Ser Ile Asp Arg Gly Glu Arg His Leu Ala Tyr Tyr Thr Leu
            915                 920                 925

Val Asp Gly Lys Gly Asn Ile Ile Lys Gln Asp Thr Phe Asn Ile Ile
    930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
            965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
            995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

| Phe | Val | Gln | Asn | Arg | Asn | Asn | Lys | Arg | Pro | Ala | Ala | Thr | Lys | Lys |
|-----|-----|-----|-----|-----|-----|-----|-----|-----|-----|-----|-----|-----|-----|-----|
| 1295 |   |   |   |   | 1300 |   |   |   |   | 1305 |   |   |   |   |

| Ala | Gly | Gln | Ala | Lys | Lys | Lys | Gly | Ser | Tyr | Pro | Tyr | Asp | Val |
|-----|-----|-----|-----|-----|-----|-----|-----|-----|-----|-----|-----|-----|-----|
| 1310 |   |   |   |   | 1315 |   |   |   |   | 1320 |   |   |   |

| Pro | Asp | Tyr | Ala | Tyr | Pro | Tyr | Asp | Val | Pro | Asp | Tyr | Ala | Tyr | Pro |
|-----|-----|-----|-----|-----|-----|-----|-----|-----|-----|-----|-----|-----|-----|-----|
| 1325 |   |   |   |   | 1330 |   |   |   |   | 1335 |   |   |   |   |

| Tyr | Asp | Val | Pro | Asp | Tyr | Ala |
|-----|-----|-----|-----|-----|-----|-----|
| 1340 |   |   |   |   | 1345 |   |

<210> SEQ ID NO 18
<211> LENGTH: 4038
<212> TYPE: DNA
<213> ORGANISM: Artificial Sequence
<220> FEATURE:
<223> OTHER INFORMATION: Synthetic-Butyrivibrio proteoclasticus (BpCpf1; pY006), including NLS and HA tag

<400> SEQUENCE: 18

```
atgagcatct accaggagtt cgtcaacaag tattcactga gtaagacact gcggttcgag      60
ctgatcccac agggcaagac actggagaac atcaaggccc gaggcctgat tctggacgat     120
gagaagcggg caaagactga taagaaagcc aagcagatca ttgataaata ccaccagttc     180
tttatcgagg aaattctgag ctccgtgtgc atcagtgagg atctgctgca gaattactca     240
gacgtgtact tcaagctgaa gaagagcgac gatgacaacc tgcagaagga cttcaagtcc     300
gccaaggaca ccatcaagaa acagattagc gagtacatca aggactccga aagtttaaa     360 aatctgttca accagaatct gatcgatgct aagaaaggcc aggagtccga cctgatcctg     420
tggctgaaac agtctaagga caatgggatt gaactgttca aggctaactc cgatatcact     480
gatattgacg aggcactgga aatcatcaag agcttcaagg atggaccac atactttaaa     540 ggcttccacg agaaccgcaa gaacgtgtac tccagcaacg acattcctac ctccatcatc     600
taccgaatcg tcgatgacaa tctgccaaag ttcctggaga acaaggccaa atatgaatct     660
ctgaaggaca aagctcccga ggcaattaat tacgaacaga tcaagaaaga tctggctgag     720
gaactgacat tcgatatcga ctataagact agcgaggtga accagagggt cttttccctg     780
gacgaggtgt ttgaaatcgc caatttcaac aattacctga accagtccgg cattactaaa     840
ttcaatacca tcattggcgg gaagtttgtg aacggggaga ataccaagcg caagggaatt     900
aacgaataca tcaatctgta tagccagcag atcaacgaca aaactctgaa gaatacaag     960 atgtctgtgc tgttcaaaca gatcctgagt gataccgagt ccaagtcttt tgtcattgat    1020
aaactggaag atgactcaga cgtggtcact accatgcaga gcttttatga gcagatcgcc    1080
gctttcaaga cagtggagga aaatctatt aaggaaactc tgagtctgct gttcgatgac    1140
ctgaaagccc agaagctgga cctgagtaag atctacttca aaaacgataa gagtctgaca    1200
gacctgtcac agcaggtgtt tgatgactat tccgtgattg gaccgccgt cctggagtac    1260 attacacagc agatcgctcc aaagaacctg ataatccct ctaagaaaga gcaggaactg    1320
atcgctaaga aaaccgagaa ggcaaaatat ctgagtctgg aaacaattaa gctggcactg    1380
gaggagttca acaagcacag ggatattgac aaacagtgcc gctttgagga atcctggcc    1440 aacttcgcag ccatccccat gattttgat gagatcgccc agaacaaaga caatctggct    1500
cagatcagta ttaagtacca gaaccagggc aagaaagacc tgctgcaggc ttcagcagaa    1560
gatgacgtga agccatcaa ggatctgctg gaccagacca caatctgct gcacaagctg    1620 aaaatcttcc atattagtca gtcagaggat aaggctaata tcctggataa agacgaacac    1680
```

```
ttctacctgg tgttcgagga atgttacttc gagctggcaa acattgtccc cctgtataac    1740
aagattagga actacatcac acagaagcct tactctgacg agaagtttaa actgaacttc    1800
gaaaatagta ccctggccaa cgggtgggat aagaacaagg agcctgacaa cacagctatc    1860
ctgttcatca aggatgacaa gtactatctg ggagtgatga ataagaaaaa caataagatc    1920
ttcgatgaca aagccattaa ggagaacaaa ggggaaggat acaagaaaat cgtgtataag    1980
ctgctgcccg cgcaaataa gatgctgcct aaggtgttct tcagcgccaa gagtatcaaa    2040
ttctacaacc catccgagga catcctgcgg attagaaatc actcaacaca tactaagaac    2100
gggagccccc agaagggata tgagaaattt gagttcaaca tcgaggattg caggaagttt    2160
attgacttct acaagcagag catctccaaa caccctgaat ggaaggattt tggcttccgg    2220
ttttccgaca cacagagata taactctatc gacgagttct accgcgaggt ggaaaatcag    2280
gggtataagc tgacttttga gaacatttct gaaagttaca tcgacagcgt ggtcaatcag    2340
ggaaagctgt acctgttcca gatctataac aaagattttt cagcatacag caagggcaga    2400
ccaaacctgc atacactgta ctggaaggcc ctgttcgatg agaggaatct gcaggacgtg    2460
gtctataaac tgaacggaga ggccgaactg ttttaccgga agcagtctat tcctaagaaa    2520
atcactcacc cagctaagga ggccatcgct aacaagaaca aggacaatcc taagaaagag    2580
agcgtgttcg aatacgatct gattaaggac aagcggttca ccgaagataa gttcttttc    2640 cattgtccaa tcaccattaa cttcaagtca agcggcgcta acaagttcaa cgacgagatc    2700
aatctgctgc tgaaggaaaa agcaaacgat gtgcacatcc tgagcattga ccgaggagag    2760
cggcatctgg cctactatac cctggtggat ggcaaaggga atatcattaa gcaggataca    2820
ttcaacatca ttggcaatga ccggatgaaa accaactacc acgataaact ggctgcaatc    2880
gagaaggata gagactcagc taggaaggac tggaagaaaa tcaacaacat taaggagatg    2940
aaggaaggct atctgagcca ggtggtccat gagattgcaa agctggtcat cgaatacaat    3000
gccattgtgg tgttcgagga tctgaacttc ggctttaaga gggggcgctt taaggtggaa    3060
aaacaggtct atcagaagct ggagaaaatg ctgatcgaaa agctgaatta cctggtgttt    3120
aaagataacg agttcgacaa gaccggaggc gtcctgagag cctaccagct gacagctccc    3180
tttgaaactt tcaagaaaat gggaaaacag acaggcatca tctactatgt gccagccgga    3240
ttcacttcca agatctgccc cgtgaccggc tttgtcaacc agctgtaccc taaatatgag    3300
tcagtgagca agtcccagga atttttcagc aagttcgata gatctgttta atctggac    3360 aaggggtact tcgagttttc cttcgattac aagaacttcg cgacaaggc cgctaagggg    3420 aaatggacca ttgcctcctt cggatctcgc ctgatcaact ttcgaaattc cgataaaaac    3480
cacaattggg acactaggga ggtgtaccca accaaggagc tggaaaagct gctgaaagac    3540
tactctatcg agtatggaca tggcgaatgc atcaaggcag ccatctgtgg cgagagtgat    3600
aagaaatttt tcgccaagct gacctcagtg ctgaatacaa tcctgcagat gcggaactca    3660
aagaccggga cagaactgga ctatctgatt agccccgtgg ctgatgtcaa cggaaacttc    3720
ttcgacagca gacaggcacc caaaaatatg cctcaggatg cagacgccaa cggggcctac    3780
cacatcgggc tgaagggact gatgctgctg ggccggatca gaacaatca ggaggggaag    3840 aagctgaacc tggtcattaa gaacgaggaa tacttcgagt ttgtccagaa tagaaataac    3900
aaaaggccgg cggccacgaa aaaggccggc caggcaaaaa agaaaaaggg atcctaccca    3960
tacgatgttc cagattacgc ttatccctac gacgtgcctg attatgcata cccatatgat    4020
gtccccgact atgcctaa                                                 4038
```

```
<210> SEQ ID NO 19
<211> LENGTH: 1522
<212> TYPE: PRT
<213> ORGANISM: Artificial Sequence
<220> FEATURE:
<223> OTHER INFORMATION: Synthetic-Peregrinibacteria bacterium
      GW2011_GWA_33_10 (PeCpf1; pY007), including NLS and HA tag

<400> SEQUENCE: 19
```

| | | | | | | | | | | | | | | |
|---|---|---|---|---|---|---|---|---|---|---|---|---|---|---|
|Met|Ser|Asn|Phe|Phe|Lys|Asn|Phe|Thr|Asn|Leu|Tyr|Glu|Leu|Ser|Lys|
|1| | | |5| | | | |10| | | | |15|

Thr Leu Arg Phe Glu Leu Lys Pro Val Gly Asp Thr Leu Thr Asn Met
                20                  25                  30

Lys Asp His Leu Glu Tyr Asp Glu Lys Leu Gln Thr Phe Leu Lys Asp
            35                  40                  45

Gln Asn Ile Asp Asp Ala Tyr Gln Ala Leu Lys Pro Gln Phe Asp Glu
        50                  55                  60

Ile His Glu Glu Phe Ile Thr Asp Ser Leu Glu Ser Lys Lys Ala Lys
65                  70                  75                  80

Glu Ile Asp Phe Ser Glu Tyr Leu Asp Leu Phe Gln Glu Lys Lys Glu
                85                  90                  95

Leu Asn Asp Ser Glu Lys Lys Leu Arg Asn Lys Ile Gly Glu Thr Phe
            100                 105                 110

Asn Lys Ala Gly Glu Lys Trp Lys Glu Lys Tyr Pro Gln Tyr Glu
        115                 120                 125

Trp Lys Lys Gly Ser Lys Ile Ala Asn Gly Ala Asp Ile Leu Ser Cys
130                 135                 140

Gln Asp Met Leu Gln Phe Ile Lys Tyr Lys Asn Pro Glu Asp Glu Lys
145                 150                 155                 160

Ile Lys Asn Tyr Ile Asp Asp Thr Leu Lys Gly Phe Phe Thr Tyr Phe
                165                 170                 175

Gly Gly Phe Asn Gln Asn Arg Ala Asn Tyr Tyr Glu Thr Lys Lys Glu
            180                 185                 190

Ala Ser Thr Ala Val Ala Thr Arg Ile Val His Glu Asn Leu Pro Lys
        195                 200                 205

Phe Cys Asp Asn Val Ile Gln Phe Lys His Ile Ile Lys Arg Lys Lys
    210                 215                 220

Asp Gly Thr Val Glu Lys Thr Glu Arg Lys Thr Glu Tyr Leu Asn Ala
225                 230                 235                 240

Tyr Gln Tyr Leu Lys Asn Asn Asn Lys Ile Thr Gln Ile Lys Asp Ala
                245                 250                 255

Glu Thr Glu Lys Met Ile Glu Ser Thr Pro Ile Ala Glu Lys Ile Phe
            260                 265                 270

Asp Val Tyr Tyr Phe Ser Ser Cys Leu Ser Gln Lys Gln Ile Glu Glu
        275                 280                 285

Tyr Asn Arg Ile Ile Gly His Tyr Asn Leu Leu Ile Asn Leu Tyr Asn
    290                 295                 300

Gln Ala Lys Arg Ser Glu Gly Lys His Leu Ser Ala Asn Glu Lys Lys
305                 310                 315                 320

Tyr Lys Asp Leu Pro Lys Phe Lys Thr Leu Tyr Lys Gln Ile Gly Cys
                325                 330                 335

Gly Lys Lys Lys Asp Leu Phe Tyr Thr Ile Lys Cys Asp Thr Glu Glu
            340                 345                 350

Glu Ala Asn Lys Ser Arg Asn Glu Gly Lys Glu Ser His Ser Val Glu

-continued

```
            355                 360                 365
Glu Ile Ile Asn Lys Ala Gln Glu Ala Ile Asn Lys Tyr Phe Lys Ser
370                 375                 380
Asn Asn Asp Cys Glu Asn Ile Asn Thr Val Pro Asp Phe Ile Asn Tyr
385                 390                 395                 400
Ile Leu Thr Lys Glu Asn Tyr Glu Gly Val Tyr Trp Ser Lys Ala Ala
                    405                 410                 415
Met Asn Thr Ile Ser Asp Lys Tyr Phe Ala Asn Tyr His Asp Leu Gln
                    420                 425                 430
Asp Arg Leu Lys Glu Ala Lys Val Phe Gln Lys Ala Asp Lys Lys Ser
            435                 440                 445
Glu Asp Asp Ile Lys Ile Pro Glu Ala Ile Glu Leu Ser Gly Leu Phe
450                 455                 460
Gly Val Leu Asp Ser Leu Ala Asp Trp Gln Thr Thr Leu Phe Lys Ser
465                 470                 475                 480
Ser Ile Leu Ser Asn Glu Asp Lys Leu Lys Ile Ile Thr Asp Ser Gln
                    485                 490                 495
Thr Pro Ser Glu Ala Leu Leu Lys Met Ile Phe Asn Asp Ile Glu Lys
                    500                 505                 510
Asn Met Glu Ser Phe Leu Lys Glu Thr Asn Asp Ile Ile Thr Leu Lys
            515                 520                 525
Lys Tyr Lys Gly Asn Lys Glu Gly Thr Glu Lys Ile Lys Gln Trp Phe
            530                 535                 540
Asp Tyr Thr Leu Ala Ile Asn Arg Met Leu Lys Tyr Phe Leu Val Lys
545                 550                 555                 560
Glu Asn Lys Ile Lys Gly Asn Ser Leu Asp Thr Asn Ile Ser Glu Ala
                    565                 570                 575
Leu Lys Thr Leu Ile Tyr Ser Asp Asp Ala Glu Trp Phe Lys Trp Tyr
                    580                 585                 590
Asp Ala Leu Arg Asn Tyr Leu Thr Gln Lys Pro Gln Asp Glu Ala Lys
            595                 600                 605
Glu Asn Lys Leu Lys Leu Asn Phe Asp Asn Pro Ser Leu Ala Gly Gly
610                 615                 620
Trp Asp Val Asn Lys Glu Cys Ser Asn Phe Cys Val Ile Leu Lys Asp
625                 630                 635                 640
Lys Asn Glu Lys Lys Tyr Leu Ala Ile Met Lys Lys Gly Glu Asn Thr
                    645                 650                 655
Leu Phe Gln Lys Glu Trp Thr Glu Gly Arg Gly Lys Asn Leu Thr Lys
                    660                 665                 670
Lys Ser Asn Pro Leu Phe Glu Ile Asn Asn Cys Glu Ile Leu Ser Lys
            675                 680                 685
Met Glu Tyr Asp Phe Trp Ala Asp Val Ser Lys Met Ile Pro Lys Cys
            690                 695                 700
Ser Thr Gln Leu Lys Ala Val Val Asn His Phe Lys Gln Ser Asp Asn
705                 710                 715                 720
Glu Phe Ile Phe Pro Ile Gly Tyr Lys Val Thr Ser Gly Glu Lys Phe
                    725                 730                 735
Arg Glu Glu Cys Lys Ile Ser Lys Gln Asp Phe Glu Leu Asn Asn Lys
                    740                 745                 750
Val Phe Asn Lys Asn Glu Leu Ser Val Thr Ala Met Arg Tyr Asp Leu
            755                 760                 765
Ser Ser Thr Gln Glu Lys Gln Tyr Ile Lys Ala Phe Gln Lys Glu Tyr
770                 775                 780
```

```
Trp Glu Leu Leu Phe Lys Gln Glu Lys Arg Asp Thr Lys Leu Thr Asn
785                 790                 795                 800

Asn Glu Ile Phe Asn Glu Trp Ile Asn Phe Cys Asn Lys Lys Tyr Ser
            805                 810                 815

Glu Leu Leu Ser Trp Glu Arg Lys Tyr Lys Asp Ala Leu Thr Asn Trp
        820                 825                 830

Ile Asn Phe Cys Lys Tyr Phe Leu Ser Lys Tyr Pro Lys Thr Thr Leu
            835                 840                 845

Phe Asn Tyr Ser Phe Lys Glu Ser Glu Asn Tyr Asn Ser Leu Asp Glu
850                 855                 860

Phe Tyr Arg Asp Val Asp Ile Cys Ser Tyr Lys Leu Asn Ile Asn Thr
865                 870                 875                 880

Thr Ile Asn Lys Ser Ile Leu Asp Arg Leu Val Glu Glu Gly Lys Leu
            885                 890                 895

Tyr Leu Phe Glu Ile Lys Asn Gln Asp Ser Asn Asp Gly Lys Ser Ile
            900                 905                 910

Gly His Lys Asn Asn Leu His Thr Ile Tyr Trp Asn Ala Ile Phe Glu
            915                 920                 925

Asn Phe Asp Asn Arg Pro Lys Leu Asn Gly Glu Ala Glu Ile Phe Tyr
930                 935                 940

Arg Lys Ala Ile Ser Lys Asp Lys Leu Gly Ile Val Lys Gly Lys Lys
945                 950                 955                 960

Thr Lys Asn Gly Thr Glu Ile Ile Lys Asn Tyr Arg Phe Ser Lys Glu
            965                 970                 975

Lys Phe Ile Leu His Val Pro Ile Thr Leu Asn Phe Cys Ser Asn Asn
            980                 985                 990

Glu Tyr Val Asn Asp Ile Val Asn Thr Lys Phe Tyr Asn Phe Ser Asn
            995                 1000                1005

Leu His Phe Leu Gly Ile Asp Arg Gly Glu Lys His Leu Ala Tyr
        1010            1015            1020

Tyr Ser Leu Val Asn Lys Asn Gly Glu Ile Val Asp Gln Gly Thr
    1025            1030            1035

Leu Asn Leu Pro Phe Thr Asp Lys Asp Gly Asn Gln Arg Ser Ile
    1040            1045            1050

Lys Lys Glu Lys Tyr Phe Tyr Asn Lys Gln Glu Asp Lys Trp Glu
    1055            1060            1065

Ala Lys Glu Val Asp Cys Trp Asn Tyr Asn Asp Leu Leu Asp Ala
    1070            1075            1080

Met Ala Ser Asn Arg Asp Met Ala Arg Lys Asn Trp Gln Arg Ile
    1085            1090            1095

Gly Thr Ile Lys Glu Ala Lys Asn Gly Tyr Val Ser Leu Val Ile
    1100            1105            1110

Arg Lys Ile Ala Asp Leu Ala Val Asn Asn Glu Arg Pro Ala Phe
    1115            1120            1125

Ile Val Leu Glu Asp Leu Asn Thr Gly Phe Lys Arg Ser Arg Gln
    1130            1135            1140

Lys Ile Asp Lys Ser Val Tyr Gln Lys Phe Glu Leu Ala Leu Ala
    1145            1150            1155

Lys Lys Leu Asn Phe Leu Val Asp Lys Asn Ala Lys Arg Asp Glu
    1160            1165            1170

Ile Gly Ser Pro Thr Lys Ala Leu Gln Leu Thr Pro Pro Val Asn
    1175            1180            1185
```

Asn Tyr Gly Asp Ile Glu Asn Lys Lys Gln Ala Gly Ile Met Leu
    1190            1195                1200

Tyr Thr Arg Ala Asn Tyr Thr Ser Gln Thr Asp Pro Ala Thr Gly
    1205            1210                1215

Trp Arg Lys Thr Ile Tyr Leu Lys Ala Gly Pro Glu Glu Thr Thr
    1220            1225                1230

Tyr Lys Lys Asp Gly Lys Ile Lys Asn Lys Ser Val Lys Asp Gln
    1235            1240                1245

Ile Ile Glu Thr Phe Thr Asp Ile Gly Phe Asp Gly Lys Asp Tyr
    1250            1255                1260

Tyr Phe Glu Tyr Asp Lys Gly Glu Phe Val Asp Glu Lys Thr Gly
    1265            1270                1275

Glu Ile Lys Pro Lys Lys Trp Arg Leu Tyr Ser Gly Glu Asn Gly
    1280            1285                1290

Lys Ser Leu Asp Arg Phe Arg Gly Glu Arg Glu Lys Asp Lys Tyr
    1295            1300                1305

Glu Trp Lys Ile Asp Lys Ile Asp Ile Val Lys Ile Leu Asp Asp
    1310            1315                1320

Leu Phe Val Asn Phe Asp Lys Asn Ile Ser Leu Leu Lys Gln Leu
    1325            1330                1335

Lys Glu Gly Val Glu Leu Thr Arg Asn Asn Glu His Gly Thr Gly
    1340            1345                1350

Glu Ser Leu Arg Phe Ala Ile Asn Leu Ile Gln Gln Ile Arg Asn
    1355            1360                1365

Thr Gly Asn Asn Glu Arg Asp Asn Asp Phe Ile Leu Ser Pro Val
    1370            1375                1380

Arg Asp Glu Asn Gly Lys His Phe Asp Ser Arg Glu Tyr Trp Asp
    1385            1390                1395

Lys Glu Thr Lys Gly Glu Lys Ile Ser Met Pro Ser Ser Gly Asp
    1400            1405                1410

Ala Asn Gly Ala Phe Asn Ile Ala Arg Lys Gly Ile Ile Met Asn
    1415            1420                1425

Ala His Ile Leu Ala Asn Ser Asp Ser Lys Asp Leu Ser Leu Phe
    1430            1435                1440

Val Ser Asp Glu Glu Trp Asp Leu His Leu Asn Asn Lys Thr Glu
    1445            1450                1455

Trp Lys Lys Gln Leu Asn Ile Phe Ser Ser Arg Lys Ala Met Ala
    1460            1465                1470

Lys Arg Lys Lys Lys Arg Pro Ala Ala Thr Lys Lys Ala Gly Gln
    1475            1480                1485

Ala Lys Lys Lys Lys Gly Ser Tyr Pro Tyr Asp Val Pro Asp Tyr
    1490            1495                1500

Ala Tyr Pro Tyr Asp Val Pro Asp Tyr Ala Tyr Pro Tyr Asp Val
    1505            1510                1515

Pro Asp Tyr Ala
    1520

<210> SEQ ID NO 20
<211> LENGTH: 4569
<212> TYPE: DNA
<213> ORGANISM: Artificial Sequence
<220> FEATURE:
<223> OTHER INFORMATION: Synthetic-Peregrinibacteria bacterium
      GW2011_GWA_33_10 (PeCpf1; pY007), including NLS and HA tag

<400> SEQUENCE: 20

```
atgtccaact tctttaagaa tttcaccaac ctgtatgagc tgtccaagac actgaggttt      60
gagctgaagc ccgtgggcga caccctgaca aacatgaagg accacctgga gtacgatgag     120
aagctgcaga ccttcctgaa ggatcagaat atcgacgatg cctatcaggc cctgaagcct     180
cagttcgacg agatccacga ggagtttatc acagattctc tggagagcaa gaaggccaag     240
gagatcgact tctccgagta cctggatctg tttcaggaga agaaggagct gaacgactct     300
gagaagaagc tgcgcaacaa gatcggcgag acattcaaca aggccggcga agtggaag      360
aaggagaagt accctcagta tgagtggaag aagggctcca agatcgccaa tggcgccgac     420
atcctgtctt gccaggatat gctgcagttt atcaagtata agaacccaga ggatgagaag     480
atcaagaatt acatcgacga tacactgaag ggcttcttta cctatttcgg cggctttaat     540
cagaacaggg ccaactacta tgagacaaag aaggaggcct ccaccgcagt ggcaacaagg     600
atcgtgcacg agaacctgcc aaagttctgt gacaatgtga tccagtttaa gcacatcatc     660
aagcggaaga aggatggcac cgtggagaaa accgagagaa agaccgagta cctgaacgcc     720
taccagtatc tgaagaacaa taacaagatc acacagatca aggacgccga gacagagaag     780
atgatcgagt ctacacccat cgccgagaag atcttcgacg tgtactactt cagcagctgc     840
ctgagccaga agcagatcga ggagtacaac cggatcatcg ccactataa tctgctgatc     900
aacctgtata accaggccaa gagatctgag ggcaagcacc tgagcgccaa cgagaagaag     960
tataaggacc tgcctaagtt caagaccctg tataagcaga tcggctgcgg caagaagaag    1020
gacctgtttt acacaatcaa gtgtgatacc gaggaggagg ccaataagtc ccggaacgag    1080
ggcaaggagt cccactctgt ggaggagatc atcaacaagg cccaggaggc catcaataag    1140
tacttcaagt ctaataacga ctgtgagaat atcaacaccg tgcccgactt catcaactat    1200
atcctgacaa aggagaatta cgagggcgtg tattggcagc aggccgccat gaacaccatc    1260
tccgacaagt acttcgccaa ttatcacgac ctgcaggata gactgaagga ggccaaggtg    1320
tttcagaagg ccgataagaa gtccgaggac gatatcaaga tcccagaggc catcgagctg    1380
tctggcctgt tcggcgtgct ggacagcctg gccgattggc agaccacact gtttaagtct    1440
agcatcctga gcaacgagga caagctgaag atcatcacag attcccagac cccctctgag    1500
gccctgctga agatgatctt caatgacatc gagaagaaca tggagtcctt tctgaaggag    1560
acaaacgata tcatcaccct gaagaagtat aagggcaata aggaggggcac cgagaagatc    1620
aagcagtggt tcgactatac actggccatc aaccggatgc tgaagtactt tctggtgaag    1680
gagaataaga tcaagggcaa ctccctggat accaatatct ctgaggccct gaaaaccctg    1740
atctacagcg acgatgccga gtggttcaag tggtacgacg ccctgagaaa ctatctgacc    1800
cagaagcctc aggatgaggc caaggagaat aagctgaagc tgaatttcga caacccatct    1860
ctggccggcg gctgggatgt gaacaaggag tgcagcaatt tttgcgtgat cctgaaggac    1920
aagaacgaga gaagtaccct ggccatcatg aagaagggcg agaataccct gttccagaag    1980
gagtggacag agggccgggg caagaacctg acaaagaagt ctaatccact gttcgagatc    2040
aataactgcg agatcctgag caagatggag tatgactttt gggccgacgt gagcaagatg    2100
atccccaagt gtagcaccca gctgaaggcc gtggtgaacc acttcaagca gtccgacaat    2160
gagttcatct ttcctatcgg ctacaaggtg acaagcggcg agaagtttag ggaggagtgc    2220
aagatctcca gcaggactt cgagctgaat aacaaggtgt ttaataagaa cgagctgagc    2280
gtgaccgcca tgcgctacga tctgtcctct acacaggaga agcagtatat caaggccttc    2340
```

```
cagaaggagt actgggagct gctgtttaag caggagaagc gggacaccaa gctgacaaat    2400
aacgagatct tcaacgagtg gatcaatttt tgcaacaaga agtatagcga gctgctgtcc    2460
tgggagagaa agtacaagga tgccctgacc aattggatca acttctgtaa gtactttctg    2520
agcaagtatc ccaagaccac actgttcaac tactctttta aggagagcga gaattataac    2580
tccctggacg agttctaccg ggacgtggat atctgttctt acaagctgaa tatcaacacc    2640
acaatcaata agagcatcct ggatagactg gtggaggagg gcaagctgta cctgtttgag    2700
atcaagaatc aggacagcaa cgatggcaag tccatcggcc acaagaataa cctgcacacc    2760
atctactgga acgccatctt cgagaatttt gacaacaggc taagctgaa tggcgaggcc     2820 gagatcttct atcgcaaggc catctccaag gataagctgg gcatcgtgaa gggcaagaaa    2880
accaagaacg gcaccgagat catcaagaat tacagattca gcaaggagaa gtttatcctg    2940
cacgtgccaa tcaccctgaa cttctgctcc aataacgagt atgtgaatga catcgtgaac    3000
acaaagttct acaattttc caacctgcac tttctgggca tcgataggg cgagaagcac      3060 ctggcctact attctctggt gaataagaac ggcgagatcg tggaccaggg cacactgaac    3120
ctgcctttca ccgacaagga tggcaatcag cgcagcatca agaaggagaa gtacttttat    3180
aacaagcagg aggacaagtg ggaggccaag gaggtggatt gttggaatta taacgacctg    3240
ctggatgcca tggcctctaa ccgggacatg gccagaaaga attggcagag gatcggcacc    3300
atcaaggagg ccaagaacgg ctacgtgagc ctggtcatca ggaagatcgc cgatctggcc    3360
gtgaataacg agcgccccgc cttcatcgtg ctggaggacc tgaatacagg ctttaagcgg    3420
tccagacaga agatcgataa gagcgtgtac cagaagttcg agctggccct ggccaagaag    3480
ctgaactttc tggtggacaa gaatgccaag cgcgatgaga tcggctcccc tacaaaggcc    3540
ctgcagctga ccccccctgt gaataactac ggcgacattg agaacaagaa gcaggccggc    3600
atcatgctgt ataccgggc caattatacc tctcagacag atccagccac aggctggaga    3660
aagaccatct atctgaaggc cggccccgag gagacaacat acaagaagga cggcaagatc    3720
aagaacaaga gcgtgaagga ccagatcatc gagacattca ccgatatcgg ctttgacggc    3780
aaggattact atttcgagta cgacaagggc gagtttgtgg atgagaaaac cggcgagatc    3840
aagcccaaga agtggcggct gtactccggc gagaatggca agtccctgga caggttccgc    3900
ggagagaggg agaaggataa gtatgagtgg aagatcgaca agatcgatat cgtgaagatc    3960
ctggacgatc tgttcgtgaa ttttgacaag aacatcagcc tgctgaagca gctgaaggag    4020
ggcgtggagc tgacccggaa taacgagcac ggcacaggcg agtccctgag attcgccatc    4080
aacctgatcc agcagatccg gaataccggc aataacgaga gagacaacga tttcatcctg    4140
tccccagtga gggacgagaa tggcaagcac tttgactctc gcgagtactg ggataaggag    4200
acaaagggcg agaagatcag catgcccagc tccggcgatg ccaatggcgc cttcaacatc    4260
gcccggaagg gcatcatcat gaacgcccac atcctggcca atagcgactc caaggatctg    4320
tccctgttcg tgtctgacga ggagtgggat ctgcacctga ataacaagac cgagtggaag    4380
aagcagctga acatctttc tagcaggaag gccatggcca agcgcaagaa gaaaaggccg    4440
gcggccacga aaaggccgg ccaggcaaaa aagaaaaagg gatcctaccc atacgatgtt    4500
ccagattacg cttatccta cgacgtgcct gattatgcat acccatatga tgtccccgac    4560
tatgcctaa                                                           4569
```

<210> SEQ ID NO 21
<211> LENGTH: 1397

<212> TYPE: PRT
<213> ORGANISM: Artificial Sequence
<220> FEATURE:
<223> OTHER INFORMATION: Synthetic-Parcubacteria bacterium
    GWC2011_GWC2_44_17 (PbCpf1; pY008), including NLS and HA tag

<400> SEQUENCE: 21

```
Met Glu Asn Ile Phe Asp Gln Phe Ile Gly Lys Tyr Ser Leu Ser Lys
1               5                   10                  15

Thr Leu Arg Phe Glu Leu Lys Pro Val Gly Lys Thr Glu Asp Phe Leu
            20                  25                  30

Lys Ile Asn Lys Val Phe Glu Lys Asp Gln Thr Ile Asp Asp Ser Tyr
        35                  40                  45

Asn Gln Ala Lys Phe Tyr Phe Asp Ser Leu His Gln Lys Phe Ile Asp
50                  55                  60

Ala Ala Leu Ala Ser Asp Lys Thr Ser Glu Leu Ser Phe Gln Asn Phe
65                  70                  75                  80

Ala Asp Val Leu Glu Lys Gln Asn Lys Ile Ile Leu Asp Lys Lys Arg
                85                  90                  95

Glu Met Gly Ala Leu Arg Lys Arg Asp Lys Asn Ala Val Gly Ile Asp
            100                 105                 110

Arg Leu Gln Lys Glu Ile Asn Asp Ala Glu Asp Ile Ile Gln Lys Glu
        115                 120                 125

Lys Glu Lys Ile Tyr Lys Asp Val Arg Thr Leu Phe Asp Asn Glu Ala
130                 135                 140

Glu Ser Trp Lys Thr Tyr Tyr Gln Glu Arg Glu Val Asp Gly Lys Lys
145                 150                 155                 160

Ile Thr Phe Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
            180                 185                 190

Lys Glu Lys Glu Phe Gln Ala Lys Asn Gln Pro Ser Leu Phe Val Glu
        195                 200                 205

Glu Lys Glu Asn Pro Gly Gln Lys Arg Tyr Ile Phe Asp Ser Phe Asp
210                 215                 220

Lys Phe Ala Gly Tyr Leu Thr Lys Phe Gln Gln Thr Lys Lys Asn Leu
225                 230                 235                 240

Tyr Ala Ala Asp Gly Thr Ser Thr Ala Val Ala Thr Arg Ile Ala Asp
                245                 250                 255

Asn Phe Ile Ile Phe His Gln Asn Thr Lys Val Phe Arg Asp Lys Tyr
            260                 265                 270

Lys Asn Asn His Thr Asp Leu Gly Phe Asp Glu Glu Asn Ile Phe Glu
        275                 280                 285

Ile Glu Arg Tyr Lys Asn Cys Leu Leu Gln Arg Glu Ile Glu His Ile
290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
            340                 345                 350

Val Glu Lys Glu Lys Gln Leu Ile Glu Lys Thr Arg Glu Lys Thr Glu
        355                 360                 365

Glu Asp Val Leu Ile Glu Arg Phe Lys Glu Phe Ile Glu Asn Asn Glu
370                 375                 380
```

```
Glu Arg Phe Thr Ala Ala Lys Lys Leu Met Asn Ala Phe Cys Asn Gly
385                 390                 395                 400

Glu Phe Glu Ser Glu Tyr Glu Gly Ile Tyr Leu Lys Asn Lys Ala Ile
            405                 410                 415

Asn Thr Ile Ser Arg Arg Trp Phe Val Ser Asp Arg Asp Phe Glu Leu
            420                 425                 430

Lys Leu Pro Gln Gln Lys Ser Lys Asn Lys Ser Glu Lys Asn Glu Pro
            435                 440                 445

Lys Val Lys Lys Phe Ile Ser Ile Ala Glu Ile Lys Asn Ala Val Glu
450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
            500                 505                 510

Lys Leu Leu Gly Tyr Asp Ser Cys Leu Lys Ile Ala Lys Gln Leu Gly
            515                 520                 525

Ile Phe Pro Gln Glu Lys Glu Ala Arg Glu Lys Ala Thr Ala Val Ile
530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
            565                 570                 575

Thr Asn Phe Tyr Ala Glu Tyr Asp Gly Tyr Tyr Lys Asp Phe Glu Phe
            580                 585                 590

Ile Lys Tyr Tyr Asn Glu Phe Arg Asn Phe Ile Thr Lys Lys Pro Phe
            595                 600                 605

Asp Glu Asp Lys Ile Lys Leu Asn Phe Glu Asn Gly Ala Leu Leu Lys
            610                 615                 620

Gly Trp Asp Glu Asn Lys Glu Tyr Asp Phe Met Gly Val Ile Leu Lys
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
            660                 665                 670

Gln Lys Met Ile Tyr Lys Gln Ile Ala Asp Ala Ser Lys Asp Val Pro
            675                 680                 685

Arg Leu Leu Leu Thr Ser Lys Lys Ala Met Glu Lys Phe Lys Pro Ser
            690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
            725                 730                 735

Asn Cys Ile Pro Gln Tyr Ser Asn Trp Ser Phe Tyr Asp Phe Gln Phe
            740                 745                 750

Gln Asp Thr Gly Lys Tyr Gln Asn Ile Lys Glu Phe Thr Asp Asp Val
            755                 760                 765

Gln Lys Tyr Gly Tyr Lys Ile Ser Phe Arg Asp Ile Asp Asp Glu Tyr
            770                 775                 780

Ile Asn Gln Ala Leu Asn Glu Gly Lys Met Tyr Leu Phe Glu Val Val
785                 790                 795                 800
```

```
Asn Lys Asp Ile Tyr Asn Thr Lys Asn Gly Ser Lys Asn Leu His Thr
                805                 810                 815
Leu Tyr Phe Glu His Ile Leu Ser Ala Glu Asn Leu Asn Asp Pro Val
            820                 825                 830
Phe Lys Leu Ser Gly Met Ala Glu Ile Phe Gln Arg Gln Pro Ser Val
            835                 840                 845
Asn Glu Arg Glu Lys Ile Thr Thr Gln Lys Asn Gln Cys Ile Leu Asp
850                 855                 860
Lys Gly Asp Arg Ala Tyr Lys Tyr Arg Arg Tyr Thr Glu Lys Lys Ile
865                 870                 875                 880
Met Phe His Met Ser Leu Val Leu Asn Thr Gly Lys Gly Glu Ile Lys
                885                 890                 895
Gln Val Gln Phe Asn Lys Ile Ile Asn Gln Arg Ile Ser Ser Ser Asp
            900                 905                 910
Asn Glu Met Arg Val Asn Val Ile Gly Ile Asp Arg Gly Glu Lys Asn
            915                 920                 925
Leu Leu Tyr Tyr Ser Val Val Lys Gln Asn Gly Glu Ile Ile Glu Gln
            930                 935                 940
Ala Ser Leu Asn Glu Ile Asn Gly Val Asn Tyr Arg Asp Lys Leu Ile
945                 950                 955                 960
Glu Arg Glu Lys Glu Arg Leu Lys Asn Arg Gln Ser Trp Lys Pro Val
                965                 970                 975
Val Lys Ile Lys Asp Leu Lys Lys Gly Tyr Ile Ser His Val Ile His
                980                 985                 990
Lys Ile Cys Gln Leu Ile Glu Lys Tyr Ser Ala Ile Val Val Leu Glu
                995                 1000                1005
Asp Leu Asn Met Arg Phe Lys Gln Ile Arg Gly Gly Ile Glu Arg
            1010                1015                1020
Ser Val Tyr Gln Gln Phe Glu Lys Ala Leu Ile Asp Lys Leu Gly
            1025                1030                1035
Tyr Leu Val Phe Lys Asp Asn Arg Asp Leu Arg Ala Pro Gly Gly
            1040                1045                1050
Val Leu Asn Gly Tyr Gln Leu Ser Ala Pro Phe Val Ser Phe Glu
            1055                1060                1065
Lys Met Arg Lys Gln Thr Gly Ile Leu Phe Tyr Thr Gln Ala Glu
            1070                1075                1080
Tyr Thr Ser Lys Thr Asp Pro Ile Thr Gly Phe Arg Lys Asn Val
            1085                1090                1095
Tyr Ile Ser Asn Ser Ala Ser Leu Asp Lys Ile Lys Glu Ala Val
            1100                1105                1110
Lys Lys Phe Asp Ala Ile Gly Trp Asp Gly Lys Glu Gln Ser Tyr
            1115                1120                1125
Phe Phe Lys Tyr Asn Pro Tyr Asn Leu Ala Asp Glu Lys Tyr Lys
            1130                1135                1140
Asn Ser Thr Val Ser Lys Glu Trp Ala Ile Phe Ala Ser Ala Pro
            1145                1150                1155
Arg Ile Arg Arg Gln Lys Gly Glu Asp Gly Tyr Trp Lys Tyr Asp
            1160                1165                1170
Arg Val Lys Val Asn Glu Glu Phe Glu Lys Leu Leu Lys Val Trp
            1175                1180                1185
Asn Phe Val Asn Pro Lys Ala Thr Asp Ile Lys Gln Glu Ile Ile
            1190                1195                1200
Lys Lys Glu Lys Ala Gly Asp Leu Gln Gly Glu Lys Glu Leu Asp
```

|   |   |   |   |   |   |   |   |   |   |
|---|---|---|---|---|---|---|---|---|---|
| | 1205 | | | | 1210 | | | | 1215 |

Gly Arg Leu Arg Asn Phe Trp His Ser Phe Ile Tyr Leu Phe Asn
                1220                    1225                    1230

Leu Val Leu Glu Leu Arg Asn Ser Phe Ser Leu Gln Ile Lys Ile
        1235                    1240                    1245

Lys Ala Gly Glu Val Ile Ala Val Asp Glu Gly Val Asp Phe Ile
    1250                    1255                    1260

Ala Ser Pro Val Lys Pro Phe Phe Thr Thr Pro Asn Pro Tyr Ile
    1265                    1270                    1275

Pro Ser Asn Leu Cys Trp Leu Ala Val Glu Asn Ala Asp Ala Asn
    1280                    1285                    1290

Gly Ala Tyr Asn Ile Ala Arg Lys Gly Val Met Ile Leu Lys Lys
    1295                    1300                    1305

Ile Arg Glu His Ala Lys Lys Asp Pro Glu Phe Lys Lys Leu Pro
    1310                    1315                    1320

Asn Leu Phe Ile Ser Asn Ala Glu Trp Asp Glu Ala Ala Arg Asp
    1325                    1330                    1335

Trp Gly Lys Tyr Ala Gly Thr Thr Ala Leu Asn Leu Asp His Lys
    1340                    1345                    1350

Arg Pro Ala Ala Thr Lys Lys Ala Gly Gln Ala Lys Lys Lys Lys
    1355                    1360                    1365

Gly Ser Tyr Pro Tyr Asp Val Pro Asp Tyr Ala Tyr Pro Tyr Asp
    1370                    1375                    1380

Val Pro Asp Tyr Ala Tyr Pro Tyr Asp Val Pro Asp Tyr Ala
    1385                    1390                    1395

<210> SEQ ID NO 22
<211> LENGTH: 4194
<212> TYPE: DNA
<213> ORGANISM: Artificial Sequence
<220> FEATURE:
<223> OTHER INFORMATION: Synthetic-Parcubacteria bacterium
    GWC2011_GWC2_44_17 (PbCpf1; pY008), including NLS and HA tag

<400> SEQUENCE: 22

| | |
|---|---|
| atggagaaca tcttcgacca gtttatcggc aagtacagcc tgtccaagac cctgagattc | 60 |
| gagctgaagc ccgtgggcaa gacagaggac ttcctgaaga tcaacaaggt gtttgagaag | 120 |
| gatcagacca tcgacgatag ctacaatcag gccaagttct atttttgattc cctgcaccag | 180 |
| aagtttatcg acgccgccct ggcctccgat aagacatccg agctgtcttt ccagaacttt | 240 |
| gccgacgtgc tggagaagca gaataagatc atcctggata agaagagaga gatgggcgcc | 300 |
| ctgaggaagc gcgacaagaa cgccgtgggc atcgataggc tgcagaagga gatcaatgac | 360 |
| gccgaggata tcatccagaa ggagaaggag aagatctaca aggacgtgcg cacactgttc | 420 |
| gataacgagg ccgagtcttg gaaaacctac tatcaggagc gggaggtgga cggcaagaag | 480 |
| atcaccttca gcaaggccga cctgaagcag aagggcgccg attttctgac agccgccggc | 540 |
| atcctgaagg tgctgaagta tgagttcccc gaggagaagg agaaggagtt caggccaag | 600 |
| aaccagccct ccctgttcgt ggaggagaag gagaatcctg ccagaagag gtacatcttc | 660 |
| gactcttttg ataagttcgc cggctatctg accaagtttc agcagacaaa gaagaatctg | 720 |
| tacgcagcag acggcaccag cacagcagtg gccacccgca tcgccgataa cttttatcatc | 780 |
| ttccaccaga ataccaaggt gttccgggac aagtacaaga caatcacac agacctgggc | 840 |
| ttcgatgagg agaacatctt tgagatcgag aggtataaga attgcctgct gcagcgcgag | 900 |

```
atcgagcaca tcaagaatga gaatagctac aacaagatca tcggccggat caataagaag   960
atcaaggagt atcgggacca gaaggccaag gataccaagc tgacaaagtc cgacttccct  1020
ttctttaaga acctggataa gcagatcctg ggcgaggtgg agaaggagaa gcagctgatc  1080
gagaaaaccc gggagaaaac cgaggaggac gtgctgatcg agcggttcaa ggagttcatc  1140
gagaacaatg aggagaggtt caccgccgcc aagaagctga tgaatgcctt ctgtaacggc  1200
gagtttgagt ccgagtacga gggcatctat ctgaagaata aggccatcaa cacaatctcc  1260
cggagatggt tcgtgtctga cagagatttt gagctgaagc tgcctcagca gaagtccaag  1320
aacaagtctg agaagaatga gccaaaggtg aagaagttca tctccatcgc cgagatcaag  1380
aacgccgtgg aggagctgga cggcgatatc tttaaggccg tgttctacga caagaagatc  1440
atcgcccagg gcggctctaa gctggagcag ttcctggtca tctggaagta cgagtttgag  1500
tatctgttcc gggacatcga gagagagaac ggcgagaagc tgctgggcta tgatagctgc  1560
ctgaagatcg ccaagcagct gggcatcttc ccacaggaga aggaggcccg cgagaaggca  1620
accgccgtga tcaagaatta cgccgacgcc ggcctgggca tcttccagat gatgaagtat  1680
tttctctctgg acgataagga tcggaagaac accccccggcc agctgagcac aaatttctac  1740
gccgagtatg acggctacta caaggatttc gagtttatca agtactacaa cgagtttagg  1800
aacttcatca ccaagaagcc tttcgacgag gataagatca gctgaacttt tgagaatggc  1860
gccctgctga gggctggga cgagaacaag gagtacgatt tcatgggcgt gatcctgaag  1920
aaggagggcc gcctgtatct gggcatcatg cacaagaacc accggaagct gtttcagtcc  1980
atgggcaatg ccaagggcga caacgccaat agataccaga gatgatcta taagcagatc  2040
gccgacgcct ctaaggatgt gcccaggctg ctgctgacca gcaagaaggc catggagaag  2100
ttcaagcctt cccaggagat cctgagaatc aagaaggaga aaaccttcaa gcgggagagc  2160
aagaactttt ccctgagaga tctgcacgcc ctgatcgagt actataggaa ctgcatccct  2220
cagtacagca attggtcctt ttatgacttc cagtttcagg ataccggcaa gtaccagaat  2280
atcaaggagt tcacagacga tgtgcagaag tacggctata gatctccttt cgcgacatc  2340
gacgatgagt atatcaatca ggccctgaac gagggcaaga tgtacctgtt cgaggtggtg  2400
aacaaggata tctataacac caagaatggc tccaagaatc tgcacacact gtactttgag  2460
cacatcctgt ctgccgagaa cctgaatgac ccagtgttca gctgtctgg catggccgag  2520
atctttcagc ggcagcccag cgtgaacgaa agagagaaga tcaccacaca gaagaatcag  2580
tgtatcctgg acaagggcga tagagcctac aagtataggc gctacaccga gaagaagatc  2640
atgttccaca tgagcctggt gctgaacaca ggcaagggcg agatcaagca ggtgcagttt  2700
aataagatca tcaaccagag gatcagctcc tctgacaacg agatgagggt gaatgtgatc  2760
ggcatcgatc gcggcgagaa gaacctgctg tactatagcg tggtgaagca gaatggcgag  2820
atcatcgagc aggcctccct gaacgagatc aatggcgtga actaccggga caagctgatc  2880
gagagggaga aggagcgcct gaagaaccgg cagagctgga gcctgtggt gaagatcaag  2940
gatctgaaga agggctacat ctcccacgtg atccacaaga tctgccagct gatcgagaag  3000
tattctgcca tcgtggtgct ggaggacctg aatatgagat tcaagcagat caggggagga  3060
atcgagcgga gcgtgtacca gcagttcgag aagggcctga tcgataagct gggctatctg  3120
gtgtttaagg acaacaggga tctgagggca ccaggaggcg tgctgaatgg ctaccagctg  3180
tctgcccct ttgtgagctt cgagaagatg cgcaagcaga ccggcatcct gttctacaca  3240
caggccgagt ataccagcaa gacagaccca atcaccggct ttcggaagaa cgtgtatatc  3300
```

-continued

```
tctaatagcg cctccctgga taagatcaag gaggccgtga agaagttcga cgccatcggc    3360
tgggatggca aggagcagtc ttacttcttt aagtacaacc cttacaacct ggccgacgag    3420
aagtataaga actctaccgt gagcaaggag tgggccatct tgccagcgc cccaagaatc     3480 cggagacaga agggcgagga cggctactgg aagtatgata gggtgaaagt gaatgaggag    3540
ttcgagaagc tgctgaaggt ctggaatttt gtgaacccaa aggccacaga tatcaagcag    3600
gagatcatca agaaggagaa ggcaggcgac ctgcagggag agaaggagct ggatggccgg    3660
ctgagaaact tttggcactc tttcatctac ctgtttaacc tggtgctgga gctgcgcaat    3720
tctttcagcc tgcagatcaa gatcaaggca ggagaagtga tcgcagtgga cgagggcgtg    3780
gacttcatcg ccagcccagt gaagcccttc tttaccacac ccaacccttta catcccctcc   3840 aacctgtgct ggctggccgt ggagaatgca acgcaaacg gagcctataa atcgccagg     3900 aagggcgtga tgatcctgaa gaagatccgc gagcacgcca agaaggaccc cgagttcaag    3960
aagctgccaa acctgtttat cagcaatgca gagtgggacg aggcagcccg ggattggggc    4020
aagtacgcag gcaccacagc cctgaacctg gaccacaaaa ggccggcggc cacgaaaaag    4080
gccggccagg caaaaaagaa aaagggatcc tacccatacg atgttccaga ttacgcttat    4140
ccctacgacg tgcctgatta tgcataccca tatgatgtcc ccgactatgc ctaa          4194
```

<210> SEQ ID NO 23
<211> LENGTH: 1295
<212> TYPE: PRT
<213> ORGANISM: Artificial Sequence
<220> FEATURE:
<223> OTHER INFORMATION: Synthetic-Smithella sp. SC_K08D17 (SsCpf1; pY009), including NLS and HA tag

<400> SEQUENCE: 23

```
Met Gln Thr Leu Phe Glu Asn Phe Thr Asn Gln Tyr Pro Val Ser Lys
1               5                   10                  15

Thr Leu Arg Phe Glu Leu Ile Pro Gln Gly Lys Thr Lys Asp Phe Ile
            20                  25                  30

Glu Gln Lys Gly Leu Leu Lys Lys Asp Glu Asp Arg Ala Glu Lys Tyr
        35                  40                  45

Lys Lys Val Lys Asn Ile Ile Asp Glu Tyr His Lys Asp Phe Ile Glu
    50                  55                  60

Lys Ser Leu Asn Gly Leu Lys Leu Asp Gly Leu Glu Lys Tyr Lys Thr
65                  70                  75                  80

Leu Tyr Leu Lys Gln Glu Lys Asp Asp Lys Asp Lys Lys Ala Phe Asp
                85                  90                  95

Lys Glu Lys Glu Asn Leu Arg Lys Gln Ile Ala Asn Ala Phe Arg Asn
            100                 105                 110

Asn Glu Lys Phe Lys Thr Leu Phe Ala Lys Glu Leu Ile Lys Asn Asp
        115                 120                 125

Leu Met Ser Phe Ala Cys Glu Glu Asp Lys Lys Asn Val Lys Glu Phe
    130                 135                 140

Glu Ala Phe Thr Thr Tyr Phe Thr Gly Phe His Gln Asn Arg Ala Asn
145                 150                 155                 160

Met Tyr Val Ala Asp Glu Lys Arg Thr Ala Ile Ala Ser Arg Leu Ile
                165                 170                 175

His Glu Asn Leu Pro Lys Phe Ile Asp Asn Ile Lys Ile Phe Glu Lys
            180                 185                 190

Met Lys Lys Glu Ala Pro Glu Leu Leu Ser Pro Phe Asn Gln Thr Leu
```

-continued

```
            195                 200                 205
Lys Asp Met Lys Asp Val Ile Lys Gly Thr Thr Leu Glu Glu Ile Phe
210                 215                 220

Ser Leu Asp Tyr Phe Asn Lys Thr Leu Thr Gln Ser Gly Ile Asp Ile
225                 230                 235                 240

Tyr Asn Ser Val Ile Gly Gly Arg Thr Pro Glu Glu Gly Lys Thr Lys
                245                 250                 255

Ile Lys Gly Leu Asn Glu Tyr Ile Asn Thr Asp Phe Asn Gln Lys Gln
                260                 265                 270

Thr Asp Lys Lys Lys Arg Gln Pro Lys Phe Lys Gln Leu Tyr Lys Gln
                275                 280                 285

Ile Leu Ser Asp Arg Gln Ser Leu Ser Phe Ile Ala Glu Ala Phe Lys
290                 295                 300

Asn Asp Thr Glu Ile Leu Glu Ala Ile Glu Lys Phe Tyr Val Asn Glu
305                 310                 315                 320

Leu Leu His Phe Ser Asn Glu Gly Lys Ser Thr Asn Val Leu Asp Ala
                325                 330                 335

Ile Lys Asn Ala Val Ser Asn Leu Glu Ser Phe Asn Leu Thr Lys Met
                340                 345                 350

Tyr Phe Arg Ser Gly Ala Ser Leu Thr Asp Val Ser Arg Lys Val Phe
                355                 360                 365

Gly Glu Trp Ser Ile Ile Asn Arg Ala Leu Asp Asn Tyr Tyr Ala Thr
370                 375                 380

Thr Tyr Pro Ile Lys Pro Arg Glu Lys Ser Glu Lys Tyr Glu Glu Arg
385                 390                 395                 400

Lys Glu Lys Trp Leu Lys Gln Asp Phe Asn Val Ser Leu Ile Gln Thr
                405                 410                 415

Ala Ile Asp Glu Tyr Asp Asn Glu Thr Val Lys Gly Lys Asn Ser Gly
                420                 425                 430

Lys Val Ile Ala Asp Tyr Phe Ala Lys Phe Cys Asp Asp Lys Glu Thr
                435                 440                 445

Asp Leu Ile Gln Lys Val Asn Glu Gly Tyr Ile Ala Val Lys Asp Leu
450                 455                 460

Leu Asn Thr Pro Cys Pro Glu Asn Glu Lys Leu Gly Ser Asn Lys Asp
465                 470                 475                 480

Gln Val Lys Gln Ile Lys Ala Phe Met Asp Ser Ile Met Asp Ile Met
                485                 490                 495

His Phe Val Arg Pro Leu Ser Leu Lys Asp Thr Asp Lys Glu Lys Asp
                500                 505                 510

Glu Thr Phe Tyr Ser Leu Phe Thr Pro Leu Tyr Asp His Leu Thr Gln
                515                 520                 525

Thr Ile Ala Leu Tyr Asn Lys Val Arg Asn Tyr Leu Thr Gln Lys Pro
530                 535                 540

Tyr Ser Thr Glu Lys Ile Lys Leu Asn Phe Glu Asn Ser Thr Leu Leu
545                 550                 555                 560

Gly Gly Trp Asp Leu Asn Lys Glu Thr Asp Asn Thr Ala Ile Ile Leu
                565                 570                 575

Arg Lys Asp Asn Leu Tyr Tyr Leu Gly Ile Met Asp Lys Arg His Asn
                580                 585                 590

Arg Ile Phe Arg Asn Val Pro Lys Ala Asp Lys Lys Asp Phe Cys Tyr
                595                 600                 605

Glu Lys Met Val Tyr Lys Leu Leu Pro Gly Ala Asn Lys Met Leu Pro
610                 615                 620
```

```
Lys Val Phe Phe Ser Gln Ser Arg Ile Gln Glu Phe Thr Pro Ser Ala
625                 630                 635                 640

Lys Leu Leu Glu Asn Tyr Ala Asn Glu Thr His Lys Lys Gly Asp Asn
                645                 650                 655

Phe Asn Leu Asn His Cys His Lys Leu Ile Asp Phe Lys Asp Ser
                660                 665                 670

Ile Asn Lys His Glu Asp Trp Lys Asn Phe Asp Phe Arg Phe Ser Ala
                675                 680                 685

Thr Ser Thr Tyr Ala Asp Leu Ser Gly Phe Tyr His Glu Val Glu His
690                 695                 700

Gln Gly Tyr Lys Ile Ser Phe Gln Ser Val Ala Asp Ser Phe Ile Asp
705                 710                 715                 720

Asp Leu Val Asn Glu Gly Lys Leu Tyr Leu Phe Gln Ile Tyr Asn Lys
                725                 730                 735

Asp Phe Ser Pro Phe Ser Lys Gly Lys Pro Asn Leu His Thr Leu Tyr
                740                 745                 750

Trp Lys Met Leu Phe Asp Glu Asn Asn Leu Lys Asp Val Val Tyr Lys
                755                 760                 765

Leu Asn Gly Glu Ala Glu Val Phe Tyr Arg Lys Lys Ser Ile Ala Glu
770                 775                 780

Lys Asn Thr Thr Ile His Lys Ala Asn Glu Ser Ile Ile Asn Lys Asn
785                 790                 795                 800

Pro Asp Asn Pro Lys Ala Thr Ser Thr Phe Asn Tyr Asp Ile Val Lys
                805                 810                 815

Asp Lys Arg Tyr Thr Ile Asp Lys Phe Gln Phe His Ile Pro Ile Thr
                820                 825                 830

Met Asn Phe Lys Ala Glu Gly Ile Phe Asn Met Asn Gln Arg Val Asn
                835                 840                 845

Gln Phe Leu Lys Ala Asn Pro Asp Ile Asn Ile Ile Gly Ile Asp Arg
850                 855                 860

Gly Glu Arg His Leu Leu Tyr Tyr Ala Leu Ile Asn Gln Lys Gly Lys
865                 870                 875                 880

Ile Leu Lys Gln Asp Thr Leu Asn Val Ile Ala Asn Glu Lys Gln Lys
                885                 890                 895

Val Asp Tyr His Asn Leu Leu Asp Lys Lys Glu Gly Asp Arg Ala Thr
                900                 905                 910

Ala Arg Gln Glu Trp Gly Val Ile Glu Thr Ile Lys Glu Leu Lys Glu
                915                 920                 925

Gly Tyr Leu Ser Gln Val Ile His Lys Leu Thr Asp Leu Met Ile Glu
                930                 935                 940

Asn Asn Ala Ile Ile Val Met Glu Asp Leu Asn Phe Gly Phe Lys Arg
945                 950                 955                 960

Gly Arg Gln Lys Val Glu Lys Gln Val Tyr Gln Lys Phe Glu Lys Met
                965                 970                 975

Leu Ile Asp Lys Leu Asn Tyr Leu Val Asp Lys Asn Lys Lys Ala Asn
                980                 985                 990

Glu Leu Gly Gly Leu Leu Asn Ala Phe Gln Leu Ala Asn Lys Phe Glu
                995                 1000                1005

Ser Phe Gln Lys Met Gly Lys Gln Asn Gly Phe Ile Phe Tyr Val
                1010                1015                1020

Pro Ala Trp Asn Thr Ser Lys Thr Asp Pro Ala Thr Gly Phe Ile
                1025                1030                1035
```

```
Asp Phe Leu Lys Pro Arg Tyr Glu Asn Leu Asn Gln Ala Lys Asp
    1040                1045                1050

Phe Phe Glu Lys Phe Asp Ser Ile Arg Leu Asn Ser Lys Ala Asp
    1055                1060                1065

Tyr Phe Glu Phe Ala Phe Asp Phe Lys Asn Phe Thr Glu Lys Ala
    1070                1075                1080

Asp Gly Gly Arg Thr Lys Trp Thr Val Cys Thr Thr Asn Glu Asp
    1085                1090                1095

Arg Tyr Ala Trp Asn Arg Ala Leu Asn Asn Asn Arg Gly Ser Gln
    1100                1105                1110

Glu Lys Tyr Asp Ile Thr Ala Glu Leu Lys Ser Leu Phe Asp Gly
    1115                1120                1125

Lys Val Asp Tyr Lys Ser Gly Lys Asp Leu Lys Gln Gln Ile Ala
    1130                1135                1140

Ser Gln Glu Ser Ala Asp Phe Phe Lys Ala Leu Met Lys Asn Leu
    1145                1150                1155

Ser Ile Thr Leu Ser Leu Arg His Asn Asn Gly Glu Lys Gly Asp
    1160                1165                1170

Asn Glu Gln Asp Tyr Ile Leu Ser Pro Val Ala Asp Ser Lys Gly
    1175                1180                1185

Arg Phe Phe Asp Ser Arg Lys Ala Asp Asp Met Pro Lys Asn
    1190                1195                1200

Ala Asp Ala Asn Gly Ala Tyr His Ile Ala Leu Lys Gly Leu Trp
    1205                1210                1215

Cys Leu Glu Gln Ile Ser Lys Thr Asp Asp Leu Lys Lys Val Lys
    1220                1225                1230

Leu Ala Ile Ser Asn Lys Glu Trp Leu Glu Phe Val Gln Thr Leu
    1235                1240                1245

Lys Gly Lys Arg Pro Ala Ala Thr Lys Lys Ala Gly Gln Ala Lys
    1250                1255                1260

Lys Lys Lys Gly Ser Tyr Pro Tyr Asp Val Pro Asp Tyr Ala Tyr
    1265                1270                1275

Pro Tyr Asp Val Pro Asp Tyr Ala Tyr Pro Tyr Asp Val Pro Asp
    1280                1285                1290

Tyr Ala
    1295

<210> SEQ ID NO 24
<211> LENGTH: 3888
<212> TYPE: DNA
<213> ORGANISM: Artificial Sequence
<220> FEATURE:
<223> OTHER INFORMATION: Synthetic-Smithella sp. SC_K08D17 (SsCpf1;
      pY009), including NLS and HA tag

<400> SEQUENCE: 24
atgcagaccc tgtttgagaa cttcacaaat cagtacccag tgtccaagac cctgcgcttt      60
gagctgatcc cccagggcaa gacaaaggac ttcatcgagc agaagggcct gctgaagaag     120
gatgaggacc gggccgagaa gtataagaag gtgaagaaca tcatcgatga gtaccacaag     180
gacttcatcg agaagtctct gaatggcctg aagctggacg cctggagaa gtacaagacc     240 ctgtatctga gcaggagaa ggacgataag gataagaagg cctttgacaa ggagaaggag     300
aacctgcgca gcagatcgc caatgccttc cggaacaatg agaagtttaa gacactgttc     360
gccaaggagc tgatcaagaa cgatctgatg tctttcgcct gcgaggagga caagaagaat     420
```

```
gtgaaggagt ttgaggcctt caccacatac ttcaccggct tccaccagaa ccgcgccaat    480
atgtacgtgg ccgatgagaa gagaacagcc atcgccagca ggctgatcca cgagaacctg    540
ccaaagttta tcgacaatat caagatcttc gagaagatga agaaggaggc ccccgagctg    600
ctgtctcctt tcaaccagac cctgaaggat atgaaggacg tgatcaaggg caccacactg    660
gaggagatct ttagcctgga ttatttcaac aagaccctga cacagagcgg catcgacatc    720
tacaattccg tgatcggcgg cagaaccccct gaggagggca agacaaagat caagggcctg    780
aacgagtaca tcaataccga cttcaaccag aagcagacag acaagaagaa gcggcagcca    840
aagttcaagc agctgtataa gcagatcctg agcgataggc agagcctgtc ctttatcgcc    900
gaggccttca gaacgacac cgagatcctg gaggccatcg agaagttta cgtgaatgag    960
ctgctgcact tcagcaatga gggcaagtcc acaaacgtgc tggacgccat caagaatgcc   1020
gtgtctaacc tggagagctt taacctgacc aagatgtatt tccgctccgg cgcctctctg   1080
acagacgtga gccggaaggt gtttggcgag tggagcatca tcaatagagc cctggacaac   1140
tactatgcca ccacatatcc aatcaagccc agagagaagt ctgagaagta cgaggagagg   1200
aaggagaagt ggctgaagca ggacttcaac gtgagcctga tccagaccgc catcgatgag   1260
tacgacaacg agacagtgaa gggcaagaac agcggcaaag tgatcgccga ttattttgcc   1320
aagttctgcg acgataagga gacagacctg atccagaagg tgaacgaggg ctacatcgcc   1380
gtgaaggatc tgctgaatac ccctgtcct gagaacgaga agctgggcag caataaggac   1440
caggtgaagc agatcaaggc ctttatggat tctatcatgg acatcatgca cttcgtgcgc   1500
cccctgagcc tgaaggatac cgacaaggag aaggatgaga cattctactc cctgttcaca   1560
cctctgtacg accacctgac ccagacaatc gccctgtata caaggtgcg gaactatctg   1620
acccagaagc cttacagcac agagaagatc aagctgaact tcgagaacag cacctgctg   1680
ggcggctggg atctgaataa ggagacagac aacacagcca tcatcctgag gaaggataac   1740
ctgtactatc tgggcatcat ggacaagagg cacaatcgca tctttcggaa cgtgcccaag   1800
gccgataaga aggacttctg ctacgagaag atggtgtata gctgctgcc tggcgccaac   1860
aagatgctgc caaaggtgtt cttttctcag agcagaatcc aggagtttac cccttccgcc   1920
aagctgctgg agaactacgc caatgagaca cacaagaagg gcgataattt caacctgaat   1980
cactgtcaca gctgatcga tttctttaag gactctatca acaagcacga ggattggaag   2040
aatttcgact ttaggttcag cgccacctcc acctacgccg acctgagcgg cttttaccac   2100
gaggtggagc accagggcta caagatctct tttcagagcg tggccgattc cttcatcgac   2160
gatctggtga cgagggcaa gctgtacctg ttccagatct ataataagga cttttcccca   2220
ttctctaagg gcaagcccaa cctgcacacc ctgtactgga gatgctgtt tgatgagaac   2280
aatctgaagg acgtggtgta aagctgaat ggcgaggccg aggtgttcta ccgcaagaag   2340
agcattgccg agaagaacac cacaatccac aaggccaatg agtccatcat caacaagaat   2400
cctgataacc caaaggccac cagcaccttc aactatgata tcgtgaagga caagagatac   2460
accatcgaca gtttcagtt ccacatccca atcacaatga actttaaggc cgagggcatc   2520
ttcaacatga atcagagggt gaatcagttc ctgaaggcca tcccgatat caacatcatc   2580
ggcatcgaca gaggcgagag gcacctgctg tactatgccc tgatcaacca gaagggcaag   2640
atcctgaagc aggataccct gaatgtgatc gccaacgaga agcagaaggt ggactaccac   2700
aatctgctgg ataagaagga gggcgaccgc gcaaccgcaa gcaggagtg gggcgtgatc   2760
gagacaatca aggagctgaa ggagggctat ctgtcccagg tcatccacaa gctgaccgat   2820
```

-continued

```
ctgatgatcg agaacaatgc catcatcgtg atggaggacc tgaactttgg cttcaagcgg    2880
ggcagacaga aggtggagaa gcaggtgtat cagaagtttg agaagatgct gatcgataag    2940
ctgaattacc tggtggacaa gaataagaag gcaaacgagc tgggaggcct gctgaacgca    3000
ttccagctgg ccaataagtt tgagtccttc cagaagatgg gcaagcagaa cggctttatc    3060
ttctacgtgc ccgcctggaa tacctctaag acagatcctg ccaccggctt tatcgacttc    3120
ctgaagcccc gctatgagaa cctgaatcag gccaaggatt ctttgagaa gtttgactct    3180 atccggctga acagcaaggc cgattacttt gagttcgcct ttgacttcaa gaatttcacc    3240
gagaaggccg atggcggcag aaccaagtgg acagtgtgca ccacaaacga ggacagatat    3300
gcctggaata gggccctgaa caataacagg ggcagccagg agaagtacga catcacagcc    3360
gagctgaagt ccctgttcga tgcaaggtg gactataagt ctggcaagga tctgaagcag    3420
cagatcgcca gccaggagtc cgccgacttc tttaaggccc tgatgaagaa cctgtccatc    3480
accctgtctc tgagacacaa taacggcgag aagggcgata tgagcagga ctacatcctg    3540 tcccctgtgg ccgattctaa gggccgcttc tttgactccc ggaaggccga cgatgacatg    3600
ccaaagaatg ccgacgccaa cggcgcctat cacatcgccc tgaagggcct gtggtgtctg    3660
gagcagatca gcaagaccga tgacctgaag aaggtgaagc tggccatctc caacaaggag    3720
tggctggagt tcgtgcagac actgaagggc aaaaggccgg cggccacgaa aaaggccggc    3780
caggcaaaaa agaaaaaggg atcctaccca tacgatgttc cagattacgc ttatccctac    3840
gacgtgcctg attatgcata cccatatgat gtccccgact atgcctaa                3888
```

<210> SEQ ID NO 25
<211> LENGTH: 1352
<212> TYPE: PRT
<213> ORGANISM: Artificial Sequence
<220> FEATURE:
<223> OTHER INFORMATION: Synthetic-Acidaminococcus sp. BV3L6 (AsCpf1; pY010), including NLS and HA tag

<400> SEQUENCE: 25

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
                20                  25                  30

Glu Gln Gly Phe Ile Glu Glu Asp Lys Ala Arg Asn Asp His Tyr Lys
            35                  40                  45

Glu Leu Lys Pro Ile Ile Asp Arg Ile Tyr Lys Thr Tyr Ala Asp Gln
        50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
```

```
            165                 170                 175
Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
            195                 200                 205

Thr Arg Leu Ile Thr Ala Val Pro Ser Leu Arg Glu His Phe Glu Asn
            210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                    245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
            275                 280                 285

Asp Glu Thr Ala His Ile Ile Ala Ser Leu Pro His Arg Phe Ile Pro
            290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
                    325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
            435                 440                 445

Ala Leu Asp Gln Pro Leu Pro Thr Thr Leu Lys Lys Gln Glu Glu Lys
            450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                    485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
            515                 520                 525

Glu Lys Phe Lys Leu Asn Phe Gln Met Pro Thr Leu Ala Ser Gly Trp
            530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                    565                 570                 575

Ala Leu Ser Phe Glu Pro Thr Glu Lys Thr Ser Glu Gly Phe Asp Lys
                580                 585                 590
```

```
Met Tyr Tyr Asp Tyr Phe Pro Asp Ala Ala Lys Met Ile Pro Lys Cys
        595                 600                 605
Ser Thr Gln Leu Lys Ala Val Thr Ala His Phe Gln Thr His Thr Thr
610                 615                 620
Pro Ile Leu Leu Ser Asn Asn Phe Ile Glu Pro Leu Glu Ile Thr Lys
625                 630                 635                 640
Glu Ile Tyr Asp Leu Asn Asn Pro Lys Glu Pro Lys Lys Phe Gln
                645                 650                 655
Thr Ala Tyr Ala Lys Lys Thr Gly Asp Gln Lys Gly Tyr Arg Glu Ala
                660                 665                 670
Leu Cys Lys Trp Ile Asp Phe Thr Arg Asp Phe Leu Ser Lys Tyr Thr
                675                 680                 685
Lys Thr Thr Ser Ile Asp Leu Ser Ser Leu Arg Pro Ser Ser Gln Tyr
        690                 695                 700
Lys Asp Leu Gly Glu Tyr Tyr Ala Glu Leu Asn Pro Leu Leu Tyr His
705                 710                 715                 720
Ile Ser Phe Gln Arg Ile Ala Glu Lys Glu Ile Met Asp Ala Val Glu
                725                 730                 735
Thr Gly Lys Leu Tyr Leu Phe Gln Ile Tyr Asn Lys Asp Phe Ala Lys
                740                 745                 750
Gly His His Gly Lys Pro Asn Leu His Thr Leu Tyr Trp Thr Gly Leu
                755                 760                 765
Phe Ser Pro Glu Asn Leu Ala Lys Thr Ser Ile Lys Leu Asn Gly Gln
        770                 775                 780
Ala Glu Leu Phe Tyr Arg Pro Lys Ser Arg Met Lys Arg Met Ala His
785                 790                 795                 800
Arg Leu Gly Glu Lys Met Leu Asn Lys Lys Leu Lys Asp Gln Lys Thr
                805                 810                 815
Pro Ile Pro Asp Thr Leu Tyr Gln Glu Leu Tyr Asp Tyr Val Asn His
                820                 825                 830
Arg Leu Ser His Asp Leu Ser Asp Glu Ala Arg Ala Leu Leu Pro Asn
        835                 840                 845
Val Ile Thr Lys Glu Val Ser His Glu Ile Ile Lys Asp Arg Arg Phe
850                 855                 860
Thr Ser Asp Lys Phe Phe Phe His Val Pro Ile Thr Leu Asn Tyr Gln
865                 870                 875                 880
Ala Ala Asn Ser Pro Ser Lys Phe Asn Gln Arg Val Asn Ala Tyr Leu
                885                 890                 895
Lys Glu His Pro Glu Thr Pro Ile Ile Gly Ile Asp Arg Gly Glu Arg
                900                 905                 910
Asn Leu Ile Tyr Ile Thr Val Ile Asp Ser Thr Gly Lys Ile Leu Glu
                915                 920                 925
Gln Arg Ser Leu Asn Thr Ile Gln Gln Phe Asp Tyr Gln Lys Lys Leu
930                 935                 940
Asp Asn Arg Glu Lys Glu Arg Val Ala Ala Arg Gln Ala Trp Ser Val
945                 950                 955                 960
Val Gly Thr Ile Lys Asp Leu Lys Gln Gly Tyr Leu Ser Gln Val Ile
                965                 970                 975
His Glu Ile Val Asp Leu Met Ile His Tyr Gln Ala Val Val Val Leu
                980                 985                 990
Glu Asn Leu Asn Phe Gly Phe Lys Ser Lys Arg Thr Gly Ile Ala Glu
                995                 1000                1005
```

| Lys | Ala | Val | Tyr | Gln | Gln | Phe | Glu | Lys | Met | Leu | Ile | Asp | Lys | Leu |
| 1010 | | | | | 1015 | | | | 1020 | | | | | |

Asn Cys Leu Val Leu Lys Asp Tyr Pro Ala Glu Lys Val Gly Gly
1025 1030 1035

Val Leu Asn Pro Tyr Gln Leu Thr Asp Gln Phe Thr Ser Phe Ala
1040 1045 1050

Lys Met Gly Thr Gln Ser Gly Phe Leu Phe Tyr Val Pro Ala Pro
1055 1060 1065

Tyr Thr Ser Lys Ile Asp Pro Leu Thr Gly Phe Val Asp Pro Phe
1070 1075 1080

Val Trp Lys Thr Ile Lys Asn His Glu Ser Arg Lys His Phe Leu
1085 1090 1095

Glu Gly Phe Asp Phe Leu His Tyr Asp Val Lys Thr Gly Asp Phe
1100 1105 1110

Ile Leu His Phe Lys Met Asn Arg Asn Leu Ser Phe Gln Arg Gly
1115 1120 1125

Leu Pro Gly Phe Met Pro Ala Trp Asp Ile Val Phe Glu Lys Asn
1130 1135 1140

Glu Thr Gln Phe Asp Ala Lys Gly Thr Pro Phe Ile Ala Gly Lys
1145 1150 1155

Arg Ile Val Pro Val Ile Glu Asn His Arg Phe Thr Gly Arg Tyr
1160 1165 1170

Arg Asp Leu Tyr Pro Ala Asn Glu Leu Ile Ala Leu Leu Glu Glu
1175 1180 1185

Lys Gly Ile Val Phe Arg Asp Gly Ser Asn Ile Leu Pro Lys Leu
1190 1195 1200

Leu Glu Asn Asp Asp Ser His Ala Ile Asp Thr Met Val Ala Leu
1205 1210 1215

Ile Arg Ser Val Leu Gln Met Arg Asn Ser Asn Ala Ala Thr Gly
1220 1225 1230

Glu Asp Tyr Ile Asn Ser Pro Val Arg Asp Leu Asn Gly Val Cys
1235 1240 1245

Phe Asp Ser Arg Phe Gln Asn Pro Glu Trp Pro Met Asp Ala Asp
1250 1255 1260

Ala Asn Gly Ala Tyr His Ile Ala Leu Lys Gly Gln Leu Leu Leu
1265 1270 1275

Asn His Leu Lys Glu Ser Lys Asp Leu Lys Leu Gln Asn Gly Ile
1280 1285 1290

Ser Asn Gln Asp Trp Leu Ala Tyr Ile Gln Glu Leu Arg Asn Lys
1295 1300 1305

Arg Pro Ala Ala Thr Lys Lys Ala Gly Gln Ala Lys Lys Lys Lys
1310 1315 1320

Gly Ser Tyr Pro Tyr Asp Val Pro Asp Tyr Ala Tyr Pro Tyr Asp
1325 1330 1335

Val Pro Asp Tyr Ala Tyr Pro Tyr Asp Val Pro Asp Tyr Ala
1340 1345 1350

<210> SEQ ID NO 26
<211> LENGTH: 4059
<212> TYPE: DNA
<213> ORGANISM: Artificial Sequence
<220> FEATURE:
<223> OTHER INFORMATION: Synthetic-Acidaminococcus sp. BV3L6 (AsCpf1;
      pY010), including NLS and HA tag

<400> SEQUENCE: 26

```
atgacacagt tcgagggctt taccaacctg tatcaggtga gcaagacact gcggtttgag      60
ctgatcccac agggcaagac cctgaagcac atccaggagc agggcttcat cgaggaggac     120
aaggcccgca atgatcacta caaggagctg aagcccatca tcgatcggat ctacaagacc     180
tatgccgacc agtgcctgca gctggtgcag ctggattggg agaacctgag cgccgccatc     240
gactcctata gaaaggagaa aaccgaggag acaaggaacg ccctgatcga ggagcaggcc     300
acatatcgca atgccatcca cgactacttc atcggccgga cagacaacct gaccgatgcc     360
atcaataaga gacacgccga gatctacaag ggcctgttca aggccgagct gtttaatggc     420
aaggtgctga agcagctggg caccgtgacc acaaccgagc acgagaacgc cctgctgcgg     480
agcttcgaca gtttacaac ctacttctcc ggcttttatg agaacaggaa gaacgtgttc      540
agcgccgagg atatcagcac agccatccca caccgcatcg tgcaggacaa cttccccaag     600
tttaaggaga attgtcacat cttcacacgc ctgatcaccg ccgtgcccag cctgcgggag     660
cactttgaga cgtgaagaa ggccatcggc atcttcgtga gcacctccat cgaggaggtg      720
ttttccttcc cttttttataa ccagctgctg acacagaccc agatcgacct gtataaccag    780
ctgctgggag gaatctctcg ggaggcaggc accgagaaga tcaagggcct gaacgaggtg     840
ctgaatctgg ccatccagaa gaatgatgag acagcccaca tcatcgcctc cctgccacac     900
agattcatcc ccctgtttaa gcagatcctg tccgatagga acaccctgtc tttcatcctg     960
gaggagttta gagcgacga ggaagtgatc cagtccttct gcaagtacaa gacactgctg    1020
agaaacgaga cgtgctggga gacagccgag gccctgttta cgagctgaa cagcatcgac     1080 ctgacacaca tcttcatcag ccacaagaag ctggagacaa tcagcagcgc cctgtgcgac    1140
cactgggata cactgaggaa tgccctgtat gagcggagaa tctccgagct gacaggcaag    1200
atcaccaagt ctgccaagga aaggtgcag cgcagcctga gcacgagga tatcaacctg      1260 caggagatca tctctgccgc aggcaaggag ctgagcgagg ccttcaagca gaaaaccagc    1320
gagatcctgt cccacgcaca cgccgccctg gatcagccac tgcctacaac cctgaagaag    1380
caggaggaga aggagatcct gaagtctcag ctggacagcc tgctgggcct gtaccacctg    1440
ctggactggt ttgccgtgga tgagtccaac gaggtggacc ccgagttctc tgcccggctg    1500
accggcatca agctggagat ggagccttct ctgagcttct acaacaaggc cagaaattat    1560
gccaccaaga agccctactc cgtggagaag ttcaagctga actttcagat gcctacactg    1620
gcctctggct gggacgtgaa taaggagaag aacaatggcg ccatcctgtt tgtgaagaac    1680
ggcctgtact atctgggcat catgccaaag cagaagggca ggtataaggc cctgagcttc    1740
gagcccacag agaaaaccag cgagggcttt gataagatgt actatgacta cttccctgat    1800
gccgccaaga tgatcccaaa gtgcagcacc cagctgaagg ccgtgacagc ccactttcag    1860
acccacacaa ccccatcct gctgtccaac aattttcatcg agcctctgga tcacaaag      1920 gagatctacg acctgaacaa tcctgagaag gagccaaaga gtttcagac agcctacgcc    1980 aagaaaaccg gcgaccagaa gggctacaga gaggccctgt gcaagtggat cgacttcaca    2040
agggattttc tgtccaagta taccaagaca acctctatcg atctgtctag cctgcggcca    2100
tcctctcagt ataaggacct gggcgagtac tatgccgagc tgaatcccct gctgtaccac    2160
atcagcttcc agagaatcgc cgagaaggag atcatggatg ccgtggagac aggcaagctg    2220
tacctgttcc agatctataa caaggacttt gccaagggcc accacggcaa gcctaatctg    2280
cacacactgt attggaccgg cctgttttct ccagagaacc tggccaagac aagcatcaag    2340
```

```
ctgaatggcc aggccgagct gttctaccgc cctaagtcca ggatgaagag gatggcacac    2400
cggctgggag agaagatgct gaacaagaag ctgaaggatc agaaaacccc aatccccgac    2460
accctgtacc aggagctgta cgactatgtg aatcacagac tgtcccacga cctgtctgat    2520
gaggccaggg ccctgctgcc caacgtgatc accaaggagg tgtctcacga gatcatcaag    2580
gataggcgct ttaccagcga caagttcttt ttccacgtgc ctatcacact gaactatcag    2640
gccgccaatt ccccatctaa gttcaaccag agggtgaatg cctacctgaa ggagcacccc    2700
gagacaccta tcatcggcat cgatcggggc gagagaaacc tgatctatat cacagtgatc    2760
gactccaccg gcaagatcct ggagcagcgg agcctgaaca ccatccagca gtttgattac    2820
cagaagaagc tggacaacag ggagaaggag agggtggcag caaggcaggc ctggtctgtg    2880
gtgggcacaa tcaaggatct gaagcagggc tatctgagcc aggtcatcca cgagatcgtg    2940
gacctgatga tccactacca ggccgtggtg gtgctggaga acctgaattt cggctttaag    3000
agcaagagga ccggcatcgc cgagaaggcc gtgtaccagc agttcgagaa gatgctgatc    3060
gataagctga attgcctggt gctgaaggac tatccagcag agaaagtggg aggcgtgctg    3120
aacccatacc agctgacaga ccagttcacc tcctttgcca agatgggcac ccagtctggc    3180
ttcctgtttt acgtgcctgc cccatataca tctaagatcg atcccctgac cggcttcgtg    3240 gacccctttcg tgtggaaaac catcaagaat cacgagagcc gcaagcactt cctggagggc    3300
ttcgactttc tgcactacga cgtgaaaacc ggcgacttca cctgcacctt taagatgaac    3360
agaaatctgt ccttccagag gggcctgccc ggctttatgc ctgcatggga tatcgtgttc    3420
gagaagaacg agacacagtt tgacgccaag ggcacccctt tcatcgccgg caagagaatc    3480
gtgccagtga tcgagaatca cagattcacc ggcagatacc gggacctgta tcctgccaac    3540
gagctgatcg ccctgctgga ggagaagggc atcgtgttca gggatggctc caacatcctg    3600
ccaaagctgc tggagaatga cgattctcac gccatcgaca ccatggtggc cctgatccgc    3660
agcgtgctgc agatgcggaa ctccaatgcc gccacaggcg aggactatat caacagcccc    3720
gtgcgcgatc tgaatggcgt gtgcttcgac tcccggtttc agaacccaga gtggcccatg    3780
gacgccgatg ccaatggcgc ctaccacatc gccctgaagg ccagctgct gctgaatcac    3840 ctgaaggaga gcaaggatct gaagctgcag aacggcatct ccaatcagga ctggctggcc    3900
tacatccagg agctgcgcaa caaaaggccg gcggccacga aaaaggccgg ccaggcaaaa    3960
aagaaaaagg atcctaccc atacgatgtt ccagattacg cttatcccta cgacgtgcct    4020
gattatgcat acccatatga tgtccccgac tatgcctaa                          4059
```

<210> SEQ ID NO 27
<211> LENGTH: 1251
<212> TYPE: PRT
<213> ORGANISM: Artificial Sequence
<220> FEATURE:
<223> OTHER INFORMATION: Synthetic-Lachnospiraceae bacterium MA2020
      (Lb2Cpf1; pY011), including NLS and HA tag

<400> SEQUENCE: 27

```
Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
            20                  25                  30

Asn Asn Ile Leu Glu Ser Asp Val Lys Arg Lys Gln Asn Tyr Glu His
        35                  40                  45

Val Lys Gly Ile Leu Asp Glu Tyr His Lys Gln Leu Ile Asn Glu Ala
```

```
                50             55                60
Leu Asp Asn Cys Thr Leu Pro Ser Leu Lys Ile Ala Ala Glu Ile Tyr
 65                  70                  75                  80

Leu Lys Asn Gln Lys Glu Val Ser Asp Arg Glu Asp Phe Asn Lys Thr
                     85                  90                  95

Gln Asp Leu Leu Arg Lys Glu Val Val Glu Lys Leu Lys Ala His Glu
                100                 105                 110

Asn Phe Thr Lys Ile Gly Lys Lys Asp Ile Leu Asp Leu Leu Glu Lys
                115                 120                 125

Leu Pro Ser Ile Ser Glu Asp Asp Tyr Asn Ala Leu Glu Ser Phe Arg
130                 135                 140

Asn Phe Tyr Thr Tyr Phe Thr Ser Tyr Asn Lys Val Arg Glu Asn Leu
145                 150                 155                 160

Tyr Ser Asp Lys Glu Lys Ser Ser Thr Val Ala Tyr Arg Leu Ile Asn
                165                 170                 175

Glu Asn Phe Pro Lys Phe Leu Asp Asn Val Lys Ser Tyr Arg Phe Val
                180                 185                 190

Lys Thr Ala Gly Ile Leu Ala Asp Gly Leu Gly Glu Glu Gln Asp
                195                 200                 205

Ser Leu Phe Ile Val Glu Thr Phe Asn Lys Thr Leu Thr Gln Asp Gly
210                 215                 220

Ile Asp Thr Tyr Asn Ser Gln Val Gly Lys Ile Asn Ser Ser Ile Asn
225                 230                 235                 240

Leu Tyr Asn Gln Lys Asn Gln Lys Ala Asn Gly Phe Arg Lys Ile Pro
                245                 250                 255

Lys Met Lys Met Leu Tyr Lys Gln Ile Leu Ser Asp Arg Glu Glu Ser
                260                 265                 270

Phe Ile Asp Glu Phe Gln Ser Asp Glu Val Leu Ile Asp Asn Val Glu
                275                 280                 285

Ser Tyr Gly Ser Val Leu Ile Glu Ser Leu Lys Ser Ser Lys Val Ser
                290                 295                 300

Ala Phe Phe Asp Ala Leu Arg Glu Ser Lys Gly Lys Asn Val Tyr Val
305                 310                 315                 320

Lys Asn Asp Leu Ala Lys Thr Ala Met Ser Asn Ile Val Phe Glu Asn
                325                 330                 335

Trp Arg Thr Phe Asp Asp Leu Leu Asn Gln Glu Tyr Asp Leu Ala Asn
                340                 345                 350

Glu Asn Lys Lys Lys Asp Asp Lys Tyr Phe Glu Lys Arg Gln Lys Glu
                355                 360                 365

Leu Lys Lys Asn Lys Ser Tyr Ser Leu Glu His Leu Cys Asn Leu Ser
                370                 375                 380

Glu Asp Ser Cys Asn Leu Ile Glu Asn Tyr Ile His Gln Ile Ser Asp
385                 390                 395                 400

Asp Ile Glu Asn Ile Ile Asn Asn Glu Thr Phe Leu Arg Ile Val
                405                 410                 415

Ile Asn Glu His Asp Arg Ser Arg Lys Leu Ala Lys Asn Arg Lys Ala
                420                 425                 430

Val Lys Ala Ile Lys Asp Phe Leu Asp Ser Ile Lys Val Leu Glu Arg
                435                 440                 445

Glu Leu Lys Leu Ile Asn Ser Ser Gly Gln Glu Leu Glu Lys Asp Leu
                450                 455                 460

Ile Val Tyr Ser Ala His Glu Glu Leu Leu Val Glu Leu Lys Gln Val
465                 470                 475                 480
```

```
Asp Ser Leu Tyr Asn Met Thr Arg Asn Tyr Leu Thr Lys Lys Pro Phe
                485                 490                 495

Ser Thr Glu Lys Val Lys Leu Asn Phe Asn Arg Ser Thr Leu Leu Asn
            500                 505                 510

Gly Trp Asp Arg Asn Lys Glu Thr Asp Asn Leu Gly Val Leu Leu Leu
        515                 520                 525

Lys Asp Gly Lys Tyr Tyr Leu Gly Ile Met Asn Thr Ser Ala Asn Lys
    530                 535                 540

Ala Phe Val Asn Pro Pro Val Ala Lys Thr Glu Lys Val Phe Lys Lys
545                 550                 555                 560

Val Asp Tyr Lys Leu Leu Pro Val Pro Asn Gln Met Leu Pro Lys Val
                565                 570                 575

Phe Phe Ala Lys Ser Asn Ile Asp Phe Tyr Asn Pro Ser Ser Glu Ile
            580                 585                 590

Tyr Ser Asn Tyr Lys Lys Gly Thr His Lys Lys Gly Asn Met Phe Ser
        595                 600                 605

Leu Glu Asp Cys His Asn Leu Ile Asp Phe Phe Lys Glu Ser Ile Ser
    610                 615                 620

Lys His Glu Asp Trp Ser Lys Phe Gly Phe Lys Phe Ser Asp Thr Ala
625                 630                 635                 640

Ser Tyr Asn Asp Ile Ser Glu Phe Tyr Arg Glu Val Glu Lys Gln Gly
                645                 650                 655

Tyr Lys Leu Thr Tyr Thr Asp Ile Asp Glu Thr Tyr Ile Asn Asp Leu
            660                 665                 670

Ile Glu Arg Asn Glu Leu Tyr Leu Phe Gln Ile Tyr Asn Lys Asp Phe
        675                 680                 685

Ser Met Tyr Ser Lys Gly Lys Leu Asn Leu His Thr Leu Tyr Phe Met
    690                 695                 700

Met Leu Phe Asp Gln Arg Asn Ile Asp Asp Val Val Tyr Lys Leu Asn
705                 710                 715                 720

Gly Glu Ala Glu Val Phe Tyr Arg Pro Ala Ser Ile Ser Glu Asp Glu
                725                 730                 735

Leu Ile Ile His Lys Ala Gly Glu Glu Ile Lys Asn Lys Asn Pro Asn
            740                 745                 750

Arg Ala Arg Thr Lys Glu Thr Ser Thr Phe Ser Tyr Asp Ile Val Lys
        755                 760                 765

Asp Lys Arg Tyr Ser Lys Asp Lys Phe Thr Leu His Ile Pro Ile Thr
    770                 775                 780

Met Asn Phe Gly Val Asp Glu Val Lys Arg Phe Asn Asp Ala Val Asn
785                 790                 795                 800

Ser Ala Ile Arg Ile Asp Glu Asn Val Asn Val Ile Gly Ile Asp Arg
                805                 810                 815

Gly Glu Arg Asn Leu Leu Tyr Val Val Ile Asp Ser Lys Gly Asn
            820                 825                 830

Ile Leu Glu Gln Ile Ser Leu Asn Ser Ile Asn Lys Glu Tyr Asp
        835                 840                 845

Ile Glu Thr Asp Tyr His Ala Leu Leu Asp Arg Glu Gly Gly Arg
    850                 855                 860

Asp Lys Ala Arg Lys Asp Trp Asn Thr Val Glu Asn Ile Arg Asp Leu
865                 870                 875                 880

Lys Ala Gly Tyr Leu Ser Gln Val Val Asn Val Val Ala Lys Leu Val
                885                 890                 895
```

```
Leu Lys Tyr Asn Ala Ile Ile Cys Leu Glu Asp Leu Asn Phe Gly Phe
            900                 905                 910

Lys Arg Gly Arg Gln Lys Val Glu Lys Gln Val Tyr Gln Lys Phe Glu
        915                 920                 925

Lys Met Leu Ile Asp Lys Leu Asn Tyr Leu Val Ile Asp Lys Ser Arg
    930                 935                 940

Glu Gln Thr Ser Pro Lys Glu Leu Gly Gly Ala Leu Asn Ala Leu Gln
945                 950                 955                 960

Leu Thr Ser Lys Phe Lys Ser Phe Lys Glu Leu Gly Lys Gln Ser Gly
                965                 970                 975

Val Ile Tyr Tyr Val Pro Ala Tyr Leu Thr Ser Lys Ile Asp Pro Thr
            980                 985                 990

Thr Gly Phe Ala Asn Leu Phe Tyr Met Lys Cys Glu Asn Val Glu Lys
        995                 1000                1005

Ser Lys Arg Phe Phe Asp Gly Phe Asp Phe Ile Arg Phe Asn Ala
    1010                1015                1020

Leu Glu Asn Val Phe Glu Phe Gly Phe Asp Tyr Arg Ser Phe Thr
    1025                1030                1035

Gln Arg Ala Cys Gly Ile Asn Ser Lys Trp Thr Val Cys Thr Asn
    1040                1045                1050

Gly Glu Arg Ile Ile Lys Tyr Arg Asn Pro Asp Lys Asn Asn Met
    1055                1060                1065

Phe Asp Glu Lys Val Val Val Thr Asp Glu Met Lys Asn Leu
    1070                1075                1080

Phe Glu Gln Tyr Lys Ile Pro Tyr Glu Asp Gly Arg Asn Val Lys
    1085                1090                1095

Asp Met Ile Ile Ser Asn Glu Glu Ala Glu Phe Tyr Arg Arg Leu
    1100                1105                1110

Tyr Arg Leu Leu Gln Gln Thr Leu Gln Met Arg Asn Ser Thr Ser
    1115                1120                1125

Asp Gly Thr Arg Asp Tyr Ile Ile Ser Pro Val Lys Asn Lys Arg
    1130                1135                1140

Glu Ala Tyr Phe Asn Ser Glu Leu Ser Asp Gly Ser Val Pro Lys
    1145                1150                1155

Asp Ala Asp Ala Asn Gly Ala Tyr Asn Ile Ala Arg Lys Gly Leu
    1160                1165                1170

Trp Val Leu Glu Gln Ile Arg Gln Lys Ser Glu Gly Glu Lys Ile
    1175                1180                1185

Asn Leu Ala Met Thr Asn Ala Glu Trp Leu Glu Tyr Ala Gln Thr
    1190                1195                1200

His Leu Leu Lys Arg Pro Ala Ala Thr Lys Lys Ala Gly Gln Ala
    1205                1210                1215

Lys Lys Lys Lys Gly Ser Tyr Pro Tyr Asp Val Pro Asp Tyr Ala
    1220                1225                1230

Tyr Pro Tyr Asp Val Pro Asp Tyr Ala Tyr Pro Tyr Asp Val Pro
    1235                1240                1245

Asp Tyr Ala
    1250

<210> SEQ ID NO 28
<211> LENGTH: 3756
<212> TYPE: DNA
<213> ORGANISM: Artificial Sequence
<220> FEATURE:
<223> OTHER INFORMATION: Synthetic-Lachnospiraceae bacterium MA2020
```

(Lb2Cpf1; pY011), including NLS and HA tag

<400> SEQUENCE: 28

```
atgtactatg agtccctgac caagcagtac cccgtgtcta agacaatccg gaatgagctg      60
atccctatcg gcaagacact ggataacatc cgccagaaca atatcctgga gagcgacgtg     120
aagcggaagc agaactacga gcacgtgaag ggcatcctgg atgagtatca aagcagctg      180
atcaacgagg ccctggacaa ttgcaccctg ccatccctga gatcgccgc cgagatctac      240
ctgaagaatc agaaggaggt gtctgacaga gaggatttca caagacaca ggacctgctg      300
aggaaggagg tggtggagaa gctgaaggcc cacgagaact taccaagat cggcaagaag      360
gacatcctgg atctgctgga gaagctgcct tccatctctg aggacgatta caatgccctg     420
gagagcttcc gcaacttta cacctatttc acatcctaca caaggtgcg ggagaatctg       480
tattctgata aggagaagag ctccacagtg gcctacagac tgatcaacga gaatttccca     540
aagtttctgg acaatgtgaa gagctatagg tttgtgaaaa ccgcaggcat cctggcagat     600
ggcctgggag aggaggagca ggactccctg ttcatcgtgg acattcaa caagaccctg       660
acacaggacg gcatcgatac ctacaattct caagtgggca agatcaactc tagcatcaat     720
ctgtataacc agaagaatca aaggccaat ggcttcagaa gatccccaa gatgaagatg       780
ctgtataagc agatcctgtc cgatagggag gagtctttca tcgacgagtt tcagagcgat     840
gaggtgctga tcgacaacgt ggagtcttat ggcagcgtgc tgatcgagtc tctgaagtcc     900
tctaaggtga gcgccttctt tgatgccctg agagagtcta agggcaagaa cgtgtacgtg     960
aagaatgacc tggccaagac agccatgagc aacatcgtgt cgagaattg gaggaccttt    1020
gacgatctgc tgaaccagga gtacgacctg gccaacgaga acaagaagaa ggacgataag    1080
tatttcgaga agcgccagaa ggagctgaag aagaataaga gctactccct ggagcacctg    1140
tgcaacctgt ccgaggattc ttgtaacctg atcgagaatt atatccacca gatctccgac    1200
gatatcgaga atatcatcat caacaatgag acattcctgc gcatcgtgat caatgagcac    1260
acaggtcccc gcaagctggc caagaaccgg aaggccgtga aggccatcaa ggactttctg    1320
gattctatca aggtgctgga gcgggagctg aagctgatca cagctccgg ccaggagctg    1380
gagaaggatc tgatcgtgta ctctgcccac gaggagctgc tggtggagct gaagcaggtg    1440
gacagcctgt ataacatgac cagaaattat ctgacaaaga agcctttctc taccgagaag    1500
gtgaagctga actttaatcg cagcacactg ctgaacggct gggatcggaa taaggagaca    1560
gacaacctgg gcgtgctgct gctgaaggac ggcaagtact atctgggcat catgaacaca    1620
agcgccaata aggccttcgt gaatcccct gtggccaaga ccgagaaggt gtttaagaag    1680
gtggattaca agctgctgcc agtgcccaac cagatgctgc caaaggtgtt ctttgccaag    1740
agcaatatcg acttctataa cccctctagc gagatctact ccaattataa aagggcacc    1800
cacaagaagg gcaatatgtt tccctggag gattgtcaca acctgatcga cttctttaag    1860
gagtctatca gcaagcacga ggactggagc aagttcggct ttaagttcag cgatacagcc    1920
tcctacaacg acatctccga gttctatcgc gaggtggaga gcagggcta agctgacc       1980
tatacagaca tcgatgagac atacatcaat gatctgatcg agcggaacga gctgtacctg    2040
ttccagatct ataataagga ctttagcatg tactccaagg gcaagctgaa cctgcacaca    2100
ctgtatttca tgatgctgtt tgatcagcgc aatatcgacg acgtggtgta taagctgaac    2160
ggagaggcag aggtgttcta taggccagcc tccatctctg aggacgagct gatcatccac    2220
aaggccggcg aggagatcaa gaacaagaat cctaaccggg ccagaaccaa ggagacaagc    2280
```

```
accttcagct acgacatcgt gaaggataag cggtatagca aggataagtt taccctgcac    2340
atccccatca caatgaactt cggcgtggat gaggtgaagc ggttcaacga cgccgtgaac    2400
agcgccatcc ggatcgatga gaatgtgaac gtgatcggca tcgaccgggg cgagagaaat    2460
ctgctgtacg tggtggtcat cgactctaag ggcaacatcc tggagcagat ctccctgaac    2520
tctatcatca ataaggagta cgacatcgag acagattatc acgcactgct ggatgagagg    2580
gagggcggca gagataaggc ccggaaggac tggaacaccg tggagaatat cagggacctg    2640
aaggccggct acctgagcca ggtggtgaac gtggtggcca agctggtgct gaagtataat    2700
gccatcatct gcctggagga cctgaacttt ggcttcaaga ggggccgcca gaaggtggag    2760
aagcaggtgt accagaagtt cgagaagatg ctgatcgata agctgaatta cctggtcatc    2820
gacaagagcc gcgagcagac atcccctaag gagctgggag cgccctgaa cgcactgcag     2880
ctgacctcta agttcaagag ctttaaggag ctgggcaagc agtccggcgt gatctactat    2940
gtgcctgcct acctgacctc taagatcgat ccaaccacag gcttcgccaa tctgttttat    3000
atgaagtgtg agaacgtgga gaagtccaag agattctttg acggctttga tttcatcagg    3060
ttcaacgccc tggagaacgt gttcgagttc ggctttgact accggagctt cacccagagg    3120
gcctgcggca tcaattccaa gtggaccgtg tgcaccaacg gcgagcgcat catcaagtat    3180
cggaatccag ataagaacaa tatgttcgac gagaaggtgg tggtggtgac cgatgagatg    3240
aagaacctgt ttgagcagta caagatcccc tatgaggatg gcagaaatgt gaaggacatg    3300
atcatcagca acgaggaggc cgagttctac cggagactgt ataggctgct gcagcagacc    3360
ctgcagatga gaaacagcac ctccgacggc acaagggatt acatcatctc ccctgtgaag    3420
aataagagag aggcctactt caacagcgag ctgtccgacg gctctgtgcc aaaggacgcc    3480
gatgccaacg gcgcctacaa tatcgccaga aagggcctgt gggtgctgga gcagatcagg    3540
cagaagagcg agggcgagaa gatcaatctg gccatgacca acgccgagtg gctggagtat    3600
gcccagacac acctgctgaa aaggccggcg gccacgaaaa aggccggcca ggcaaaaaag    3660
aaaaagggat cctacccata cgatgttcca gattacgctt atccctacga cgtgcctgat    3720
tatgcatacc catatgatgt ccccgactat gcctaa                              3756
```

<210> SEQ ID NO 29
<211> LENGTH: 1283
<212> TYPE: PRT
<213> ORGANISM: Artificial Sequence
<220> FEATURE:
<223> OTHER INFORMATION: Synthetic-Candidatus Methanoplasma termitum
    (CMtCpf1; pY012), including NLS and HA tag

<400> SEQUENCE: 29

Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
            20                  25                  30

Thr Phe Asn Phe Phe Glu Glu Asp Arg Asp Arg Ala Glu Lys Tyr Lys
        35                  40                  45

Ile Leu Lys Glu Ala Ile Asp Glu Tyr His Lys Phe Ile Asp Glu
    50                  55                  60

His Leu Thr Asn Met Ser Leu Asp Trp Asn Ser Leu Lys Gln Ile Ser
65                  70                  75                  80

Glu Lys Tyr Tyr Lys Ser Arg Glu Glu Lys Asp Lys Lys Val Phe Leu
            85                  90                  95

```
Ser Glu Gln Lys Arg Met Arg Gln Glu Ile Val Ser Glu Phe Lys Lys
            100                 105                 110

Asp Asp Arg Phe Lys Asp Leu Phe Ser Lys Lys Leu Phe Ser Glu Leu
            115                 120                 125

Leu Lys Glu Glu Ile Tyr Lys Lys Gly Asn His Gln Glu Ile Asp Ala
145         130                 135                 140

Leu Lys Ser Phe Asp Lys Phe Ser Gly Tyr Phe Ile Gly Leu His Glu
145                 150                 155                 160

Asn Arg Lys Asn Met Tyr Ser Asp Gly Asp Glu Ile Thr Ala Ile Ser
                165                 170                 175

Asn Arg Ile Val Asn Glu Asn Phe Pro Lys Phe Leu Asp Asn Leu Gln
                180                 185                 190

Lys Tyr Gln Glu Ala Arg Lys Lys Tyr Pro Glu Trp Ile Ile Lys Ala
            195                 200                 205

Glu Ser Ala Leu Val Ala His Asn Ile Lys Met Asp Glu Val Phe Ser
            210                 215                 220

Leu Glu Tyr Phe Asn Lys Val Leu Asn Gln Glu Gly Ile Gln Arg Tyr
225                 230                 235                 240

Asn Leu Ala Leu Gly Gly Tyr Val Thr Lys Ser Gly Glu Lys Met Met
                245                 250                 255

Gly Leu Asn Asp Ala Leu Asn Leu Ala His Gln Ser Gly Lys Ser Ser
                260                 265                 270

Lys Gly Arg Ile His Met Thr Pro Leu Phe Lys Gln Ile Leu Ser Glu
            275                 280                 285

Lys Glu Ser Phe Ser Tyr Ile Pro Asp Val Phe Thr Glu Asp Ser Gln
            290                 295                 300

Leu Leu Pro Ser Ile Gly Gly Phe Phe Ala Gln Ile Glu Asn Asp Lys
305                 310                 315                 320

Asp Gly Asn Ile Phe Asp Arg Ala Leu Glu Leu Ile Ser Ser Tyr Ala
                325                 330                 335

Glu Tyr Asp Thr Glu Arg Ile Tyr Ile Arg Gln Ala Asp Ile Asn Arg
                340                 345                 350

Val Ser Asn Val Ile Phe Gly Glu Trp Gly Thr Leu Gly Gly Leu Met
            355                 360                 365

Arg Glu Tyr Lys Ala Asp Ser Ile Asn Asp Ile Asn Leu Glu Arg Thr
            370                 375                 380

Cys Lys Lys Val Asp Lys Trp Leu Asp Ser Lys Glu Phe Ala Leu Ser
385                 390                 395                 400

Asp Val Leu Glu Ala Ile Lys Arg Thr Gly Asn Asn Asp Ala Phe Asn
                405                 410                 415

Glu Tyr Ile Ser Lys Met Arg Thr Ala Arg Glu Lys Ile Asp Ala Ala
            420                 425                 430

Arg Lys Glu Met Lys Phe Ile Ser Glu Lys Ile Ser Gly Asp Glu Glu
            435                 440                 445

Ser Ile His Ile Ile Lys Thr Leu Leu Asp Ser Val Gln Gln Phe Leu
            450                 455                 460

His Phe Phe Asn Leu Phe Lys Ala Arg Gln Asp Ile Pro Leu Asp Gly
465                 470                 475                 480

Ala Phe Tyr Ala Glu Phe Asp Glu Val His Ser Lys Leu Phe Ala Ile
                485                 490                 495

Val Pro Leu Tyr Asn Lys Val Arg Asn Tyr Leu Thr Lys Asn Asn Leu
            500                 505                 510
```

```
Asn Thr Lys Lys Ile Lys Leu Asn Phe Lys Asn Pro Thr Leu Ala Asn
            515                 520                 525

Gly Trp Asp Gln Asn Lys Val Tyr Asp Tyr Ala Ser Leu Ile Phe Leu
530                 535                 540

Arg Asp Gly Asn Tyr Tyr Leu Gly Ile Ile Asn Pro Lys Arg Lys Lys
545                 550                 555                 560

Asn Ile Lys Phe Glu Gln Gly Ser Gly Asn Gly Pro Phe Tyr Arg Lys
                565                 570                 575

Met Val Tyr Lys Gln Ile Pro Gly Pro Asn Lys Asn Leu Pro Arg Val
            580                 585                 590

Phe Leu Thr Ser Thr Lys Gly Lys Lys Glu Tyr Lys Pro Ser Lys Glu
        595                 600                 605

Ile Ile Glu Gly Tyr Glu Ala Asp Lys His Ile Arg Gly Asp Lys Phe
    610                 615                 620

Asp Leu Asp Phe Cys His Lys Leu Ile Asp Phe Phe Lys Glu Ser Ile
625                 630                 635                 640

Glu Lys His Lys Asp Trp Ser Lys Phe Asn Phe Tyr Phe Ser Pro Thr
                645                 650                 655

Glu Ser Tyr Gly Asp Ile Ser Glu Phe Tyr Leu Asp Val Glu Lys Gln
            660                 665                 670

Gly Tyr Arg Met His Phe Glu Asn Ile Ser Ala Glu Thr Ile Asp Glu
        675                 680                 685

Tyr Val Glu Lys Gly Asp Leu Phe Leu Phe Gln Ile Tyr Asn Lys Asp
    690                 695                 700

Phe Val Lys Ala Ala Thr Gly Lys Lys Asp Met His Thr Ile Tyr Trp
705                 710                 715                 720

Asn Ala Ala Phe Ser Pro Glu Asn Leu Gln Asp Val Val Lys Leu
                725                 730                 735

Asn Gly Glu Ala Glu Leu Phe Tyr Arg Asp Lys Ser Asp Ile Lys Glu
            740                 745                 750

Ile Val His Arg Glu Gly Glu Ile Leu Val Asn Arg Thr Tyr Asn Gly
        755                 760                 765

Arg Thr Pro Val Pro Asp Lys Ile His Lys Lys Leu Thr Asp Tyr His
770                 775                 780

Asn Gly Arg Thr Lys Asp Leu Gly Glu Ala Lys Glu Tyr Leu Asp Lys
785                 790                 795                 800

Val Arg Tyr Phe Lys Ala His Tyr Asp Ile Thr Lys Asp Arg Arg Tyr
                805                 810                 815

Leu Asn Asp Lys Ile Tyr Phe His Val Pro Leu Thr Leu Asn Phe Lys
            820                 825                 830

Ala Asn Gly Lys Lys Asn Leu Asn Lys Met Val Ile Glu Lys Phe Leu
        835                 840                 845

Ser Asp Glu Lys Ala His Ile Ile Gly Ile Asp Arg Gly Glu Arg Asn
850                 855                 860

Leu Leu Tyr Tyr Ser Ile Ile Asp Arg Ser Gly Lys Ile Ile Asp Gln
865                 870                 875                 880

Gln Ser Leu Asn Val Ile Asp Gly Phe Asp Tyr Arg Glu Lys Leu Asn
                885                 890                 895

Gln Arg Glu Ile Glu Met Lys Asp Ala Arg Gln Ser Trp Asn Ala Ile
            900                 905                 910

Gly Lys Ile Lys Asp Leu Lys Glu Gly Tyr Leu Ser Lys Ala Val His
        915                 920                 925

Glu Ile Thr Lys Met Ala Ile Gln Tyr Asn Ala Ile Val Val Met Glu
```

930             935             940
Glu Leu Asn Tyr Gly Phe Lys Arg Gly Arg Phe Lys Val Glu Lys Gln
945                 950                 955                 960

Ile Tyr Gln Lys Phe Glu Asn Met Leu Ile Asp Lys Met Asn Tyr Leu
            965                 970                 975

Val Phe Lys Asp Ala Pro Asp Glu Ser Pro Gly Gly Val Leu Asn Ala
                980                 985                 990

Tyr Gln Leu Thr Asn Pro Leu Glu Ser Phe Ala Lys Leu Gly Lys Gln
        995                 1000                1005

Thr Gly Ile Leu Phe Tyr Val Pro Ala Ala Tyr Thr Ser Lys Ile
    1010                1015                1020

Asp Pro Thr Thr Gly Phe Val Asn Leu Phe Asn Thr Ser Ser Lys
    1025                1030                1035

Thr Asn Ala Gln Glu Arg Lys Glu Phe Leu Gln Lys Phe Glu Ser
    1040                1045                1050

Ile Ser Tyr Ser Ala Lys Asp Gly Gly Ile Phe Ala Phe Ala Phe
    1055                1060                1065

Asp Tyr Arg Lys Phe Gly Thr Ser Lys Thr Asp His Lys Asn Val
    1070                1075                1080

Trp Thr Ala Tyr Thr Asn Gly Glu Arg Met Arg Tyr Ile Lys Glu
    1085                1090                1095

Lys Lys Arg Asn Glu Leu Phe Asp Pro Ser Lys Glu Ile Lys Glu
    1100                1105                1110

Ala Leu Thr Ser Ser Gly Ile Lys Tyr Asp Gly Gly Gln Asn Ile
    1115                1120                1125

Leu Pro Asp Ile Leu Arg Ser Asn Asn Asn Gly Leu Ile Tyr Thr
    1130                1135                1140

Met Tyr Ser Ser Phe Ile Ala Ala Ile Gln Met Arg Val Tyr Asp
    1145                1150                1155

Gly Lys Glu Asp Tyr Ile Ile Ser Pro Ile Lys Asn Ser Lys Gly
    1160                1165                1170

Glu Phe Phe Arg Thr Asp Pro Lys Arg Arg Glu Leu Pro Ile Asp
    1175                1180                1185

Ala Asp Ala Asn Gly Ala Tyr Asn Ile Ala Leu Arg Gly Glu Leu
    1190                1195                1200

Thr Met Arg Ala Ile Ala Glu Lys Phe Asp Pro Asp Ser Glu Lys
    1205                1210                1215

Met Ala Lys Leu Glu Leu Lys His Lys Asp Trp Phe Glu Phe Met
    1220                1225                1230

Gln Thr Arg Gly Asp Lys Arg Pro Ala Ala Thr Lys Lys Ala Gly
    1235                1240                1245

Gln Ala Lys Lys Lys Lys Gly Ser Tyr Pro Tyr Asp Val Pro Asp
    1250                1255                1260

Tyr Ala Tyr Pro Tyr Asp Val Pro Asp Tyr Ala Tyr Pro Tyr Asp
    1265                1270                1275

Val Pro Asp Tyr Ala
    1280

<210> SEQ ID NO 30
<211> LENGTH: 3852
<212> TYPE: DNA
<213> ORGANISM: Artificial Sequence
<220> FEATURE:
<223> OTHER INFORMATION: Synthetic-Candidatus Methanoplasma termitum
      (CMtCpf1; pY012), including NLS and HA tag

<400> SEQUENCE: 30

```
atgaacaatt acgacgagtt caccaagctg tatcctatcc agaaaaccat ccggtttgag      60
ctgaagccac agggcagaac catggagcac ctggagacat tcaacttctt tgaggaggac     120
cgggatagag ccgagaagta taagatcctg aaggaggcca tcgacgagta ccacaagaag     180
tttatcgatg agcacctgac caatatgtcc ctggattgga actctctgaa gcagatcagc     240
gagaagtact ataagagcag ggaggagaag gacaagaagg tgttcctgtc cgagcagaag     300
aggatgcgcc aggagatcgt gtctgagttt aagaaggacg atcgcttcaa ggacctgttt     360
tccaagaagc tgttctctga gctgctgaag gaggagatct acaagaaggg caaccaccag     420
gagatcgacg ccctgaagag cttcgataag ttttccggct atttcatcgg cctgcacgag     480
aataggaaga acatgtactc cgacggcgat gagatcaccg ccatctccaa tcgcatcgtg     540
aatgagaact tccccaagtt tctggataac ctgcagaagt accaggaggc caggaagaag     600
tatcctgagt ggatcatcaa ggccgagagc gccctggtgg cccacaatat caagatggac     660
gaggtgttct ccctggagta ctttaataag gtgctgaacc aggagggcat ccagcggtac     720
aacctggccc tgggcggcta tgtgaccaag agcggcgaga gatgatgggg cctgaatgat     780
gccctgaacc tggcccacca gtccgagaag agctccaagg gcagaatcca catgacccc     840
ctgttcaagc agatcctgtc cgagaaggag tccttctctt acatcccga cgtgtttaca     900
gaggattctc agctgctgcc tagcatcggc ggcttctttg cccagatcga aatgacaag      960
gatggcaaca tcttcgaccg ggccctggag ctgatctcta gctacgccga gtatgatacc    1020
gagcggatct atatcagaca ggccgacatc aatagagtgt ccaacgtgat ctttggagag    1080
tgggcacccc tggaggcct gatgaggag tacaaggccg actctatcaa tgatatcaac     1140
ctggagcgca catgcaagaa ggtggacaag tggctggatt ctaaggagtt tgccctgagc    1200
gatgtgctgg aggccatcaa gaggaccggc aacaatgacg ccttcaacga gtatatctcc    1260
aagatgcgga cagccagaga aagatcgat gccgcccgca aggagatgaa gttcatcagc    1320
gagaagatct ccggcgatga ggagtctatc cacatcatca gaccctgct ggacagcgtg    1380
cagcagttcc tgcacttctt taatctgttt aaggcaaggc aggacatccc actggatgga    1440
gccttctacg ccgagtttga cgaggtgcac agcaagctgt ttgccatcgt gcccctgtat    1500
aacaaggtgc ggaactatct gaccaagaac aatctgaaca caagaagat caagctgaat    1560
ttcaagaacc ctacactggc caatggctgg gaccagaaca aggtgtacga ttatgcctcc    1620
ctgatctttc tgcgggacgg caattactat ctgggcatca tcaatcctaa gagaaagaag    1680
aacatcaagt tcgagcaggg ctctggcaac ggccccttct accggaagat ggtgtataag    1740
cagatccccg ccctaataa gaacctgcca agagtgttcc tgacctccac aaagggcaag    1800
aaggagtata gccctctaa ggagatcatc gagggctacg aggccgacaa gcacatcagg    1860
ggcgataagt tcgacctgga ttttttgtcac aagctgatcg atttctttaa ggagtccatc    1920
gagaagcaca aggactggtc taagttcaac ttctacttca gcccaaccga gagctatggc    1980
gacatctctg agttctaccte ggatgtggag aagcagggct atcgcatgca ctttgagaat    2040
atcagcgccg agacaatcga cgagtatgtg gagaagggcg atctgtttct gttccagatc    2100
tacaacaagg attttgtgaa ggccgccacc ggcaagaagg acatgcacac aatctactgg    2160
aatgccgcct tcagccccga gaacctgcag gacgtggtgg tgaagctgaa cggcgaggcc    2220
gagctgtttt ataggacaa gtccgatatc aaggagatcg tgcaccgcga gggcgagatc    2280
```

-continued

```
ctggtgaata ggacctacaa cggccgcaca ccagtgcccg acaagatcca caagaagctg    2340
accgattatc acaatggccg gacaaaggac ctgggcgagg ccaaggagta cctggataag    2400
gtgagatact tcaaggccca ctatgacatc accaaggatc ggagatacct gaacgacaag    2460
atctatttcc acgtgcctct gaccctgaac ttcaaggcca acggcaagaa gaatctgaac    2520
aagatggtca tcgagaagtt cctgtccgat gagaaggccc acatcatcgg catcgacagg    2580
ggcgagcgca atctgctgta ctattccatc atcgacaggt ctggcaagat catcgatcag    2640
cagagcctga atgtgatcga cggctttgat tatcgggaga agctgaacca gagagagatc    2700
gagatgaagg atgcccgcca gtcttggaac gccatcggca agatcaagga cctgaaggag    2760
ggctacctga gcaaggccgt gcacgagatc accaagatgg ccatccagta taatgccatc    2820
gtggtcatgg aggagctgaa ctacggcttc aagcggggcc ggttcaaggt ggagaagcag    2880
atctatcaga gttcgagaa tatgctgatc gataagatga actacctggt gtttaaggac    2940
gcacctgatg agtccccagg aggcgtgctg aatgcctacc agctgacaaa cccactggag    3000
tctttcgcca gctgggcaa gcagaccggc atcctgtttt acgtgccagc cgcctataca    3060
tccaagatcg accccaccac aggcttcgtg aatctgttta acacctcctc taagacaaac    3120
gcccaggagc ggaaggagtt cctgcagaag tttgagagca tctcctattc tgccaaggat    3180
ggcggcatct ttgccttcgc ctttgactac agaaagttcg gcaccagcaa gacagatcac    3240
aagaacgtgt ggaccgccta taaacggc gagaggatgc gctacatcaa ggagaagaag    3300
cggaatgagc tgtttgaccc ttctaaggag atcaaggagg ccctgaccag ctccggcatc    3360
aagtacgatg gcgccagaa catcctgcca gacatcctga ggagcaacaa taacggcctg    3420
atctacacaa tgtattctag cttcatcgcc gccatccaga tgcgcgtgta cgacggcaag    3480
gaggattata tcatcagccc catcaagaac tccaagggcg agttctttag gaccgaccccc    3540 aagaggcgcg agctgcctat cgacgccgat gccaatggcg cctacaacat cgccctgagg    3600
ggagagctga caatgagggc aatcgcgag aagttcgacc ctgatagcga gaagatggcc    3660
aagctggagc tgaagcacaa ggattggttc gagtttatgc agaccagagg cgacaaaagg    3720
ccggcggcca cgaaaaaggc cggccaggca aaaaagaaaa agggatccta cccatacgat    3780
gttccagatt acgcttatcc ctacgacgtg cctgattatg catacccata tgatgtcccc    3840
gactatgcct aa                                                        3852
```

```
<210> SEQ ID NO 31
<211> LENGTH: 1327
<212> TYPE: PRT
<213> ORGANISM: Artificial Sequence
<220> FEATURE:
<223> OTHER INFORMATION: Synthetic-Eubacterium eligens (EeCpf1; pY013),
      including NLS and HA tag

<400> SEQUENCE: 31

Met Asn Gly Asn Arg Ser Ile Val Tyr Arg Glu Phe Val Gly Val Ile
1               5                   10                  15

Pro Val Ala Lys Thr Leu Arg Asn Glu Leu Arg Pro Val Gly His Thr
                20                  25                  30

Gln Glu His Ile Ile Gln Asn Gly Leu Ile Gln Glu Asp Glu Leu Arg
            35                  40                  45

Gln Glu Lys Ser Thr Glu Leu Lys Asn Ile Met Asp Asp Tyr Tyr Arg
        50                  55                  60

Glu Tyr Ile Asp Lys Ser Leu Ser Gly Val Thr Asp Leu Asp Phe Thr
65                  70                  75                  80
```

```
Leu Leu Phe Glu Leu Met Asn Leu Val Gln Ser Ser Pro Ser Lys Asp
                85                  90                  95

Asn Lys Lys Ala Leu Glu Lys Glu Gln Ser Lys Met Arg Glu Gln Ile
            100                 105                 110

Cys Thr His Leu Gln Ser Asp Ser Asn Tyr Lys Asn Ile Phe Asn Ala
            115                 120                 125

Lys Leu Leu Lys Glu Ile Leu Pro Asp Phe Ile Lys Asn Tyr Asn Gln
130                 135                 140

Tyr Asp Val Lys Asp Lys Ala Gly Lys Leu Glu Thr Leu Ala Leu Phe
145                 150                 155                 160

Asn Gly Phe Ser Thr Tyr Phe Thr Asp Phe Phe Glu Lys Arg Lys Asn
                165                 170                 175

Val Phe Thr Lys Glu Ala Val Ser Thr Ser Ile Ala Tyr Arg Ile Val
            180                 185                 190

His Glu Asn Ser Leu Ile Phe Leu Ala Asn Met Thr Ser Tyr Lys Lys
            195                 200                 205

Ile Ser Glu Lys Ala Leu Asp Glu Ile Glu Val Ile Glu Lys Asn Asn
210                 215                 220

Gln Asp Lys Met Gly Asp Trp Glu Leu Asn Gln Ile Phe Asn Pro Asp
225                 230                 235                 240

Phe Tyr Asn Met Val Leu Ile Gln Ser Gly Ile Asp Phe Tyr Asn Glu
                245                 250                 255

Ile Cys Gly Val Val Asn Ala His Met Asn Leu Tyr Cys Gln Gln Thr
            260                 265                 270

Lys Asn Asn Tyr Asn Leu Phe Lys Met Arg Lys Leu His Lys Gln Ile
            275                 280                 285

Leu Ala Tyr Thr Ser Thr Ser Phe Glu Val Pro Lys Met Phe Glu Asp
290                 295                 300

Asp Met Ser Val Tyr Asn Ala Val Asn Ala Phe Ile Asp Glu Thr Glu
305                 310                 315                 320

Lys Gly Asn Ile Ile Gly Lys Leu Lys Asp Ile Val Asn Lys Tyr Asp
                325                 330                 335

Glu Leu Asp Glu Lys Arg Ile Tyr Ile Ser Lys Asp Phe Tyr Glu Thr
            340                 345                 350

Leu Ser Cys Phe Met Ser Gly Asn Trp Asn Leu Ile Thr Gly Cys Val
            355                 360                 365

Glu Asn Phe Tyr Asp Glu Asn Ile His Ala Lys Gly Lys Ser Lys Glu
370                 375                 380

Glu Lys Val Lys Lys Ala Val Lys Glu Asp Lys Tyr Lys Ser Ile Asn
385                 390                 395                 400

Asp Val Asn Asp Leu Val Glu Lys Tyr Ile Asp Glu Lys Glu Arg Asn
                405                 410                 415

Glu Phe Lys Asn Ser Asn Ala Lys Gln Tyr Ile Arg Glu Ile Ser Asn
            420                 425                 430

Ile Ile Thr Asp Thr Glu Thr Ala His Leu Glu Tyr Asp Asp His Ile
            435                 440                 445

Ser Leu Ile Glu Ser Glu Glu Lys Ala Asp Glu Met Lys Lys Arg Leu
450                 455                 460

Asp Met Tyr Met Asn Met Tyr His Trp Ala Lys Ala Phe Ile Val Asp
465                 470                 475                 480

Glu Val Leu Asp Arg Asp Glu Met Phe Tyr Ser Asp Ile Asp Asp Ile
                485                 490                 495
```

Tyr Asn Ile Leu Glu Asn Ile Val Pro Leu Tyr Asn Arg Val Arg Asn
            500                 505                 510

Tyr Val Thr Gln Lys Pro Tyr Asn Ser Lys Lys Ile Lys Leu Asn Phe
        515                 520                 525

Gln Ser Pro Thr Leu Ala Asn Gly Trp Ser Gln Ser Lys Glu Phe Asp
    530                 535                 540

Asn Asn Ala Ile Ile Leu Ile Arg Asp Asn Lys Tyr Tyr Leu Ala Ile
545                 550                 555                 560

Phe Asn Ala Lys Asn Lys Pro Asp Lys Lys Ile Ile Gln Gly Asn Ser
            565                 570                 575

Asp Lys Lys Asn Asp Asn Asp Tyr Lys Lys Met Val Tyr Asn Leu Leu
        580                 585                 590

Pro Gly Ala Asn Lys Met Leu Pro Lys Val Phe Leu Ser Lys Lys Gly
    595                 600                 605

Ile Glu Thr Phe Lys Pro Ser Asp Tyr Ile Ile Ser Gly Tyr Asn Ala
    610                 615                 620

His Lys His Ile Lys Thr Ser Glu Asn Phe Asp Ile Ser Phe Cys Arg
625                 630                 635                 640

Asp Leu Ile Asp Tyr Phe Lys Asn Ser Ile Glu Lys His Ala Glu Trp
            645                 650                 655

Arg Lys Tyr Glu Phe Lys Phe Ser Ala Thr Asp Ser Tyr Ser Asp Ile
        660                 665                 670

Ser Glu Phe Tyr Arg Glu Val Glu Met Gln Gly Tyr Arg Ile Asp Trp
    675                 680                 685

Thr Tyr Ile Ser Glu Ala Asp Ile Asn Lys Leu Asp Glu Glu Gly Lys
    690                 695                 700

Ile Tyr Leu Phe Gln Ile Tyr Asn Lys Asp Phe Ala Glu Asn Ser Thr
705                 710                 715                 720

Gly Lys Glu Asn Leu His Thr Met Tyr Phe Lys Asn Ile Phe Ser Glu
            725                 730                 735

Glu Asn Leu Lys Asp Ile Ile Lys Leu Asn Gly Gln Ala Glu Leu
        740                 745                 750

Phe Tyr Arg Arg Ala Ser Val Lys Asn Pro Val Lys His Lys Lys Asp
    755                 760                 765

Ser Val Leu Val Asn Lys Thr Tyr Lys Asn Gln Leu Asp Asn Gly Asp
    770                 775                 780

Val Val Arg Ile Pro Ile Pro Asp Asp Ile Tyr Asn Glu Ile Tyr Lys
785                 790                 795                 800

Met Tyr Asn Gly Tyr Ile Lys Glu Ser Asp Leu Ser Glu Ala Ala Lys
            805                 810                 815

Glu Tyr Leu Asp Lys Val Glu Val Arg Thr Ala Gln Lys Asp Ile Val
        820                 825                 830

Lys Asp Tyr Arg Tyr Thr Val Asp Lys Tyr Phe Ile His Thr Pro Ile
    835                 840                 845

Thr Ile Asn Tyr Lys Val Thr Ala Arg Asn Asn Val Asn Asp Met Val
    850                 855                 860

Val Lys Tyr Ile Ala Gln Asn Asp Asp Ile His Val Ile Gly Ile Asp
865                 870                 875                 880

Arg Gly Glu Arg Asn Leu Ile Tyr Ile Ser Val Ile Asp Ser His Gly
            885                 890                 895

Asn Ile Val Lys Gln Lys Ser Tyr Asn Ile Leu Asn Asn Tyr Asp Tyr
        900                 905                 910

Lys Lys Lys Leu Val Glu Lys Glu Lys Thr Arg Glu Tyr Ala Arg Lys

-continued

```
             915                 920                 925
Asn Trp Lys Ser Ile Gly Asn Ile Lys Glu Leu Lys Glu Gly Tyr Ile
         930                 935                 940
Ser Gly Val Val His Glu Ile Ala Met Leu Ile Val Glu Tyr Asn Ala
 945                 950                 955                 960
Ile Ile Ala Met Glu Asp Leu Asn Tyr Gly Phe Lys Arg Gly Arg Phe
                 965                 970                 975
Lys Val Glu Arg Gln Val Tyr Gln Lys Phe Glu Ser Met Leu Ile Asn
             980                 985                 990
Lys Leu Asn Tyr Phe Ala Ser Lys Glu Lys Ser Val Asp Glu Pro Gly
         995                 1000                1005
Gly Leu Leu Lys Gly Tyr Gln Leu Thr Tyr Val Pro Asp Asn Ile
     1010                1015                1020
Lys Asn Leu Gly Lys Gln Cys Gly Val Ile Phe Tyr Val Pro Ala
     1025                1030                1035
Ala Phe Thr Ser Lys Ile Asp Pro Ser Thr Gly Phe Ile Ser Ala
     1040                1045                1050
Phe Asn Phe Lys Ser Ile Ser Thr Asn Ala Ser Arg Lys Gln Phe
     1055                1060                1065
Phe Met Gln Phe Asp Glu Ile Arg Tyr Cys Ala Glu Lys Asp Met
     1070                1075                1080
Phe Ser Phe Gly Phe Asp Tyr Asn Asn Phe Asp Thr Tyr Asn Ile
     1085                1090                1095
Thr Met Gly Lys Thr Gln Trp Thr Val Tyr Thr Asn Gly Glu Arg
     1100                1105                1110
Leu Gln Ser Glu Phe Asn Asn Ala Arg Arg Thr Gly Lys Thr Lys
     1115                1120                1125
Ser Ile Asn Leu Thr Glu Thr Ile Lys Leu Leu Leu Glu Asp Asn
     1130                1135                1140
Glu Ile Asn Tyr Ala Asp Gly His Asp Ile Arg Ile Asp Met Glu
     1145                1150                1155
Lys Met Asp Glu Asp Lys Lys Ser Glu Phe Phe Ala Gln Leu Leu
     1160                1165                1170
Ser Leu Tyr Lys Leu Thr Val Gln Met Arg Asn Ser Tyr Thr Glu
     1175                1180                1185
Ala Glu Glu Gln Glu Asn Gly Ile Ser Tyr Asp Lys Ile Ile Ser
     1190                1195                1200
Pro Val Ile Asn Asp Glu Gly Glu Phe Phe Asp Ser Asp Asn Tyr
     1205                1210                1215
Lys Glu Ser Asp Asp Lys Glu Cys Lys Met Pro Lys Asp Ala Asp
     1220                1225                1230
Ala Asn Gly Ala Tyr Cys Ile Ala Leu Lys Gly Leu Tyr Glu Val
     1235                1240                1245
Leu Lys Ile Lys Ser Glu Trp Thr Glu Asp Gly Phe Asp Arg Asn
     1250                1255                1260
Cys Leu Lys Leu Pro His Ala Glu Trp Leu Asp Phe Ile Gln Asn
     1265                1270                1275
Lys Arg Tyr Glu Lys Arg Pro Ala Ala Thr Lys Lys Ala Gly Gln
     1280                1285                1290
Ala Lys Lys Lys Lys Gly Ser Tyr Pro Tyr Asp Val Pro Asp Tyr
     1295                1300                1305
Ala Tyr Pro Tyr Asp Val Pro Asp Tyr Ala Tyr Pro Tyr Asp Val
     1310                1315                1320
```

Pro Asp Tyr Ala
    1325

<210> SEQ ID NO 32
<211> LENGTH: 3984
<212> TYPE: DNA
<213> ORGANISM: Artificial Sequence
<220> FEATURE:
<223> OTHER INFORMATION: Synthetic-Eubacterium eligens (EeCpf1; pY013),
      including NLS and HA tag

<400> SEQUENCE: 32

| | | |
|---|---|---|
| atgaacggca ataggtccat cgtgtaccgc gagttcgtgg cgtgatccc cgtggccaag | 60 |
| accctgagga atgagctgcg ccctgtgggc cacacacagg agcacatcat ccagaacggc | 120 |
| ctgatccagg aggacgagct gcggcaggag aagagcaccg agctgaagaa catcatggac | 180 |
| gattactata gagagtacat cgataagtct ctgagcggcg tgaccgacct ggacttcacc | 240 |
| ctgctgttcg agctgatgaa cctggtgcag agctcccct ccaaggacaa taagaaggcc | 300 |
| ctggagaagg agcagtctaa gatgagggag cagatctgca cccacctgca gtccgactct | 360 |
| aactacaaga atatctttaa cgccaagctg ctgaaggaga tcctgcctga tttcatcaag | 420 |
| aactacaatc agtatgacgt gaaggataag gccggcaagc tggagacact ggccctgttt | 480 |
| aatggcttca gcacatactt taccgacttc tttgagaaga ggaagaacgt gttcaccaag | 540 |
| gaggccgtga gcacatccat cgcctaccgc atcgtgcacg agaactccct gatcttcctg | 600 |
| gccaatatga cctcttataa gaagatcagc gagaaggccc tggatgagat cgaagtgatc | 660 |
| gagaagaaca atcaggacaa gatgggcgat tgggagctga atcagatctt taaccctgac | 720 |
| ttctacaata tggtgctgat ccagtccggc atcgacttct acaacgagat ctgcggcgtg | 780 |
| gtgaatgccc acatgaacct gtactgtcag cagaccaaga acaattataa cctgttcaag | 840 |
| atgcggaagc tgcacaagca gatcctggcc tacaccagca ccagcttcga ggtgccaag | 900 |
| atgttcgagg acgatatgag cgtgtataac gccgtgaacg ccttcatcga cgagacagag | 960 |
| aagggcaaca tcatcggcaa gctgaaggat atcgtgaata agtacgacga gctggatgag | 1020 |
| aagagaatct atatcagcaa ggactttac gagacactga gctgcttcat gtccggcaac | 1080 |
| tggaatctga tcacaggctg cgtggagaac ttctacgatg agaacatcca cgccaagggc | 1140 |
| aagtccaagg aggagaaggt gaagaaggcc gtgaaggagg acagtacaa gtctatcaat | 1200 |
| gacgtgaacg atctggtgga agtatatc gatgagaagg agaggaatga gttcaagaac | 1260 |
| agcaatgcca agcagtacat ccgcgagatc tccaacatca tcaccgacac agagacagcc | 1320 |
| cacctggagt atgacgatca catctctctg atcgagagcg aggagaaggc cgacgagatg | 1380 |
| aagaagcggc tggatatgta tatgaacatg taccactggg ccaaggcctt tatcgtggac | 1440 |
| gaggtgctgg acagagatga gatgttctac agcgatatcg acgatatcta atatatcctg | 1500 |
| gagaacatcg tgccactgta taatcgggtg agaaactacg tgacccagaa gccctacaac | 1560 |
| tctaagaaga tcaagctgaa tttccagagc cctacactgg ccaatggctg gtcccagtct | 1620 |
| aaggagttcg acaacaatgc catcatcctg atcagagata acaagtacta tctggccatc | 1680 |
| ttcaatgcca gaacaagcc agacaagaag atcatccagg gcaactccga taagaagaac | 1740 |
| gacaacgatt acaagaagat ggtgtataac ctgctgccag cgccaacaa gatgctgccc | 1800 |
| aaggtgtttc tgtctaagaa gggcatcgag acattcaagc cctccgacta tatcatctct | 1860 |
| ggctacaacg cccacaagca catcaagaca agcgagaatt ttgatatctc cttctgtcgg | 1920 |

```
gacctgatcg attacttcaa gaacagcatc gagaagcacg ccgagtggag aaagtatgag    1980
ttcaagtttt ccgccaccga cagctactcc gatatctctg agttctatcg ggaggtggag    2040
atgcagggct acagaatcga ctggacatat atcagcgagg ccgacatcaa caagctggat    2100
gaggagggca agatctatct gtttcagatc tacaataagg atttcgccga gaacagcacc    2160
ggcaaggaga atctgcacac aatgtacttt aagaacatct tctccgagga gaatctgaag    2220
gacatcatca tcaagctgaa cggccaggcc gagctgtttt atcggagagc ctctgtgaag    2280
aatcccgtga agcacaagaa ggatagcgtg ctggtgaaca agacctacaa gaatcagctg    2340
gacaacggcg acgtggtgag aatccccatc cctgacgata tctataacga gatctacaag    2400
atgtataatg gctacatcaa ggagtccgac ctgtctgagg ccgccaagga gtacctggat    2460
aaggtggagg tgaggaccgc ccagaaggac atcgtgaagg attaccgcta tacagtggac    2520
aagtacttca tccacacacc tatcaccatc aactataagg tgaccgcccg caacaatgtg    2580
aatgatatgg tggtgaagta catcgcccag aacgacgata tccacgtgat cggcatcgac    2640
cggggcgaga gaaacctgat ctacatctcc gtgatcgatt ctcacggcaa catcgtgaag    2700
cagaaatcct acaacatcct gaacaactac gactacaaga agaagctggt ggagaaggag    2760
aaaacccggg agtacgccag aaagaactgg aagagcatcg gcaatatcaa ggagctgaag    2820
gagggctata tctccggcgt ggtgcacgag atcgccatgc tgatcgtgga gtacaacgcc    2880
atcatcgcca tggaggacct gaattatggc tttaagaggg ccgcttcaa ggtggagcgg    2940
caggtgtacc agaagtttga gagcatgctg atcaataagc tgaactattt cgccagcaag    3000
gagaagtccg tggacgagcc aggaggcctg ctgaagggct atcagctgac ctacgtgccc    3060
gataatatca gaacctgggc aagcagtgc ggcgtgatct tttacgtgcc tgccgccttc    3120
accagcaaga tcgacccatc cacaggcttt atctctgcct tcaactttaa gtctatcagc    3180
acaaatgcct ctcggaagca gttctttatg cagtttgacg agatcagata ctgtgccgag    3240
aaggatatgt tcagctttgg cttcgactac aacaacttcg ataacctacaa catcacaatg    3300
ggcaagacac agtggaccgt gtatacaaac ggcgagagac tgcagtctga gttcaacaat    3360
gccaggcgca ccggcaagac aaagagcatc aatctgacag agacaatcaa gctgctgctg    3420
gaggacaatg agatcaacta cgccgacggc cacgatatca ggatcgatat ggagaagatg    3480
gacgaggata gaagagcga gttctttgcc cagctgctga gcctgtataa gctgaccgtg    3540
cagatgcgca attcctatac agaggccgag gagcaggaga acggcatctc ttacgacaag    3600
atcatcagcc ctgtgatcaa tgatgagggc gagttctttg actccgataa ctataaggag    3660
tctgacgata aggagtgcaa gatgccaaag gacgccgatg ccaacggcgc ctactgtatc    3720
gccctgaagg gcctgtatga ggtgctgaag atcaagagcg agtggaccga ggacggcttt    3780
gataggaatt gcctgaagct gccacacgca gagtggctgg acttcatcca gaacaagcgg    3840
tacgagaaaa ggccggcggc cacgaaaaag gccggccagg caaaaaagaa aaagggatcc    3900
tacccatacg atgttccaga ttacgcttat ccctacgacg tgcctgatta tgcatacccca    3960
tatgatgtcc ccgactatgc ctaa                                            3984
```

<210> SEQ ID NO 33
<211> LENGTH: 1418
<212> TYPE: PRT
<213> ORGANISM: Artificial Sequence
<220> FEATURE:
<223> OTHER INFORMATION: Synthetic-Moraxella bovoculi 237 (MbCpf1;
      pY014), including NLS and HA tag

<400> SEQUENCE: 33

Met Leu Phe Gln Asp Phe Thr His Leu Tyr Pro Leu Ser Lys Thr Val
1               5                   10                  15

Arg Phe Glu Leu Lys Pro Ile Asp Arg Thr Leu Glu His Ile His Ala
            20                  25                  30

Lys Asn Phe Leu Ser Gln Asp Glu Thr Met Ala Asp Met His Gln Lys
                35                  40                  45

Val Lys Val Ile Leu Asp Asp Tyr His Arg Asp Phe Ile Ala Asp Met
    50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Asp Glu Leu Gln Lys Gln Leu
                85                  90                  95

Lys Asp Leu Gln Ala Val Leu Arg Lys Glu Ile Val Lys Pro Ile Gly
            100                 105                 110

Asn Gly Gly Lys Tyr Lys Ala Gly Tyr Asp Arg Leu Phe Gly Ala Lys
                115                 120                 125

Leu Phe Lys Asp Gly Lys Glu Leu Gly Asp Leu Ala Lys Phe Val Ile
130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
        195                 200                 205

Ile Lys Gln Lys His Ser Ala Leu Tyr Asp Gln Ile Ile Asn Glu Leu
210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
                245                 250                 255

Gly Gly Ile Ser Gly Glu Ala Gly Ser Pro Lys Ile Gln Gly Ile Asn
            260                 265                 270

Glu Leu Ile Asn Ser His His Asn Gln His Cys His Lys Ser Glu Arg
        275                 280                 285

Ile Ala Lys Leu Arg Pro Leu His Lys Gln Ile Leu Ser Asp Gly Met
290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
            340                 345                 350

Tyr Val Glu His Lys Asn Leu Asn Glu Leu Ser Lys Gln Ala Phe Gly
        355                 360                 365

Asp Phe Ala Leu Leu Gly Arg Val Leu Asp Gly Tyr Tyr Val Asp Val
370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

```
His Ser Leu Ala Ser Leu Glu Gln Ala Ile Glu His Tyr Thr Ala Arg
            420                 425                 430

His Asp Asp Glu Ser Val Gln Ala Gly Lys Leu Gly Gln Tyr Phe Lys
            435                 440                 445

His Gly Leu Ala Gly Val Asp Asn Pro Ile Gln Lys Ile His Asn Asn
450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
                485                 490                 495

Leu Arg Gln Leu Lys Glu Leu Leu Asp Asn Ala Leu Asn Val Ala His
            500                 505                 510

Phe Ala Lys Leu Leu Thr Thr Lys Thr Thr Leu Asp Asn Gln Asp Gly
            515                 520                 525

Asn Phe Tyr Gly Glu Phe Gly Val Leu Tyr Asp Glu Leu Ala Lys Ile
530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
                565                 570                 575

Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
            595                 600                 605

Val Phe Asp Asn Ala Pro Asn Thr Gly Lys Ser Ile Tyr Gln Lys Met
            610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
                645                 650                 655

Glu Ile Lys Asp Lys Gly Arg Gln Arg Ser Asp Asp Glu Arg Leu Lys
            660                 665                 670

Leu Tyr Arg Phe Ile Leu Glu Cys Leu Lys Ile His Pro Lys Tyr Asp
            675                 680                 685

Lys Lys Phe Glu Gly Ala Ile Gly Asp Ile Gln Leu Phe Lys Lys Asp
            690                 695                 700

Lys Lys Gly Arg Glu Val Pro Ile Ser Glu Lys Asp Leu Phe Asp Lys
705                 710                 715                 720

Ile Asn Gly Ile Phe Ser Ser Lys Pro Lys Leu Glu Met Glu Asp Phe
                725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
            755                 760                 765

Glu Asn Phe Tyr Asn Asn His Pro Lys Phe Lys Lys Asp Leu Val Arg
            770                 775                 780

Tyr Tyr Tyr Glu Ser Met Cys Lys His Glu Glu Trp Glu Glu Ser Phe
785                 790                 795                 800

Glu Phe Ser Lys Lys Leu Gln Asp Ile Gly Cys Tyr Val Asp Val Asn
                805                 810                 815

Glu Leu Phe Thr Glu Ile Glu Thr Arg Arg Leu Asn Tyr Lys Ile Ser
            820                 825                 830
```

```
Phe Cys Asn Ile Asn Ala Asp Tyr Ile Asp Glu Leu Val Glu Gln Gly
            835                 840                 845

Gln Leu Tyr Leu Phe Gln Ile Tyr Asn Lys Asp Phe Ser Pro Lys Ala
    850                 855                 860

His Gly Lys Pro Asn Leu His Thr Leu Tyr Phe Lys Ala Leu Phe Ser
865                 870                 875                 880

Glu Asp Asn Leu Ala Asp Pro Ile Tyr Lys Leu Asn Gly Glu Ala Gln
                885                 890                 895

Ile Phe Tyr Arg Lys Ala Ser Leu Asp Met Asn Glu Thr Thr Ile His
            900                 905                 910

Arg Ala Gly Glu Val Leu Glu Asn Lys Asn Pro Asp Asn Pro Lys Lys
            915                 920                 925

Arg Gln Phe Val Tyr Asp Ile Ile Lys Asp Lys Arg Tyr Thr Gln Asp
            930                 935                 940

Lys Phe Met Leu His Val Pro Ile Thr Met Asn Phe Gly Val Gln Gly
945                 950                 955                 960

Met Thr Ile Lys Glu Phe Asn Lys Lys Val Asn Gln Ser Ile Gln Gln
                965                 970                 975

Tyr Asp Glu Val Asn Val Ile Gly Ile Asp Arg Gly Glu Arg His Leu
            980                 985                 990

Leu Tyr Leu Thr Val Ile Asn Ser  Lys Gly Glu Ile Leu  Glu Gln Cys
        995                 1000                1005

Ser Leu Asn Asp Ile Thr Thr  Ala Ser Ala Asn Gly  Thr Gln Met
    1010                1015                1020

Thr Thr Pro Tyr His Lys Ile  Leu Asp Lys Arg Glu  Ile Glu Arg
    1025                1030                1035

Leu Asn Ala Arg Val Gly Trp  Gly Glu Ile Glu Thr  Ile Lys Glu
    1040                1045                1050

Leu Lys Ser Gly Tyr Leu Ser  His Val Val His Gln  Ile Ser Gln
    1055                1060                1065

Leu Met Leu Lys Tyr Asn Ala  Ile Val Val Leu Glu  Asp Leu Asn
    1070                1075                1080

Phe Gly Phe Lys Arg Gly Arg  Phe Lys Val Glu Lys  Gln Ile Tyr
    1085                1090                1095

Gln Asn Phe Glu Asn Ala Leu  Ile Lys Lys Leu Asn  His Leu Val
    1100                1105                1110

Leu Lys Asp Lys Ala Asp Asp  Glu Ile Gly Ser Tyr  Lys Asn Ala
    1115                1120                1125

Leu Gln Leu Thr Asn Asn Phe  Thr Asp Leu Lys Ser  Ile Gly Lys
    1130                1135                1140

Gln Thr Gly Phe Leu Phe Tyr  Val Pro Ala Trp Asn  Thr Ser Lys
    1145                1150                1155

Ile Asp Pro Glu Thr Gly Phe  Val Asp Leu Leu Lys  Pro Arg Tyr
    1160                1165                1170

Glu Asn Ile Ala Gln Ser Gln  Ala Phe Phe Gly Lys  Phe Asp Lys
    1175                1180                1185

Ile Cys Tyr Asn Ala Asp Lys  Asp Tyr Phe Glu Phe  His Ile Asp
    1190                1195                1200

Tyr Ala Lys Phe Thr Asp Lys  Ala Lys Asn Ser Arg  Gln Ile Trp
    1205                1210                1215

Thr Ile Cys Ser His Gly Asp  Lys Arg Tyr Val Tyr  Asp Lys Thr
    1220                1225                1230

Ala Asn Gln Asn Lys Gly Ala  Ala Lys Gly Ile Asn  Val Asn Asp
```

1235                1240                1245
Glu Leu Lys Ser Leu Phe Ala Arg His His Ile Asn Glu Lys Gln
              1250                1255                1260
Pro Asn Leu Val Met Asp Ile Cys Gln Asn Asn Asp Lys Glu Phe
          1265                1270                1275
His Lys Ser Leu Met Tyr Leu Leu Lys Thr Leu Leu Ala Leu Arg
      1280                1285                1290
Tyr Ser Asn Ala Ser Ser Asp Glu Asp Phe Ile Leu Ser Pro Val
  1295                1300                1305
Ala Asn Asp Glu Gly Val Phe Phe Asn Ser Ala Leu Ala Asp Asp
  1310                1315                1320
Thr Gln Pro Gln Asn Ala Asp Ala Asn Gly Ala Tyr His Ile Ala
      1325                1330                1335
Leu Lys Gly Leu Trp Leu Leu Asn Glu Leu Lys Asn Ser Asp Asp
      1340                1345                1350
Leu Asn Lys Val Lys Leu Ala Ile Asp Asn Gln Thr Trp Leu Asn
      1355                1360                1365
Phe Ala Gln Asn Arg Lys Arg Pro Ala Ala Thr Lys Lys Ala Gly
      1370                1375                1380
Gln Ala Lys Lys Lys Lys Gly Ser Tyr Pro Tyr Asp Val Pro Asp
      1385                1390                1395
Tyr Ala Tyr Pro Tyr Asp Val Pro Asp Tyr Ala Tyr Pro Tyr Asp
      1400                1405                1410
Val Pro Asp Tyr Ala
      1415

<210> SEQ ID NO 34
<211> LENGTH: 4257
<212> TYPE: DNA
<213> ORGANISM: Artificial Sequence
<220> FEATURE:
<223> OTHER INFORMATION: Synthetic-Moraxella bovoculi 237 (MbCpf1;
      pY014), including NLS and HA tag

<400> SEQUENCE: 34
atgctgttcc aggactttac ccacctgtat ccactgtcca agacagtgag atttgagctg      60
aagcccatcg ataggaccct ggagcacatc cacgccaaga acttcctgtc tcaggacgag     120
acaatggccg atatgcacca gaaggtgaaa gtgatcctgg acgattacca ccgcgacttc     180
atcgccgata tgatgggcga ggtgaagctg accaagctgg ccgagttcta tgacgtgtac     240
ctgaagtttc ggaagaaccc aaaggacgat gagctgcaga gcagctgaa ggatctgcag      300 gccgtgctga aaggagat cgtgaagccc atcggcaatg cggcaagta taaggccggc        360 tacgacaggc tgttcggcgc caagctgttt aaggacggca aggagctggg cgatctggcc     420
aagttcgtga tcgcacagga gggagagagc tccccaaagc tggcccacct ggcccacttc     480
gagaagtttt ccacctattt cacaggcttt cacgataacc ggaagaatat gtattctgac     540
gaggataagc acaccgccat cgcctaccgc ctgatccacg agaacctgcc ccggtttatc     600
gacaatctgc agatcctgac cacaatcaag cagaagcact ctgccctgta cgatcagatc     660
atcaacgagc tgaccgccag cggcctggac gtgtctctgg ccagccacct ggatggctat     720
cacaagctgc tgacacagga gggcatcacc gcctacaata cactgctggg aggaatctcc     780
ggagaggcag gctctcctaa gatccagggc atcaacgagc tgatcaattc tcaccacaac     840
cagcactgcc acaagagcga gagaatcgcc aagctgaggc cactgcacaa gcagatcctg     900

```
tccgacggca tgagcgtgtc cttcctgccc tctaagtttg ccgacgatag cgagatgtgc    960
caggccgtga acgagttcta tcgccactac gccgacgtgt cgccaaggt gcagagcctg    1020
ttcgacggct ttgacgatca ccagaaggat ggcatctacg tggagcacaa gaacctgaat   1080
gagctgtcca agcaggcctt cggcgacttt gcactgctgg acgcgtgct ggacggatac    1140
tatgtggatg tggtgaatcc agagttcaac gagcggtttg ccaaggccaa gaccgacaat   1200
gccaaggcca agctgacaaa ggagaaggat aagttcatca agggcgtgca ctccctggcc   1260
tctctggagc aggccatcga gcactatacc gcaaggcacg acgatgagag cgtgcaggca   1320
ggcaagctgg acagtactt caagcacggc ctggccggag tggacaaccc catccagaag    1380
atccacaaca atcacagcac catcaagggc tttctggaga gggagcgccc tgcaggagag   1440
agagccctgc aaagatcaa gtccggcaag aatcctgaga tgacacagct gaggcagctg    1500
aaggagctgc tggataacgc cctgaatgtg gcccacttcg ccaagctgct gaccacaaag   1560
accacactgg acaatcagga tgcaacttc tatggcgagt ttggcgtgct gtacgacgag    1620
ctggccaaga tccccaccct gtataacaag gtgagagatt acctgagcca gaagcctttc   1680
tccaccgaga agtacaagct gaactttggc aatccaacac tgctgaatgg ctgggacctg   1740
aacaaggaga aggataattt cggcgtgatc ctgcagaagg acggctgcta ctatctggcc   1800
ctgctggaca aggcccacaa gaaggtgttt gataacgccc ctaatacagg caagagcatc   1860
tatcagaaga tgatctataa gtacctggag gtgaggaagc agttccccaa ggtgttcttt   1920
tccaaggagg ccatcgccat caactaccac ccttctaagg agctggtgga gatcaaggac   1980
aagggccggc agagatccga cgatgagcgc ctgaagctgt atcggtttat cctggagtgt   2040
ctgaagatcc accctaagta cgataagaag ttcgagggcg ccatcggcga catccagctg   2100
tttaagaagg ataagaaggg cagagaggtg ccaatcagcg agaaggacct gttcgataag   2160
atcaacggca tcttttctag caagcctaag ctggagatgg aggacttctt tatcggcgag   2220
ttcaagaggt ataacccaag ccaggacctg gtggatcagt ataatatcta caagaagatc   2280
gactccaacg ataatcgcaa gaaggagaat ttctacaaca atcaccccaa gtttaagaag   2340
gatctggtgc ggtactatta cgagtctatg tgcaagcacg aggagtggga ggagagcttc   2400
gagttttcca agaagctgca ggacatcggc tgttacgtgg atgtgaacga gctgtttacc   2460
gagatcgaga cacggagact gaattataag atctccttct gcaacatcaa tgccgactac   2520
atcgatgagc tggtggagca gggccagctg tatctgttcc agatctacaa caaggacttt   2580
tccccaaagg cccacggcaa gcccaatctg cacaccctgt acttcaaggc cctgtttttct  2640
gaggacaacc tggccgatcc tatctataag ctgaatggcg aggcccagat cttctacaga   2700
aaggcctccc tggacatgaa cgagacaaca atccacaggg ccggcgaggt gctggagaac   2760
aagaatcccg ataatcctaa gagagacag ttcgtgtacg acatcatcaa ggataagagg   2820
tacacacagg acaagttcat gctgcacgtg ccaatcacca tgaactttgg cgtgcagggc   2880
atgacaatca aggagttcaa taagaaggtg aaccagtcta ccagcagta tgacgaggtg   2940
aacgtgatcg gcatcgatcg gggcgagaga cacctgctgt acctgaccgt gatcaatagc   3000
aagggcgaga tcctggagca gtgttccctg aacgacatca ccacagcctc tgccaatggc   3060
acacagatga ccacaccttta ccacaagatc ctggataaga gggagatcga gcgcctgaac   3120
gcccgggtgg atggggcga gatcgagaca atcaaggagc tgaagtctgg ctatctgagc   3180
cacgtggtgc accagatcag ccagctgatg ctgaagtaca acgccatcgt ggtgctggag   3240
gacctgaatt tcggctttaa gaggggccgc tttaaggtgg agaagcagat ctatcagaac   3300
```

```
ttcgagaatg ccctgatcaa gaagctgaac cacctggtgc tgaaggacaa ggccgacgat    3360
gagatcggct cttacaagaa tgccctgcag ctgaccaaca atttcacaga tctgaagagc    3420
atcggcaagc agaccggctt cctgttttat gtgcccgcct ggaacacctc taagatcgac    3480
cctgagacag gctttgtgga tctgctgaag ccaagatacg agaacatcgc ccagagccag    3540
gccttctttg gcaagttcga caagatctgc tataatgccg acaaggatta cttcgagttt    3600
cacatcgact acgccaagtt taccgataag gccaagaata ccgccagat ctggacaatc    3660 tgttcccacg gcgacaagcg gtacgtgtac gataagacag ccaaccagaa taagggcgcc    3720
gccaagggca tcaacgtgaa tgatgagctg aagtccctgt cgcccgcca ccacatcaac    3780 gagaagcagc ccaacctggt catggacatc tgccagaaca atgataagga gtttcacaag    3840
tctctgatgt acctgctgaa aaccctgctg gccctgcggt acagcaacgc ctcctctgac    3900
gaggatttca tcctgtcccc cgtggcaaac gacgagggcg tgttctttaa tagcgccctg    3960
gccgacgata cacagcctca gaatgccgat gccaacggcg cctaccacat cgccctgaag    4020
ggcctgtggc tgctgaatga gctgaagaac tccgacgatc tgaacaaggt gaagctggcc    4080
atcgacaatc agacctggct gaatttcgcc cagaacagga aaggccggc ggccacgaaa    4140 aaggccggcc aggcaaaaaa gaaaaaggga tcctacccat cgatgttcc agattacgct    4200 tatccctacg acgtgcctga ttatgcatac ccatatgatg tccccgacta tgcctaa      4257
```

<210> SEQ ID NO 35
<211> LENGTH: 1308
<212> TYPE: PRT
<213> ORGANISM: Artificial Sequence
<220> FEATURE:
<223> OTHER INFORMATION: Synthetic-Leptospira inadai (LiCpf1; pY015),
      including NLS and HA tag

<400> SEQUENCE: 35

```
Met Glu Asp Tyr Ser Gly Phe Val Asn Ile Tyr Ser Ile Gln Lys Thr
1               5                   10                  15

Leu Arg Phe Glu Leu Lys Pro Val Gly Lys Thr Leu Glu His Ile Glu
            20                  25                  30

Lys Lys Gly Phe Leu Lys Lys Asp Lys Ile Arg Ala Glu Asp Tyr Lys
        35                  40                  45

Ala Val Lys Lys Ile Ile Asp Lys Tyr His Arg Ala Tyr Ile Glu Glu
    50                  55                  60

Val Phe Asp Ser Val Leu His Gln Lys Lys Lys Asp Lys Thr Arg
65                  70                  75                  80

Phe Ser Thr Gln Phe Ile Lys Glu Ile Lys Glu Phe Ser Glu Leu Tyr
                85                  90                  95

Tyr Lys Thr Glu Lys Asn Ile Pro Asp Lys Glu Arg Leu Glu Ala Leu
            100                 105                 110

Ser Glu Lys Leu Arg Lys Met Leu Val Gly Ala Phe Lys Gly Glu Phe
        115                 120                 125

Ser Glu Glu Val Ala Glu Lys Tyr Lys Asn Leu Phe Ser Lys Glu Leu
    130                 135                 140

Ile Arg Asn Glu Ile Glu Lys Phe Cys Glu Thr Asp Glu Glu Arg Lys
145                 150                 155                 160

Gln Val Ser Asn Phe Lys Ser Phe Thr Thr Tyr Phe Thr Gly Phe His
                165                 170                 175

Ser Asn Arg Gln Asn Ile Tyr Ser Asp Glu Lys Lys Ser Thr Ala Ile
            180                 185                 190
```

```
Gly Tyr Arg Ile Ile His Gln Asn Leu Pro Lys Phe Leu Asp Asn Leu
        195                 200                 205
Lys Ile Ile Glu Ser Ile Gln Arg Arg Phe Lys Asp Phe Pro Trp Ser
210                 215                 220
Asp Leu Lys Lys Asn Leu Lys Lys Ile Asp Lys Asn Ile Lys Leu Thr
225                 230                 235                 240
Glu Tyr Phe Ser Ile Asp Gly Phe Val Asn Val Leu Asn Gln Lys Gly
                245                 250                 255
Ile Asp Ala Tyr Asn Thr Ile Leu Gly Gly Lys Ser Glu Glu Ser Gly
                260                 265                 270
Glu Lys Ile Gln Gly Leu Asn Glu Tyr Ile Asn Leu Tyr Arg Gln Lys
            275                 280                 285
Asn Asn Ile Asp Arg Lys Asn Leu Pro Asn Val Lys Ile Leu Phe Lys
290                 295                 300
Gln Ile Leu Gly Asp Arg Glu Thr Lys Ser Phe Ile Pro Glu Ala Phe
305                 310                 315                 320
Pro Asp Asp Gln Ser Val Leu Asn Ser Ile Thr Glu Phe Ala Lys Tyr
                325                 330                 335
Leu Lys Leu Asp Lys Lys Lys Ser Ile Ile Ala Glu Leu Lys Lys
            340                 345                 350
Phe Leu Ser Ser Phe Asn Arg Tyr Glu Leu Asp Gly Ile Tyr Leu Ala
            355                 360                 365
Asn Asp Asn Ser Leu Ala Ser Ile Ser Thr Phe Leu Phe Asp Asp Trp
370                 375                 380
Ser Phe Ile Lys Lys Ser Val Ser Phe Lys Tyr Asp Glu Ser Val Gly
385                 390                 395                 400
Asp Pro Lys Lys Ile Lys Ser Pro Leu Lys Tyr Glu Lys Glu Lys
                405                 410                 415
Glu Lys Trp Leu Lys Gln Lys Tyr Tyr Thr Ile Ser Phe Leu Asn Asp
            420                 425                 430
Ala Ile Glu Ser Tyr Ser Lys Ser Gln Asp Glu Lys Arg Val Lys Ile
        435                 440                 445
Arg Leu Glu Ala Tyr Phe Ala Glu Phe Lys Ser Lys Asp Asp Ala Lys
    450                 455                 460
Lys Gln Phe Asp Leu Leu Glu Arg Ile Glu Glu Ala Tyr Ala Ile Val
465                 470                 475                 480
Glu Pro Leu Leu Gly Ala Glu Tyr Pro Arg Asp Arg Asn Leu Lys Ala
                485                 490                 495
Asp Lys Lys Glu Val Gly Lys Ile Lys Asp Phe Leu Asp Ser Ile Lys
                500                 505                 510
Ser Leu Gln Phe Phe Leu Lys Pro Leu Leu Ser Ala Glu Ile Phe Asp
            515                 520                 525
Glu Lys Asp Leu Gly Phe Tyr Asn Gln Leu Glu Gly Tyr Tyr Glu Glu
            530                 535                 540
Ile Asp Ser Ile Gly His Leu Tyr Asn Lys Val Arg Asn Tyr Leu Thr
545                 550                 555                 560
Gly Lys Ile Tyr Ser Lys Glu Lys Phe Lys Leu Asn Phe Glu Asn Ser
                565                 570                 575
Thr Leu Leu Lys Gly Trp Asp Glu Asn Arg Glu Val Ala Asn Leu Cys
            580                 585                 590
Val Ile Phe Arg Glu Asp Gln Lys Tyr Tyr Leu Gly Val Met Asp Lys
            595                 600                 605
```

```
Glu Asn Asn Thr Ile Leu Ser Asp Ile Pro Lys Val Lys Pro Asn Glu
    610                 615                 620
Leu Phe Tyr Glu Lys Met Val Tyr Lys Leu Ile Pro Thr Pro His Met
625                 630                 635                 640
Gln Leu Pro Arg Ile Ile Phe Ser Ser Asp Asn Leu Ser Ile Tyr Asn
                645                 650                 655
Pro Ser Lys Ser Ile Leu Lys Ile Arg Glu Ala Lys Ser Phe Lys Glu
                660                 665                 670
Gly Lys Asn Phe Lys Leu Lys Asp Cys His Lys Phe Ile Asp Phe Tyr
                675                 680                 685
Lys Glu Ser Ile Ser Lys Asn Glu Asp Trp Ser Arg Phe Asp Phe Lys
    690                 695                 700
Phe Ser Lys Thr Ser Ser Tyr Glu Asn Ile Ser Glu Phe Tyr Arg Glu
705                 710                 715                 720
Val Glu Arg Gln Gly Tyr Asn Leu Asp Phe Lys Lys Val Ser Lys Phe
                725                 730                 735
Tyr Ile Asp Ser Leu Val Glu Asp Gly Lys Leu Tyr Leu Phe Gln Ile
                740                 745                 750
Tyr Asn Lys Asp Phe Ser Ile Phe Ser Lys Gly Lys Pro Asn Leu His
                755                 760                 765
Thr Ile Tyr Phe Arg Ser Leu Phe Ser Lys Glu Asn Leu Lys Asp Val
    770                 775                 780
Cys Leu Lys Leu Asn Gly Glu Ala Glu Met Phe Arg Lys Lys Ser
785                 790                 795                 800
Ile Asn Tyr Asp Glu Lys Lys Arg Glu Gly His His Pro Glu Leu
                805                 810                 815
Phe Glu Lys Leu Lys Tyr Pro Ile Leu Lys Asp Lys Arg Tyr Ser Glu
                820                 825                 830
Asp Lys Phe Gln Phe His Leu Pro Ile Ser Leu Asn Phe Lys Ser Lys
                835                 840                 845
Glu Arg Leu Asn Phe Asn Leu Lys Val Asn Glu Phe Leu Lys Arg Asn
    850                 855                 860
Lys Asp Ile Asn Ile Ile Gly Ile Asp Arg Gly Glu Arg Asn Leu Leu
865                 870                 875                 880
Tyr Leu Val Met Ile Asn Gln Lys Gly Glu Ile Leu Lys Gln Thr Leu
                885                 890                 895
Leu Asp Ser Met Gln Ser Gly Lys Gly Arg Pro Glu Ile Asn Tyr Lys
                900                 905                 910
Glu Lys Leu Gln Glu Lys Glu Ile Glu Arg Asp Lys Ala Arg Lys Ser
                915                 920                 925
Trp Gly Thr Val Glu Asn Ile Lys Glu Leu Lys Glu Gly Tyr Leu Ser
    930                 935                 940
Ile Val Ile His Gln Ile Ser Lys Leu Met Val Glu Asn Asn Ala Ile
945                 950                 955                 960
Val Val Leu Glu Asp Leu Asn Ile Gly Phe Lys Arg Gly Arg Gln Lys
                965                 970                 975
Val Glu Arg Gln Val Tyr Gln Lys Phe Glu Lys Met Leu Ile Asp Lys
                980                 985                 990
Leu Asn Phe Leu Val Phe Lys Glu Asn Lys Pro Thr Glu Pro Gly Gly
                995                 1000                1005
Val Leu Lys Ala Tyr Gln Leu Thr Asp Glu Phe Gln Ser Phe Glu
    1010                1015                1020
Lys Leu Ser Lys Gln Thr Gly Phe Leu Phe Tyr Val Pro Ser Trp
```

|      |      |      |      | 1025 |      |      |      |      | 1030 |      |      |      |      | 1035 |
|------|------|------|------|------|------|------|------|------|------|------|------|------|------|------|

Asn Thr Ser Lys Ile Asp Pro Arg Thr Gly Phe Ile Asp Phe Leu
           1040                1045               1050

His Pro Ala Tyr Glu Asn Ile Glu Lys Ala Lys Gln Trp Ile Asn
           1055                1060               1065

Lys Phe Asp Ser Ile Arg Phe Asn Ser Lys Met Asp Trp Phe Glu
           1070                1075               1080

Phe Thr Ala Asp Thr Arg Lys Phe Ser Glu Asn Leu Met Leu Gly
           1085                1090               1095

Lys Asn Arg Val Trp Val Ile Cys Thr Thr Asn Val Glu Arg Tyr
           1100                1105               1110

Phe Thr Ser Lys Thr Ala Asn Ser Ser Ile Gln Tyr Asn Ser Ile
           1115                1120               1125

Gln Ile Thr Glu Lys Leu Lys Glu Leu Phe Val Asp Ile Pro Phe
           1130                1135               1140

Ser Asn Gly Gln Asp Leu Lys Pro Glu Ile Leu Arg Lys Asn Asp
           1145                1150               1155

Ala Val Phe Phe Lys Ser Leu Leu Phe Tyr Ile Lys Thr Thr Leu
           1160                1165               1170

Ser Leu Arg Gln Asn Asn Gly Lys Lys Gly Glu Glu Glu Lys Asp
           1175                1180               1185

Phe Ile Leu Ser Pro Val Val Asp Ser Lys Gly Arg Phe Phe Asn
           1190                1195               1200

Ser Leu Glu Ala Ser Asp Asp Glu Pro Lys Asp Ala Asp Ala Asn
           1205                1210               1215

Gly Ala Tyr His Ile Ala Leu Lys Gly Leu Met Asn Leu Leu Val
           1220                1225               1230

Leu Asn Glu Thr Lys Glu Glu Asn Leu Ser Arg Pro Lys Trp Lys
           1235                1240               1245

Ile Lys Asn Lys Asp Trp Leu Glu Phe Val Trp Glu Arg Asn Arg
           1250                1255               1260

Lys Arg Pro Ala Ala Thr Lys Lys Ala Gly Gln Ala Lys Lys Lys
           1265                1270               1275

Lys Gly Ser Tyr Pro Tyr Asp Val Pro Asp Tyr Ala Tyr Pro Tyr
           1280                1285               1290

Asp Val Pro Asp Tyr Ala Tyr Pro Tyr Asp Val Pro Asp Tyr Ala
           1295                1300               1305

<210> SEQ ID NO 36
<211> LENGTH: 3927
<212> TYPE: DNA
<213> ORGANISM: Artificial Sequence
<220> FEATURE:
<223> OTHER INFORMATION: Synthetic-Leptospira inadai (LiCpf1; pY015),
      including NLS and HA tag

<400> SEQUENCE: 36

```
atggaggact attccggctt tgtgaacatc tactctatcc agaaaaccct gaggttcgag      60
ctgaagccag tgggcaagac actggagcac atcgagaaga agggcttcct gaagaaggac     120
aagatccggg ccgaggatta caaggccgtg aagaagatca tcgataagta ccacagagcc     180
tatatcgagg aggtgtttga ttccgtgctg caccagaaga agaagaagga caagacccgc     240
ttttctacac agttcatcaa ggagatcaag gagttcagcg agctgtacta taagaccgag     300
aagaacatcc ccgacaagga gaggctggag gccctgagcg agaagctgcg caagatgctg     360
```

```
gtgggcgcct ttaagggcga gttctccgag gaggtggccg agaagtataa gaacctgttt      420
tctaaggagc tgatcaggaa tgagatcgag aagttctgcg agacagacga ggagcgcaag      480
caggtgtcta acttcaagag cttcaccaca tactttaccg gcttccactc caacaggcag      540
aatatctatt ccgacgagaa gaagtctaca gccatcggct accgcatcat ccaccagaac      600
ctgcctaagt tcctggataa tctgaagatc atcgagtcca tccagcggcg gttcaaggac      660
ttcccatggt ctgatctgaa gaagaacctg aagaagatcg ataagaatat caagctgacc      720
gagtacttca gcatcgacgg cttcgtgaac gtgctgaatc agaagggcat cgatgcctac      780
aacacaatcc tgggcggcaa gtccgaggag tctggcgaga agatccaggg cctgaacgag      840
tacatcaatc tgtatcggca agaacaat atcgacagaa agaacctgcc caatgtgaag      900
atcctgttta gcagatcct gggcgatagg gagacaaaga gctttatccc tgaggccttc      960
ccagacgatc agtccgtgct gaactctatc acagagttcg ccaagtacct gaagctggat     1020
aagaagaaga gagcatcat cgccgagctg aagaagtttc tgagctcctt caatcgctac     1080
gagctggacg gcatctatct ggccaacgat aatagcctgg cctctatcag caccttcctg     1140
tttgacgatt ggtcctttat caagaagtcc gtgtctttca gtatgacga gtccgtgggc     1200 gaccccaaga agaagatcaa gtctcccctg aagtacgaga ggagaagga gaagtggctg     1260 aagcagaagt actatacaat ctctttcctg aacgatgcca tcgagagcta ttccaagtct     1320
caggacgaga gagggtgaa gatccgcctg gaggcctact tgccgagtt caagagcaag     1380 gacgatgcca agaagcagtt cgacctgctg gagaggatcg aggaggccta tgccatcgtg     1440
gagcctctgc tgggagcaga gtacccaagg gaccgcaacc tgaaggccga taagaaggaa     1500
gtgggcaaga tcaaggactt cctggatagc atcaagtccc tgcagttctt tctgaagcct     1560
ctgctgtccg ccgagatctt tgacgagaag gatctgggct tctacaatca gctggagggc     1620
tactatgagg agatcgattc tatcggccac ctgtataaca aggtgcggaa ttatctgacc     1680
ggcaagatct acagcaagga gaagtttaag ctgaacttcg agaacagcac cctgctgaag     1740
ggctgggacg agaaccggga ggtggccaat ctgtgcgtga tcttcagaga ggaccagaag     1800
tactatctgg gcgtgatgga taaggagaac aataccatcc tgtccgacat ccccaaggtg     1860
aagcctaacg agctgtttta cgagaagatg gtgtataagc tgatccccac acctcacatg     1920
cagctgcccc ggatcatctt ctctagcgac aacctgtcta tctataatcc tagcaagtcc     1980
atcctgaaga tcagagaggc caagagcttt aaggagggca gaacttcaa gctgaaggac     2040 tgtcacaagt ttatcgattt ctacaaggag tctatcagca agaatgagga ctggagcaga     2100
ttcgacttca gttcagcaa gaccagcagc tacgagaaca tcagcgagtt ttaccgggag     2160
gtggagagac agggctataa cctggacttc aagaaggtgt ctaagttcta catcgacagc     2220
ctggtggagg atggcaagct gtacctgttc cagatctata caaggacttt ttctatcttc     2280
agcaagggca gcccaatct gcacaccatc tattttcggt ccctgttctc taaggagaac     2340
ctgaaggacg tgtgcctgaa gctgaatggc gaggccgaga tgttctttcg gaagaagtcc     2400
atcaactacg atgagaagaa gaagcgggag ggccaccacc ccgagctgtt tgagaagctg     2460
aagtatccta tcctgaagga caagagatac agcgaggata gtttcagtt ccacctgccc     2520 atcagcctga acttcaagtc caaggagcgg ctgaacttta tctgaaagt gaatgagttc     2580 ctgaagagaa acaaggacat caatatcatc ggcatcgatc ggggcgagag aaacctgctg     2640
tacctggtca tgatcaatca gaagggcgag atcctgaagc agaccctgct ggacagcatg     2700
cagtccggca agggccggcc tgagatcaac tacaaggaga agctgcagga aaggagatc     2760
```

-continued

```
gagagggata aggcccgcaa gagctggggc acagtggaga atatcaagga gctgaaggag    2820
ggctatctgt ctatcgtgat ccaccagatc agcaagctga tggtggagaa caatgccatc    2880
gtggtgctgg aggacctgaa catcggcttt aagcggggca gacagaaggt ggagcggcag    2940
gtgtaccaga agttcgagaa gatgctgatc gataagctga actttctggt gttcaaggag    3000
aataagccaa ccgagccagg aggcgtgctg aaggcctatc agctgacaga cgagtttcag    3060
tctttcgaga gctgagcaa gcagaccggc tttctgttct acgtgccaag ctggaacacc    3120
tccaagatcg accccagaac aggctttatc gatttcctgc accctgccta cgagaatatc    3180
gagaaggcca agcagtggat caacaagttt gattccatca ggttcaattc taagatggac    3240
tggtttgagt tcaccgccga tacacgcaag tttttcgaga acctgatgct gggcaagaat    3300
cgggtgtggg tcatctgcac cacaaatgtg gagcggtact tcaccagcaa gaccgccaac    3360
agctccatcc agtacaatag catccagatc accgagaagc tgaaggagct gtttgtggac    3420
atcccttca gcaacggcca ggatctgaag ccagagatcc tgaggaagaa tgacgccgtg    3480
ttctttaaga gcctgctgtt ttacatcaag accacactgt ccctgcgcca gaacaatggc    3540
aagaagggcg aggaggagaa ggacttcatc ctgagcccag tggtggattc caagggccgg    3600
ttctttaact ctctggaggc cagcgacgat gagcccaagg acgccgatgc caatggcgcc    3660
taccacatcg ccctgaaggg cctgatgaac ctgctggtgc tgaatgagac aaaggaggag    3720
aacctgagca gaccaaagtg gaagatcaag aataaggact ggctggagtt cgtgtgggag    3780
aggaaccgca aaggccggc ggccacgaaa aaggccggcc aggcaaaaaa gaaaaaggga    3840
tcctacccat acgatgttcc agattacgct tatccctacg acgtgcctga ttatgcatac    3900
ccatatgatg tccccgacta tgcctaa                                          3927
```

<210> SEQ ID NO 37
<211> LENGTH: 1273
<212> TYPE: PRT
<213> ORGANISM: Artificial Sequence
<220> FEATURE:
<223> OTHER INFORMATION: Synthetic-Lachnospiraceae bacterium ND2006
      (LbCpf1; pY016), including NLS and HA tag

<400> SEQUENCE: 37

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140
```

```
Asn Gly Phe Thr Thr Ala Phe Thr Gly Phe Phe Asp Asn Arg Glu Asn
145                 150                 155                 160
Met Phe Ser Glu Glu Ala Lys Ser Thr Ser Ile Ala Phe Arg Cys Ile
                165                 170                 175
Asn Glu Asn Leu Thr Arg Tyr Ile Ser Asn Met Asp Ile Phe Glu Lys
            180                 185                 190
Val Asp Ala Ile Phe Asp Lys His Glu Val Gln Glu Ile Lys Glu Lys
        195                 200                 205
Ile Leu Asn Ser Asp Tyr Asp Val Glu Asp Phe Phe Glu Gly Glu Phe
    210                 215                 220
Phe Asn Phe Val Leu Thr Gln Glu Gly Ile Asp Val Tyr Asn Ala Ile
225                 230                 235                 240
Ile Gly Gly Phe Val Thr Glu Ser Gly Glu Lys Ile Lys Gly Leu Asn
                245                 250                 255
Glu Tyr Ile Asn Leu Tyr Asn Gln Lys Thr Lys Gln Lys Leu Pro Lys
            260                 265                 270
Phe Lys Pro Leu Tyr Lys Gln Val Leu Ser Asp Arg Glu Ser Leu Ser
        275                 280                 285
Phe Tyr Gly Glu Gly Tyr Thr Ser Asp Glu Glu Val Leu Glu Val Phe
    290                 295                 300
Arg Asn Thr Leu Asn Lys Asn Ser Glu Ile Phe Ser Ser Ile Lys Lys
305                 310                 315                 320
Leu Glu Lys Leu Phe Lys Asn Phe Asp Glu Tyr Ser Ser Ala Gly Ile
                325                 330                 335
Phe Val Lys Asn Gly Pro Ala Ile Ser Thr Ile Ser Lys Asp Ile Phe
            340                 345                 350
Gly Glu Trp Asn Val Ile Arg Asp Lys Trp Asn Ala Glu Tyr Asp Asp
        355                 360                 365
Ile His Leu Lys Lys Lys Ala Val Val Thr Glu Lys Tyr Glu Asp Asp
    370                 375                 380
Arg Arg Lys Ser Phe Lys Lys Ile Gly Ser Phe Ser Leu Glu Gln Leu
385                 390                 395                 400
Gln Glu Tyr Ala Asp Ala Asp Leu Ser Val Val Glu Lys Leu Lys Glu
                405                 410                 415
Ile Ile Ile Gln Lys Val Asp Glu Ile Tyr Lys Val Tyr Gly Ser Ser
            420                 425                 430
Glu Lys Leu Phe Asp Ala Asp Phe Val Leu Glu Lys Ser Leu Lys Lys
        435                 440                 445
Asn Asp Ala Val Val Ala Ile Met Lys Asp Leu Leu Asp Ser Val Lys
    450                 455                 460
Ser Phe Glu Asn Tyr Ile Lys Ala Phe Phe Gly Glu Gly Lys Glu Thr
465                 470                 475                 480
Asn Arg Asp Glu Ser Phe Tyr Gly Asp Phe Val Leu Ala Tyr Asp Ile
                485                 490                 495
Leu Leu Lys Val Asp His Ile Tyr Asp Ala Ile Arg Asn Tyr Val Thr
            500                 505                 510
Gln Lys Pro Tyr Ser Lys Asp Lys Phe Lys Leu Tyr Phe Gln Asn Pro
        515                 520                 525
Gln Phe Met Gly Gly Trp Asp Lys Asp Lys Glu Thr Asp Tyr Arg Ala
    530                 535                 540
Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
```

-continued

```
                565                 570                 575
Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
            610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
                675                 680                 685

Glu Val Asp Lys Leu Val Glu Glu Gly Lys Leu Tyr Met Phe Gln Ile
                690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
                740                 745                 750

Lys Glu Glu Leu Val Val His Pro Ala Asn Ser Pro Ile Ala Asn Lys
                755                 760                 765

Asn Pro Asp Asn Pro Lys Lys Thr Thr Thr Leu Ser Tyr Asp Val Tyr
770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
                820                 825                 830

Arg Gly Glu Arg Asn Leu Leu Tyr Ile Val Val Val Asp Gly Lys Gly
                835                 840                 845

Asn Ile Val Glu Gln Tyr Ser Leu Asn Glu Ile Ile Asn Asn Phe Asn
                850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
                900                 905                 910

Glu Leu Val Glu Lys Tyr Asp Ala Val Ile Ala Leu Glu Asp Leu Asn
                915                 920                 925

Ser Gly Phe Lys Asn Ser Arg Val Lys Val Glu Lys Gln Val Tyr Gln
                930                 935                 940

Lys Phe Glu Lys Met Leu Ile Asp Lys Leu Asn Tyr Met Val Asp Lys
945                 950                 955                 960

Lys Ser Asn Pro Cys Ala Thr Gly Gly Ala Leu Lys Gly Tyr Gln Ile
                965                 970                 975

Thr Asn Lys Phe Glu Ser Phe Lys Ser Met Ser Thr Gln Asn Gly Phe
                980                 985                 990
```

```
Ile Phe Tyr Ile Pro Ala Trp Leu Thr Ser Lys Ile Asp Pro Ser Thr
            995                 1000                1005

Gly Phe Val Asn Leu Leu Lys Thr Lys Tyr Thr Ser Ile Ala Asp
    1010                1015                1020

Ser Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ile Ser Asn Lys Glu Trp
    1205                1210                1215

Leu Glu Tyr Ala Gln Thr Ser Val Lys His Lys Arg Pro Ala Ala
    1220                1225                1230

Thr Lys Lys Ala Gly Gln Ala Lys Lys Lys Lys Gly Ser Tyr Pro
    1235                1240                1245

Tyr Asp Val Pro Asp Tyr Ala Tyr Pro Tyr Asp Val Pro Asp Tyr
    1250                1255                1260

Ala Tyr Pro Tyr Asp Val Pro Asp Tyr Ala
    1265                1270

<210> SEQ ID NO 38
<211> LENGTH: 3822
<212> TYPE: DNA
<213> ORGANISM: Artificial Sequence
<220> FEATURE:
<223> OTHER INFORMATION: Synthetic-Lachnospiraceae bacterium ND2006
      (LbCpf1; pY016), including NLS and HA tag

<400> SEQUENCE: 38
atgagcaagc tggagaagtt tacaaactgc tactccctgt ctaagaccct gaggttcaag      60
gccatccctg tgggcaagac ccaggagaac atcgacaata gcggctgct ggtggaggac     120 gagaagagag ccgaggatta aagggcgtg aagaagctgc tggatcgcta ctatctgtct     180
tttatcaacg acgtgctgca cagcatcaag ctgaagaatc tgaacaatta catcagcctg     240
ttccggaaga aaccagaac cgagaaggag aataaggagc tggagaacct ggagatcaat     300
```

-continued

```
ctgcggaagg agatcgccaa ggccttcaag ggcaacgagg gctacaagtc cctgtttaag      360
aaggatatca tcgagacaat cctgccagag ttcctggacg ataaggacga gatcgccctg      420
gtgaacagct tcaatggctt taccacagcc ttcaccggct tctttgataa cagagagaat      480
atgttttccg aggaggccaa gagcacatcc atcgccttca ggtgtatcaa cgagaatctg      540
acccgctaca tctctaatat ggacatcttc gagaaggtgg acgccatctt tgataagcac      600
gaggtgcagg agatcaagga gaagatcctg aacagcgact atgatgtgga ggatttcttt      660
gagggcgagt tctttaactt tgtgctgaca caggagggca tcgacgtgta aacgccatc       720 atcggcggct tcgtgaccga gagcggcgag aagatcaagg gcctgaacga gtacatcaac      780
ctgtataatc agaaaaccaa gcagaagctg cctaagttta agccactgta taagcaggtg      840
ctgagcgatc gggagtctct gagcttctac ggcgagggct atacatccga tgaggaggtg      900
ctggaggtgt ttagaaacac cctgaacaag aacagcgaga tcttcagctc catcaagaag      960
ctggagaagc tgttcaagaa ttttgacgag tactctagcg ccggcatctt tgtgaagaac     1020 ggcccccgcca tcagcacaat ctccaaggat atcttcggcg agtggaacgt gatccgggac     1080
aagtggaatg ccgagtatga cgatatccac ctgaagaaga aggccgtggt gaccgagaag     1140
tacgaggacg atcggagaaa gtccttcaag aagatcggct ccttttctct ggagcagctg     1200
caggagtacg ccgacgccga tctgtctgtg gtggagaagc tgaaggagat catcatccag     1260
aaggtggatg agatctacaa ggtgtatggc tcctctgaga gctgttcga cgccgatttt      1320 gtgctggaga gagcctgaa gaagaacgac gccgtggtgg ccatcatgaa ggacctgctg      1380
gattctgtga gagcttcga gaattacatc aaggccttct tggcgaggg caaggagaca      1440 aacagggacg agtccttcta tggcgatttt gtgctggcct acgacatcct gctgaaggtg     1500
gaccacatct acgatgccat ccgcaattat gtgacccaga gcccctactc taaggataag     1560
ttcaagctgt attttcagaa ccctcagttc atgggcggct gggacaagga taaggagaca     1620
gactatcggg ccaccatcct gagatacggc tccaagtact atctggccat catggataag     1680
aagtacgcca agtgcctgca gaagatcgac aaggacgatg tgaacggcaa ttacgagaag     1740
atcaactata gctgctgcc cggccctaat aagatgctgc caaaggtgtt cttttctaag     1800
aagtggatgg cctactataa ccccagcgag gacatccaga gatctacaa gaatggcaca     1860 ttcaagaagg gcgatatgtt taacctgaat gactgtcaca gctgatcga cttctttaag     1920 gatagcatct cccggtatcc aaagtggtcc aatgcctacg atttcaactt ttctgagaca     1980
gagaagtata aggacatcgc cggcttttac agagaggtgg aggagcaggg ctataaggtg      2040
agcttcgagt ctgccagcaa gaaggaggtg gataagctgg tggaggaggg caagctgtat     2100
atgttccaga tctataacaa ggacttttcc gataagtctc acggcacacc caatctgcac     2160
accatgtact tcaagctgct gtttgacgag aacaatcacg acagatcag gctgagcgga     2220 ggagcagagc tgttcatgag gcgcgcctcc ctgaagaagg aggagctggt ggtgcaccca     2280
gccaactccc ctatcgccaa caagaatcca gataatccca agaaaccac aaccctgtcc     2340 tacgacgtgt ataaggataa gaggttttct gaggaccagt acgagctgca catcccaatc     2400
gccatcaata gtgccccaa gaacatcttc aagatcaata cagaggtgcg cgtgctgctg     2460
aagcacgacg ataaccccta tgtgatcggc atcgataggg gcgagcgcaa tctgctgtat     2520
atcgtggtgg tggacggcaa gggcaacatc gtggagcagt attccctgaa cgagatcatc     2580
aacaacttca acggcatcag gatcaagaca gattaccact ctctgctgga caagaaggag     2640
aaggagaggt tcgaggcccg ccagaactgg acctccatcg agaatatcaa ggagctgaag     2700
```

```
gccggctata tctctcaggt ggtgcacaag atctgcgagc tggtggagaa gtacgatgcc    2760
gtgatcgccc tggaggacct gaactctggc tttaagaata gccgcgtgaa ggtggagaag    2820
caggtgtatc agaagttcga gaagatgctg atcgataagc tgaactacat ggtggacaag    2880
aagtctaatc cttgtgcaac aggcggcgcc ctgaagggct atcagatcac caataagttc    2940
gagagcttta gtccatgtc tacccagaac ggcttcatct tttacatccc tgcctggctg    3000
acatccaaga tcgatccatc taccggcttt gtgaacctgc tgaaaaccaa gtataccagc    3060
atcgccgatt ccaagaagtt catcagctcc tttgacagga tcatgtacgt gcccgaggag    3120
gatctgttcg agtttgccct ggactataag aacttctctc gcacagacgc cgattacatc    3180
aagaagtgga agctgtactc ctacggcaac cggatcagaa tcttccggaa tcctaagaag    3240
aacaacgtgt cgactggga ggaggtgtgc ctgaccagcg cctataagga gctgttcaac    3300
aagtacggca tcaattatca gcagggcgat atcagagccc tgctgtgcga gcagtccgac    3360
aaggccttct actctagctt tatggccctg atgagcctga tgctgcagat gcggaacagc    3420
atcacaggcc gcaccgacgt ggatttctg atcagccctg tgaagaactc cgacggcatc    3480
ttctacgata gccggaacta tgaggcccag gagaatgcca tcctgccaaa gaacgccgac    3540
gccaatggcg cctataacat cgccagaaag gtgctgtggg ccatcggcca gttcaagaag    3600
gccgaggacg agaagctgga taaggtgaag atcgccatct ctaacaagga gtggctggag    3660
tacgcccaga ccagcgtgaa gcacaaaagg ccggcggcca cgaaaaaggc cggccaggca    3720
aaaaagaaaa agggatccta cccatacgat gttccagatt acgcttatcc ctacgacgtg    3780
cctgattatg catacccata tgatgtcccc gactatgcct aa                      3822
```

<210> SEQ ID NO 39
<211> LENGTH: 1305
<212> TYPE: PRT
<213> ORGANISM: Artificial Sequence
<220> FEATURE:
<223> OTHER INFORMATION: Synthetic-Porphyromonas crevioricanis (PcCpf1; pY017), including NLS and HA tag

<400> SEQUENCE: 39

```
Met Asp Ser Leu Lys Asp Phe Thr Asn Leu Tyr Pro Val Ser Lys Thr
1               5                   10                  15

Leu Arg Phe Glu Leu Lys Pro Val Gly Lys Thr Leu Glu Asn Ile Glu
            20                  25                  30

Lys Ala Gly Ile Leu Lys Glu Asp Glu His Arg Ala Glu Ser Tyr Arg
        35                  40                  45

Arg Val Lys Lys Ile Ile Asp Thr Tyr His Lys Val Phe Ile Asp Ser
    50                  55                  60

Ser Leu Glu Asn Met Ala Lys Met Gly Ile Glu Asn Ile Lys Ala
65                  70                  75                  80

Met Leu Gln Ser Phe Cys Glu Leu Tyr Lys Lys Asp His Arg Thr Glu
                85                  90                  95

Gly Glu Asp Lys Ala Leu Asp Lys Ile Arg Ala Val Leu Arg Gly Leu
            100                 105                 110

Ile Val Gly Ala Phe Thr Gly Val Cys Gly Arg Arg Glu Asn Thr Val
        115                 120                 125

Gln Asn Glu Lys Tyr Glu Ser Leu Phe Lys Glu Lys Leu Ile Lys Glu
    130                 135                 140

Ile Leu Pro Asp Phe Val Leu Ser Thr Glu Ala Glu Ser Leu Pro Phe
145                 150                 155                 160
```

```
Ser Val Glu Glu Ala Thr Arg Ser Leu Lys Glu Phe Asp Ser Phe Thr
                165                 170                 175

Ser Tyr Phe Ala Gly Phe Tyr Glu Asn Arg Lys Asn Ile Tyr Ser Thr
                180                 185                 190

Lys Pro Gln Ser Thr Ala Ile Ala Tyr Arg Leu Ile His Glu Asn Leu
                195                 200                 205

Pro Lys Phe Ile Asp Asn Ile Leu Val Phe Gln Lys Ile Lys Glu Pro
                210                 215                 220

Ile Ala Lys Glu Leu Glu His Ile Arg Ala Asp Phe Ser Ala Gly Gly
225                 230                 235                 240

Tyr Ile Lys Lys Asp Glu Arg Leu Glu Asp Ile Phe Ser Leu Asn Tyr
                245                 250                 255

Tyr Ile His Val Leu Ser Gln Ala Gly Ile Glu Lys Tyr Asn Ala Leu
                260                 265                 270

Ile Gly Lys Ile Val Thr Glu Gly Asp Gly Glu Met Lys Gly Leu Asn
                275                 280                 285

Glu His Ile Asn Leu Tyr Asn Gln Gln Arg Gly Arg Glu Asp Arg Leu
                290                 295                 300

Pro Leu Phe Arg Pro Leu Tyr Lys Gln Ile Leu Ser Asp Arg Glu Gln
305                 310                 315                 320

Leu Ser Tyr Leu Pro Glu Ser Phe Glu Lys Asp Glu Glu Leu Leu Arg
                325                 330                 335

Ala Leu Lys Glu Phe Tyr Asp His Ile Ala Glu Asp Ile Leu Gly Arg
                340                 345                 350

Thr Gln Gln Leu Met Thr Ser Ile Ser Glu Tyr Asp Leu Ser Arg Ile
                355                 360                 365

Tyr Val Arg Asn Asp Ser Gln Leu Thr Asp Ile Ser Lys Lys Met Leu
                370                 375                 380

Gly Asp Trp Asn Ala Ile Tyr Met Ala Arg Glu Arg Ala Tyr Asp His
385                 390                 395                 400

Glu Gln Ala Pro Lys Arg Ile Thr Ala Lys Tyr Glu Arg Asp Arg Ile
                405                 410                 415

Lys Ala Leu Lys Gly Glu Glu Ser Ile Ser Leu Ala Asn Leu Asn Ser
                420                 425                 430

Cys Ile Ala Phe Leu Asp Asn Val Arg Asp Cys Arg Val Asp Thr Tyr
                435                 440                 445

Leu Ser Thr Leu Gly Gln Lys Glu Gly Pro His Gly Leu Ser Asn Leu
                450                 455                 460

Val Glu Asn Val Phe Ala Ser Tyr His Glu Ala Glu Gln Leu Leu Ser
465                 470                 475                 480

Phe Pro Tyr Pro Glu Glu Asn Asn Leu Ile Gln Asp Lys Asp Asn Val
                485                 490                 495

Val Leu Ile Lys Asn Leu Leu Asp Asn Ile Ser Asp Leu Gln Arg Phe
                500                 505                 510

Leu Lys Pro Leu Trp Gly Met Gly Asp Glu Pro Asp Lys Asp Glu Arg
                515                 520                 525

Phe Tyr Gly Glu Tyr Asn Tyr Ile Arg Gly Ala Leu Asp Gln Val Ile
                530                 535                 540

Pro Leu Tyr Asn Lys Val Arg Asn Tyr Leu Thr Arg Lys Pro Tyr Ser
545                 550                 555                 560

Thr Arg Lys Val Lys Leu Asn Phe Gly Asn Ser Gln Leu Leu Ser Gly
                565                 570                 575
```

```
Trp Asp Arg Asn Lys Glu Lys Asp Asn Ser Cys Val Ile Leu Arg Lys
            580                 585                 590

Gly Gln Asn Phe Tyr Leu Ala Ile Met Asn Asn Arg His Lys Arg Ser
        595                 600                 605

Phe Glu Asn Lys Met Leu Pro Glu Tyr Lys Glu Gly Glu Pro Tyr Phe
    610                 615                 620

Glu Lys Met Asp Tyr Lys Phe Leu Pro Asp Pro Asn Lys Met Leu Pro
625                 630                 635                 640

Lys Val Phe Leu Ser Lys Lys Gly Ile Glu Ile Tyr Lys Pro Ser Pro
                645                 650                 655

Lys Leu Leu Glu Gln Tyr Gly His Gly Thr His Lys Lys Gly Asp Thr
            660                 665                 670

Phe Ser Met Asp Asp Leu His Glu Leu Ile Asp Phe Phe Lys His Ser
        675                 680                 685

Ile Glu Ala His Glu Asp Trp Lys Gln Phe Gly Phe Lys Phe Ser Asp
    690                 695                 700

Thr Ala Thr Tyr Glu Asn Val Ser Ser Phe Tyr Arg Glu Val Glu Asp
705                 710                 715                 720

Gln Gly Tyr Lys Leu Ser Phe Arg Lys Val Ser Glu Ser Tyr Val Tyr
                725                 730                 735

Ser Leu Ile Asp Gln Gly Lys Leu Tyr Leu Phe Gln Ile Tyr Asn Lys
            740                 745                 750

Asp Phe Ser Pro Cys Ser Lys Gly Thr Pro Asn Leu His Thr Leu Tyr
        755                 760                 765

Trp Arg Met Leu Phe Asp Glu Arg Asn Leu Ala Asp Val Ile Tyr Lys
    770                 775                 780

Leu Asp Gly Lys Ala Glu Ile Phe Phe Arg Glu Lys Ser Leu Lys Asn
785                 790                 795                 800

Asp His Pro Thr His Pro Ala Gly Lys Pro Ile Lys Lys Lys Ser Arg
                805                 810                 815

Gln Lys Lys Gly Glu Glu Ser Leu Phe Glu Tyr Asp Leu Val Lys Asp
            820                 825                 830

Arg Arg Tyr Thr Met Asp Lys Phe Gln Phe His Val Pro Ile Thr Met
        835                 840                 845

Asn Phe Lys Cys Ser Ala Gly Ser Lys Val Asn Asp Met Val Asn Ala
    850                 855                 860

His Ile Arg Glu Ala Lys Asp Met His Val Ile Gly Ile Asp Arg Gly
865                 870                 875                 880

Glu Arg Asn Leu Leu Tyr Ile Cys Val Ile Asp Ser Arg Gly Thr Ile
                885                 890                 895

Leu Asp Gln Ile Ser Leu Asn Thr Ile Asn Asp Ile Asp Tyr His Asp
            900                 905                 910

Leu Leu Glu Ser Arg Asp Lys Asp Arg Gln Gln Glu His Arg Asn Trp
        915                 920                 925

Gln Thr Ile Glu Gly Ile Lys Glu Leu Lys Gln Gly Tyr Leu Ser Gln
    930                 935                 940

Ala Val His Arg Ile Ala Glu Leu Met Val Ala Tyr Lys Ala Val Val
945                 950                 955                 960

Ala Leu Glu Asp Leu Asn Met Gly Phe Lys Arg Gly Arg Gln Lys Val
                965                 970                 975

Glu Ser Ser Val Tyr Gln Gln Phe Glu Lys Gln Leu Ile Asp Lys Leu
            980                 985                 990

Asn Tyr Leu Val Asp Lys Lys Lys  Arg Pro Glu Asp Ile  Gly Gly Leu
```

-continued

| | 995 | | | 1000 | | | 1005 | | |
|---|---|---|---|---|---|---|---|---|---|
| Leu | Arg | Ala | Tyr | Gln | Phe | Thr | Ala | Pro | Phe | Lys | Ser | Phe | Lys | Glu |
| | | 1010 | | | | 1015 | | | | 1020 | | | |

Leu Arg Ala Tyr Gln Phe Thr Ala Pro Phe Lys Ser Phe Lys Glu
          1010                   1015                    1020

Met Gly Lys Gln Asn Gly Phe Leu Phe Tyr Ile Pro Ala Trp Asn
          1025                   1030                    1035

Thr Ser Asn Ile Asp Pro Thr Thr Gly Phe Val Asn Leu Phe His
          1040                   1045                    1050

Val Gln Tyr Glu Asn Val Asp Lys Ala Lys Ser Phe Phe Gln Lys
          1055                   1060                    1065

Phe Asp Ser Ile Ser Tyr Asn Pro Lys Lys Asp Trp Phe Glu Phe
          1070                   1075                    1080

Ala Phe Asp Tyr Lys Asn Phe Thr Lys Lys Ala Glu Gly Ser Arg
          1085                   1090                    1095

Ser Met Trp Ile Leu Cys Thr His Gly Ser Arg Ile Lys Asn Phe
          1100                   1105                    1110

Arg Asn Ser Gln Lys Asn Gly Gln Trp Asp Ser Glu Glu Phe Ala
          1115                   1120                    1125

Leu Thr Glu Ala Phe Lys Ser Leu Phe Val Arg Tyr Glu Ile Asp
          1130                   1135                    1140

Tyr Thr Ala Asp Leu Lys Thr Ala Ile Val Asp Glu Lys Gln Lys
          1145                   1150                    1155

Asp Phe Phe Val Asp Leu Leu Lys Leu Phe Lys Leu Thr Val Gln
          1160                   1165                    1170

Met Arg Asn Ser Trp Lys Glu Lys Asp Leu Asp Tyr Leu Ile Ser
          1175                   1180                    1185

Pro Val Ala Gly Ala Asp Gly Arg Phe Phe Asp Thr Arg Glu Gly
          1190                   1195                    1200

Asn Lys Ser Leu Pro Lys Asp Ala Asp Ala Asn Gly Ala Tyr Asn
          1205                   1210                    1215

Ile Ala Leu Lys Gly Leu Trp Ala Leu Arg Gln Ile Arg Gln Thr
          1220                   1225                    1230

Ser Glu Gly Gly Lys Leu Lys Leu Ala Ile Ser Asn Lys Glu Trp
          1235                   1240                    1245

Leu Gln Phe Val Gln Glu Arg Ser Tyr Glu Lys Asp Lys Arg Pro
          1250                   1255                    1260

Ala Ala Thr Lys Lys Ala Gly Gln Ala Lys Lys Lys Lys Gly Ser
          1265                   1270                    1275

Tyr Pro Tyr Asp Val Pro Asp Tyr Ala Tyr Pro Tyr Asp Val Pro
          1280                   1285                    1290

Asp Tyr Ala Tyr Pro Tyr Asp Val Pro Asp Tyr Ala
          1295                   1300                    1305

<210> SEQ ID NO 40
<211> LENGTH: 3918
<212> TYPE: DNA
<213> ORGANISM: Artificial Sequence
<220> FEATURE:
<223> OTHER INFORMATION: Synthetic-Porphyromonas crevioricanis (PcCpf1; pY017), including NLS and HA tag

<400> SEQUENCE: 40
atggacagcc tgaaggattt caccaacctg taccccgtgt ccaagacact gcggtttgag    60
ctgaagcctg tgggcaagac cctggagaat atcgagaagg ccggcatcct gaaggaggat   120
gagcacagag ccgagagcta ccggagagtg aagaagatca tcgatacata tcacaaggtg   180

| | |
|---|---|
| ttcatcgaca gctccctgga gaacatggcc aagatgggca tcgagaatga gatcaaggcc | 240 |
| atgctgcagt cctttttgcga gctgtataag aaggaccaca ggaccgaggg agaggacaag | 300 |
| gccctggata agatcagggc cgtgctgagg ggcctgatcg tgggagcctt caccggcgtg | 360 |
| tgcggccggc gggagaacac agtgcagaat gagaagtatg agagcctgtt taaggagaag | 420 |
| ctgatcaagg agatcctgcc agatttcgtg ctgtctacag aggccgagtc cctgcccttt | 480 |
| tctgtggagg aggccaccag aagcctgaag gagttcgact cctttacatc ttacttcgcc | 540 |
| ggcttttatg agaaccggaa gaatatctac tctaccaagc cccagagcac agccatcgcc | 600 |
| tatagactga tccacgagaa cctgcctaag ttcatcgata atatcctggt gtttcagaag | 660 |
| atcaaggagc caatcgccaa ggagctggag cacatcaggg cagacttcag cgccggcggc | 720 |
| tacatcaaga aggatgagcg cctggaggac atcttttccc tgaactacta tatccacgtg | 780 |
| ctgtctcagg ccggcatcga gaagtacaat gccctgatcg gcaagatcgt gaccgagggc | 840 |
| gatggcgaga tgaagggcct gaacgagcac atcaacctgt ataatcagca gaggggccgc | 900 |
| gaggaccggc tgccactgtt cagacccctg tataagcaga tcctgtctga tagggagcag | 960 |
| ctgtcctatc tgccagagtc tttcgagaag gacgaggagc tgctgagggc cctgaaggag | 1020 |
| ttttacgatc acatcgcaga ggacatcctg gaaggaccc agcagctgat gacaagcatc | 1080 |
| tccgagtacg atctgtcccg gatctatgtg agaaacgata gccagctgac cgacatctcc | 1140 |
| aagaagatgc tgggcgattg gaatgccatc tacatggccc gggagagagc ctatgaccac | 1200 |
| gagcaggccc ccaagcgcat cacagccaag tacgagaggg accgcatcaa ggccctgaag | 1260 |
| ggcgaggagt ctatcagcct ggccaacctg aacagctgca tcgccttcct ggacaacgtg | 1320 |
| agggattgtc gcgtggacac ctatctgtct acactgggac agaaggaggg acctcacggc | 1380 |
| ctgagcaacc tggtggagaa cgtgttcgcc tcctaccacg aggccgagca gctgctgtct | 1440 |
| tttccctatc ctgaggagaa caatctgatc caggacaagg ataacgtggt gctgatcaag | 1500 |
| aacctgctgg ataatatcag cgacctgcag aggttcctga gccactgtg gggcatgggc | 1560 |
| gatgagcccg acaaggatga gaggttttac ggcgagtaca attatatcag gggcgccctg | 1620 |
| gaccaggtca tccctctgta taacaaggtg cggaattatc tgacccgcaa gccatactcc | 1680 |
| acacgcaagg tgaagctgaa cttcggcaat agccagctgc tgtccggctg ggataggaac | 1740 |
| aaggagaagg acaattcttg cgtgatcctg cgcaagggcc agaacttcta cctggccatc | 1800 |
| atgaacaatc ggcacaagcg gagcttcgag aataagatgc tgcccgagta taaggagggc | 1860 |
| gagccttact tcgagaagat ggattataag tttctgccag accccaacaa gatgctgccc | 1920 |
| aaggtgttcc tgtctaagaa gggcatcgag atctacaagc ctagcccaaa gctgctggag | 1980 |
| cagtatggcc acggcaccca caagaagggc gataccttca gcatggacga tctgcacgag | 2040 |
| ctgatcgact ctttaagca ctccatcgag gcccacgagg attggaagca gttcggcttt | 2100 |
| aagttcagcg acaccgccac atacgagaac gtgagcagct ctaccgggga ggtggaggac | 2160 |
| cagggctaca agctgtcttt tagaaaggtg tccgagtctt acgtgtatag cctgatcgat | 2220 |
| cagggcaagc tgtacctgtt ccagatctat aacaaggact ttagcccttg ttccaagggc | 2280 |
| acccccaaatc tgcacacact gtactggcgg atgctgttcg atgagagaaa cctgccgac | 2340 |
| gtgatctata agctggatgg caaggccgag atcttctttc gggagaagtc cctgaagaat | 2400 |
| gaccacccaa cccaccctgc aggcaagccc atcaagaaga agagccggca gaagaagggc | 2460 |
| gaggagagcc tgttcgagta cgatctggtg aaggaccgga gatataccat ggataagttt | 2520 |
| cagttccacg tgccaatcac aatgaacttt aagtgctctg ccggcagcaa ggtgaacgac | 2580 |

```
atggtgaatg cccacatcag ggaggccaag gacatgcacg tgatcggcat cgataggggc    2640
gagcgcaatc tgctgtatat ctgcgtgatc gacagccgcg gcaccatcct ggatcagatc    2700
tccctgaaca caatcaatga catcgattat cacgatctgc tggagtccag ggacaaggat    2760
cgccagcagg agcacaggaa ctggcagacc atcgagggca tcaaggagct gaagcagggc    2820
tacctgtctc aggccgtgca ccgcatcgcc gagctgatgg tggcctataa ggccgtggtg    2880
gccctggagg acctgaacat gggcttcaag cggggcagac agaaggtgga gagcagcgtg    2940
taccagcagt ttgagaagca gctgatcgac aagctgaatt atctggtgga taagaagaag    3000
cggcccgagg acatcggagg cctgctgaga gcctaccagt tcaccgcccc tttcaagagc    3060
tttaaggaga tgggcaagca gaacggcttt ctgttctata tccctgcctg gaacacatcc    3120
aatatcgacc caaccacagg cttcgtgaac ctgtttcacg tgcagtacga gaatgtggat    3180
aaggccaaga gcttctttca gaagttcgac agcatctcct acaaccctaa gaaggattgg    3240
tttgagttcg cctttgacta taagaacttc accaagaagg ccgagggctc taggagcatg    3300
tggattctgt gcacccacgg ctcccggatc aagaacttca gaaattctca gaagaatggc    3360
cagtgggata gcgaggagtt tgccctgacc gaggccttca gtccctgtt tgtgcggtac     3420 gagatcgatt ataccgccga cctgaaaacc gccatcgtgg acgagaagca gaaggatttc    3480
tttgtggacc tgctgaagct gttcaagctg accgtgcaga tgagaaactc ctggaaggag    3540
aaggacctgg attacctgat ctctccagtg gccggcgccg atggcaggtt ctttgacaca    3600
cgcgagggca ataagagcct gcccaaggac gcagatgcaa acggagccta taatatcgcc    3660
ctgaagggcc tgtgggcact gaggcagatc agacagacct ccgagggcgg caagctgaag    3720
ctggccatct ctaacaagga gtggctgcag tttgtgcagg agagatccta cgagaaggac    3780
aaaaggccgg cggccacgaa aaaggccggc caggcaaaaa agaaaaaggg atcctaccca    3840
tacgatgttc cagattacgc ttatccctac gacgtgcctg attatgcata cccatatgat    3900
gtccccgact atgcctaa                                                  3918
```

<210> SEQ ID NO 41
<211> LENGTH: 1368
<212> TYPE: PRT
<213> ORGANISM: Artificial Sequence
<220> FEATURE:
<223> OTHER INFORMATION: Synthetic-Prevotella disiens (PdCpf1; pY018),
    including NLS and HA tag

<400> SEQUENCE: 41

```
Met Glu Asn Tyr Gln Glu Phe Thr Asn Leu Phe Gln Leu Asn Lys Thr
 1               5                  10                  15

Leu Arg Phe Glu Leu Lys Pro Ile Gly Lys Thr Cys Glu Leu Leu Glu
            20                  25                  30

Glu Gly Lys Ile Phe Ala Ser Gly Ser Phe Leu Glu Lys Asp Lys Val
        35                  40                  45

Arg Ala Asp Asn Val Ser Tyr Val Lys Lys Glu Ile Asp Lys Lys His
    50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Glu Leu Lys Ala Phe Lys
                85                  90                  95

Lys Asp Cys Lys Ser Asp Glu Glu Val Lys Lys Thr Ala Leu Arg
            100                 105                 110
```

```
Asn Lys Cys Thr Ser Ile Gln Arg Ala Met Arg Glu Ala Ile Ser Gln
            115                 120                 125

Ala Phe Leu Lys Ser Pro Gln Lys Lys Leu Leu Ala Ile Lys Asn Leu
        130                 135                 140

Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175

Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
        195                 200                 205

Glu Gln Phe Asp Ala Lys Thr Leu Ser Glu Ile Phe Glu Asn Tyr Lys
    210                 215                 220

Leu Tyr Val Ala Gly Ser Ser Leu Asp Glu Val Phe Ser Leu Glu Tyr
225                 230                 235                 240

Phe Asn Asn Thr Leu Thr Gln Lys Gly Ile Asp Asn Tyr Asn Ala Val
                245                 250                 255

Ile Gly Lys Ile Val Lys Glu Asp Lys Gln Glu Ile Gln Gly Leu Asn
            260                 265                 270

Glu His Ile Asn Leu Tyr Asn Gln Lys His Lys Asp Arg Arg Leu Pro
        275                 280                 285

Phe Phe Ile Ser Leu Lys Lys Gln Ile Leu Ser Asp Arg Glu Ala Leu
    290                 295                 300

Ser Trp Leu Pro Asp Met Phe Lys Asn Asp Ser Glu Val Ile Lys Ala
305                 310                 315                 320

Leu Lys Gly Phe Tyr Ile Glu Asp Gly Phe Glu Asn Asn Val Leu Thr
                325                 330                 335

Pro Leu Ala Thr Leu Leu Ser Ser Leu Asp Lys Tyr Asn Leu Asn Gly
            340                 345                 350

Ile Phe Ile Arg Asn Asn Glu Ala Leu Ser Ser Leu Ser Gln Asn Val
        355                 360                 365

Tyr Arg Asn Phe Ser Ile Asp Glu Ala Ile Asp Ala Asn Ala Glu Leu
    370                 375                 380

Gln Thr Phe Asn Asn Tyr Glu Leu Ile Ala Asn Ala Leu Arg Ala Lys
385                 390                 395                 400

Ile Lys Lys Glu Thr Lys Gln Gly Arg Lys Ser Phe Glu Lys Tyr Glu
                405                 410                 415

Glu Tyr Ile Asp Lys Lys Val Lys Ala Ile Asp Ser Leu Ser Ile Gln
            420                 425                 430

Glu Ile Asn Glu Leu Val Glu Asn Tyr Val Ser Glu Phe Asn Ser Asn
        435                 440                 445

Ser Gly Asn Met Pro Arg Lys Val Glu Asp Tyr Phe Ser Leu Met Arg
    450                 455                 460

Lys Gly Asp Phe Gly Ser Asn Asp Leu Ile Glu Asn Ile Lys Thr Lys
465                 470                 475                 480

Leu Ser Ala Ala Glu Lys Leu Leu Gly Thr Lys Tyr Gln Glu Thr Ala
                485                 490                 495

Lys Asp Ile Phe Lys Lys Asp Glu Asn Ser Lys Leu Ile Lys Glu Leu
            500                 505                 510

Leu Asp Ala Thr Lys Gln Phe Gln His Phe Ile Lys Pro Leu Leu Gly
        515                 520                 525

Thr Gly Glu Glu Ala Asp Arg Asp Leu Val Phe Tyr Gly Asp Phe Leu
```

```
                530               535               540
Pro Leu Tyr Glu Lys Phe Glu Leu Thr Leu Leu Tyr Asn Lys Val
545                 550               555               560

Arg Asn Arg Leu Thr Gln Lys Pro Tyr Ser Lys Asp Lys Ile Arg Leu
                565               570               575

Cys Phe Asn Lys Pro Lys Leu Met Thr Gly Trp Val Asp Ser Lys Thr
                580               585               590

Glu Lys Ser Asp Asn Gly Thr Gln Tyr Gly Tyr Leu Phe Arg Lys
                595               600               605

Lys Asn Glu Ile Gly Glu Tyr Asp Tyr Phe Leu Gly Ile Ser Ser Lys
            610               615               620

Ala Gln Leu Phe Arg Lys Asn Glu Ala Val Ile Gly Asp Tyr Glu Arg
625               630               635               640

Leu Asp Tyr Tyr Gln Pro Lys Ala Asn Thr Ile Tyr Gly Ser Ala Tyr
                645               650               655

Glu Gly Glu Asn Ser Tyr Lys Glu Asp Lys Lys Arg Leu Asn Lys Val
                660               665               670

Ile Ile Ala Tyr Ile Glu Gln Ile Lys Gln Thr Asn Ile Lys Lys Ser
            675               680               685

Ile Ile Glu Ser Ile Ser Lys Tyr Pro Asn Ile Ser Asp Asp Asp Lys
            690               695               700

Val Thr Pro Ser Ser Leu Leu Glu Lys Ile Lys Lys Val Ser Ile Asp
705               710               715               720

Ser Tyr Asn Gly Ile Leu Ser Phe Lys Ser Phe Gln Ser Val Asn Lys
                725               730               735

Glu Val Ile Asp Asn Leu Leu Lys Thr Ile Ser Pro Leu Lys Asn Lys
                740               745               750

Ala Glu Phe Leu Asp Leu Ile Asn Lys Asp Tyr Gln Ile Phe Thr Glu
                755               760               765

Val Gln Ala Val Ile Asp Glu Ile Cys Lys Gln Lys Thr Phe Ile Tyr
                770               775               780

Phe Pro Ile Ser Asn Val Glu Leu Glu Lys Glu Met Gly Asp Lys Asp
785               790               795               800

Lys Pro Leu Cys Leu Phe Gln Ile Ser Asn Lys Asp Leu Ser Phe Ala
                805               810               815

Lys Thr Phe Ser Ala Asn Leu Arg Lys Lys Arg Gly Ala Glu Asn Leu
                820               825               830

His Thr Met Leu Phe Lys Ala Leu Met Glu Gly Asn Gln Asp Asn Leu
                835               840               845

Asp Leu Gly Ser Gly Ala Ile Phe Tyr Arg Ala Lys Ser Leu Asp Gly
850               855               860

Asn Lys Pro Thr His Pro Ala Asn Glu Ala Ile Lys Cys Arg Asn Val
865               870               875               880

Ala Asn Lys Asp Lys Val Ser Leu Phe Thr Tyr Asp Ile Tyr Lys Asn
                885               890               895

Arg Arg Tyr Met Glu Asn Lys Phe Leu Phe His Leu Ser Ile Val Gln
                900               905               910

Asn Tyr Lys Ala Ala Asn Asp Ser Ala Gln Leu Asn Ser Ser Ala Thr
            915               920               925

Glu Tyr Ile Arg Lys Ala Asp Asp Leu His Ile Ile Gly Ile Asp Arg
                930               935               940

Gly Glu Arg Asn Leu Leu Tyr Tyr Ser Val Ile Asp Met Lys Gly Asn
945               950               955               960
```

-continued

```
Ile Val Glu Gln Asp Ser Leu Asn Ile Ile Arg Asn Asp Leu Glu
            965                 970                 975

Thr Asp Tyr His Asp Leu Leu Asp Lys Arg Glu Lys Glu Arg Lys Ala
            980                 985                 990

Asn Arg Gln Asn Trp Glu Ala Val  Glu Gly Ile Lys Asp  Leu Lys Lys
            995                 1000                1005

Gly Tyr  Leu Ser Gln Ala Val  His Gln Ile Ala Gln  Leu Met Leu
            1010                1015                1020

Lys Tyr  Asn Ala Ile Ile Ala  Leu Glu Asp Leu Gly  Gln Met Phe
            1025                1030                1035

Val Thr  Arg Gly Gln Lys Ile  Glu Lys Ala Val Tyr  Gln Gln Phe
            1040                1045                1050

Glu Lys  Ser Leu Val Asp Lys  Leu Ser Tyr Leu Val  Asp Lys Lys
            1055                1060                1065

Arg Pro  Tyr Asn Glu Leu Gly  Gly Ile Leu Lys Ala  Tyr Gln Leu
            1070                1075                1080

Ala Ser  Ser Ile Thr Lys Asn  Asn Ser Asp Lys Gln  Asn Gly Phe
            1085                1090                1095

Leu Phe  Tyr Val Pro Ala Trp  Asn Thr Ser Lys Ile  Asp Pro Val
            1100                1105                1110

Thr Gly  Phe Thr Asp Leu Leu  Arg Pro Lys Ala Met  Thr Ile Lys
            1115                1120                1125

Glu Ala  Gln Asp Phe Phe Gly  Ala Phe Asp Asn Ile  Ser Tyr Asn
            1130                1135                1140

Asp Lys  Gly Tyr Phe Glu Phe  Glu Thr Asn Tyr Asp  Lys Phe Lys
            1145                1150                1155

Ile Arg  Met Lys Ser Ala Gln  Thr Arg Trp Thr Ile  Cys Thr Phe
            1160                1165                1170

Gly Asn  Arg Ile Lys Arg Lys  Lys Asp Lys Asn Tyr  Trp Asn Tyr
            1175                1180                1185

Glu Glu  Val Glu Leu Thr Glu  Glu Phe Lys Lys Leu  Phe Lys Asp
            1190                1195                1200

Ser Asn  Ile Asp Tyr Glu Asn  Cys Asn Leu Lys Glu  Glu Ile Gln
            1205                1210                1215

Asn Lys  Asp Asn Arg Lys Phe  Phe Asp Asp Leu Ile  Lys Leu Leu
            1220                1225                1230

Gln Leu  Thr Leu Gln Met Arg  Asn Ser Asp Asp Lys  Gly Asn Asp
            1235                1240                1245

Tyr Ile  Ile Ser Pro Val Ala  Asn Ala Glu Gly Gln  Phe Phe Asp
            1250                1255                1260

Ser Arg  Asn Gly Asp Lys Lys  Leu Pro Leu Asp Ala  Asp Ala Asn
            1265                1270                1275

Gly Ala  Tyr Asn Ile Ala Arg  Lys Gly Leu Trp Asn  Ile Arg Gln
            1280                1285                1290

Ile Lys  Gln Thr Lys Asn Asp  Lys Lys Leu Asn Leu  Ser Ile Ser
            1295                1300                1305

Ser Thr  Glu Trp Leu Asp Phe  Val Arg Glu Lys Pro  Tyr Leu Lys
            1310                1315                1320

Lys Arg  Pro Ala Ala Thr Lys  Lys Ala Gly Gln Ala  Lys Lys Lys
            1325                1330                1335

Lys Gly  Ser Tyr Pro Tyr Asp  Val Pro Asp Tyr Ala  Tyr Pro Tyr
            1340                1345                1350
```

| Asp | Val | Pro | Asp | Tyr | Ala | Tyr | Pro | Tyr | Asp | Val | Pro | Asp | Tyr | Ala |
|-----|-----|-----|-----|-----|-----|-----|-----|-----|-----|-----|-----|-----|-----|-----|
| 1355 | | | | 1360 | | | | | 1365 | | | | | |

<210> SEQ ID NO 42
<211> LENGTH: 4107
<212> TYPE: DNA
<213> ORGANISM: Artificial Sequence
<220> FEATURE:
<223> OTHER INFORMATION: Synthetic-Prevotella disiens (PdCpf1; pY018), including NLS and HA tag

<400> SEQUENCE: 42

```
atggagaact atcaggagtt caccaacctg tttcagctga ataagacact gagattcgag    60
ctgaagccca tcggcaagac ctgcgagctg ctggaggagg cgaagatctt cgccagcggc   120
tcctttctgg agaaggacaa ggtgagggcc gataacgtga gctacgtgaa gaaggagatc   180
gacaagaagc acaagatctt tatcgaggag acactgagcc ccttctctat cagcaacgat   240
ctgctgaagc agtactttga ctgctataat gagctgaagg ccttcaagaa ggactgtaag   300
agcgatgagg aggaggtgaa gaaaaccgcc ctgcgcaaca agtgtacctc catccagagg   360
gccatgcgcg aggccatctc tcaggccttt ctgaagagcc ccagaagaa gctgctggcc   420
atcaagaacc tgatcgagaa cgtgttcaag gccgacgaga atgtgcagca cttctccgag   480
tttaccagct atttctccgg cttttgagaca acagagaga atttctactc tgacgaggag   540
aagtccacat ctatcgccta taggctggtg cacgataacc tgcctatctt catcaagaac   600
atctacatct tcgagaagct gaaggagcag ttcgacgcca agaccctgag cgagatcttc   660
gagaactaca agctgtatgt ggccggctct agcctggatg aggtgttctc cctggagtac   720
tttaacaata ccctgacaca agagggcatc gacaactata tgccgtgat cggcaagatc   780
gtgaaggagg ataagcagga gatccagggc ctgaacgagc acatcaacct gtataatcag   840
aagcacaagg accggagact gccccttcttt atctccctga gaagcagat cctgtccgat   900
cgggaggccc tgtcttggct gcctgacatg ttcaagaatg attctgaagt gatcaaggcc   960
ctgaagggct tctacatcga ggacggcttt gagaacaatg tgctgacacc tctggccacc  1020
ctgctgtcct ctctggataa gtacaacctg aatggcatct ttatccgcaa caatgaggcc  1080
ctgagctccc tgtcccagaa cgtgtatcgg aattttttcta tcgacgaggc catcgatgcc  1140
aacgccgagc tgcagacctt caacaattac gagctgatcg ccaatgccct gcgcgccaag  1200
atcaagaagg agacaaagca gggccggaag tctttcgaga gtacgagga gtatatcgat  1260
aagaaggtga aggccatcga cagcctgtcc atccaggaga tcaacgagct ggtggagaat  1320
tacgtgagcg agtttaactc taatagcggc aacatgccaa gaaggtgga ggactacttc  1380
agcctgatga ggaagggcga cttcggctcc aacgatctga tcgaaaatat caagaccaag  1440
ctgagcgccg cagagaagct gctgggcaca aagtaccagg agacagccaa ggacatcttc  1500
aagaaggatg agaactccaa gctgatcaag gagctgctgg acgccaccaa gcagttccag  1560
cactttatca gccactgct gggcacaggc gaggaggcag atcgggacct ggtgttctac  1620
ggcgattttc tgccctgta tgagaagttt gaggagctga cctgctgta taacaaggtg  1680
cggaatagac tgcacagaa gcccctattcc aaggacaaga tccgcctgtg cttcaacaag  1740
cctaagctga tgacaggctg ggtggattcc aagaccgaga gtctgacaa cggcacacag  1800
tacggcggct atctgtttcg gaagaagaat gagatcggcg agtacgatta ttttctgggc  1860
atctctagca aggcccagct gttcagaaag aacgaggccg tgatcggcga ctacgagagg  1920
ctggattact atcagccaaa ggccaatacc atctacggct ctgcctatga gggcgagaac  1980
```

```
agctacaagg aggacaagaa gcggctgaac aaagtgatca tcgcctatat cgagcagatc    2040
aagcagacaa acatcaagaa gtctatcatc gagtccatct ctaagtatcc taatatcagc    2100
gacgatgaca aggtgacccc atcctctctg ctggagaaga tcaagaaggt gtctatcgac    2160
agctacaacg gcatcctgtc cttcaagtct tttcagagcg tgaacaagga agtgatcgat    2220
aacctgctga aaaccatcag cccccctgaag aacaaggccg agtttctgga cctgatcaat    2280
aaggattatc agatcttcac cgaggtgcag gccgtgatcg acgagatctg caagcagaaa    2340
accttcatct actttccaat ctccaacgtg gagctggaga aggagatggg cgataaggac    2400
aagcccctgt gcctgttcca gatcagcaat aaggatctgt ccttcgccaa gacctttagc    2460
gccaacctgc ggaagaagag aggcgccgag aatctgcaca caatgctgtt taaggccctg    2520
atggagggca accaggataa tctggacctg ggctctggcg ccatcttcta cagagccaag    2580
agcctggacg gcaacaagcc cacacaccct gccaatgagg ccatcaagtg taggaacgtg    2640
gccaataagg ataaggtgtc cctgttcacc tacgacatct ataagaacag cgctacatg    2700 gagaataagt tcctgtttca cctgagcatc gtgcagaact ataaggccgc caatgactcc    2760
gcccagctga acagctccgc caccgagtat atcagaaagg ccgatgacct gcacatcatc    2820
ggcatcgata ggggcgagcg caatctgctg tactattccg tgatcgatat gaagggcaac    2880
atcgtggagc aggactctct gaatatcatc aggaacaatg acctgagac agattaccac    2940 gacctgctgg ataagaggga aaggagcgc aaggccaacc ggcagaattg ggaggccgtg    3000
gagggcatca aggacctgaa gaagggctac ctgagccagg ccgtgcacca gatcgcccag    3060
ctgatgctga agtataacgc catcatcgcc ctggaggatc tgggccagat gtttgtgacc    3120
cgcggccaga gatcgagaa ggccgtgtac cagcagttcg agaagagcct ggtggataag    3180
ctgtcctacc tggtggacaa gaagcggcct tataatgagc tgggcggcat cctgaaggcc    3240
taccagctgg cctctagcat caccaagaac aattctgaca gcagaacgg cttcctgttt    3300 tatgtgccag cctggaatac aagcaagatc gatcccgtga ccggctttac agacctgctg    3360
cggcccaagg ccatgaccat caaggaggcc aggacttct ttggcgcctt cgataacatc    3420
tcttacaatg acaagggcta tttcgagttt gagacaaact acgacaagtt taagatcaga    3480
atgaagagcg cccagaccag gtggacaatc tgcaccttcg caatcggat caagagaaag    3540 aaggataaga actactggaa ttatgaggag gtggagctga ccgaggagtt caagaagctg    3600
tttaaggaca gcaacatcga ttacgagaac tgtaatctga aggaggagat ccagaacaag    3660
gacaatcgca agttctttga tgacctgatc aagctgctgc agctgacact gcagatgcgg    3720
aactccgatg acaagggcaa tgattatatc atctctcctg tggccaacgc cgagggccag    3780
ttctttgact cccgcaatgg cgataagaag ctgccactgg atgcagacgc aaacggagcc    3840
tacaatatcg cccgcaaggg cctgtggaac atccggcaga tcaagcagac caagaacgac    3900
aagaagctga atctgagcat ctcctctaca gagtggctgg atttcgtgcg ggagaagcct    3960
tacctgaaga aaaggccggc ggccacgaaa aaggccggcc aggcaaaaaa gaaaaaggga    4020
tcctacccat acgatgttcc agattacgct tatccctacg acgtgcctga ttatgcatac    4080
ccatatgatg tccccgacta tgcctaa                                       4107
```

<210> SEQ ID NO 43
<211> LENGTH: 1291
<212> TYPE: PRT
<213> ORGANISM: Artificial Sequence
<220> FEATURE:

<223> OTHER INFORMATION: Synthetic-Porphyromonas macacae (PmCpf1; pY09), including NLS and HA tag

<400> SEQUENCE: 43

```
Met Lys Thr Gln His Phe Phe Glu Asp Phe Thr Ser Leu Tyr Ser Leu
1               5                   10                  15

Ser Lys Thr Ile Arg Phe Glu Leu Lys Pro Ile Gly Lys Thr Leu Glu
            20                  25                  30

Asn Ile Lys Lys Asn Gly Leu Ile Arg Arg Asp Glu Gln Arg Leu Asp
        35                  40                  45

Asp Tyr Glu Lys Leu Lys Lys Val Ile Asp Glu Tyr His Glu Asp Phe
    50                  55                  60

Ile Ala Asn Ile Leu Ser Ser Phe Ser Phe Ser Glu Glu Ile Leu Gln
65                  70                  75                  80

Ser Tyr Ile Gln Asn Leu Ser Glu Ser Glu Ala Arg Ala Lys Ile Glu
                85                  90                  95

Lys Thr Met Arg Asp Thr Leu Ala Lys Ala Phe Ser Glu Asp Glu Arg
            100                 105                 110

Tyr Lys Ser Ile Phe Lys Lys Glu Leu Val Lys Lys Asp Ile Pro Val
        115                 120                 125

Trp Cys Pro Ala Tyr Lys Ser Leu Cys Lys Lys Phe Asp Asn Phe Thr
    130                 135                 140

Thr Ser Leu Val Pro Phe His Glu Asn Arg Lys Asn Leu Tyr Thr Ser
145                 150                 155                 160

Asn Glu Ile Thr Ala Ser Ile Pro Tyr Arg Ile Val His Val Asn Leu
                165                 170                 175

Pro Lys Phe Ile Gln Asn Ile Glu Ala Leu Cys Glu Leu Gln Lys Lys
            180                 185                 190

Met Gly Ala Asp Leu Tyr Leu Glu Met Met Glu Asn Leu Arg Asn Val
        195                 200                 205

Trp Pro Ser Phe Val Lys Thr Pro Asp Asp Leu Cys Asn Leu Lys Thr
    210                 215                 220

Tyr Asn His Leu Met Val Gln Ser Ser Ile Ser Glu Tyr Asn Arg Phe
225                 230                 235                 240

Val Gly Gly Tyr Ser Thr Glu Asp Gly Thr Lys His Gln Gly Ile Asn
                245                 250                 255

Glu Trp Ile Asn Ile Tyr Arg Gln Arg Asn Lys Glu Met Arg Leu Pro
            260                 265                 270

Gly Leu Val Phe Leu His Lys Gln Ile Leu Ala Lys Val Asp Ser Ser
        275                 280                 285

Ser Phe Ile Ser Asp Thr Leu Glu Asn Asp Asp Gln Val Phe Cys Val
    290                 295                 300

Leu Arg Gln Phe Arg Lys Leu Phe Trp Asn Thr Val Ser Ser Lys Glu
305                 310                 315                 320

Asp Asp Ala Ala Ser Leu Lys Asp Leu Phe Cys Gly Leu Ser Gly Tyr
                325                 330                 335

Asp Pro Glu Ala Ile Tyr Val Ser Asp Ala His Leu Ala Thr Ile Ser
            340                 345                 350

Lys Asn Ile Phe Asp Arg Trp Asn Tyr Ile Ser Asp Ala Ile Arg Arg
        355                 360                 365

Lys Thr Glu Val Leu Met Pro Arg Lys Glu Ser Val Glu Arg Tyr
    370                 375                 380

Ala Glu Lys Ile Ser Lys Gln Ile Lys Lys Arg Gln Ser Tyr Ser Leu
385                 390                 395                 400
```

```
Ala Glu Leu Asp Asp Leu Leu Ala His Tyr Ser Glu Ser Leu Pro
                405                 410                 415
Ala Gly Phe Ser Leu Leu Ser Tyr Phe Thr Ser Leu Gly Gly Gln Lys
            420                 425                 430
Tyr Leu Val Ser Asp Gly Glu Val Ile Leu Tyr Glu Gly Gly Ser Asn
                435                 440                 445
Ile Trp Asp Glu Val Leu Ile Ala Phe Arg Asp Leu Gln Val Ile Leu
    450                 455                 460
Asp Lys Asp Phe Thr Glu Lys Lys Leu Gly Lys Asp Glu Glu Ala Val
465                 470                 475                 480
Ser Val Ile Lys Lys Ala Leu Asp Ser Ala Leu Arg Leu Arg Lys Phe
                485                 490                 495
Phe Asp Leu Leu Ser Gly Thr Gly Ala Glu Ile Arg Arg Asp Ser Ser
                500                 505                 510
Phe Tyr Ala Leu Tyr Thr Asp Arg Met Asp Lys Leu Lys Gly Leu Leu
                515                 520                 525
Lys Met Tyr Asp Lys Val Arg Asn Tyr Leu Thr Lys Lys Pro Tyr Ser
                530                 535                 540
Ile Glu Lys Phe Lys Leu His Phe Asp Asn Pro Ser Leu Leu Ser Gly
545                 550                 555                 560
Trp Asp Lys Asn Lys Glu Leu Asn Asn Leu Ser Val Ile Phe Arg Gln
                565                 570                 575
Asn Gly Tyr Tyr Tyr Leu Gly Ile Met Thr Pro Lys Gly Lys Asn Leu
                580                 585                 590
Phe Lys Thr Leu Pro Lys Leu Gly Ala Glu Met Phe Tyr Glu Lys
                595                 600                 605
Met Glu Tyr Lys Gln Ile Ala Glu Pro Met Leu Met Leu Pro Lys Val
                610                 615                 620
Phe Phe Pro Lys Lys Thr Lys Pro Ala Phe Ala Pro Asp Gln Ser Val
625                 630                 635                 640
Val Asp Ile Tyr Asn Lys Lys Thr Phe Lys Thr Gly Gln Lys Gly Phe
                645                 650                 655
Asn Lys Lys Asp Leu Tyr Arg Leu Ile Asp Phe Tyr Lys Glu Ala Leu
                660                 665                 670
Thr Val His Glu Trp Lys Leu Phe Asn Phe Ser Phe Ser Pro Thr Glu
                675                 680                 685
Gln Tyr Arg Asn Ile Gly Glu Phe Phe Asp Glu Val Arg Glu Gln Ala
            690                 695                 700
Tyr Lys Val Ser Met Val Asn Val Pro Ala Ser Tyr Ile Asp Glu Ala
705                 710                 715                 720
Val Glu Asn Gly Lys Leu Tyr Leu Phe Gln Ile Tyr Asn Lys Asp Phe
                725                 730                 735
Ser Pro Tyr Ser Lys Gly Ile Pro Asn Leu His Thr Leu Tyr Trp Lys
                740                 745                 750
Ala Leu Phe Ser Glu Gln Asn Gln Ser Arg Val Tyr Lys Leu Cys Gly
                755                 760                 765
Gly Gly Glu Leu Phe Tyr Arg Lys Ala Ser Leu His Met Gln Asp Thr
    770                 775                 780
Thr Val His Pro Lys Gly Ile Ser Ile His Lys Lys Asn Leu Asn Lys
785                 790                 795                 800
Lys Gly Glu Thr Ser Leu Phe Asn Tyr Asp Leu Val Lys Asp Lys Arg
                805                 810                 815
```

```
Phe Thr Glu Asp Lys Phe Phe His Val Pro Ile Ser Ile Asn Tyr
            820                 825                 830

Lys Asn Lys Lys Ile Thr Asn Val Asn Gln Met Val Arg Asp Tyr Ile
        835                 840                 845

Ala Gln Asn Asp Asp Leu Gln Ile Ile Gly Ile Asp Arg Gly Glu Arg
    850                 855                 860

Asn Leu Leu Tyr Ile Ser Arg Ile Asp Thr Arg Gly Asn Leu Leu Glu
865                 870                 875                 880

Gln Phe Ser Leu Asn Val Ile Glu Ser Asp Lys Gly Asp Leu Arg Thr
            885                 890                 895

Asp Tyr Gln Lys Ile Leu Gly Asp Arg Glu Gln Glu Arg Leu Arg Arg
        900                 905                 910

Arg Gln Glu Trp Lys Ser Ile Glu Ser Ile Lys Asp Leu Lys Asp Gly
    915                 920                 925

Tyr Met Ser Gln Val Val His Lys Ile Cys Asn Met Val Glu His
            930                 935                 940

Lys Ala Ile Val Val Leu Glu Asn Leu Asn Leu Ser Phe Met Lys Gly
945                 950                 955                 960

Arg Lys Lys Val Glu Lys Ser Val Tyr Glu Lys Phe Glu Arg Met Leu
            965                 970                 975

Val Asp Lys Leu Asn Tyr Leu Val Val Asp Lys Lys Asn Leu Ser Asn
        980                 985                 990

Glu Pro Gly Gly Leu Tyr Ala Ala Tyr Gln Leu Thr Asn Pro Leu Phe
    995                 1000                1005

Ser Phe Glu Glu Leu His Arg Tyr Pro Gln Ser Gly Ile Leu Phe
    1010                1015                1020

Phe Val Asp Pro Trp Asn Thr Ser Leu Thr Asp Pro Ser Thr Gly
    1025                1030                1035

Phe Val Asn Leu Leu Gly Arg Ile Asn Tyr Thr Asn Val Gly Asp
    1040                1045                1050

Ala Arg Lys Phe Phe Asp Arg Phe Asn Ala Ile Arg Tyr Asp Gly
    1055                1060                1065

Lys Gly Asn Ile Leu Phe Asp Leu Asp Leu Ser Arg Phe Asp Val
    1070                1075                1080

Arg Val Glu Thr Gln Arg Lys Leu Trp Thr Leu Thr Thr Phe Gly
    1085                1090                1095

Ser Arg Ile Ala Lys Ser Lys Lys Ser Gly Lys Trp Met Val Glu
    1100                1105                1110

Arg Ile Glu Asn Leu Ser Leu Cys Phe Leu Glu Leu Phe Glu Gln
    1115                1120                1125

Phe Asn Ile Gly Tyr Arg Val Glu Lys Asp Leu Lys Lys Ala Ile
    1130                1135                1140

Leu Ser Gln Asp Arg Lys Glu Phe Tyr Val Arg Leu Ile Tyr Leu
    1145                1150                1155

Phe Asn Leu Met Met Gln Ile Arg Asn Ser Asp Gly Glu Glu Asp
    1160                1165                1170

Tyr Ile Leu Ser Pro Ala Leu Asn Glu Lys Asn Leu Gln Phe Asp
    1175                1180                1185

Ser Arg Leu Ile Glu Ala Lys Asp Leu Pro Val Asp Ala Asp Ala
    1190                1195                1200

Asn Gly Ala Tyr Asn Val Ala Arg Lys Gly Leu Met Val Val Gln
    1205                1210                1215

Arg Ile Lys Arg Gly Asp His Glu Ser Ile His Arg Ile Gly Arg
```

| | | | |
|---|---|---|---|
| | 1220 | 1225 | 1230 |

Ala Gln Trp Leu Arg Tyr Val Gln Glu Gly Ile Val Glu Lys Arg
 1235                1240                1245

Pro Ala Ala Thr Lys Lys Ala Gly Gln Ala Lys Lys Lys Lys Gly
 1250                1255                1260

Ser Tyr Pro Tyr Asp Val Pro Asp Tyr Ala Tyr Pro Tyr Asp Val
 1265                1270                1275

Pro Asp Tyr Ala Tyr Pro Tyr Asp Val Pro Asp Tyr Ala
 1280                1285                1290

<210> SEQ ID NO 44
<211> LENGTH: 3876
<212> TYPE: DNA
<213> ORGANISM: Artificial Sequence
<220> FEATURE:
<223> OTHER INFORMATION: Synthetic-Porphyromonas macacae (PmCpf1; pY09),
      including NLS and HA tag

<400> SEQUENCE: 44

| | |
|---|---|
| atgaaaaccc agcacttctt tgaggacttc acaagcctgt actctctgag caagaccatc | 60 |
| cggtttgagc tgaagccaat cggcaagacc ctggagaaca tcaagaagaa tggcctgatc | 120 |
| cggagagatg agcagagact ggacgattac gagaagctga agaaagtgat cgacgagtat | 180 |
| cacgaggatt tcatcgccaa catcctgagc tccttttcct tctctgagga gatcctgcag | 240 |
| tcctacatcc agaatctgag cgagtccgag gccagggcca gatcgagaa accatgcgc | 300 |
| gacacactgg ccaaggcctt ctctgaggat gagaggtaca agagcatctt taagaaggag | 360 |
| ctggtgaaga aggacatccc cgtgtggtgc cctgcctata gagcctgtg caagaagttc | 420 |
| gataacttta ccacatctct ggtgcccttc acgagaaca ggaagaacct gtataccagc | 480 |
| aatgagatca cagcctctat cccttatcgc atcgtgcacg tgaacctgcc aaagtttatc | 540 |
| cagaatatcg aggccctgtg cgagctgcag aagaagatgg gcgccgacct gtacctggag | 600 |
| atgatggaga acctgcgcaa cgtgtggccc agcttcgtga aaccccaga cgacctgtgc | 660 |
| aacctgaaaa cctataatca cctgatggtg cagtctagca tcagcgagta caacaggttt | 720 |
| gtgggcggct attccaccga ggacggcaca aagcaccagg gcatcaacga gtggatcaat | 780 |
| atctacagac agaggaataa ggagatgcgc tgcctggcc tggtgttcct gcacaagcag | 840 |
| atcctggcca aggtggactc ctctagcttc atcagcgata cactggagaa cgacgatcag | 900 |
| gtgttttgcg tgctgagaca gttcaggaag ctgttttgga ataccgtgtc ctctaaggag | 960 |
| gacgatgccg cctccctgaa ggacctgttc tgtggcctgt ctggctatga ccctgaggcc | 1020 |
| atctacgtga gcgatgccca cctggccaca atctccaaga acatctttga cagatggaat | 1080 |
| tacatctccg atgccatcag cgcaagacc gaggtgctga tgccacggaa gaaggagagc | 1140 |
| gtggagagat atgccgagaa gatctccaag cagatcaaga gagacagtc ttacagcctg | 1200 |
| gccgagctgg acgatctgct ggcccactat agcgaggagt ccctgcccgc aggcttctct | 1260 |
| ctgctgagct actttacatc tctgggcggc cagaagtatc tggtgagcga cggcgaagtg | 1320 |
| atcctgtacg aggagggcag caacatctgg gacgaggtgc tgatcgcctt cagggatctg | 1380 |
| caggtcatcc tggacaagga cttcaccgag aagaagctgg caaggatga ggaggccgtg | 1440 |
| tctgtgatca agaaggccct ggacagcgcc ctgcgcctgc ggaagttctt tgatctgctg | 1500 |
| tccggcacag cgcagagat caggagagac agctccttct atgccctgta taccgaccgg | 1560 |
| atggataagc tgaagggcct gctgaagatg tatgataagg tgagaaacta cctgaccaag | 1620 |

```
aagccttatt ccatcgagaa gttcaagctg cactttgaca acccatccct gctgtctggc    1680
tgggataaga ataaggagct gaacaatctg tctgtgatct tccggcagaa cggctactat    1740
tacctgggca tcatgacacc caagggcaag aatctgttca agaccctgcc taagctgggc    1800
gccgaggaga tgttttatga aagatggag tacaagcaga tcgccgagcc tatgctgatg    1860
ctgccaaagg tgttctttcc aagaaaacc aagccagcct tcgcccaga ccagagcgtg     1920 gtggatatct acaacaagaa aaccttcaag acaggccaga agggctttaa taagaaggac    1980
ctgtaccggc tgatcgactt ctacaaggag ccctgacag tgcacgagtg aagctgttt     2040 aacttctcct tttctccaac cgagcagtat cggaatatcg gcgagttctt tgacgaggtg    2100
agagagcagg cctacaaggt gtccatggtg aacgtgcccg cctcttatat cgacgaggcc    2160
gtggagaacg gcaagctgta tctgttccag atctacaata aggacttcag ccctactcc    2220 aagggcatcc ctaacctgca cacactgtat tggaaggccc tgttcagcga gcagaatcag    2280
agccgggtgt ataagctgtg cggaggagga gagctgtttt atagaaaggc cagcctgcac    2340
atgcaggaca ccacagtgca ccccaagggc atctctatcc acaagaagaa cctgaataag    2400
aagggcgaga caagcctgtt caactacgac ctggtgaagg ataagaggtt taccgaggac    2460 aagttcttt tccacgtgcc tatctctatc aactacaaga ataagaagat caccaacgtg    2520
aatcagatgg tgcgcgatta tatcgcccag aacgacgatc tgcagatcat cggcatcgac    2580
cgcggcgagc ggaatctgct gtatatcagc cggatcgata aaggggcaa cctgctggag    2640 cagttcagcc tgaatgtgat cgagtccgac aagggcgatc tgagaaccga ctatcagaag    2700
atcctgggcg atcgcgagca ggagcggctg aggcgccggc aggagtggaa gtctatcgag    2760
agcatcaagg acctgaagga tggctacatg agccaggtgg tgcacaagat ctgtaacatg    2820
gtggtggagc acaaggccat cgtggtgctg agaaacctga atctgagctt catgaagggc    2880
aggaagaagg tggagaagtc cgtgtacgag aagtttgagc gcatgctggt ggacaagctg    2940
aactatctgg tggtggataa gaagaacctg tccaatgagc aggaggcct gtatgcagca     3000 taccagctga ccaatccact gttctctttt gaggagctgc acagataccc ccagagcggc    3060
atcctgtttt tcgtgacccc atggaacacc tctctgacag atcccagcac aggcttcgtg    3120
aatctgctgg gcagaatcaa ctacaccaat gtgggcgacg cccgcaagtt tttcgatcgg    3180
tttaacgcca tcagatatga cggcaagggc aatatcctgt cgacctgga tctgtccaga    3240 tttgatgtga gggtggagac acagaggaag ctgtggacac tgaccacatt cggctctcgc    3300
atcgccaaat ccaagaagtc tggcaagtgg atggtggagc ggatcgagaa cctgagcctg    3360
tgctttctgg agctgttcga gcagtttaat atcggctaca gagtggagaa ggacctgaag    3420
aaggccatcc tgagccagga taggaaggag ttctatgtgc gcctgatcta cctgtttaac    3480
ctgatgatgc agatccggaa cagcgacggc gaggaggatt atatcctgtc tccgcctg     3540 aacgagaaga atctgcagtt cgacagcagg ctgatcgagg ccaaggatct gcctgtggac    3600
gcagatgcaa acggagcata caatgtggcc cgcaagggcc tgatggtggt gcagagaatc    3660
aagaggggcg accacgagtc catccacagg atcggaaggg cacagtggct gagatatgtg    3720
caggagggca tcgtggagaa aaggccggcg gccacgaaaa aggccggcca ggcaaaaaag    3780
aaaaagggat cctacccata cgatgttcca gattacgctt atccctacga cgtgcctgat    3840
tatgcatacc catatgatgt ccccgactat gcctaa                              3876
```

<210> SEQ ID NO 45
<211> LENGTH: 7

```
<212> TYPE: PRT
<213> ORGANISM: Artificial Sequence
<220> FEATURE:
<223> OTHER INFORMATION: Synthetic-Nuclear Localization Signal

<400> SEQUENCE: 45

Pro Lys Lys Lys Arg Lys Val
1               5

<210> SEQ ID NO 46
<211> LENGTH: 16
<212> TYPE: PRT
<213> ORGANISM: Artificial Sequence
<220> FEATURE:
<223> OTHER INFORMATION: Synthetic-Nuclear Localization Signal

<400> SEQUENCE: 46

Lys Arg Pro Ala Ala Thr Lys Lys Ala Gly Gln Ala Lys Lys Lys Lys
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Synthetic-Nuclear Localization Signal
<220> FEATURE:
<221> NAME/KEY: misc_feature
<222> LOCATION: (3)..(12)
<223> OTHER INFORMATION: X is any amino acid.

<400> SEQUENCE: 47

Lys Arg Xaa Xaa Xaa Xaa Xaa Xaa Xaa Xaa Xaa Xaa Lys Lys Lys Lys
1               5                   10                  15

<210> SEQ ID NO 48
<211> LENGTH: 4
<212> TYPE: PRT
<213> ORGANISM: Artificial Sequence
<220> FEATURE:
<223> OTHER INFORMATION: Synthetic-Nuclear Localization Signal
<220> FEATURE:
<221> NAME/KEY: misc_feature
<222> LOCATION: (3)..(3)
<223> OTHER INFORMATION: X is any amino acid

<400> SEQUENCE: 48

Lys Lys Xaa Lys
1

<210> SEQ ID NO 49
<211> LENGTH: 4
<212> TYPE: PRT
<213> ORGANISM: Artificial Sequence
<220> FEATURE:
<223> OTHER INFORMATION: Synthetic-Nuclear Localization Signal
<220> FEATURE:
<221> NAME/KEY: misc_feature
<222> LOCATION: (3)..(3)
<223> OTHER INFORMATION: X is any amino acid

<400> SEQUENCE: 49

Lys Arg Xaa Lys
1

<210> SEQ ID NO 50
<211> LENGTH: 4
<212> TYPE: PRT
<213> ORGANISM: Artificial Sequence
```

```
<220> FEATURE:
<223> OTHER INFORMATION: Synthetic-Nuclear Localization Signal
<220> FEATURE:
<221> NAME/KEY: misc_feature
<222> LOCATION: (3)..(3)
<223> OTHER INFORMATION: X is any amino acid

<400> SEQUENCE: 50

Lys Lys Xaa Arg
1

<210> SEQ ID NO 51
<211> LENGTH: 4
<212> TYPE: PRT
<213> ORGANISM: Artificial Sequence
<220> FEATURE:
<223> OTHER INFORMATION: Synthetic-Nuclear Localization Signal
<220> FEATURE:
<221> NAME/KEY: misc_feature
<222> LOCATION: (3)..(3)
<223> OTHER INFORMATION: X is any amino acid

<400> SEQUENCE: 51

Lys Arg Xaa Arg
1

<210> SEQ ID NO 52
<211> LENGTH: 20
<212> TYPE: PRT
<213> ORGANISM: Artificial Sequence
<220> FEATURE:
<223> OTHER INFORMATION: Synthetic-Nuclear Localization Signal

<400> SEQUENCE: 52

Ala Val Lys Arg Pro Ala Ala Thr Lys Lys Ala Gly Gln Ala Lys Lys
1               5                   10                  15

Lys Lys Leu Asp
            20

<210> SEQ ID NO 53
<211> LENGTH: 25
<212> TYPE: PRT
<213> ORGANISM: Artificial Sequence
<220> FEATURE:
<223> OTHER INFORMATION: Synthetic-Nuclear Localization Signal

<400> SEQUENCE: 53

Met Ser Arg Arg Arg Lys Ala Asn Pro Thr Lys Leu Ser Glu Asn Ala
1               5                   10                  15

Lys Lys Leu Ala Lys Glu Val Glu Asn
            20                  25

<210> SEQ ID NO 54
<211> LENGTH: 9
<212> TYPE: PRT
<213> ORGANISM: Artificial Sequence
<220> FEATURE:
<223> OTHER INFORMATION: Synthetic-Nuclear Localization Signal

<400> SEQUENCE: 54

Pro Ala Ala Lys Arg Val Lys Leu Asp
1               5

<210> SEQ ID NO 55
<211> LENGTH: 9
<212> TYPE: PRT
<213> ORGANISM: Artificial Sequence
```

```
<220> FEATURE:
<223> OTHER INFORMATION: Synthetic-Nuclear Localization Signal

<400> SEQUENCE: 55

Lys Leu Lys Ile Lys Arg Pro Val Lys
1               5

<210> SEQ ID NO 56
<211> LENGTH: 15591
<212> TYPE: DNA
<213> ORGANISM: Homo sapiens

<400> SEQUENCE: 56 tagggatga cagtgggctc tccgctttct cctccatgaa gtaacttaca tgcccctcac      60
cctctgtggg aggggtgttg caggggtgc  agaactcccc tcgccgggta gttcaagcaa     120
tggggaccat atcaattcca tctataggga aactgaggcc tggagtaggg cgaggcctct    180
gggaacccag ccctattctg tctctttccc tggcatttcc catccacaca tagagcttca    240
gattctcttt ctttccccag agaccctcaa atatcctctc actcacagaa tggtgtctct    300
gcctgcctcg ggttggccct gtgatttatt ttagttcttt tcccttgttt ttttttttc     360 aaactctata cactttttgtt ttaaaaactg tggtttctca tgagccctat tatctcattg    420
atacctctca cctctgtggt gaggggaaga atcatatttt tcagatgact cgtaaagggc    480
aaagaaaaaa acccaaaatt tcaaaatttc cgtttaagtc tcataatcaa gaaaaggaga    540
aacacagaga gagagaaaaa aaaaactatg agaacccctc cccacccccgt gattatcagc    600 gcacacactc atcgaaaaaa atttggatta ttagaagaga gaggtctgcg gcttccacac    660
cgtacagcgt ggttttttctt ctcggtataa aagcaaagtt gttttttgata cgtgacagtt    720 tcccacaagc caggctgatc cttttctgtc agtccacttc accaaggtga gtgtccctgc    780
tctcccctac cagatgtggg ccccattgga ggagatggca gggaggtagg cacggcgggg    840
gggtcagggg ccctctggta cagtgggatg tacccagcta ccgtgattcc agccaggtaa    900 ggtcttttaaa aaaataatag aataaatggc agaagactta aaggtgaagt acttaatgca   960
tgggcagggg caaaaataaa tgaattcatc aattgatacg tagatggata ggattttttaa   1020 aatatgtcag ctgccagtct ttatggattt cagagctttg aacaacttga aatgctgtcc    1080
aggtgcaact gaaaatttca actgcatctc tctcatctct ttgtctctta gctcttgatg    1140
cctctcatcc ttctctgtct ctctgctcac cctgtcttgc tctttttacat gtttctctgc    1200 ctctcttttct cccgccatct gtctgtcgct acactcagac tctctttccc cgcatctctc   1260
ctggcctctg accatctccc ctatctctgt ctcctccatc ttgaccacac tccatcgatc    1320
tcctttcctc catctctccc gctctctttt cttgccttcc cccacctgcc ttcccagcca    1380
gcatccagcc tagagctttg tacacagctg gcgtttaata atagtaatgt cgccgaggac    1440
ctttacattt tatgagagtg agcatcagtt ctgttcaccc tagtagcagg aggattgcaa    1500
ggtgccgggg caagctgagc acttaactga actttgcttg tatcgcttta gaggagaccc    1560
ttggggcggg ggggcaggga gcacttcaca ccattgtcaa ccgtagttta gctgtgtgga    1620
cctaccccag gactgcatgt gtgtgaccag agtccatatt caggaagcaa acaggttgtt    1680
cagggctggg gtgagctcga ttctgcaggc ttagcacagc gtttggcaca agtaagtgc     1740 tcacgaagtg ttagctatta gtatttctgt aaccaaatta gaatcatgct atatattggt    1800
tttgttcctg ctttattcaa ttaacagtag tgttttttgaa gcttactaaa aattgtttga    1860
acacatgatc tttcatgatg gacaagactg tcctcacatc agcatgaact ttgattgatt    1920
```

```
tgaccaagtg ccgattgttg gacattccgg ttgtttctcg ttttttttcta taaacatccc   1980 tgactgcttc cttggattcc tgaaaaggga gttgctgggg caaaggggggc gtgcatttttt  2040 aaagtttatg accctctctg ctaattctcc ttccaaaagg ttgtcctatt ttatgctccc   2100
tctacttaag ctaaccctag gtgagtatta ttatgtttta attatttccc aacatgacag   2160
gtaagaaaaa cacattatca cattgttgaa atttgcatct tgtgattact tttactattc   2220
attggccatt catgcttttt ttttttttttt tttggttgtc tggtcatgtc cttactccta   2280
atagggtgtt catcttattt ttcccttatt gatttgccac agctctttat ttggaatggt   2340
tattaacctt tcatcagcca ttacatatat agcaaatatt ttccccaatt catcatttgc   2400
tttttttcta tttgtttatg gtgttttttg tgatgcttat gatggtttta tacagtcaaa   2460
taggttagtc tttttttctg tggcttctgt ctctggtttt gtgcttagaa agtccttttcc  2520 tacttgaaaa tgagataaat gttcacctat gttggcttct agtctctttt atggcttcat   2580
tttttccatt tactatagag gttaagagtg tgggtactgg agccagactg tctgggacaa   2640
acccagcgtc accccaagcc ctatgtgtga ttttttagcca ggcacttaac ctctccatac  2700
ctccatttcc tcatatgtac tgcaatggtt ataatagtac cttcctcagg agtctttgtt   2760
tagattaaaa ttttttaacca cagtaaatac ttagcacaag gcctgacaca caataaaccc   2820
aagatcagca ttaggtgtta aaacttatat cttgaatgga tctgggcatt ttagggtata   2880
tgatgatggt gacatttcaa actgggcagg gaggggttgt tgggataatg gactgactat   2940
tcactcaata actttatctt ctccctaatt atctcagaca catttgttaa accatactcc   3000
atggtcctcc agtttgaaat gccacattca tcacaaattc agttctctcc atatgtgggt   3060
ccatgtccaa gctttctatt ctgttctctt ccccagtatc tgttcttata ccagggccac   3120
actgttttgc tgattgttgc tttgcaatac aattcaatac ccagccatgg gtgtccctgg   3180
caccttgccc ttctttattc ttgattattt caggcagcat cagttgaacc agccagagac   3240
cagcaaatgt tcttatttga ggcaatcctc ctctcgcaca catgcactct ggctctccat   3300
gcatgtgtcc atttctctca atgtctctca ctatctcttg ttctctcttg ctcgctcttt   3360
gtgtgtgtct ctttgtctct atgtatccct atctctcagc cagtccctg gatagagggg    3420 caattgtcaa cttgaagccc tgcagacacc taatgactta accagacagc gtagaagggc   3480 cctggcccctt gtctactcca cgcctctccg tgctcagtgt agaagggcaa attgaagacc   3540
agagatctca gggcctcacc gaaatgcagc ggcagagttg aaatccaagc ctagatctca   3600
ggactctagg tgggacccctg gttctggctc tctccccaac tgcaggcctc agtttacccc  3660
tcagcaccca gaagggggaa ggggaacctg ggctaccatt ccccccttctg ccttctcaca   3720 cgttggaccc caacttccca caggttggac gatccacgat cacagtgtgg ggcccagcct   3780
cacaagagct gggctaggtg aggccccgga ctccataggt caggaggcct agttggccag   3840
agcgtggtga tgatggaggc atgtcagtca gtcaggctgt gtgtcccccag agctggtgct   3900 ggtccccgaa aaccttgatt gtggggcccc tctagagagt ctgatgatgg gctctgtatt   3960
ggcgaaggct gaggcttttc cagctccccc catgaggccc agaccaaagg cacaccagcc   4020
tcaacctcct cctcccccctg ttgccatctc tggcggagtg gccatgtatt tgggaacgtt   4080
gttccagagt ggacagggag actgaggccc tagggaggct ggctctgttt ccaggcctgg   4140
taggcaagag gccctatgaa gcagcaagct gcctgacttt cagatggttc caaggagttt   4200
ggacaccagg gacactggcc tacacatact gagactttgg gaccgtagac cccacagtct   4260
```

```
gtggttttga gattctagga tcctttaaat ctaagaaatg ctgttctatg attctgaggt    4320
cctggtgtta tactatttga agaccccagg ggtcccagta tctgtggagc ctgcctggca    4380
ctctcagagc ttcaaacctg ggtcctctcc acaacccaag aagggccagg tcttcagagc    4440
taggggcttg tcatagtggc cagatggaca tcacctacca catccaccag cacccatgtc    4500
accccacctg ggccaagcct gctgcaggac agggcagcca gttctcggaa cgaaacctgt    4560
ggggtggggt atctgccctc ttctcttcct ccgtggtgtc gatgaagccc ggcgcatccg    4620
gccgccatga cgtcaatggc ggaaaaatct gggcaagtcg ggggctgtga acagggcc     4680 cagatgcaga ccccgatatg aaaacataat ctgtgtccca gaaacatccc ccattcagct    4740
tctgagaaac ccagtcagaa agggacgtcc caacagacag tgcaggaagc cggctgccca    4800
gcccggccct ctaggtcctc taccccccaga cagatcatct ccatgtccct gtctgagaat    4860
gtatctatgc tttgctgagt caggccatcc cacatgtgtt tggggagaat tcttagctct    4920
ggccaagtgt ccaggcagct tcagaagtga ccacaggcca gccacatggg ccaggccaga    4980
gtggtggaaa acatccattt gcaccgaaat cggtattagt ttgttctggc tgctataaca    5040
aagtaccaca actgagtggc ttcagcaaca gaaattgatc atctcacagt tctggaggcc    5100
agagtccaag atcaaggtgt tgccagggtt ggttccttct gggggccata agggagaagc    5160
tgctccaggc ctctccccca gcttctggtg gttgctggca atctttgtta tttcttggct    5220
tgaaggagca tcaccccatc tctggcttca ttcattcact caccttctca tctcaccagt    5280
gctctcccag gcccttgttc ggagcctcca cagacccaca ctcctgtttc tcacgcagta    5340
atgttctaag ccccccaggag actaagaact taatacctgg attctcacac tcatctccct    5400
cagcaccaca gctctgacaa ccaccccccag gaggtgacag caaagaaagg aaggagcaac    5460
tgctccccca gaacccttct atactccccc gggctgctct cagcagctgt gtgcccaact    5520
cagtgctgtg aggtggaacg gggagatgga gacacacaca cacacacacc agagagttta    5580
taaaatgtgc acacggaaac acttcctaaa gaaagaagtg gagttctcaa gtcactatgg    5640
gactacggaa ctcggcatct gagcatcccc ttctgtataa tggggttggc tgggcagtcc    5700
cttccagctc tggcttcctc tcagaccagg attataggat cctgaaaagc cagtgcttcc    5760
ctcagggagt ggaaggttct ggggctcagc agggggcccg gagccattgt ggagggcttt    5820
caaggtgagg acaatagaag agcaggtctt gcgtggcttg gacagggaaa gaggagaagg    5880
agtgggcatt tgaggcaggg ggtgtagcat gagccaggct tgagggccag aaattggggt    5940
gaactctgat gggggctggg tagagaagct tctacaggcc ccagctcaag gaccccatc    6000 tctcctcctc tctgtcactt gccatgctgg atccgtgcat gatcacactc ctggactcgc    6060
ctccttgccc tgagatccag accccgtat tcagctgccc cctcagctcc tccactcaca    6120
tatttaatgc cagactcttc atgtctatct acacctgcac ttttgcaccc aatccaactc    6180
cccgccatgt cccccatctc aggtaatgtc agctcggtcc ttccagctgc tcaagctaaa    6240
acccatgtca ctttgactct ccctcttgcc cactacatcc aagctgctag cactgctcct    6300
gatccagctt cagattaagt ctcagaatct acccacttct cgccttctcc actgccacca    6360
gcccattctg tgccagcatc atcacttgcc aggactgtta caatagcctc ctcactagcc    6420
ccactcacag cagccagatg aatctttttga gtccatgcct agtcactggg gcaaaatagg    6480
actccgagga gaaagtccga gaccagctcc ggcaagatga gcaaacacag cctgtgcagg    6540
gtgcagggag ggctagaggc ctgaggcttg aaacagctct caagtggagg gggaaacaac    6600
cattgccctc atagaggaca catccacacc agggctgtgc tagcgtgggc aggcaagcca    6660
```

-continued

```
ggtgctggac ctctgcacgt ggggcatgtg tgggtatgta catgtacctg tgttcttggt    6720
gtgtgtgtgt gtgtgtgtgt gtgtgtgtgt ctagagctgg ggtgcaacta tggggccccct   6780 cgggacatgt cccagccaat gcctgctttg accagaggag tgtccacgtg gctcaggtgg    6840
tcgagtatct cataccgccc tagcacacgt gtgactcctt tccctattg tctacgcagc     6900 ctgcccttgg acaaggaccc gatgcccaac cccaggcctg gcaagccctc ggccccttcc    6960
ttggcccttg gccatcccc aggagcctcg cccagctgga gggctgcacc caaagcctca     7020
gacctgctgg ggcccgggg cccaggggga accttccagg gccgagatct tcgaggcggg     7080
gcccatgcct cctcttcttc cttgaacccc atgccaccat cgcagctgca ggtgaggccc    7140
tgggcccagg atgggcagg cagggtgggg tacctggacc tacaggtgcc gacctttact    7200
gtggcactgg gcgggagggg ggctggctgg ggcacaggaa gtggtttctg ggtcccaggc    7260
aagtctgtga cttatgcaga tgttgcaggg ccaagaaaat ccccacctgc caggcctcag    7320
agattggagg ctctccccga cctcccaatc cctgtctcag gagaggagga ggccgtattg    7380
tagtcccatg agcatagcta tgtgtcccca tccccatgtg acaagagaag aggactgggg    7440
ccaagtaggt gaggtgacag ggctgaggcc agctctgcaa cttattagct gtttgatctt    7500
taaaaagtta ctcgatctcc atgagcctca gtttccatac gtgtaaaagg gggatgatca    7560
tagcatctac catgtgggct tgcagtgcag agtatttgaa ttagacacag aacagtgagg    7620
atcaggatgg cctctcaccc acctgccttt ctgcccagct gcccacactg ccctagtca     7680 tggtggcacc ctccggggca cggctgggcc ccttgcccca cttacaggca ctcctccagg    7740
acaggccaca tttcatgcac caggtatgga cggtgaatgg gcagggagga gggagcaggt    7800
gggagaactg tggggagggg ccccgagtca ggctgaacca cagcccacat gtgcccccca    7860
gctctcaacg gtggatgccc acgcccggac ccctgtgctg caggtgcacc ccctggagag    7920
cccagccatg atcagcctca caccacccac caccgccact ggggtcttct ccctcaaggc    7980
ccggcctggc ctcccacctg gtaacacctc agcccgtacc ccatggcttc acagaacccc    8040
caagtcccca gatccttggc tgtgagcagt gtaggctatt ctgaattgca gtactctggg    8100
ggtcaaaggt gtcaggtctc agaggcttgg aaactccacc ctccaaaaaa cgtcaggtgc    8160
agaaccttaa agatgcagaa tgtcaaaatc acaaaaccac agagctttac aaagctagtc    8220
aaaatgtcag cacctgcgaa tggccgtctt taagcttctc tgccagaagc ctgggacttt    8280
ggggacagca gagccccctg ggagtcaggg ttttcgaggc tcaggagggt gggaagctca    8340
aaatgagagg ccttgtgggc caagctccag agcccagccc acagcctcca taggtgccct    8400
gtccccaccc acagggatca acgtggccag cctggaatgg gtgtccaggg agccggcact    8460
gctctgcacc ttcccaaatc ccagtgcacc caggaaggac aggtcagtgg acagggctgg    8520
gaaggatcct cgccctccta tccctcccc tgacaccctc tgtcccccca gcaccctttc    8580
ggctgtgccc cagagctcct acccactgct ggcaaatggt gtctgcaagt ggcccggatg    8640
tgagaaggtc ttcgaagagc cagaggactt cctcaagtga gtggcccagg cctgtgccag    8700
tctaccggcc ctggcttgtg gggagaggtc tagggtgcag atctcagctc aggcttcatc    8760
ccaataagta gtaagatgca agagctaaac tctgagactt tgggttcaaa tcccagctcc    8820
atccctgact ggctgtgtga ccttggacaa attacttagc ttctctcgac ctcagttttc    8880
tcgtatgtat aataagaaac gtttgtgctg ttatttaccc ccattttaca gacaaggaga    8940
ctgaggccaa agaggttaag tgtcttgatc aaaatctccc agttcctgag tgacagagct    9000
```

```
gggatttgaa cccatgtagc caggctctag aatctgcact cctgctttgc cctgctactc    9060
ctcatgccaa catgccagcc ttattccact gttcccaaag ttctagctcc tctagatggc    9120
tgctgctgcc tcccctcagt cccccatat gtctctctct ctctctctct ctctctctct    9180
ctctctctct ctctctctct ctctctttct ctctctctca cacacacaca cacacaaata    9240
cacaccacac tacacacaac ccttagcagc aaccccacat gtcctgtcct ccttgcagcc    9300
aggcctttgc acaggccgtc cctccaccca gaatgctttg cccactctca cctccctggc    9360
ccattctcaa ctcaccacac ttccaacatt atctccagca ctctggccag gctcaagtgg    9420
tgagttcagg cctgacatgc agtaggtgct gaggggcatg tgttaaggga acgaggggtg    9480
tgagagggag actgaggtag agagggagg ggagctgggg ctcagaggag agaactccca    9540
gagggtctgg gccctcccca ttcagagcat tgagccagac caggcctgtc gtggtcacct    9600
gcatggaatc ttctccctac ttaggcactg ccaggcggac catcttctgg atgagaaggg    9660
cagggcacaa tgtctcctcc agagagagat ggtacagtct ctggagcagc aggtaatgcc    9720
agggcggtgg agggtaaggg atagggatag tgcgcaaaac cttctgtcca ccatgtgcca    9780
gaaaccaagt tcacctggga cgagggctgg tataaaggaa ggaagaggag cgggcactcc    9840
cagggaagac cgtagcctgg gcaaagatgt ggcagagaag ggccaggctg aggcctcatg    9900
tttgtgccat ttcacagctg gtgctggaga aggagaagct gagtgccatg caggcccacc    9960
tggctgggaa aatggcactg accaaggctt catctgtggt gagcgacccc aggactggtg   10020
gtggcagact cagactgctg gggggcaggg aggaggtctg cacggtgcag ggaacctaac   10080
ctcacattca ggtcctgaga gctagggcc cctgtcccca gctccaaaca tgcccagacc   10140
tggaaatctg tccccttcta cttacaaacc ctctgacccc ggctgggcgt ggtggctcac   10200
gcctgtaatc ccagcacttt gggaggccga ggcgggtgga tcacgaggtc aggagttcaa   10260
gaccagcctc gccaagatgg tgaaaccctg tgtctactaa aagtacaaaa aattagccag   10320
gcgtggtggc aggtgtctgt agtcccaact acttgggagg ctgaggcaga gaattgcttg   10380
aacctgggag gcggagtttg cagtgagctg agatcatacc actgcactcc agcctaggcg   10440
acagatcaag actccgtctc aagaaaaaaa aaaaaaaaaa accctctgac tctaagatcc   10500
ccaaacactg tgatcctgag ttgttaaagc aaatgcaaat agccagactt gccagatgca   10560
ggctgtgtgc cagcaggacc agctatgtaa cctgcagggc cccttgttca gatttcaaga   10620
tggcgaccac agagcattaa acaaagcaca gggtgccaca taaccacata ggtcacacgc   10680
ccatgaagcc agcctggag gccaggcact gtttctgagc gctttgctgg tggtaattta   10740
tttctcatga tgcgaatgta cagatgagga atattgaggc cagggggtt taggtgactt   10800
tcccaaggtc acagttgggt ggtaaagagc cctattcaac cccagttcat ggtcccagca   10860
tcagtggcca catacgacat ccgcacctgt gctctaataa atacggctca tgctgttttg   10920
tgggattcca cctcagactg gaatttagaa gagggcgtcc ttgctttgaa aaacactgat   10980
ttaaaaataa agtggagcca ggcgcagtgg ctcatgcctg taatcccagc actttgggag   11040
gctgaagcgg gtggatcaca tgaggtcagg agttcgagac cagcctggct aacatggtga   11100
aaccccatct ctaccaaaaa tacaaaaatt agctgggcgt agtgacggc acctgtagtc   11160
ccagctactc gggaggctga ggcagaagac ttgcttgaat ctgggaggtg ggggttgcag   11220
tgagccgaga ttgcaccact gcactccagc ctgggcgaca gagcaagact cagtatcaaa   11280
aaaaataaaa aacataaaat agaaagtaaa aagtgggaag tttaagcctc tgggtcacca   11340
gcctctcccc ctcacccagg catcatccga caagggctcc tgctgcatcg tagctgctgg   11400
```

```
cagccaaggc cctgtcgtcc cagcctggtc tggcccccgg gaggcccctg acagcctgtt   11460
tgctgtccgg aggcacctgt ggggtagcca tggaaacagc acattcccag gtaagaatgg   11520
tccttgcact acacggtgcc cccaagctcc taatcctgac aggctctggg tggagggtgc   11580
aaaggagctc catgctgccc cttcccacca ccaccaccac tgcagctgcc gccactcagc   11640
ctttgggaaa atgcatccgc tcacaaaagc ttcctttcgg gatgtccgtg cctgaaagc    11700 cccccatatg gtctcgagtg tcgggcccct agccctgact cccttgggga ttggggccat   11760
gcctcaccca ctctggactc cagctactat attcggccat cagaagggag ggaccctgct   11820
aagtaattcc aggagcacct cctttcctcc cctgaccaag gaaaatcggg gtggattcgc   11880
ccgagctcac ctatccactg ctctccacca ggcctggcct gtgggcttag cagggatcag   11940
agaccttgac tgtcatcctg gctctgccat ttaacctctt gcatcctttg gtgtgcaagt   12000
tactccgctt cttttcaacc tcggggagaa ctattttggc agaagtggtg caaagaataa   12060
atgatacaac ttatgtcagg tgctcagcaa acagtacctg tgcccgtgga cacgggtgtt   12120
gacggtgaga tctcaggcct gtagactcac cttgtagggg gaggggacag ggagctagct   12180
aggaggtcct gcatggggct tgattcatcc ccaccctctg acagagttcc tccacaacat   12240
ggactacttc aagttccaca acatgcgacc cccttccacc tacgccacgc tcatccgctg   12300
ggtaagcagg gcagctcggc cccaaggagg aggaagacaa agatggggtg ggggacctgc   12360
ctcccaaact cctgtctccc tctgagtgcc ctcagagtgg gttcctccat tcccaagccc   12420
cagccccaag gatccccaag ccgtgcctca aatgtgaccc ctcatgctgg cttcacccca   12480
aacctgtccg caaatccaaa cctaaaccac catccaggcc agagcatgcc aaattctgac   12540
cctaaaccta cccctttcca gatgtccacc tcagccccat acctaaccct ctcctggacc   12600
cataaaatag cctaaagcta accccatctc tgcaccttgc cctaaacgta ccccagctct   12660
tactctaact ccttcccag cctttatgcc aacccaaccc catctccttc cctggcccca   12720
acgtacccca gtatgtcaat acaccccaa ctgggcacca ttcccaacct ttccttgtaa   12780
cacccatttg atccttaact tcatcacccc atcccaactc cttcatctca gcctccccaa   12840
tgccttctca gaaccttcat cctagcgcca cacctaaccc caaacctgaa cctcacccct   12900
acatgatacc agatattccc cgactgtctc tgaactgaaa ccctgaccta gccccatcct   12960
gactgatagc ctcactgcaa tcatcatcgc tgactctgta atcccattcc tgaatccaaa   13020
ctgatcaaat tccctgaccc tcagcctcac tccacaccga accccacaac taacctcatc   13080
cttgccctga gcctaaccac ctaaccatgt ccctgacacg taagatactc gataattcaa   13140
accatctctg gcttctgacc taaagccaag tcatcccatc cctcacccct agaccccca    13200 cctgagtcca ccccagcctg actcttaacc caccccttcc ctgacccttta agttggcctg   13260 gccctttacc ccttccaaat ccttgacccc acttctgacc cttcaccttc cccaaccctg   13320
aaatgtcacc tccacagaga ccccaactc caactccatc ccagaccttt cacctcactt    13380
cagccctagc cctgaacaag accccactcc caacctcagt cctgatccct tacctaatcc   13440
cagaacaacc ataccacac ccatctaacc ctgcccaacc cgacacttca cccctttct    13500 aaccccatct ttgaccccat gcttcacccc acatctagtc ctgtccctga ttacctgccc   13560
ctacaattcc gcccccatgt cagatggctc ggggtaggtc atagcccctc taaaccccaa   13620
gtttggggaa tgtgcccctt accccacccc caacttcca ggccatcctg gaggctccag    13680
agaagcagcg gacactcaat gagatctacc actggttcac acgcatgttt gccttcttca   13740
```

-continued

```
gaaaccatcc tgccacctgg aaggtgagct cctctgaggt ggcggtgact gggatggcct    13800
caagtgccat cgcagctcaa agtgggcagg cctgggtctg ggctcatagg cacattgggg    13860
aggaacggga tgtgggttgt tggtggtggc tgctggcctc agaggttgac gcccacctgc    13920
tccctgtccc cggccttcca cagaacgcca tccgccacaa cctgagtctg cacaagtgct    13980
ttgtgcgggt ggagagcgag aagggggctg tgtggaccgt ggatgagctg gagttccgca    14040
agaaacggag ccagaggccc agcaggtgtt ccaaccctac acctggcccc tgacctcaag    14100
atcaaggaaa ggaggatgga cgaacagggg ccaaactggt gggaggcaga ggtggtgggg    14160
gcagggatga taggccctgg atgtgcccac agggaccaag aagtgaggtt tccactgtct    14220
tgcctgccag ggcccctgtt ccccgctgg cagccacccc ctcccccatc atatcctttg     14280
ccccaaggct gctcagaggg gccccggtcc tggcccagc ccccacctcc gcccagaca     14340
caccccccag tcgagccctg cagccaaaca gagccttcac aaccagccac acagagcctg    14400
cctcagctgc tcgcacagat tacttcaggg ctggaaaagt cacacagaca cacaaaatgt    14460
cacaatcctg tccctcactc aacacaaacc caaaacaca gagagcctgc ctcagtacac     14520
tcaaacaacc tcaaagctgc atcatcacac aatcacacac aagcacagcc ctgacaaccc    14580
acacacccca aggcacgcac ccacagccag cctcagggcc cacaggggca ctgtcaacac    14640
aggggtgtgc ccagaggcct acacagaagc agcgtcagta ccctcaggat ctgaggtccc    14700
aacacgtgct cgctcacaca cacggcctgt tagaattcac ctgtgtatct cacgcatatg    14760
cacacgcaca gcccccagt gggtctcttg agtcccgtgc agacacacac agccacacac     14820
actgccttgc caaaaatacc ccgtgtctcc cctgccactc acctcactcc cattccctga    14880
gccctgatcc atgcctcagc ttagactgca gaggaactac tcatttattt gggatccaag    14940
gcccccaacc cacagtaccg tccccaataa actgcagccg agctcccac atgctggact      15000
atcaccccat ataaggggttg cggtcagtgg gcaggggtct gggtccaagg ccgcagcagg    15060
aggaactgga cagcggagga agtagctagg gcatgtgctt ggccactgcc tccagcaccc    15120
caaatccctg cctgaggctg gggagagacc tctgccggcg gctcctcagg cctcccggac    15180
ccggcctagg aggccagcgt tctcctggcg gagggctcgg tagtcctccc ggatcttctc    15240
caggttgctg agggtcttct tgcccagctc tgtctcgatc tgaggcaatg tgaacacatg    15300
ccccctcagc acacacagcc cctttcccag ctcctgctca ccagccccca tcacagccac    15360
tctgggcccc tcccaccaac tccaacagcc tgctctgtcc catggccagg cctcgtgtgg    15420
tgttccctct acccaaagca tccttcgcca tgtggcagga ttccccctac atctttaagc    15480
tgaagcctct gcccatggcc ctgggaggca gacaggaggg cccttggggt ggaagctggg    15540
gctcacagta ggccacttgc ctgtcccagg tcacaggcac taagggggcag g             15591
```

<210> SEQ ID NO 57
<211> LENGTH: 431
<212> TYPE: PRT
<213> ORGANISM: Homo sapiens

<400> SEQUENCE: 57

```
Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
                20                  25                  30

Ser Asp Leu Leu Gly Ala Arg Gly Pro Gly Gly Thr Phe Gln Gly Arg
            35                  40                  45
```

Asp Leu Arg Gly Gly Ala His Ala Ser Ser Ser Leu Asn Pro Met
 50                 55                  60

Pro Pro Ser Gln Leu Gln Leu Pro Thr Leu Pro Leu Val Met Val Ala
 65                  70                  75                  80

Pro Ser Gly Ala Arg Leu Gly Pro Leu Pro His Leu Gln Ala Leu Leu
                 85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
        115                 120                 125

Ile Ser Leu Thr Pro Pro Thr Thr Ala Thr Gly Val Phe Ser Leu Lys
130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430

<210> SEQ ID NO 58
<211> LENGTH: 16049
<212> TYPE: DNA
<213> ORGANISM: Homo sapiens

<400> SEQUENCE: 58

-continued

```
catgaccctg ccaccccatg ggcctgctgc tggtggcagc gtggccgcct cctgagagtt      60
ggccctccct tgtgccactg ccaggggagg aaaggccttg atgttccaga caataataaa     120
tgcgcctgtg acttagcctt ggtgtcagtc tcttgcggac ctgacaaccc ccatctctcc     180
ttccctgatt ccctctgcct ttccaggccc catcccctg aacagctcct ccctatggtc      240
ctggctgggc ctaaccctgc cccagggcct aaccctacct gaggctcctc cccttccccc     300
ggggcaggtt gagaggctgg agtgggtccc tcagcgccct gggtgggtgg gcctgcacag     360
ggggtacctc cttctctgag gaactgggct gttagggatt ttccttaggc cctttggttt     420
ccgcctacgg agaggtttcc cccattggtt gctcttcctc agccagggtt acttcctggt     480
ctgttcccct acccaatacc ccgccgctct gtcagcttga gctccaggtg gagctccagg     540
tggctcctcc tctcccgggg gaaggcggcc ctggaccagc aggcgggcct gctgtactcc     600
cgctttgggg ctgcagggaa gctggccgct gtgggcggtc tcgggccagc ccgccccac      660 ctgtcctttt cctggagact attagtccag ggtttgtccc tgcagtgcca ttggcctggc     720
aggcaggatc gaggaggaag tggctgatta ctgagcggtt cttcctcacc tggcttgggc     780
cactgtgcac agctgtgccg ctggctcagc ccgccccct gcggccctct gccgtggctt      840 cccctccct acagagagat gctgtcccgt gggtaagtcc cgggcaccat cggggtccca     900
gtctcctgtt agttttggag ggagggaggg ctttgttgat gctcactccg acgtgtgtga     960
acgtgagtgc gatctgccgc tgccctgcgc ctgtttccgg tccctatgaa cttcccttc     1020 ccgcaaggtg tgaggacccc cggctcactc atgctcctct gcccctctt taacattttc     1080 ccctggacaa gtgtgtatct gttctctcca ttgcatttct acttccagcc tctgggctcc    1140
tgcttctgcc tcctgcttag gacctgtccc cctgggtagc tcacaacacc tcaaacatag    1200
cagtcagagg ccaccgcga aggccctccc acgtccagcc aacttctccg cacttcccaa     1260
catcagactt tggtcccatc ttctttgttt cctttcactt cccttccccc tgcatcattc    1320
attcaacagg tacgtgttga gcatctatta tgcaccaggt gctgtttaag atgctggtaa    1380
tactggagtg aacaagacag acatggtctc tgctctcacg gagcttacat tccagtggga    1440
ggttacagac cgaacaaata acccaataaa ttggatcatt gcagattctc agaagtatta    1500
cgcagaaaat agacagcctt ggccgggtgt agtggttcac acctgtgatc ccagcactgt    1560
gggaggctga ggcgagagga ttgcttgagc ccaggagttt gagaccagcc tggccaatat    1620
agtgagaccc tgtctctaca aaaataaga aattagctgg gtgtggtggc acacgtcctg     1680
tggttccagc tatggagagg ctaaggtgag aggcttgctt gagcctggga ggtcaaggct    1740
gcagtcagcg atgattgcac cactgcacac cagcctgggc gacagagtga gaccttgtct    1800 caaaaaaaa aaaaaaaaa gaaatgaac cagcttcata tgctagcaag tgactgggtg      1860
tgcaggtgac attactagct ggagggatca gggaggcctt cccgaggagg tgacatttga    1920
gctgagaccc ggatgaggag gaagaggagc tggccatgtg acgtagtgat caagagtcaa    1980
gcatctctgg gcagaggaga tggtgagcac aaagccctaa tgtgggaaca acaaaaaaaa   2040
ggacagtgtg cccgtggcag aggacccag tggagcggag gcagggccac agcaggttag    2100
accatgttgg agctaggatg ttgaaagtga aaacctgacg agatgaggtg gcgcacgtct    2160
gtgatcccag cactttggga ggccgaaggg ggaagattgc ttgagctcag gagtttaaaa    2220
ccagcctggg caacatagag agaccccatc tctattaaaa aaaaatactg ggtatgatgg    2280
cccaagcatg tggtagtcct agcagtttgg gaggctgagg tgggaggatc acttgagccc    2340
```

```
aagagttcaa gaccaccctg ggcaacatag ggagagacct catctctact acgactacga    2400
ctactactac tactaataaa tagctggatg tagtggcatg cacctgtggt ctcagttact    2460
tggaaggctg aggcaggagg atcacctgag ccaaggaggt cgacgctgca gtgagttgga    2520
ttgtgacact gcacttcagc ctgggtgata agcaagatt ctgtgtcaaa aaaaaaaaa     2580 aaagagaggg aaggaaagaa ggaagggaag gaagaaagaa aaagagaaag aaggaaaaaa    2640
aggaaagagc gagaaagaag aaagaaaagg aaggaaggaa agaaagaaaa gaaaggaaag    2700
aaaaagaaaa agtgacaccc agtcgaaaga agaaggaaa gaaaagaaa aagtgacaac     2760 cggtcgaaag aaaaaagaaa aagtgacaac cggctgggca tggtggctca agcctgtaat    2820
cccagcactt tgggaggccg aggcaggtgg atcacgaggt caggagttca agaccagcct    2880
ggccaacatg gtgaaaccct gtctcaacta aagatacaaa aaaaaaatta ggctggcaca    2940
gtggtgcgca cctgtgagtc ccagctacta gggaggctga ggcaggagaa ttgcttgaac    3000
ccaggaggcg gaggttgcag tgagccgaga ttgcgtcact gcactccagc ctgagtgcag    3060
cgggagagac tccatctcaa aaaaaaaaaa aaagaaaag aaaagtgac aacctgctta     3120 cagagtactg gcgagtttgt gggtgggtgg ctccctagcc ctgctgattc ttgcttctca    3180
cactcatgtc tgccctgcc ccagtgcaca tcttgtcact gtcggcccca ccgatggggt     3240
tcctactgag tcttctggtc cctgatcccg tctgtggtca ttttcctgcc aggtagcttg    3300
gccaggcctc cctggtgca gatttcatcc ttggtttctc agcctggcct tgaatgaccc     3360
tctacagcag ggtccccacc tctcagaaca actttgctcc agccacatgg cttgctcacg    3420
gccaggcact gccatgtggg actctgtgcg tgccacctct tgccctgac ccatgttgcc     3480 tctgggggag cacttcttcc tccaccttcc atcatgggct gtggcagtgc ccatcccatc    3540 tgccccgac gctgtctgct gcagtatggt tgttgggga agggcacca ggctccggcg       3600 tctgacagcc gtgttttacc caccttccta ctcactagct tgtgaccttg gcaattact     3660 taacatctct gagtcttagt ttctgtttct aaaattgggt gaataacacc tactaagtag    3720
ggttggcctg aggattaata gtataatgta aaagctggca gcactgaaac cctgccactt    3780
accagctttt cacatcagta tttgggaaat attgttaagc tcatttgtca ggcggggatt    3840
ctgaggctca gagcagttcc agaactttct acagattatt ttgccttgtt tgcgcttcca    3900
gactgcctat cttcttgtat caccattgat cttgatctgt atggttttta atttttttt     3960 ttttgagacg gagtttcact ctgttgccca ggctggagtg cggtggcatg atctcggctc    4020
actgcaacct ccacctcctg agaagctggg attacaggca tgtgccacca cacccggcta    4080
atctttgtat ttttagtaga gttggggttt cactatgttg gccaggctgg tctcgatctc    4140
ctgacctcgt gatccgccag ccttggcctc ccaaagtgct gggattacag gcgtgagcca    4200
ctgcgcccgg ccaacttcac gtttatacac acccatgcaa acagcatcca gatagagaca    4260
aagagccttc cctgtaccct aaagttttcc cagaaattgt tcccagttag catatttatt    4320
tttataaagg taatgcatgc ccatcatata acattcaaaa aggtatgtag agaaccaagt    4380 gtctcccca gcctgtcct ccagccaccc agtttccctc cctagggaa gccaccaata       4440 tgtgtttctt atgtatcccc tgttgagctg cttttcctcg ttttggtttg gcggtgttga    4500
tgtttgtatt tggaattaca ggtaggcagc atcatatacc ttagtgttta gggcctctaa    4560
gatcaaccag ccctgagaaa atcagccatg tgaggacct tgtcccccag ccccccagga     4620
gataggcccc ctggtgggag tgctggggca ggcagaggc ctaggacaa gaattagaaa      4680 ggacccatgt tgacagggct gctcagggtc atgttgtcca tccctctgcc acagtggcat    4740
```

```
ggacaaactg catatgttgg ttagaggagg gcacccttct ctcttgcaag cattggcaag    4800
gtcttaacta ttagtctcct gctcccatgg cagccccttt ggacaaggag gctcttaatc    4860
tctgttcttt gaagccctga gggctggtgt ataggagttc aaagcactgg cttttggaacc   4920
ggactgtctg ggtttgaatc ctggcactgc agctgactca ctgatggact caggcaatgc    4980
cttaaactcc ctgagcctca ggttccttgt ctgtaaaatg ataaagatag cccctgtttc    5040
atagggctgt ggtgagaaac caatcagaca aggcatgtga acgccattat agcacagcgc    5100
ccggcatcca gcaggactca ctcgatgaca gttgtcaccg ccatcattgt tattagcgtg    5160
ggccagggag ggctgcgtaa aagcagctgg tggaggaggg agagatgccg tgggaccgtc    5220
tgggttcgca tgcgtgaagt attatctggg cctggagtgt gcaaggcaca catgtgtcct    5280
tactgcatgt gttgtcacat atgtgcaatg ccatgctcct gagcctttga ttgcagacgt    5340
gtgggaagtg ggccccgtcc ccaccccag tgccaccctg ctctgcttct cttcccttgc     5400
tgtgctctaa aacgagaagt acaagtgagt tcccccaagg ggtcggccgc gcctcttcct   5460
gtccccgccc tgccggctgc cccaggccag tggagtggca gccccagaac tgggaccacc    5520
gggggtggtg aggcggcccg gcactgggag ctgcatctga ggcttagtcc ctgagctctc    5580
tgcctgccca gactagctgc acctcctcat tccctgcgcc ccttcctct ccggaagccc     5640
ccaggatggt gaggtaaggg cctgccaccc acgtgtagaca ggaggcaagg gtgcctggtg   5700
cccacgggac ccctcctcac tgccctgcct gggccgccca ggtggtttca ccgagacctc    5760
agtgggctgg atgcagagac cctgctcaag ggccgaggtg tccacggtag cttcctggct    5820
cggcccagtc gcaagaacca gggtgacttc tcgctctccg tcaggtaggt gggccccccg    5880
caacccgggg catttggcc actctcttgt gccatccagg ccctgaacca ctcattcctg     5940
gttcccgtg gcagtgctga ctccccgtct gttcccttgc ccccaacccc cacactcccc     6000
atccctgtct gtgcccaccc atgcccatgt gtgcccccac ccaggacctc agccgatccc    6060
tgccctcctg cctctactcc tgcaccgact ggcctcaccg cctggtgccc tgcagggtgg    6120
gggatcaggt gacccatatt cggatccaga actcagggga tttctatgac ctgtatggag    6180
gggagaagtt tgcgactctg acagagctgg tggagtacta cactcagcag cagggtgtcc    6240
tgcaggaccg cgacggcacc atcatccacc tcaagtaccc gctgaactgc tccgatccca    6300
ctagtgagag gtgagggctc cgcacccccg ccattcccaa gcaggatga gccggctccc     6360
accctgaaca gccagggagg cagggagact ggcagccggc gctgcctacc ctccatcccc    6420
tcccctccct gcaccagctg gggctctcaa tgtccctcct ccctgctgtc ctgggacctg    6480
gtgtctcaga gcctaaccta ccacccttc cacctaaccc cgaggaagcc acagaaagct     6540
gcctcgccct actccgggag ccctggccgc tgcaacccag gtcccactgg agacaggag     6600
gccactgctg gtggccagca tgtcgtgcag gccagctctg ttgttagaaa gctcttcttc    6660
ctctggaatc gagcctgcct tcctccgtct gcccctcacc ccagcacatg ttaggacagt    6720
gaggagctga cactggggtg aagatgggga tgaatgcttg ccaagacact tgatgccttg    6780
tcccagccgc cccgtgggga tgggtctgtc ctgtggggtc aaataggtct ccggcccaaa    6840
cagagatcat tgagagcacg atgtgaagtg ttcacctgtg taaagtgtct cacgctgtcc    6900
cgggcacaga gtaatactcc aggcatttcc ttcctgtggc ctccccgact cctcctgtgg    6960
tctcccaaag gcatgggctg ggggctgggg gctctgaatg ctcctcatga caccatggct    7020
cctttcagca gccgcatctc aatgccagat ccccttagag taaagggcag cggaataacg    7080
```

```
ctaggggtt ttcacatgca cccctgggcc aagccgactt gcccttgccg tggatccctg    7140
cattcatgga tcggttattg aaatgatcgg gaaccttgct cctgccagct tgcagcctct   7200
ctgagattcg ggcctccaaa ctgcatcaat attttggtc aaggcactga ttgaaactta    7260
gagctggatt cggtcacggt gcagcccgtg ggcccacctg ggaggcctcc tttcctggat   7320
cggcctcctt caaggccttc cctctctctg tgagcctcac atggctggct ccgtgtctgc   7380
cccctgccct tcctcttccc caccgcaaca ctcaggggc ttttggcacc gagaccctct    7440
aaagctcatg tcctctcttt ctccttgcct ccagccagga gaggaggacg ggctgaccag   7500
tgcctggagg tggaagagag gagcagggcc ccaggaggcc cctgcagagg aggctgaggc   7560
ctgggttcaa ggagaagaga aagagagag aaggaaggga gggcagtgcc ggggcgggag    7620
gttaagacca gggaagccgc actggaggcc cttttgggtg acccgtccca ggagccagtg   7680
tcaccctga gcctgggagt gtgtgagagg ctctttctcc caggttctgc tgtgtcctct    7740
gccttgtctg tgcgcctcct cctctgcgag aatttgcatc tgtccctcgg tggctctgcg   7800
cttcctgtgg tcagcctgac atttgcatgg agacttcctc atcctgggc ctgagggaag    7860
gggctcagcc ccctccccgc tacctggggt cctagcctgt ccccaggcgg tgggctgaag   7920
tagcccagtg gggttaggag gctctggggg tctctcggct ggagtcacct ccgggcaggg   7980
gtgagatggg ttgggacaga ctggtcctcc cctccttccc cccatccctg cggttggaaa   8040
atttgcccgc cctcccctcg tccctgggct gaggaaacct cacaacctca cttctcactc   8100
tctccccaga aggagttttg tgttttttcc atcacgtggt ttcctgtggg gctgggcttt   8160
gtggggctac agtttcctcc tgggaaaggg gtgtgcttcg gggaaagggc ttagttctgc   8220
tttctgccct gacagcccct tcaaatccgt ttgaaccctg gctccccttt cagtgacatc   8280
atccagggca ccccagaacc ccctacacca ctctttcccc agtggggttg tcttccccgc   8340
ctccctggcg gagcgcaccc catccgcctt ccttgtgact tgagtctgtg tgtccatctc   8400
ccaccactcc ctgtggtgtg gcctcggtct gcgtttctct ttgcctctgg tctctgctgg   8460
ggcacagtcc catccttcac ggagattcat ccttagcttc tctcctccaa atattttgaa   8520
tattgccagc ctttctgcct ttcagaggtg ggctctgggt tcgaagcccg gttagaactc   8580
tggaggctag gatggcttga acctgggagg tcgaggctgc agagagctgt aaccgcgcca   8640
ctgcactcca gcctgggcaa cagagctctg gaagcttgcc ctagagtcag tcaagggccc   8700
taggccagtg agtaacagct cagcgtcagt ttcctcatct ataaaatggg ggtaatatca   8760
tacctagctc tcagcatgtt tgtgagagac ctaaatgagg tggtggattt ggaagcatgt   8820
agcgcagtgc ctggcacaca gtaggtgctt gatttccggc ccctctctgt gaatgtctct   8880
gctcagcgcc ttccctgtg gcctgggtct taccttccct gacgctgcct tctctaggtg    8940
gtaccatggc cacatgtctg gcgggcaggc agagacgctg ctgcaggcca agggcgagcc   9000
ctggacgttt cttgtgcgtg agagcctcag ccagcctgga gacttcgtgc tttctgtgct   9060
cagtgaccag cccaaggctg gcccaggctc cccgctcagg gtcacccaca tcaaggtcat   9120
gtgcgaggta aggcagccag gcggcggggg agcctctgct gaggctcctg tctgtgacca   9180
cagtgtgggt ggcaggagg gtctgcctgg gcttgaattc aaggctgggg acccaggag    9240
ggagactcaa gtcctgtgaa tggcctaatt tggctccccc cagggtggac gctacacagt   9300
gggtggttg gagaccttcg acagcctcac ggacctggtg gagcatttca agaagacggg   9360
gattgaggag gcctcaggcg cctttgtcta cctgcgcag gtcaggggtg ggcccagctg    9420
cctcccact tcccctgagc tgtccccag atgtgagctt ctgggatctc tgagttgctg    9480
```

```
acttctcgct cttccccacc ccagccgtac tatgccacga gggtgaatgc ggctgacatt    9540
gagaaccgag tgttggaact gaacaagaag caggagtccg aggatacagc caaggctggc    9600
ttctgggagg agtttgaggt gcatggtggg gaccggcagg gctggggcag ctgaggtggt    9660
ggcagcggcc tggggcccca ggcggacacc ttcccctcct tgcccacctc tgctcctgac    9720 ccacccacg tgagctcccc cgatggatgc cctctttggg agctgatgct catttcccca    9780
cccacatctc agagtttgca gaagcaggag gtgaagaact tgcaccagcg tctggaaggg    9840
cagcggccag agaacaaggg caagaaccgc tacaagaaca ttctcccctg tgagcccca    9900 ggctgcccca ttcacccagg ataccgcccc tgccccagct gcctcccctc atctcacagg    9960
tctccaccct ccacgccagg aggggccatc tccccacacc cccacagag cctccccctt   10020 ctccaaaagg cctctactcc tcccagaagt gcctccccac caccagcagg caggttgccc   10080
cctgctccca acctccttgt gaactccctc actccctcca tacagatgat cccccacccc   10140
tgctgcccac agtccccgc aagcctcatg gcttctgaga ccagaatggc ctgttagctc   10200
aggagggtct gacccaggtg tggtgagtcc ctggctaacc cagaccatct cgcctcctct   10260
ccgcccactc ccagttgacc acagccgagt gatcctgcag ggacgggaca gtaacatccc   10320
cgggtccgac tacatcaatg ccaactacat caaggtcagc agtgtgggcc acgtgggagg   10380
agaggctggg ccctgggaat tccctgtctg gtgggggac cctagatcca gagacagctg   10440
ggcaaagccg aagctggctt cttgcatggg tgagggtggc agtggttcag ggcctgtgct   10500
gggccaaggg gctcactgtc ttggggtgcg tctctccacg cttgcgtcca gaaccagctg   10560
ctaggccctg atgagaacgc taagacctac atcgccagcc agggttgtct ggaggccacg   10620
gtcaatgact tctggcagat ggcgtggcag gagaacagcc gtgtcatcgt catgaccacc   10680
cgagaggtgg agaaaggccg ggtagggcgc ccccccttcc ccgcatccgc ccccgtgctt   10740
gtggtcatgc cattaagtcg aagagcagtc agatgccagg gcagaaaggg atctcagggg   10800
tgagggtccg gcccttgttg ggaaactgag ggctagtgac aaagtctcga ctacacaacg   10860 tgaccccccag atccctgcat gcatccctgg gctcttctga gctccagacc caggttccag   10920
gctgtcctcc ttcctcctac ccctgcccca cctgtctgca tccaggcccc tcctgtcctc   10980
cctgccccat agatctctct ggagtctgcc ccttaccctg caggctcccc ctacacagca   11040
ccctctgtgc tgccattgaa gtgatcccat ccgtgacaca aactgggtca agttccttcc   11100
tttctgaaat ctcttccatg gctcctggtc acctttggga taaagtcgca ctctaaggcc   11160
tggcattcaa ggtctggtgg cttccctctg acccgcacgc ttctcttgaa ggctcaccgc   11220
ccccagcagc cccagctctt tcaggttccc agcctttctt tgcacaagct cattttctgc   11280
taggaaatga ctctctccac actatctctg cctggcagat gcctcgtttt tgaagacaca   11340
gccggagcgc tgcctcctct gtgaatccag gtcttgtttc ctccaggacc tagagggaga   11400
attacgtctt tccagccac gctcctcagc gcggtgtctc ccccggtcac ctgtctctgt   11460
gagctcctcg aggcacaggg gcacagactg ggtgttattt gtgtctgtga agctgtgtgg   11520
tttgcacagc ttcggggaca atgcctgccc tggcaacgtt tgttaatga caaacggatg   11580 taccggtgaa gtggctggcc aggcctcacc acctgttggt ggttgatctg agacgagagc   11640
ccaggtctcc tgcctctctg ccagcccatc cgtccatcca acaaatgttt gggccggtgc   11700
caggcactca gaacatagag caggacctgg gatgggccac agtgccctgc tctgtgcctc   11760
atccccaccc gaccctccct ttccagaaca aatgcgtccc atactggccc gaggtgggca   11820
```

```
tgcagcgtgc ttatgggccc tactctgtga ccaactgcgg ggagcatgac acaaccgaat    11880
acaaactccg taccttacag gtctccccgc tggacaatgt gagtggcccc cacgccctgc    11940
cccattccgg gagtccctcc ctggacttgt tctcctctct ggtcgggtag ggtgagatgg    12000
atgaggtgtt ccgagagagg aggggcact  gaccctatgt cctcggctta gggagacctg    12060
attcgggaga tctggcatta ccagtacctg agctggcccg accatggggt ccccagtgag    12120
cctgggggtg tcctcagctt cctggaccag atcaaccagc ggcaggaaag tctgcctcac    12180
gcagggccca tcatcgtgca ctgcaggtga ggatgataat cctgatggta gtagtgacag    12240
ctgagaagta aatactgcta agtgccatga gctgttataa gcaatataaa cgttagctcg    12300
cacattgagt gccctccgct cacccccggc ttctcctggg tcccctcatg gctccagaac    12360
cctgggtgga tcgtgctgg  aaccagcccc actttggccc tctgcctgtg ggtatcttcc    12420
tcagagccct ctccggatgt accatctcgc ccaaccctgc caaatacaga ggaggagccc    12480
gggacccagt tgctggccag gcccaagcta gtcaggcaa  ggccgggcag gcacccacag    12540
taggcctgtg tcccggctgc tccgcttct  ctcgaggtcc cattctgttg gtttcttctc    12600
ccaggaacat ctatgaggca tgtgctcccc attcctcctc tttttccatc ggtagccgca    12660
gggcttcggc ttcttcctga ctctgccctc tctcccagct tccccaggca gtgccccatc    12720
ctggccccca gggctgtgtg gggatgggtg atgcttcttt ggggctgcac ataactcctc    12780
tgtctatcta cccgcatgtt tgtgatcagg agacctctgg taaggtgcag aggtgggggc    12840
tgcaaggagg agcagggggtt ccacaggtga gcccactgag ctggcctggc ctgggtggat    12900
gagaggcagt gggtgcaggg cccctccgct taccagctgt gtggtcttgg acaaattact    12960
taacttttct aaccctcagc ttcctcatct gtaaaatcag gatctcaggg ttgtcgtgag    13020
aactcaatga gaccctatcg ttgtggctgg aattccgtca gccctcaaaa actgggcgct    13080
gttactagtt tagtaactca catcaggcag agaataggg  aatgggaacc tgccttgccc    13140
cggtcccttc ccactccctc cgtggacccc aggcctgcga cggcctctgg cttcctcctc    13200
ttcccccagc agctgtttgt cctgggacag ggcaagtcgg ctgaatctag aggtgccccc    13260
gatgggctgt ccggggacgc ggctctgtcc tgtgctctct cagggacagg cccatccccg    13320
agagctaccc tcctgctcac ccgccacaca cacattcaca cacttcttga aagccccatg    13380
gcctttattt agacgttaca ggaaggaagt gggtgtgggg ggttattttt gacaatctgg    13440
gtttgaaatt agacagcgcg actcagggca tcagcttgct gggctcagct gagggtgggc    13500
ctggggtctc cctgaggtct gtttgcccag ggctgggaaa ggagagaaac ttcctactgc    13560
actgctcccc tgagtcccct gaccctgtgc ccccgcaccc tgctgtctca gggctatcct    13620
ttccctgacg tcagggtttg aaggaaaagg gaagtgaagc catgctgaga gacgctccat    13680
aactccttca gggagaggcg gggagggctc agggtacctg ggagccggca ggacagtggt    13740
gggatttggg ggtcccaggt cttccggggt gggggcagcc actcactagg agtgaggagt    13800
cggcgcgagg agtggaggag ggaaggatgg tgcagctgg  ggagccagcg tcagcaccgc    13860
agagcccgag gtggagcgtg tccatgcaga gctgggcaaa cctccatcat cacttgcccg    13920
gtgaccctgg gcacattccc tcccatcact ggaggctcag gctgctcctg tggtgcctgg    13980
ggctggagct gagcgctggg taccccctt  cccggggagg gcttgactgg cctctgatgg    14040 caccccgtc  tttccccagc gccggcatcg gccgcacagg caccatcatt gtcatcgaca    14100
tgctcatgga gaacatctcc accaagggtg aggggcacct gggggtttgg gggtgggggg    14160
tgagcagccc ctcggtgtcc gcctatgcct ggacctgagg tttgactgcc ccccacccag    14220
```

```
gcctggactg tgacattgac atccagaaga ccatccagat ggtgcggggcg cagcgctcgg    14280 gcatggtgca gacggaggcg cagtacaagt tcatctacgt ggccatcgcc cagttcattg    14340
aaaccactaa gaagaagctg gaggtcctgc aggtgcgtgc agagcagggc ctggggggg     14400 gggggggctgc agtgcaggat gggtgccacc tggccctgct gggaccacca ccttcccact   14460
gtccctctgc ccacagtcgc agaagggcca ggagtcggag tacgggaaca tcacctatcc    14520
cccagccatg aagaatgccc atgccaaggc ctcccgcacc tcgtccaagt gagtggccct    14580
gactgccact gcccggcatc caccccttg tcctgcccag cccgatcctc actttctgga     14640
gaggacaagt gttgcagctg gggggacctg gcttcaagtt caggcttggt tctcaccct    14700 tctgttcata agcatttcct gagtgcccac acgtgtgggc ctctgctagg taccagcagc    14760
gcactcgtgt atgagatgta gcctctgtcc tctaggagct tggagtctag tgcagggacc   14820
gtggctgcgt cacctgtgag acggggtggc cagaggggac tgccagtgcc gggtccccct    14880
gtgctgtctc ctgacctgca ccaactgcct gtacttgccc cctgcaccc ggctgcagac    14940 acaaggagga tgtgtatgag aacctgcaca ctaagaacaa gagggaggag aaagtgaaga   15000
agcagcggtc agcagacaag gagaagagca agggttccct caagaggaag tgagcggtgc   15060
tgtcctcagg tggccatggt acagctcttc tgcctgggtg tcctccctgc cctgccctgt    15120
gtccttggct ccactgcctt ccctgggtgg atggggtggc cgcagcctca ttctgtgctt    15180
cccagctgcc ccagaccctc ttgttccacc tccaggttcc agctaccctc tcactccctc   15240
actcccttct cttggcagcc tcagcccga ccctgtggaa gcatttcgcg atggacagac    15300
tcacaacctg aacctaggag tgccccattc ttttgtaatt taaatggctg catcccccc    15360 acctctccct gaccctgtat atagcccagc caggcccag gcagggccaa cccttctcct    15420
cttgtaaata aagccctggg atcactgtgt gtcgcctctg agccctttgc ttgcccagtg   15480
agtgggcggc cagagggcag ggcaggatgg gtaactgtgt gtgcctccgt gcgtgcctcg   15540
cgtgaaagct ccgccttccg tcagacggac gtgggtcggg actccgcctc gcacgtggga   15600
gggtgaccgt gggtgaagct ccccagtctc cttcttaaa atggagggcg atcataacag    15660
ggtggttgtg aaaagcaccg agatgacggc tgacgataag acgggcacag tgactcatca   15720
cacgcttgcc atgtgcccag gcactaaaag actacacacg ttagttcagt ctaggcactt   15780
ctgtcattct cattttaccg tggcggaaac tgagggacag aaaaactaag taacttggtc   15840
acttgcccaa ggtcacaggg ctatggaaca gtgaggctgg gattcgaacc caggctgtct   15900
gaccccagag cccacactcc ttaccctgga gttgcagctg ggccaccct cagggggcc     15960 ctgatcacac tcccctgatg ctgagttcca gatctgaact aagaagagta gttaacagcc   16020
ggaagcgcag acctgaggcc agcccggct                                     16049
```

<210> SEQ ID NO 59
<211> LENGTH: 624
<212> TYPE: PRT
<213> ORGANISM: Homo sapiens

<400> SEQUENCE: 59

Met Val Arg Trp Phe His Arg Asp Leu Ser Gly Leu Asp Ala Glu Thr
1               5                   10                  15

Leu Leu Lys Gly Arg Gly Val His Gly Ser Phe Leu Ala Arg Pro Ser
            20                  25                  30

Arg Lys Asn Gln Gly Asp Phe Ser Leu Ser Val Arg Val Gly Asp Gln
        35                  40                  45

```
Val Thr His Ile Arg Ile Gln Asn Ser Gly Asp Phe Tyr Asp Leu Tyr
     50                  55                  60
Gly Gly Glu Lys Phe Ala Thr Leu Thr Glu Leu Val Glu Tyr Tyr Thr
 65                  70                  75                  80
Gln Gln Gln Gly Val Leu Gln Asp Arg Asp Gly Thr Ile Ile His Leu
                     85                  90                  95
Lys Tyr Pro Leu Asn Cys Ser Asp Pro Thr Ser Glu Arg Trp Tyr His
                100                 105                 110
Gly His Met Ser Gly Gly Gln Ala Glu Thr Leu Leu Gln Ala Lys Gly
                115                 120                 125
Glu Pro Trp Thr Phe Leu Val Arg Glu Ser Leu Ser Gln Pro Gly Asp
            130                 135                 140
Phe Val Leu Ser Val Leu Ser Asp Gln Pro Lys Ala Gly Pro Gly Ser
145                 150                 155                 160
Pro Leu Arg Val Thr His Ile Lys Val Met Cys Glu Gly Gly Arg Tyr
                    165                 170                 175
Thr Val Gly Gly Leu Glu Thr Phe Asp Ser Leu Thr Asp Leu Val Glu
                180                 185                 190
His Phe Lys Lys Thr Gly Ile Glu Glu Ala Ser Gly Ala Phe Val Tyr
                195                 200                 205
Leu Arg Gln Pro Tyr Tyr Ala Thr Arg Val Asn Ala Ala Asp Ile Glu
    210                 215                 220
Asn Arg Val Leu Glu Leu Asn Lys Lys Gln Glu Ser Glu Asp Thr Ala
225                 230                 235                 240
Lys Ala Gly Phe Trp Glu Glu Phe Glu Ser Leu Gln Lys Gln Glu Val
                    245                 250                 255
Lys Asn Leu His Gln Arg Leu Glu Gly Gln Arg Pro Glu Asn Lys Gly
                260                 265                 270
Lys Asn Arg Tyr Lys Asn Ile Leu Pro Phe Asp His Ser Arg Val Ile
                275                 280                 285
Leu Gln Gly Arg Asp Ser Asn Ile Pro Gly Ser Asp Tyr Ile Asn Ala
    290                 295                 300
Asn Tyr Ile Lys Asn Gln Leu Leu Gly Pro Asp Glu Asn Ala Lys Thr
305                 310                 315                 320
Tyr Ile Ala Ser Gln Gly Cys Leu Glu Ala Thr Val Asn Asp Phe Trp
                    325                 330                 335
Gln Met Ala Trp Gln Glu Asn Ser Arg Val Ile Val Met Thr Thr Arg
                340                 345                 350
Glu Val Glu Lys Gly Arg Asn Lys Cys Val Pro Tyr Trp Pro Glu Val
                355                 360                 365
Gly Met Gln Arg Ala Tyr Gly Pro Tyr Ser Val Thr Asn Cys Gly Glu
    370                 375                 380
His Asp Thr Thr Glu Tyr Lys Leu Arg Thr Leu Gln Val Ser Pro Leu
385                 390                 395                 400
Asp Asn Gly Asp Leu Ile Arg Glu Ile Trp His Tyr Gln Tyr Leu Ser
                    405                 410                 415
Trp Pro Asp His Gly Val Pro Ser Glu Pro Gly Gly Val Leu Ser Phe
                420                 425                 430
Leu Asp Gln Ile Asn Gln Arg Gln Glu Ser Leu Pro His Ala Gly Pro
    435                 440                 445
Ile Ile Val His Cys Ser Ala Gly Ile Gly Arg Thr Gly Thr Ile Ile
450                 455                 460
```

```
Val Ile Asp Met Leu Met Glu Asn Ile Ser Thr Lys Gly Leu Asp Cys
465                 470                 475                 480

Asp Ile Asp Ile Gln Lys Thr Ile Gln Met Val Arg Ala Gln Arg Ser
            485                 490                 495

Gly Met Val Gln Thr Glu Ala Gln Tyr Lys Phe Ile Tyr Val Ala Ile
                500                 505                 510

Ala Gln Phe Ile Glu Thr Thr Lys Lys Leu Glu Val Leu Gln Ser
        515                 520                 525

Gln Lys Gly Gln Glu Ser Glu Tyr Gly Asn Ile Thr Tyr Pro Pro Ala
        530                 535                 540

Met Lys Asn Ala His Ala Lys Ala Ser Arg Thr Ser Ser Lys Ser Leu
545                 550                 555                 560

Glu Ser Ser Ala Gly Thr Val Ala Ala Ser Pro Val Arg Arg Gly Gly
                565                 570                 575

Gln Arg Gly Leu Pro Val Pro Gly Pro Pro Val Leu Ser Pro Asp Leu
            580                 585                 590

His Gln Leu Pro Val Leu Ala Pro Leu His Pro Ala Ala Asp Thr Arg
            595                 600                 605

Arg Met Cys Met Arg Thr Cys Thr Leu Arg Thr Arg Gly Arg Arg Lys
610                 615                 620
```

<210> SEQ ID NO 60
<211> LENGTH: 92763
<212> TYPE: DNA
<213> ORGANISM: Homo sapiens

<400> SEQUENCE: 60

```
aggctcaagc aatcctctca cctcagcctc ccgagtagct gggactacag gcgcgcgcca        60
ccacgcccgg ctaattttttg tattttttgt agagatggga tttcactatt ttgcccgggc     120
tggttcccaa ctcctggact caagcgattc gcccgcctca gcctcccaaa gggaagtgct     180
gggatttcag gcgtgtgcca ccgctcccac cccaaagtag tatttattgt aattattatt     240
attatttttga acggagtct cgctctattg ccaggctgga gtgcagtggc gcgatctcgg     300
ctcaatgcaa cctctgcctc ccgggttcaa gcgattctcc tgcttcagac tcccaagcag     360
ctgggactac aggcgccccc caccacgcca ggctaattct tgaattttta gtggagacgg     420
ggtttcacca tgttggccag gatggtctcg atctcttgac ctcgtgatcc gcccacctcg     480
gcctcccaaa gtgctgggat tacaggcgtg agccaccgcg cccagcctat tattatttt     540
ttaggcagtg tcttgccctg tcgctcaggg tgtagtgcag tggcgtgatc acgactcact     600
gcagccccga cttctcgggc ttaagttatc ttcccgccgc agcctccacg cccggttagt     660
tttttgcatt ttttgtagag atgaggtctt gctttttgc ccaggctggc ctcgaactcc     720
ttggcttaag cgaacctctt gccgcagcct cccaaagtgt tgggattacg ggcgtgaacc     780
accgcgccca gcctactatc tttatcttac agaaagaaaa gaatggagga aaccgaggct     840
cggagacagt aggtaatttc cccaaggttc cacagctaat gagtggagcg gcgatttgtg     900
gaacgaaatg aatgaaatcg atgtggcagc gggcccggac gggtcggtgg cgtagacgcg     960
gagcgcgcag ctcacacctg gcggccgcgg tttccaggag gaagcaagga tgctttggac    1020
actgtgcgtg gcgcctccgc ggagcccccg cgctgccatt cccggccgtc gctcggtcct    1080
ccgctgacgg gaagcaggaa gtggcggcgg gcgtcgcgag cggtgacatc acggggcga     1140
cggcggcgaa gggcgggggc ggaggaggag cgagccgggc cggggggcag ctgcacagtc    1200
tccgggatcc ccaggcctgg agggggtct gtgcgcggcc ggctggctct gccccgcgtc    1260
```

-continued

```
cggtcccgag cgggcctccc tcgggccagc ccgatgtgac cgagcccagc ggagcctgag    1320
caaggagcgg gtccgtcgcg gagccggagg gcgggaggaa catgacatcg cggaggtgag    1380
gagccccgag gggcccggcg cgggcctcgg cccggccacc gccgcgttcg gttagccccg    1440
tccggaaggg ggcgccccgg ccgggcttcg ggctcccgcc ccgggtcggg gttggggggcc   1500 ggttccctcc tcgtcccctc gccctccagg ggccggggc  cggccccacc gcgccccac    1560 ccctcgggtc cccattcatt tcctgcctcc ccgagttccg gctgcggcag ccccggggat    1620
gcccgtcagg cccggggcag gtagagccgc cgagggaacc acgggtgcca gcggccaggc    1680
tcagcgccgc attcctgacc cattgcctca tgagaattgc ctcatggtga ttccgaaata    1740
accctgctca cttggggagg ctccttggga cacgagaggg gagttgcgcg gggccgggcc    1800
cccagtggtc tagtcgttct ggctcactgt gccactttcg tgcatttggg gacttcacgc    1860
aggacccctg accttttat  atgcctcttt gtgtcttctt ttcctcctac ccctcacgtg    1920
ccagaaatgg aaaaactgac tgtatctgca gccactagaa gtatttcctt cctctgcgat    1980
cttcgctttg ggagatggaa aggaagggag ccgcatctcg ttatttaatc cttcactgca    2040
accttaacag tcaggtcact ttactggtac ccgttttatg gatgaggaaa ccgaggccca    2100
gaagcaacat gctagtaaat gacaagattt gaaacttagg aggattagtg agttaatgag    2160
atcctttgaa aggtcagggt aatactacta ctaatagcta acatttgctt agttctgacc    2220
acagccctat cagatggcta ctattatccc cattgtaaag atgagtaaac cgagtttcag    2280
aggttaagta aattgcctaa cctcacagct agtaggtggt ggagacagaa tccctacttt    2340
taatcactat gttgcttcta ttattttgta actattgcta accatttgta agccttaatt    2400
ttgttgtcaa acagtagtgt gacctgttgt tttcagatag tgatcctgct attttgtata    2460
gtcactctat ataccactca cacttaagac ccattgtcta ttcttttcca tgattgttca    2520
attatggtca ctgtctcaga catttaaaaa acgattcaag ctattgaggc tatttgaatg    2580
agattttctt ttctttttttt ctttttttt  ttggagacgg aggctcactc tgttgcccag    2640
gctggagtgc agtggcgcaa tctcggctca ccacaatctc cgcctcctag gttcaagcga    2700
ttctcctgcc tcagcctccc aagtaactag gactacaggc gcaccactat gcccggctaa    2760
tttttgtatt tttagtagag acagggtttc actatgttgg ccaggctggt ctcaaactcc    2820
tgacctcgtg atccgcccgc cttggcctcc caaagtgctg gaattacagg cgtgagccac    2880
cgtacccagc ctgaatgaga ttttcaaaa  tattaggaat gtctcctcca aacacacctg    2940
gcatgttatt catacatgga tctggaattt aaaaagggga gaaaagaaa  actgagaact    3000 cgtaggaagt gagtgacttg gacaggtcgg ttggcaagtg cttacagatc tgggtaatat    3060
ataactgcat ttcaacagaa cagtgtatag cctcaaatgt tctaattctt tagggagctt    3120
ttaaataaac agttgtctat tctttaatct gtcaaatagt cattgagcct tttgttcctg    3180
gtgtctgctc ttccagacaa gtaaggatct gctgctttag gagacatcag acggggctgg    3240
gggttgggaa aaggtctggg tagtaataga ccctacattg tccagtttgt tcatttagaa    3300
gcatagaagt gtgggcatag tcaaagtagc aagtggtaaa gatgacagtt tgaaatggag    3360
taattccttc tcccctccag ccctggtatt atgcaccacc caaaaagccg ggttatgaac    3420
ataatacaca taattttgaa tgattcatta ttttttggat tataagcctg ttttatttgt    3480
taaccagcct taatgaggta taaatgcat  gcaattaatt gcatatattt aaatgtacaa    3540
tttgatcagt tttgacatac atatacactt gggaaaccac caccatagtc aagataatga    3600
```

```
acacatctat caccoctggt aattttgcct tatgttcttt ataatccttc ctttgttctt    3660
aggcagccac tattctgctt tctgtcacta tgtattagtt tgcatttcct agaattttat    3720
ttttaaaaat tttaaaattg tttgaataga gatggggtct cactgtgttg cccagggcag    3780
tctcaaactc ctgggttcaa gtgatcctct caccttggcc tcctgaagtg ttgggattat    3840
aggcatgaga caccctgccc agccctagaa ttttattatt attgttatta ttgtgttttt    3900
ttgagatagg gtctcacttt gttgcccagg ctggagtgca gtggtgcaat cactgcagcc    3960
ttgtttttcct aggctcaatc catcccccct cctcagcttt ccggttactg ggctacagg    4020
tgtgcaccac cacacccggc taattttttgt attttttttat agagacaggg ttttgccatg    4080
ttggccaggc tggtctcaaa ctcccgggct caagcgatct tcctgcctcg gcctcccaaa    4140
gtgctgggat tacaggcatg agctattgcg tcccgccttc aaattacttt aacctagtat    4200
taattcattc aacaggaagt taatgagcca ggcaggataa agcagtaaga taggaaaata    4260
ttgctatttt catggctgag agagagcaga caaacacatg actaaatagg gcaatttcag    4320
gtagtaataa attctaggag ggaaaaaatc ccacagaaat gtgaggatgg gagaatgcag    4380
ttagttttga taggtggttt agagaaggtg atcgtgtgag ctgacacctg aatgacaatt    4440
agtagtctga attttgtttt gcttaattat caaaataact cctcttgggt tcggctttta    4500
tatgcatcca gtaattaaaa tgtaagtata ttcaatgtac tgatatctct cagcatcata    4560
ggtaggaaaa ctaaggcatt cagcaattaa gtgactcctc ccttgatcat gtagcagtga    4620
tagtactgga tttagatttt gaggttgctt ctctgcccct ttctgccttt gtgaaaccaa    4680
caaagctgcc tgtattttcc aactcttcct tcagcatgtg gtacctcctt tacatctgtt    4740
tttgttgctc tgaaatccat acgcgacgat gagctgagag gggcagaaaa ttgagcttgt    4800
tctgagactg gaggcttttg gtttatctct tgcaggtcaa gtacattttg tcctgggctc    4860
tccctggtgg ccacgtttgt ttatctcctg cgggagtaaa taaacttgcc ttgctgaaaa    4920
ataacagttc tgtgtctttg cagtggaaac tgggatgtct ttattaacgt taggtcctga    4980
tgtaaggcca agttttttggt tagagttgct caagtgcaga ggccactgct aagatgactt    5040
accccctcgtg tccatggtca atgtggagac tgttatgagt ggcacatgat gctggaaaag    5100
cagagccaac tcatgtttgt aattgtccta gcaggccgtg gtgtactttg ttaggcagcc    5160
acagaacaat agagaaactc agcttattcc ccttccctct gggaaacaca gacagtactt    5220
gccatccaac gccaatgttt ttaaggaaga aagaggcaaa aagtgatgtt ggcaaggtct    5280
ctgggagttg tggaccccaa ccaaggattg gagaccctga aatggattca gatgccctaa    5340
aatgcagccc agttcattac tatgaatttt ggaggacttt gtgccttgag caaatgtgta    5400
tatgtgacgc tctttgacaa cactgaaata ggaaaaatac tatccatgtt cgcgaggagc    5460
actgaattta gagagggaga cagactttta tgccagcatc aaatgaattt gataaagcta    5520
gtaccaaaat gaaatttgaa attttttttt tttgaaatag agtcttactc agtcacccag    5580
gctggagtgc agtgatacaa tattggctca ctgcaacctc cacctcttgg gttcaaacaa    5640
ttcttgtgcc tcagtctcct gagtagctgg gattacaggt gcgtgccacc atgtctggct    5700
aattttttata ttttttagtag ggatggggtt tcaccatgtt ggccaggccg gtcttgaact    5760
cctggcctca agtgatctgc ccaccttggc cttccaaagt gctgggatta taggcatgag    5820
ctaccacaca agcctgaaat ttgaaatgta ttggtataga atatactgtt tagaatgtat    5880
gtgtatatat gtatatttgt atactcatat aaacacaaat acacattgta tgtgtttctg    5940
taatatgtat atctgtctac acatacatgt atatacacac atacaatgtc tttttttttt    6000
```

```
tttttttttt ttgagacagg gtcttaccct gttgcccagg ctggagactg cagtggcata    6060
atcttggctc actgcagcct cgacctcctg ggctcaagtg atcctcccat ctcagcctcc    6120
tgagtagctg ggactgacta caggcacgtg gcatcaaact tgtccaattt ttctattttt    6180
ttgtagagtt agggtcttgc tctgttgccc aggctggtct caaattcctg ggctcaagct    6240
gtctgcctgc ctcggccttc caaagtacta ggattacaga tgtgaaccac tgtacctggc    6300
ctttacaatg tctattttaa agataatggt tcaagttttt atcatcccac tggcctactc    6360
taatgaaaca tctatccatt cattgaagaa ttatttatgg tgggataact ctgtgccagg    6420
taccgtgcta ggcattgagt attccaggtt ttaggaaaca gcacatgcaa agtgctgaa     6480
gtgggagaag atctcggagt gattgaaggc taggagagag caagtgtggg agctgtgagg    6540
ctgggaaggt gggaggtagg tgggagcaga ccacataggg attcttaatg tctttagtgt    6600
catgtggacc atggagagga gtgtagattg tatttttaga gcaatgcaaa atcatagaag    6660
gatgtgatcg ggggagtggc atgagctgat ctatttaaaa atatttctct ggctgctgtg    6720
aaggaaggat tgtaggaggc aggagtagat tcagggagat gagacaagtg atgagagagg    6780
ctttgaactt gggtaaaagt agtttgtgga aagtcttttt tggaggtagt ttttgtttat    6840
tgccttgtca tcaaagcaga gatgctgacc aatgaaactc catgagaaaa tagtgattta    6900
taaagacata tctatgcact gccattaaaa agctgcttgg aaaaaaagga taaaaagctg    6960
ctttaacaac ttttttttttt gagatggggt cttactctgt cacccaggct cacgacctca    7020
gctcactgca acctctgcct cccaggctca agcattctcc cacctcagcc tcccgagtgg    7080
ctgggactgc aggcacacgc caccatgtca ggctaattgt gtgtgtgtgt gtgtgtgtgt    7140
atgtgtgtgt gtgtgtgtgt gtgtgtgtgc tgggactgca ggcacacacc accatgtcag    7200
gctaattgtg tgtgtgtgtg tgtgtgtgtg tgtgtgtgtg tgtgtgtgta    7260
tgtagagatg gggttttgcc atgttgccca ggctggtctc aaaatgttgc ccaggctggt    7320
ctcaaactcc tgagctcagg tgatccaccc gcctcggcct ccaaagtgct ggagattaca    7380
gacgtgagcc actgtgccca cctaacaact taaaaaaat tttgacattt agtaggatat    7440
ttattgcatt attgttgaga tggcaaaata ttggagacaa ctgaaatgtt catcagtggg    7500
gggggctagt taaatgaaat acagtgtagc atgcattaga acacttttca agaatttaac    7560
ttttttttgta gccttttact tataatgctt gtccctattg atgccttttt tttcagcatg    7620
acttactctt ttactatagg atattaaaat ttaattagat tagaaatgag gaatattctt    7680
gtaatctgta gaaagtaaca aactataaac ttattcccca agaacaaata taataatttt    7740
tctggagtag caggtaagaa agatataaat ttatatgtat acaagaaact gaaattagac    7800
tttatacatt taaaggttac aagtgcagtt ttattacatg aatgtattat ccagcattga    7860
agtctgggct tttagtgtaa ccagcacctg aataacatac attgtaccca ttaagtaatt    7920
tctcatccct caaaccccctc ccaccctgaa attagacttt ggatccctag tttaaattcc    7980
accccctctct tttttttgaga caaggtctca ctctgtcacc caggctggag gcaatgttg    8040
caatgatagc ttactgtagc ctcaacctcc tgggctcaag ggatacaccc tcctcagcct    8100
cctgagtagc tggaactgca ggcgtgcacc accacattca gctaattttt tgatttttt    8160
atagagatga ggtcggaact cctgggctca agcgattctc cccaagtgct ggggttacac    8220
acatgggcca ctgcccccag cctaaacctc ctttctcagt atagcagcct tgagatgaag    8280
ttcctgaaat tactggccag cttgactgtt tccccacatc actggaggag ggggatgcat    8340
```

```
agataaaaca aaatattcag catcattgta ttttcttttt gtttcatcag catcttttt      8400
taaaactcac ttgacataag tccctagcct caaagagtaa agcctttgca gaatctgcat      8460
tcagatttcg ggtgtgattt cctgacagat agttcaggtt tgtaaactct ttttttttc      8520
tttgagacag agtttcactc ttgtagcgca ggctggagtg cagtggcacc atcttgcctc      8580
actgcaactt ctgccccctt gattcacgcg attctcctgc ctcagcctcc tgagtagctg      8640
ggattacagg catgcgccac cacacctggg taattttgt attttagta gagatggggt        8700
ttcaccatgt tggccaggct ggttttgaac tcctgacttc aggtgatcta cctgcctcag      8760
cctcccaaag tgatgggatt acaggtgtga gccaccgcag ccggccaaaa ctttgttttt      8820
tttcctcttt ttgttgctga gaaatgtaaa ctcttacaga cacaaattat gtctcccatt      8880
ttttaaaacc cactcaacac aggggtcatg tgtaataggc cctggagctt attttagaca      8940
ttgatttgag gctctttcc ccaagtgctg gtttgtgtgt gtgtgtatgt gtgtgtaagt       9000
ctttctatga gatgagtggt acctacctgg gctgtgtgat cttttttatt ttatttattt      9060
tattttgta gatacgaggt ctcactatgt tgctcaggct ggtcttgaac tctggggctc       9120
aacctatcct ccctccttgg cctcctagag tgctgagatt acaggtgtga gccactgcac      9180
ctggccagcg atccttaata aatatagata atggccgggc gtggtggctc acacctataa      9240
taccagtact ttgaggggcc gaggctggca ggtcacctga gctgaggagt ttgagaccag      9300
cctgggtaac gtgggtgaaa ccctgtctct acagaaaata gaaaaattag ccaggtgtgg      9360
tggtgcatgc ctgtagtcac agctacttgg gaggttgaga caggagaatt gcttgaacct      9420
ggaaggtgga ggttgcagtg agccgagatc gtgtctttga actccagcct gggtgacaga      9480
gtgagacctt gtctcaaaaa aaaatataga tataggctgg gcgtggtggc tcacacctgt      9540
aatcccagca ctttgggagg ccgaggcggg tggatcagga ggtcaggaga tcgagaccat      9600
cctagctaac atggtgaaac cctgtctcta ctaaaaatac aaacaattag ccaggcctgg      9660
tggtgggtgc ctgtagtccc agctactcgg gaggctgagg caggagaatg gcgtgaaccc      9720
gggaggtgga ggttgcagtg agccgagact gtgccactgc cctccagcct gggcgacaga      9780
gcgagactct gtctcaaaaa aaaaaaatct atatatctat atatctatat ctatatagat      9840
atagatatag ataatgccag atgatggctg gttagaaggg attgtcaggg gctggcaggt      9900
tttgcaggtg ttagaatgag caagatgagg agaaggatgc ttacttccct ctccttgtaa      9960
ctctctaccc cctcccctca gtgttttttt attttatttt ttatttattt attttttg       10020
agacaaggtc ttgctctgtc acccacactg gattgcagtg atgcaatcat agctcattga      10080
agcccaaaact cctgggctca agtgatcctc ttgcctcagc ctcccaagta actgggacca      10140
caggtgcgta caactatgcc cagttaagtt tttcatttt tatacagacg gggtcttgct       10200
atgctgtcca ggctggactt gcacttctgg cttcaagtga ttctcttgcc tcagtttccc      10260
aaagtgctgg cattatgggc ataagccact gtgcctagcc catcagtgtc tttttatcct      10320
ttactcctat caaaattcat tcactcagca gccattgatc aagtgcctac tatatacatg      10380
ttgaggactg gaaatttatt tgtctcttct catcttatct ggaccctctg tgttaattgt      10440
aattaactgt aatcattctg tattaattgt aataaacttg ttgataaact caaatgaggc      10500
cataccgttt tgccacttcc cctccttcca ggttatatgg atgtacttac attgcaggtt      10560
tcatttgttg gttcagtttt taaactaagc cctattgtgt caaattatgc taggtgtgag      10620
atggggagtt caagctgtgt gttgtctttt ttttttttt tttttttgcc tcacttacta       10680
atatacaagc gcttataacc tttgaggctg gccctataca ttaagatttt tattaattcc      10740
```

-continued

```
actgttcttt atcttctctt actaagttct cagggtcgaa tgaactctaa ctgctccttg    10800
ctagtgataa gcaagttgca aattacagaa ttgtcagtga ttgaatacac gtattaaacc    10860
tgtaactggg aagcattttt ggtaattatg aatactttg gaaaaaaaaa agctatggaa     10920
ggaaagttta aaatctacga aagctcaagt agatggtcat ggaatagcta tttcaatttc    10980
taactatata ttacttattt atttatttat ttttgagacg gagtttagct cttgttgccc    11040
aggctggagt gtaatggcgt gatctcagct cactgcaacc tccacctccc gggttcaagc    11100
tattctcctg cctcagcctc ccgagtagct gggattatag acatgtgcca ccacgccagg    11160
ctaattttgt attttagta gagacggggt ttctccacat tggtcaggct ggtctcgaac      11220
tcccaacctc agctgatccg cctgcctcgg cctcccaaag tgctgggatt acaggcgtga    11280
gccaccgcgt ccggcctctt aactattgtt tgaaataatg tagagacagc tccagagcca    11340
tgaagaagtg tatgaagaag cagtgttagc ttaaatgaca tacatgtcac aattgcctat    11400
gtgaaactat cataattatg catgagaagt atctatcctg cataacctcc accaataata    11460
ataatgttaa taatagtgaa aactaatgtt tattaagtcc ttactgtctc cagcctctgt    11520
gctaaatact ggttactaag tttccctgaa aatactattc tcatctgttt gttcttaata    11580
acaggatagc ataattgtaa gttgtaaatg aaataataca gtttatgtaa taaaagggta    11640
aaagagaaga ccacctacct tatcttctgt tgctgatctg gatggatgta ggtggtgttt    11700
acctagtttc acctttggca gttgaaacta cttttttttt tttttttttt tttttaaga    11760 gacagggtgg gccaggcgca gtggctcacg cctgtaatcc ccgcactttg ggaggctgag    11820
gcggacagat cacttgaggt cagaagttcg agaccagcct ggccaacatg gtgaaaccct    11880
gtctctacta aaaatacaga aaaattaact gggtgtggtg gtacacacct gtaattccag    11940
ctacgtggga ggctgaagca ggagaatcgc ttgaacccgg gagtggaggt tgcagtgagc    12000
tgagattgtg ccactgcact ccagcctggg tgacagagca ggactccgtc tcaaaaaaaa    12060
aaacaacaac aaaaaaagaa attttagaa atatgagatg acagcaagaa tgagggtatt    12120 aaaagaaat ttttagaact aaatagcaga atgtaatggt gaaagtttg atttctcaag     12180 tctgctttgc acacaggcat gtggcaaaca ttcagtaagt atagctgtaa ttttaaccag    12240
ctgtaatgta taatagccaa catatcacat ttttcttttt tcttttttga cacagagtct    12300
tgctctgttg cccaggctgg agtgcagtgg caccatctcg gctcactgca acctctgcct    12360
cctgagttca agtgattctt gtgcctcagc ctctcaagta gctgggatta caggtgtgtg    12420
ccaccacact cggctatttt ttgcattttt agtagagatg gggctggtct tgaactccca    12480
gcctcaggtg atctgcctgc ctcagcctcc caaagtgctg agattacagg tgtgagccac    12540
agcgcctggc catatattgc ttttttctta ttatcagagc cagttcataa ttgtggaaaa    12600
atagtgtttg taacaatgta agtatggata aatcatcttt ttaattttgt gattcatata    12660
ggtttgttgt tgttgttgtt gttttgtttt tatcttgaga cagagtcttg gtctgtcacc    12720
caggctggag tgtaatggca caaccatggc tcactgcagc ctcagatgcc tgggttcaag    12780
caatcctccc gtctcagcct ctagagtaga tgggaccaca ggtgtgggcc accatgcctg    12840
ggtaattaca aaactttttt ttttttttct agagatgagg tctcactatg ttgcccaggc    12900
tggtctcaaa cctttgacct cgcttcagcc tttagagtag ctatgactat aggcatgtgc    12960
catcacccag ctaattaaaa tttttttttct tttttttttt ggtggagatg cggtcttact    13020
ttgttaccca gactgcaagt tagttccaga tatcaacatt tggtgtttcc aaatgcacgg    13080
```

```
ggaggctttg gagcaagttt ttggctcata tgcataggtg tcctagacat tcactttgca    13140
aattcttatt aaaatgacta cagtagcata cagataggga aaaatatcct tgtcagtacc    13200
accgattggg tgagaagaga ctgtatatta aaaacaatga ccatcttttt gccacataaa    13260
ttgctggtgg ggccagtttg aagagggctt tgtcagctgc cttctgcctc ttcctcttga    13320
gtacgtggag ttggagtcat ccttgacagc ctcctgttga caccacccgg gtcacagatg    13380
tgaaactgtg tggatgtagg agagagcagt gatgggcctt accccaaggt tgctcttcct    13440
tccctctggc cacaaatgtt tagtaaggaa ctgctctgta ttaaccatt t gctagggct     13500 gcagatacgg tggtgaagaa atagacatgt tcctactcgg gatgctgagg tgggaggatt    13560
gcttgagccc aggagttgga gctgcagtga gccatgatca caccactgca ctccagcctg    13620
ggggacagag cgagacccta tctctaaaaa acaataaaag aaatagatgt gtccttcacc    13680
ctcatggaac tgccagtcta gccttcaacc tggtgactgt agaaatgtgt gattagatgc    13740
tatattgcca tgttgagtgt caccc ctgag aagcagggtt ttttttgaga aggtaggatg    13800
ggggatctga ctgtgggacc accagaggga aaagcacatg taaaagctgc gtgtaccaac    13860
tggaggaaat cggagacgtg atcagagaac cagagtcaac caggggccat gccgtacagg    13920
gtcctgttaa gatctgtgac ttttttctaa acgttttctt ctggataaca tctaaatttc    13980
tagttccaaa tgtgaaactc caagggcgtt ctgtgctaaa cattttgcat gtattaatta    14040
atttccacca cacaacattg ctgtgaatta agacagtttc taagcatggc aagaaaccca    14100
gaaatcataa tggaaaaatc tgataaattt aacaatgcca acatgaacct ctgtaggaaa    14160
aaaaatacca cagactaaaa aggggggaaa aaaccagag acaaatattt gcaacacata    14220
cagtaaaggg taattttctg gttatatcaa gagctcctac aaatcagtaa gaaaaaaat    14280 ctaataggaa atgagcaacg acaaactgac aactcataga aaaggaaaca caagtggtct    14340
gaaaacatga aaaagtgctc agtctcacaa agaaatgcaa actaacatgg taccattttc    14400
cattaatcag atagacaaag atgaaagagt ttggtaatgt atgtagtatt ggcacaagtg    14460
agggaaaaca ggggatttca cactctatgc ccgtccaaac cagtacctta ttttgagggt    14520
ggtttgacaa tatttgtcaa aataaaaaaa ttatatatag tcatttgcca cataatgatg    14580
gttcagttga tgatggacgg catacataat ggtggtccca taagaatata atgggctggg    14640
tgcagtggct ctcacctgca atcccagcac tttgggaggc cgaggtgggt ggattgcctg    14700
aggtcaggag tttgagacca gcctggccaa catggtgaaa ccctgtctct gctaaaaaca    14760
tacaaacaat tagccaggca tggtggcggg tgcctgtaat cccagctact caggaggcag    14820
aggcaggaga atcgcttgaa cccggaaggc ggaggttgca gtgaggtgag attgggccac    14880
tgcactccca tctagatgac aaggcaaaac tccatctcaa aaaaaaaaaa aaaaagaat     14940 attatgggcc cagccacagt ggctcacacc tgtaatccca gtactttggt aggccaaggc    15000
aggagaatca tttgaactca ggagtttgag actagtgggg acaacatagc aagacccc at    15060 ctcaaaaaaa aaagattatg gtggagctgt cctgtataga cataccattt ttaactttt t    15120 tttttttga gatggagtct tgctgtgtca cccaggctga tgtgtagtgg cgtgatctgg    15180
gcttactgaa acctccacct cctgggttca agcgattctc ctgcctcagc ttcctgagta    15240
gctgggactg caggcgcagg acaccatatc tggctaattt ttatatattt agtagagatg    15300
gggtttcacc atgttggcca ggctggtctt gaactcctga cctcaagtga tccgcctgcc    15360
tcagcctccc aaagtgctgg gattacaggc attagccacc atttacaggc acctggccac    15420 cattttaat cttttatatt gtatttaaac tgtacctttt ctatgtatgg atgtgtttag    15480
```

```
atacacaaat accattgtgt tacagttact tacagtattc agtacagtag catgctgtac   15540
aggtgtgtag cctaggagca ataggttata ccatatagcc caggtgtgta gtaggctctg   15600
ccatctaggt ttgtgtaagt acgctccatg atgttaccac agtgacgaaa tcgcctaatg   15660
atgcatttct cagaacatat tcctgttgtt aagcaatgca tgaccgtatc ttgacaaagc   15720
cattttattt ctaaaacttt aattttacag atttatttgt aaaagtatgt aaaaatgatt   15780
gtaaaggata tgttctgctg cattatttgt aataacaaaa aaccagagga taacataaat   15840
gtcctataag aagggttaga ttatggatgg cacattcata caatggggta ttatgtagcc   15900
attgaataaa agggtactgg ctgggcgcag tggctcatgc ctataatctc aacactttgg   15960
gtggccaaag aaggaggatt gcttgaagcc aggagcttgg ggccagcctg gcaacatag    16020 caagacccta tctctacaaa ggaaaaataa aacaattagc caggtttggt attggacacc   16080
ttcatggtcc cagctactga ggaggctgag attggaggga tcgcttgtgc ctggcaggtt   16140
gaggctgtag tgagccatga ttgtgccact gcactccagg ctgggagata gagtgggacc   16200
ctatctcaaa aaacaaaaa caaaaacaaa acctcctgta aaatgtcaag aagtcctaga    16260
tgtgggccag gtgtggtggc tcacacttgt aatcccctgca cttttgggagg ctgaggccag   16320 gagtttgaga ccaggcagag caagatagca agactccatt tctacaaaaa ataaaaaaaa   16380
ttagttgggc atagtggtgc attcctgtag tcccagctac tcaggaggct gaggtgggag   16440
gattgcttga gcctgggagg ttgaggctgc agtgagccat gatcacacct ctgcactcca   16500
acctgcgcaa cagagtgaga ccctgtctct aaaaacaaca accaaaaaaa cccagcaaag   16560
tactgataaa gatctttggc tgggcgcagt ggctcacacc tgtaatccca cacttcagg    16620 aggctgaggc gggcaggtca caagatcaag agatcaagac catcctggcc aacatggtga   16680
aacccggtct ctactaaaaa tacaaaaatt agctgggcat ggtggcgtgc acctgtagtc   16740
tctgctactc gggaggctga ggcaggagaa tcacttgaac ccaggtggca gaggttgcag   16800
tgagccgaga tcacgccact gcattccagc ctggcgacag agcaagactc cgtctcaaaa   16860
aaaaaaaaaa gagagaaaga tcttcaagtt gtagtatgtg aaaaaatcag ggtgtaaaac    16920
aagagaatcc catttgtgtg tgtgtcgagt gtgtttcaca caggctcaga gggagtagtg   16980
tgtatatgca catgaacata cgtgtcagtg tatatatgta tatatacaag gttgtgggtt   17040
tgtttgtttt ttttgagaca gagtcttact ctgttgccca ggctggggtg cagtggtgca   17100
atcttgaccc actgcaacct tcacctccca ggttcaagtg attcttgtgc ctcagcctcc   17160
caagtagctg agactacagg cacgcaccac catgcccagt taattttttgt attttttagta   17220 gagatggggt ttcatcatgt tgcccaggct ggtctggaac tcctggcctc aagtgctctg   17280
cccgccttgg cctccgaaag tgctgttgcc caggctggag ctcagtggca aatcgcagc    17340 tcactgcaac cccgacgtcc caggctcagg caatctttcc gtcttagctt cccaagtaac   17400
tgggactaca ggtgtgtgcc atcaatgccc caccaatttt ttaattttttt gtagagatgg   17460 ggtttcccta cgttgcccag gctgatcttg aactcctggt ctcaagcaat cctcccacct   17520
cagcctccca aagtgctgcg attacaggtg tgagccacct tgccctgccc tgtacaaaga   17580
tctgcataaa agcagttaat aatactatgt ttgaggctgc catcacaggg gtgaggtcaa   17640
ggacaagtgt gagaaattct tttagaatct attttaaaaa aagaagagat gacagtggtg   17700
acagtcaggg aacagataag caggtagatt gtggggtct aggctgtcta actggtgttt     17760
aaaatgaagc aaccgctgag cctgctgtat ttcatttaat ggagactagt aaaacaacag   17820
```

```
ccagaaattc ttcactttcc atctaagaga ggcaaaagtt attttcccctt caataacctg   17880 ggactgtagg attaaggttt ttttttttttt ttttttaaat actacaatat gactaccagt   17940
ataatttaaa aatgattaga attctatttg agtaagaaat aggtgtctgc ctgaagtaga   18000
cagtcactga agtcactaag tggcaaaaga cagaaaaaaa attgaaagta ggaaacaatc   18060
agcagatatg ataccaaaca tgagctgtca gtgataatgg attaagtcct tcaataatgg   18120
ctgagccaga tggaattaaa agaaaaaatc caggccgggc atggtggctc acacctgtaa   18180
tcccagcact ttgggaggct gaggtgggag gatcacttga gtccaggagt ttgagaccag   18240
cctgaacaac atagtgggac cccatctcta tttataaaa atattttgaa aaagaaaaa     18300 aaaattcagt tgtgttctgc tttaaaaaga caaattggca cagaatgtca aagaataaat   18360
aaaacaaaca tgggcaaaag agattcaggt ggtaccaata tcgggctaag tagcattcaa   18420
gataaagatt attaaataat aagttagtta atactagagt aattgcatat taatgaaaca   18480
taatctatgg tagagatatt atagtcaata attgttttat gtattcatta aggtaacaac   18540
aagcaaacaa gctttaatag ttttaaatgc tttatatgct ttatagttct tttatgtgca   18600
ttaattcatt aattctcatt tcctatgagg taaacactat tattatccac attttacaga   18660
tgtaaaaacc gaagcagaga gattaattag cttgcccagg agatgtggca ttctgggatt   18720
tgagacagtg gtttggctct gtaggttgct tcaataacca agagatgctt caaatcagat   18780
ttttaaaata tgttttttcag aagcattttc ctgatacttc tcccccttaca tgggtgttag   18840 tcttttgggt tgaaaaacat gagtaagtgc tagaagagca aaatatgcat ccagattaa    18900 tagtatgtct gtttttctga gccttggcat ttcattgctt ttataataga aatgaaggct   18960 ttttttttttt tttggctgag aatagcactg aactcagtgg gagggactgt gggttgtaag   19020
ttgtccgcct ctgaatggag ttgaatttaa gtttcttggt ttccaaagaa tgattgatttt  19080 aaagaccctc aaattgcaag ttagaactga cttcagtcct tgaggttttt taccatttaa   19140
tgaataatta aatttatggt aataaatggt aataaatggt aaaaatggta ataaatttta   19200 ccattttaatg aatttttctt aaaaagcaat tgaattgttg atgaaaggtg atgttaaaat   19260
tatcccagat ttatcaatct ttttttttatt gcccctggat tttgagtcat agaaagcctt   19320
tccttattct aaggttaaca agacattcac ccatgttttc ctctagtatt gcattgtttc    19380 atctttacg tttattattt attttatttt atttttttga cagggtct cactgtgtca      19440 ctcaggctgg agtgcagtgg aatgatcttg gctcactgca gcctctgcct cccgcctccc   19500
gggttcaagc gattctgctg cctcggcctc ccaagtagct gggattacag gcacctgcca   19560
ccgcgcctgg ctaattttttg tatttttttt ttagtacaga tggggttttg ctgttggcca   19620
ggctggtctc gaactcctga ccttaagtga tccaccccgcc ttggcctccc aaagtgctgg   19680
gattacaggc atgagccacc gtgccggccc taaaatttat tctgatatgt gatatgatgt   19740
atggttctaa ctactttgtt acggtgcatt attttctaaa tgtggtattg gattcttttta  19800 tattttgttt agaagttctg catcaatatt catgagtacc attggtctct gttgtttttc   19860
ttgtgccatc tttattggta taggtatcag tgttatattt agtttgtaaa aggaagttgg   19920
aagttttcct ttcttttttag tactcaggaa tgatttttaag aattgagact atttggtctt  19980
tgaaggtttg gtagaagtcc attgggaatc catctgggcc tggtgattttt ctgtgcggta   20040 gttccttaat tgtttttccct attttttctt attttttaatc aggtagcctc tgaaccagaa   20100
taggttcaga gaggctccct ctattttttt taatacaagt tggtctgcct aagtttttctt   20160 actctaatgg gttaattttt gtagactgca tttccctgaa aaattacacg tttgttctag   20220
```

```
gttttctgac ttatttccac aacttttag tctttccccc tggaatcatg cccctttcca    20280
taaacaggac tctgatgtac ctgaagtatt ttcacacttc gggtggactt tctgtttctg    20340
ggggtggttt tagagcaatt ttaggcctgc cactagctac cctgttctct acaccatgct    20400
gttttctca gaatgctctt cttttgcaca aaggcttgga gtaggaggtt gagcagtcac    20460
tcactgacgt ttggtatatt ttcttttttt tgcttacagg taatctggaa gtttgggcat    20520
tctctttaag ttgagggtgt ggttttcatg tcattttatt tgtttattgt tttcttgtgt    20580
gtgtttctta gagacagggt cccactcttg ccctggctgg agtgcagtgg cgtcttgatc    20640
atagcttact gcatcctcaa gctgctgggc ttagatgaac ctcccacctc agcctcctga    20700
gtagctggga ctacaggagc acaccaccat acctaatttt tttttttttg agacgaagtc    20760
ttgctctgtc cccagattg gagtgtagtg gtgcaatctc ggctcactgc aacctctgcc    20820
tcccgggttc aagcgattct ctcacctcag cctcccgagt agctgagact gcaggtgcat    20880
gccaccatac ccggctaatt tttgtatttt ttagtagaaa cagggtttca ccatgttggc    20940
taggctggtc tcaaactctt gacctcaagt gatccaccca ccttggcctc ccaaagtgct    21000
gggattacag gcttgagcca ctgtgcctgg tccctggcta atttttaatt tttttgtaga    21060
gatgggatct tgctatgttg cccaggctgg tcttgaacac ctggccttaa gcaatcctcc    21120
caccctagcc tgccaaaaca ctgggattta caggcatgaa ccattgtgcc tggcttgttt    21180
tgtttttaat tctatgttgt ttttgaagga tgtatgggga gagatggatt taggcaatca    21240
tcgttgtcct tggctacctg aaagtccagg cactcttcta gatactttat aaatattaac    21300
tcatttatc ctctcaacaa cactatgaca tgggtactgt tacaccttcc attttatagg    21360
acttaacaga gaggttaaat atgtagccca gggtcacaga gagctgggct tcagaccaag    21420
acaatctggc accagagtct atgtggctac ccctaaggct ttgccaccat gtgttagtga    21480
ttctcagcct gtcatttggg gaggggattg ccctttttt taaactttt aaaaaattta    21540
ttcttatttt attatatttt tgagacagag tctccctctt ttgccgaggc tggagtggag    21600
tggtgtgatt tcagctcact gtaacctctg cctctggggt tcaagtgatt ctcatgcctc    21660
agcctcccaa gtagctggga ttacagttgc cagccaccat gcccagctaa ttttttgtatt    21720
attattatta ttatttgaga cggagtctcg ctcttttgtt caggctggag tgcagtgctg    21780
tgatctcggc tctctgtaac cttcgtctcc tgggttcagg tgattctcct gcctcagcct    21840
ccggagtagc tgggactata ggcgcgcacc accatacttg gctaattttt tgtatttta    21900
gtagagacgg ggtttcacta tgttggccag gctggtctcg aactcctgac ctcaggtgat    21960
ctacctgcct tggccttcca aagtgctggg attacaggtg tgagccacca tgcatggctg    22020
gattgtcctt ttttaaaaaa aaaacaaaa acaaaaaaaa aaacccaaac cataaaccca    22080
atattctgaa agatttggtc tccacacctg tgttatataa taattagttt ttccattttt    22140
ttcctcttgg tagaaggcac atatgccact cagtttccag ttgccacacc caattaacat    22200
aattgttttg cagccaaaag caaaagagag ttgacatttt aattagctta tgtaggtaga    22260
caaattgagg cctaatgtaa gagtttcatt ataccttttt gaaaaactat aaatagctag    22320
aagccagttg tcattacttt ttgattcctt agaattctgg gcatctttca tctggaacca    22380
cagatgaaag aagctgcaag gaaggatttt ttttcttaac ggaatagttt aaccattctg    22440
aatgcaaaag tattggatgc tagaataata ggtatcacat aaattgaggt tgacgttttc    22500
ccggggtgaaa ttctattctg tctcaatttt ccttttttt tgagacggaa tcttgctctg    22560
```

```
tcgcccaggc tggagtgcag tggcatgatc tcggctcact gcaagctcca cctcctgggt    22620
tcatgccatt ttcctgcctc agcctcccga gtagctggga ttacaggggc ctgccacaac    22680
acccagctaa ttttttttgta tttttagtag agacggggtt tcccaggatg gtctcaatct   22740
cctgacctcg tgatccgcct gcctcggcct cccaaagtgc cgggattaca ggcgtgagcc    22800
actgtgcctg gccttttttt tttttttttt tttttttttt taagacagag tctcgctttg    22860
ttgcctaggc tggagcgcag tggcatgatc tcagcttatt gcaacctccg cctcccgggt    22920
tcaagtgatt ctcctgcctc agcctcccga gtatctgaga ttacagatgt gtgccaccat    22980
gcctggctaa ttttttgtatt tttagtacag atgaggtttt gccatgttgc ccaggctggc   23040
ctcaaactcc tgacctcagg taatcctcct gcctcagctc ttcccaaagt gctgggatta    23100
taggcatgag tcaccggggcc cagactcaat cttctgacaa gctctcagag agagtaaaaa   23160
gcaaatgaat atttcattat tttgatctga gctttacgat ttttcttttc ttttcttttt    23220
tttttttttt tgagatggag ttttcgcgttg ttgcccaggc tagagtgcag tggtggcgat   23280
cttggctcac cgcaccctcc gcttcccggg ttcaagcgat tcttctgcct cagcctcctg    23340
agtaactggg attacaggca tgcgccacca tgcccggctg attttgtatt tttagtaggg    23400 acagggttttc tccatgttgg tcaggctggt cttaagctcc cgacctcagg tgatccacct    23460
gcctcggcct cccaaagtgc tgggattaca agcatgagcc accttgccca gcctttttt     23520 tttaaatctg agaagaggtc ttgctcgatt gcctaggctg gagtgcagtg gtgcgatctc    23580
tgctcactgc attctctgcc tcccagactc aagcaatcct cccaccttag cctcctgagt    23640
agctgggact acaggcatat gccaccacac ctggctaatg ttcgtatttt tttgtagaga    23700
cagggttttg ccattttgcc caggctggtc ttgaactcct gacctcaggt gatcctccca    23760
ccttggcctc ccaaagtgct gggattacag gtgtgagcca ctgtgcctgg tctccttcac    23820
tgttgtaaga tacttgaatt gggtcaatat ttgtggagaa gtctcttaaa agttcacttg    23880
attgtcagta ctagaactct acatttaata ttgacatatt cctgggagca tttcagagca    23940
ttctattagc ttagaaaggt ccaggataat ttgactttag aagttactgt taccatgaat    24000
ctcaatgact tttgaaatcc atgaagaata tcttttttttt tttttttgaga cggagtctca   24060 ctctgtcgcc caggctggag tgcagtggtg atctggctc actgcaagct ccgcctactg     24120
ggttcacgcc attctcctgc ctcagcctcc cgagtagctg ggattacagg cacatgccac    24180
cacgcctggc taatttttttt gcattttttag tagagagggg gtttcactgt gttagccagg   24240
atggtctcga tctcctgacc ttgtgatccg cccgcctcgg cctcccaaag tgctgggatt    24300
acaggcgtga gccaccgcgc ctgcccaaga atatcttttt gctggtaact agagaggact    24360
cctctgaagc agatgccatt catgatggat ttcatcattt atgggtttta aaaaacattt    24420
tattttgaaa taattttcaaa tttaaataag agttgcaaaa tagtacaaat aattcgtgtt   24480
aacttttcat ccagatttac aagtcaacct tatacaggtt gagtatccct tatccaaaat    24540
gcttgggacc agaagtgttt tggatttcag attttttcga attttggaat attttttatta   24600 tatacttaag catctctaat ccccaaatct caaatctgaa atatctgaaa tgctatgatg    24660
agcatttcct ttgagtgtta tgtgggcact ttttaaattt atttaattaa tttattttt     24720 gagatggagt attgctccat cacccaggct ggagtgcagt gagcgatctt ggcttattgc    24780
aaacttcacc ttctgggttc aagtgattct cctgcctcag cccctgagt agttgggact     24840 ataggcgctt gccaccacgg ccggctaatt tttgtatttt tagtagagac agggtttcac    24900
cgtgttggcc aggctggtct cgaactcctg acctcaggtg gtccacctgc ctccgcctcc    24960
```

```
caaagtgctg ggattacagg agtgaaccac cgcgcctggc catgattttt gcagcatttt   25020
agatttggga tactcaacct gtaccatgtt tactctctct cctctctctc tctctctttt   25080
tatatatata tatatatata tatatatata tatatatata tatatataaa ttatatatac   25140
actacacata tatgtatgta tatgtatgta ttttatatat aaaatacata tctacatata   25200
aaatacacat gtatatatac atgtgtacat atatgtgtct ctatatttaa gttttgttgg   25260
aaccacttga gggtaagttg cagacatggc gtctcattgc tccaaaatac ttcagtgtgt   25320
atttcttaaa tacaaggaca cttggttaca taaccacagt atatcaccaa atgtatatta   25380
taacaagact accatcaaat ccttatatct ctttcaaatt gttttagtaa tatccttata   25440
gcaaaagaca aaacaacaac aaaaactgtt ccctttattt ttgtttgttt tggtccatta   25500
tatgtccagg ttatgcatta atgcattgtg ttacttgcta agtcttgtta ctggcccttta  25560
attaggatat ttctttgcat cccgccaaac tcctcttcat ggttgtatct ttttttttt    25620
ttttggagat ggaattttgc ttatgttgcc caggctggag tataatgatg cgatcttggc   25680
tcactgcaac ctccgtctcc cgggttcaag cgattctcct gcctcagcct cccgagtaac   25740
tgggattgca ggcctgcgcc accttgccca gctaattttg gaatttttgtg agacggggtt   25800
ttgccatgtt ggtcagacta gtctcgaact cctgacctca tgatccgccc gccttggcct   25860
cccaaactgt tgggattaca ggtgtgagcc actgtgcccg gtcttttttt tttttttttt   25920
gagacagggt cttattctgt tgcctggcct ggagtgcagt ggtatgatct tggctcactg   25980
caacctggac ctcctgggct caggcgatcc tcccacctca gcctccttag tagctgggac   26040
tataggcaca caccaccatg catggctaat ttttatattt ttttgtagag actgggtttc   26100
gccatgttgc ccaagctggt cttgaactcc tgggctcaag tgatccacct gccttggcct   26160
cccaaaatgc taggattaca ggtgtaagcc actgcgcctg gccctaattt ttgcattttt   26220
tgtagagatg gggtttcact atattgccca ggctggtctt gaactcctgg gctcaagtga   26280
tcttcccatc acagccccct aaagtgctgg gattataggc gtgaaccact gtgcctggct   26340
gaggattaag tttcaacctc aggggagcgg cattcaaact atagcattgt cctttagtga   26400
ctggcttagt tcacttagaa tgtttgtcta ttcatccatc tatagacact gttttctttc   26460
accttttggc tttgcaaata atgctgctgt gaatatgagt tatagaaaaa taccaatttg   26520
aatccgtgtt tcaattact ttgagtatat acctggaagt ggaatttctg gatcatatgg    26580
tacttccaag ttttttttttt ttcttttttg agacaaggtc tcactctgtc acccaggctg   26640
gagtgtagtg gcacgatctt ggctcactgc aacctccgcc tcccgggttc aagcgattct   26700
cctgcctcag cctctcaagt agctgggatt acaggcacgc gccaccacgc ccaactaatt   26760
ttgtatttt agtagagatg ggtttctcca tgttggtcag gctgctcccg aactcccgac   26820
ctcaggtgat ctgcctgcct cagcctccca aaattctggg attacaggtg tgagccaccg   26880
cacctggcct ccatgtttca atttttaaac aaacaattag ttaaaaaaat aggaaactaa   26940
gagaatgaac tatttcctgt tttattcagt gggttataat ctgttactat cattgtttat   27000
tttgaggtac aaattgtccc tactttggcc agcagaggat cctgcagttt gtctcctgtg   27060
tccttttcat agctccttgt tggaactctt actggcccac aataggatgt tccaagttca   27120
tcttcttact tttactgccc caacgctggg atcagccatt tcttcaagga ggccagttcc   27180
tttcattgga gaatggaaaa cccaatatgt agaaaccaag atagaggtgt taggtgtgat   27240
tgctactgga gtgtcattgc ttccaaaccc tttcagaaga gacctaggaa atgtgtgtgt   27300
```

```
gtgtgtatat atatatgtgt gtgtgtgtgt gtattcataa aagcacatac acatacacat   27360
accccgaagc atgtatttct gtattattat tatttttttg agatggagtc ttgctctgtc   27420
gcccaggctg gagtacagtg gcacgatcat ggctcactgc aacctctgcc tcctggattc   27480
aagcaattct cctgtctcag cctcctgagt agctgggatt acaggtgtcc accaccacgc   27540
ccacctaatt tttgtatttt tagtagagat ggggtttcac cacattggcc aggatggtct   27600
tgaactcctg acgtcaagtg atctgcccgc ctcggcctcc caaagtgctg ggattatagg   27660
cgtgagccac tgttcccatc cagaagcata catatctatt tctatatcta catttctgtc   27720
tttacatgta tatattaaaa attacagttt gcactaatac ctccaattac aatctaacat   27780
catgggattt attctggctt tctcccttct catatttgtg tctccccaac agtgagaaac   27840
ctggcttgct atcctcaaca tggtaactta tttattaaga aacttattct ttttttttt   27900 tttttctga gattgagttt cgctcttgtt gcccaagctg gagtgcagtg gtgtgatctt   27960
ggctcaccgc aacctctgcc tcctgggttc aagcgattct cctgcctcag cttctcaagt   28020
agctgggatt acaggcatgc accaccatgc ccagctaatt tcgtattttt agtagagatg   28080 gggtttctcca tgttggtcag gctgctctgg aactcccgac cccagctgat ctgcctgcct   28140
cggcctccca aagtcctggg attacaggcg tgagccaccg tgccctgcct ctagtttatt   28200 tattttatt ccatgtgctc agtcttgcga gcacgtggtc tgttttcttg ggcctggccc   28260
cctcagtgca ctgtcttaat accctagccc ccagtccctc tgatcatatc cccagacacc   28320
cctactgaat cccaggtctc taccaaggga aaggcaggga ggaggcattg accaaggaga   28380
agagggggaa gggacaggga aggtcttgat ttgtattttc taaaattttc tactctgctc   28440
ataatgcgtc ttagctgtgt tgttgtggaa agtagtgctg acagtgtctt gttttttat   28500 tacttacttt gtctttcttt ttaagatggt ttcacccaaa tatcactggt gtggaggcag   28560
aaaacctact gttgacaaga ggagttgatg gcagtttttt ggcaaggcct agtaaaagta   28620
accctggaga cttcacactt tccgttaggt aagttggaat gaaaagagag gatcctgaga   28680
gtgttttcta ggtaggaagt ggtaaaacca tgcttggata gcttgctgcc tgcatttcga   28740
gtttgaaggc cttatctgag ccctgggctg ccttcagggt tggggagtg gcctcctgga   28800 catttagcag aagaggagta aggagggccc ttcttctccc tctgagacct catggaaggt   28860
gagttggagc aggtcataga agttcttaag ccctccagtg cttgagactt gttccacaca   28920
tcttgaacct ggtttctgca ttttctttt ccttcctgtt gatttattta aaatttat    28980 ttcttttcaa ttttttttt tttttaaata gaggtgggat cttccaatgt tggccaggtt   29040
ggccttgaac ttctggcctc aagcaatcct gcctcggcct cccaaagtgt taggattaca   29100
ggcgtgagcc actatgcctg gccttctttt tttgagacaa gctgttgctc tgttgcccag   29160
gctggagtgc agtggtacga tcacagctta cagcagcctt gaactcctgg gcttaagtga   29220
tcctcccgcc tcagcctccc gggtagctgg gactccaggc ttgtgccacc atgctcagca   29280
tttttaaaaa atatttttg tagagatgag gtctcactgt attaccaagg ctgatctta   29340 actcttagcc tcaagtgatc ctcctgcctc agcctcccaa agtgttggga ttacaggcat   29400
gagccaccac actcagactt tgttgacttc ttaataagaa aaatacttgt taagagtttc   29460
ttcagatcac tttcctttat caacaagtaa aacatgactg aggaagttgt ggtcccctt   29520 gcttccctgc ccaggcccgt ttccctccct cttcccccag aggaaaccac caagaggttg   29580
gcatatattc ttcctgaacg tgtttttata gttgtactgc acttgtactg tgtatgaaca   29640
atataaagtt ggtttgtgtg tttaaaaaat tcacatacat ggatttataa tgtatgtatc   29700
```

```
attttgcaac ttaaaaattt tttttttgagc tccatgctga ttgataacga tctattttttt   29760 tttttttgaga tggagtttca gtcttattgc ccaggctgaa gtgcaatggc gtgatctcag   29820
ctcactgcaa cctcagcctc ctgggttcaa gctattctcc tgtctcagcc tccggagtgg   29880
ctgggattac aggtgcatgc caccatgccc agctaatttt tgtattttta gtagagatgg   29940
ggtttcacca tgtcgaccag gctggtctca aactcctgac ctcaggtgat ctgcctgcct   30000
tggcctccca aagtgctgga attacaggca tgagctacca tgcctggcct ttttttttt   30060 tttttttga gacaaagtct tgctcttttt cccaggctgg agtgcagtgg ccacaatctt   30120
ggctcactgc aacctctgcc tcctgagttc aagcagttct cctgcctcag cctcctgagt   30180
agctgggatt acagacatgt accaccatgc caagttaatt tttgtatttt ttgtagagac   30240
taggttttac catgttggcc aggctggtcc tgaactcctg acttaaagtg atccatctgc   30300
cttggcttcc caaagtgctg gggttacagg catgagctat cgcgcctggc ctgagaaatc   30360
tcattcttac tcctactccc ttgcacacta tctccattct gtaggtagcc atttctatta   30420
atttcttgtt taccettctg tgtttctttc attctttttc ttttttttctt tttttttttt   30480 gagacaatct tgctctgttg cccagactgg agtgcagtgg tgtgatcttg gctcaccgca   30540
acctccacct cctgggttca gtgattttc atgactcagc cacctaagta gttgggatta   30600
cagcgcctgg tgtacactac cacacccagc taatttgtgt attttttagta gagatggggt   30660 ttcaccatgt tgtccaggct aatctccaac tcttggcctc aagggatctg cctgtctcag   30720
cctcccaaag tgctgggatt ataggcatga gccaccatgc ctggccctat gtttcttttt   30780
ataaaaataa gcaaattaat attttatta ctattttcct tttattttta cacatcaagt   30840
agaacattaa atatatttct ctgtaatttt tttcagttac ctaaatcttt tagtgatctc   30900
tctcatcttt ttaatcagct ggatcgcatt ctatcatgtg aatattttat aacttctata   30960
tactgtcacc agcaggtagc gatttagttg tgtctaatat tttaaaatga tatataatgc   31020
ctcaatgaat atagtaacct tttgcatata ttgttttgtg ctttgggata acactacctc   31080
gtattggaaa ctgtgtcatt acatgtgtct ttaaaattac atgtgtcttt ttattttat   31140 ttttatttt tttgagtggg agtttcactc ttgttgccca ggctggagtg cagtggtgag   31200
atctcggccg actgcaactt ccgcctcccg ggttcaagcg attctcctgc ctcagcctcc   31260
ccagtaggtg agattacagg tgcctgccac cacgcccagc taattttttgt attttttagta   31320 gggacggggt ttcaccatgt tggccaggct ggtatcggtc tgctgacctc aggtgatcct   31380
cccacctcag cctcccaaag tgctgggatt acagacgtga gccaccatgc ctggccatca   31440
cttttttttt tttcttaatt gctgcatagt ggccgggcac agtggctcac gcctgtaatc   31500
ccagcacttt ggaggccaa gcaggcggc ggatcatgag gtcaggagac caataccatc   31560
ctggctaaca tggtgaaacc ccgtctctac taaaaataca aaaaaattta gctgggcgtc   31620
gtggcgggcg cctgtagtcc cagctacttg ggaggttgag gcaggagaat ggtgtgaacc   31680
cgggacgtgg agcttgcagt gagccaagat tgcaccactg cactccagcc tgggtgatgg   31740
agtgagactc tgtctcaaaa acaaacaaac aaacaaaaaa attgctgcat agtattccat   31800
tgtatgagta gtaacacaac aattttttata atgcatagta ttccattgta tgaatagtaa   31860
tgtagcacta tttgtttata cattttatg attaaaaaac aaaatgtttt tctattatga   31920
ataaagtggc aatgaatatt tttgtacaag tgttttggta gctatacagt tattgtcact   31980
taatatatgc aattcgatag gccagtcatt caaaatagaa gatatacaag gtaggccggg   32040
```

```
cgtggtggct cacgcctgta atctcagcac tttgggaggc cgaggtgggt ggatcacctg   32100
tggttaggag tttcagacca gcctgaccaa catgggagaaa cctcatctct actaaaaata   32160
caaaagtagc tgagcgtggt ggcgcattcc tgtaatccca gcttcttggg aggctgaggt   32220
aggagaatca cttgaacctg gatttataat gtatgtaaat ccaccgcgaa ggttgcggtg   32280
aaccgagatc acgtcattgc actccagcct gggcaataag agcgaaactc catctcaaaa   32340
aaaaaaaaaa aagatatgca aggtaaagat actaataaag acctttgtgt tgagttggtt   32400
gacatgtggt tatttcaccc atcgtatttc ttatagggaa taggtaaatt cgttccttgg   32460
gtttctttca cacttaggt aaaatccgac gtggaagatg agatctgatt ttactggtgt   32520
aactctttat ttgtcccctt gcctcccttt ccaatggact attttagaag aaatggagct   32580
gtcacccaca tcaagattca gaacactggt gattactatg acctgtatgg aggggagaaa   32640
tttgccactt tggctgagtt ggtccagtat tacatggaac atcacgggca attaaaagag   32700
aagaatggag atgtcattga gcttaaatat cctctgaact gtgcagatcc tacctctgaa   32760
aggtcagtaa cattttagtg accacaaagt ctgctgctcc cttgtgccct gagtgtcaga   32820
aatgcatgac ggtctgtgta tgactctctg actccaaagg cttgtgactg ttttttgagc   32880
tgtaatcttt aaagaattac taaagtgaga ctaatagcat caaattattt tcagagtacc   32940
tttttcctgc aaaagtttta atcagtgtta cttacactca tcctataggg gttgcatacc   33000
attcctgcat atacttggta cgtgtattag ttttaagact tattgaactt cagcagataa   33060 tcttgagag ttattagagg aaaacaaatg ataatggaga caccaaaata gcagcagttt   33120
tctatggtgg ctctcgacca gttattcagc aatgtcacca acagatgtca gtttaagctc   33180
agaagtggaa aagcagagag ctcagagggt cagcttttc atcagttctt ttaatgttat   33240
caccacaatt atgtgagaat gaccttgctt agagaaaatt atgttatttt cgagatcttt   33300 cccctgtgt tggaactagg ctgatgaaag catgggcttg acttatttat tgattgtatt   33360
cgttttgtac attcccaatc tcctctctga cttggtgcaa attcaggatc tcttagttag   33420
tttgtatatt ttgtgtcttc aggtatgatt ttttcagctt atacctttat gtcagtgcta   33480
ttatgtgctg ataatttgtt tctctagcta ccaccgtagc ttcaggcaaa aggctgtcag   33540
ccaactctgt acagtttatt tctaaatttt actgttttca gttgagtatg gatgaagaat   33600
aactcaaagt ttattctttt gatgatgagc ccttaacacc cctgccatg atagtacttg   33660 ctttctgacc aagatcctga gggaaaaagc cactttatta ttagaactat gttaagatgc   33720
ttcccaaaaa acatggagca gtattgtctc aaagtctgtc cttggatggc tttggatgcc   33780
tacatcagga ctgtctgatg tgctggttaa aatgcagatt cctgggcctc attcagactt   33840
acatgtattg atattgctgg ttgtggagcc tgggaattca tatttttagc aaaatccctc   33900
atttttactc caagtcttat gtgcattata cagtttgaga tgatcaccca ggatatagtc   33960
caaagacact ggaggctgtt gaagtatagg ttgtatatat ggaaaaggtt ggaatgtttg   34020
aattaattta taatgaagat cctttttaat tgagtgttca catgccaagg caaggacaaa   34080
cattcaaaat gattttctgt ctctgttaca acttttttctt tctttttttt aatttattta   34140
tttgagatgg agtctcactc tgtcacccag gctggagtca agtgacgcga tctcggctca   34200
ctacaacctc cgcctcccag attcaagtaa ttctcttgcc tcagcctccc gagtagctgg   34260
gactacaggc atgtgccacc atgcccagtt aattttgta tttttagtag agacagggtt   34320
ttgtcatgtt tgccaggctg gtctcaaact cctgaactca ggtgatccgc ccaccttgac   34380
ctctcaaagt gctgggatta taggcgtgag ccaccgtgcc tgtctctatt acaactttttt   34440
```

-continued

```
attacaactt ctttattttg actttatttt tacaaattat ttatttattt tttttgagat   34500
ggagtttcgc tcgtcaccca ggctggagtg caatggtgcg atctcagctc actgcaacct   34560
ccgcctccca ggttcaagtg attctcctgc ctcagcctcc tgagtagctg ggattacagg   34620
cacttgccac cacacccggc caattttgta tttttagcag agacagggtt tcaccatgtt   34680
ggtcaggctg gtctcgaatt cttgacctca ggtgatccac ctgcctcggc ctcccaaagt   34740
gttgggatta caggcatgag ccaccacgtc cggccgactt ttattttttt ttcttgagac   34800
agggtcttgc tctgtcaccc aagctggagt gcggtggcat gatcatagcg cactgcagcc   34860
tcgacctcct ggactcaagt gatcctcctg cctcggcctt gtgtatagct gggattacag   34920
gcagttgcca ccatgccagg ctaattttta attgttttgt gaagatgggg atttcactgt   34980
gttgcccaga ctggtcttga actcctggcc tcaagtgatc ttcctgcctt ggccttccaa   35040
agtgttggga ttacaggcat aagccactat gcatggcctg taacttcttt aaatggctat   35100
aattaaacag ttggtccttt taagattggg caatggacga atggcaaatt gcattttaa    35160
aagaggaggg atttaaaaaa aaacaggaaa gattggggca tttgtctcta aaggactgtg   35220
gactcattta agaagtttag tggtcattct taccatcttt gtggtttttc ctgcctgcat   35280
gggatgcaga ttttctgtct caggtgggat tgatcaatcc cttggaggaa tgtgtctact   35340
ttttaattgt gtttaggaga gctgactgta tacagtagtt ttgtgaaaga acaacatgaa   35400
cccatagtag agctaaattc ttttttattt tttaaaaact ttaggtggtt tcatggacat   35460
ctctctggga aagaagcaga gaaattatta actgaaaaag gaaaacatgg tagttttctt   35520
gtacgagaga gccagagcca ccctggagat tttgttcttt ctgtgcgcac tggtgatgac   35580
aaaggggaga gcaatgacgg caagtctaaa gtgacccatg ttatgattcg ctgtcaggta   35640
aatctccagt tgaaaaatgg gtctggcaag atgttaacctt tgggtgattt ttctgctgac   35700
agaagacaga caccattaca ttcaaagtca gattgtcttt tatttattta tttatttatt   35760
tatttatttg agacagggtc ttgctctatc acctacagat ggggtttcac cacgttgggt   35820
ctggtgaccc aaatctttgg gtgatttttc tgctggaaga ggacaaacac cattacattc   35880
aaagtcagat tttctgtttt ttttttttt ttgtttttgt tttttaata ttcatttgtt    35940
tattcatttg agactgggtc ttgctctgtc acgcaggctg gagtgcaacc tccctgggct   36000
cagttgatct tccctcagcc tcttgagtag ctgggactac aggtgtgtgc caccatgccc   36060
agctagtgtt tgtatttttt gtggagatgg tgttttgccg cattgcccag tgtggtcttg   36120
aactagtgct caagaggcct gcctccttca acctctcaaa gtgttaggat tacagatgtg   36180
aactactgtg cctgatccaa agtcagattt tctttgctta cttagtcaag ttcgtctatg   36240
cttttattat acttaatata ttagtatagt tactgtatta gtatattagc atatttaata   36300
tattattata cttatcatac ttgagtatat tgagtatatt tacactttta gtatatttgt   36360
atacacacac cacattttta ttatttatct tttttttgag acagagtctc cctctgtctc   36420
ccaggctgaa gcacagttgg ctcactgcaa cctctgcctc ttgggctcaa gtgattctcg   36480
tgcctcaccc tcctgagtag cagggattac aggtgtccac caccaagcct ggctaatttt   36540
tgtatttta gtggatatgg ggttttacca tgttggccag gctggtctcg aactcctgac   36600
ctcaaatgat ctgcccgcct tggcctccca aagtgctgga attactggcg tgagccactg   36660
cacccagcct attatctgtc ttttgatgga catttaagtt gtctctatat actagctatt   36720
gtgaataatg ctgcagtgaa catgagagtg cttgaaaaca ctaatgtaac ataaaggtaa   36780
```

```
caaataataa atgtcatgtg tttatcttga aaggaactga aatacgacgt tggtggagga    36840
gaacggtttg attctttgac agatcttgtg gaacattata agaagaatcc tatggtggaa    36900
acattgggta cagtactaca actcaagcag gtgagcagat tggaaagctc aagctttctc    36960
cttaaaaact taaacaaat cctaatagag aattttgcaa acatacagag gtagacagaa    37020
tagtatcatc agcctccatg tacccattgc agcttcaact atcaaatctt tttttttttt    37080
ttttttttg agacagtctt actctgtcac ccagtctgga gtacagtgtt gcaatcttgg    37140
ctcactacaa cctctgcttc ctgggttcaa gcgattctcc tgcctcagcc tcctgagtag    37200
ctgggactac aggtgcccac caccatgccc ggctagtttt tgtgttttta atagagatgg    37260
ggtttcacca tgttggcctg gctggtcttg aattcccgac ctcaggtttt ctgcccgcct    37320
tggcctcccg aagttttggg attacaggcg tgagctacca cgcccggccc taaatctttt    37380
cttattatga ttccactcac tgactgccgc tatagtactt ggaaacatat tccagattta    37440
tattattccc atatttatct gtaaaaggca ttacagaggt tctttttttt tttttttttt    37500
tttgagatgg agttttgctc tgtcgcccag gctggagtgc agtggcgtgt tcttggctca    37560
ctgcaacctc tgcgtcccgg gttcaagagc ttctcctgcc tcagcctcct gagtagctgg    37620
gattataggt ggtgccacta cacccagcta attttttgtat ttttagtaga gatggggttt    37680
caccatgtta gccaggctgg tcttgaactc ctgacctcaa gtgatctgcc tgcctcagcc    37740
tctcaaagtg ctgggattat aggcatgagc cactgcatct ggcctaaggc tgtacagagt    37800
tttaaagcaa gttttcatta tagatccact tctggttacc tttaggtaac ctcacttatt    37860
cactttggca ttgttgctat ttcaaatttc acctttatga tagtgaaaaa tgatataatc    37920
tctctaaata atgtggtcta ttcataaaga aaaataggct tgaatttata tcagcagagt    37980
aaagtgtatg tgaagactga agaaagatac attttctggc tgaacagaaa acacggtgaa    38040
acgatttgaa aacttttatt gtgaattaca gggtcctatg aaccctctgt ccgtgccttt    38100
atgaatatca acatagacat gttttttttt tttttttgc attaacaccg ttttctgtaa    38160
tattttcttt attttacatc aactgctgta ctcgatcagc cccttaacac gactcgtata    38220
aatgctgctg aaatagaaag cagagttcga gaactaagca aattagctga gaccacagat    38280
aaagtcaaac aaggcttttg ggaagaattt gaggtaagtt attaaaaaac tgtttttacg    38340
tgagttgtta tatcctatt ttagtggagg agaagttgct cttgtgtttg gaattggacc    38400
tgagagactt gaaactgacg tccttttta attcggccat tgattgacac ggagcaagtt    38460
gctgagaggg cttcttcgaa acagaagagc attgtgttct gagggaaggg agttggcagt    38520
gagtagtcaa tggatgtgct agccgctcca tttggctctt ttggtttgga ctggtggcaa    38580
aatctcagaa aaacaaaagg atctaatttc ttcgaaagat ttccagcatg cactgggtc     38640
tttagaaaca atctatagcc ttagtgcagc aaatgagtat gagtaaaaga gaaacacctt    38700
gtggtggctt ttttttttt ttttttgaga cagggtctcg ctctgtcgcc gaagctggag    38760
tgtagtggcg tgatctcggt ttactgcagc cccgtcctcc ctgggctcaa gtgatcttcc    38820
catctcagcc tactgagtag ctgggactac aggcacatgc cctatgcct ggctaatttt    38880
tgtattttg gtagagatga ggttttgcag tgttgcccag gctggtcttg aactcttggg    38940
ctcaagtgat cctcctactt aagcttcccg agtagctggg actacaggca cacgatacca    39000
tgcccatcta atttttgtat ttttttgtag agatgggggtt ttgcagtgtt gcccaggctg    39060
gtcttgaact cttgggctca agtgatcctc cagcttgac gtgccaaatg tggtggcttt    39120
aatttcagag ttcaaattga taactctggt aagttaagtg aactgatttc tttttttttt    39180
```

```
aaattatttt tgttgattat actttaagtt ctgggatata tgtgcagaac gtgcaggttt    39240
gtacataggt atacatgtgc catcatggtt tgctgcacac attaacccat catttaggtt    39300
ttaagtcctg catgcattag gtgtttgtcc taatgctctc cctcccttt aatgcatcag     39360 tgaaaaagtg atgataggct gggcgtggtg gctcactcct gtaatctcag cactttgaga    39420
gggtgaggca ggtggaccac ttgaatccag gagtttgccc ccatcccag acagtgtgtg     39480 tgatgttccc ctccctgtgt ccatgtgttc tcattgtttg gttttctgtt cctgtgttag    39540
tttgctgaga atgatggttt ccagcttcat ccatgaccct gcaaaggaca tgaactcatt    39600 cttttttat ggctgcatag tattccatgg tgtgtatgtg ccacatttc tttatccggt      39660 ctatcattga tgggcatttg ggttggttcc aagtctttgc tattgtaaat agtgctgcaa    39720
taaacatatg tgtgcatatg tctttatagt agaatgtttt ataatccttt gggtatatac    39780
ccagtaatgg gattgctggg tcaaatggta tttctggttc tagatccttg aggagtcacc    39840
acactgtctt ccacaatggt tcaactaatt tacactccca ccaacagtgt aaaagcattc    39900
ctatttctcc acatcttctc cagcatctgt tgtttcctga ctttaagtga actgatctct    39960
ttcctgaaac taacttgggt tggagaatgt ccctgatggg aatgtgctgt gttcccattg    40020
cactcttcta tatcacttac ccattgacaa tgtgatctct ttcattttct cctcatccat    40080
ttgacagaaa acttcaaaaa caaggattct ggcatattta cctttgcagt tgtccccagc    40140
atgtagcacg gtgcctagta cacagaagaa actccataaa tgtttgttga atgagattta    40200
catttaactc atgtttacat cattttattt tcctgttctg ttttatggga atgattattc    40260
tatgcttttt gaggactaca atttataaat atttgtggat tgaatgaata agtgaatact    40320
gggcaaataa agtcctttta gccagagtat gtctgaacaa cttgctgaga tagatatgat    40380
ttcccatttt ccagctgagg ggcctaaggg aggttaagta aattattcaa tcttcatacc    40440 acagttttg ttttgttttg ttttgttttt tttcctcctg agacagagtc tcactttgct     40500
gccatactgg agtacagtgg tgcaatcata gctcactgca gcgtccaact tctgggctca    40560
cgccatcctc ccacctcagc ctcctgagta gctggtacta caggtgtgca ccaccatagc    40620
cggctaattt ttcattttt gtagatatgg ggtctcactg tgttactcag gttggtcttg      40680
aacttctgag ctcaaacaat tctcctgtct tggcctctca agtgttggg attacaggtg      40740 tgagccactg tgcccggccc ataccacaga tattgattga attccagcag tggggaggag    40800
tgtggaatag aacattctca gtccttgctc aacattactg aacagagact tgaatttgag    40860
tttattctct catcccaggc ttcgcgttag gctctgaaga cactagtgaa caagacagac    40920
agggttactg cctttaaagg gagcttttag ttgagagaag gaaaacagtg atgaaaagca    40980
tcagtgaaaa agtgatgata ggctggggcg tagtggctac tcctgtaatc tcagcacttt    41040
tagagggtga ggcaggcagc tcacttgatt ccaggagttt gagaccaggc tgggcaacat    41100
ggtaaaaccc cgtctctaca aaaatacaaa aaagtagctg ggtgtggggg tgcgcaccca    41160
cagtcccagc tactctgggg gttgaggtgg gaggattgct cgagcctggg agattgaggc    41220
tgcagtgagc tgagatcacg tcactgctct ccagcctgag caacagagcc agaacctgtc    41280
ccaaaaaaaa aaaaaattga tgataaacat agtgagacag aatttgaaa tctcagcctc      41340 actgttgcct tccttgtccc ctgcctgcct aaataataaa aggcagcatt tcagcagtca    41400
ttcatttcat tactttcact tcatttcacc ttcataaagc ctcatgaggt aagatgggaa    41460
gatacagaag tttagaaac cgctcatcaa aattgaatgg aaagccgatt gttccaaaac      41520
```

```
tttttagtgt ggaaaatttc tattatatgc aaaagtagag agaatgggat agttatagca    41580
gtatacctga cacccagcat taacaactgt tgataaatatg gccaatctttt ttcgactctg   41640
```



```
tttttagtgt ggaaaatttc tattatatgc aaaagtagag agaatgggat agttatagca    41580
gtatacctga cacccagcat taacaactgt tgataaatatg gccaatcttt ttcgactctg    41640
ccccactcac ttccccagcc ctgacttgtc ttgaagcaaa tacttttttt ttttttttga    41700
gatagagttt tgttttgttt tgttttttgt ttttgagatg gagtctcact ctgtccccca    41760
agctggagtg ctgtggcttg atcttggctc actacaacct ccgcctcctg ggttcaagtg    41820
attcttgtgc ctcagcctcc tgagtaactg ggattacagg tgtgtaccac catgcccagc    41880 taattttttgt atttttagta gggacagggt tttcactatg ttggccacgc tggtctcaaa    41940
ctcctgacct caggtgatcc gcctgacttg gcctccgaaa gtgctgggat tgtaggtgtg    42000
agccactgct cccggccttg aagcaaatct taacacatca tttcgtctgt aactatttta    42060
tttcaaaaaa ttataacctg aatagcatta tcatatctaa aactattaac agtatttcct    42120
taatattaac acatatcagt cacattttcc tgattgctac acacacacac acacacacac    42180
acacacacac acttgcaatt tgtgtttttt tcttttagaa tggatctcac tctgttgccc    42240
aggctggagt gcaatggtgc attctcagct cactgcaacc tccacctcct gggctcaact    42300
gattctcttg cctcagcctc ctgagtagct gggactacag gtgcccacca cctcacctgg    42360 ctagttttttg tattttttagt agaggtgggg tttcaccatg ttggccaggt tggtctcaaa    42420
cttccgacct caggtgatcc acccaccttg gcctcccaaa gtgctgggat tacaggcatg    42480
agccactgtg cccagcagca atttgtttga attgggagtg cttcttcca ccttgattat    42540 gaaaaaattt caaatgtgta taaaacagat tcatataaag gatcctgata tgccattatc    42600
agctttatca attatccctg tcatcatatt ttttattttat aaatatttca atatttgtgg    42660
aatccttaaa aatgcatcac ataacccaac attgttcata ttataccaat tgtcttataa    42720
tttaaaaata ttttgttcaa tcatttttca gataagcttc acacactgtg gttggctaag    42780
tctcataata tttctgttgt aaaaatctta agtctgggcg tggtggcaca cggctgtcat    42840
tccagcactt tgggaggctg aggtgggcgg atcacgaggt caagagatcg agaccatcct    42900
ggccaacatg gtgaaacccg gtctctacta aaaatacaaa aattagctgg gcgtggtagt    42960
gcgtgcctgt agtcccagct actcgggagg ctgaggcagg agaatcgctt gaacccagaa    43020
ggtggcagtt gcagtgagcc gagatcgcgc cactgcactc cagcctagag acagagtgcg    43080
gcttcatctc aaaacgaaac aaaacaaaac aatcttaagt ctcttagaat actttgatgc    43140
cccttccatc tctctttttc tgtcttcctt cccctctcc ctgtcttttc tgctgttgaa    43200
gaaagcagat catttgtcct gagagttact tatagtctga attttgctga gtgcctctct    43260
gtggtggact taagcatgta tccatccctt atatttcttg taagttgata tatctagaga    43320
cttcattgga tacaagtttt ctttggcaag atagcatgta tggtggtgta tcaggaggtg    43380
tttatgtcct gttgtttctt ctctgatttt cttagcagct cctgatcatt attacttaga    43440
tccattaatt cataagggac tatatggtag tgatattgta attttatcat tcttcttcat    43500
ttgttaggtt ggcatatttc tataaaaagc ttttcatcgc cgagggttga ttttttcctt    43560
cttactaagc agttttcttt tcttttttctt tttttttttt ttgaggtagg tctcactgtg    43620
ttgctcaggc tggtgtgcag tggcgcaaac acacagttgc gaactcttgg gctgaggtga    43680
tcctcctgcc tcagtttcct gtgtagttgg gaccacaggt gcatgccacc atgcctggct    43740
aattttttga ttcttttgta gagatgaggt ctcactttat ttcccaggct ggtcttgaat    43800
gtctgggctc aagcaatctt tctacctcag cctcctgagt agctgggact acaggcacat    43860
accaccatgc ccagctaatt ttttaatttt tatttttagt agagatgtgg tcgtattatg    43920
```

-continued

```
ttgctcagga tggtctcgaa ctgcagagct caagtgatcc tcctgcctca gcctcccagt    43980
gtgctgggat tataggtgta ctacaggcaa gagccaatga gcctggtcag atttttttt     44040 cctgatttga atctgttat gggttcaatt gatacttcca aatcaaactc agggtttcag     44100 gattttact aacctcattg atcttaccca tgtatctcct ttctctaatg ccaaaaatcc     44160
tacttcttga agccataata agattattca tttgttttat cccacattac acacaacaat    44220
cttagaataa tgacttccca ataatatgat tactgaaaac agtttaattt ttttgcgct     44280 tttcaaaaaa atccttcaga gatgtgtagt caagttactg tattctgctg ggcacagtgg    44340
ctcacgccta taatcccagt actttgggag gacaagaagg gaggatcgct ggacctcagg    44400
agtttgagac cagccggggc aatatagtga gaccctgtct ctacaaaaga aaattaaaaa    44460
ttaaccagac atggtggcat gtccctatag tcccagctat tgagaggctg tggcgagagt    44520
aggcttaagc ccaggagttt gaagctgcag tgagatacga ttgtgacact gtactctagg    44580
gtgacagagc agggaccctg ttttaaaaa aaaaaaatga aaaaacttcc tgtgccttag     44640
actcatttgt aatcgtcctt ctctctgtgt ggctatatgc taactgggta tatggttagt    44700
ttatttgttt catttaaaaa atctctttct gttaagtttt atttataatt acacaaatac    44760
tggctttgat agtcaaattg aaaaaacaaa gtgtattcaa agaagtctac cttctatcct    44820
tgtcctttcc tatgttttag ccatagtata aaaagttatg gttatcatt atatttcaaa     44880 aatataagaa gatattccca tatcccactt tttcttaaac agtagcataa ctttacatac    44940
ttttttctaa ccttgctttt ttaaatatcc tggacatcct ggatatccat aatagtgtct    45000
agagatagtc ttcattcttt ttttactgta tagtaatcca ctgtgtactt gtaccatagt    45060
ttattcaacc tattgatggg catttgggta gtttccaaat gtatcacaga gaggattaca    45120
gtgaatagcc ttgtgtatgc atcctgcttt acttttgctg actactggta atattaacat    45180 ttttatgtt ctgtatttaa aaaatggtgg ttattattca tctataactt ttattataca    45240
tgactttggt tagcatgctt taacctttta gcataacatt tgcaagctac ttgttttaat    45300
taaaattttg gttaaatgta aaaaatagtg agctattttg taatctagat tcaatagaat    45360
cttatacttc ctttacaaat gatagctgag ttgatcattt gtgtaaatga ctgtgaactt    45420
aaaaattaca gcatttttta aaataaattt ttttaacatt ttaaaattat ttaaataat    45480 agacacacaa agtaaaaaga gaagaaaaaa aaaagagaca gggtcttgct atgttgccca    45540
ggctggtctc aaactcccag gctcaaatga tcctcctgcc ttggcctcct aaagtgtaag    45600
ccaccacact tggcaaaaat tagtttcttt aaaacaaaaa cattacaggt tatctggtac    45660
catggtagct tctttaacac taggttcact tagaacaaag cttaggaaca agtcagact    45720 ttcacaaaga gcttgtgtgg caatgggta ttttttgcaa attccattgg tggggtcaag    45780
atgtgagttt agaaggaact cttagcctga ctcttctggc catggaaaaa gatggttgct    45840
tctaaatgct gacctggtga ttttacactg tcacatctca aattgtggtc atcttttata    45900
cattattaac aacaaaggg aaaaattgag ttgactttaa gaggaagtgg aaaataacga    45960
gatcacatct gtactctaca ggctctccac agaggtcaga ctgaggtggt aaaattgttg    46020
tgcactaaat tagggcatta acgtttcatg gaaactgaag ctatatctaa atagctgatg    46080
gcctgctttc tagatctcct atatacctgc ttctcaaatt cagtctgttt taaaaaattg    46140 cccttttgagg ttgaaccag cgaaataagg ctgaaaacag aataagccat tattgaaaaa    46200
attaggaact tggaagcaga tactcataat ctaaatcctc tgaagctaaa gtttgatcca    46260
```

```
caatagcaaa gcattatcat tttagtgatt gtaccttagt tgtttcctgg caggtgataa    46320
atttgggatc actttcttct tacagtgtgc tctgatagtc tttaaaacaa accagagctc    46380
taaattgtaa tgccattggt aatttaactc tgatttgtct ctatgcctgt ctcctggtgt    46440
tctgtaaaat tctacacgtc atttcaggta tcactatcca gaagacgtta cttttgcctt    46500
tgatgcactt taaaatgtga agtctcttgt gaagctcttt ggttattttc tcctttgctg    46560
ctgaaataaa ttcaggttga tgattttctt gtaggatatg ttgtgtgatc tagacattgc    46620
aaacccaagt ctttgatttt ttttttccta cagattgcct gtttcttttt tattttaatt    46680
tttattagtt attattattt ttgagatgga gtctcactct gtcacccagg ctggagtgca    46740
gaggtgtgat agctcactgc aacctccacc tcccgggttc ttgtgcctca gccacccagg    46800
tagctgggat tacaggcacg taccaccact ctcagctaat tttttttgtat ttttagtagg    46860 gatgggattt ctccatgttg gccaggctga tctcaaactc ctgaccttaa gtgatcttcc    46920
tgccttggtc tctgaaagtg ttgggattac aggtgtgagc cactgtgcct ggccagttat    46980 taatttttt aaagagatgg ggtctcacta tcttgcccag gctggagtgc agtggctctt    47040
tacaggcact gttgtagtgc actgcagcct tgaactcctg ggctcaagtg atcctcctga    47100
gaggctggaa ttacaggcac acaccactgt gtccaacaga ttgcccattt gtgatctgtg    47160
taaatatctc tcacttcctg cagtatctct gctcaagaat gtaaagagat ggataatatt    47220
tttagatttg ttgaaacaaa gtaaagttct gctcaaatga gaatgacact aactaaatga    47280
aaaggccggt tataattctg taattttgtg cctgcaatgt gtgtgttatt gtacacttga    47340
atcggccctg tgcattgtgg cgaggtgcat attgcatggt tgtattgaaa aggtgcttgg    47400
gccgggcgtg gtggctcaca cctgtaatcc cagcaatttg ggaggctgag gcagctggat    47460
tacctgaggt taggagttca agaccagcct ggccaacatg gtgaaaccct gtttctagta    47520
aaaaatacaa aaaattagct gggtgtggtg gtgggtgcct gtaataccag ctactaggga    47580
ggctaaggca gggagaattg cttaaacctg ggaggcagag gttgcagtga gctgagattg    47640
tgccactgca ctccagcctg agtgtatcac aaaaaaaaaa aaaaaaggtt tttgccctct    47700
ctctgtgcct gctgctccct gttgagtcct ataggcctga gctgccaggg ggtactgtgg    47760
gctgagactg gacattgcaa ccgactgcaa ggcaccgtgg gacccaggtt gtggatggac    47820
tgtctctcgg gctttcttct ttccattcat cttcctcctc taactcccct ctgtatccag    47880
tatccttgct ctccatacac ctgcttcatt cttttttcctt cagtagattt ttctgcttct    47940
tgacttacaa acccctactt ctagcccctt cagatattga aactagcaac tttcaggctt    48000
tgtaccaaag tctcagagat tctcattgac tcggatgcca tccatctcta gtccaaagaa    48060
caatgtcaag gacatgaaca tgtggaacaa aagtgtctgc tgtggacacc tttggggaga    48120
aatagttttc agtgatgagg gttgtagtga gttgggcaga tatcccaaaa atatctgcca    48180
aaaactatag acacttctgg ttgcagtgac ttattccttc cttcattcag caaatactga    48240
ttgaacaccg actgtatgtc tggatctatt ctaggttttg ggggtggagc agtgaacaaa    48300
tcagtcttta tctttataga gtgtacagtc aagtgggaga acaggcagt aaacaaagaa     48360 acagttcaat attcaatctg tgagatggtg ataagtgcta cagagaaaac aaactagtgt    48420
aagataaaaa gggtgttttg ataggccttt actatttagg tctctttgat aaggtggcat    48480
ttgaacaaag ctctgaagga aataatggag ccaaccatgc atataacctc agggagaaca    48540
ttctaggtag agggaacagc aagtgcaaag gccctgaagt gggggtttgt ttaccttgtt    48600
gcacaatctg cacacaggcc agtacaattg gaatggatgg gaaatgtaaa agagagaagt    48660
```

```
tgaaaaggcc aggtgcagtg gctcatgcct acaatcccag cattttggga ggctgaagtg   48720
ggaggaattt gagatcagcc tgggcaacag aaccagacct cgggctaatt tttgtatttt   48780
tagtagagac agggtttcac catattggcc aggctgatct caaactcctg acctcaggtg   48840
atcctcctgc ctcagcctcc caaagtgcta ggattacagg tgtgagccat ggcccccagc   48900
cgtatctttg tcttaaaaag taatctctgt gcttggtagg ccaagaattt aaaatataaa   48960
aaatttaaga aagaaaaaaa ataagtaaag taactataca ggttggtctg gccgtaatgg   49020
tgagtgtcat tattttttctt ccctaggtat tttggctctg ttgctcagag cagtgcaggc   49080
gaaatggtca ttagggcatc gtcatggtgc ctggggatgc ctggctcagc cagtttattt   49140
tctgtctgcc tctctccttg gtccttttcc tccactttca ttcatgaaat tctagtcaag   49200
agctgggtcc agtggttttc aatccaaggg ctttggaagc ctctggggtc tattttggtc   49260
attgcagtca ctggctgct gctcctggca tttaggttgg caggggtctg ggctgggaag   49320
caggaatgtt cagtggccat aaatgtaagg gttggtctta catttacata agggagacaa   49380
tgaaaactta actcctccac agtagtggag tagtgccgtt gggtactcac agtcagtagt   49440
gccgttgggt actcacatgt acaacatgga tcaggacatt gactttctgt ggatacccttt   49500 taatagttta ttagatgtgt taggctgttt tgcactgctc taaaggaata tctgagtcta   49560
ggtaatttat aaagacaaga ggtttaattg gctcatggtt ctgaaggctg tacaagcatg   49620
gctccagcat ctgcttctgg tgagggcctc aggaagcttc cggtcatagt ggaaggcaaa   49680
aggagggcag acgatcacat ggccggagtg gtggcaaggg tggggtggga gccacgctct   49740 tttttttaatt ttattttaat ttgagacagt gtctcactct tttgcccagc ctggagtgca   49800
gtggcgtgat ctcagctcac tgcagcctct gcctcccagg ttcaagcaat tctcctgcct   49860
cagcctcctg agtagttggg actacaggcg cgcatcacaa tgcccagctg attttttgtat   49920 ttttagcaga gacagggttt caccatgttg gccaggctgg tctcggactc ctgatctcaa   49980
gtaatccgcc tgcctcggcc tcccaaagtg ctgggattac aggcatgagc cactgcgcac   50040
ggccaccaca ctgttttaaa caaccagatt gcacgtgaac ttagagtgag aactcactgt   50100
gaggatggca ccaaaacatt catgaaggat ccaccaccct cctttaggcc ccacctccaa   50160
cactggaggt catatttcaa cttgagattt ggagggggaca gacatccaaa ccgtatcatt   50220
aaatttaata gttttatgca gttttttttgg ctctagatct gtttagactc ctgcagtcag   50280
gtgtctgtaa ctagcctctg gtccttttttg agagttcaca gtttggtgca aaccctttgg   50340
atgtattatt tgggaaaatg ggatatctgg cagcctgtgt ccctgcttta cattatcctt   50400
tttgctgcct gccccaagcc tcctcattag catccctgcc aaggccagtg agaaggatg   50460 gagatgcggt gacattcagc ttgacaggtc attagcagct tttgtgccct agggactgct   50520
ggtgggaggg aggttgtgga agataaaccc tgacaggaat gtattctcct cgagggcagg   50580
gtttatttga tattttttctg gagcttagaa ccataagcct ggtgctgggg aggaagcgcc   50640
cttagcattt ggtagcctct gtgggcagag catggaaagt cacaacttct gaattgtttg   50700
tattttcagt ctcactctag atggatggca tcttctgcta tgggaaatga aatatgttta   50760
ggcaacttga gtcccaggtg cagatgaggc tgggctaattt ggtgcactag ggaaggagcc   50820
gggggagaga tgtgctgtta gctattatca atctgtgaca actgtcagct gctggcagtt   50880
agcacccacc tgagcctggg atgcaggggt gcctctcctg tcctctgtgg aagcctctgg   50940
acccagcagc catcttgact gtgcactgtt caagccccaa gtccgcctgg aagaggtgat   51000
```

```
tgagaactta ctgcaggata aggaaagcgc aggacaggtg cagtggctca cgcctgtaat   51060
ctcagtgctt tgggaggctg aggccggagg agggctggag tccttgagtg cgagaccagc   51120
ctgggcaaca tagtgagacc ctgtctttac aaaaaggaaa agaattagcc agatgtggtg   51180
gtgcgtgcct gtagtcccag ccactcaaga ggctgaggtg cgaggatcac ttgagcccag   51240
gagtttgagg ttacagtgag ctatgatcat accactgcat tccagcctgg gtgagagagc   51300
atgactctgt cccaacaaca aaaaaaaaga ttaaggaaag cctctggcag acctgatgat   51360
gggtggccca gccaaaatga gtattgatga ggatttccct ggtctggaac tctgaattta   51420
gtctggcaaa gtattccctt tgtgttgtga gatgattctt ggtgttaccc catcacggta   51480
ggtaagatga attagcaaat gagaaaggct ttctcttttt catccttatc tagtccgtag   51540
atgaagcctg aagaaggtct ccatatggta gtagtaagtg tttaacatct acctctaaca   51600
cttgcctgtg tcttttttttt tttgcaaagc ctcaggaatg ccccagtatc taggtagaat   51660
ttgataatat ttcatttttg ttatattccc ttttctgttt accttctata tacagcaaaa   51720
tgaaaaaatt tttaaaattt gtgcaagtaa gggcaatttc tttttctttt tctttttttt   51780
ttgagacagg gtcttgctct ggcacccagg ctggagtgca gtgacacaat ctcggctcac   51840
tgcaacctct gcttcctggg tttaagcgat tctcctgcct caggcttcca gtagctggg   51900
attacaggtg cctgccacca ctcccagcta attttcatat ttttagtaga gaccaggttt   51960
tgccatgttg actgggctgg tcttgaactc ctgacctcag gtgatccatc cccttggcc   52020
tcccaaagtg ctgggattat aggcttgagc cactgggcct ggctgaggca gtttctttt   52080
gaaatatatt ttgtgaagga gaaaagagg agttcagttt aaagaaacaa atgacataag   52140
aggtggtatg cagagatgcc aaagcatctt gaaggtgctt ttttttttgg aaacagagtc   52200
ttgcttcatt gcccagtctg gtctgcagtg gtgcaatcat ggttccctgc agccttgacc   52260
ttctgggctc aagtaatcct cccacctcag cctctcaagt agctgggact acagatgcat   52320
gccactatgt ctggctaatc tttaaatttt ttgtagaagc cagctctcac catattgccc   52380
aggctggtct tgacctcctg tcctcgagca aaaataccga ttttgattaa gtctggggta   52440
ggacctgggg ctgggattct aaccagctcc caggtggtgc taatgctgct ggtctacaga   52500
ccacacgtgg agtagccagt gtagagttca tgtagcaata gtgatgtcat agaaatagcc   52560
agtatctgta tacttgcttt gttgtatgtc acgcactgta tagtgatgta catgcatctc   52620
atttgaccct caccccgccc cttgtggggt agaaaggatt gtgctcattt cacactcaag   52680
gaaactgagg cacagacagg caaagtagct tggcgaaaca gaaggaact tagaggcagg   52740
ccctgattag ctcagagact agaaggcctt gtgcgtcatc ctgaacagct tggacttgat   52800
cttgaaggtg gagggagaaa ttgaagggta attaaacagg aactgtagga aattcacctt   52860
gcatagtgat tgctttggcc acgtgtgccc tgccaccgcc cccccacctc agtgaagtgt   52920
catgcgaagt tgggttcgta aatgaaggcc cgaatgcttt cctgacaagt ttgttttaaa   52980
tcaagctgct aattagtccc agtcccctc ccccggtatg tattttttg ttgatgtcgt    53040
ttcacttcat ttagttgaag tgattgattc agttcagtgt ttgaacttct ttttgaacct   53100
caccttaata acctgtctaa acatcaaggt taaaccttct tgctaacaca gcagtattgc   53160
ttggtaagac tggctcacag tccaaggaaa tgcttgccca gagagggcaa actgccttaa   53220
ctccttaacc tgagctcatt aaaaaaaatt caaatgactg attccttgtc acagttctac   53280
ctacattgtt tttatttttg tccaggtttc agctagttaa atgcttttgt gatgagctta   53340
tgtccaggct gaaggttgca ttttgaaact gagcgtcaaa taccaattta aagtccagac   53400
```

```
ctttacactt gtgaaattca gataaatgaa atggaaataa aacagggctg ctgtgttgtg   53460
aaatatgact gtgtttttcc ttgtaggact ctttgagggt agccattttg gcattttata   53520
tataaatttt cttttcttag cctacctttt actttcttga tttgcctatt tgtgatttcc   53580
cattaaacac taggcttttt gtaaaccaat tatcccttga aattgacttt tttttttttt   53640
gagacaggat cttgttttgc cacacaggct ggagtgccgt ggctccatca tatgataaac   53700
agaaagagag agagagagag agagagagag agagagagag accctgtctt atttaaaaca   53760
aaaaagaag aagaaaaaaa gaatatagat cacagctgtt atttgtatat gctacgccaa    53820
tccttgttgg gtttcattct ttataattgt tattttttaaa gattttttctt atgaatattc  53880
tattgtttca ttgtagaaaa tttaagggag aacacagtgg gaaaaaaaaa acaagaaaag   53940
gacttcataa tcctgctacc ctgggagaaa aaaaaaatca ccattaccta tttggttctt   54000
ctcccacttt ttttttttttc gagatggagt ctcccttttgt tacccaggct ggagggcagg  54060
gacgtgatct tggctctctg caacctctgc ctcctgggtt caagcgattc tcgtgcctca   54120
gcctcccgag tatctgggat tacaggggtg tgccatcaca cctggctaat ttttgtattt   54180
ttagtagaga cggggttttg tcatgttggc caggctggtt tgttggccat gtctggtttt   54240
ttgtcatatt ggccagtctg tttgtcatgt caggctgaca tgttttgtca tgttggccag   54300
gctggtcttt aactcctgac ttcaggtaat cctgaagtgc taggattata ggcgtgagcc   54360
attgcacctg gccttctgcc tttttttttaa agaaaaaaaa ttaaaacatt ttttctttt   54420
taagatagcg tctcattttg ttgcccaggc tggtcttgaa ctcctgggct caagtgatcc   54480
tccagcctca gcctctggag tagctgggac tacagatgca catcatggtg tccttatgcc   54540
atttctttttg tacgtaggtg aatgcaagtg tatgattaca tcatatgcta ttttggaggt   54600
ttgactttct tttcactttc atcatctttc caaggtgtta ttttcctagt acatcttttt   54660
aaatggacat agaacattct tttgtatgaa caaacaatag ttttatttag gcggtccttt   54720
cctgttggac atttatatta ttttcagcat ttctccacag ttgttgcagc attcagatga   54780
accttctttt tttttttttt tgagacggag tctcgctctt tcgcccaggc tggagtgcag   54840
tggcacaatc tctcctcaag tgattcctgt gtcaccctcc cacgtagctg ggattacagg   54900
tgcccatgtc tggctaattt ttgtgttttt ggtagagctg tggttttacc atgttggcca   54960
ggctggtttc gaactcctgc cctgaagtga tctgcccacc tcagcctccc aaagtgtggg   55020
gattacaggt gtaagccatc acgcctgacc cagatgaaca ttcttgtagc tatcgcacac   55080
aattctgaac atttcctagg atgaattcct taaagaagta atgctgatcc aggcttttt    55140
cttttttctgt gactctttga cacgtaataa tattgacttt tctttctttc cagacactac   55200
aacaacagga gtgcaaactt ctctacagcc gaaagagggg tcaaaggcaa gaaaacaaaa   55260
acaaaaatag atataaaaac atcctgccct gtaagtatca atattccgct cagtaatagt   55320
cactcttgga gattttgatt cctagcacct ctgtaccttt cctcagggtc gtgtgctctt   55380
gttagcacat cggaggcctt agcttcttta attgcaagca gtttccaaaa taatcaacca   55440
tggtgggtgt tgatgacttc attcactgag ctcccgtgat gctgattact gagtaaagtt   55500
gccactaggt ggctttgtct gtggttggtt ccttctgtta attaattttc tgtctgccca   55560
agatagatca tctcaaggct tgggatctct cagtgtcagg gaccttaggg tgccagattt   55620
gtgtcttgac tcctcctcac tgggcctgtg agtcctgggg aaggcctgcc tcctttctgg   55680
gactcagttc ccttaagtgg gaaacagaca aaacctcct gagggctcct agaactgttc     55740
```

```
tgcttgctga tccccctgagc tcaagttact ggagaaaggg tatataccta aactgctcag    55800
aagaagactt tgtgggccgg gcgcagtggc tcacacctgt aatcccagca ctttcggagg    55860
ccgaggcaag cggatcacct ctgatcagga gttcaagacc agcctggcca acatggtgaa    55920 acccatctc tactaaaaat acaaaaatta gccatatgtg gtggtgtgcg cctgtaatcc    55980
cagctactcg ggaggctgag gcgggaaatt ggttgaaccc aggagatgga ggttgcagtg    56040
agccgagatg tgccattgca ctccagcctg ggtgacaaga gcaaaactcc gtctcaaaaa    56100 aaaaaagga agactttgtg aatattcgca aagctgtaaa gctgtacctt tcaattttt    56160 tttgagacat agtctcactc tgttgctcag ggtgcagtca cagctcactg tagcctcaac    56220
ctcctgggct caagcgattc tcccacctca gcctcctgat tagctgggac aataggcagg    56280
caccagtaca cctggttgat tttacagttt ttctgtaggc cggcgcagtg gcttacgcct    56340
gtaatcccag caccctggga ggccgaggtg ggcggatcac ctgaggttag gagttcgaga    56400
gtagcctggc caacatggtg aaacccccatc tctattaaaa attacaaaaa ttagctgggc    56460
gtggtggtgg atgcctgtaa tcccagctac ttgggaggct gaggctgagg caggagaatc    56520
gcttgaacct gggaggcgga ggttgcaatg agccggaggt gctatgtgca ccactgcact    56580
ccaggctggg cgacagagtg agactctgtc tcaaaacaaa aaacgattta aaaataata    56640 aaatttttc tagggcgggg tctccctatg ttgcccaggc tggtcttgaa ctcctgggct    56700
caagtagtcc tcctgcctca gcctcccaaa ctgttgggat taccagtgca agccattgtg    56760
cctggctgta ccttctgtaa cacccaaatg ccacctggca aagcccaagt tgaatcatga    56820
ggaaaaaagg cctggaagga tgtagacctt ccttttttct acttatttat ttatttattt    56880
ttgagatagg gtcttactct gttgcccagg ctggagtgca gtggcatgat catgggtcac    56940
tgcagcctca acctcccggg ctcaagtggt ccttcccacc ccagcctgca atgtagctgg    57000
gactacaggc atgtgctacc atgcccagct aatttttgta ttttttgtaa ttatttttt    57060 tgtagagaca gggtttcgtc atgttgccta ggctggtctc gaattcctgg gctcaaacga    57120
tctgcctgca tcggcctccc aaagtgttgg gattacaggt gtgaaccact gtgtctggct    57180
atatcttctg taacacccaa atgccaccag gcaaagccca agttgaacca ggagggaaaa    57240
aggcctggca ggatgtaggc cttgcatgag gatctcagaa actgcactaa accagtcaca    57300
gttcctctct cccagaggtct aactctatgc tgaactcttt gcattttat ctcacttaat    57360 ccatatcaca tgcacaggaa ggaagcattc gtagtatcct ggtttcctag accatttag    57420 caaggttata agtgaagggg agtgggtggg agaactggca ctagagcccc caaagtcact    57480
gttcttagca ccactctaat gcatggggtt ctccattgat gtgctatgca aggcagtgca    57540
ctgaggagaa aggaaggaac atttacaact tctctttatt tatatcctgt ccctaaaaaa    57600
aaaagaaaaa gaaaaatttg tctgaggcct agattgattg cagggagtgc ataatgtttt    57660
attgattgat tgattgattg tatatagaga tgggggtct cactatattg cccaggctga    57720
tctcgaactc ctaggctcaa gcaatcctcc tgctttggct tcccaaagtg ctgggattac    57780
aggcatgagc gactgcacct ggctatgcat actatattta tccaacttac aaataaggct    57840
tgcttgcctg tagtgcatat gtgtatacat ttcagcatag aaaaactgtg tgattggggg    57900
ttgtgatcaa atttggagag cattgctctc atgtcttatc aggtcagagt cattttgtca    57960
aatcttgtaa accattcttt gtgtgtgtct atgcatgaaa catagtcttt ctctttctgc    58020
atgcatatgt acatatacat ggtatatatg tatatcatat ctacatggat attgtaatgt    58080
atatgtatga ggatgggga aagtggagac atttgtaata ctgagaaaag gcagtgagga    58140
```

```
atttgcagag aagcagtttg agctgtagca tggtactagt gaccttgagg aagccttatc   58200 ctttttttt ggaatttatt ttttcaattt ttagaaatag acaagagttt ctctatgttg    58260
cccaggctgg tcttgacctc ctgggcccaa actatcctcc tgccttggct tcccaaagtg   58320
ccaggattac aggtgtggac caccatgcct ggccaccttg tcctttctat gtctaagttg   58380
tgacatctgc tcagggtca  ggtggtatta aatggtataa aatgtatggg aaagtgaagg   58440
gatcaatggt atgcagtatc taaatagaat atcgcttttt cctcccttaa aggtctcatt   58500
cagatgtttc ctctgatgaa catctcattt ccttaaagat gaggagtctg aagcaaaaaa   58560
gacattattc ttttaagaca catggctgtc ttactaattc ccattgcaaa atatgttgtt   58620
taggtagagc actcagattt ttatacgaat aatagacttt tgtacagaat ttggacagtt   58680
gatactatca gagccttgtg atattccact gcattatgct tcactaaaaa atacctggct   58740
gggtgcggtg gctcacaact gtaatcccag cactttggga ggctgaggtg gcagatcac   58800 ctgaggtcag gagttcaaga tcagcctggc taacatggca aaaccccatc tctactaaaa   58860
atacaaaaat tagccagatg tggtggcacg ctcctgtaat cccagttact caggaggctg   58920
aggtatgaga attgcttgag cccaggaggc agaggttgca gagagccgag atagtgctat   58980
tgcactccaa cctgggtgac agaggaaaac cctgtctcaa aaataaatt  taaaacaaca   59040 acaacaacaa caacaaaaac ccctctttat tatgggaaatt ttcaaatata ttcaagagca  59100
taaagaaccc acatgtaccc atcacccagc ttcaacaatt atcaactcat gcccagtctt   59160
ggtttcatct atactctgat ccacatctcc tctctccttg aattattttg aagcccatct   59220
cagacatcat gtcatatatg tatacttcaa tcttctttt  ttttaaaact cccctcccc   59280 ttttctttt  tcttgagact gtgtctcact ctgtcatcca ggctggagtg atcttggctc   59340
actgcaatgt ccgcctctcg ggttcaagcg attttgtac  ctcagcctcc ctagtagcta   59400
ggattacaga tgtggaccaa catgcctggc taattttgt  attttaata  gagacagggt   59460 tttgtcatgt tggccaggct ggtcttgacc tcctgacctc atatgatcca cctgccttgg   59520
cctcccaaag tgctgaaatt ataggccact gcgcccagcc caaaatttct tggtttgaaa   59580
taattttgga actcataaga agttacacat atagtagaga gaattttctt gtaccttctc   59640
tgagcttcct atatacccaa tgataacatc ctatatacc  atagtatatg atcaaaacta   59700
ggaaattgtg aagatggcat tttgagacat caggcagtgt tcacgttact gttttgctta   59760
cctgggcttt aattttatg tgttttttt tcaatcattg aatgaacaaa acttggacta   59820
ggctggggag taactgattt gaactgtttt ttcctgaagc agtccaggac ttatgtgacc   59880
gtggtctctt tttcttctag ttgatcatac cagggttgtc ctacacgatg gtgatcccaa   59940
tgagcctgtt tcagattaca tcaatgcaaa tatcatcatg gtaagctttg cttttcacag   60000
tgttttctga ccatacattt ctagcctatt tttgtatttt aaatccttcc tcatgtcctg   60060
aaagtaactt taaggtgttt gaaggatttt cttcctaaat ttctagcctg aatttgaaac   60120
caagtgcaac aattcaaagc ccaaaaagag ttacattgcc acacaaggct gcctgcaaaa   60180
cacggtgaat gacttttggc ggatggtgtt ccaagaaaac tcccgagtga ttgtcatgac   60240
aacgaaagaa gtggagagag gaaaggtaaa tcacagaaac ttcttttctg ctaaactgtt   60300
tttaaagtat cagacatgtc agattggcca tgtttaggaa ttgaataaat gaattaagct   60360
tactgtaact gattctctgg aaaaaaggga ctaggagaaa tttgattatg ttattccttg   60420
gtgtagtttt ctttatgttt cttctgcttg ggatttgttg agcttcttgg ctccatggat   60480
```

```
ttgtagtttt ccttaaattt ggataatgtt cagtcttagt ttcttcagat acatatcctg    60540
ggctgggcat ggtggctcat gcctgtagtc ccagcactgt ggggtgttga ggtgggcgga    60600
tcacttgagg tcaggagttt gagaccagcc tgggcaatgt agtaagaccc catctcttaa    60660
aaaaaaaaaa tgtaccctgc acaaccttgt cctaggacag cagtcatacg tgtattagac    60720
tacttgaagt tgtctcatag cccactgata cttggtttat tttattcagt ttttttctccc    60780 cgtgtttcat ttcgaatagc ttcttttgct atgtctccaa gttaatcttc tgcaatatgt    60840
catccgctct taatcctatc cagagtattt ttcatcacag acattgtatt tttcatctct    60900
agaagtgtta atgtcatcta tagctttcct tttaacatgt gtagcatttt ccttacctttt    60960 tgaatgtatg gagtatttct gttgttgttt tttgttttgt agagacaggg tctcggtctg    61020
ttgcccaggc cggagtgcag tggcatgatc tcagctcact gcagcctctg cctcccggtt    61080
caaatgattc tcatgcctca gcctcccaag tagctgggac tacaggtgcg tgccaccacg    61140
cctggctaat ttttgtattt ttagtagaga tggggttttg ccatgttggc caggctggtt    61200
ttggaacccc tgagcttagg tgatccacct tccttgacct cccaaagtgt tgggattata    61260
ggtgtgagcc accatgcctg gccatgttgt ctgttttaat taactctgcc taactgtcct    61320
cccaaatggt tgctgcagtg ctcactccca ccagcagcac ctgcctagga ctcattactc    61380
catactcttc aagacacttc agattaaaaa aataaattgt aacaccccac acctacagaa    61440
gagcggacag atcttattga gtgacagccc tctgtgttat ctcaaagtga gcccaccatg    61500 gtggttttt tttaaatat ggaaaagttc tgtgttttg tttgtgttct agtgaaagtt    61560
cttttttaga tatcctttaa ttggtttata taagatttta tgtggaatgt agcagtcata    61620
cctataaatt aaacctaagg cagatggaga actttggagt tgagccttcc tactgtaatt    61680
ttcatattgg atgtgaaggg cagtgtgatt ttcataagac tttcattgtt gtactcctag    61740
ttggtatact tctgaatacc tttgaggcca gttctggtca tcgtgaaaca aggtttcct    61800 tcagcaaatg cctgtggtaa cattaggtgt tcttgaatta atggaccaat gaaaacatct    61860
ttgtagtttc tgcttcaggc aagggttttt tgccctaaat gtggatagga agaatgaagc    61920
ccttcatcct ccttttttgcc tgattatagc tataggaggt tcacctgttc tcagaagaca    61980
tgaggattgt gaagagaggg gtcttgtgtt gcttcagagg aatcagtatc agtccctttc    62040
agaagctctc ctggatagac aggcattagg gccaaatcac tctgccccac ccctcaccac    62100
catgtcctac tctctgctcc ctgtctcatt cttcctcttt actttggtgg tgccgagagg    62160
atgacatgat gggtattgat tctctccaca gacctttctg acatcctact ttcagtatcc    62220
ccccagtgca cagaagacaa gccagactgt ggactgtgtt tgattcctgg gctctatttt    62280
aaaagacagt gtattagttc tcacatttta gaatttgttt gccaaggttt ccacgggagt    62340
ttagaaacta gggggagggc tgatgtttaa agttagctaa aatgttcttt tcagggtcat    62400
gatttaattt tatattctct ggtgagttcc ctatagtgac tgggagcagt cctcagtctt    62460
gattggccag tgacagcata gagtacaatt aatattagga gtgctcattt ggggaaacta    62520
aaatttgcat caaatctgtc agaggtgttt ggatctacaa aataccggag ggaaagctga    62580
attgagaatc ataataaata aaagaccaca tcgttctttt ttttttttttt ttttgggact    62640 gtatcttgct ctgtcactca ggctgcagtg cagtggcact atcttggatc actgcaggct    62700
ccgcctcccg gattcaagcg attttcctgc ctcagtgcct gagtagctgg gattacaggc    62760
gtgtgccact acacctggct aattttttgta atttttagtag agacaggttt caccatgttg    62820
gccaggctgg tctcaaactc ctggcctcaa gtgatccacc cggcttccca aagtgctggg    62880
```

```
attacaggcg tgagccactg cgcccaacca agaccacatc cttttattga acgttcctcc    62940
taccatgttt tctttttct ttcaattaat cattgactca ttgactctca ctgttgatgt    63000
ctgtagctgc tctcttattt ccagttttat agctgtaaat ttctctgtct tcctaagata    63060
caaggtaaat ttctcttgct gatattggtg gttttggaaa gtgagtggtg tggatgactg    63120
cccagaaaac aacagaacac aaaagcattc tctgcccaga acacatcacc aaatagatac    63180
aaactcatct cttactgagt gaaatagctt ccttttggc agcaagaatg attttcttgg     63240
tgccatattt ttcaatccgc ctgctcttga agccagcagc tattgcagac ttggcattcc    63300
caggcaccca gttaagggaa agtgacgtgt agaggaggta tcagatgggg ctggatatag    63360
aaaaagcagc tggttcaaaa ccccatgggc tgcctttctg tgatagagtt attcacactt    63420
gggttagata aggcacagag tcctcctaca ctggtgcgga aatgaaacag acagtctggc    63480
tcgttgggca gcctagcctc ctccagaatc tgtgcttgcc ttccctatgg agtgactggt    63540
agatcttaga attcagacct cagtggttgc tagccagcac tctcacattg gttggtcctt    63600
ctctctgcat ctttgattct ttagagatag ataaaccaag caccgactct cctttgacat    63660
gtgcttggaa cagacacctg cacgagctgc ctttctcctc ccacttctgc ctggtcttcc    63720
aaacacctgc ttttcttgtt tgaactcttc cttttttttt gagacagaac ctctctctgt    63780
cacccaggct ggagtgcagt ggcatgatct cagctcactg caacctctgc ctcccaggtt    63840
caaataattc tcctgcctca gcctcccaag tagctgggat tacaggtgcc tgctatcacg    63900
cctggctaat ttttgtattt ttagtagaga cacggtttca ccatttggcc aggttggtct    63960
caaacctctg gtctcaagtg atctgcccgc ctcggccacc cgaactgctg ggattacagg    64020
catgagccac tgcgcccag ctgattcttt acagataaac aaacattgac tctgctttga     64080
catgtgcttg gatcaggtaa ctgcaccagc tgcctttctc ctcccacttc tgcctggtcc    64140
tccgaatgcc tgcttttctt atttgaactc ttctgtcctt ttctgaaaac ctaacagatg    64200
cgaaacaggc cattttccat gttggtggtt attaagcaag acttgaacat ttgtttgttg    64260
cttgttaagg ctttttattt cagagttcaca gaattaactt tcttttttc tgatctcttc    64320 cagagtaaat gtgtcaaata ctggcctgat gagtatgctc taaaagaata tggcgtcatg    64380
cgtgttagga acgtcaaaga aagcgccgct catgactata cgctaagaga acttaaactt    64440
tcaaaggttg gacaagtaag tatattgtcg tattctagag actttgggaa ctgttgatgg    64500
tgtgtaggaa ttcagggtct tgccgttact catgtttgca tacatgcatg cattcgctca    64560
ctcattgatt cagtagccat ttattagctt ccttctatgt gccaggtaca gtttaagcag    64620
tactggtaca ttgtgaacaa ggcaggtagt gttcctgccc tcatcgagcc tagggagata    64680
gacaatttaa aaacaaataa ctggccaggc gccgtggctc aggcctgtaa tcccagcact    64740
ttgggaggct gaggtgggtg gatcgcttga gccggggagt tcgagaccag ccctgggtgg    64800
gagactggga tagggtgacc tgagtggcta caagtctgt taggaggcct ccgcagggc     64860 ctatgttgat ggcctcctct ccaagtatcc acagacttca gcagttgttc ttttttgttc    64920
cttcctttgg aatggaatat tatataaaat ggcagaataa actggaagag aagcagtaga    64980
tgtgagaggt gccgggggt gaagtctgca ggatgtgggg attgtttggc ttttggagga     65040
ggaaggaggg attcaagaca cattgtagag gtttgagtct gagcggacag tggtgctgtg    65100
gcagacacca caaagctgg aaggagaact gatgtgggca gtgatttgtt ttcttctgga     65160
tgtgttcagc tgggcatctg aacagtcatg tggacattca tctattcatt cagagatatt    65220
```

```
tgttcaatga cctcttggtt cctggcacca tgctgcttgc tggagataga gctggggaac  65280
aaaacagatg gaatccctgc actcccaagt gtacactata ctggccagta atctaccagc  65340
ccagtaattg cacatataaa tatatcatta taaactgtaa tcagggctag aaagaaaaaa  65400
tgcaggagtt tagggttcat ttggaggggg aagggacttt ttttttttt ttttgaaac   65460 agaatcttgt tctgtcaccc agactggagt gcactggtgc attcacggct cactgcagcc  65520
acaacctcct aagctcaagt gatcctctca cctcagcctc ccatgtagct ggggctaca  65580 ggtgtgtgcc accatgccca cccaattgtt aaattttta tagagacggt tgtctcatta  65640
tgttgcccag gctggtcttg aactcctggg cttaagcgat cctgctgcca catgcagcct  65700
cccaaggtgc tggaattaca ggcgtgagcc agcgcacccg gccaagggag gggaggttct  65760
taaggcatag gaacaatgt gtttgagtca gcaaaggagg ttgtggggt ttgtcctaag  65820 tgtggtaagc agccagagtt ggatttaagt ttttaagaga ttccctcca ccctgtagag  65880 actggagggg gcaggagttg ttctagggat taggaccaat ttggaggtag tgcagccgtc  65940
agagtaaaaa ataataggga ttgaactagg ccagtgccca gggtgcctga aagaaggaga  66000
cccagtagag ctgactggag gcagacatgc aggattcag tgaaggagtg taccaagggc  66060
gagggtggtg tgcagggtga ctggcaattt tctagcttga gaaaggtccg gggggatggc  66120
agtggagttg aggaagctgg gaggatcaag gacctttttg tgaacacaca aagtttgaga  66180
tgccttggac acattgaagt ggagcggtca gggaggcaag ggtggaggtg ggatgcggag  66240
gggaggtggg atgcagagcg tcgtggatgg atcagttttg ctcgatagag ggacatgttt  66300
ttctgtggca acaggagggc aaaggagaa ggtggccaca gatgccggta gatgagctga  66360
gagtgattgt attccctatc ctctcggaag cttgaggcaa ggccatcaac agacaatcag  66420
agggaataag aagagataga atatatgaag aaagggagaa aagatgaaat cgtaattgtg  66480
tagcagggca agaagtccag aaatttctgt gctgtgccaa gttcccagtt gaggcggtga  66540
acatgaaaat atactgatac ccattgcctg gttttctcc aaggcacttt ggctcctagg  66600
gcacaaaaca gaaagtacgt ggtttgtcca ggccgagggc tttgcatagt tgcagtggat  66660
ggagaggagg tcaaggaatg gaggcacatg gtagagagag actgtcccca gagcacgggg  66720
actcctggcc ggatgagggg gacaggggca ggaggaggca ggtggaaagt agagggaggg  66780
ctcagtggtc tggaggctac aggaagtgac ggggggacca aaggagctg gaaaccagtg  66840 tggttgtggc ccagggtggg atgtttggat ttctgatgtc agagagggtc cagtccttct  66900
gatgatgggg aggggtggag gctgaatcta tggtagagat agtgagagga actgaacaa  66960 tgtagctgtc aagtggaaat gggagaaagg gctgggcgtg gtggctcacg cctgtaatcc  67020
cagcatattg ggaggctgag gcaagaggat cgtgttagct caggagttct gggctgcatt  67080
gagctgtgat tgtgccactg cactccagcc ttggcaacag agtgcccagt aaaaataaa  67140 aataaaataa aataaaaaaa ttaaaaaaaa aagaagaaga aaaagagaaa aagtgtcctt  67200
ttacatccct tttaaaaatg tcacttaagg ctgggcaaag tggctcatgc ctgtaatccc  67260
tgcactttgg gaggctgaag tgggtggatt acttgaggtc aggagtacaa gaccagcctg  67320
gccaacatgc gaaactcct tctctactaa aattagctgg atgtggtaca tgcctgtagt  67380
cccagctact cgggagtcga gtctgaggcc caagaattgc ttgaatcggg gaggcgtagg  67440
ttgcagtgag ctgtgatcag gtcactgtgc accagcctgg atgacagagt gagactctgt  67500
ctcaaaaaaa aaagtcactt agcttagatt gtctctacat ataggaag aagatgtagg  67560 aatgaatggt gctgctacaa ttacgtcatc tggatagacc cagaaacatg atacttttg  67620
```

-continued

```
gttttctgta gccttggtgc cattgttgat ctttattaat tatcattatc ctcaaaatag    67680
ccataatgtg ctgagtctct tcctatttgc tgggcagagg ctgagtattt cagcgagctc    67740
actgagtcct taaaattgca ttatgataga gagaaagaga ttattatttg cattttgcaa    67800
aatgaagaaa ttgaggttta gagataccca agggccacgt gagtgtgagt gcctggaatt    67860
ggagcctaaa tctagtcatc tgatagcaaa gcctgttttc ttatctgctt tgcattaaat    67920
ataagtttaa aatagaacaa tactggccag gctgggtggc tcacgcctgt aatcccagca    67980
ctttgggagg tcgaggcagg cagatcacct gaggtcagga gtttgcaacc agcctggcca    68040
atatggcgaa agaaacccca tcgctactaa aaatacaaaa attagccagg catggtgatg    68100
tgtgcctgta atcccagcta cttgggaggc tgaggcagga aatggcttg aacccgggag    68160 gcagaggttg cagtgagcca agatcacgcc actgcactcc agcctgggca acagagtaag    68220
actctgtctt ggaaaaaaaa aaaaaaagaa atgatactat agtctgtgtt tatatggtgg    68280
ggaaggttga gtatcaaaaa aataacaaag aggaatgaat gtcttaagtg aatgcctgtt    68340
tccccatctg cttcctcttc tgctgggagg agagacctgg atccctagag gtttcagttg    68400
cctccagagc tgagtgccac agggatgcag gggaataggg atgttacctg tcgctggtaa    68460
ttcagagaga tgattcaggg tatagttacc tgaaagaaca aattgccatg ccagacgtct    68520
tggttcttat gacagaggca aagagttgcc tccaggattg cccaaaagga gacgagttct    68580
gggaacctca cgaagaggac ctttcagtgg aacctgggga gattctcttc ctctccattg    68640
gatttaggaa agcttagaac cgggtgattc ctcaacctct tgatttattt aattcttttc    68700 tggttttttct tggctctact ccaggggaat acggagagaa cggtctggca ataccacttt    68760
cggacctggc cggaccacgg cgtgcccagc gaccctgggg gcgtgctgga cttcctggag    68820
gaggtgcacc ataagcagga gagcatcatg gatgcagggc cggtcgtggt gcactgcagg    68880
tgacagctcc tgctgcccct ctaggccaca gcctgtccct gtctcctagc gcccagggct    68940 tgctttacc tacccactcc tagctctta actgtaggaa gaatttaata tctgtttgag    69000
gcatagagca actgcattga gggacatttt gatcccaagg catatttctc ctagacccta    69060
cagcactgcc attggccatg gccatggcaa catgctcagt taaaacagca aagactaagt    69120
cagcattatc tctgagtcca ccagaagttg tgcattaaac aacttcatcc tggctctgca    69180
gtttctcctt attcttcatg atgtttgctt tgtagctgtt gactgctttg taggtattga    69240
ggtggtgggg gtgtggtgga aataggcctg actcttgagg atcccttaag tcatttttgc    69300
ttggttctct ttttccttct tttcttctac tcttctatga ttcatctctt tgattgtgat    69360
tctgttctct ctctctctct ctctttttt ttttcgtttt ttgagacaga gtcttgtttt    69420
gttgcccagc ctagagtgca gtggtgccat cttggctcac tgcaacctcc gcctccggg    69480 ttcaggccat tctcctgcct cagcctccca agtagctggg attacaggca tctgacacta    69540
cgcccggcta ttttttgtat tttaatagag acaaggtttt gtcatgttgg ccaggctggt    69600
ctcgaaccct tgacctcagg tgatccacct gccttgtcct tccaaagtgc tgggattaca    69660
ggtatgagct accatgcccg gcccattctg ttctcttcta ccataaatat atttctcccc    69720
taacactata tttgtttgct tcacaagatt ccagctgctt ttccaccaag gcctttgatg    69780
gaagctgtgc tgtgacctct gtaatgagtc tgtgggctgc tgattctcca gtttgggctt    69840
catgattata ctgggaata ttgggttttcc taaatctcat tcatttcttg ggcaagtaga    69900
tatatgtgaa agtgtttatt tgtccagttg ttaaagaagc taccatttat tgagccagcc    69960
```

```
tctgagcaca atgtttttttg ttttgttttg tttttaattt ttaaaattat ttacttcttc    70020
tatttcaata actttattat tattatttttt tgagacagag tctcactctg tcacccaggc    70080
tagagtgcaa ttgagcgatc ttagctcact gcaacctctg ctttctgggt tcaagcaatt    70140
ctcatgtctc agcctcccga gtagctggga ttactggtac gtgacaacat gcctggctaa    70200
tttttgtgtt tttagtagag acgaggtttt gctatgttgg ccaggctggt ctggaactcc    70260
tggccccaag tgatcctcct gcctcggcct cccaaagtgc tggtattata ggtgagagcc    70320
actgcgcccg gccctctttc agtaatttg atgtattttt ttgtatatga ttcctgtttc    70380
attctgtcca accagcactc tgtatggtat gtgctgttgt ccccatttca cagatgcaga    70440
aattaagggt cagagaggtt aagggactta cctcaggcac gttgtactgg agaagctgaa    70500
ctccaagagc aggtttgggc tgactccaaa gccctatgct ttttgccaac atattttcaa    70560
acataaatag acaattttat aaatagctcc aaagagtaga cattgtttct gttgatatta    70620
atggcttggt tttgagtctg aaaccccat gaatgattct gttgtccctg ctttttgtcc    70680
ttctgcccgc agtgctggaa ttggccggac agggacgttc attgtgattg atattcttat    70740
tgacatcatc agagagaaag gtgggtcatc tggtgggcaa aagcgacag tttctgtttt    70800
tagtttatgg aaggaaagtg ctcacgaaaa cagtctgggg aagagaggtt gaatgggaaa    70860
attcttcac aaaaatctgg gctgaagact tcagtgtgtc tgcctgagaa cagaagtgac    70920
actatttgag cttttggcat aaaatgaagt ctaggagctg cagaacccac tgccatggcc    70980
ttttgttgca tacacagtgg tggtctctat ccagccacct gaccttgttt acagtatggg    71040
gtgatttgtt ggcaagtgag ggaatcctga cttctgccac ttcgttattt atgtagtctt    71100
ctgggatcat tggtattggt cagaagttca acactgtagc cattgcaaca tgctcagtta    71160
aaacagcaaa gactaaatta gcattgtctc tgagtccact aaaagttgtg cattaaacaa    71220
cttcatcctg gctctgcagt ttctctttat tcttcatgat gtttccttcg taggtgttga    71280
ctgcgatatt gacgttccca aaaccatcca gatggtgcgg tctcagaggt cagggatggt    71340
ccagacagaa gcacagtacc gatttatcta tatggcggtc cagcattata ttgaaacact    71400
acagcgcagg attgaagaag agcaggtacc agcctgaggg ctggcatgcg gattctcatt    71460
ctcttgctag gcctcttgga tacgctctcc ttttgagcag gaggacaggc tctgatagac    71520
aactgtttga tttcggaatg ggaaacaaac tcccaactaa aagggcctct ggaaactgtc    71580
aattattctc cacttctcag ctctgatttt tcactgcaga ggagcttagg gaagggcacc    71640
atcctatcag cctggcctgc cagattgaag aactgccatg cagaaaggtt ctgatgttct    71700
caggctcatg tggcaagcgt aaaactcaaa gccttgaagt ttctagcctg ttccagcctt    71760
gatccaggcc atgtttatcc tgattccatc ctttaaaacg aatgcctcac tcttaatagc    71820
gcacggcagt ttgaaccact aatttggtcg agttggaaac agtgaaattt caattttaat    71880
aagctgtgca taatgaagag gaatgtggaa ttggagcctt tccatctgaa gctattcata    71940
acaggcacaa agctgagtta attaggaata tgctgagatg aaggaaatga ggagagctgc    72000
tcttttgggg gctgtgcttc tctccccaac ccctcaaccc cattgccatg ctgcagatgg    72060
ggtggtgtct aaacatcagt ggcgagtgcc tgcattactc tgctcgttgc cttccagaga    72120
actcagcttc tccaaatgct gagctctttt cagaatggga cctgccacca gtatttgaaa    72180
gatttctagc ctagcagaac agcagccacg ttatcaaagt ttggttggcc aaaggaaggt    72240
acttgctaat tagtttagta ggttttcagt ccgcacagac atacgggatt gttttattgt    72300
acatagacat cttcagaaac agtgtatgta tagaaatgta aggtcaaaat ttgaacctca    72360
```

```
gtgctttaaa tctgaatttg tattaactga tatgaaatat ttagacggtt actttatttt    72420
atatctgtct tccattatac ttaatttggc tcaagaatag ttaggcaaaa agttgcccaa    72480
agagaaggat ctcctagtaa atacaaagag aatgtaacat agttgctaca agttggagca    72540
tgttcaggga tgtctttttt tttttttttt tttgagagag aggtctctct ctgttgccca    72600
ggctggagtg cagtggtgta atcatggctc actgcagcct caatctccca ggcttaagcg    72660
atcctcccac ctcagcctcc caagtagctg ggactatagg catgcgccac cacacctagc    72720
taattttcgc attttttgta gtgtcacagt ttcgccatgt tgcccaggct agtctcgaat    72780
tcctaggctc aagcagtgct tctgcctcag cctctctgag tagttaggac tacaaatttg    72840
tggctccatg cccggctaat ttttttatct ttattttgta gagacaaggt ctcactgtgt    72900
tgcccaggct agtcttgaac tcctgggctc aaacaaccct cccactttgg gtttccaaag    72960
tgctgggatt acaagtgtga gccactgagc ccagtgacct ctgggtttta aaaatgtgta    73020
ggcttcaatt atttatttta aaaaatgaaa tcctgcaata tatagttttc tgcgttgtgt    73080
ggtttgaatc aatctgggaa ctggcttgct ggctgattgt ggtaaagtaa aagtactta    73140 atttagtaga aagtttaaat ggcagacata acattaaacc cagctgattt ataaatgaag    73200
caaaagaaca aaactcattc aggataattg gttattctaa aatacagtca tttctaaaat    73260
tatgaagtgt tcaggacctt tgggagtgaa agaatttgct aaagaaggat cagtgaaaaa    73320
aaggaatgat gggtgaagag ctgtggagaa ggaagagaag aaacagcaca aggaaggaag    73380
aatataaaat cagatgtggg aatccagggg aaagtgcaaa cgaagcaaga ttgagaaaat    73440
tctcaagttt ttataaacag ttctcacact ctgccagttc cttggaggta gacttttttg    73500
ttaacttcca actacagtag tgaaaaaaaa aaaaaaccc tcaaatttgc aaaagcagtc    73560
tgtggaattt tctttaccca gctttcctga ctgttaactt tttagcacac ttaactttat    73620
cattcgttta ttctctctgt ttaaaattaa aaatgtaaat tttaaaaagt aaaatgtttg    73680
ttggttacaa acatttatac ccctttgtct ctaaatatca tttcatttta aaaaatgaat    73740
aatctaagcc tacacattct aaaatgtgta tattttctaa aaataagggc attctcttac    73800
ataaccaatg tcacaattat ttgatacagt gatcaaaatc aggaaactaa cattgatata    73860
acactattat ctaacctaca gaccatcttc aaattttgtc ctgctagtat cttttatggg    73920
tccagggtca cacagtgcat ttggctataa tgtatctttt ttctcttttt ttgagacagg    73980
gtctcacttt gttgcccagg ttggagtgca gtggtgcaat tatggctcac ggcagccttg    74040
acctccttgg gctcaggtga tcctcccacc tcagcctctc gagtagctgg agaccacagg    74100
tgtgcaccac catgcctggc taagttttgt atttttgta gagatggagc ttcgccgtgt    74160
tgccccggct ggccttgaac tcctgggctc aagtgaccct cccgccttgg cctcccaaag    74220
tgctgggatt acaggcgtga gtcaccacac ctggccagtt attagtatgt ttagtctctt    74280
taatctggaa cagtttctca gtcattcttt attttcatg acctggatgt ttttgaagag    74340
tttaggccag ctatttagca gaatgccttt cagtttggat ttgtccagtg tttctcttg    74400 actatattct agtcatgcat ttttggcagg actgtcacag aaatgttgtt gtagtcttct    74460
tagtacatca catcaggtac acactgttga tctgattcat tactagtggt gttaactttg    74520
atcacttgaa taaggtggtg tctgtcaaat ttgtccaccg taaagttact tgagcaaaac    74580
gtagctggga ctacaggcgt agcaaaaaat gtagcaaaaa gtagtatttt tgctacatttt   74640 ttttttttagg aacaaagtat ttttcccttt taagttaatc tcttgtccat aaagttatta   74700
```

```
tttttccctt ttaagttaat atcttgtggg tagatactgg agactgcgta aattacctat    74760
ttctcataat actttttttt ttttttgagat ggagtctcgc accgtctccc aggctggagt    74820
gcagtggtgc aatctcgggt cactgcaagc tccacctccc gggttgacgc cattctcctg    74880
cctcagcctc ccaagtagtt gggactacag gcgcccgcca tcacacctgg ctaattttttt   74940
gtatttttag tagagacggg gtctcaccgt gttagccagg atggtcttga tctcctgacc    75000
ttgtgatctg cccgccttgg cctcccaaag tgctgggatt acagatgtga gtcactgcgc    75060
ccggctctca taatactttt tgcctactaa ttttatattc attgattaaa ttcttgcctg    75120
aaaaaattat tactgtggta tttgccaaat ggcaattttc tgtttccatc attgcctttc    75180
ccccgctttt aaaagtataa gtgacaaaga aaaactgtat ataaagtgta caccatgata    75240
ttttgatata tgtatacttt gtgaaatgat tatcaaaatt gagttaaata atgcatccaa    75300
catctcagtt actttttttt tttttgaga cagagtcttg gtttgtcact aaggctggag    75360
tgcagtgcca caatctcggc tcattacaac ctccacctcc caggttcaag tgattctcct    75420
gccttggcct ccccagtagc tgggattaca ggtgcccacc atcacacccg gctaatttttt   75480
gtatttttag tagaggtggg gtttcactac gttggccagg ctggtctcga actcctgacc    75540
tcaaatgatc ctcccgtctc agcttttccaa agtggtggga ttacaggcgt gagccactgt    75600
gcccggccac tcttagtaaa ttttaagtgt acattttttt ttttttttt ttgagatgga    75660
gtctcacttt gtcaccctgg ctggagtgca gtggcatgat cttgccacac tggaacctct    75720
gcctcctggg ttcattcagg tgcttctccc acctcagcct cccaagtagc tgagactaca    75780
ggtacccgcc accatgcctg gctaattatt gtatttttag tagagatggg ggttcaccat    75840
gttagccagg ctggcctcaa actcctgacc tcaggtgatc tacccacctc ggcctcccaa    75900
agtactgaga ttacaggcat gagccaccac acccagccac attacgttag tattaactat    75960
aatcaccatg ctgtacatta gatctccaaa atgtattcat cttatgtaac ttcaagtttg    76020
tacccttgga ccaagtgtctc cttgttttcc ctacccccaa cccctggtaa tcactgcttt    76080
aatctcagtt tttatgagtt tgactggttt agattccaca tacaaatgag atcaggcagt    76140
gatggtttat ttcacttagc ataatgtcat ccatgttctt gcaaatgaca ggattttctt    76200
cttttttaaaa ctaatatcca tgctggacac ggtggctcat gcctgtaatc ccagcacttt    76260
ggaaggctga ggagggtgga tcacttgagg tcaggagttc gagaccagcc tggccaacat    76320
ggtgaaaccc catctctacc aaaaatataa aaaattagct ggatgtggtg gcgcacacct    76380
gtgatcccag ctactgggga cactgaggca ggaggatcgc ttgaacccgg gaggcggagg    76440
ttgcagtgag ccaagatggt gccactgcac tttagcctgg atgttgatgt tgttccactt    76500
gtttattttt atttgttcc ctgtgctttt ggtatcaaat cctaaaaacc attgccatga    76560
ccattgtcat gttactttcc ccatatgctt tcttctagaa cttttaaggt tcatcattcc    76620
cttttctgtt tttagttgca agcctactat aaggaagggc ttttcttttct tccttattta    76680
tttattcatg tctatcagaa tgggcacctt actactattt tgttgttat tgcttgaatt    76740
gacttgaatt tggctagtgg aaaccttttc agatcgggta ctctgtcctt ttgatctctt    76800
tccattttca agcacttctt tagacttaag atggtctagg ctcatcttct cctttcccag    76860
ccatttttca aaggaacctg attccttta gtgaagagca gtattttgaa accaagatct    76920
gggcactggg tctacttgtt tgtactggta cagtgttctt tgaattgcta attagctgat    76980
caattactgc tctatttgag ttccctcttt ctaaaacctc acatatgtgt acagacggtc    77040
cctgacttat gatggttcga cttatgattt ttgatttat gatggtttga gagcaataca    77100
```

```
tccattctgt ttttcacttt tcattcaaca ctttatttta aaatagggat tgtgagatga   77160
tattgcccac gtgtaggcta atgtaagtgt tctgagcacg tttaaagtag gctaggctaa   77220
gctgtggtgt ttggtaggtt agatatgtta aatgcatttt cgactagtga tattttcaac   77280
ttatgatgag tttattggga tgtatcccca taaagtcgag gagcattata catatctctg   77340
tataacagag tgagttcctt atacctttca tccactttcc cctgaagtta acattttacc   77400
taaccatgat acatttatca aaactaaaac attaacatca atacattgct attaactaaa   77460
ctagagttta attggatttt gccagttttc caatgaatat ccttttctg ttccttgatc    77520 caattcatgg tcacacactg agtttggtca cttgtcactg tagtcttctc caatctgcga   77580
cagcttctta ggctttcctt gtttttcatg tactcttgac gattttaag agtactggtc    77640 agatatcttg taggatatcc cacaacttgt gtttaatctt atgttttctc atgattagac   77700
ttgagtaatg gattttgggg aagaatacca cagaggtata ttgttaagtg ttctcatcac   77760
ttggaggtaa atgttatcaa catggcctgg tgatgttaaa cttgtcagtt tgtttagtta   77820
gtatctgcca gattttctc actgcataat tacaaatcct ccttaactta tgatggggtt    77880
acagcctgat aagcccatca taaattgaaa atatcataag tcaaaaatgc atttaatgca   77940
tctaaactac taaacatcac agcttagcct agcctgcctt gaacgtattc aggacactta   78000
cattagccta cagttgggca aaatcatctc atgggaagcc tgttttataa tgtgttgcat   78060
atcttatgta atgtgttgag tactgtactc agaatgaaaa acagaagggt tgtattgctt   78120
ttgcaccatc ataaaatcaa aaaaaccata aggcaaacca tcatgaagtt ggggactgcc   78180
tgtacttttt tcctctttcc ctgttcaatt ccttggaaga aagtcattta gttcagacca   78240
tactcaagaa aagggaaata aagctccatc tcttggagct taattgaaac tggaatgact   78300
agtttctata tacattattt agaatccttt tgtaagaaag atttgttcct tctctccatt   78360
tatttattcc attatttata ttgatagaga cgcatgtaca tttattttat actttgggtt   78420
ataatctatt tttcttgctc aaattgttac agctttggtc actgggaggt tcttcagatt   78480
ggctcctgtg tcatttgaca tgtccccacc ctctcgtttc tgagtacttc tctactttgg   78540
cattacaaaa gatgttccag gctcctctta tatttttccc tgccgcagcc ctagaatcat   78600 ccattttct atggtgccct ggttcctttt actttagatg ggggtttaga aaccaatctg    78660
ggtgttgggt gtgctcattg ctactggaat cactgcttct aggccctctc agcagataga   78720
gctagaaaac atatggctgt atatgaatcc atggattcat atatatctat aattgttttc   78780
tgtatctggc catctatata tatattaagc taaacatgaa ttcatactga tgtctcagac   78840
tcgaatccat tgccgcaggg ctcattcttg ccttcctctt gcttatttgt gacttctttc   78900
tctaacaggg agaaacccca gtctcattat caccaaccta tctactcatt tgttcaaccc   78960
tggtataggt gtaaagtagt ttcagaatta ctaacctata cccatgtgag aattgtattt   79020
gcacttcttg tttgaaggaa atacatacaa cacaggtagc gtctctacac ttcagtatac   79080
agagatctga acagtgttct ctctgagtga atcatattgc aggacagaaa ttacttttaa   79140
aaattctgta atgggtcagg cctataatcc tagcactttg ggaggctgag gtgggcagat   79200
cacctgaggt caggagttcg agaccagcct ggccaaaatg gtaaaccccc atctctacaa   79260
aaaatacaaa aattagccag gcgtagtggt gtgtgcctgt aatcccagct actcaggagg   79320
ctgaggcacg agaatcactt gaacctggga ggcagagctt gcagtgagct gagattgagc   79380
cactgcactc cagtctgggc gacagagcga gactctgtct caaaaaaaaa aaaaaaaaaa   79440
```

```
aattccataa tgatagcaga gctggaatag aaatgggatt gcacaggctg aatctgagtt    79500
gttgcaacag taaacgagca agatttaaac tggccttgtg tagcacttgc tatttggctc    79560
ctcatatttt attagacgct tattctttt  tgtttggtgt cattcctttg agaaatattt    79620
gagtgccttt tctgttgcag acattgatta gatgctgagg ttgtaacaat gaagaagata    79680
gccatcgctg ttgcctcatg gaactgaagt tttactagat gtaaaatttg agttaacatg    79740
aggccgtgcc cctatgtgcc ctattgtttc ttcacacagc tcccttcatc tccttggtcc    79800
aatgaaaagg ttttttcata cttgttcatt cattcctgca ttaattaaag taggttgtac    79860
tgtgccaggc actgggaata tttaagtagt tgtgttcctg aattggaaat gaatccagca    79920
tggttggagt agaaggagct gggggggcaat gtggagtgtg atggggagat tggaaaagta    79980
agctgagacc agattttttca gtttggaggg agaggtgggc cttgtaggcc atattacaga    80040
ttgtagactt tatttggagg gacatggaag tcattgagga gtctgaagca ggggaatgac    80100
ataaaaagat cctcatttta ggccggatgt ggtggctcac gcctgtaatc ccagcacttt    80160
gggaggttga agtgggtgga ttgcttgagg ccaagagttt gagactagcc tgggcaacat    80220
ggtgaaaccc tgtctctatc aaaaatacaa aaattagctg gcatggtgg  ctcacacctg    80280 tagtcccagc tacttgggag gctgaggcat gagaatcgct tgaacccggg aggcagagat    80340
tgcagtgagc cgagattgtg ccactgcatt ccagcctggg tgacagagtg agacttcgtg    80400
tcaaaaaaaa aacaaaaaac ccctcatttt gaaagggaac cctggcttga gggtgaagaa    80460
tgggtgggca ctaggctaga gcagctgcag ggtcagtgag gagctgccgc agtgctgcac    80520
gtgagaaccc gtcatggttt ggtcagggtg ggcaggactg acagtgagca cagagcgaag    80580
taaaaccagc aaaatttcat gattggatag tggaaggaat catggtgttt gtagtcttca    80640
aatgtgaacc cagagtgcac tggacaagta gtctaggctg ctctgtaacc aaggcaagtg    80700
ttttcatttt accctctctt cctgctcttg gcctttggat ttttttgtaat ttaaggttta    80760 tgaatgtaat cagttactta acatggaaag atacttaata ccagatgatt ttggagtctt    80820
gtgatcaata ccttctctca atcttgggtg tgtgtcagtt ggcaaggcca taaaatttgt    80880
tataaacatt gcagaaggct tggttactgt gctgtgacgt tgaatttggg tggagataga    80940
tcaatttcag ttgattttct aggcttcaga aacacattac cctctactcc acaaacacaa    81000
atcaaaacaa aacaatccct attccctgag catttctctt gatctataac acagcctggg    81060
ctgtcacagt actaagacaa gcccatctga tttgtgagtc agttttattt cttggtcttc    81120
tacataagct aaaaagtttc aacattttaa tgcttttcct tggattcctt tgagtcattg    81180
aagtaattcc tgtttcattt gtactaatta ttccacacta gaaaattctg ttgtaatcac    81240
tttatgtatt aatagaaata ctgattttta ttttcaagga agtattgagt agggaggggg    81300
aaatagggat ttgctgttca atgggtatag agtttcagta atacaagaca aaaaacttca    81360
gagatcttct atacagcagt gggtatatag ttaacaatac tgcacatcta acagtttgtt    81420
aagagggtag atctcatgtc atgtgttttt aaaaattgct tttaaaaaaa gtatcgtagta    81480 aaaagcagt  tttactcctc agtttctatt tatatttaaa attttattt  aaaaagtgag    81540 ttgagatttt taaacctcag gataagtttt atttttaa   aaatttatttt ttattattt    81600 tttgagatgg agtctcactc catctcaagt cacccaggct ggagtgcagt ggtgtcttgg    81660
ctcactgcga cctctatctc ccaggttcaa gtgtttctgc tgcttcagcc tcctgagtag    81720
ctgggattac aggtctgcac caccacgcct ggctaatttt tgtatttta  gtagagatgg    81780 ggtgtcacca tgttggccag gtttgtcttg aactcctaac ctcaagtgac cacctgcctt    81840
```

```
ggcctctcaa agtgctggga ttacaggtat gagccacagt gcccggcggg ataagtttta   81900
aaataatatt ctctgctggc tgggcatggt ggctcatgcc tgtaaaccca gcactttggg   81960
aggctgaggc aggagcatca ctcgaggcca agagtttgag accagtctgg caacataat   82020
gagacccct ctctacaaaa aataaaaaaa atttggctga gtgtggcatg ttcctgtagc    82080
tatcgggagg ctgagatggg aggattgctt gagcccagga gtttgaggct gcagtgagct   82140
atgattgcac cactgcgctc tagtctgggt gacagtgtga gaccctgtct cttaaaaaaa   82200
aaaaaaaaaa aggccaggca cagtggctca ggcctgtaac cccagcactt tgggaggccg   82260
aggcgggtgg atcacttgag gccaggaatt tgagaccagg ctggccaaca tgatgaaacc   82320
ccgtctctac taaaaataca aaaataagct gggtgttgtg gtgcacacct gtaatcccag   82380
ctacttggga ggctgaggga gaaattgct tgaacctggg aggcagaggc tacagtgagc    82440
cgagatcaca ccactgcact ccagcctggg tgacagagca agactccatc tcaaaaacaa   82500
caacaacaaa aaaccaaat gttcttgcca attcttccat ttaatattta attttgaatt    82560
atattgtatc tttctaagga ttgtttctta tataagcaaa gattttttcag tgctaaacat  82620
ttacgactgc tattcagaaa tggttattta caagtctttt tgttttaaga aaatggctgt   82680
tcaaaaaatt aaaatagtat ataaaccaaa caaatatttt ttgctttgga tgtctgtttt   82740
gcagcttctt ccctacacta taagttctta ctgactgctt tatcacttaa taaattggtt   82800
tggctacttt aacagaggca aatagtatca ggcaaaaaat tatttttat ttttattttt    82860
tgagacagtc tcactccatc acccaggctg cagtgcagtg gcctgatctt ggctcactgc   82920
aacctccacc tcccaggttc aagcgattct catgcctcag cctcctgagt agctggaatt   82980
ataggcatgc accaccacac tcagctaatt tttgtatttt tagtagagac agggttttgc   83040
catgttgacc aggctagtct tgaactcctg acctcaagtg atccatctgc tttggcctcc   83100
caaagtgctg ggataacagg catgagccac catgcccagc cctatttttt attttttaga   83160
gatgggtctc gcttttaga gatgggtctt gttgcccagg ccagagtgca gtggtgcgat    83220
catagcttac tgcagccttg aattcctggg ctcaagcaat tctcctgcct cagcctcccg   83280
agtagctggg actacaggcc tgtgccacca ggcctggctt gtacattagt atttgatatg   83340
gctaccctaa gggcaatcct atagtgaagt caacattaga taatgatgct catctgatgg   83400
attagattt cagagttggc tgtttccagg tgcctatagg agtagaaaag ggtgacaaac    83460
ctcctaacta gatgtcctac caaatatagt tcactccaca tctgagatga gactgcatga   83520
ctgctggttt tctttgcctt ttccccccca gggtatcatc agaaccaaaa ataaagtttt   83580
aaaggtgggt caggtgtgtg ttggctcatg cctgtaatcc tagcactttg ggaggctgag   83640
gcaggtggat catctgagct caggagttca agaccagcct ggctaataac atggttaagc   83700
cccatctcta ctaaaataca aaagttagc tgggcatggt ggtgggcacc tgtaatccca    83760
gctactcagg aggctgaggc atgaaaatcg cttgaaccc agaggcgggg gttgcagtga    83820
gccgagatca tgccactgca cactagcctg aacaacagag caaggctctg tctccaaaca   83880
aacaaaaatg gtgccagagt cttttccagg gctgagggga gatacaatga agtgtgttat   83940
tttttctgat aagagtgcta ccatctttca ttcttgtgtg ccatttctag ttggggtgaa   84000
tttgttttcg gagttccttt cccagctgtt tgcctgaaaa accatgaaat gtgttccaca   84060
tgaactatga aatgattaga tgctaatgtg gcaaagaaag tgtgaattct cttgtagaaa   84120
cagggacatt tggttcggta cagtaagttg ttaatgcgtg actctgtgct ttcaaattct   84180
```

```
gtggttcaaa agtactttc actcctactg tgtatttacc ttgagaaggt gaatccccta    84240
acaatttggt caatgtatca gtattctcaa cccgtctatc aattttttt tctttctccc    84300 tctttttct tttttgggc aaaatacctt ttttgctttt tatccccttaa aataaccat     84360 tgtccctcac atgtgcactc ttccaaattt cagaaaagca agaggaaagg gcacgaatat    84420
acaaatatta agtattctct agcggaccag acgagtggag atcagagccc tctcccgcct    84480
tgtactccaa cgccaccctg tgcagagtaa gtagtgctga aggaaattct ttttacctgg    84540
tcatggtggt ttaaaaaggt ttaaaaaaca aaaacaaaaa caaaacacaa gtttgtagca    84600
catgcctttc actggtgcac gttcctgttg ccctactgtt agtgtatctg tgactggtga    84660
tatctattga ttgtgttaat gctatctcaa ccacgtttta attttcctaa gctggccagg    84720
cacggtggct aacgcctgta atcccagtgc tttgggaggc cgaggttcat ggattacttt    84780
gaagtcagga gttcgagacc agcctggcca acatggtgaa accctgtctc tactaaaaat    84840
acaaaaatta gccgggcatg gtggcgcatg cctgtaatcc cagctactca ggaggctgag    84900
gcaggagaat cgcttgaacc caggaaacgg atgttgcagt gagccgagat catgccactg    84960
cactccagcc tgggcgatag agtgagcctc tgtctaaaaa taaaataaaa taaaataaat    85020
tcctaaactg aaggctgact gctatgctag ctaggattat atgggatttt aagtatatca    85080
agtggtggtt ctccaagaag aatctaattt ttcttttgat gggctgggga ttgtaacaaa    85140
ggaaggtcat atgtcttaat gatgtgttaa ggctctttgc aaaatcaaag taaataaatt    85200
gaccactaat gtgtcagccc agccatgttc tgctcatttg ccaccagtca acagaaatct    85260
actttgggtg tttaaaccag gagtcagcaa actacagctc acaaggccag atgtgggcca    85320
tggcctgtta ctgtatggcc tgttaatggt tttaaagggt tgtaaaacaa agaacacaa     85380 aacaaagacc caataacaaa acaaagcccg aagaataata tgcgacagag accatgtatg    85440
gcatatagag cctaaaatac tgactctcaa gcccttccca gaaatccttc ccgactcctt    85500
gttgaaaaca cggtaggaaa gcatttgtca aattgaggat atgaatagca attgtaagtt    85560 attattttc tatatattcg aaagtcactt gctagtataa catttacctt ttatttttcc     85620
ctaagaatct tctctctgtt tgctttcgac atggatttt aaacccctgc agattttaat     85680
attctatata aatgttttag gtggcatata tgaggtttgt attaacattt gctttctatt    85740
taacattgaa atgaaattat acagcagagg tattttctcg tccaagttgc cacttctttc    85800 tatcttttt cttttctttc ccagtggact gcctgggaaa attgatattt taaattgctc     85860
tctgcaataa tttgcaatgg aactggaatg ccagggttct gagtccttgc cagacagctc    85920
gtccctcctg ttggcatgac tgagtcagct gtcatgattc cctcagtacc agtggcatgc    85980
ctgtgacaga cagcctgtct gcctttcatt cccgtcgtct cccttgtagg gttcagatcc    86040
aggatacact ggtcctggag cccctctcag cctggcaccc acagctgctg ggttccttac    86100
tctcctggac tgctctgatg tcatctccct gctcagcaga aagaagtctg ggatcttgat    86160
gctttggccc tctgtcctag gccctaaacc acccattgcc cttcacataa cctgagctgg    86220
ggctaaatag atctctcatc actgcctgcc tgctcctgta ttttcccttc ttggagcttt    86280
tgcctgttca gatccctcta ctggaaatta ataggatttc attctatgtg tgcatttcca    86340
acctttcttc acagtgcgat ccaaatgcct catcctacag gcctccttaa aacaacctgc    86400
tttctgccag accccaggga gcaccaggac ttgaggcttt tattgcactt ctgttgtttt    86460
tttgagatgg agtctcgctc tgtcgcccag gctggagtgc agtggcacga tctctgctca    86520
ctgcaacctc catctcccga gttcaagaga ttcttctgcc tcagcctctc aagcagctgg    86580
```

```
gactacaggc atgtgccatg acacccggat aattttttgta ttttttagtag agacggggtt    86640
caccatattg gccaggctgg tctcaaactc ctgacctcgt gatccaccca cctgggcctc    86700
ccaaagttct gggattacag gcgtgagcca ccatgcccag cgttatttca cttctgcctc    86760
tgtaattata ttgctgtatg gctatctctt ctctccctgg gaatgtcagg tcctaggcac    86820
aggaactgtg tctgtaccat atctggtgcc caaagaatgt agtatgtgtt ttatagatat    86880
catgtaagct taaacagcgt ggtctacatt tttgtaaatg tctttctttt tcttttctct    86940
ccagaatgag agaagacagt gctagagtct atgaaaacgt gggcctgatg caacagcaga    87000
aaagtttcag atgagaaaac ctgccaaaac ttcagcacag aaataggtat ttaaatgcaa    87060
gtgctctatt ggttaattgt ttatataatt ggcagtattt ttaagcaggc aagcaatttg    87120
ggaatgtttt agcaaagtgt accataattg agttttacaa accaggctcc ttttttcctct    87180
ccctgtactt cttttttccaa gatggtttta gtttagagtt cattaaacat taaaatcaaa    87240
cacagaatta attctgcatg aggcaaggct agcacttatt ccagagaaat ggctgatact    87300
ggtggtagag tgcaggtatc actgttcctg caatttttat tagagttggt tagcccaggc    87360
tgtgctgggg gatgatctgt agggatctgg gaagcatcgg gactcagcac tgggtggttg    87420
ggagtcagga agcctgagtt ctcatttcag tcagtctctg accaactgtg tggcatgggg    87480
tgctagacca cttggctgcc gactgggtca ccgacatccc ttccagctct gctgctggaa    87540
attcatctct cccatatgtt gcctccccat caattacgtt ttttaagtgt gacccaagta    87600
tatgatgtat gttttcatga taaattagaa acttatctgg gcatggtggc tcataccccgt    87660
aatcccagca ctttgggagg ctgaggtggg cggatcacct gaggtcagga gttcgagacc    87720
agcctgacca actaaaatag tagagaccaa cccgtctcta ctaaaaatag aaaattagct    87780
gagcatggtg gtgcatgcct ataatcccag ctactcagga ggctgaggca ggagaggcag    87840
cggttgcagt gtgccaagat cgcgccattg cactccacct gggccacaag agtgaaactc    87900
catctcaaaa aaaaaaaaa aaaaaaaaa actcagtgtc agtatttcat gtcgaaattc    87960
cacttcaatg ggtagtgtag ttaaaagctc taagtctacc ttaaaatcac ctaatgcttt    88020
gttaagcttt tagatatatg ttccttaaaa actcttaact tatttcttcc ccagatgtgg    88080
actttcaccc tctccctaaa aagatcaaga acagacgcaa gaaagtttat gtgaagacag    88140
aatttggatt tggaaggctt gcaatgtggt tgactacctt ttgataagca aaatttgaaa    88200
ccatttaaag accactgtat tttaactcaa caatacctgc ttcccaatta ctcatttcct    88260
cagataagaa gaaatcatct ctacaatgta gacaacatta tattttatag aatttgtttg    88320
aaattgagga agcagttaaa ttgtgcgctg tattttgcag attatgggga ttcaaattct    88380
agtaataggc ttttttattt ttatttttat acccttaacc agtttaattt tttttttcct    88440
cattgttggg gatgatgaga agaaatgatt tgggaaaatt aagtaacaac gacctagaaa    88500
agtgagaaca atctcattta ccatcatgta tccagtagtg gataattcat tttgatggct    88560
tctatttttg gccaaatgag aattaagcca gtgcctgaga ctgtcagaag ttgacctttg    88620
cactggcatt aaagagtcat agaaaaagaa tcatggatat ttatgaatta aggtaagagg    88680
tgtggctttt ttttttttct tttttccagc cgttgaccaa ttatagttcg gctgttgact    88740
gagaagtttg tggtgggaaa acgtttgcca tattttcttt gcatttgaat aattgtcttg    88800
tacttagaaa aaaggcgtct atgaatgacc agtgtttttg gtcgccaaat gttgctgaca    88860
aacttatccc aaaactttag tggcttaaaa aaacctgccc ccaactgtta gtcaatctga    88920
```

```
gctgggctca gctgggctgt tcttctgcca gcctgcaggt ggccactcat gtggtcagca    88980
ggtcggcgga gagactggga tggctgggct tctctctctg cctgcagtcc tgagtctctc    89040
cttcttcgtg tagtctcttt cagtggcctg gctggcaggg tagctagacc tctcacatgc    89100
agctcagagc tcccaagagc tcaaaagcag aaatggccag gccttctgaa aacttaagtc    89160
cagaattgtc acagtgtccc ttctacttcc ctctattgat gatgatgatg atgatgatga    89220
tgatgatgat gatgatgtgg atggtttttt ctaatcagaa gaaagctggg gtatgccctc    89280
tacttactaa acaagtcaca agcccagctc agattcaaga aaagggtgtg aagtagaggt    89340
gcagttaagt gggggggccac tagtctaaca gacggtcaca accagtgcca tggaaaacca    89400
aggatattag caaaagcaga agttgctagt gaccttggga agccgaagct gcttacagta    89460
gctgggacaa gctgaaagtc agactaagaa ataaagagag ggccttcaag aagcttcctg    89520
aatgatttct gctagccctg agcctatttt tggaaccagc acttgggaaa actgatcttg    89580
tgaggatgga tgtgtttagg gacacagggc ttttgagagc agcaccaccc cactgggca    89640 tccccagact tgggaaacgt gactcttcct taatgccact gggttttagt caggccacag    89700
tgagaaggaa cagccctaac aggcctccag ccaggttgaa tgagctcatt tttgttgtag    89760
ccaaccagta agatttgcta atgttctaca ttaagtgcct tctccaaaga catccctctt    89820
tgcctcatat gttgaatcat ccagtgcgga tatttcaatg aaaatatcat tggttgactt    89880
ttgtgatggt aataatgcta tggcatcttt gccatgaagt tgtggcctcc ttggattctt    89940
ctgactttgg cttctgaaag gaaggcctag atccagccct ggtggtagtt cctttctgag    90000
gtctctcagt cccttgagac tttggggtag tttggctgcc attctcactg acaaaatgta    90060
tatcagcccc cacctccacc ccccaatatt ccttgaactt tgaattgctt cagaacacag    90120
gtgtggcctg aagtattcc cttattaggg aagtgtcact gctgtcttct agtcaaactt    90180
gtaaagaaaa agattccagt tcagtatttg cagcaagaag cttgaatgct gttctttta    90240 tcgcattgtt acatcgactc attctccatt ttgctttggt tttgtcttga cttgacttga    90300
ctttgggggt aaagtctttc accagcacac aagagtttga ttgtacaaat atatcttctg    90360
cattaacatc tctgcctgtt gcttaagatc agttgctttt atactcagaa tggaaatacc    90420
tgatcttggc tagttttgtt ataagatatt gatttcattt agatttccct ccacgaggtc    90480
agcaaactat catgttctta tgtaaactta ggccaaggcc agagttatca tagtccctag    90540
gttgctacgg cttatcatgt gcttggtaaa aggtgatcgc aggttctcag acgagtttac    90600
tttacatgag atggaatcag gcagagaggc tgggatgatg gagaaagctc gaggtgaagt    90660
tttaaaaaaa aagttgtgga aaggaaagtt ccaaagaggt ggtttctgag gaagtcagag    90720
cgcccagggc cagagcagtc agtaatgggt gaatgaggtt gtttggaaag tcggtgtgac    90780
agacacatgg atgccatcta cttctaggtt gctggtgggt attaaatatg cacaatattc    90840
catagctcac tgaggatttt aaaattataa gcataggatt ttatattttg gggtgaaaga    90900
attatctggc acattaggta ttggagttta aaaaaaagc caaatttcac agtcttaata    90960 actttttta aaaaaacta aaaggcgctt catgtccagt gtgtggccct tctgaaactt    91020
atggtcatct ctcccactga aaccaagtc ttttcaaatg tggctaaatg gggatgagga    91080
gacacgggta ggactttctt ggtgtgtgtg cattctttaa agagccaagt tgcttcgggg    91140
aaacagccag gaaatggtc aagattattt ttagaggtta ttttattggg gattttaaga    91200
actaataaca tcttgagtta ttttttaattc agggggatgt ggaaaggttt gcaattgtca    91260
agtgttttgt tgtagcttag tatccataag ggaaacttag actatagaca taactacaaa    91320
```

-continued

```
gccagtgcag cttttgtttt ctgtatgttg ttgggggatc aactttcaca catagcaagc    91380
acatggcctc cctgatgtca ggatgccttt gttaggatct gtatttgccc ttaattttgt    91440
tgaaatcttt tttccttctt cctcttgaaa agttccaaaa tatagtttat tgtatctttc    91500
atcactaaaa atttgttcct ttttcactat gggcagttca cacaaggcaa aaactattga    91560
acagttggtt ttagtgtgtt gtataacttt gctgtatatc aaactaattt tgacaagttt    91620
tcatcctaag cctcaaatca tgtaattaat aatttgcctg tttatttatg acctaattgt    91680
gattctttta ttaataaaag ctaatgggaa aaggatccct gattaagctg atgactagac    91740
ctacaattaa ttttcctgca gtatatgaag tattgtacca gagtattaaa agatatgtaa    91800
tattttattg ataaatctat cctttaaaag gaatacgttt taggatgtca tcattttgat    91860
gtgaatcatg taaatgttga taatatgctg tttattatac atttagtgtt tcaagagatt    91920
cacttaattg ccttttttgcc cacgtatatt atgtagtcta tttgcaactg ttcttaaaaa    91980
aatgacatta aaagaatagt ttatgtagag aaacattagt ggatgttaat tgtctcccca    92040
cctatattta tgggtgttag cgcaactgct ttgctagttg caaagctgta ttatcagagt    92100
aaaagtgtat ttgtaaactg tatgggaact aaaaattagg aataaaacca ttttcttata    92160
tgatggcatt tgtcgtttgc ttcatcagaa atgtccagga aaaaaatggg attattggtc    92220
actccacctc tcacactggc aaaatactga catttagcag ctcttatcta gaagtgactt    92280
ggaacataga ataaaggcat gagttcctga agaattcatt gagtgtttcc tgtagaaata    92340
gctttaggag atagggagtt ctatctggga gaacatatga gtaactcaag agtaaaaagt    92400
atagtctgtg taaactatag aagaaatgct gggcatggtg gcgcgcccct gtaatctcag    92460
ctacttggag gctgagacgg gaggattcct tgaacccagg agcccaggag ttttagacca    92520
gtctgggtaa catagtgaga ccctttctca cctactctca ctgcatgccc cccaaaaata    92580
tatatgtgcg cgcacgcgcg cgcacacaca catacacaca cacacacaca cacacacaca    92640
cagaggaaat tgttagaaaa cacacagaac tgaatgtaaa tagtattagg tgggaataag    92700
aagtaaaggg atggtaagga ggcttggagg aggagtaaat tatctgctat gggacatcag    92760
ctc                                                                92763
```

<210> SEQ ID NO 61
<211> LENGTH: 593
<212> TYPE: PRT
<213> ORGANISM: Homo sapiens
<400> SEQUENCE: 61

```
Met Thr Ser Arg Arg Trp Phe His Pro Asn Ile Thr Gly Val Glu Ala
1               5                   10                  15

Glu Asn Leu Leu Leu Thr Arg Gly Val Asp Gly Ser Phe Leu Ala Arg
            20                  25                  30

Pro Ser Lys Ser Asn Pro Gly Asp Phe Thr Leu Ser Val Arg Arg Asn
        35                  40                  45

Gly Ala Val Thr His Ile Lys Ile Gln Asn Thr Gly Asp Tyr Tyr Asp
    50                  55                  60

Leu Tyr Gly Gly Glu Lys Phe Ala Thr Leu Ala Glu Leu Val Gln Tyr
65                  70                  75                  80

Tyr Met Glu His His Gly Gln Leu Lys Glu Lys Asn Gly Asp Val Ile
                85                  90                  95

Glu Leu Lys Tyr Pro Leu Asn Cys Ala Asp Pro Thr Ser Glu Arg Trp
            100                 105                 110
```

-continued

Phe His Gly His Leu Ser Gly Lys Glu Ala Glu Lys Leu Leu Thr Glu
        115                 120                 125

Lys Gly Lys His Gly Ser Phe Leu Val Arg Glu Ser Gln Ser His Pro
    130                 135                 140

Gly Asp Phe Val Leu Ser Val Arg Thr Gly Asp Asp Lys Gly Glu Ser
145                 150                 155                 160

Asn Asp Gly Lys Ser Lys Val Thr His Val Met Ile Arg Cys Gln Glu
                165                 170                 175

Leu Lys Tyr Asp Val Gly Gly Gly Glu Arg Phe Asp Ser Leu Thr Asp
            180                 185                 190

Leu Val Glu His Tyr Lys Lys Asn Pro Met Val Glu Thr Leu Gly Thr
        195                 200                 205

Val Leu Gln Leu Lys Gln Pro Leu Asn Thr Thr Arg Ile Asn Ala Ala
    210                 215                 220

Glu Ile Glu Ser Arg Val Arg Glu Leu Ser Lys Leu Ala Glu Thr Thr
225                 230                 235                 240

Asp Lys Val Lys Gln Gly Phe Trp Glu Glu Phe Glu Thr Leu Gln Gln
                245                 250                 255

Gln Glu Cys Lys Leu Leu Tyr Ser Arg Lys Glu Gly Gln Arg Gln Glu
            260                 265                 270

Asn Lys Asn Lys Asn Arg Tyr Lys Asn Ile Leu Pro Phe Asp His Thr
        275                 280                 285

Arg Val Val Leu His Asp Gly Asp Pro Asn Glu Pro Val Ser Asp Tyr
    290                 295                 300

Ile Asn Ala Asn Ile Ile Met Pro Glu Phe Glu Thr Lys Cys Asn Asn
305                 310                 315                 320

Ser Lys Pro Lys Lys Ser Tyr Ile Ala Thr Gln Gly Cys Leu Gln Asn
                325                 330                 335

Thr Val Asn Asp Phe Trp Arg Met Val Phe Gln Glu Asn Ser Arg Val
            340                 345                 350

Ile Val Met Thr Thr Lys Glu Val Glu Arg Gly Lys Ser Lys Cys Val
        355                 360                 365

Lys Tyr Trp Pro Asp Glu Tyr Ala Leu Lys Glu Tyr Gly Val Met Arg
    370                 375                 380

Val Arg Asn Val Lys Glu Ser Ala Ala His Asp Tyr Thr Leu Arg Glu
385                 390                 395                 400

Leu Lys Leu Ser Lys Val Gly Gln Gly Asn Thr Glu Arg Thr Val Trp
                405                 410                 415

Gln Tyr His Phe Arg Thr Trp Pro Asp His Gly Val Pro Ser Asp Pro
            420                 425                 430

Gly Gly Val Leu Asp Phe Leu Glu Glu Val His His Lys Gln Glu Ser
        435                 440                 445

Ile Met Asp Ala Gly Pro Val Val His Cys Ser Ala Gly Ile Gly
        450                 455                 460

Arg Thr Gly Thr Phe Ile Val Ile Asp Ile Leu Ile Asp Ile Ile Arg
465                 470                 475                 480

Glu Lys Gly Val Asp Cys Asp Ile Asp Val Pro Lys Thr Ile Gln Met
                485                 490                 495

Val Arg Ser Gln Arg Ser Gly Met Val Gln Thr Glu Ala Gln Tyr Arg
            500                 505                 510

Phe Ile Tyr Met Ala Val Gln His Tyr Ile Glu Thr Leu Gln Arg Arg
        515                 520                 525

```
Ile Glu Glu Gln Lys Ser Lys Arg Lys Gly His Glu Tyr Thr Asn
    530             535                 540

Ile Lys Tyr Ser Leu Ala Asp Gln Thr Ser Gly Asp Gln Ser Pro Leu
545             550                 555                 560

Pro Pro Cys Thr Pro Thr Pro Pro Cys Ala Glu Met Arg Glu Asp Ser
            565             570                 575

Ala Arg Val Tyr Glu Asn Val Gly Leu Met Gln Gln Gln Lys Ser Phe
            580             585                 590

Arg

<210> SEQ ID NO 62
<211> LENGTH: 1296
<212> TYPE: DNA
<213> ORGANISM: Homo sapiens

<400> SEQUENCE: 62
```

| | | | | | |
|---|---|---|---|---|---|
| atgcccaacc | ccaggcctgg | caagccctcg | gccccttcct | tggcccttgg | cccatcccca | 60 |
| ggagcctcgc | ccagctggag | ggctgcaccc | aaagcctcag | acctgctggg | ggcccggggc | 120 |
| ccaggggaa | ccttccaggg | ccgagatctt | cgaggcgggg | cccatgcctc | ctcttcttcc | 180 |
| ttgaacccca | tgccaccatc | gcagctgcag | ctgcccacac | tgcccctagt | catggtggca | 240 |
| ccctccgggg | cacggctggg | cccttgccc | cacttacagg | cactcctcca | ggacaggcca | 300 |
| catttcatgc | accagctctc | aacggtggat | gcccacgccc | ggacccctgt | gctgcaggtg | 360 |
| cacccctgg | agagcccagc | catgatcagc | ctcacaccac | ccaccaccgc | cactggggtc | 420 |
| ttctccctca | aggcccggcc | tggcctccca | cctgggatca | acgtggccag | cctggaatgg | 480 |
| gtgtccaggg | agccggcact | gctctgcacc | ttcccaaatc | ccagtgcacc | caggaaggac | 540 |
| agcacccttt | cggctgtgcc | ccagagctcc | tacccactgc | tggcaaatgg | tgtctgcaag | 600 |
| tggcccggat | gtgagaaggt | cttcgaagag | ccagaggact | tcctcaagca | ctgccaggcg | 660 |
| gaccatcttc | tggatgagaa | gggcagggca | caatgtctcc | tccagagaga | gatggtacag | 720 |
| tctctggagc | agcagctggt | gctggagaag | gagaagctga | gtgccatgca | ggcccacctg | 780 |
| gctgggaaaa | tggcactgac | caaggcttca | tctgtggcat | catccgacaa | gggctcctgc | 840 |
| tgcatcgtag | ctgctggcag | ccaaggccct | gtcgtcccag | cctggtctgg | ccccgggag | 900 |
| gcccctgaca | gcctgtttgc | tgtccggagg | cacctgtggg | gtagccatgg | aaacagcaca | 960 |
| ttcccagagt | tcctccacaa | catggactac | ttcaagttcc | acaacatgcg | accccctttc | 1020 |
| acctacgcca | cgctcatccg | ctgggccatc | ctggaggctc | cagagaagca | gcggacactc | 1080 |
| aatgagatct | accactggtt | cacacgcatg | tttgccttct | tcagaaacca | tcctgccacc | 1140 |
| tggaagaacg | ccatccgcca | caacctgagt | ctgcacaagt | gctttgtgcg | ggtggagagc | 1200 |
| gagaaggggg | ctgtgtggac | cgtggatgag | ctggagttcc | gcaagaaacg | gagccagagg | 1260 |
| cccagcaggt | gttccaaccc | tacacctggc | ccctga | | | 1296 |

```
<210> SEQ ID NO 63
<211> LENGTH: 1875
<212> TYPE: DNA
<213> ORGANISM: Homo sapiens

<400> SEQUENCE: 63
```

| | | | | | |
|---|---|---|---|---|---|
| atggtgaggt | ggtttcaccg | agacctcagt | gggctggatg | cagagaccct | gctcaagggc | 60 |
| cgaggtgtcc | acggtagctt | cctggctcgg | cccagtcgca | agaaccaggg | tgacttctcg | 120 |
| ctctccgtca | gggtggggga | tcaggtgacc | catattcgga | tccagaactc | agggattttc | 180 |

```
tatgacctgt atggagggga gaagtttgcg actctgacag agctggtgga gtactacact      240
cagcagcagg gtgtcctgca ggaccgcgac ggcaccatca tccacctcaa gtacccgctg      300
aactgctccg atcccactag tgagaggtgg taccatggcc acatgtctgg cgggcaggca      360
gagacgctgc tgcaggccaa gggcgagccc tggacgtttc ttgtgcgtga gagcctcagc      420
cagcctggag acttcgtgct ttctgtgctc agtgaccagc ccaaggctgg cccaggctcc      480
ccgctcaggg tcacccacat caaggtcatg tgcgagggtg gacgctacac agtgggtggt      540
ttggagacct tcgacagcct cacggacctg gtggagcatt tcaagaagac ggggattgag      600
gaggcctcag gcgcctttgt ctacctgcgg cagccgtact atgccacgag ggtgaatgcg      660
gctgacattg agaaccgagt gttggaactg aacaagaagc aggagtccga ggatacagcc      720
aaggctggct ctgggagga gtttgagagt ttgcagaagc aggaggtgaa gaacttgcac      780
cagcgtctgg aagggcagcg gccagagaac aagggcaaga accgctacaa gaacattctc      840
ccctttgacc acagccgagt gatcctgcag ggacgggaca gtaacatccc cgggtccgac      900
tacatcaatg ccaactacat caagaaccag ctgctaggcc ctgatgagaa cgctaagacc      960
tacatcgcca gccaggggttg tctggaggcc acggtcaatg acttctggca gatggcgtgg     1020
caggagaaca gccgtgtcat cgtcatgacc acccgagagg tggagaaagg ccggaacaaa     1080
tgcgtcccat actggcccga ggtgggcatg cagcgtgctt atgggcccta ctctgtgacc     1140
aactgcgggg agcatgacac aaccgaatac aaactccgta ccttacaggt ctcccgctg      1200 gacaatggag acctgattcg ggagatctgg cattaccagt acctgagctg gcccgaccat     1260
ggggtcccca gtgagcctgg gggtgtcctc agcttcctgg accagatcaa ccagcggcag     1320
gaaagtctgc ctcacgcagg gcccatcatc gtgcactgca gcgccggcat cggccgcaca     1380
ggcaccatca ttgtcatcga catgctcatg gagaacatct ccaccaaggg cctggactgt     1440
gacattgaca tccagaagac catccagatg gtgcgggcgc agcgctcggg catggtgcag     1500
acggaggcgc agtacaagtt catctacgtg gccatcgccc agttcattga aaccactaag     1560
aagaagctgg aggtcctgca gtcgcagaag ggccaggagt cggagtacgg gaacatcacc     1620
tatcccccag ccatgaagaa tgcccatgcc aaggcctccc gcacctcgtc caagagcttg     1680
gagtctagtg cagggaccgt ggctgcgtca cctgtgagac ggggtggcca gagggactg      1740 ccagtgccgg gtcccctgt gctgtctcct gacctgcacc aactgcctgt acttgccccc     1800
ctgcacccgg ctgcagacac aaggaggatg tgtatgagaa cctgcacact aagaacaaga     1860
gggaggagaa agtga                                                      1875
```

<210> SEQ ID NO 64
<211> LENGTH: 1782
<212> TYPE: DNA
<213> ORGANISM: Homo sapiens

<400> SEQUENCE: 64

```
atgacatcgc ggagatggtt tcacccaaat atcactggtg tggaggcaga aaacctactg       60
ttgacaagag gagttgatgg cagttttttg gcaaggccta gtaaaagtaa ccctggagac      120
ttcacacttt ccgttagaag aaatggagct gtcacccaca tcaagattca gaacactggt      180
gattactatg acctgtatgg aggggagaaa tttgccactt ggctgagtt ggtccagtat      240 tacatggaac atcacgggca attaaaagag aagaatggag atgtcattga gcttaaatat      300
cctctgaact gtgcagatcc tacctctgaa aggtggtttc atggacatct ctctgggaaa      360
```

```
gaagcagaga aattattaac tgaaaaagga aaacatggta gttttcttgt acgagagagc    420
cagagccacc ctggagattt tgttctttct gtgcgcactg gtgatgacaa aggggagagc    480
aatgacggca agtctaaagt gacccatgtt atgattcgct gtcaggaact gaaatacgac    540
gttggtggag gagaacggtt tgattctttg acagatcttg tggaacatta taagaagaat    600
cctatggtgg aaacattggg tacagtacta caactcaagc agcccttaa cacgactcgt    660 ataaatgctg ctgaaataga aagcagagtt cgagaactaa gcaaattagc tgagaccaca    720
gataaagtca aacaaggctt tgggaagaa tttgagacac tacaacaaca ggagtgcaaa    780
cttctctaca gccgaaaaga gggtcaaagg caagaaaaca aaaacaaaaa tagatataaa    840
aacatcctgc cctttgatca taccagggtt gtcctacacg atggtgatcc caatgagcct    900
gtttcagatt acatcaatgc aaatatcatc atgcctgaat ttgaaaccaa gtgcaacaat    960
tcaaagccca aaagagtta cattgccaca caaggctgcc tgcaaaacac ggtgaatgac   1020
ttttggcgga tggtgttcca agaaaactcc cgagtgattg tcatgacaac gaaagaagtg   1080
gagagaggaa agagtaaatg tgtcaaatac tggcctgatg agtatgctct aaaagaatat   1140
ggcgtcatgc gtgttaggaa cgtcaaagaa agcgccgctc atgactatac gctaagagaa   1200
cttaaacttt caaggttgg acaagggaat acggagagaa cggtctggca ataccacttt   1260
cggacctggc cggaccacgg cgtgcccagc gaccctgggg gcgtgctgga cttcctggag   1320
gaggtgcacc ataagcagga gagcatcatg gatgcagggc cggtcgtggt gcactgcagt   1380
gctggaattg gccggacagg gacgttcatt gtgattgata ttcttattga catcatcaga   1440
gagaaaggtg ttgactgcga tattgacgtt cccaaaacca tccagatggt gcggtctcag   1500
aggtcaggga tggtccagac agaagcacag taccgattta tctatatggc ggtccagcat   1560
tatattgaaa cactacagcg caggattgaa gaagagcaga aaagcaagag gaaagggcac   1620
gaatatacaa atattaagta ttctctagcg gaccagacga gtggagatca gagccctctc   1680
ccgccttgta ctccaacgcc accctgtgca gaaatgagag aagacagtgc tagagtctat   1740
gaaaacgtgg gcctgatgca acagcagaaa agtttcagat ga                     1782
```

<210> SEQ ID NO 65
<211> LENGTH: 930
<212> TYPE: PRT
<213> ORGANISM: Artificial Sequence
<220> FEATURE:
<223> OTHER INFORMATION: Synthetic-Generic TALEN amino acid sequence (to
      recognize 15bp DNA sequences)
<220> FEATURE:
<221> NAME/KEY: misc_feature
<222> LOCATION: (187)..(188)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (221)..(222)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (255)..(256)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (289)..(290)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (323)..(344)

```
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (356)..(357)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (390)..(391)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (424)..(425)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (458)..(459)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (492)..(493)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (526)..(527)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (560)..(561)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (594)..(595)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (628)..(629)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (662)..(663)
<223> OTHER INFORMATION: To recognize C: XX = HD; To recognize T: XX =
      NG; To recognize A: XX = NI; To recognize G: XX = NK

<400> SEQUENCE: 65

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ser Arg Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Thr Tyr Cys His Ile Ile Thr Ala Leu Pro Glu Ala Thr His Glu Asp
            100                 105                 110

Ile Val Gly Val Gly Lys Gln Trp Ser Gly Ala Arg Ala Leu Glu Ala
        115                 120                 125
```

```
Leu Leu Thr Asp Ala Gly Glu Leu Arg Gly Pro Pro Leu Gln Leu Asp
    130                 135                 140

Thr Gly Gln Leu Val Lys Ile Ala Lys Arg Gly Gly Val Thr Ala Met
145                 150                 155                 160

Glu Ala Val His Ala Arg Asn Ala Leu Thr Gly Ala Pro Leu Asn Leu
                165                 170                 175

Thr Pro Glu Gln Val Val Ala Ile Ala Ser Xaa Xaa Gly Gly Lys Gln
                180                 185                 190

Ala Leu Glu Thr Val Gln Arg Leu Leu Pro Val Leu Cys Gln Ala His
            195                 200                 205

Gly Leu Thr Pro Glu Gln Val Val Ala Ile Ala Ser Xaa Xaa Gly Gly
    210                 215                 220

Lys Gln Ala Leu Glu Thr Val Gln Arg Leu Leu Pro Val Leu Cys Gln
225                 230                 235                 240

Ala His Gly Leu Thr Pro Glu Gln Val Val Ala Ile Ala Ser Xaa Xaa
                245                 250                 255

Gly Gly Lys Gln Ala Leu Glu Thr Val Gln Arg Leu Leu Pro Val Leu
                260                 265                 270

Cys Gln Ala His Gly Leu Thr Pro Glu Gln Val Val Ala Ile Ala Ser
            275                 280                 285

Xaa Xaa Gly Gly Lys Gln Ala Leu Glu Thr Val Gln Arg Leu Leu Pro
    290                 295                 300

Val Leu Cys Gln Ala His Gly Leu Thr Pro Glu Gln Val Val Ala Ile
305                 310                 315                 320

Ala Ser Xaa Xaa Gly Gly Lys Gln Ala Leu Glu Thr Val Gln Arg Leu
                325                 330                 335

Leu Val Leu Cys Gln Ala His Gly Leu Thr Pro Glu Gln Val Val Ala
            340                 345                 350

Ile Ala Ser Xaa Xaa Gly Gly Lys Gln Ala Leu Glu Thr Val Gln Arg
    355                 360                 365

Leu Leu Pro Val Leu Cys Gln Ala His Gly Leu Thr Pro Glu Gln Val
370                 375                 380

Val Ala Thr Ala Ser Xaa Xaa Gly Gly Lys Gln Ala Leu Glu Thr Val
385                 390                 395                 400

Gln Arg Leu Leu Pro Val Leu Cys Gln Ala Asn Gly Leu Thr Pro Glu
                405                 410                 415

Gln Val Val Ala Ile Ala Ser Xaa Xaa Gly Gly Lys Gln Ala Leu Glu
                420                 425                 430

Thr Val Gln Arg Leu Leu Pro Val Leu Cys Gln Ala His Gly Leu Thr
            435                 440                 445

Pro Glu Gln Val Val Ala Ile Ala Ser Xaa Xaa Gly Gly Lys Gln Ala
    450                 455                 460

Leu Glu Thr Val Gln Arg Leu Leu Pro Val Leu Cys Gln Ala His Gly
465                 470                 475                 480

Leu Thr Pro Glu Gln Val Val Ala Ile Ala Ser Xaa Xaa Gly Gly Lys
                485                 490                 495

Gln Ala Leu Glu Thr Val Gln Arg Leu Leu Pro Val Leu Cys Gln Ala
                500                 505                 510

His Gly Leu Thr Pro Glu Gln Val Val Ala Ile Ala Ser Xaa Xaa Gly
            515                 520                 525

Gly Lys Gln Ala Leu Glu Thr Val Gln Arg Leu Leu Pro Val Leu Cys
    530                 535                 540

Gln Ala His Gly Leu Thr Pro Glu Gln Val Val Ala Ile Ala Ser Xaa
```

```
                    545                 550                 555                 560
Xaa Gly Gly Lys Gln Ala Leu Glu Thr Val Gln Arg Leu Leu Pro Val
                565                 570                 575

Leu Cys Gln Ala His Gly Leu Thr Pro Glu Gln Val Val Ala Ile Ala
            580                 585                 590

Ser Xaa Xaa Gly Gly Lys Gln Ala Leu Glu Thr Val Gln Arg Leu Leu
        595                 600                 605

Pro Val Leu Cys Gln Ala His Gly Leu Thr Pro Glu Gln Val Val Ala
    610                 615                 620

Thr Ala Ser Xaa Xaa Gly Gly Lys Gln Ala Leu Glu Thr Val Gln Arg
625                 630                 635                 640

Leu Leu Pro Val Leu Cys Gln Ala His Gly Leu Thr Pro Glu Gln Val
                645                 650                 655

Val Ala Thr Ala Ser Xaa Xaa Gly Gly Arg Pro Ala Leu Glu Ser Ile
            660                 665                 670

Val Ala Gln Leu Ser Arg Pro Asp Pro Ala Leu Ala Ala Leu Thr Asn
        675                 680                 685

Asp His Leu Val Ala Leu Ala Cys Leu Gly Gly Arg Pro Ala Met Asp
    690                 695                 700

Ala Val Lys Lys Gly Leu Pro His Ala Pro Glu Leu Ile Arg Arg Val
705                 710                 715                 720

Asn Arg Arg Ile Gly Glu Arg Thr Ser His Arg Val Ala Gly Ser Gln
                725                 730                 735

Leu Val Lys Ser Glu Leu Glu Glu Lys Lys Ser Glu Leu Arg His Lys
            740                 745                 750

Leu Lys Tyr Val Pro His Glu Tyr Ile Glu Leu Ile Glu Ile Ala Arg
        755                 760                 765

Asn Pro Thr Gln Asp Arg Ile Leu Glu Met Lys Val Met Glu Phe Phe
    770                 775                 780

Met Lys Val Tyr Gly Tyr Arg Gly Glu His Leu Gly Gly Ser Arg Lys
785                 790                 795                 800

Pro Asp Gly Ala Ile Tyr Thr Val Gly Pro Ile Asp Tyr Gly Val Ile
                805                 810                 815

Val Asp Thr Lys Ala Tyr Ser Gly Gly Tyr Asn Leu Pro Ile Gly Gln
            820                 825                 830

Ala Asp Glu Met Gln Arg Tyr Val Lys Glu Asn Gln Thr Arg Asn Lys
        835                 840                 845

His Ile Asn Pro Asn Glu Trp Trp Lys Val Tyr Pro Ser Ser Val Thr
    850                 855                 860

Glu Phe Lys Phe Leu Phe Val Ser Gly His Phe Lys Gly Asn Tyr Lys
865                 870                 875                 880

Ala Gln Leu Thr Arg Leu Asn Arg Lys Thr Asn Cys Asn Gly Ala Val
                885                 890                 895

Leu Ser Val Glu Glu Leu Leu Ile Gly Gly Glu Met Ile Lys Ala Gly
            900                 905                 910

Thr Leu Thr Leu Glu Glu Val Arg Arg Lys Phe Asn Asn Gly Glu Ile
        915                 920                 925

Asn Phe
    930

<210> SEQ ID NO 66
<211> LENGTH: 933
<212> TYPE: PRT
<213> ORGANISM: Artificial Sequence
```

```
<220> FEATURE:
<223> OTHER INFORMATION: Synthetic-Generic TALEN amino acid sequence (to
      recognize 15bp DNA sequences)
<220> FEATURE:
<221> NAME/KEY: misc_feature
<222> LOCATION: (188)..(189)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (222)..(223)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (256)..(257)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (290)..(291)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (324)..(325)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (358)..(359)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (392)..(393)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (426)..(427)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (460)..(461)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (494)..(495)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (528)..(529)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (562)..(563)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (596)..(597)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (630)..(631)
<223> OTHER INFORMATION: To recognize C: XX = HD; To recognize T: XX =
      NG; To recognize A: XX = NI; To recognize G: XX = NN
<220> FEATURE:
<221> NAME/KEY: misc_feature
<222> LOCATION: (664)..(665)
<223> OTHER INFORMATION: To recognize C: XX = HD; To recognize T: XX =
      NG; To recognize A: XX = NI; To recognize G: XX = NK
```

```
<400> SEQUENCE: 66

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Arg Val Asp Leu Arg Thr Leu Gly Tyr
            35                  40                  45

Ser Gln Gln Gln Gln Glu Lys Ile Lys Pro Lys Val Arg Ser Thr Val
            50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Thr Tyr Gln His Ile Ile Thr Ala Leu Pro Glu Ala Thr His Glu Asp
            100                 105                 110

Ile Val Gly Val Gly Lys Gln Trp Ser Gly Ala Arg Ala Leu Glu Ala
            115                 120                 125

Leu Leu Thr Asp Ala Gly Glu Leu Arg Gly Pro Pro Leu Gln Leu Asp
130                 135                 140

Thr Gly Gln Leu Val Lys Ile Ala Lys Arg Gly Gly Val Thr Ala Met
145                 150                 155                 160

Glu Ala Val His Ala Ser Arg Asn Ala Leu Thr Gly Ala Pro Leu Asn
                165                 170                 175

Leu Thr Pro Glu Gln Val Val Ala Ile Ala Ser Xaa Xaa Gly Gly Lys
            180                 185                 190

Gln Ala Leu Glu Thr Val Gln Arg Leu Leu Pro Val Leu Cys Gln Ala
            195                 200                 205

His Gly Leu Thr Pro Glu Gln Val Val Ala Ile Ala Ser Xaa Xaa Gly
            210                 215                 220

Gly Lys Gln Ala Leu Glu Thr Val Gln Arg Leu Leu Pro Val Leu Cys
225                 230                 235                 240

Gln Ala His Gly Leu Thr Pro Glu Gln Val Val Ala Ile Ala Ser Xaa
                245                 250                 255

Xaa Gly Gly Lys Gln Ala Leu Glu Thr Val Gln Arg Leu Leu Pro Val
            260                 265                 270

Leu Cys Gln Ala His Gly Leu Thr Pro Glu Gln Val Val Ala Ile Ala
            275                 280                 285

Ser Xaa Xaa Gly Gly Lys Gln Ala Leu Glu Thr Val Gln Arg Leu Leu
            290                 295                 300

Pro Val Leu Cys Gln Ala His Gly Leu Thr Pro Glu Gln Val Val Ala
305                 310                 315                 320

Ile Ala Ser Xaa Xaa Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser Xaa Xaa Gly Gly Lys Gln Ala Leu Glu Thr Val
            355                 360                 365

Gln Arg Leu Leu Pro Val Leu Cys Gln Ala His Gly Leu Thr Pro Glu
            370                 375                 380

Gln Val Val Ala Ile Ala Ser Xaa Xaa Gly Gly Lys Gln Ala Leu Glu
385                 390                 395                 400

Thr Val Gln Arg Leu Leu Pro Val Leu Cys Gln Ala His Gly Leu Thr
                405                 410                 415
```

```
Pro Glu Gln Val Val Ala Ile Ala Ser Xaa Xaa Gly Gly Lys Gln Ala
                420                 425                 430

Leu Glu Thr Val Gln Arg Leu Leu Pro Val Leu Cys Gln Ala His Gly
            435                 440                 445

Leu Thr Pro Glu Gln Val Val Ala Ile Ala Ser Xaa Xaa Gly Gly Lys
        450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Xaa Xaa Gly
                485                 490                 495

Gly Lys Gln Ala Leu Glu Thr Val Gln Arg Leu Leu Pro Val Leu Cys
                500                 505                 510

Gln Ala His Gly Leu Thr Pro Glu Gln Val Val Ala Ile Ala Ser Xaa
                515                 520                 525

Xaa Gly Gly Lys Gln Ala Leu Glu Thr Val Gln Arg Leu Leu Pro Val
        530                 535                 540

Leu Cys Gln Ala His Gly Leu Thr Pro Glu Gln Val Val Ala Ile Ala
545                 550                 555                 560

Ser Xaa Xaa Gly Gly Lys Gln Ala Leu Glu Thr Val Gln Arg Leu Leu
                565                 570                 575

Pro Val Leu Cys Gln Ala His Gly Leu Thr Pro Glu Gln Val Val Ala
            580                 585                 590

Ile Ala Ser Xaa Xaa Gly Gly Lys Gln Ala Leu Glu Thr Val Gln Arg
        595                 600                 605

Leu Leu Pro Val Leu Cys Gln Ala His Gly Leu Thr Pro Glu Gln Val
    610                 615                 620

Val Ala Ile Ala Ser Xaa Xaa Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser Xaa Xaa Gly Gly Arg Pro Ala Leu Glu
                660                 665                 670

Ser Ile Val Ala Gln Leu Ser Arg Pro Asp Pro Ala Leu Ala Ala Leu
                675                 680                 685

Thr Asn Asp His Leu Val Ala Leu Ala Cys Leu Gly Gly Arg Pro Ala
            690                 695                 700

Met Asp Ala Val Lys Lys Gly Leu Pro His Ala Pro Glu Leu Ile Arg
705                 710                 715                 720

Arg Val Asn Arg Arg Ile Gly Glu Arg Thr Ser His Arg Val Ala Gly
                725                 730                 735

Ser Gln Leu Val Lys Ser Glu Leu Glu Glu Lys Ser Glu Leu Arg
                740                 745                 750

His Lys Leu Lys Tyr Val Pro His Glu Tyr Ile Glu Leu Ile Glu Ile
            755                 760                 765

Ala Arg Asn Pro Thr Gln Asp Arg Ile Leu Glu Met Lys Val Met Glu
            770                 775                 780

Phe Phe Met Lys Val Tyr Gly Tyr Arg Gly Glu His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830
```

-continued

```
Ile Gly Gln Ala Asp Glu Met Glu Arg Tyr Val Glu Glu Asn Gln Thr
            835                 840                 845

Arg Asp Lys His Leu Asn Pro Asn Glu Trp Trp Lys Val Tyr Pro Ser
    850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
            915                 920                 925

Gly Glu Ile Asn Phe
    930
```